United States Patent
Corman et al.

(10) Patent No.: US 10,214,531 B2
(45) Date of Patent: Feb. 26, 2019

(54) SUBSTITUTED AMINO TRIAZOLES, AND METHODS USING SAME

(71) Applicant: Institute for Drug Discovery, LLC, Guilford, CT (US)

(72) Inventors: Michael L. Corman, Salem, CT (US); William M. Hungerford, Niantic, CT (US); Adam Golebiowski, Madison, CT (US); Raymond P. Beckett, Yorktown Heights, NY (US); Marzena Mazur, Lodz (PL); Sylwia Olejniczak, Zgierz (PL); Jacek Olczak, Lodz (PL)

(73) Assignee: Institute for Drug Discovery, LLC, Guilford, CT (US)

( * ) Notice: Subject to any disclaimer, the term of this patent is extended or adjusted under 35 U.S.C. 154(b) by 0 days.

(21) Appl. No.: 15/037,090

(22) PCT Filed: Dec. 19, 2014

(86) PCT No.: PCT/US2014/071490
§ 371 (c)(1),
(2) Date: May 17, 2016

(87) PCT Pub. No.: WO2015/095701
PCT Pub. Date: Jun. 25, 2015

(65) Prior Publication Data
US 2016/0297823 A1  Oct. 13, 2016

Related U.S. Application Data

(60) Provisional application No. 61/919,117, filed on Dec. 20, 2013.

(51) Int. Cl.
*A61K 31/4196* (2006.01)
*C07D 401/04* (2006.01)
*C07D 487/04* (2006.01)
*C07D 403/12* (2006.01)
*C07D 401/14* (2006.01)
*C07D 405/14* (2006.01)
*C07D 413/14* (2006.01)
*C07D 249/14* (2006.01)
*C07D 471/04* (2006.01)
*C07D 405/12* (2006.01)

(52) U.S. Cl.
CPC ......... *C07D 487/04* (2013.01); *C07D 249/14* (2013.01); *C07D 401/04* (2013.01); *C07D 401/14* (2013.01); *C07D 403/12* (2013.01); *C07D 405/12* (2013.01); *C07D 405/14* (2013.01); *C07D 413/14* (2013.01); *C07D 471/04* (2013.01)

(58) Field of Classification Search
CPC ................. A61K 31/4196; C07D 401/04
See application file for complete search history.

(56) References Cited

U.S. PATENT DOCUMENTS

| 4,421,753 | A | 12/1983 | Tomcufcik et al. |
| 4,582,833 | A | 4/1986 | Tomcufcik et al. |
| 8,288,371 | B2 | 10/2012 | Paradkar et al. |
| 8,586,623 | B2 | 11/2013 | Kenda et al. |

FOREIGN PATENT DOCUMENTS

| WO | 2005047250 A1 | 5/2005 |
| WO | 2012126984 A1 | 9/2012 |

OTHER PUBLICATIONS

PCT International Search Report and Written Opinion for PCT International Application No. PCT/US2014/071490 dated May 22, 2015.
Cole, et al., "Identification and characterization of acidic mammalian chitinase inhibitors", J Med Chem. 53(16), 2010, 6122-6128.
Gloster, et al., "Developing inhibitors of glycan processing enzymes as tools for enabling glycobiology", Nat Chem Biol. 8(8), 2012, 683-694.
European Search Report for European Patent Application No. 14871777.0 dated Apr. 12, 2017.
NCBI PubChem Substance SID151760441, 2012.
Meyer, et al., "5-(1-piperazinyl)-1H-1,2,4-triazol-3-amines as antihypertensive agents", J Med Chem. 32(3), 1989, 593-597.

*Primary Examiner* — Zohreh A Fay
(74) *Attorney, Agent, or Firm* — Saul Ewing Arnstein & Lehr LLP; Kathryn Doyle; Domingos J. Silva

(57) ABSTRACT

The invention provides novel substituted amino triazoles of Formula (I), or a pharmaceutically acceptable salt, hydrate or solvate thereof, as well as pharmaceutical compositions comprising the same. The compounds of the invention are inhibitors of acidic mammalian chitinase (AMCase) and are useful, in a non-limiting embodiment, for treating asthma. The invention further provides methods of using compounds and/or compositions of the invention to treat asthma and/or to monitor asthma treatment.

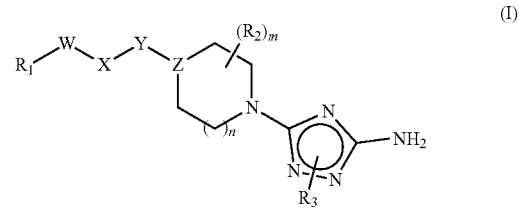

10 Claims, No Drawings

SUBSTITUTED AMINO TRIAZOLES, AND METHODS USING SAME

CROSS-REFERENCE TO RELATED APPLICATIONS

The present application is a 35 U.S.C. § 371 national phase application from, and claims priority to, International Application No. PCT/US2014/071490, filed Dec. 19, 2014, and published under PCT Article 21(2) in English, which claims priority under 35 U.S.C. § 119(e) to U.S. Provisional Patent Application No. 61/919,117, filed Dec. 20, 2013, all of which applications are incorporated herein by reference in their entireties.

BACKGROUND OF THE INVENTION

Acidic mammalian chitinase (AMCase) is a secreted enzyme of molecular weight of about 52.2 kD and typically found in the stomach, salivary gland, and lungs. The enzyme catalyzes the hydrolysis of artificial chitin-like substrates, and is unique among mammalian enzymes by having an acidic pH optimum. AMCase is induced during $T_H2$ inflammation through an IL-13-dependent mechanism. Chitinases are believed to play a key role in the innate immunity to parasites and other infectious agents. It has been suggested that, when produced in a dysregulated fashion, chitinases also play an important role in the pathogenesis of allergy and/or asthma.

Asthma is a chronic inflammatory disease of the airways characterized by recurrent episodes of reversible airway obstruction and airway hyperresponsiveness (AHR). Typical clinical manifestations include shortness of breath, wheezing, coughing and chest tightness that can become life threatening or fatal. While existing therapies focus on reducing the symptomatic bronchospasm and pulmonary inflammation, there is a growing awareness of the role of long-term airway remodeling in accelerated lung deterioration in asthmatics. Airway remodeling refers to a number of pathological features including epithelial smooth muscle and myofibroblast hyperplasia and/or metaplasia, subepithelial fibrosis and matrix deposition.

It is generally accepted that allergic asthma is initiated by an inappropriate inflammatory reaction to airborne allergens. The lungs of asthmatics demonstrate an intense infiltration of lymphocytes, mast cells and especially eosinophils. AMCase is prominently expressed in lungs from antigen-sensitized and challenged and IL-13-transgenic mice. AMCase mRNA is not readily detected in lung tissues from patients without known lung disease, but has been detected, histologically and morphometrically, in the epithelial cells and subepithelial cells in tissues from patients with asthma. In accordance with $T_H2$ inflammation and IL-13 transgenic models, AMCase is expressed in an exaggerated fashion in lung tissues from patients with asthma.

There is a need in the art for novel compounds that inhibit acidic mammalian chitinase. Such compounds could be used for treating diseases or disorders, such as asthma. The present invention addresses this need.

BRIEF SUMMARY OF THE INVENTION

The present invention includes compounds of formula (I), pharmaceutical compositions containing the same, and methods of using such compounds and/or compositions to treat asthma and/or to monitor asthma treatment.

The present invention further includes pharmaceutical compositions comprising at least one compound of the present invention, or a pharmaceutically acceptable salt, hydrate or solvate thereof, and at least one pharmaceutically acceptable carrier, solvent, adjuvant or diluent.

The present invention further includes synthetic intermediates that are useful in making the compounds of the present invention, and methods of preparing compounds of the present invention and the intermediates used within the methods.

The present invention further includes methods for inhibiting acidic mammalian chitinase, and/or methods of treating asthma in a subject in need thereof. In certain embodiments, the method comprises administering to the subject a therapeutically effective amount of at least one compound or one pharmaceutical composition of the invention. The present invention also includes a compound, or a pharmaceutical composition thereof, in a kit with instructions for using the compound or composition within the methods of the invention.

In certain embodiments, the invention provides a compound of formula (I), or any acceptable salt, hydrate, and/or solvate thereof:

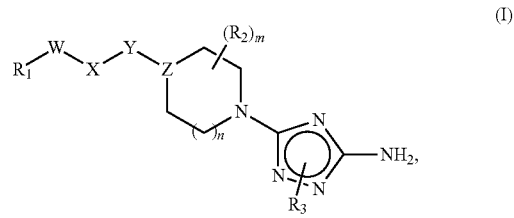

wherein in (I):

m is 0, 1, 2, 3, or 4;

n is 0, 1, or 2;

$R_1$ is aryl or heteroaryl, each of which is optionally substituted with one or more of $R_4$;

each $R_2$ is individually selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, hydroxy($C_1$-$C_6$ alkyl), $C_1$-$C_6$ acyloxy($C_1$-$C_6$ alkyl), alkoxy($C_1$-$C_6$ alkyl), and $C_1$-$C_6$ haloalkoxy;

$R_3$ is a substituent on one nitrogen atom, and is hydrogen or $C_1$-$C_6$ alkyl;

W is absent, —O—, —N($R_5$)—, —$X_1$—N($R_5$)—, —$X_1$—O—, —N($R_5$)C(=O)—, —C(=O)N($R_5$)—, —N($R_5$)S(=O)$_2$—, or —S(=O)$_2$N($R_5$)—, where $X_1$ is $C_1$-$C_3$ alkylene optionally substituted with one or more substituents selected from the group consisting of $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)N($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);

X is —C(=O)— or $C_1$-$C_6$ alkylene optionally substituted with one or more substituents selected from the group consisting of $C_1$-$C_6$ alkyl, $C_1$-$C_6$ haloalkyl, benzyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N (C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

Y is absent, —C(=O)—, —OC(=O)—, —N(R$_5$), —N(R$_5$)C(=O)—, —C(=O)N(R$_5$)—, —N(R$_5$)S(=O)$_2$—, —S(=O)$_2$N(R$_5$)—, —N(R$_5$)CH$_2$—, or —S(=O)$_2$—;

or W—X—Y represent a heteroarylene, heterocyclylene, or C$_3$-C$_8$ cycloalkylene, each optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, or C$_1$-C$_6$ haloalkoxy;

Z is CH, C(C$_1$-C$_6$ alkyl), or N, wherein the C$_1$-C$_6$ alkyl is optionally substituted with one or more substituents selected from halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

or Y—Z, together with one carbon atom to which Z is attached, form a heterocyclyl;

or Y—Z combine to form a bicyclic heterocycle selected from the group consisting of:

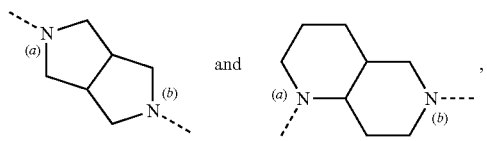

wherein the N labelled as (a) is covalently bonded to X and the N labelled as (b) is covalently bonded to the 1,3,4-triazole ring;

or Y is absent, X is a bond or as defined above, and Z is a carbon atom that is covalently connected to W by a C$_1$-C$_4$ alkylene chain optionally containing a nitrogen, oxygen, or sulfur atom, whereby Z—X—Y—W together form a 3-7 membered carbocyclic or heterocyclic ring;

each R$_4$ is independently selected from the group consisting of halogen, —NO$_2$, —CN, C$_1$-C$_6$ alkyl, C$_3$-C$_7$ cycloalkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(=O)$_{0-2}$(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)NHNH$_2$, —C(=O)H, —C(=O)O(C$_1$-C$_6$ alkyl), —OC(=O)(C$_1$-C$_6$ alkyl), —NHC(=O)(C$_1$-C$_6$ alkoxy), —NHC(=O)(C$_1$-C$_6$ alkyl), —NHC(=O)NH$_2$, —NHC(=O)NH(C$_1$-C$_6$ alkyl), —NHC(=NH)NH$_2$, —NH—S(=O)$_{0-2}$—(C$_1$-C$_6$ alkyl), —NH—S(=O)$_{0-2}$-aryl, and —NH—S(=O)$_{0-2}$-heteroaryl; and, each R$_5$ is independently selected from hydrogen and C$_1$-C$_6$ alkyl optionally substituted with at least one substituent selected from the group consisting of halogen, hydroxy, C$_1$-C$_6$ haloalkyl, C$_3$-C$_7$ cycloalkyl, C$_1$-C$_6$ alkoxy, and R$_{5a}$, where R$_{5a}$ is phenyl, naphthyl or a bicyclic heteroaryl, and R$_{5a}$ is optionally substituted with 1-3 substituents independently selected from the group consisting of halogen, hydroxy, C$_1$-C$_6$ alkyl, cyano, hydroxy C$_1$-C$_6$ alkyl, phenyl, C$_1$-C$_6$ alkoxy, haloalkyl, —NH$_2$, —NH(C$_1$-C$_6$ alkyl), —N(C$_1$-C$_6$ alkyl)$_2$, and C$_1$-C$_6$ haloalkoxy;

provided the compound of formula (I) is not:
5-[4-(1-naphthalenylmethyl)-1-piperazinyl]-1H-1,2,4-triazol-3-amine;
5-[4-(1,3-benzodioxol-5-ylmethyl)-1-piperazinyl]-1H-1,2,4-triazol-3-amine;
5-[4-(1-phenylethyl)-1-piperazinyl]-1H-1,2,4-triazol-3-amine;
5-[4-[[2-chloro-4-(dimethylamino)phenyl]methyl]-1-piperazinyl]-1H-1,2,4-triazol-3-amine;
5-[4-[[3-bromo-4-(dimethylamino)phenyl]methyl]-1-piperazinyl]-1H-1,2,4-triazol-3-amine;
5-[4-[(2,3,4-trimethoxyphenyl)methyl]-1-piperazinyl]-1H-1,2,4-triazol-3-amine;
5-[4-[(2-chloro-4-fluorophenyl)methyl]-1-piperazinyl]-1H-1,2,4-triazol-3-amine;
5-[4-[[3-(trifluoromethyl)phenyl]methyl]-1-piperazinyl]-1H-1,2,4-triazol-3-amine;
5-[4-[(2,4,6-trimethylphenyl)methyl]-1-piperazinyl]-1H-1,2,4-triazol-3-amine;
5-[4-[(2,5-dimethylphenyl)methyl]-1-piperazinyl]-1H-1,2,4-triazol-3-amine;
5-[4-[(2,6-dichlorophenyl)methyl]-1-piperazinyl]-1H-1,2,4-triazol-3-amine;
5-[4-(2-phenoxyethyl)-1-piperazinyl]-1H-1,2,4-triazol-3-amine;
5-[4-(4-phenoxybutyl)-1-piperazinyl]-1H-1,2,4-triazol-3-amine;
5-[4-[2-(4-bromophenoxy)ethyl]-1-piperazinyl]-1H-1,2,4-triazol-3-amine;
5-[4-[(3,4-dichlorophenyl)methyl]-1-piperazinyl]-1H-1,2,4-triazol-3-amine;
5-[4-(4-pyridinylmethyl)-1-piperazinyl]-1H-1,2,4-triazol-3-amine;
5-[4-[(4-methylphenyl)methyl]-1-piperazinyl]-1H-1,2,4-triazol-3-amine;
5-[4-(phenylmethyl)-1-piperazinyl]-1H-1,2,4-triazol-3-amine;
5-[4-[(4-aminophenyl)methyl]-1-piperazinyl]-1H-1,2,4-triazol-3-amine;
5-[4-[[3-chloro-4-(dimethylamino)phenyl]methyl]-1-piperazinyl]-1H-1,2,4-triazol-3-amine;
5-[4-[(3-chlorophenyl)methyl]-1-piperazinyl]-1H-1,2,4-triazol-3-amine;
5-[4-[[2-bromo-4-(dimethylamino)phenyl]methyl]-1-piperazinyl]-1H-1,2,4-triazol-3-amine;
5-[4-(3-phenylpropyl)-1-piperazinyl]-1H-1,2,4-triazol-3-amine;
5-[4-[[4-(dimethylamino)phenyl]methyl]-1-piperazinyl]-1H-1,2,4-triazol-3-amine;
5-[4-(2-furanylmethyl)-1-piperazinyl]-1H-1,2,4-triazol-3-amine;
5-[4-(2-quinolinylmethyl)-1-piperazinyl]-1H-1,2,4-triazol-3-amine;
4-[[4-(3-amino-1H-1,2,4-triazol-5-yl)-1-piperazinyl]methyl]-benzonitrile;
5-[4-[(2-fluorophenyl)methyl]-1-piperazinyl]-1H-1,2,4-triazol-3-amine;
5-[4-(2-phenylethyl)-1-piperazinyl]-1H-1,2,4-triazol-3-amine;
5-[4-[(4-fluorophenyl)methyl]-1-piperazinyl]-1H-1,2,4-triazol-3-amine;
5-[4-[(2-nitrophenyl)methyl]-1-piperazinyl]-1H-1,2,4-triazol-3-amine;
5-[4-(3-phenoxypropyl)-1-piperazinyl]-1H-1,2,4-triazol-3-amine;
5-[4-[[4-(1,1-dimethylethyl)phenyl]methyl]-1-piperazinyl]-1H-1,2,4-triazol-3-amine;

5-[4-[(4-butylphenyl)methyl]-1-piperazinyl]-1H-1,2,4-triazol-3-amine;

5-[4-[(3-methylphenyl)methyl]-1-piperazinyl]-1H-1,2,4-triazol-3-amine;

benzyl 4-(3-amino-1H-1,2,4-triazol-5-yl)piperazine-1-carboxylate;

5-[4-[(3,4,5-trimethoxyphenyl)methyl]-1-piperazinyl]-1H-1,2,4-triazol-3-amine; or 5-[4-[(2-methylphenyl)methyl]-1-piperazinyl]-1H-1,2,4-triazol-3-amine.

In certain embodiments, the compound of formula (I) is a compound of formula (II) or any pharmaceutically acceptable salt, hydrate, and/or solvate thereof:

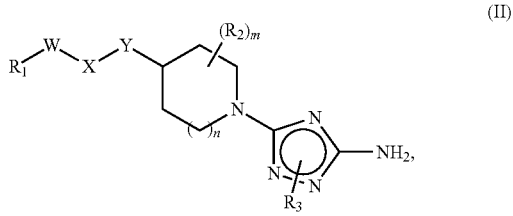

(II)

wherein in (II):

W is absent, —O—, —X₁—O—, —N(R₅)—, —N(R₅)C(=O)—, —C(=O)N(R₅)—, —N(R₅)S(=O)₂—, or —S(=O)₂N(R₅)—;

X is $C_1$-$C_6$ alkylene optionally substituted with one or more of $C_1$-$C_6$ alkyl, benzyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, or —S($C_1$-$C_6$ alkyl);

Y is absent, —C(=O)—, —N(R₅)—, —N(R₅)C(=O)—, —C(=O)N(R₅)—, —N(R₅)S(=O)₂—, —S(=O)₂N(R₅)—, —N(R₅)CH₂—, or —S(=O)₂—.

In certain embodiments, the compound of formula (I) is a compound of formula (III) or any pharmaceutically acceptable salt, hydrate, or solvate thereof:

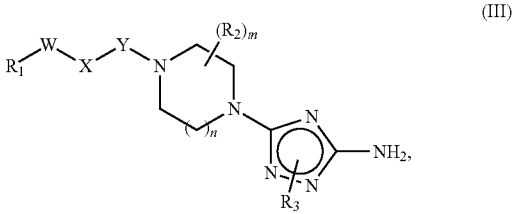

(III)

wherein in (III):

W is absent, —O—, —N(R₅)—, —N(R₅)C(=O)—, —C(=O)N(R₅)—, —N(R₅)S(=O)₂—, or —S(=O)₂N(R₅)—;

X is $C_1$-$C_6$ alkylene optionally substituted with one or more substituents selected from the group consisting of $C_1$-$C_6$ alkyl, benzyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, and —S($C_1$-$C_6$ alkyl);

Y is absent, —C(=O)—, —N(R₅)—, —N(R₅)C(=O)—, —C(=O)N(R₅)—, —N(R₅)S(=O)₂—, —S(=O)₂N(R₅)—, —N(R₅)CH₂—, or —S(=O)₂—;

provided that, when both W and Y are absent, X is not optionally substituted methylene;

provided the compound is not:

5-[4-(2-phenoxyethyl)-1-piperazinyl]-1H-1,2,4-triazol-3-amine;

5-[4-(4-phenoxybutyl)-1-piperazinyl]-1H-1,2,4-triazol-3-amine;

5-[4-[2-(4-bromophenoxy)ethyl]-1-piperazinyl]-1H-1,2,4-triazol-3-amine;

5-[4-(3-phenylpropyl)-1-piperazinyl]-1H-1,2,4-triazol-3-amine;

45-[4-(2-phenylethyl)-1-piperazinyl]-1H-1,2,4-triazol-3-amine; or

5-[4-(3-phenoxypropyl)-1-piperazinyl]-1H-1,2,4-triazol-3-amine.

In certain embodiments, W is absent, —X₁O—, —O—, —N(R₅)—, —N(R₅)C(=O)—, —C(=O)N(R₅)—, —N(R₅)S(=O)₂—, or —S(=O)₂N(R₅)—; X is $C_1$-$C_6$ alkylene optionally substituted with one or more substituents selected from the group consisting of $C_1$-$C_6$ alkyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, and —S($C_1$-$C_6$ alkyl); provided that W—X—Y is not —CH₂—, and provided that when R₁ is phenyl optionally substituted with halogen, W—X—Y is not —CH(CH₃)—, —(CH₂)₂—, —(CH₂)₃—, —O(CH₂)₂—, —O(CH₂)₃—, or —O(CH₂)₄—.

In certain embodiments, W is absent, —O—, —N(R₅)—, —N(R₅)C(=O)—, —C(=O)N(R₅)—, —N(R₅)S(=O)₂—, or —S(=O)₂N(R₅)—; X is $C_1$-$C_6$ alkylene optionally substituted with one or more of $C_1$-$C_6$ alkyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, or —S($C_1$-$C_6$ alkyl).

In certain embodiments, the compound of formula (I) is a compound of formula (IV) or any pharmaceutically acceptable salt, hydrate, or solvate thereof:

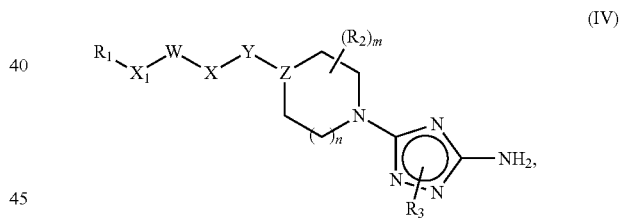

(IV)

wherein in (IV):

W is —O—, —X₁O—, —N(R₅)—, —N(R₅)C(=O)—, —C(=O)N(R₅)—, —N(R₅)S(=O)₂—, or —S(=O)₂N(R₅)—;

X is $C_1$-$C_3$ alkylene optionally substituted with one or more of $C_1$-$C_6$ alkyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH₂, —C(=O)NH($C_1$-$C_6$ alkyl), —C(=O)N($C_1$-$C_6$ alkyl)₂, —C(=O)O($C_1$-$C_6$ alkyl), —NHC(=O)($C_1$-$C_6$ alkoxy), or —NHC(=O)($C_1$-$C_6$ alkyl);

X₁ is $C_1$-$C_3$ alkylene optionally substituted with one or more of $C_1$-$C_6$ alkyl, $C_1$-$C_6$ haloalkyl, —NH₂, —NH($C_1$-$C_6$ alkyl), —N($C_1$-$C_6$ alkyl)₂, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH₂, —C(=O)NH($C_1$-$C_6$ alkyl), —C(=O)N($C_1$-$C_6$ alkyl)₂, —C(=O)O($C_1$-$C_6$ alkyl), —NHC(=O)($C_1$-$C_6$ alkoxy), or —NHC(=O)($C_1$-$C_6$ alkyl);

Y is absent, —C(═O)—, —OC(═O)—, —N(R$_5$)—, —N(R$_5$)C(═O)—, —C(═O)N(R$_5$)—, —N(R$_5$)S(═O)$_2$—, —S(═O)$_2$N(R$_5$)—, —N(R$_5$)CH$_2$—, or —S(═O)$_2$—;

provided that the compound is not benzyl 4-(3-amino-1H-1,2,4-triazol-5-yl)piperazine-1-carboxylate.

In certain embodiments, the compound of formula (I) is a compound of formula (V) or any pharmaceutically acceptable salt, hydrate, or solvate thereof:

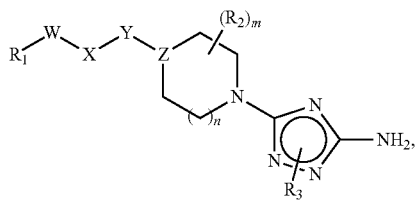
(V)

wherein in (V):

W is —O— or —N(R$_5$)—;

X is C$_1$-C$_6$ alkylene optionally substituted with one or more of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(═O)NH$_2$, —C(═O)NH(C$_1$-C$_6$ alkyl), —C(═O)N(C$_1$-C$_6$ alkyl)$_2$, —C(═O)O(C$_1$-C$_6$ alkyl), —NHC(═O)(C$_1$-C$_6$ alkoxy), or —NHC(═O)(C$_1$-C$_6$ alkyl); or X together with one of R$_4$ forms a C$_1$-C$_3$ alkylene or C$_1$-C$_3$ alkenylene group;

Y is —C(═O)—, —OC(═O)—, —N(R$_5$)—, —N(R$_5$)C(═O)—, —C(═O)N(R$_5$)—, —N(R$_5$)SO$_2$—, —S(═O)$_2$N(R$_5$)—, —N(R$_5$)CH$_2$—, or —SO$_2$—.

In certain embodiments, the compound of formula (I) is a compound of formula (VI) or any acceptable salt, hydrate, or solvate thereof:

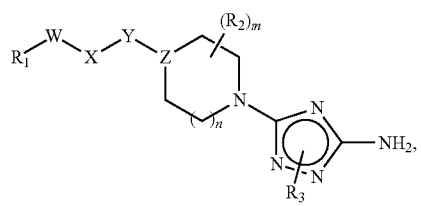
(VI)

wherein in (VI):

W is —N(R$_5$)—; X is —C(═O)—; Y is —N(R$_5$)—; Z is CH, C(C$_1$-C$_6$ alkyl), or N.

In certain embodiments, W—X—Y form at least one selected from the group consisting of:

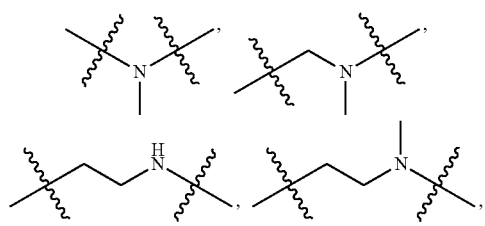

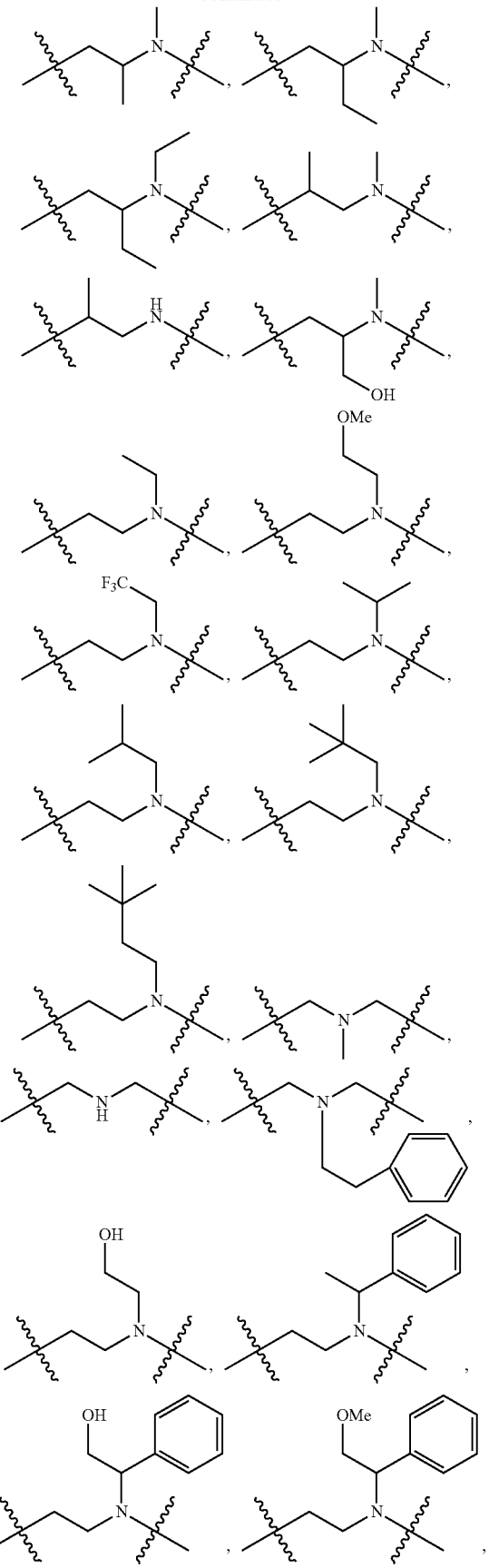

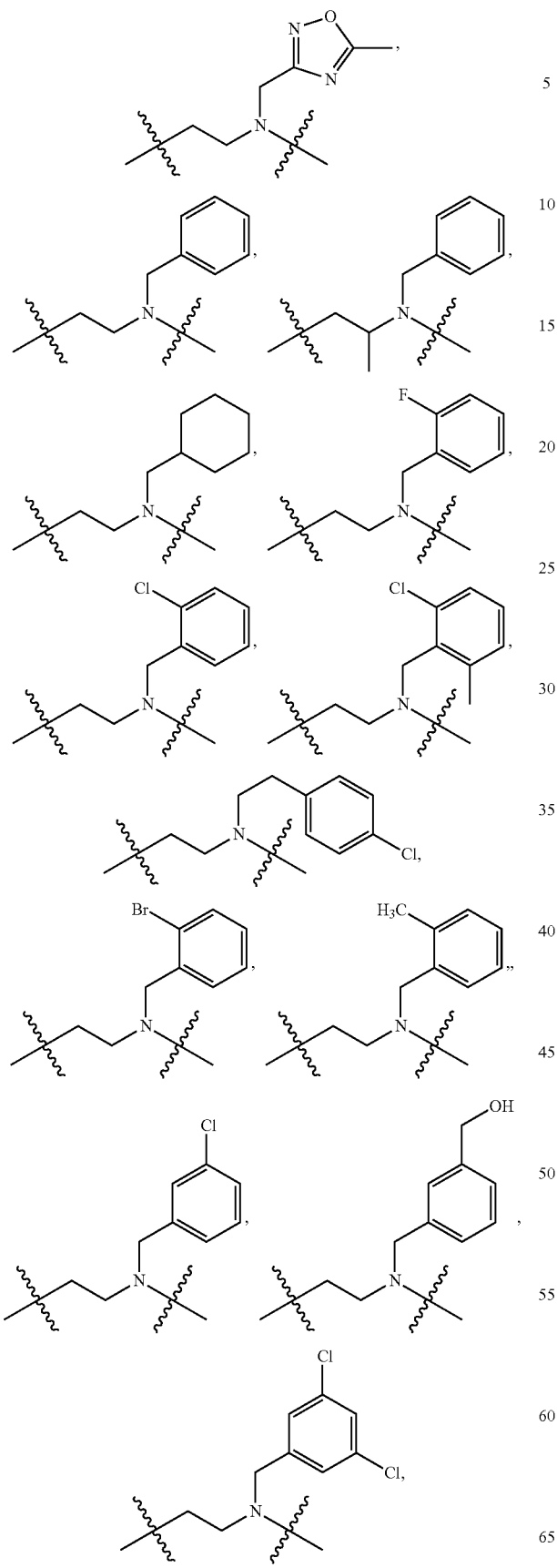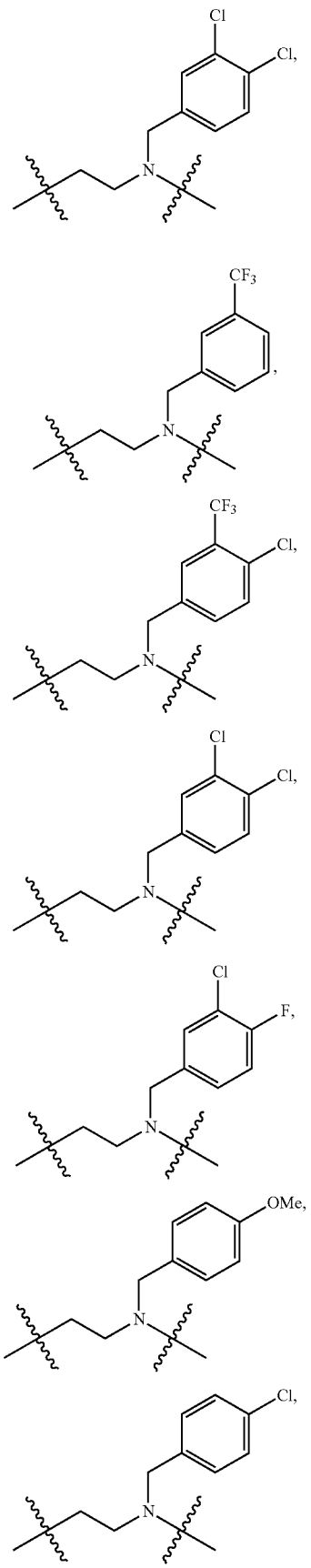

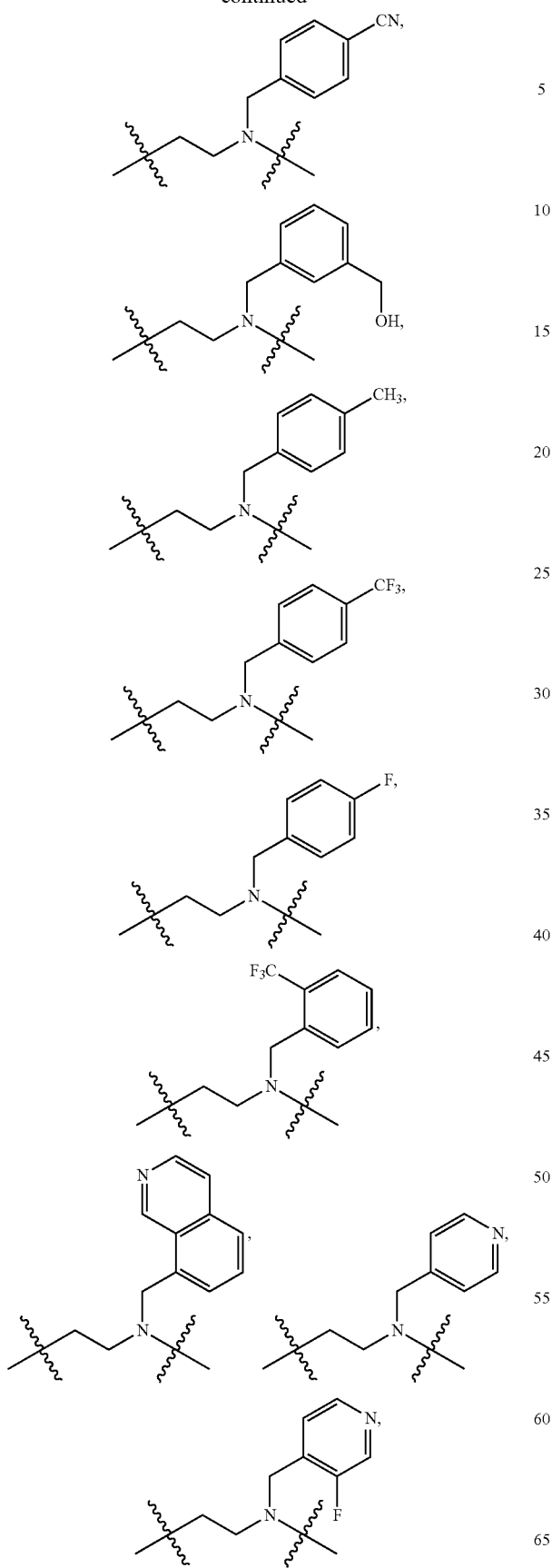
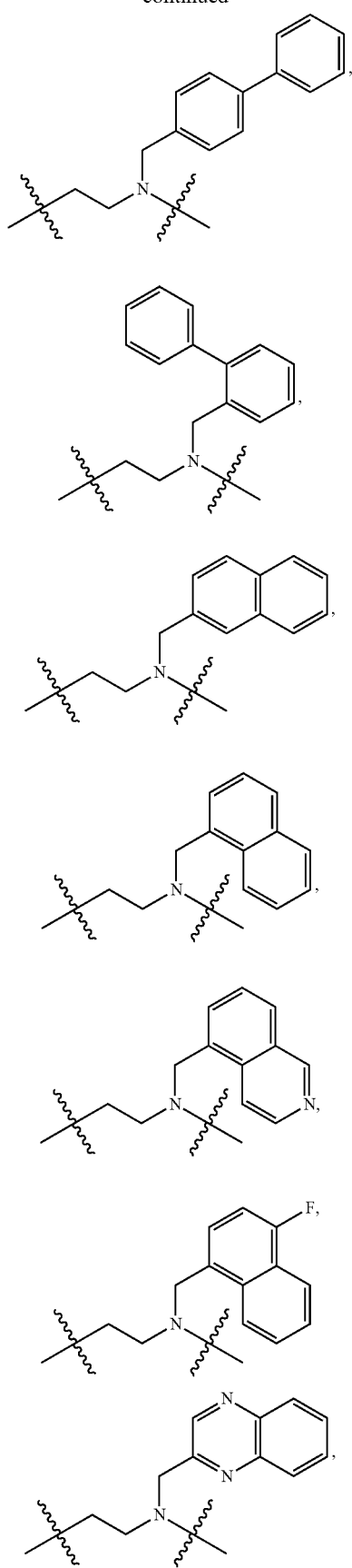

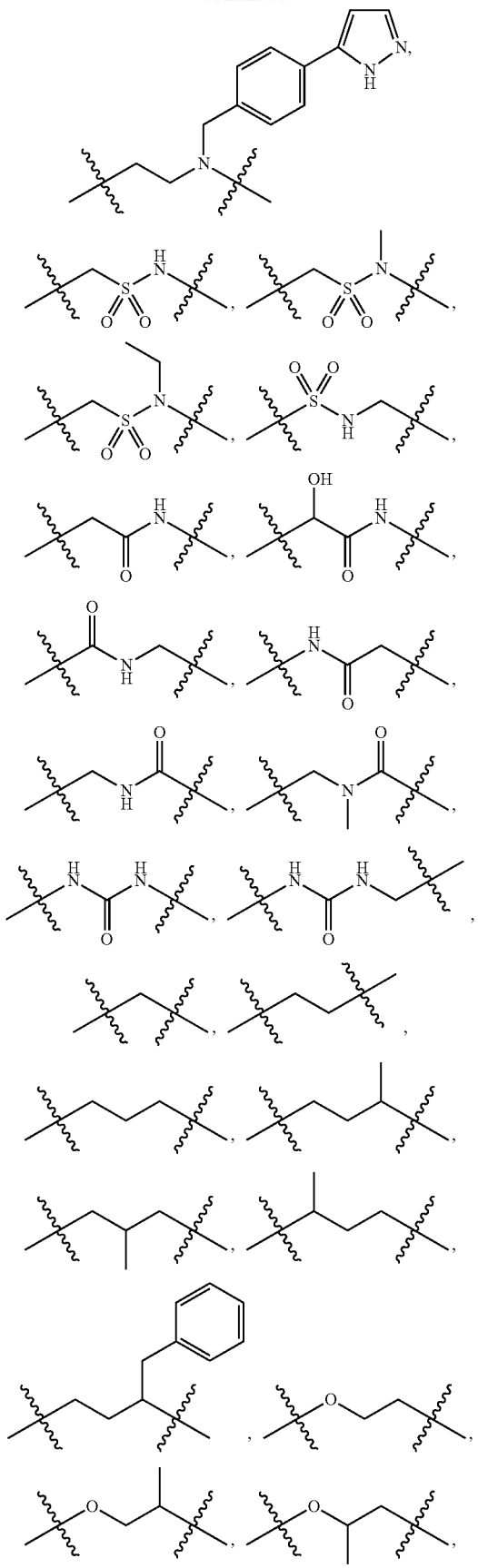
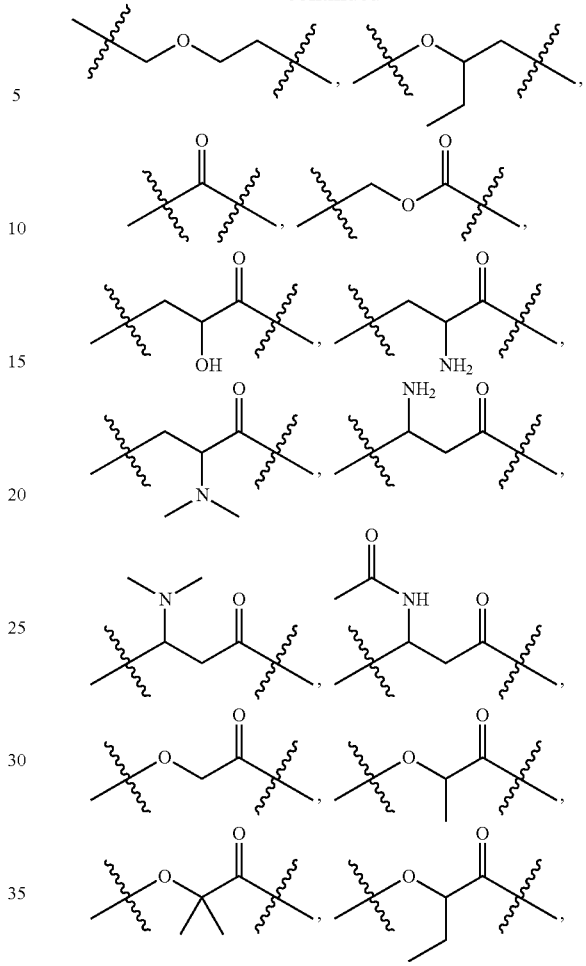

and oxadiazolylene.

In certain embodiments, the compound is selected from the group consisting of:

5-(4-(2-(4-fluorophenoxy)ethyl) piperazin-1-yl)-1H-1,2,4-triazol-3-amine;
5-(4-(2-(4-chlorophenoxy)ethyl) piperazin-1-yl)-1H-1,2,4-triazol-3-amine;
5-(4-(4-ethoxybenzyl) piperazin-1-yl)-1H-1,2,4-triazol-3-amine;
1-(4-(3-amino-1H-1,2,4-triazol-5-yl)piperazin-1-yl)-2-(4-bromophenoxy)ethan-1-one;
1-(4-(3-amino-1H-1,2,4-triazol-5-yl)piperazin-1-yl)-2-(4-bromophenoxy)butan-1-one;
(R)-1-(4-(3-amino-1H-1,2,4-triazol-5-yl)piperazin-1-yl)-2-(4-bromophenoxy)propan-1-one;
(S)-1-(4-(3-amino-1H-1,2,4-triazol-5-yl)piperazin-1-yl)-2-(4-bromophenoxy)propan-1-one;
1-(4-(3-amino-1H-1,2,4-triazol-5-yl)piperazin-1-yl)-2-(4-chlorophenoxy)butan-1-one;
(R)-1-(4-(3-amino-1H-1,2,4-triazol-5-yl)piperazin-1-yl)-2-(4-chlorophenoxy)propan-1-one;
(S)-1-(4-(3-amino-1H-1,2,4-triazol-5-yl)piperazin-1-yl)-2-(4-chlorophenoxy)propan-1-one;
N-((1-(3-amino-1H-1,2,4-triazol-5-yl)piperidin-4-yl)methyl)-4-bromobenzamide;
N-((1-(3-amino-1H-1,2,4-triazol-5-yl)piperidin-4-yl)methyl)-4-bromobenzenesulfonamide;

N-(1-(3-amino-1H-1,2,4-triazol-5-yl)piperidin-4-yl)-1-(4-bromophenyl)methanesulfonamide;
N-(1-(3-amino-1H-1,2,4-triazol-5-yl)piperidin-4-yl)-1-(4-chlorophenyl)methanesulfonamide;
N-(1-(3-amino-1H-1,2,4-triazol-5-yl)piperidin-4-yl)-1-(3,4-dichlorophenyl) methanesulfonamide;
N-(1-(3-amino-1H-1,2,4-triazol-5-yl)piperidin-4-yl)-2-(4-bromophenyl)acetamide;
1-(3-amino-1H-1,2,4-triazol-5-yl)-N-(3,4-dichlorobenzyl) piperidine-4-carboxamide;
1-(3-amino-1H-1,2,4-triazol-5-yl)-N-(4-bromobenzyl)piperidine-4-carboxamide;
5-(4-(4-(4-bromophenyl)butan-2-yl)piperazin-1-yl)-1H-1,2,4-triazol-3-amine;
5-(4-(2-(4-bromophenoxy)propyl)piperazin-1-yl)-1H-1,2,4-triazol-3-amine;
5-(4-(1-(4-bromophenoxy)propan-2-yl)piperazin-1-yl)-1H-1,2,4-triazol-3-amine;
1-(3-amino-1H-1,2,4-triazol-5-yl)-N-(4-bromophenethyl)-N-methylpiperidin-4-amine;
1-(3-amino-1H-1,2,4-triazol-5-yl)-N-(4-bromophenethyl)piperidin-4-amine;
5-(4-(2-((4-chloronaphthalen-1-yl)oxy)ethyl)piperazin-1-yl)-1H-1,2,4-triazol-3-amine;
1-(4-(3-amino-1H-1,2,4-triazol-5-yl)piperazin-1-yl)-2-(4-chlorophenoxy)ethan-1-one;
1-(4-(3-amino-1H-1,2,4-triazol-5-yl)piperazin-1-yl)-2-(naphthalen-2-yloxy)ethan-1-one;
5-(4-(2-(4-bromophenoxy)ethyl)-3-methylpiperazin-1-yl)-1H-1,2,4-triazol-3-amine;
3-(4-(2-(4-bromophenoxy)ethyl)piperazin-1-yl)-1-methyl-1H-1,2,4-triazol-5-amine;
5-(4-(2-(4-bromophenoxy)ethyl)piperazin-1-yl)-1-methyl-1H-1,2,4-triazol-3-amine;
5-(4-(2-(4-bromophenoxy)ethyl)-1,4-diazepan-1-yl)-1H-1,2,4-triazol-3-amine;
5-(5-(2-(4-bromophenoxy)ethyl)hexahydropyrrolo[3,4-c]pyrrol-2(1H)-yl)-1H-1,2,4-triazol-3-amine;
1-(4-(3-amino-1H-1,2,4-triazol-5-yl)piperazin-1-yl)-2-phenoxyethan-1-one;
1-(4-(3-amino-1H-1,2,4-triazol-5-yl)piperazin-1-yl)-2-(4-ethylphenoxy)propan-1-one;
1-(4-(3-amino-1H-1,2,4-triazol-5-yl)piperazin-1-yl)-2-(o-tolyloxy)propan-1-one;
1-(4-(3-amino-1H-1,2,4-triazol-5-yl)piperazin-1-yl)-2-(2-ethylphenoxy)propan-1-one;
1-(4-(3-amino-1H-1,2,4-triazol-5-yl)piperazin-1-yl)-2-(2,5-dimethylphenoxy)propan-1-one;
1-(4-(3-amino-1H-1,2,4-triazol-5-yl)piperazin-1-yl)-2-(2,4-dimethylphenoxy)propan-1-one;
1-(4-(3-amino-1H-1,2,4-triazol-5-yl)piperazin-1-yl)-2-(m-tolyloxy)propan-1-one;
1-(4-(3-amino-1H-1,2,4-triazol-5-yl)piperazin-1-yl)-2-(2,3-difluorophenoxy)propan-1-one;
5-(4-(3-(4-bromophenyl)-2-methylpropyl)piperazin-1-yl)-1H-1,2,4-triazol-3-amine;
3-amino-1-(4-(3-amino-1H-1,2,4-triazol-5-yl)piperazin-1-yl)-3-(4-chlorophenyl)propan-1-one;
5-(4-(3-(benzo[d][1,3]dioxol-5-yl)-1,2,4-oxadiazol-5-yl)piperidin-1-yl)-1H-1,2,4-triazol-3-amine;
5-(4-(3-(4-(methylsulfonyl)phenyl)-1,2,4-oxadiazol-5-yl)piperidin-1-yl)-1H-1,2,4-triazol-3-amine;
5-(4-(5-(4-fluorophenyl)-1,3,4-oxadiazol-2-yl)piperidin-1-yl)-1H-1,2,4-triazol-3-amine;
1-(4-(3-amino-1H-1,2,4-triazol-5-yl)piperazin-1-yl)-2-(2-fluorophenoxy)propan-1-one;
1-(4-(3-amino-1H-1,2,4-triazol-5-yl)piperazin-1-yl)-2-(2-chloro-4-methylphenoxy)propan-1-one;
benzyl 4-(3-amino-1H-1,2,4-triazol-5-yl)piperazine-1-carboxylate;
(4-(3-amino-1H-1,2,4-triazol-5-yl)piperazin-1-yl)(benzofuran-2-yl)methanone;
1-(3-amino-1H-1,2,4-triazol-5-yl)-N-(4-fluorobenzyl)piperidine-4-carboxamide;
1-(3-amino-1H-1,2,4-triazol-5-yl)-N-(4-fluoro-2-(trifluoromethyl)benzyl)piperidine-4-carboxamide;
1-(3-amino-1H-1,2,4-triazol-5-yl)-N-(2-fluorobenzyl)piperidine-4-carboxamide;
1-(3-amino-1H-1,2,4-triazol-5-yl)-N-(4-chlorobenzyl)piperidine-4-carboxamide;
1-(3-amino-1H-1,2,4-triazol-5-yl)-N-(2-bromobenzyl)piperidine-4-carboxamide;
1-(3-amino-1H-1,2,4-triazol-5-yl)-N-(4-fluoro-3-(trifluoromethyl)benzyl)piperidine-4-carboxamide;
5-(4-(((4-bromobenzyl)(methyl)amino)methyl)piperidin-1-yl)-1H-1,2,4-triazol-3-amine;
N-(1-(3-amino-1H-1,2,4-triazol-5-yl)piperidin-4-yl)-1-(3-fluorophenyl)methanesulfonamide;
N-(1-(3-amino-1H-1,2,4-triazol-5-yl)piperidin-4-yl)-1-(4-fluorophenyl)methanesulfonamide;
N-(1-(3-amino-1H-1,2,4-triazol-5-yl)piperidin-4-yl)-1-(3,5-dichlorophenyl) methanesulfonamide;
N-(1-(3-amino-1H-1,2,4-triazol-5-yl)piperidin-4-yl)-1-(3-chlorophenyl)methanesulfonamide;
5-(4-(2-(4-bromophenoxy)butyl)piperazin-1-yl)-1H-1,2,4-triazol-3-amine;
(R)-5-(4-(2-(4-bromophenoxy)propyl)piperazin-1-yl)-1H-1,2,4-triazol-3-amine;
(S)-5-(4-(2-(4-bromophenoxy)propyl)piperazin-1-yl)-1H-1,2,4-triazol-3-amine;
5-(4-(2-(4-chlorophenoxy)butyl)piperazin-1-yl)-1H-1,2,4-triazol-3-amine;
(R)-5-(4-(2-(4-chlorophenoxy)propyl)piperazin-1-yl)-1H-1,2,4-triazol-3-amine;
(S)-5-(4-(2-(4-chlorophenoxy)propyl)piperazin-1-yl)-1H-1,2,4-triazol-3-amine;
(4-(3-amino-1H-1,2,4-triazol-5-yl)-1-(3-(4-chlorophenyl)propyl)piperazin-2-yl)methanol;
1-(1-(3-amino-1H-1,2,4-triazol-5-yl)piperidin-4-yl)-3-(4-chlorophenyl)urea;
1-(1-(3-amino-1H-1,2,4-triazol-5-yl)piperidin-4-yl)-3-(3,4-difluorophenyl)urea;
N-((1-(3-amino-1H-1,2,4-triazol-5-yl)piperidin-4-yl)methyl)-3-bromobenzamide;
2-(1-(3-amino-1H-1,2,4-triazol-5-yl)piperidin-4-yl)-N-(4-bromophenyl)acetamide;
N-(1-(3-amino-1H-1,2,4-triazol-5-yl)piperidin-4-yl)-2-(4-chlorophenyl)-2-hydroxyacetamide;
(R)-1-(4-(3-amino-1H-1,2,4-triazol-5-yl)piperazin-1-yl)-3-(4-chlorophenyl)-2-hydroxypropan-1-one;
1-(4-(3-amino-1H-1,2,4-triazol-5-yl)piperazin-1-yl)-3-(2-chlorophenyl)-2-hydroxypropan-1-one;
1-(4-(3-amino-1H-1,2,4-triazol-5-yl)piperazin-1-yl)-2-(4-chloro-3-nitrophenoxy)ethan-1-one;
(S)-2-amino-1-(4-(3-amino-1H-1,2,4-triazol-5-yl)piperazin-1-yl)-3-(2,4-dichlorophenyl)propan-1-one;
(S)-2-amino-1-(4-(3-amino-1H-1,2,4-triazol-5-yl)piperazin-1-yl)-3-(2-chlorophenyl)propan-1-one;
N-(3-(4-(3-amino-1H-1,2,4-triazol-5-yl)piperazin-1-yl)-1-(4-fluorophenyl)-3-oxopropyl)acetamide;
5-(4-(2-phenoxyethyl)piperazin-1-yl)-1H-1,2,4-triazol-3-amine;

5-(4-(2-(2-chlorophenoxy)ethyl)piperazin-1-yl)-1H-1,2,4-triazol-3-amine;
5-(4-(2-(benzyloxy)ethyl)piperazin-1-yl)-1H-1,2,4-triazol-3-amine;
5-(4-(2-(4-methoxyphenoxy)ethyl)piperazin-1-yl)-1H-1,2,4-triazol-3-amine;
5-(4-(2-((1H-indol-5-yl)oxy)ethyl)piperazin-1-yl)-1H-1,2,4-triazol-3-amine;
5-(4-(2-([1,1'-biphenyl]-2-yloxy)ethyl)piperazin-1-yl)-1H-1,2,4-triazol-3-amine;
5-(4-(2-(2-isopropylphenoxy)ethyl)piperazin-1-yl)-1H-1,2,4-triazol-3-amine;
5-(4-(2-(2-fluorophenoxy)ethyl)piperazin-1-yl)-1H-1,2,4-triazol-3-amine;
5-(4-(2-(3-chlorophenoxy)ethyl)piperazin-1-yl)-1H-1,2,4-triazol-3-amine;
5-(4-(2-(2-chloro-6-methylphenoxy)ethyl)piperazin-1-yl)-1H-1,2,4-triazol-3-amine;
1-(3-amino-1H-1,2,4-triazol-5-yl)-N-(4-chlorophenethyl) piperidin-4-amine;
1-(3-amino-1H-1,2,4-triazol-5-yl)-N-(4-chlorophenethyl)-N-ethylpiperidin-4-amine;
(R)-5-(4-(2-(4-bromophenoxy)propyl)piperazin-1-yl)-1H-1,2,4-triazol-3-amine;
1-(3-amino-1H-1,2,4-triazol-5-yl)-N-(4-chlorobenzyl)-N,4-dimethylpiperidine-4-carboxamide;
1-(3-amino-1H-1,2,4-triazol-5-yl)-N-(4-chlorophenethyl)-N-isobutylpiperidin-4-amine;
1-(3-amino-1H-1,2,4-triazol-5-yl)-N-(4-chlorophenethyl)-N-(3,3-dimethylbutyl)piperidin-4-amine;
1-(3-amino-1H-1,2,4-triazol-5-yl)-N-(4-chlorophenethyl)-N-neopentylpiperidin-4-amine;
1-(3-amino-1H-1,2,4-triazol-5-yl)-N-(2-chlorobenzyl)-N-(4-chlorophenethyl)piperidin-4-amine;
1-(3-amino-1H-1,2,4-triazol-5-yl)-N-(4-bromophenethyl)-N-isobutylpiperidin-4-amine;
1-(3-amino-1H-1,2,4-triazol-5-yl)-N-(4-bromophenethyl)-N-(2-chlorobenzyl)piperidin-4-amine;
1-(3-amino-1H-1,2,4-triazol-5-yl)-N-benzyl-N-(4-chlorophenethyl) piperidin-4-amine;
(3-(((1-(3-amino-1H-1,2,4-triazol-5-yl)piperidin-4-yl)(4-chlorophenethyl)amino) methyl)phenyl)methanol;
1-(3-amino-1H-1,2,4-triazol-5-yl)-N-(4-bromophenethyl)-N-ethylpiperidin-4-amine;
1-(3-amino-1H-1,2,4-triazol-5-yl)-N-(4-chlorophenethyl)-N-(4-methylbenzyl)piperidin-4-amine;
(S)-1-(3-amino-1H-1,2,4-triazol-5-yl)-N-(4-chlorophenethyl)-N-(1-phenylethyl)piperidin-4-amine;
1-(3-amino-1H-1,2,4-triazol-5-yl)-N-(4-chlorophenethyl)-N-(4-(trifluoromethyl)benzyl) piperidin-4-amine;
1-(3-amino-1H-1,2,4-triazol-5-yl)-N-(4-bromophenethyl)-N-(isoquinolin-8-ylmethyl) piperidin-4-amine;
1-(3-amino-1H-1,2,4-triazol-5-yl)-N-(4-cyclopropylphenethyl)-N-methylpiperidin-4-amine;
(R)-2-((1-(3-amino-1H-1,2,4-triazol-5-yl)piperidin-4-yl)(4-chlorophenethyl)amino)-2-phenylethan-1-ol;
1-(3-amino-1H-1,2,4-triazol-5-yl)-N-(4-chlorophenethyl)-N-(pyridin-4-ylmethyl)piperidin-4-amine;
(R)-1-(3-amino-1H-1,2,4-triazol-5-yl)-N-(4-chlorophenethyl)-N-(2-methoxy-1-phenylethyl) piperidin-4-amine;
1-(3-amino-1H-1,2,4-triazol-5-yl)-N-(3-chlorobenzyl)-N-(4-chlorophenethyl)piperidin-4-amine;
N-([1,1'-biphenyl]-4-ylmethyl)-1-(3-amino-1H-1,2,4-triazol-5-yl)-N-(4-chlorophenethyl) piperidin-4-amine;
1-(3-amino-1H-1,2,4-triazol-5-yl)-N-(4-chlorophenethyl)-N-(naphthalen-2-ylmethyl) piperidin-4-amine;
1-(3-amino-1H-1,2,4-triazol-5-yl)-N-(4-chlorophenethyl)-N-(2-(trifluoromethyl)benzyl) piperidin-4-amine;
N-([1,1'-biphenyl]-2-ylmethyl)-1-(3-amino-1H-1,2,4-triazol-5-yl)-N-(4-chlorophenethyl) piperidin-4-amine;
N-(4-(1H-pyrazol-5-yl)benzyl)-1-(3-amino-1H-1,2,4-triazol-5-yl)-N-(4-chlorophenethyl) piperidin-4-amine;
1-(3-amino-1H-1,2,4-triazol-5-yl)-N-(4-chlorophenethyl)-N-(quinoxalin-2-ylmethyl) piperidin-4-amine;
2-((1-(3-amino-1H-1,2,4-triazol-5-yl)piperidin-4-yl)(4-chlorophenethyl)amino)ethan-1-ol;
(R)-1-(3-amino-1H-1,2,4-triazol-5-yl)-N-(4-chlorophenethyl)-N-(1-phenylethyl)piperidin-4-amine;
1-(3-amino-1H-1,2,4-triazol-5-yl)-N-(4-chlorophenethyl)-N-((3-fluoropyridin-4-yl)methyl)piperidin-4-amine;
1-(3-amino-1H-1,2,4-triazol-5-yl)-N-(4-isopropylphenethyl)-N-methylpiperidin-4-amine;
1-(3-amino-1H-1,2,4-triazol-5-yl)-N-(4-ethylphenethyl)-N-methylpiperidin-4-amine;
1-(3-amino-1H-1,2,4-triazol-5-yl)-N-(4-bromophenethyl)-3-methylpiperidin-4-amine;
1-(3-amino-1H-1,2,4-triazol-5-yl)-N-(4-chlorophenethyl)-N-(4-fluorobenzyl)piperidin-4-amine;
1-(3-amino-1H-1,2,4-triazol-5-yl)-N-(4-chlorophenethyl)-N-(2-methylbenzyl)piperidin-4-amine;
1-(3-amino-1H-1,2,4-triazol-5-yl)-N-(4-chloro-3-(trifluoromethyl)benzyl)-N-(4-chlorophenethyl)piperidin-4-amine;
1-(3-amino-1H-1,2,4-triazol-5-yl)-N-(2-bromobenzyl)-N-(4-chlorophenethyl)piperidin-4-amine;
1-(3-amino-1H-1,2,4-triazol-5-yl)-N-(4-chlorophenethyl)-N-isopropylpiperidin-4-amine;
1-(3-amino-1H-1,2,4-triazol-5-yl)-N-(4-bromophenethyl)-N-(naphthalen-1-ylmethyl) piperidin-4-amine;
2-((1-(3-amino-1H-1,2,4-triazol-5-yl)piperidin-4-yl)(methyl)amino)-3-(4-chlorophenyl) propan-1-ol;
1-(3-amino-1H-1,2,4-triazol-5-yl)-N-methyl-N-(2-(pyridin-3-yl)ethyl)piperidin-4-amine;
1-(3-amino-1H-1,2,4-triazol-5-yl)-N-(4-chlorophenethyl)-3-methylpiperidin-4-amine;
1-(3-amino-1H-1,2,4-triazol-5-yl)-N-(4-chlorophenethyl)-N-(naphthalen-1-ylmethyl)piperidin-4-amine;
1-(3-amino-1H-1,2,4-triazol-5-yl)-N-(4-chlorobenzyl)-N-(4-chlorophenethyl)piperidin-4-amine;
(S)-2-((1-(3-amino-1H-1,2,4-triazol-5-yl)piperidin-4-yl)(4-chlorophenethyl)amino)-2-phenylethan-1-ol;
N-((1H-benzo[d]imidazol-2-yl)methyl)-1-(3-amino-1H-1,2,4-triazol-5-yl)-N-methylpiperidin-4-amine;
1-(3-amino-1H-1,2,4-triazol-5-yl)-N-(4-chlorophenethyl)-N-(2-fluorobenzyl)piperidin-4-amine;
1-(3-amino-1H-1,2,4-triazol-5-yl)-N-(4-chlorophenethyl)-N-methylpiperidin-4-amine;
(R)-1-(3-amino-1H-1,2,4-triazol-5-yl)-N-(1-(4-chlorophenyl)propan-2-yl)-N-methylpiperidin-4-amine;
1-(3-amino-1H-1,2,4-triazol-5-yl)-N-(2-(4-chlorophenyl)propyl)-N-methylpiperidin-4-amine;
1-(3-amino-1H-1,2,4-triazol-5-yl)-N-(1-(4-chlorophenyl)propan-2-yl)-N-methylpiperidin-4-amine;
4-(((1-(3-amino-1H-1,2,4-triazol-5-yl)piperidin-4-yl)(4-chlorophenethyl) amino)methyl)benzonitrile;
1-(3-amino-1H-1,2,4-triazol-5-yl)-N-(4-chlorophenethyl)-N-(cyclohexylmethyl)piperidin-4-amine;
1-(3-amino-1H-1,2,4-triazol-5-yl)-N-(4-chlorophenethyl)-N-((4-fluoronaphthalen-1-yl)methyl)piperidin-4-amine;
1-(3-amino-1H-1,2,4-triazol-5-yl)-N-(2-chloro-4-fluorobenzyl)-N-(4-chlorophenethyl)piperidin-4-amine;
1-(3-amino-1H-1,2,4-triazol-5-yl)-N-benzyl-N-(4-bromophenethyl)piperidin-4-amine;

1-(3-amino-1H-1,2,4-triazol-5-yl)-N-(2-(4-chlorophenyl)propyl)piperidin-4-amine;
1-(3-amino-1H-1,2,4-triazol-5-yl)-N-(4-chlorobenzyl)-N-methylpiperidin-4-amine;
1-(3-amino-1H-1,2,4-triazol-5-yl)-N-(4-chlorophenethyl)-N-(3,5-dichlorobenzyl)piperidin-4-amine;
1-(3-amino-1H-1,2,4-triazol-5-yl)-N-(4-chlorophenethyl)-3-fluoro-N-methylpiperidin-4-amine;
1-(3-amino-1H-1,2,4-triazol-5-yl)-N-(1-(4-chlorophenyl)propan-2-yl)piperidin-4-amine;
1-(3-amino-1H-1,2,4-triazol-5-yl)-N-(4-chlorophenethyl)-N-(4-methoxybenzyl)piperidin-4-amine;
(S)-2-((1-(3-amino-1H-1,2,4-triazol-5-yl)piperidin-4-yl)(methyl)amino)-3-(4-chlorophenyl)propan-1-ol;
1-(3-amino-1H-1,2,4-triazol-5-yl)-N-(4-chlorophenethyl)-N,3-dimethylpiperidin-4-amine;
1-(3-amino-1H-1,2,4-triazol-5-yl)-N-(4-chlorophenethyl)-N-ethylpiperidin-4-amine;
1-(3-amino-1H-1,2,4-triazol-5-yl)-N-(4-chlorophenethyl)-N-(3-(trifluoromethyl)benzyl) piperidin-4-amine;
1-(3-amino-1H-1,2,4-triazol-5-yl)-N-methyl-N-(2-(pyridin-2-yl)ethyl)piperidin-4-amine;
1-(3-amino-1H-1,2,4-triazol-5-yl)-N-(4-chlorophenethyl)-N-(2,4-dichlorobenzyl)piperidin-4-amine;
1-(3-amino-1H-1,2,4-triazol-5-yl)-N-benzyl-N-(1-(4-chlorophenyl)propan-2-yl)piperidin-4-amine;
1-(3-amino-1H-1,2,4-triazol-5-yl)-N-(1-(4-chlorophenyl)butan-2-yl)-N-methylpiperidin-4-amine;
1-(3-amino-1H-1,2,4-triazol-5-yl)-N-(2-chloro-6-methylbenzyl)-N-(4-chlorophenethyl) piperidin-4-amine;
1-(3-amino-1H-1,2,4-triazol-5-yl)-N,N-bis(4-chlorophenethyl) piperidin-4-amine;
1-(3-amino-1H-1,2,4-triazol-5-yl)-N-(4-chlorophenethyl)-N-(2,4-dichlorobenzyl)piperidin-4-amine;
(2-(((1-(3-amino-1H-1,2,4-triazol-5-yl)piperidin-4-yl)(4-chlorophenethyl)amino)methyl) phenyl)methanol;
1-(3-amino-1H-1,2,4-triazol-5-yl)-N-(4-(tert-butyl)phenethyl)-N-methylpiperidin-4-amine;
1-(5-amino-1-methyl-1H-1,2,4-triazol-3-yl)-N-(4-bromophenethyl)-N-methylpiperidin-4-amine;
1-(3-amino-1H-1,2,4-triazol-5-yl)-N-(4-bromophenethyl)-N-((4-fluoronaphthalen-1-yl)methyl)piperidin-4-amine;
1-(3-amino-1H-1,2,4-triazol-5-yl)-N-(4-bromophenethyl)-N-(isoquinolin-5-ylmethyl)piperidin-4-amine;
1-(3-amino-1H-1,2,4-triazol-5-yl)-N-methyl-N-(2-(trifluoromethyl)phenethyl)piperidin-4-amine;
1-(3-amino-1H-1,2,4-triazol-5-yl)-N-(2-(benzo[d][1,3]dioxol-5-yl)ethyl)-N-methylpiperidin-4-amine;
1-(3-amino-1H-1,2,4-triazol-5-yl)-N-methyl-N-(4-methylphenethyl)piperidin-4-amine;
1-(3-amino-1H-1,2,4-triazol-5-yl)-N-(2-methoxyphenethyl)-N-methylpiperidin-4-amine;
1-(3-amino-1H-1,2,4-triazol-5-yl)-N-(3,4-dimethoxyphenethyl)-N-methylpiperidin-4-amine;
1-(3-amino-1H-1,2,4-triazol-5-yl)-N-methyl-N-(2-(trifluoromethoxy)phenethyl)piperidin-4-amine;
1-(3-amino-1H-1,2,4-triazol-5-yl)-N-(2,4-dichlorophenethyl)-N-methylpiperidin-4-amine;
1-(3-amino-1H-1,2,4-triazol-5-yl)-N-(3,4-dichlorophenethyl)-N-methylpiperidin-4-amine;
1-(3-amino-1H-1,2,4-triazol-5-yl)-N-(2,3-dimethoxyphenethyl)-N-methylpiperidin-4-amine;
1-(3-amino-1H-1,2,4-triazol-5-yl)-N-(4-(dimethylamino)phenethyl)-N-methylpiperidin-4-amine;
1-(3-amino-1H-1,2,4-triazol-5-yl)-N-methyl-N-(2-methylphenethyl)piperidin-4-amine;
1-(3-amino-1H-1,2,4-triazol-5-yl)-N-methyl-N-(3-(trifluoromethyl)phenethyl)piperidin-4-amine;
1-(3-amino-1H-1,2,4-triazol-5-yl)-N-methyl-N-phenethylpiperidin-4-amine;
1-(3-amino-1H-1,2,4-triazol-5-yl)-N-(2,5-dimethoxyphenethyl)-N-methylpiperidin-4-amine;
1-(3-amino-1H-1,2,4-triazol-5-yl)-N-(4-fluorophenethyl)-N-methylpiperidin-4-amine;
1-(3-amino-1H-1,2,4-triazol-5-yl)-N-(2,6-dichlorophenethyl)-N-methylpiperidin-4-amine;
1-(3-amino-1H-1,2,4-triazol-5-yl)-N-(4-chlorophenethyl)-N-(2,2,2-trifluoroethyl)piperidin-4-amine;
1-(3-amino-1H-1,2,4-triazol-5-yl)-N-(4-chlorophenethyl)-N-(2-methoxyethyl)piperidin-4-amine;
N-(1-(3-amino-1H-1,2,4-triazol-5-yl)piperidin-4-yl)-1-(3-bromophenyl)methanesulfonamide;
N-(1-(3-amino-1H-1,2,4-triazol-5-yl)piperidin-4-yl)-1-(3-(trifluoromethyl)phenyl) methanesulfonamide;
5-(4-(2-(2-(trifluoromethyl)-phenoxy)ethyl)piperazin-1-yl)-1H-1,2,4-triazol-3-amine;
5-(4-(2-(2,6-dichlorophenoxy)ethyl)piperazin-1-yl)-1H-1,2,4-triazol-3-amine;
1-(3-amino-1H-1,2,4-triazol-5-yl)-N-(naphthalen-1-ylmethyl)piperidine-4-carboxamide;
1-(3-amino-1H-1,2,4-triazol-5-yl)-N-(3-fluorobenzyl)piperidine-4-carboxamide;
1-(3-amino-1H-1,2,4-triazol-5-yl)-N-(2-methoxybenzyl)piperidine-4-carboxamide;
1-(3-amino-1H-1,2,4-triazol-5-yl)-N-(2-chlorobenzyl)piperidine-4-carboxamide;
1-(3-amino-1H-1,2,4-triazol-5-yl)-N-(3,4-difluorobenzyl) piperidine-4-carboxamide;
1-(3-amino-1H-1,2,4-triazol-5-yl)-N-(1-(4-chlorophenyl)propan-2-yl)-N-methylpiperidin-4-amine;
1-(3-amino-1H-1,2,4-triazol-5-yl)-N-(2,4-dimethoxybenzyl)piperidine-4-carboxamide;
1-(3-amino-1H-1,2,4-triazol-5-yl)-N-((2-methyl-5-(trifluoromethyl)furan-3-yl)methyl) piperidine-4-carboxamide;
1-(3-amino-1H-1,2,4-triazol-5-yl)-N-(3,4-difluorobenzyl) piperidine-4-carboxamide;
1-(3-amino-1H-1,2,4-triazol-5-yl)-N-(2,5-dimethylbenzyl) piperidine-4-carboxamide;
1-(3-amino-1H-1,2,4-triazol-5-yl)-N-(4-(trifluoromethoxy) benzyl) piperidine-4-carboxamide;
1-(3-amino-1H-1,2,4-triazol-5-yl)-N-(4-methoxybenzyl)piperidine-4-carboxamide;
N-((1-(3-amino-1H-1,2,4-triazol-5-yl)piperidin-4-yl)methyl)-3-fluorobenzamide;
N-((1-(3-amino-1H-1,2,4-triazol-5-yl)piperidin-4-yl)methyl)-3,5-dibromobenzamide;
N-((1-(3-amino-1H-1,2,4-triazol-5-yl)piperidin-4-yl)methyl)-2,3-dimethylbenzamide;
N-((1-(3-amino-1H-1,2,4-triazol-5-yl)piperidin-4-yl)methyl)-3,4-dimethoxybenzamide;
N-((1-(3-amino-1H-1,2,4-triazol-5-yl)piperidin-4-yl)methyl)-2-methylbenzamide;
N-((1-(3-amino-1H-1,2,4-triazol-5-yl)piperidin-4-yl)methyl)-2,4-difluorobenzamide;
3-amino-1-(4-(3-amino-1H-1,2,4-triazol-5-yl)piperazin-1-yl)-3-(2-fluorophenyl)propan-1-one;
3-amino-1-(4-(3-amino-1H-1,2,4-triazol-5-yl)piperazin-1-yl)-3-(4-fluorophenyl)propan-1-one;
5-(4-(2-(4-chlorophenoxy)butyl) piperazin-1-yl)-1H-1,2,4-triazol-3-amine;
1-(1-(3-amino-1H-1,2,4-triazol-5-yl)piperidin-4-yl)-3-(2,4,5-trichlorophenyl)urea;

1-((1-(3-amino-1H-1,2,4-triazol-5-yl)piperidin-4-yl)methyl)-3-(3-chlorophenyl)urea;
1-(1-(3-amino-1H-1,2,4-triazol-5-yl)piperidin-4-yl)-3-(4-bromophenyl)urea;
N-((1-(3-amino-1H-1,2,4-triazol-5-yl)piperidin-4-yl)methyl)-3,4-difluorobenzamide;
(S)-1-(4-(3-amino-1H-1,2,4-triazol-5-yl)piperazin-1-yl)-3-(4-chlorophenyl)-2-hydroxypropan-1-one;
N-(3-(4-(3-amino-1H-1,2,4-triazol-5-yl)piperazin-1-yl)-1-(3-fluorophenyl)-3-oxopropyl)acetamide;
3-(4-(3-amino-1H-1,2,4-triazol-5-yl)-1-(3-(4-(trifluoromethyl)phenyl)propyl)piperazin-2-yl)propan-1-ol;
3-(4-(3-amino-1H-1,2,4-triazol-5-yl)-1-(3-(4-bromophenyl)propyl)piperazin-2-yl)propyl acetate;
3-(4-(3-amino-1H-1,2,4-triazol-5-yl)-1-(3-(4-bromophenyl)propyl) piperazin-2-yl)propan-1-ol;
3-(4-(3-amino-1H-1,2,4-triazol-5-yl)-1-(3-phenylpropyl)piperazin-2-yl)propan-1-ol;
N-(1-(3-amino-1H-1,2,4-triazol-5-yl)-3-(hydroxymethyl)piperidin-4-yl)-1-(4-bromophenyl) methanesulfonamide;
2-(1-(3-amino-1H-1,2,4-triazol-5-yl)-4-((4-chlorophenethyl)(methyl)amino)piperidin-4-yl)ethanol;
4-(4-(3-amino-1H-1,2,4-triazol-5-yl)-1-(3-(4-bromophenyl)propyl)piperazin-2-yl)-2-methylbutan-2-ol;
1-(3-amino-1H-1,2,4-triazol-5-yl)-N-(4-bromophenethyl)-N,3-dimethylpiperidin-4-amine;
1-(3-amino-1H-1,2,4-triazol-5-yl)-N-(4-chlorophenethyl)-3-propylpiperidin-4-amine;
1-(3-amino-1H-1,2,4-triazol-5-yl)-N-(1-(4-chlorophenyl)butan-2-yl)-N-ethylpiperidin-4-amine;
3-amino-1-(4-(3-amino-1H-1,2,4-triazol-5-yl)piperazin-1-yl)-3-(3-fluorophenyl)propan-1-one;
1-(3-amino-1H-1,2,4-triazol-5-yl)-N-(4-chlorophenethyl)-3-propylpiperidin-4-amine;
1-(3-amino-1H-1,2,4-triazol-5-yl)-N-(4-chlorobenzyl)-4-methylpiperidine-4-carboxamide;
1-(3-amino-1H-1,2,4-triazol-5-yl)-N-(4-bromobenzyl)-4-methylpiperidine-4-carboxamide;
N-(1-(3-amino-1H-1,2,4-triazol-5-yl)piperidin-4-yl)-1-(3-chlorophenyl)-N-ethylmethanesulfonamide;
N-(1-(3-amino-1H-1,2,4-triazol-5-yl)piperidin-4-yl)-1-(4-bromophenyl)-N-methylmethanesulfonamide;
1-(4-(3-amino-1H-1,2,4-triazol-5-yl)piperazin-1-yl)-3-(2,4-dichlorophenyl)-2-(dimethylamino)propan-1-one;
(R)-5-(4-(2-(4-chlorophenoxy)propyl)piperazin-1-yl)-1H-1,2,4-triazol-3-amine;
1-(4-(3-amino-1H-1,2,4-triazol-5-yl)piperazin-1-yl)-3-(dimethylamino)-3-(2-fluorophenyl)propan-1-one;
N-((1-(3-amino-1H-1,2,4-triazol-5-yl)piperidin-4-yl)methyl)-3,5-dichlorobenzamide;
N-(1-(3-amino-1H-1,2,4-triazol-5-yl)-3-methylpiperidin-4-yl)-1-(4-bromophenyl)methanesulfonamide;
3-(1-(3-amino-1H-1,2,4-triazol-5-yl)-4-((4-chlorophenethyl)(methyl)amino)piperidin-4-yl)propan-1-ol;
3-(1-(3-amino-1H-1,2,4-triazol-5-yl)-4-((4-bromophenethyl)(methyl)amino)piperidin-3-yl)propan-1-ol;
1-(3-amino-1H-1,2,4-triazol-5-yl)-N-(4-bromophenethyl)-4-propylpiperidin-4-amine;
N-(1-(3-amino-1H-1,2,4-triazol-5-yl)piperidin-4-yl)-1-(3-chlorophenyl)-N-methylmethanesulfonamide;
1-(3-amino-1H-1,2,4-triazol-5-yl)-N-(4-chlorophenethyl)-3-fluoro-N-methylpiperidin-4-amine;
1-(3-amino-1H-1,2,4-triazol-5-yl)-N-methyl-N-(1,2,3,4-tetrahydronaphthalen-2-yl)piperidin-4-amine;
3-(1-(3-amino-1H-1,2,4-triazol-5-yl)-4-((4-chlorophenethyl)amino)piperidin-3-yl)propan-1-ol;
5-(4-(((3,4-dichlorobenzyl)amino) methyl)piperidin-1-yl)-1H-1,2,4-triazol-3-amine;
5-(1-(4-bromophenethyl)octahydro-1,6-naphthyridin-6(2H)-yl)-1H-1,2,4-triazol-3-amine;
5-(4-(((4-bromobenzyl)amino) methyl)piperidin-1-yl)-1H-1,2,4-triazol-3-amine;
1-(3-amino-1H-1,2,4-triazol-5-yl)-N-(3,5-bis(trifluoromethyl)benzyl) piperidine-4-carboxamide;
N-(1-(3-amino-1H-1,2,4-triazol-5-yl)-4-(4-hydroxybutyl)piperidin-4-yl)-1-(4-bromophenyl)methane sulfonamide;
5-(4-(4-(4-bromophenyl)-1-phenylbutan-2-yl)piperazin-1-yl)-1H-1,2,4-triazol-3-amine trifluoroacetate;
1-(4-(3-amino-1H-1,2,4-triazol-5-yl)piperazin-1-yl)-2-(4-chlorophenoxy)-2-methylpropan-1-one, and
1-(4-(3-amino-1H-1,2,4-triazol-5-yl)piperazin-1-yl)-2-(4-bromophenoxy)ethan-1-one.

In certain embodiments, the invention provides a pharmaceutical formulation comprising a compound of formula (X), or a pharmaceutically acceptable salt, hydrate, or solvate thereof, and at least one pharmaceutically acceptable carrier, solvent, adjuvant or diluent, wherein the compound of formula (X) is:

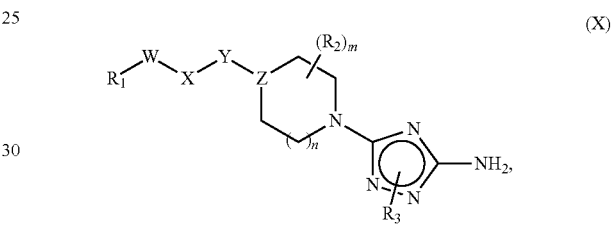

wherein in (X):
m is 0, 1, 2, 3, or 4;
n is 0, 1, or 2;
$R_1$ is aryl or heteroaryl, each of which is optionally substituted with one or more of $R_4$;
each $R_2$ is individually selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, hydroxy($C_1$-$C_6$ alkyl), $C_1$-$C_6$ acyloxy($C_1$-$C_6$ alkyl), alkoxy($C_1$-$C_6$ alkyl), and $C_1$-$C_6$ haloalkoxy;
$R_3$ is a substituent on one nitrogen atom, and is hydrogen or $C_1$-$C_6$ alkyl;
W is absent, —O—, —N($R_5$)—, —$X_1$—N($R_5$)—, —$X_1$—O—, —N($R_5$)C(=O)—, —C(=O)N($R_5$)—, —N($R_5$)S(=O)$_2$—, or —S(=O)$_2$N($R_5$)—, where $X_1$ is $C_1$-$C_3$ alkylene optionally substituted with one or more substituents selected from the group consisting of $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)N($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);
X is —C(=O)— or $C_1$-$C_6$ alkylene optionally substituted with one or more substituents selected from the group consisting of $C_1$-$C_6$ alkyl, $C_1$-$C_6$ haloalkyl, benzyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);

Y is absent, —C(=O)—, —OC(=O)—, —N(R$_5$), —N(R$_5$)C(=O)—, —C(=O)N(R$_5$)—, —N(R$_5$)S(=O)$_2$—, —S(=O)$_2$N(R$_5$)—, —N(R$_5$)CH$_2$—, or —S(=O)$_2$—;

or W—X—Y represent a heteroarylene, heterocyclylene, or C$_3$-C$_8$ cycloalkylene, each optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, or C$_1$-C$_6$ haloalkoxy;

Z is CH, C(C$_1$-C$_6$ alkyl), or N, wherein the C$_1$-C$_6$ alkyl is optionally substituted with one or more substituents selected from halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

or Y—Z, together with one carbon atom to which Z is attached, form a heterocyclyl;

or Y—Z combine to form a bicyclic heterocycle selected from the group consisting of:

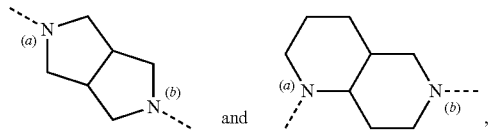

wherein the N labelled as (a) is covalently bonded to X and the N labelled as (b) is covalently bonded to the 1,3,4-triazole ring;

or Y is absent, X is a bond or as defined above, and Z is a carbon atom that is covalently connected to W by a C$_1$-C$_4$ alkylene chain optionally containing a nitrogen, oxygen, or sulfur atom, whereby Z—X—Y—W together form a 3-7 membered carbocyclic or heterocyclic ring;

each R$_4$ is independently selected from the group consisting of halogen, —NO$_2$, —CN, C$_1$-C$_6$ alkyl, C$_3$-C$_7$ cycloalkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(=O)$_{0-2}$(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)NHNH$_2$, —C(=O)H, —C(=O)O(C$_1$-C$_6$ alkyl), —OC(=O)(C$_1$-C$_6$ alkyl), —NHC(=O)(C$_1$-C$_6$ alkoxy), —NHC(=O)(C$_1$-C$_6$ alkyl), —NHC(=O)NH$_2$, —NHC(=O)NH(C$_1$-C$_6$ alkyl), —NHC(=NH)NH$_2$, —NH—S(=O)$_{0-2}$—(C$_1$-C$_6$ alkyl), —NH—S(=O)$_{0-2}$-aryl, and —NH—S(=O)$_{0-2}$-heteroaryl; and, each R$_5$ is independently selected from hydrogen and C$_1$-C$_6$ alkyl optionally substituted with at least one substituent selected from the group consisting of halogen, hydroxy, C$_1$-C$_6$ haloalkyl, C$_3$-C$_7$ cycloalkyl, C$_1$-C$_6$ alkoxy, and R$_{5a}$, where R$_{5a}$ is phenyl, naphthyl or a bicyclic heteroaryl, and R$_{5a}$ is optionally substituted with 1-3 substituents independently selected from the group consisting of halogen, hydroxy, C$_1$-C$_6$ alkyl, cyano, hydroxy C$_1$-C$_6$ alkyl, phenyl, C$_1$-C$_6$ alkoxy, haloalkyl, —NH$_2$, —NH(C$_1$-C$_6$ alkyl), —N(C$_1$-C$_6$ alkyl)$_2$, and C$_1$-C$_6$ haloalkoxy.

DETAILED DESCRIPTION OF THE INVENTION

In a broad aspect, the present invention includes compounds of formula (I), any acceptable salt, hydrate, or solvate thereof, pharmaceutical compositions containing the same, and methods of using compounds and/or compositions to treat asthma and/or to monitor asthma treatment.

In certain embodiments, the invention includes a compound of formula (I), or any acceptable salt, hydrate, and/or solvate thereof:

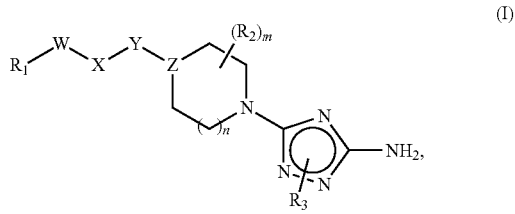

wherein in (I):

m is 0, 1, 2, 3, or 4;

n is 0, 1, or 2;

R$_1$ is aryl or heteroaryl, each of which is optionally substituted with one or more of R$_4$;

each R$_2$ is individually selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, hydroxy(C$_1$-C$_6$ alkyl), C$_1$-C$_6$ acyloxy(C$_1$-C$_6$ alkyl), alkoxy(C$_1$-C$_6$ alkyl), and C$_1$-C$_6$ haloalkoxy;

R$_3$ is a substituent on one nitrogen atom, and is hydrogen or C$_1$-C$_6$ alkyl;

W is absent, —O—, —N(R$_5$)—, —X$_1$—N(R$_5$)—, —X$_1$—O—, —N(R$_5$)C(=O)—, —C(=O)N(R$_5$)—, —N(R$_5$)S(=O)$_2$—, or —S(=O)$_2$N(R$_5$)—, where X$_1$ is C$_1$-C$_3$ alkylene optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

X is —C(=O)— or C$_1$-C$_6$ alkylene optionally substituted with one or more substituents selected from the group consisting of C$_1$-C$_6$ alkyl, C$_1$-C$_6$ haloalkyl, benzyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

Y is absent, —C(=O)—, —OC(=O)—, —N(R$_5$), —N(R$_5$)C(=O)—, —C(=O)N(R$_5$)—, —N(R$_5$)S(=O)$_2$—, —S(=O)$_2$N(R$_5$)—, —N(R$_5$)CH$_2$—, or —S(=O)$_2$—;

or W—X—Y represent a heteroarylene, heterocyclylene, or C$_3$-C$_8$ cycloalkylene, each optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, or C$_1$-C$_6$ haloalkoxy;

Z is CH, C(C$_1$-C$_6$ alkyl), or N, wherein the C$_1$-C$_6$ alkyl is optionally substituted with one or more substituents selected from halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)

NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

or Y—Z, together with one carbon atom to which Z is attached, form a heterocyclyl;

or Y—Z combine to form a bicyclic heterocycle selected from the group

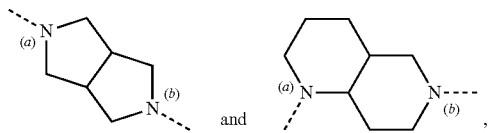

consisting of:

wherein the N labelled as (a) is covalently bonded to X and the N labelled as (b) is covalently bonded to the 1,3,4-triazole ring;

or Y is absent, X is a bond or as defined above, and Z is a carbon atom that is covalently connected to W by a C$_1$-C$_4$ alkylene chain optionally containing a nitrogen, oxygen, or sulfur atom, whereby Z—X—Y—W together form a 3-7 membered carbocyclic or heterocyclic ring;

each R$_4$ is independently selected from the group consisting of halogen, —NO$_2$, —CN, C$_1$-C$_6$ alkyl, C$_3$-C$_7$ cycloalkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(=O)$_{0-2}$(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)NHNH$_2$, —C(=O)H, —C(=O)O(C$_1$-C$_6$ alkyl), —OC(=O)(C$_1$-C$_6$ alkyl), —NHC(=O)(C$_1$-C$_6$ alkoxy), —NHC(=O)(C$_1$-C$_6$ alkyl), —NHC(=O)NH$_2$, —NHC(=O)NH(C$_1$-C$_6$ alkyl), —NHC(=NH)NH$_2$, —NH—S(=O)$_{0-2}$—(C$_1$-C$_6$ alkyl), —NH—S(=O)$_{0-2}$-aryl, and —NH—S(=O)$_{0-2}$-heteroaryl; and, each R$_5$ is independently selected from hydrogen and C$_1$-C$_6$ alkyl optionally substituted with at least one substituent selected from the group consisting of halogen, hydroxy, C$_1$-C$_6$ haloalkyl, C$_3$-C$_7$ cycloalkyl, C$_1$-C$_6$ alkoxy, and R$_{5a}$, where R$_{5a}$ is phenyl, naphthyl or a bicyclic heteroaryl, and R$_{5a}$ is optionally substituted with 1-3 substituents independently selected from the group consisting of halogen, hydroxy, C$_1$-C$_6$ alkyl, cyano, hydroxy C$_1$-C$_6$ alkyl, phenyl, C$_1$-C$_6$ alkoxy, haloalkyl, —NH$_2$, —NH(C$_1$-C$_6$ alkyl), —N(C$_1$-C$_6$ alkyl)$_2$, and C$_1$-C$_6$ haloalkoxy;

provided the compound of formula (I) is not:

5-[4-(1-naphthalenylmethyl)-1-piperazinyl]-1H-1,2,4-triazol-3-amine;

5-[4-(1,3-benzodioxol-5-ylmethyl)-1-piperazinyl]-1H-1,2,4-triazol-3-amine;

5-[4-(1-phenylethyl)-1-piperazinyl]-1H-1,2,4-triazol-3-amine;

5-[4-[[2-chloro-4-(dimethylamino)phenyl]methyl]-1-piperazinyl]-1H-1,2,4-triazol-3-amine;

5-[4-[[3-bromo-4-(dimethylamino)phenyl]methyl]-1-piperazinyl]-1H-1,2,4-triazol-3-amine;

5-[4-[(2,3,4-trimethoxyphenyl)methyl]-1-piperazinyl]-1H-1,2,4-triazol-3-amine;

5-[4-[(2-chloro-4-fluorophenyl)methyl]-1-piperazinyl]-1H-1,2,4-triazol-3-amine;

5-[4-[[3-(trifluoromethyl)phenyl]methyl]-1-piperazinyl]-1H-1,2,4-triazol-3-amine;

5-[4-[(2,4,6-trimethylphenyl)methyl]-1-piperazinyl]-1H-1,2,4-triazol-3-amine;

5-[4-[(2,5-dimethylphenyl)methyl]-1-piperazinyl]-1H-1,2,4-triazol-3-amine;

5-[4-[(2,6-dichlorophenyl)methyl]-1-piperazinyl]-1H-1,2,4-triazol-3-amine;

5-[4-(2-phenoxyethyl)-1-piperazinyl]-1H-1,2,4-triazol-3-amine;

5-[4-(4-phenoxybutyl)-1-piperazinyl]-1H-1,2,4-triazol-3-amine;

5-[4-[2-(4-bromophenoxy)ethyl]-1-piperazinyl]-1H-1,2,4-triazol-3-amine;

5-[4-[(3,4-dichlorophenyl)methyl]-1-piperazinyl]-1H-1,2,4-triazol-3-amine;

5-[4-(4-pyridinylmethyl)-1-piperazinyl]-1H-1,2,4-triazol-3-amine;

5-[4-[(4-methylphenyl)methyl]-1-piperazinyl]-1H-1,2,4-triazol-3-amine;

5-[4-(phenylmethyl)-1-piperazinyl]-1H-1,2,4-triazol-3-amine;

5-[4-[(4-aminophenyl)methyl]-1-piperazinyl]-1H-1,2,4-triazol-3-amine;

5-[4-[[3-chloro-4-(dimethylamino)phenyl]methyl]-1-piperazinyl]-1H-1,2,4-triazol-3-amine;

5-[4-[(3-chlorophenyl)methyl]-1-piperazinyl]-1H-1,2,4-triazol-3-amine;

5-[4-[[2-bromo-4-(dimethylamino)phenyl]methyl]-1-piperazinyl]-1H-1,2,4-triazol-3-amine;

5-[4-(3-phenylpropyl)-1-piperazinyl]-1H-1,2,4-triazol-3-amine;

5-[4-[[4-(dimethylamino)phenyl]methyl]-1-piperazinyl]-1H-1,2,4-triazol-3-amine;

5-[4-(2-furanylmethyl)-1-piperazinyl]-1H-1,2,4-triazol-3-amine;

5-[4-(2-quinolinylmethyl)-1-piperazinyl]-1H-1,2,4-triazol-3-amine;

4-[[4-(3-amino-1H-1,2,4-triazol-5-yl)-1-piperazinyl]methyl]-benzonitrile;

5-[4-[(2-fluorophenyl)methyl]-1-piperazinyl]-1H-1,2,4-triazol-3-amine;

5-[4-(2-phenylethyl)-1-piperazinyl]-1H-1,2,4-triazol-3-amine;

5-[4-[(4-fluorophenyl)methyl]-1-piperazinyl]-1H-1,2,4-triazol-3-amine;

5-[4-[(2-nitrophenyl)methyl]-1-piperazinyl]-1H-1,2,4-triazol-3-amine;

5-[4-(3-phenoxypropyl)-1-piperazinyl]-1H-1,2,4-triazol-3-amine;

5-[4-[[4-(1,1-dimethylethyl)phenyl]methyl]-1-piperazinyl]-1H-1,2,4-triazol-3-amine;

5-[4-[(4-butylphenyl)methyl]-1-piperazinyl]-1H-1,2,4-triazol-3-amine;

5-[4-[(3-methylphenyl)methyl]-1-piperazinyl]-1H-1,2,4-triazol-3-amine;

benzyl 4-(3-amino-1H-1,2,4-triazol-5-yl)piperazine-1-carboxylate;

5-[4-[(3,4,5-trimethoxyphenyl)methyl]-1-piperazinyl]-1H-1,2,4-triazol-3-amine; or 5-[4-[(2-methylphenyl)methyl]-1-piperazinyl]-1H-1,2,4-triazol-3-amine.

In certain embodiments, the compound of formula (I) is a compound of formula (II) or any pharmaceutically acceptable salt, hydrate, and/or solvate thereof:

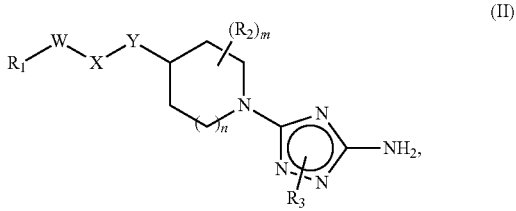

(II)

wherein in (II):

W is absent, —O—, —$X_1$—O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more of $C_1$-$C_6$ alkyl, benzyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, or —S($C_1$-$C_6$ alkyl);

Y is absent, —C(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)CH$_2$—, or —S(=O)$_2$—.

In certain embodiments, the compound of formula (I) is a compound of formula (III) or any pharmaceutically acceptable salt, hydrate, and/or solvate thereof:

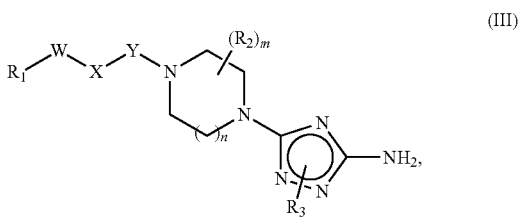

(III)

wherein in (III):

W is absent, —O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more substituents selected from the group consisting of $C_1$-$C_6$ alkyl, benzyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, and —S($C_1$-$C_6$ alkyl);

Y is absent, —C(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)CH$_2$—, or —S(=O)$_2$—;

provided that, when both W and Y are absent, X is not optionally substituted methylene;

provided the compound is not:

5-[4-(2-phenoxyethyl)-1-piperazinyl]-1H-1,2,4-triazol-3-amine;

5-[4-(4-phenoxybutyl)-1-piperazinyl]-1H-1,2,4-triazol-3-amine;

5-[4-[2-(4-bromophenoxy)ethyl]-1-piperazinyl]-1H-1,2,4-triazol-3-amine;

5-[4-(3-phenylpropyl)-1-piperazinyl]-1H-1,2,4-triazol-3-amine;

45-[4-(2-phenylethyl)-1-piperazinyl]-1H-1,2,4-triazol-3-amine; or

5-[4-(3-phenoxypropyl)-1-piperazinyl]-1H-1,2,4-triazol-3-amine.

In certain embodiments, in formula (III), W is absent, —$X_1$O—, —O—, —N($R_5$)—, —N($R_5$)C(=O)—, —C(=O)N($R_5$)—, —N($R_5$)S(=O)$_2$—, or —S(=O)$_2$N($R_5$)—; X is $C_1$-$C_6$ alkylene optionally substituted with one or more substituents selected from the group consisting of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, and —S($C_1$-$C_6$ alkyl); provided that W—X—Y is not —CH$_2$—, and provided that when $R_1$ is phenyl optionally substituted with halogen, W—X—Y is not —CH(CH$_3$)—, —(CH$_2$)$_2$—, —(CH$_2$)$_3$—, —O(CH$_2$)$_2$—, —O(CH$_2$)$_3$—, or —O(CH$_2$)$_4$—.

In other embodiments, in formula (III), W is absent, —O—, —N($R_5$)—, —N($R_5$)C(=O)—, —C(=O)N($R_5$)—, —N($R_5$)S(=O)$_2$—, or —S(=O)$_2$N($R_5$)—; X is $C_1$-$C_6$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, or —S($C_1$-$C_6$ alkyl).

In certain embodiments, the compound of formula (I) is a compound of formula (IV) or any pharmaceutically acceptable salt, hydrate, and/or solvate thereof:

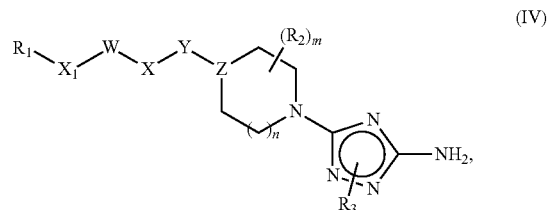

(IV)

wherein in (IV):

W is —O—, —$X_1$O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_3$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), or —NHC(=O)($C_1$-$C_6$ alkyl);

$X_1$ is $C_1$-$C_3$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), or —NHC(=O)($C_1$-$C_6$ alkyl);

Y is absent, —C(=O)—, —OC(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)CH$_2$—, or —S(=O)$_2$—;

provided that the compound is not benzyl 4-(3-amino-1H-1,2,4-triazol-5-yl)piperazine-1-carboxylate.

In certain embodiments, W is —O— or —N($R_5$)—.

In certain embodiments, Y is absent. In other embodiments, Y is —C(=O)— or —SO$_2$—. In yet other embodiments, Y is absent, W is NR$_5$ and R$_5$ is $C_1$-$C_3$ alkyl substituted with phenyl which is optionally substituted with 1-3 substituents independently selected from the group consisting of halogen, hydroxy, $C_1$-$C_6$ alkyl, $C_1$-$C_6$ alkoxy, haloalkyl, —NH$_2$, —NH($C_1$-$C_6$ alkyl), —N($C_1$-$C_6$ alkyl)$_2$, and $C_1$-$C_6$ haloalkoxy In certain embodiments, Y is absent, W is NR$_5$ and R$_5$ is hydrogen or $C_1$-$C_6$ alkyl. In certain embodiments, Y is absent, W is NR$_5$ and R$_5$ is hydrogen. In certain embodiments, Y is absent, W is NR$_5$ and R$_5$ is C$_1$-C$_6$ alkyl; In other embodiments, W is NR$_5$ and R$_5$ is methyl or ethyl.

In certain embodiments, the compound of formula (I) is a compound of formula (V), or any pharmaceutically acceptable salt, hydrate, and/or solvate thereof:

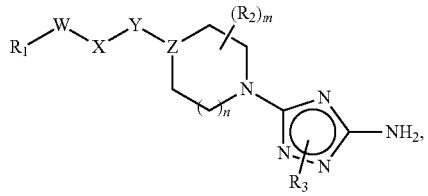
(V)

wherein in (V):

W is —O— or —N(R$_5$)—;

X is C$_1$-C$_6$ alkylene optionally substituted with one or more of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), or —NHC(=O)(C$_1$-C$_6$ alkyl); or X together with one of R$_4$ forms a C$_1$-C$_3$ alkylene or C$_1$-C$_3$ alkenylene group;

Y is —C(=O)—, —OC(=O)—, —N(R$_5$)—, —N(R$_5$)C(=O)—, —C(=O)N(R$_5$)—, —N(R$_5$)SO$_2$—, —S(=O)$_2$N(R$_5$)—, —N(R$_5$)CH$_2$—, or —SO$_2$—.

In certain embodiments, Y is —C(=O)— or —S(=O)$_2$—. In certain embodiments, X—R$_4$ is a C$_2$-C$_3$ alkylene or C$_1$-C$_3$alkenylene group. In certain embodiments, Y is —C(=O)— and W is O.

In certain embodiments, the compound of formula (I) is a compound of formula (VI), or any acceptable salt, hydrate, and/or solvate thereof:

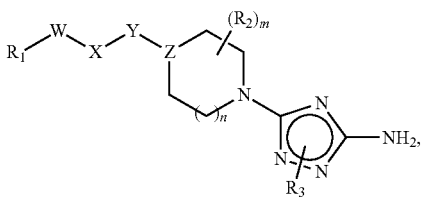
(VI)

wherein in (VI):

W is —N(R$_5$)—; X is —C(=O)—; Y is —N(R$_5$)—; Z is CH, C(C$_1$-C$_6$ alkyl), or N.

In certain embodiments, both W and Y are NH.

In certain embodiments, the invention includes pharmaceutical formulations comprising a compound of Formula (X), or a pharmaceutically acceptable salt, hydrate, and/or solvate thereof, and methods of using such formulations to treat diseases and disorders involving acidic mammalian chitinase, including, for example, asthma:

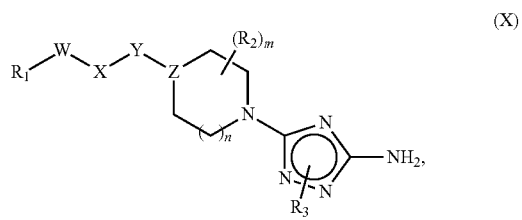
(X)

wherein in (X):

m is 0, 1, 2, 3, or 4;

n is 0, 1, or 2;

R$_1$ is aryl or heteroaryl, each of which is optionally substituted with one or more of R$_4$;

each R$_2$ is individually selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, hydroxy(C$_1$-C$_6$ alkyl), C$_1$-C$_6$ acyloxy(C$_1$-C$_6$ alkyl), alkoxy(C$_1$-C$_6$ alkyl), and C$_1$-C$_6$ haloalkoxy;

R$_3$ is a substituent on one nitrogen atom, and is hydrogen or C$_1$-C$_6$ alkyl;

W is absent, —O—, —N(R$_5$)—, —X$_1$—N(R$_5$)—, —X$_1$—O—, —N(R$_5$)C(=O)—, —C(=O)N(R$_5$)—, —N(R$_5$)S(=O)$_2$—, or —S(=O)$_2$N(R$_5$)—, where X$_1$ is C$_1$-C$_3$ alkylene optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

X is —C(=O)— or C$_1$-C$_6$ alkylene optionally substituted with one or more substituents selected from the group consisting of C$_1$-C$_6$ alkyl, C$_1$-C$_6$ haloalkyl, benzyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)NH(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

Y is absent, —C(=O)—, —OC(=O)—, —N(R$_5$), —N(R$_5$)C(=O)—, —C(=O)N(R$_5$)—, —N(R$_5$)S(=O)$_2$—, —S(=O)$_2$N(R$_5$)—, —N(R$_5$)CH$_2$—, or —S(=O)$_2$—;

or W—X—Y represent a heteroarylene, heterocyclylene, or C$_3$-C$_8$ cycloalkylene, each optionally substituted with one or more substituents selected from the group consisting of C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, or C$_1$-C$_6$ haloalkoxy;

Z is CH, C(C$_1$-C$_6$ alkyl), or N, wherein the C$_1$-C$_6$ alkyl is optionally substituted with one or more substituents selected from halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —C(=O)NH$_2$, —C(=O)N(C$_1$-C$_6$ alkyl), —C(=O)N(C$_1$-C$_6$ alkyl)$_2$, —C(=O)O(C$_1$-C$_6$ alkyl), —NHC(=O)(C$_1$-C$_6$ alkoxy), and —NHC(=O)(C$_1$-C$_6$ alkyl);

or Y—Z, together with one carbon atom to which Z is attached, form a heterocyclyl;

or Y—Z combine to form a bicyclic heterocycle selected from the group consisting of:

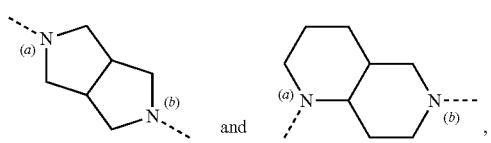

wherein the N labelled as (a) is covalently bonded to X and the N labelled as (b) is covalently bonded to the 1,3,4-triazole ring;

or Y is absent, X is a bond or as defined above, and Z is a carbon atom that is covalently connected to W by a $C_1$-$C_4$ alkylene chain optionally containing a nitrogen, oxygen, or sulfur atom, whereby Z—X—Y—W together form a 3-7 membered carbocyclic or heterocyclic ring;

each $R_4$ is independently selected from the group consisting of halogen, —$NO_2$, —CN, $C_1$-$C_6$ alkyl, $C_3$-$C_7$ cycloalkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S(=O)$_{0-2}$($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)$NHNH_2$, —C(=O)H, —C(=O)O($C_1$-$C_6$ alkyl), —OC(=O)($C_1$-$C_6$ alkyl), —NHC(=O)($C_1$-$C_6$ alkoxy), —NHC(=O)($C_1$-$C_6$ alkyl), —NHC(=O)$NH_2$, —NHC(=O)NH($C_1$-$C_6$ alkyl), —NHC(=NH)$NH_2$, —NH—S(=O)$_{0-2}$—($C_1$-$C_6$ alkyl), —NH—S(=O)$_{0-2}$-aryl, and —NH—S(=O)$_{0-2}$-heteroaryl; and, each $R_5$ is independently selected from hydrogen and $C_1$-$C_6$ alkyl optionally substituted with at least one substituent selected from the group consisting of halogen, hydroxy, $C_1$-$C_6$ haloalkyl, $C_3$-$C_7$ cycloalkyl, $C_1$-$C_6$ alkoxy, and $R_{5a}$, where $R_{5a}$ is phenyl, naphthyl or a bicyclic heteroaryl, and $R_{5a}$ is optionally substituted with 1-3 substituents independently selected from the group consisting of halogen, hydroxy, $C_1$-$C_6$ alkyl, cyano, hydroxy $C_1$-$C_6$ alkyl, phenyl, $C_1$-$C_6$ alkoxy, haloalkyl, —$NH_2$, —NH($C_1$-$C_6$ alkyl), —N($C_1$-$C_6$ alkyl)$_2$, and $C_1$-$C_6$ haloalkoxy.

In certain embodiments, if W is —N($R_5$)C(=O)—, —C(=O)N($R_5$)—, —N($R_5$)S(=O)$_2$—, or —S(=O)$_2$N($R_5$)—, then X is not C(=O)—.

In certain embodiments, the compound of formula (I) is at least one selected from the group consisting of Examples 1-37, 39-45, 47-76, 78-96, 98-123, 125-184, 186, 188, 191-206, 208-235 and 237-259.

In certain embodiments, W is absent, —O—, —N($R_5$)—, —$X_1$—N($R_5$)—, —$X_1$—O—, —N($R_5$)C(=O)—, —C(=O)N($R_5$)—, —N($R_5$)S(=O)$_2$—, or —S(=O)$_2$N($R_5$)—. In other embodiments, W is absent, —O—, —N($R_5$)—, —N($R_5$)C(=O)—, —C(=O)N($R_5$)—, —N($R_5$)S(=O)$_2$—, or —S(=O)$_2$N($R_5$)—.

In certain embodiments, Y is $NR_5$, and $R_5$ is $C_1$-$C_3$ alkyl substituted with phenyl which is optionally substituted with 1-3 substituents independently selected from the group consisting of halogen, hydroxy, $C_1$-$C_6$ alkyl, $C_1$-$C_6$ alkoxy, haloalkyl, —$NH_2$, —NH($C_1$-$C_6$ alkyl), —N($C_1$-$C_6$ alkyl)$_2$, and $C_1$-$C_6$ haloalkoxy. In other embodiments, Y is $NR_5$, and $R_5$ is hydrogen or $C_1$-$C_6$ alkyl. In yet other embodiments, Y is $NR_5$, and $R_5$ is hydrogen. In yet other embodiments, Y is $NR_5$, and $R_5$ is $C_1$-$C_6$ alkyl. In yet other embodiments, Y is $NR_5$, and $R_5$ is methyl or ethyl.

In certain embodiments, W is $NR_5$, and $R_5$ is $C_1$-$C_3$ alkyl substituted with phenyl which is optionally substituted with 1-3 substituents independently selected from the group consisting of halogen, hydroxy, $C_1$-$C_6$ alkyl, $C_1$-$C_6$ alkoxy, haloalkyl, —$NH_2$, —NH($C_1$-$C_6$ alkyl), —N($C_1$-$C_6$ alkyl)$_2$, and $C_1$-$C_6$ haloalkoxy. In other embodiments, W is $NR_5$, and $R_5$ is hydrogen or $C_1$-$C_6$ alkyl. In yet other embodiments, W is $NR_5$, and $R_5$ is hydrogen. In yet other embodiments, W is $NR_5$, and $R_5$ is $C_1$-$C_6$ alkyl. In yet other embodiments, W is $NR_5$, and $R_5$ is methyl or ethyl.

In certain embodiments, X is $C_1$-$C_6$ alkylene optionally substituted with one or more substituents independently selected from the group consisting of $C_1$-$C_6$ alkyl, $C_1$-$C_6$ haloalkyl, benzyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)N($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);

In certain embodiments, $R_1$ is aryl optionally substituted with one or more of $R_4$. In other embodiments, $R_1$ is phenyl optionally substituted with one or more of $R_4$. In yet other embodiments, $R_1$ is naphthyl optionally substituted with one or more of $R_4$.

In certain embodiments, each $R_4$ is independently selected from the group consisting of halogen, —$NO_2$, —CN, $C_1$-$C_6$ alkyl, $C_1$-$C_6$ haloalkyl, $C_3$-$C_7$ cycloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S(=O)$_2$($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)$NHNH_2$, —C(=O)H, and —C(=O)O($C_1$-$C_6$ alkyl). In other embodiments, each $R_4$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —C(=O)$NH_2$, —C(=O)NH($C_1$-$C_6$ alkyl), —C(=O)N($C_1$-$C_6$ alkyl)$_2$, —C(=O)$NHNH_2$, —C(=O)H, and —C(=O)O($C_1$-$C_6$ alkyl). In yet other embodiments, each $R_4$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. In yet other embodiments, each $R_4$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy. In yet other embodiments, each $R_4$ is independently selected from the group consisting of halogen, —$NO_2$, $C_1$-$C_6$ alkyl, and $C_1$-$C_6$ alkoxy.

In certain embodiments, at least one $R_4$ is present. In other embodiments, $R_4$ is halogen. In yet other embodiments, $R_1$ is phenyl and $R_4$ is 4-bromo. In yet other embodiments, $R_1$ is phenyl and $R_4$ is 4-chloro. In yet other embodiments, $R_1$ is phenyl and $R_4$ is 3-chloro. In yet other embodiments, $R_1$ is phenyl and one $R_4$ is 3-chloro and the other $R_4$ is 4-chloro. In yet other embodiments, $R_1$ is phenyl and one $R_4$ is 3-chloro and the other $R_4$ is 5-chloro. In yet other embodiments, $R_1$ is phenyl and $R_4$ is 3-fluoro or 4-fluoro. In yet other embodiments, $R_1$ is phenyl and $R_4$ is $C_1$-$C_6$ alkyl.

In certain embodiments, $R_4$ is methyl or ethyl. In other embodiments, two $R_4$ are present and each is independently $C_1$-$C_6$ alkyl. In yet other embodiments, one $R_4$ is $C_1$-$C_6$ alkyl, and the other $R_4$ is halogen. In yet other embodiments, $R_4$ is $C_1$-$C_6$ alkoxy. In yet other embodiments, $R_4$ is methoxy or ethoxy.

In certain embodiments, $R_1$ is heteroaryl optionally substituted with one or more of $R_4$. In yet other embodiments, $R_1$ is furyl, imidazolyl, isoxazolyl, oxazolyl, pyridinyl, pyridazinyl, pyrimidinyl, pyrazinyl, pyrazolyl, pyrrolyl, triazolyl, benzimidazolyl, benzofuranyl, indazolyl, indolyl, quinolinyl, or purinyl, each of which is optionally substituted with one or more of $R_4$.

In certain embodiments, $R_1$ is unsubstituted. In other embodiments, $R_1$ is substituted with one or more of $R_4$, and each $R_4$ is independently selected from the group consisting of halogen, $-NO_2$, $-CN$, $C_1$-$C_6$ alkyl, $C_1$-$C_6$ haloalkyl, $-NH_2$, $-NH(C_1$-$C_6$ alkyl), $-N(C_1$-$C_6$ alkyl)$_2$, $-OH$, $C_1$-$C_6$ alkoxy, $C_1$-$C_6$ haloalkoxy, $-C(=O)NH_2$, $-C(=O)NH(C_1$-$C_6$ alkyl), $-C(=O)N(C_1$-$C_6$ alkyl)$_2$, $-C(=O)NHNH_2$, $-C(=O)H$, and $-C(=O)O(C_1$-$C_6$ alkyl). In yet other embodiments, each $R_4$ is independently selected from the group consisting of halogen, $-NO_2$, $-CN$, $C_1$-$C_6$ alkyl, $C_1$-$C_6$ haloalkyl, $-NH_2$, $-NH(C_1$-$C_6$ alkyl), $-N(C_1$-$C_6$ alkyl)$_2$, $-OH$, $C_1$-$C_6$ alkoxy, and $C_1$-$C_6$ haloalkoxy.

In certain embodiments, n is 1 or 2. In other embodiments, n is 1. In yet other embodiments, m is 0, 1, or 2. In yet other embodiments, m is 0. In yet other embodiments, m is 1 or 2.

In certain embodiments, each $R_2$ is individually selected from the group consisting of halogen, $C_1$-$C_6$ alkyl, $C_1$-$C_6$ haloalkyl, $-OH$, $C_1$-$C_6$ alkoxy, hydroxy($C_1$-$C_6$ alkyl), alkoxy($C_1$-$C_6$ alkyl), $C_1$-$C_6$ acyloxy($C_1$-$C_6$ alkyl), and $C_1$-$C_6$ haloalkoxy. In yet other embodiments, each $R_2$ is individually selected from the group consisting of halogen, $C_1$-$C_6$ alkyl, $-OH$, $C_1$-$C_6$ alkoxy, hydroxy($C_1$-$C_6$ alkyl), and alkoxy($C_1$-$C_6$ alkyl). In yet other embodiments, each $R_2$ is individually selected from the group consisting of $C_1$-$C_6$ alkyl and hydroxy($C_1$-$C_6$ alkyl).

In certain embodiments, $R_3$ is hydrogen. In other embodiments, $R_3$ is $C_1$-$C_6$ alkyl.

In certain embodiments, Z is CH. In other embodiments, Z is C($C_1$-$C_6$ alkyl), wherein the alkyl is optionally substituted with one or more substituents selected halogen, hydroxy, $C_1$-$C_6$ alkyl, cyano, hydroxy $C_1$-$C_6$ alkyl, phenyl, $C_1$-$C_6$ alkoxy, haloalkyl, $-NH_2$, $-NH(C_1$-$C_6$ alkyl), $-N(C_1$-$C_6$ alkyl)$_2$, and $C_1$-$C_6$ haloalkoxy. In yet other embodiments, Z is C(CH$_3$).

In certain embodiments, Y is $-N(R_5)-$, $-N(R_5)C(=O)-$, $-C(=O)N(R_5)-$, or $-N(R_5)S(=O)_2-$. In yet other embodiments, Y is $-N(R_5)-$. In yet other embodiments, Y is $-N(R_5)C(=O)-$ or $-C(=O)N(R_5)-$. In yet other embodiments, Y is $-N(R_5)S(=O)_2-$.

In certain embodiments, $R_5$ is hydrogen. In other embodiments, $R_5$ is hydrogen, methyl or ethyl.

In certain embodiments, X is optionally substituted $C_1$-$C_3$ alkylene. In other embodiments, X is optionally substituted $C_1$-$C_2$ alkylene. Optional substituents include $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy.

In certain embodiments, X is methylene. In other embodiments, X is ethylene.

In certain embodiments, Y—Z combine to form a bicyclic heterocycle selected from the group consisting of:

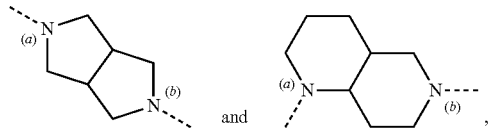

wherein the N labelled as (a) is covalently bonded to X and the N labelled as (b) is covalently bonded to the 1,3,4-triazole ring In certain embodiments, Y is absent. In other embodiments, X is optionally substituted $C_1$-$C_3$ alkylene. In yet other embodiments, X is optionally substituted $C_1$-$C_2$ alkylene. Optional substituents include $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In yet other embodiments, X is methylene. In yet other embodiments, X is ethylene.

In certain embodiments, W is $-N(R_5)-$, $-N(R_5)C(=O)-$, $-C(=O)N(R_5)-$, $-N(R_5)S(=O)_2-$, or $-S(=O)_2N(R_5)-$. In other embodiments, W is $-N(R_5)C(=O)-$ or $-C(=O)N(R_5)-$. In yet other embodiments, W is $-S(=O)_2N(R_5)-$. In certain embodiments, W is absent.

In certain embodiments, W—X—Y represent a heteroarylene optionally substituted with one or more of $C_1$-$C_6$ alkyl, $C_1$-$C_6$ haloalkyl, $-NH_2$, $-NH(C_1$-$C_6$ alkyl), $-N(C_1$-$C_6$ alkyl)$_2$, $-OH$, $C_1$-$C_6$ alkoxy, or $C_1$-$C_6$ haloalkoxy. In other embodiments, W—X—Y represent oxadiazolylene moiety, such as 3,5-oxadiazolylene or 2,5-oxadiazolylene.

In certain embodiments, Z is N.

In certain embodiments, X is optionally substituted $C_1$-$C_3$ alkylene. Optional substituents include $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In other embodiments, X is methylene. In yet other embodiments, X is propylene optionally substituted with $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In yet other embodiments, X is propylene optionally substituted with methyl or ethyl.

In certain embodiments, W is $-O-$ or $-N(R_5)-$, and Y is absent. In other embodiments, W is $-O-$, and Y is absent. In yet other embodiments, X is optionally substituted $C_1$-$C_3$ alkylene. In yet other embodiments, X is $C_1$-$C_3$ alkylene optionally substituted with $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In certain embodiments, W is absent and Y is absent.

In certain embodiments, X is ethylene optionally substituted with $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In other embodiments, X is ethylene optionally substituted with methyl or ethyl.

In certain embodiments, W is absent, and Y is $-C(=O)-$ or $-OC(=O)-$. In other embodiments, W is absent, and Y is $-C(=O)-$. In yet other embodiments, X is optionally substituted $C_1$-$C_3$ alkylene. In yet other embodiments, X is $C_1$-$C_3$ alkylene optionally substituted with $C_1$-$C_6$ alkyl, $-NH_2$, $-NH(C_1$-$C_6$ alkyl), $-N(C_1$-$C_6$ alkyl)$_2$, $-OH$, $C_1$-$C_6$ alkoxy, or $-NHC(=O)(C_1$-$C_6$ alkyl).

In certain embodiments, X is ethylene optionally substituted with $C_1$-$C_6$ alkyl, $-NH_2$, $-NH(C_1$-$C_6$ alkyl), $-N(C_1$-$C_6$ alkyl)$_2$, $-OH$, $C_1$-$C_6$ alkoxy or $-NHC(=O)(C_1$-$C_6$ alkyl). In other embodiments, X is ethylene optionally substituted with $-NH_2$, $-OH$ or $-NHCO(C_1$-$C_6$ alkyl).

In certain embodiments, W is $-O-$ or $-N(R_5)-$, and Y is $-C(=O)-$ or $-OC(=O)-$. In other embodiments, W is $-O-$ or $-N(R_5)-$, and Y is $-C(=O)-$. In yet other embodiments, W is $-O-$, and Y is $-C(=O)-$. In yet other embodiments, X is optionally substituted $C_1$-$C_3$ alkylene. In yet other embodiments, X is $C_1$-$C_3$ alkylene optionally substituted with $C_1$-$C_6$ alkyl, $-NH_2$, $-NH(C_1$-$C_6$ alkyl), $-N(C_1$-$C_6$ alkyl)$_2$, $-OH$, $C_1$-$C_6$ alkoxy, or $-NHCO(C_1$-$C_6$ alkyl).

In certain embodiment, X is methylene optionally substituted with $C_1$-$C_6$ alkyl, $-NH_2$, $-NH(C_1$-$C_6$ alkyl), $-N(C_1$-$C_6$ alkyl)$_2$, $-OH$, or $C_1$-$C_6$ alkoxy. In other embodiments, X is methylene optionally substituted with methyl or ethyl.

In certain embodiments, W—X—Y form:
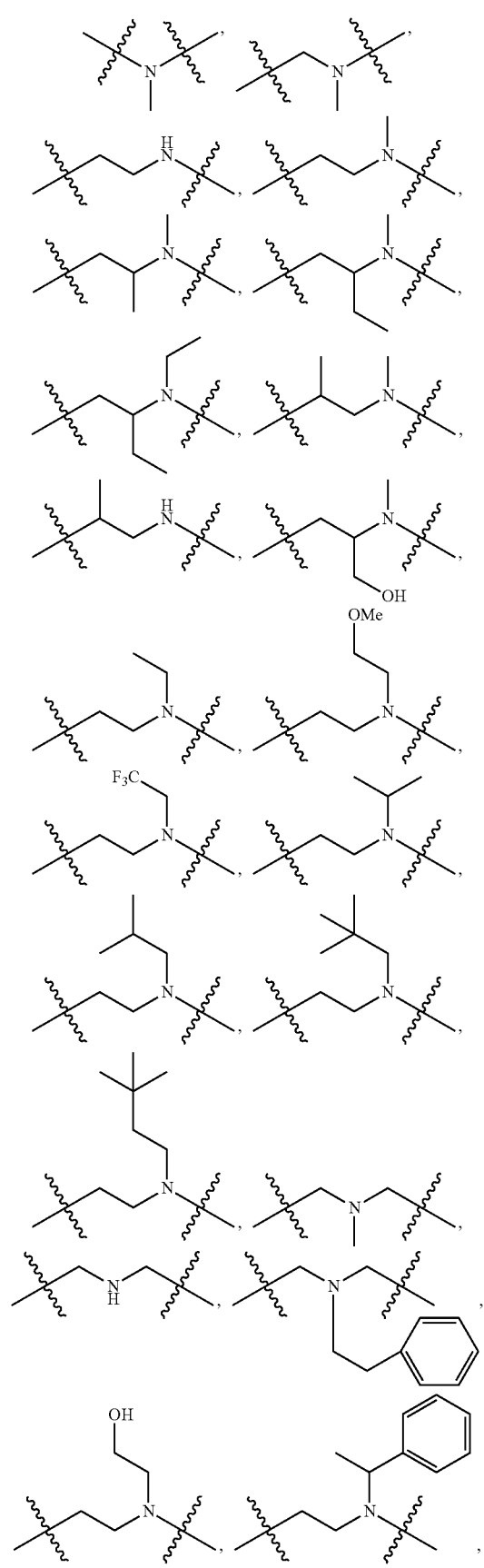
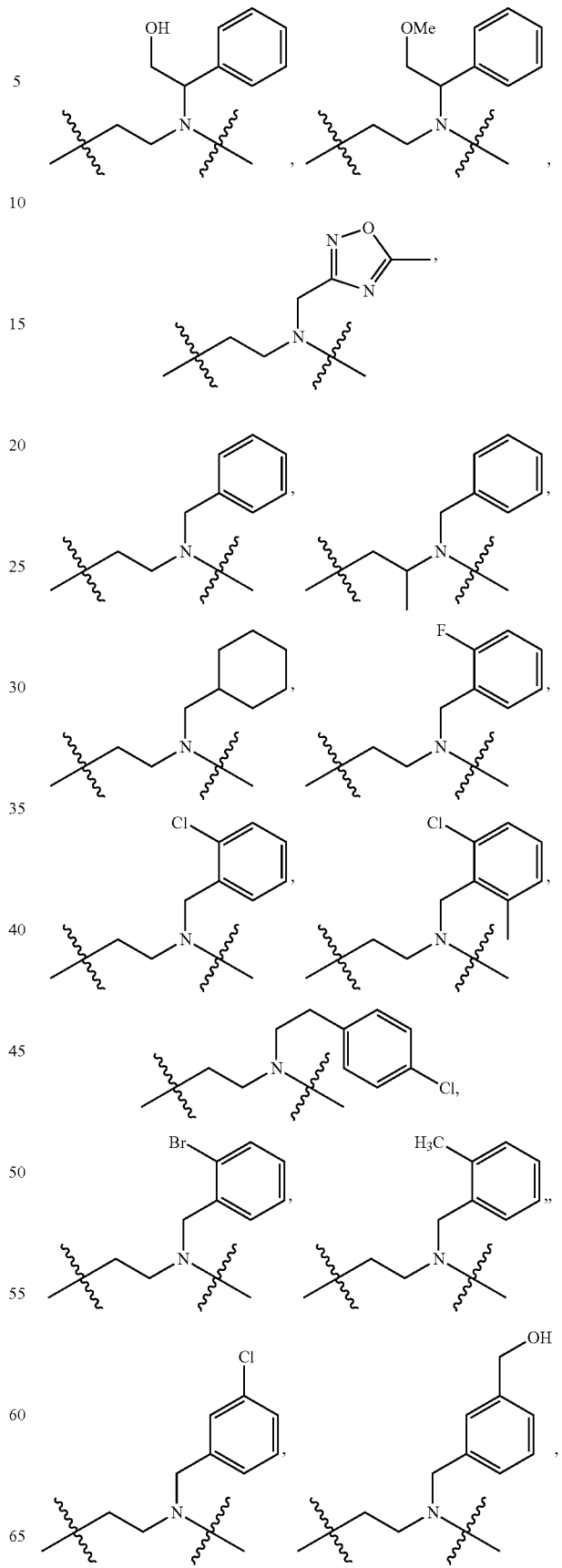
-continued

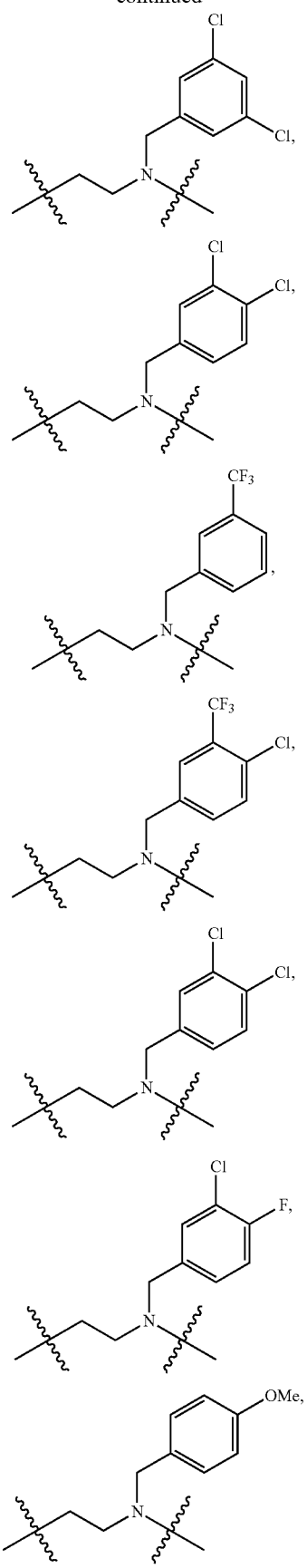
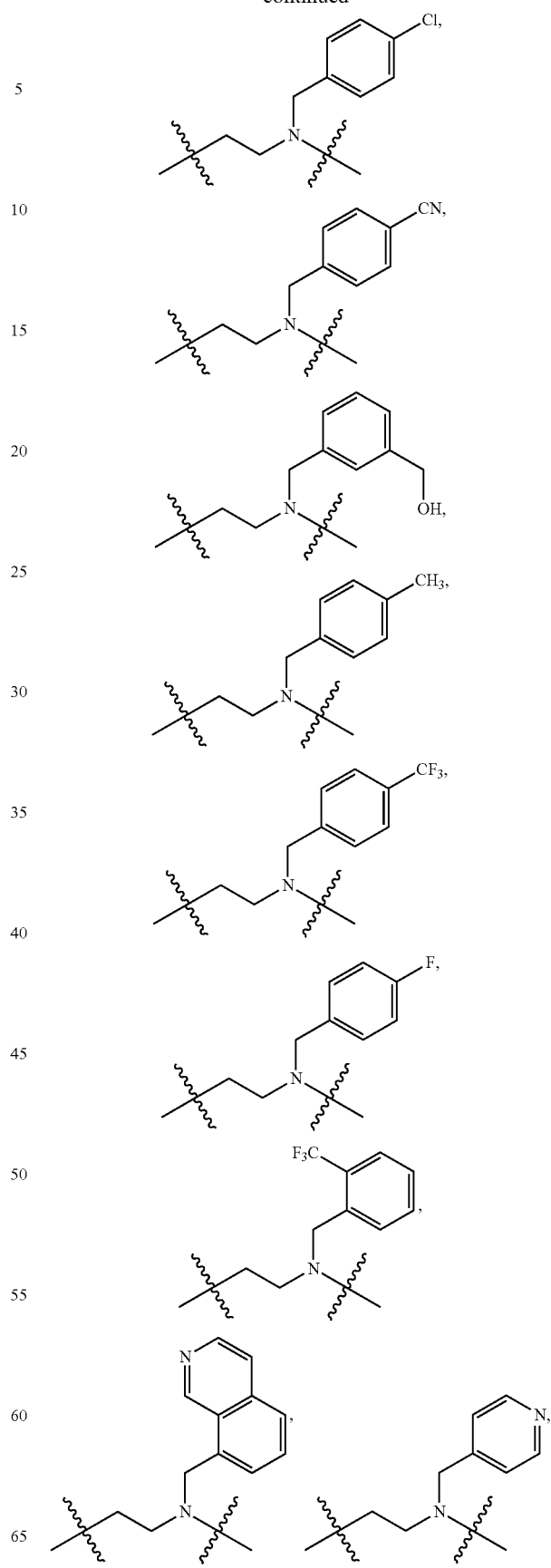

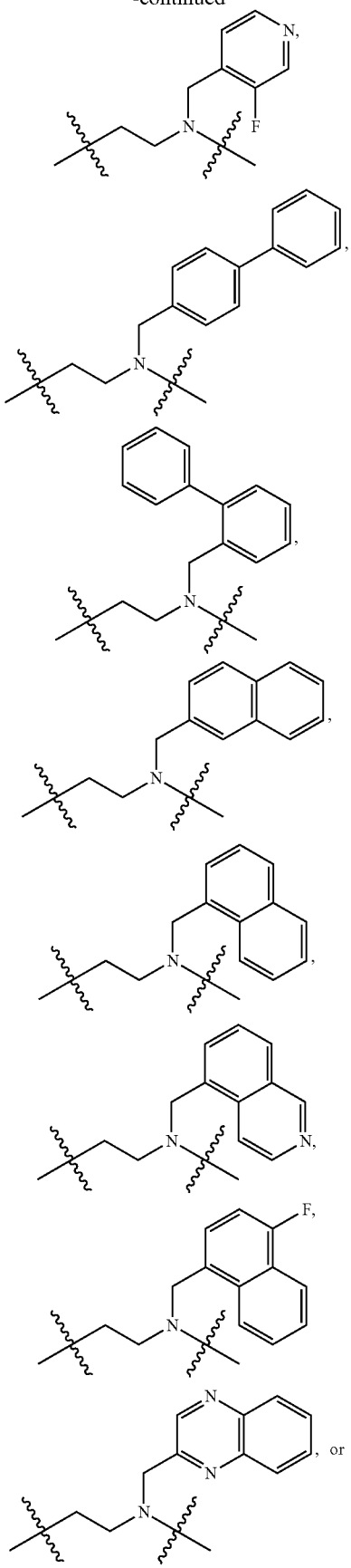
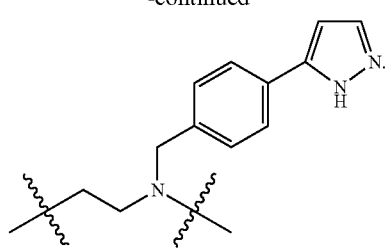
In certain embodiments, W—X—Y form:
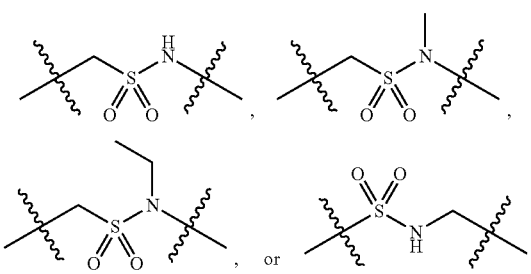
In certain embodiments, W—X—Y form:
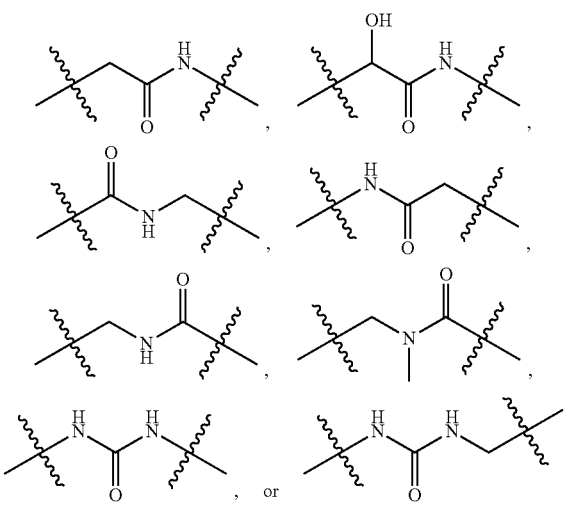
In certain embodiments, W—X—Y form:
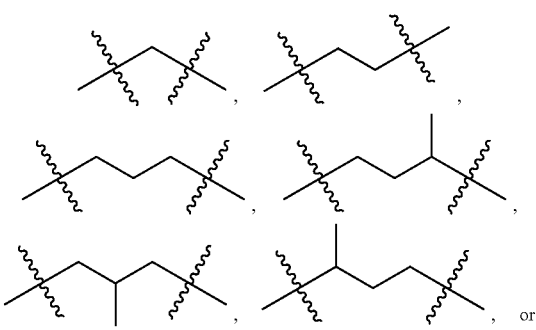

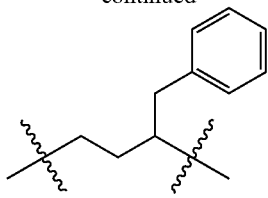

In certain embodiments, W—X—Y form:

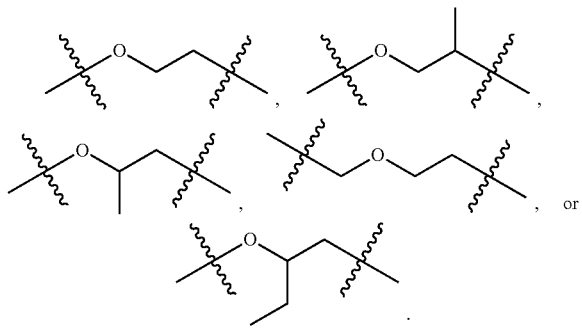

In certain embodiments, W—X—Y form:

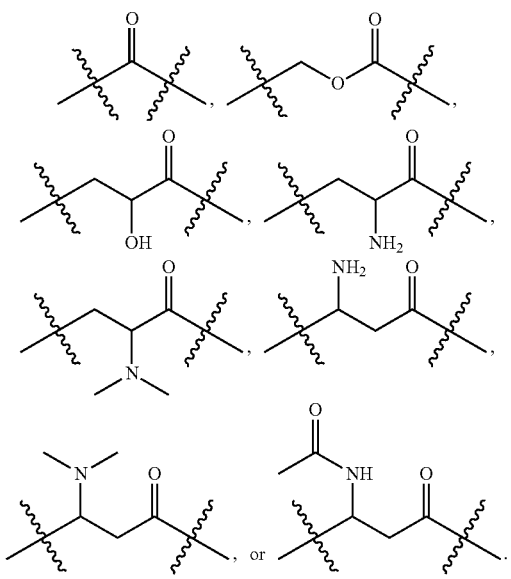

In certain embodiments, W—X—Y form:

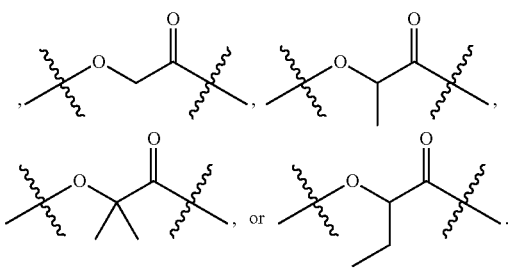

Therapeutics Applications

The invention provides methods of treating asthma and/or other allergic diseases, the method comprising administering to a subject in need of such treatment an effective amount of one or more compounds of the invention.

In another aspect, the invention provides a method of screening for agents for treating asthma in a mammal. Such method may comprise one or more of the following steps: (a) contacting an acidic mammalian chitinase protein with a compound of the invention and a substrate of the chitinase; (b) determining if the compound inhibits the activity of the chitinase; and (c) classifying the compound as an agent for treating asthma if the compound inhibits the activity of the chitinase.

In another aspect, the invention provides methods for monitoring the efficacy of a treatment for asthma. Such method may comprise one or more of the following steps: (a) administering a compound of the invention to a mammal, and (b) monitoring the expression of acidic mammalian chitinase in the mammal after administration of the compound, wherein a decrease in the expression of acidic mammalian chitinase indicates that the compound is useful in treating asthma, allergic diseases such as hay fever, allergic rhinitis, atopic dermatitis or other Th-2 mediated or associated diseases.

In another aspect, the invention provides methods for monitoring the efficacy of a treatment for asthma and/or other allergic diseases. Such methods may comprise one or more of the following steps: (a) administering a compound of the invention to a mammal, and (b) monitoring the expression of inflammatory mediators including, but not limited to IL-13, IL-5, IL-4, eotaxin, IgE or inflammatory cells such as eosinophils, neutrophils, or lymphocytes in broncho-alveolar washings, sputum or tissues obtained from the mammal after administration of the compound, wherein a decrease indicates that the compound is useful in treating asthma or allergic diseases such as hay fever, allergic rhinitis, atopic dermatitis or other Th-2 mediated or associated diseases.

The invention further provides methods of treating diseases caused by infectious agents, such as fungi, worms, and parasites, the method comprising administering to a subject in need of such treatment an effective amount of one or more compounds of the invention. The invention also provides methods of treating allergies, the method comprising administering to a subject in need of such treatment an effective amount of one or more compounds of the invention. Such allergies can be caused by a variety of antigens including biological sources such as dust mites and mold, cock roaches and other insects, dander from pets or other mammals, pollens, and other plant antigens, spores, mold, and other fungal sources, and chemicals such as isocyanates.

The salts, hydrates, and solvates of the compounds of the invention are preferably pharmaceutically acceptable salts, hydrates, and solvates.

Pharmaceutical Compositions

In another aspect, the present invention provides compositions comprising one or more of compounds as described elsewhere herein, and an appropriate carrier, excipient or diluent. The exact nature of the carrier, excipient or diluent will depend upon the desired use for the composition, and may range from being suitable or acceptable for veterinary uses to human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture/combination with other agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound (s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries, which facilitate processing of the compounds into preparations that can be used pharmaceutically.

The compounds may be formulated in the pharmaceutical composition per se, or in the form of a hydrate, solvate, N-oxide or pharmaceutically acceptable salt, as described elsewhere herein. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, and so forth, or a form suitable for administration by inhalation or insufflation.

For topical administration, the compound(s) may be formulated as solutions, gels, ointments, creams, suspensions, and so forth, as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, and so forth.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) that are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans are able to optimize effective local dosages without undue experimentation.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, and —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means an aromatic hydrocarbon ring system containing at least one aromatic ring, e.g., a phenyl (i.e., monocyclic aryl), or a bicyclic ring system containing at least one aromatic hydrocarbon ring, e.g., phenyl, or an aromatic bicyclic ring containing only carbon atoms in the aromatic portion of the ring system. Preferred aryl groups have from 6-14 ring members, and more preferably from 6-10 ring members. Examples of aryl groups include, for example, phenyl, naphthyl, anthracenyl, azulenyl, 1,2,3,4-tetrahydronaphthalenyl, indenyl, 2,3-dihydroindenyl, and biphenyl. In certain embodiments, the bicyclic aryl can be azulenyl, naphthyl, or a phenyl fused to a monocyclic cycloalkyl, a monocyclic cycloalkenyl, or a monocyclic heterocyclyl. In certain embodiments, the aryl groups are phenyl and naphthyl groups. In certain embodiments, the aryl groups are phenyl. The bicyclic aryl is attached to the parent molecular moiety through any carbon atom contained within the aromatic portion of the ring system, e.g., the phenyl portion of the bicyclic system, or any carbon atom within the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The aryl groups of the invention may be substituted with various groups as provided herein. Thus, any carbon atom present within an aryl ring system and available for substitution may be further covalently bonded to a variety of ring substituents, such as, for example, halogen, —OH, —NO$_2$, —CN, —NH$_2$, $C_1$-$C_8$ alkyl, $C_1$-$C_8$ alkoxy, —NH($C_1$-$C_8$ alkyl), N($C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$) alkyl, halo($C_1$-$C_8$)alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, and/or $C_1$-$C_8$ aminosulfonyl.

An "aralkyl" or "arylalkyl" group comprises an aryl group as defined herein covalently attached to an alkyl group, either of which independently is optionally substituted. Preferably, the aralkyl group is aryl($C_1$-$C_6$)alkyl, including, without limitation, benzyl, phenethyl, and naphthylmethyl. As used herein, the terms "aralkyl" and "arylalkyl" are interchangeable.

The terms "cyano" and "nitrile" as used herein, mean a —CN group.

The term "cycloalkyl" as used herein means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5- or 6-membered monocyclic cycloalkyl ring fused to either a phenyl ring, a 5- or 6-membered monocyclic cycloalkyl, a 5- or 6-membered monocyclic cycloalkenyl, a 5- or 6-membered monocyclic heterocyclyl, or a 5- or 6-membered monocyclic heteroaryl, wherein the fused bicyclic cycloalkyl is optionally substituted by one or two groups which are independently oxo or thia.

The cycloalkyl groups of the invention may be substituted with various groups as provided herein. Thus, any carbon atom present within a cycloalkyl ring system and available for substitution may be further bonded to a variety of ring substituents, such as, for example, halogen, —OH, —NO$_2$, —CN, —NH$_2$, $C_1$-$C_8$ alkyl, $C_1$-$C_8$ alkoxy, —NH($C_1$-$C_8$ alkyl), —N($C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$) alkyl, halo($C_1$-$C_8$)alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, and $C_1$-$C_8$ aminosulfonyl.

The term "halo" or "halogen" as used herein, means —Cl, —Br, —I and/or —F.

The terms "haloalkyl", "haloalkenyl" and "haloalkoxy" refer to an aliphatic, alkyl, alkenyl or alkoxy group, as the case may be, which is substituted with one or more halogen atoms.

The term "heteroaryl" as used herein means a monocyclic heteroaryl or a bicyclic ring system containing at least one heteroaromatic ring. Preferred heteroaryl groups have from 5-14 ring members wherein 1-4 ring members are hetero atoms selected from the group consisting of O, N, and S, the remaining ring atoms being C. In certain embodiments, heteroaryl groups have from 5-10 ring members wherein 1-4 ring members are hetero atoms selected from the group consisting of O, N, and S, the remaining ring atoms being C. Examples of aryl groups include, for example, phenyl, naphthyl, anthracenyl, azulenyl 1,2,3,4-tetrahydronaphthalenyl, indenyl, 2,3-dihydroindenyl, and biphenyl. In certain embodiments, heteroaryl groups are monocyclic heteroaryl groups having a 5- or 6-membered ring. The 5-membered ring consists of two double bonds and one, two, three or four nitrogen atoms and optionally one oxygen or sulfur atom. The 6-membered ring consists of three double bonds and one, two, three or four nitrogen atoms. The 5- or 6-membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5- or 6-membered monocyclic heteroaryl ring fused to either a phenyl ring, a 5- or 6-membered monocyclic cycloalkyl, a 5- or 6-membered monocyclic cycloalkenyl, a 5- or 6-membered monocyclic heterocyclyl, or a 5- or 6-membered monocyclic heteroaryl, wherein the fused cycloalkyl, cycloalkenyl, and heterocyclyl groups are optionally substituted with one or two groups which are independently oxo or thia.

The heteroaryl groups of the invention may be substituted with various groups as provided herein. Thus, any carbon atom present within an heteroaryl ring system and available for substitution may be further bonded to a variety of ring substituents, such as, for example, halogen, —OH, —NO$_2$, —CN, —NH$_2$, C$_1$-C$_8$ alkyl, C$_1$-C$_8$ alkoxy, —NH(C$_1$-C$_8$ alkyl), —N(C$_1$-C$_8$ alkyl)(C$_1$-C$_8$ alkyl), C$_3$-C$_{10}$ cycloalkyl, (C$_3$-C$_{10}$ cycloalkyl)alkyl, (C$_3$-C$_{10}$ cycloalkyl)alkoxy, C$_2$-C$_9$ heterocycloalkyl, C$_1$-C$_8$ alkenyl, C$_1$-C$_8$ alkynyl, halo(C$_1$-C$_8$) alkyl, halo(C$_1$-C$_8$)alkoxy, oxo, amino(C$_1$-C$_8$)alkyl, mono- and di(C$_1$-C$_8$ alkyl)amino(C$_1$-C$_8$)alkyl, C$_1$-C$_8$ acyl, C$_1$-C$_8$ acyloxy, C$_1$-C$_8$ sulfonyl, C$_1$-C$_8$ thio, C$_1$-C$_8$ sulfonamido, and C$_1$-C$_8$ aminosulfonyl.

The terms "heterocyclyl" and "heterocycloalkyl" as used herein are interchangeable and mean a monocyclic heterocycle or a bicyclic heterocycle. Heterocycloalkyl aryl groups of the invention have 3-14 ring members wherein 1-4 of the ring members are hetero atoms selected from the group consisting of O, N, and S, the remaining ring atoms being C. In certain embodiments, heterocycloalkyl groups have 5-10 ring members wherein 1-4 ring members are heteroatoms selected from the group consisting of O, N, and S, the remaining ring atoms being C. Thus, the monocyclic heterocycle is a 3-, 4-, 5-, 6- or 7-membered ring containing at least one heteroatom independently selected from the group consisting of O, N, and S where the ring is saturated or unsaturated, but not aromatic. The 3- or 4-membered ring contains 1 heteroatom selected from the group consisting of O, N and S. The 5-membered ring can contain zero or one double bond and one, two or three heteroatoms selected from the group consisting of O, N and S. The 6- or 7-membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5- or 6-membered monocyclic heterocyclyl ring fused to phenyl ring, a 5- or 6-membered monocyclic cycloalkyl, a 5- or 6-membered monocyclic cycloalkenyl, a 5- or 6-membered monocyclic heterocyclyl, or a 5- or 6-membered monocyclic heteroaryl, wherein the bicyclic heterocyclyl is optionally substituted by one or two groups which are independently oxo or thia.

The heterocycloalkyl groups of the invention may be substituted with various groups as provided herein. Thus, any carbon atom present within an heterocycloalkyl ring system and available for substitution may be further bonded to a variety of ring substituents, such as, for example, halogen, —OH, —NO$_2$, —CN, —NH$_2$, C$_1$-C$_8$ alkyl, C$_1$-C$_8$ alkoxy, —NH(C$_1$-C$_8$ alkyl), —N(C$_1$-C$_8$ alkyl)(C$_1$-C$_8$ alkyl), C$_3$-C$_{10}$ cycloalkyl, (C$_3$-C$_{10}$ cycloalkyl)alkyl, (C$_3$-C$_{10}$ cycloalkyl)alkoxy, C$_2$-C$_9$ heterocycloalkyl, C$_1$-C$_8$ alkenyl, C$_1$-C$_8$ alkynyl, halo(C$_1$-C$_8$)alkyl, halo(C$_1$-C$_8$)alkoxy, oxo, amino(C$_1$-C$_8$)alkyl, mono- and di(C$_1$-C$_8$ alkyl)amino(C$_1$-C$_8$)alkyl, C$_1$-C$_8$ acyl, C$_1$-C$_8$ acyloxy, C$_1$-C$_8$ sulfonyl, C$_1$-C$_8$ thio, C$_1$-C$_8$ sulfonamido, and C$_1$-C$_8$ aminosulfonyl.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclyl group.

The term "nitro" as used herein means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted" as used herein means that a hydrogen radical of the designated moiety is replaced with the radical of a specified substituent, provided that the substitution results in a stable or chemically feasible compound. The term "substitutable" when used in reference to a designated atom means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Both the R and the S stereochemical isomers, as well as all mixtures thereof, are included within the scope of the invention.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder, such as but not limited to asthma.

"Treating" or "treatment" as used herein covers the treatment of a disease or disorder described herein, in a subject, preferably a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, ameliorating, or slowing progression of one or more symptoms of the disease or disorder.

"Subject" refers to a warm blooded animal such as a mammal, such as a human, or a human child, which is afflicted with, or has the potential to be afflicted with one or more diseases and disorders described herein.

"EC$_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Methods of Preparation

The compounds of the invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present invention, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those skilled in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Representative synthetic procedures for the preparation of compounds of the invention are outlined below. Substituents carry the same meaning as defined above, unless otherwise noted.

Scheme 1:

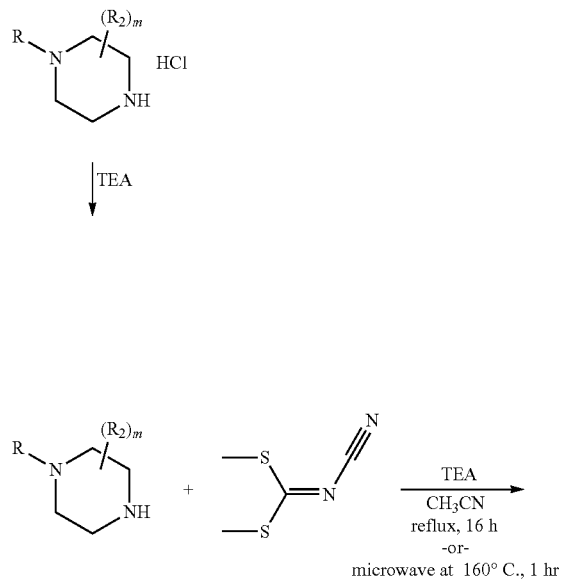

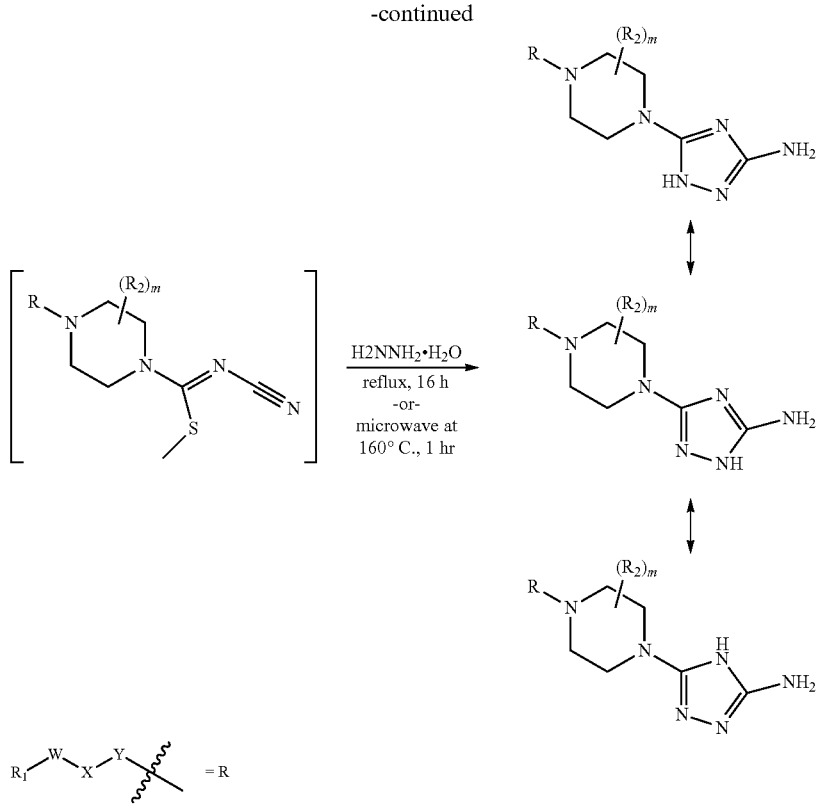

Scheme 1 illustrates the preparation of aminotriazolopiperazine. Reaction yields three possible tautomers, which are interchangeable. For convenience, only one triazole tautomer is depicted throughout the specification. In one method (method A), the substituted piperazine and dimethyl cyanocarbonimidodithioate are combined in anhydrous acetonitrile and refluxed overnight. After formation of the intermediate, hydrazine hydrate monohydrate is added to the reaction mixture, and reflux is continued until the reaction is complete. In another method (method B), the above reactions are carried out by microwave irradiation at 160° C. for 1 hour for each step.

Scheme 2:

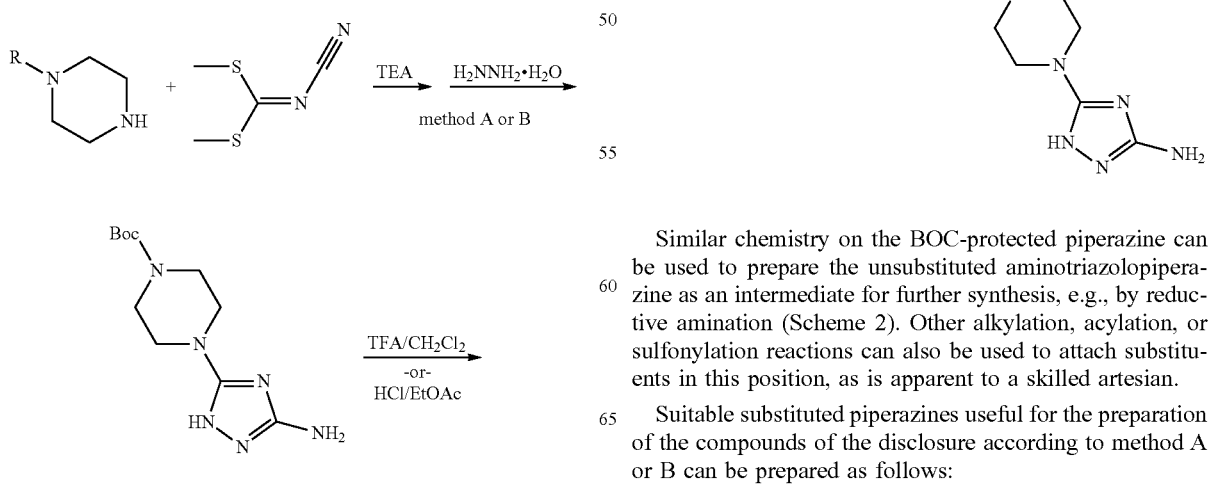

Similar chemistry on the BOC-protected piperazine can be used to prepare the unsubstituted aminotriazolopiperazine as an intermediate for further synthesis, e.g., by reductive amination (Scheme 2). Other alkylation, acylation, or sulfonylation reactions can also be used to attach substituents in this position, as is apparent to a skilled artesian.

Suitable substituted piperazines useful for the preparation of the compounds of the disclosure according to method A or B can be prepared as follows:

Scheme 3:

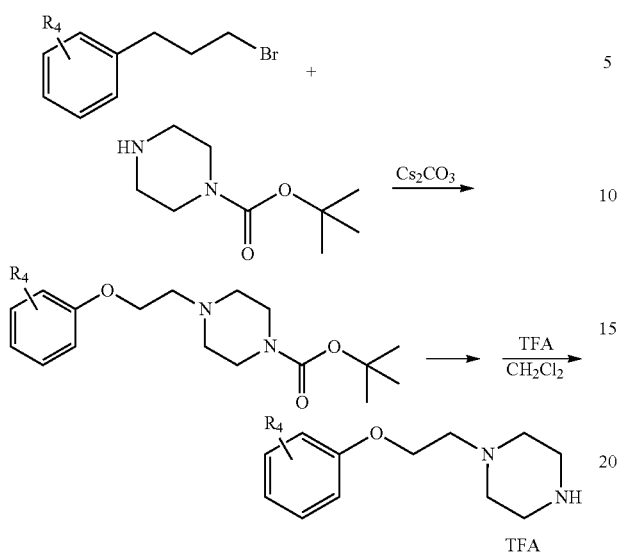

Alkyl bromide and cesium carbonate are added to protected piperazine in dimethylformamide, and the system is stirred at room temperature until reaction is complete. The protecting group is removed by stirring at room temperature in TFA/CH$_2$Cl$_2$ to give a substituted piperazine.

Scheme 3:

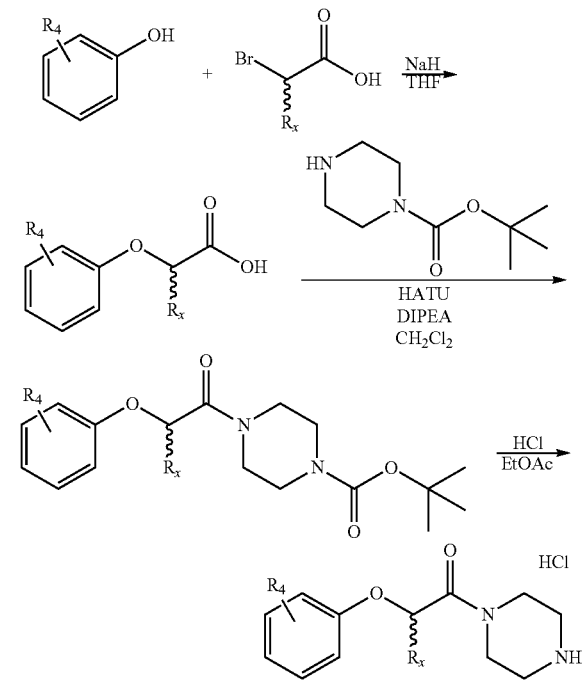

A solution of a phenol in dry THF is treated with sodium hydride, followed by a solution of an α-bromo carboxylic acid (R$_x$ is hydrogen or the optional substituents on X-variable above). The resulting α-aryloxycarboxylic acid is treated with protected piperazine, HATU, and DIPEA in dichloromethane. The protecting group is removed to yield a substituted piperazine.

Suitable substituted piperidines useful for the preparation of the compounds of the disclosure according to method A or B can be prepared as follows:

Scheme 5:

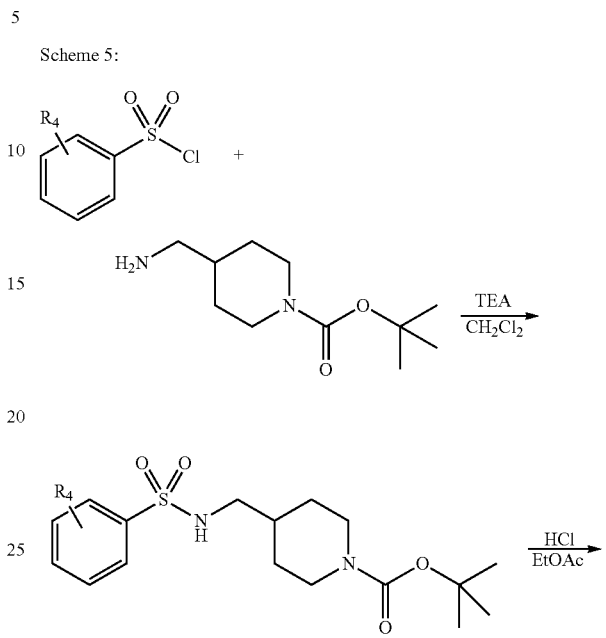

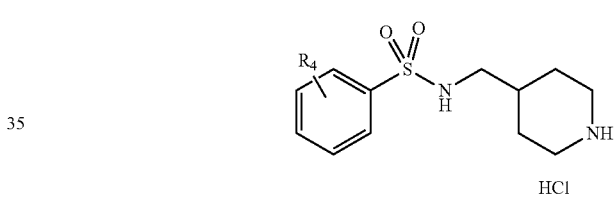

Protected piperidine is treated with substituted benzenesulfonylchloride, triethylamine and a solvent. The protecting group is removed to give a substituted piperidine.

EXAMPLES

The preparation of the compounds of the invention is illustrated further by the following examples, which are not to be construed as limiting the invention in scope or spirit to the specific procedures and compounds described in them. In all cases, unless otherwise specified, the column chromatography is performed using a silica gel solid phase.

Example 1: 5-(4-(2-(4-fluorophenoxy)ethyl)piperazin-1-yl)-1H-1,2,4-triazol-3-amine

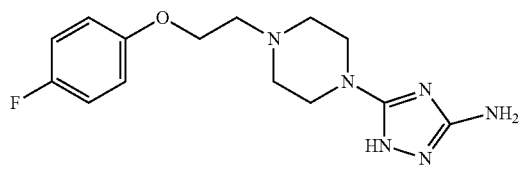 [SMILES: Nc1n[nH]c(N2CCN(CCOc3ccc(F)cc3)CC2)n1]

Step 1: methyl N-cyano-4-(2-(4-fluorophenoxy)ethyl)piperazine-1-carbimidothioate

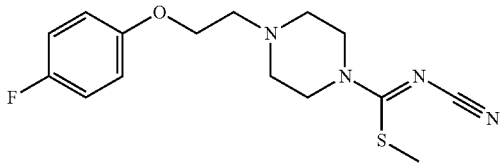 [SMILES: CS/C(=N\C#N)N1CCN(CCOc2ccc(F)cc2)CC1]

To a 100 mL single neck RBF equipped with nitrogen inlet tube, reflux condenser, and bleach trap was added 1-[2-(4-fluorophenoxy)ethyl]piperazine (0.0553 g, 0.2466 mmol), dimethyl cyanocarbonimidodithioate (0.0361 g, 0.2466 mmol), and anhydrous acetonitrile (20 mL). Reaction solution was refluxed overnight under nitrogen. TLC and MS confirmed presence of the desired intermediate. The reaction solution was carried forward without purification. ESI-LCMS m/z calculated for $C_{15}H_{19}FN_4OS$: expected 322.4; found 323.2 [M+H]$^+$.

Step 2: 5-(4-(2-(4-fluorophenoxy)ethyl)piperazin-1-yl)-1H-1,2,4-triazol-3-amine To the reaction solution from step 1 was added hydrazine hydrate monohydrate (0.1929 g, 2.466 mmol, 187 μL). The reaction was refluxed for 16 hours. The solvent was removed, and the residue was purified by reverse-phase HPLC to give the desired product as a white solid (0.020 g, 26.5% yield). $^1$H NMR (CD$_3$OD, 300 MHz) δ (ppm) 7.09-6.99 (m, 4H), 5.48 (s, 2H), 4.38 (t, J=5.0 Hz, 2H), 3.67 (t, J=5.0 Hz, 6H), 3.35 (s, 2H); ESI-LCMS m/z calculated for $C_{14}H_{19}FN_6O$: expected 306.4; found 307.2 [M+H]$^+$.

Example 2: 5-(4-(2-(4-chlorophenoxy)ethyl)piperazin-1-yl)-1H-1,2,4-triazol-3-amine

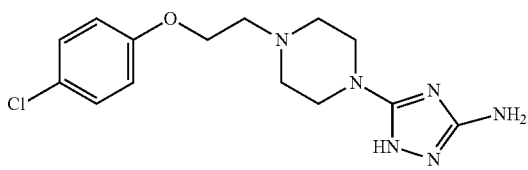 [SMILES: Nc1n[nH]c(N2CCN(CCOc3ccc(Cl)cc3)CC2)n1]

Step 1: methyl 4-(2-(4-chlorophenoxy)ethyl)-N-cyanopiperazine-1-carbimidothioate

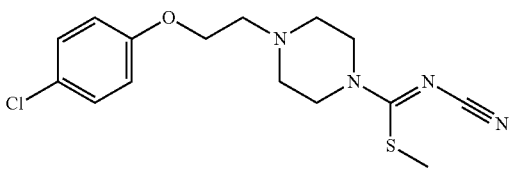 [SMILES: CS/C(=N\C#N)N1CCN(CCOc2ccc(Cl)cc2)CC1]

Preparation in a manner similar to Example 1 (step 1) from 1-[2-(4-chlorophenoxy)-ethyl] piperazine. ESI-LCMS m/z calculated for $C_{15}H_{19}ClN_4OS$: expected 338.9; found 339.2 [M+H]$^+$.

Step 2: 5-(4-(2-(4-chlorophenoxy)ethyl)piperazin-1-yl)-1H-1,2,4-triazol-3-amine Preparation and purification in a manner similar to Example 1 (step 2) from methyl 4-(2-(4-chlorophenoxy)ethyl)-N-cyanopiperazine-1-carbimidothioate gave the desired product as a white solid. (0.100 g, 62% yield). $^1$H NMR (CD$_3$OD, 300 MHz) δ (ppm) 7.09-6.99 (m, 4H), 5.48 (s, 2H), 4.38 (t, J=5.0 Hz, 2H), 3.67 (t, J=5.0 Hz, 6H), 3.35 (s, 2H); ESI-LCMS m/z calculated for $C_{14}H_{19}ClN_6O$: expected 322.8; found 323.2 [M+H]$^+$.

Example 3: 5-(4-(4-ethoxybenzyl)piperazin-1-yl)-1H-1,2,4-triazol-3-amine

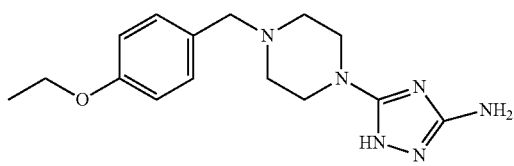 [SMILES: CCOc1ccc(CN2CCN(c3nc(N)n[nH]3)CC2)cc1]

Step 1: methyl N-cyano-4-(4-ethoxybenzyl)piperazine-1-carbimidothioate

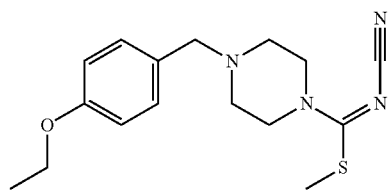 [SMILES: CCOc1ccc(CN2CCN(/C(=N\C#N)SC)CC2)cc1]

Prepared in a manner similar to Example 1 (step 1) from 1-[(4-ethoxyphenyl)methyl]-piperazine. ESI-LCMS m/z calculated for $C_{16}H_{22}N_4OS$: expected 318.4; found 319.2 [M+H]$^+$.

Step 2: 5-(4-(4-ethoxyphenyl)methyl)piperazin-1-yl)-1H-1,2,4-triazol-3-amine Preparation and purification in a manner similar to Example 1 (step 2) from methyl N-cyano-4-(4-ethoxybenzyl)piperazine-1-carbimidothioate gave the desired product as a white solid. (0.108 g, 72% yield). $^1$H NMR (CD$_3$OD, 400 MHz) δ (ppm) 7.26 (dd, J=8.4, J=5.2, 2H), 7.00 (dd, J=8.4, J=5.2, 2H), 4.02 (2H, q, J=7.003), 3.70-3.61 (m, 6H), 2.62-2.56 (bs, 4H), 1.24 (t, J=7.003, 3H); ESI-LCMS m/z calculated for $C_{15}H_{22}N_6O$: expected 302.4; found 303.2 [M+H]$^+$.

Example 4: 1-[4-(3-amino-1H-1,2,4-triazol-5-yl)piperazin-1-yl]-2-(4-bromophenoxy)-ethan-1-one

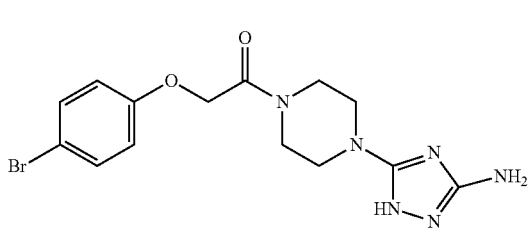 [SMILES: Nc1n[nH]c(N2CCN(C(=O)COc3ccc(Br)cc3)CC2)n1]

Step 1: methyl 4-(2-(4-bromophenoxy)acetyl)-N-cyanopiperazine-1-carbimidothioate

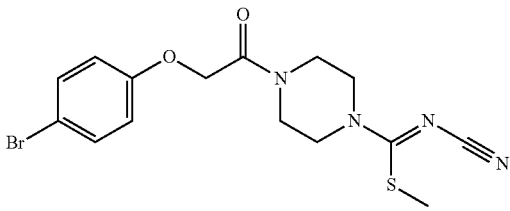

Prepared in a manner similar to Example 1 (step 1) from 2-(4-bromophenoxy)-1-(1-piperazinyl) ethanone. ESI-LCMS m/z calculated for $C_{15}H_{17}BrN_4O_2S$: expected 397.3; found 398.2 $[M+H]^+$.

Step 2: 1-[4-(3-amino-1H-1,2,4-triazol-5-yl)piperazin-1-yl]-2-(4-bromophenoxy)-ethan-1-one Preparation and purification in a manner similar to Example 1 (step 2) from methyl 4-(2-(4-bromophenoxy)acetyl)-N-cyanopiperazine-1-carbimidothioate gave the desired product as a white solid. (0.102 g, 54% yield). $^1$H NMR (CD$_3$OD, 400 MHz) δ (ppm) 7.12 (dd, J=8.5, J=5.5, 2H), 6.893 (dd, J=8.5, J=5.5, 2H), 4.18 (s, 2H), 3.59 (m, 4H), 3.46 (dd, J=12.0, J=3.2, 2H), 3.06 (dd, J=12.0, J=3.2, 2H); ESI-LCMS m/z calculated for $C_{14}H_{17}BrN_6O_2$: expected 381.2; found 382.2 $[M+H]^+$.

Example 5: 1-[4-(3-amino-1H-1,2,4-triazol-5-yl)piperazin-1-yl]-2-(4-bromophenoxy)butan-1-one

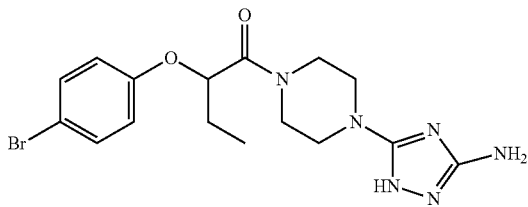 [SMILES: CCC(Oc1ccc(Br)cc1)C(=O)N1CCN(c2nc(N)n[nH]2)CC1]

Step 1: 2-(4-bromophenoxy)butanoic Acid

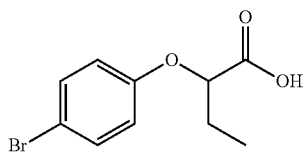

Sodium hydride (3 eq, 60% in mineral oil) was added to a three-neck flask with dry THF (1 ml/mmol) under argon. A solution of 4-bromophenol in dry THF (0.1 ml/mmol) was added dropwise (generation of hydrogen, and exothermic effect of formation of the sodium salt of phenol, were observed). When addition of phenol was finished the reaction mixture was stirred at ambient temperature for 15 minutes. After that time, a solution of 2-bromobutyric acid (1.2 eq.) in dry THF (0.1 ml/mmol) was added dropwise under argon (generation of hydrogen and exothermic effect of formation of the sodium salt of acid were observed). When addition of acid was finished the reaction mixture was stirred at ambient temperature for 30 minutes. TLC showed no starting phenol. The reaction mixture was carefully quenched with methanol, solvents were removed under reduced pressure, the residue was dissolved in 1M NaOH and washed with ether (removing mineral oil). The basic aqueous layer was acidified to pH=2 by 6M HCl and product was extracted with ether (3 times). Combined organic extracts were washed with brine and dried over anhydrous MgSO4. The drying agent was filtered off, solvent was removed under reduced pressure to give product as off-white solid. The product was recrystallized from Et$_2$O/hexane to give title compound as white solid (88% yield), ESI MS for $C_{10}H_{11}BrO_3$; expected 259.1; found m/z 258.3/260.3 in ratio ~1/1 (isotopes of Br) $[M-H]^-$. $^1$H NMR (DMSO-d$_6$, 600 MHz): δ (ppm) 13.02 (bs, 1H), 7.40 (d, J=8.8 Hz, 2H), 6.81 (d, J=8.8 Hz, 2H), 4.63 (q, J=4.9 Hz, J=7.0 Hz, 1H), 1.90-1.78 (m, 2H), 0.95 (t, J=7.4 Hz, 3H).

Step 2: tert-butyl 4-(2-(4-bromophenoxy)butanoyl)piperazine-1-carboxylate

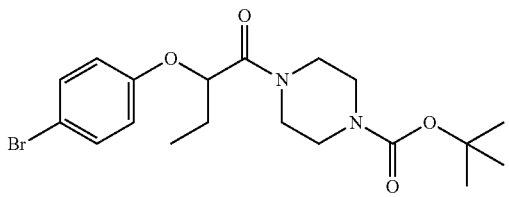

2-(4-bromophenoxy)butanoic acid (1 eq) was dissolved in dichloromethane (2 mL/mmol) and diisopropylethylamine (1.1 eq) was added at ambient temperature followed by addition of BOC-piperazine (1.1 eq). When the solution was clear, coupling reagent O-(7-azabenzotriazol-1-yl)-N,N,N',N'-tetramethyluronium hexafluorophosphate (HATU) (1 eq) was added. The reaction mixture was stirred at ambient temperature overnight, diluted with dichloromethane and washed with 1M NaOH, 2M HCl, brine and dried over MgSO$_4$. The solvent was evaporated and product was crystallized from ethyl acetate/hexane solvent system to give the title compound as an off-white solids (93% yield), ESI MS for $C_{19}H_{27}BrN_2O_4$; expected 427.34; found m/z 427.3/429.3 in ratio ~1/1 (isotopes of Br) $[M+H]^+$. $^1$H NMR (DMSO-d$_6$, 600 MHz): δ (ppm) 7.39 (d, J=9.0 Hz, 2H), 6.77 (d, J=9.0 Hz, 2H), 5.03-4.98 (m, 1H), 3.62-3.57 (m, 1H), 3.52-3.41 (m, 1H), 3.36-3.18 (m, 6H), 1.82-1.70 (m, 2H), 1.37 (s, 9H), 0.94 (t, J=7.3 Hz, 3H).

Step 3: 2-(4-bromophenoxy)-1-(piperazin-1-yl)butan-1-one

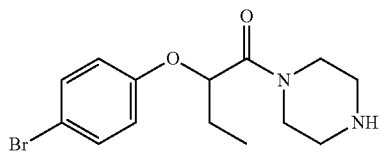 [SMILES: CCC(Oc1ccc(Br)cc1)C(=O)N1CCNCC1]

tert-Butyl 4-(2-(4-bromophenoxy)butanoyl)piperazine-1-carboxylate was dissolved in ethyl acetate and treated with hydrogen chloride (4M solution in ethyl acetate). The reaction mixture was stirred at ambient temperature and followed by TLC (chloroform/methanol 9:1). When substrate was no longer detected, the precipitate was filtered off and washed with ether to give the title compound as the hydrochloride salt (white solid). The hydrochloride salt was dissolved in 1M NaOH, and the free amine was extracted into dichloromethane, washed with brine, and dried over anhydrous MgSO$_4$. The solvent was removed under reduced pressure to give the title compound as a colorless oil (91% yield), ESI MS for C$_{14}$H$_{19}$BrN$_2$O$_2$; expected 327.22; found m/z 327.3/329.3 in ratio ~1/1 (isotopes of Br) [M+H]$^+$. $^1$H NMR (DMSO-d$_6$, 600 MHz): δ (ppm) 9.46 (bs, 1H), 7.43 (d, J=9.0 Hz, 2H), 6.83 (d, J=9.0 Hz, 2H), 5.08-5.05 (m, 1H), 3.93-3.86 (m, 1H), 3.79-3.69 (m, 2H), 3.64-3.57 (m, 1H), 3.17-3.09 (m, 1H), 3.07-2.99 (m, 3H), 1.86-1.72 (m, 2H), 0.97 (t, J=7.3 Hz, 3H).

Step 4: methyl 4-(2-(4-bromophenoxy)butanoyl)-N-cyanopiperazine-1-carbimidothioate

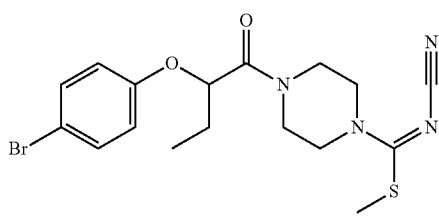 [SMILES: CCC(Oc1ccc(Br)cc1)C(=O)N1CCN(/C(=N\C#N)SC)CC1]

Prepared in a manner similar to Example 1 (step 1) from 2-(4-bromophenoxy)-1-(piperazin-1-yl)butan-1-one. Reaction mixture was carried on without further characterization.

Step 5: 1-[4-(3-amino-1H-1,2,4-triazol-5-yl)piperazin-1-yl]-2-(4-bromophenoxy)butan-1-one Preparation and purification in a manner similar to Example 1 (step 2) from methyl 4-(2-(4-bromophenoxy)butanoyl)-N-cyanopiperazine-1-carbimidothioate gave the desired product as a white solid, (69% yield), ESI MS for C$_{16}$H$_{21}$BrN$_6$O$_2$; expected 409.29; found m/z 409.4/411.4 in ratio ~1/1 (isotopes of Br) [M+H]$^+$. $^1$H NMR (DMSO-d$_6$, 600 MHz): δ (ppm) 10.99 (bs, 1H); 7.39 (d, J=9.0 Hz, 2H), 6.77 (d, J=9.0 Hz, 2H), 5.76 (bs, 2H); 5.05-5.01 (m, 1H), 3.71-3.63 (m, 1H), 3.61-3.55 (m, 1H), 3.55-3.48 (m, 1H), 3.45-3.38 (m, 1H), 3.19-3.02 (m, 4H), 1.83-1.71 (m, 2H), 0.95 (t, J=7.3 Hz, 3H).

Example 6: (R)-1-(4-(3-amino-1H-1,2,4-triazol-5-yl)piperazin-1-yl)-2-(4-bromophenoxy)propan-1-one

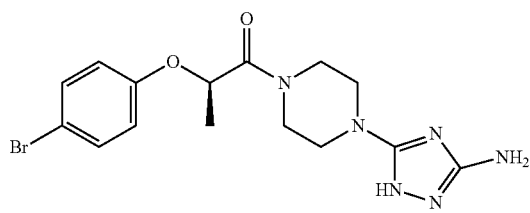 [SMILES: C[C@@H](Oc1ccc(Br)cc1)C(=O)N1CCN(c2nc(N)n[nH]2)CC1]

Step 1: (R)-2-(4-bromophenoxy)propanoic Acid

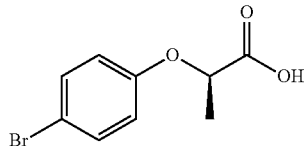

Prepared in a manner similar to Example 5 (step 1) from 4-bromophenol and (R)-2-bromopropionic acid (77% yield). ESI MS for C$_9$H$_9$BrO$_3$; expected 245.07; found m/z 244.0/246.0 in ratio ~1/1 (isotopes of Br) [M–H]$^-$. $^1$H NMR (DMSO-d$_6$, 600 MHz): δ (ppm) 13.08 (bs, 1H), 7.46 (d, J=9.0 Hz, 2H), 6.87 (d, J=9.0 Hz, 2H), 4.86 (q, J=6.8 Hz, J=13.5 Hz, 1H), 1.52 (t, J=6.8 Hz, 3H).

Step 2: (R)-tert-butyl 4-(2-(4-bromophenoxy)propanoyl)piperazine-1-carboxylate

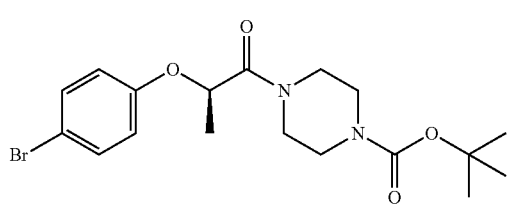

Prepared in a manner similar to Example 5 (step 2) from (R)-2-(4-bromophenoxy)-propanoic acid (86% yield), ESI MS for C$_{18}$H$_{25}$BrN$_2$O$_4$; expected 413.31; found m/z 413.3/415.3 in ratio ~1/1 (isotopes of Br) [M+H]$^+$. $^1$H NMR (DMSO-d$_6$, 600 MHz): δ (ppm) 7.39 (d, J=9.0 Hz, 2H), 6.79 (d, J=9.0 Hz, 2H), 5.22 (q, J=6.4 Hz, J=13.0 Hz, 1H), 3.58-3.53 (m, 1H), 3.48-3.43 (m, 2H), 3.35-3.19 (m, 5H), 1.38 (d, J=6.8 Hz, 3H), 1.37 (s, 9H).

Step 3: (R)-2-(4-bromophenoxy)-1-(piperazin-1-yl)-propan-1-one

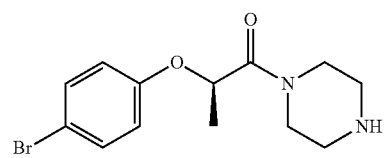

Prepared in a manner similar to Example 5 (step 3) from (R)-tert-butyl 4-(2-(4-bromophenoxy)propanoyl)piperazine-1-carboxylate (88% yield), ESI MS for C$_{13}$H$_{17}$BrN$_2$O$_2$; expected 313.20; found m/z 313.3/315.3 in ratio ~1/1 (isotopes of Br) [M+H]$^+$. $^1$H NMR (DMSO-d$_6$, 600 MHz): δ (ppm) 9.60 (bs, 1H), 7.43 (d, J=9.0 Hz, 2H), 6.83 (d, J=9.0 Hz, 2H), 5.28 (q, J=6.6 Hz, J=13.2 Hz, 1H), 3.89-3.82 (m, 1H), 3.76-3.68 (m, 2H), 3.67-3.60 (m, 1H), 3.16-3.09 (m, 1H), 3.08-3.02 (m, 3H), 1.41 (d, J=6.4 Hz, 3H).

Step 4: methyl (R)-4-(2-(4-bromophenoxy)pro-
panoyl)-N-cyanopiperazine-1-carbimidothioate

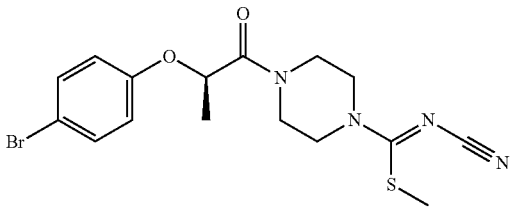

Prepared in a manner similar to Example 1 (step 1) from (R)-2-(4-bromophenoxy)-1-(piperazin-1-yl)propan-1-one. Reaction mixture was carried on without further characterization.

Step 5: (R)-1-(4-(3-amino-1H-1,2,4-triazol-5-yl)
piperazin-1-yl)-2-(4-bromophenoxy)-propan-1-one Preparation and purification in a manner similar to Example 1 (step 2) from methyl (R)-4-(2-(4-bromophenoxy) propanoyl)-N-cyanopiperazine-1-carbimidothioate gave the desired product as a white solid (75% yield), ESI MS for $C_{15}H_{19}BrN_6O_2$; expected 395.26; found m/z 395.3/397.3 in ratio ~1/1 (isotopes of Br) [M+H]$^+$. $^1$H NMR (DMSO-d$_6$, 600 MHz): δ (ppm) 11.00 (bs, 1H); 7.40 (d, J=9.0 Hz, 2H), 6.78 (d, J=9.0 Hz, 2H), 5.76 (bs, 2H); 5.24 (q, J=6.4 Hz, J=13.1 Hz, 1H), 3.66-3.60 (m, 1H), 3.58-3.48 (m, 2H), 3.43-3.37 (m, 1H), 3.21-3.03 (m, 4H), 1.39 (d, J=6.6 Hz, 3H).

Example 7: (S)-1-(4-(3-amino-1H-1,2,4-triazol-5-yl)
piperazin-1-yl)-2-(4-bromophenoxy)-propan-1-one

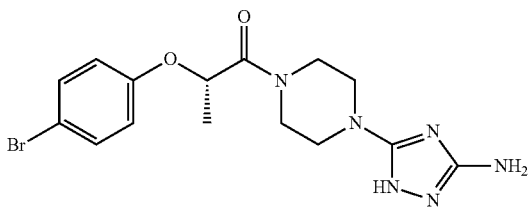 [SMILES: C[C@H](Oc1ccc(Br)cc1)C(=O)N1CCN(c2nc(N)n[nH]2)CC1]

Step 1: (S)-2-(4-bromophenoxy)-propanoic Acid

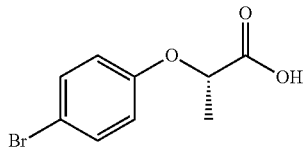

Prepared in a manner similar to Example 5 (step 1) from 4-bromophenol and (S)-2-bromopropionic acid (88% yield), ESI MS for $C_9H_9BrO_3$; expected 245.07; found m/z 244.0/246.0 in ratio ~1/1 (isotopes of Br) [M−H]$^-$. $^1$H NMR (DMSO-d$_6$, 600 MHz): δ (ppm) 13.06 (bs, 1H), 7.46 (d, J=9.0 Hz, 2H), 6.87 (d, J=9.0 Hz, 2H), 4.86 (q, J=6.8 Hz, J=13.5 Hz, 1H), 1.52 (t, J=6.8 Hz, 3H).

Step 2: (S)-tert-butyl 4-(2-(4-bromophenoxy)pro-
panoyl)-piperazine-1-carboxylate

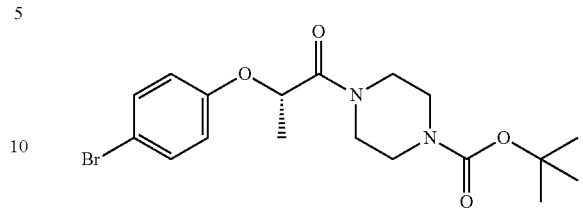

Prepared in a manner similar to Example 5 (step 2) from (S)-2-(4-bromophenoxy) propanoic acid (81% yield), ESI MS for $C_{18}H_{25}BrN_2O_4$; expected 413.31; found m/z 413.3/415.3 in ratio ~1/1 (isotopes of Br) [M+H]$^+$. $^1$H NMR (DMSO-d$_6$, 600 MHz): δ (ppm) 7.39 (d, J=9.0 Hz, 2H), 6.79 (d, J=9.0 Hz, 2H), 5.22 (q, J=6.5 Hz, J=13.1 Hz, 1H), 3.58-3.51 (m, 1H), 3.49-3.41 (m, 2H), 3.35-3.18 (m, 5H), 1.38 (d, J=6.8 Hz, 3H), 1.37 (s, 9H).

Step 3: (S)-2-(4-bromophenoxy)-1-(piperazin-1-yl)-
propan-1-one

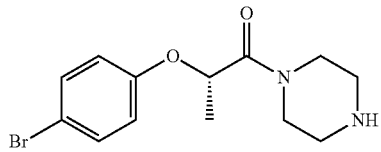

Prepared in a manner similar to Example 5 (step 3) from (S)-tert-butyl 4-(2-(4-bromophenoxy)propanoyl)piperazine-1-carboxylate (93% yield), ESI MS for $C_{13}H_{17}BrN_2O_2$; expected 313.20; found m/z 313.2/315.2 in ratio ~1/1 (isotopes of Br) [M+H]$^+$. $^1$H NMR (DMSO-d$_6$, 600 MHz): δ (ppm) 9.54 (bs, 1H), 7.42 (d, J=9.0 Hz, 2H), 6.84 (d, J=9.0 Hz, 2H), 5.28 (q, J=6.5 Hz, J=13.1 Hz, 1H), 3.86-3.79 (m, 1H), 3.77-3.67 (m, 2H), 3.66-3.57 (m, 1H), 3.16-3.10 (m, 1H), 3.09-3.01 (m, 3H), 1.40 (d, J=6.5 Hz, 3H).

Step 4: methyl (S)-4-(2-(4-bromophenoxy)pro-
panoyl)-N-cyanopiperazine-1-carbimidothioate

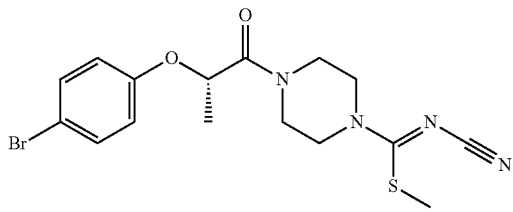

Prepared in a manner similar to Example 1 (step 1) from (S)-2-(4-bromophenoxy)-1-(piperazin-1-yl)propan-1-one. Reaction mixture was carried on without further characterization.

Step 5: (S)-1-(4-(3-amino-1H-1,2,4-triazol-5-yl)
piperazin-1-yl)-2-(4-bromophenoxy)-propan-1-one Preparation and purification in a manner similar to Example 1 (step 2) from methyl (S)-4-(2-(4-bromophenoxy)

propanoyl)-N-cyanopiperazine-1-carbimidothioate gave the desired product as a white solid (61% yield), ESI MS for C$_{15}$H$_{19}$BrN$_6$O$_2$; expected 395.26; found m/z 395.3/397.3 in ratio ~1/1 (isotopes of Br) [M+H]$^+$. $^1$H NMR (DMSO-d$_6$, 600 MHz): δ (ppm) 10.99 (bs, 1H); 7.40 (d, J=9.0 Hz, 2H), 6.78 (d, J=9.0 Hz, 2H), 5.75 (bs, 2H); 5.24 (q, J=6.4 Hz, J=13.1 Hz, 1H), 3.66-3.59 (m, 1H), 3.58-3.47 (m, 2H), 3.45-3.37 (m, 1H), 3.22-3.03 (m, 4H), 1.39 (d, J=6.6 Hz, 3H).

Example 8: 1-(4-(3-amino-1H-1,2,4-triazol-5-yl)piperazin-1-yl)-2-(4-chlorophenoxy)-butan-1-one

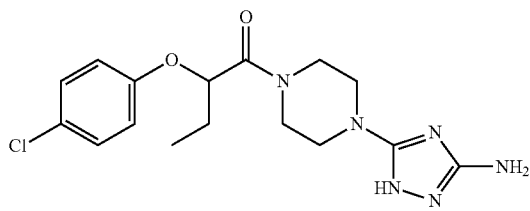 [SMILES: CCC(Oc1ccc(Cl)cc1)C(=O)N1CCN(c2nc(N)n[nH]2)CC1]

Step 1: 2-(4-chlorophenoxy)butanoic Acid

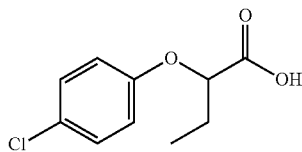

Prepared in a manner similar to Example 5 (step 1) from 4-chlorophenol and 2-bromobutyric acid (92% yield), ESI MS for C$_{10}$H$_{11}$ClO$_3$; expected 214.65; found m/z 213.2/215.2 in ratio ~3/1 (isotopes of Cl) [M−H]$^−$. $^1$H NMR (DMSO-d$_6$, 600 MHz): δ (ppm) 13.03 (bs, 1H), 7.28 (d, J=9.0 Hz, 2H), 6.86 (d, J=9.0 Hz, 2H), 4.63 (q, J=4.9 Hz, J=7.0 Hz, 1H), 1.89-1.78 (m, 2H), 0.95 (t, J=7.4 Hz, 3H).

Step 2: tert-butyl 4-(2-(4-chlorophenoxy)butanoyl)piperazine-1-carboxylate

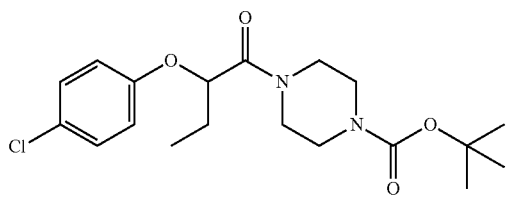 [SMILES: CCC(Oc1ccc(Cl)cc1)C(=O)N1CCN(C(=O)OC(C)(C)C)CC1]

Prepared in a manner similar to Example 5 (step 2) from 2-(4-chlorophenoxy) butanoic acid, (84% yield), ESI MS for C$_{19}$H$_{27}$ClN$_2$O$_4$; expected 382.89; found m/z 381.4/383.4 in ratio ~3/1 (isotopes of Cl) [M−H]$^−$. $^1$H NMR (DMSO-d$_6$, 600 MHz): δ (ppm) 7.28 (d, J=9.0 Hz, 2H), 6.82 (d, J=9.0 Hz, 2H), 5.01-4.97 (m, 1H), 3.65-3.53 (m, 1H), 3.52-3.37 (m, 5H), 3.29-3.19 (m, 2H), 1.88-1.72 (m, 2H), 1.37 (s, 9H), 0.94 (t, J=7.3 Hz, 3H).

Step 3: 2-(4-chlorophenoxy)-1-(piperazin-1-yl)butan-1-one

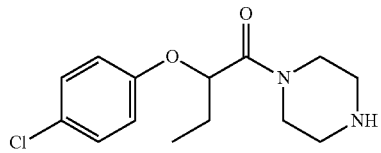 [SMILES: CCC(Oc1ccc(Cl)cc1)C(=O)N1CCNCC1]

Prepared in a manner similar to Example 5 (step 3) from tert-butyl 4-(2-(4-chlorophenoxy)butanoyl)piperazine-1-carboxylate (81% yield), ESI MS for C$_{14}$H$_{19}$ClN$_2$O$_2$; expected 282.77; found m/z 283.3/285.3 in ratio ~3/1 (isotopes of Cl) [M+H]$^+$.

Step 4: methyl 4-(2-(4-chlorophenoxy)butanoyl)-N-cyanopiperazine-1-carbimidothioate

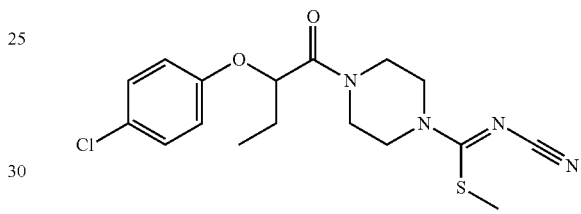

Prepared in a manner similar to Example 1 (step 1) from 2-(4-chlorophenoxy)-1-(piperazin-1-yl)butan-1-one. Reaction mixture was carried on without further characterization.

Step 5: 1-(4-(3-amino-1H-1,2,4-triazol-5-yl)piperazin-1-yl)-2-(4-chlorophenoxy)butan-1-one Preparation and purification in a manner similar to Example 1 (step 2) from methyl 4-(2-(4-chlorophenoxy)butanoyl)-N-cyanopiperazine-1-carbimidothioate gave the desired product as a white solid (52% yield), ESI MS for C$_{16}$H$_{21}$ClN$_6$O$_2$; expected 364.84; found m/z 365.4/367.4 in ratio ~3/1 (isotopes of Cl) [M+H]$^+$. $^1$H NMR (DMSO-d$_6$, 600 MHz): δ (ppm) 10.99 (bs, 1H); 7.28 (d, J=9.0 Hz, 2H), 6.82 (d, J=9.0 Hz, 2H), 5.76 (bs, 2H); 5.05-5.00 (m, 1H), 3.71-3.63 (m, 1H), 3.62-3.55 (m, 1H), 3.55-3.46 (m, 1H), 3.46-3.39 (m, 1H), 3.21-3.01 (m, 4H), 1.83-1.70 (m, 2H), 0.95 (t, J=7.4 Hz, 3H).

Example 9: (R)-1-(4-(3-amino-1H-1,2,4-triazol-5-yl)piperazin-1-yl)-2-(4-chlorophenoxy)-propan-1-one

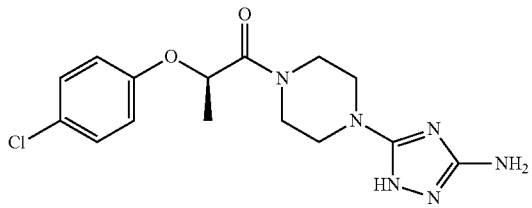 [SMILES: C[C@@H](Oc1ccc(Cl)cc1)C(=O)N1CCN(c2nc(N)n[nH]2)CC1]

Step 1: (R)-2-(4-chlorophenoxy-)propanoic Acid

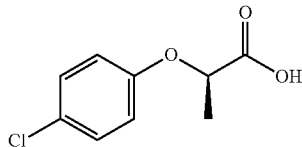

Prepared in a manner similar to Example 5 (step 1) from 4-chlorophenol and (R)-2-bromopropanoic acid, (77% yield), ESI MS for $C_9H_9ClO_3$; expected 200.62; found m/z 199.3/201.3 in ratio ~3/1 (isotopes of Cl) [M–H]−. $^1$H NMR (DMSO-$d_6$, 600 MHz): δ (ppm) 13.01 (bs, 1H), 7.27 (d, J=9.0 Hz, 2H), 6.85 (d, J=9.0 Hz, 2H), 4.80 (q, J=6.8 Hz, J=13.5 Hz, 1H), 1.46 (t, J=6.8 Hz, 3H).

Step 2: (R)-tert-butyl 4-(2-(4-chlorophenoxy)propanoyl)piperazine-1-carboxylate

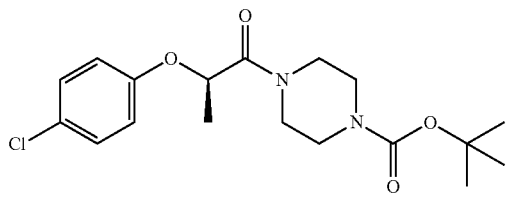 [SMILES: C[C@@H](Oc1ccc(Cl)cc1)C(=O)N1CCN(C(=O)OC(C)(C)C)CC1]

Prepared in a manner similar to Example 5 (step 2) from (R)-2-(4-chlorophenoxy)-propanoic acid, (74% yield), ESI MS for $C_{18}H_{25}ClN_2O_4$; expected 368.86; found m/z 369.2/371.2 in ratio ~3/1 (isotopes of Cl) [M+H]+.

Step 3: (R)-2-(4-chlorophenoxy)-1-(piperazin-1-yl)propan-1-one

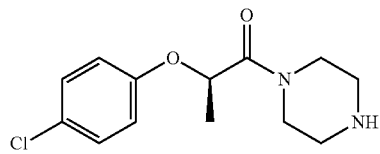 [SMILES: C[C@@H](Oc1ccc(Cl)cc1)C(=O)N1CCNCC1]

Prepared in a manner similar to Example 5 (step 3) from (R)-tert-butyl 4-(2-(4-chlorophenoxy)propanoyl)piperazine-1-carboxylate (78% yield), ESI MS for $C_{13}H_{17}ClN_2O_2$; expected 268.75; found m/z 269.3/271.3 in ratio ~3/1 (isotopes of Cl) [M+H]+. $^1$H NMR (DMSO-$d_6$, 600 MHz): δ (ppm) 9.54 (bs, 1H), 7.31 (d, J=9.0 Hz, 2H), 6.88 (d, J=9.0 Hz, 2H), 5.28 (q, J=6.5 Hz, J=13.1 Hz, 1H), 3.86-3.81 (m, 1H), 3.77-3.67 (m, 2H), 3.66-3.59 (m, 1H), 3.15-3.10 (m, 1H), 3.09-3.00 (m, 3H), 1.40 (d, J=6.6 Hz, 3H).

Step 4: methyl (R)-4-(2-(4-chlorophenoxy)propanoyl)-N-cyanopiperazine-1-carbimidothioate

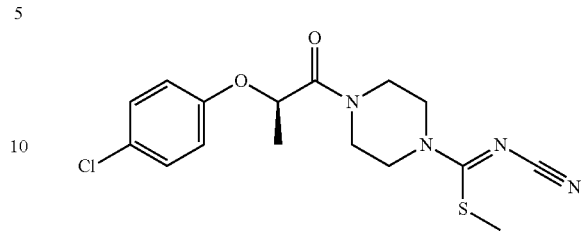

Prepared in a manner similar to Example 1 (step 1) from (R)-2-(4-chlorophenoxy)-1-(piperazin-1-yl)propan-1-one. Reaction mixture was carried on without further characterization.

Step 5: (R)-1-(4-(3-amino-1H-1,2,4-triazol-5-yl)piperazin-1-yl)-2-(4-chlorophenoxy)propan-1-one Preparation and purification in a manner similar to Example 1 (step 2) from methyl (R)-4-(2-(4-chlorophenoxy)propanoyl)-N-cyanopiperazine-1-carbimidothioate gave the desired product as a white solid (42% yield), ESI MS for $C_{15}H_{19}ClN_6O_2$; expected 350.81; found m/z 351.4/353.4 in ratio ~3/1 (isotopes of Cl) [M+H]+. $^1$H NMR (DMSO-$d_6$, 600 MHz): δ (ppm) 7.28 (d, J=8.8 Hz, 2H), 6.85 (d, J=8.8 Hz, 2H), 5.28 (q, J=6.4 Hz, J=13.0 Hz, 1H), 3.74-3.64 (m, 1H), 3.64-3.55 (m, 2H), 3.47-3.41 (m, 1H), 3.31-3.19 (m, 4H), 1.38 (d, J=6.6 Hz, 3H).

Example 10: (S)-1-(4-(3-amino-1H-1,2,4-triazol-5-yl)piperazin-1-yl)-2-(4-chlorophenoxy)propan-1-one

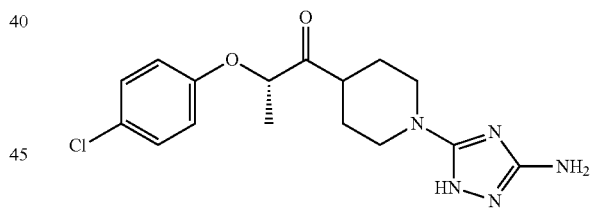

Step 1: (S)-2-(4-chlorophenoxy)-propanoic Acid

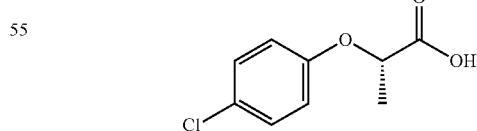

Prepared in a manner similar to Example 5 (step 1) from 4-chlorophenol and (S)-2-bromopropanoic acid, (77% yield), ESI MS for $C_9H_9ClO_3$; expected 200.62; found m/z 199.3/201.3 in ratio ~3/1 (isotopes of Cl) [M–H]−. $^1$H NMR (DMSO-$d_6$, 600 MHz): δ (ppm) 12.93 (bs, 1H), 7.31 (d, J=9.0 Hz, 2H), 6.88 (d, J=9.0 Hz, 2H), 4.82 (q, J=6.8 Hz, J=13.5 Hz, 1H), 1.48 (t, J=7.0 Hz, 3H).

Step 2: (S)-tert-butyl 4-(2-(4-chlorophenoxy)propanoyl)piperazine-1-carboxylate

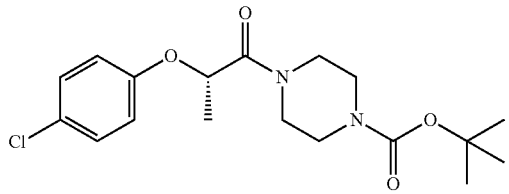 [SMILES: C[C@H](Oc1ccc(Cl)cc1)C(=O)N1CCN(C(=O)OC(C)(C)C)CC1]

Prepared in a manner similar to Example 5 (step 2) from (S)-2-(4-chlorophenoxy)-propanoic acid (88% yield), ESI MS for $C_{18}H_{25}ClN_2O_4$; expected 368.86; found m/z 369.3/371.3 in ratio ~3/1 (isotopes of Cl) [M+H]⁺.

Step 3: (S)-2-(4-chlorophenoxy)-1-(piperazin-1-yl)-propan-1-one

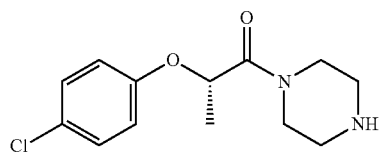 [SMILES: C[C@H](Oc1ccc(Cl)cc1)C(=O)N1CCNCC1]

Prepared in a manner similar to Example 5 (step 3) from (S)-tert-butyl 4-(2-(4-chlorophenoxy)propanoyl)piperazine-1-carboxylate (83% yield), ESI MS for $C_{13}H_{17}ClN_2O_2$; expected 268.75; found m/z 269.3271.3 in ratio ~3/1 (isotopes of Cl) [M+H]⁺. ¹H NMR (DMSO-d₆, 600 MHz): δ (ppm) 9.43 (bs, 1H), 7.31 (d, J=9.0 Hz, 2H), 6.88 (d, J=9.0 Hz, 2H), 5.29 (q, J=6.5 Hz, J=13.1 Hz, 1H), 3.87-3.78 (m, 1H), 3.77-3.68 (m, 2H), 3.66-3.58 (m, 1H), 3.18-3.10 (m, 1H), 3.09-3.01 (m, 3H), 1.40 (d, J=6.6 Hz, 3H).

Step 4: methyl (S)-4-(2-(4-chlorophenoxy)propanoyl)-N-cyanopiperazine-1-carbimidothioate

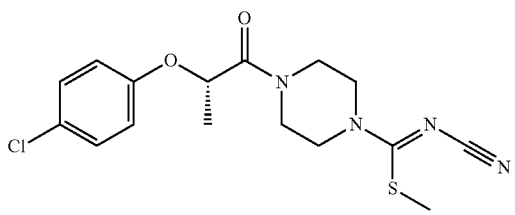 [SMILES: CS/C(=N\C#N)N1CCN(C(=O)[C@H](C)Oc2ccc(Cl)cc2)CC1]

Prepared in a manner similar to Example 1 (step 1) from (S)-2-(4-chlorophenoxy)-1-(piperazin-1-yl)-propan-1-one. Reaction mixture was carried on without further characterization.

Step 5: (S)-1-(4-(3-amino-1H-1,2,4-triazol-5-yl)piperazin-1-yl)-2-(4-chlorophenoxy)-propan-1-one Preparation and purification in a manner similar to Example 1 (step 2) from methyl (S)-4-(2-(4-chlorophenoxy)propanoyl)-N-cyanopiperazine-1-carbimidothioate gave the desired product as a white solid (33% yield), ESI MS for $C_{15}H_{19}ClN_6O_2$; expected 350.81; found m/z 351.4/353.4 in ratio ~3/1 (isotopes of Cl) [M+H]⁺. ¹H NMR (DMSO-d₆, 600 MHz): δ (ppm) 7.28 (d, J=9.0 Hz, 2H), 6.85 (d, J=9.0 Hz, 2H), 5.28 (q, J=6.4 Hz, J=13.0 Hz, 1H), 3.74-3.67 (m, 1H), 3.63-3.54 (m, 2H), 3.49-3.43 (m, 1H), 3.32-3.19 (m, 4H), 1.38 (d, J=6.6 Hz, 3H).

Example 11: N-((1-(3-amino-1H-1,2,4-triazol-5-yl)piperidin-4-yl)methyl)-4-bromobenzamide

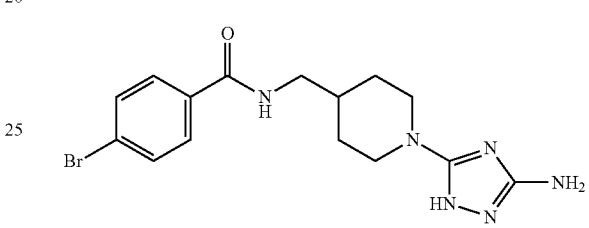

Step 1: tert-butyl 4-((4-bromobenzamido)methyl)piperidine-1-carboxylate

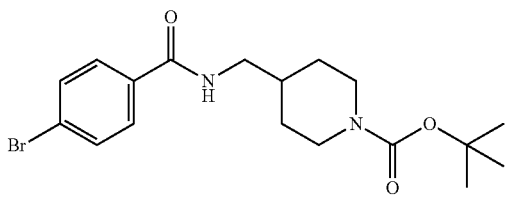 [SMILES: CC(C)(C)OC(=O)N1CCC(CNC(=O)c2ccc(Br)cc2)CC1]

Prepared in a manner similar to Example 5 (step 2) from 4-bromobenzoic acid (0.61 g, 3 mmol) and 1-N-Boc-4-(aminomethyl)piperidine (0.65 g, 3 mmol); white solid, 0.9 g (82% yield). Used without further characterization.

Step 2: 4-bromo-N-(piperidin-4-ylmethyl)benzamide

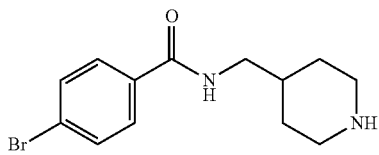 [SMILES: O=C(NCC1CCNCC1)c1ccc(Br)cc1]

Prepared in a manner similar to Example 5 (step 3) from tert-butyl 4-((4-bromobenzamido) methyl)piperidine-1-carboxylate to give 0.61 g (91% yield). Used without further characterization.

Step 3: methyl 4-((4-bromobenzamido)methyl)-N-cyanopiperidine-1-carbimidothioate

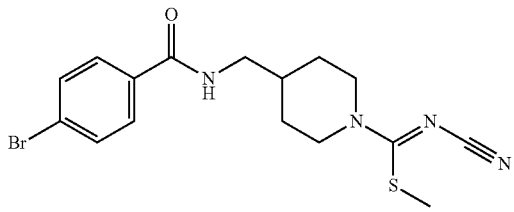 [SMILES: CS/C(=N\C#N)N1CCC(CNC(=O)c2ccc(Br)cc2)CC1]

Prepared in a manner similar to Example 1 (step 1) 4-bromo-N-(piperidin-4-ylmethyl)benzamide. Reaction mixture was carried on without further characterization.

Step 4: N-((1-(3-amino-1H-1,2,4-triazol-5-yl)piperidin-4-yl)methyl)-4-bromobenzamide Preparation and purification in a manner similar to Example 1 (step 2) methyl 4-((4-bromobenzamido)methyl)-N-cyanopiperidine-1-carbimidothioate gave the desired product as a white solid, 200 mg (28%). $^1$H NMR (DMSO, 500 MHz) δ (ppm) 10.86 (brs, 1H), 8.65-8.42 (m, 1H), 7.81-7.65 (m, 4H), 5.80-5.34 (brs, 1H), 3.87-3.60 (m, 2H), 3.17-2.94 (m, 2H), 2.71-2.49 (m, 2H), 1.76-146 (m, 3H), 1.26-0.95 (m, 2H). ESI-LCMS m/z for $C_{15}H_{19}BrN_6O$: calculated 378.08, found 379/381 [M+H]+.

Example 12: N-((1-(3-amino-1H-1,2,4-triazol-5-yl)piperidin-4-yl)methyl)-4-bromobenzenesulfonamide

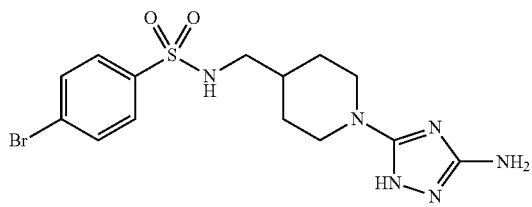 [SMILES: Nc1n[nH]c(N2CCC(CNS(=O)(=O)c3ccc(Br)cc3)CC2)n1]

Step 1: tert-butyl 4-((4-bromophenylsulfonamido)methyl)piperidine-1-carboxylate

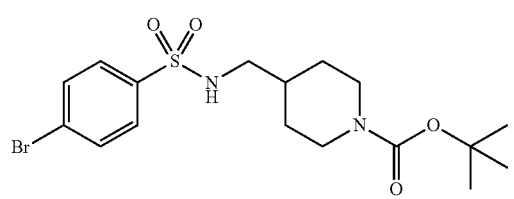 [SMILES: CC(C)(C)OC(=O)N1CCC(CNS(=O)(=O)c2ccc(Br)cc2)CC1]

Triethylamine (0.61 ml, 4.41 mmol) and 4-bromobenzenesulfonyl chloride (0.800 g, 3.73 mmol) were added to a solution of 1-BOC-4-(aminomethyl)piperidine (0.867 g, 3.39 mmol) in dichloromethane and stirred at room temperature overnight. Reaction progress was monitored by LCMS. The resulting mixture was diluted with dichloromethane and washed with aqueous 1M HCl, aqueous 5% NaHCO$_3$, and brine, and dried over MgSO$_4$. The solvent was evaporated to give the title compound as a white foam, 1.390 g (94% yield). $^1$H NMR (CDCl$_3$, 500 MHz) δ (ppm) 7.74-7.63 (m, 4H), 4.67 (t, J=6.6 Hz, 1H), 4.05-4.12 (m, 2H), 2.82 (t, J=6.6 Hz, 2H), 2.56-2.70 (m, 2H), 1.62-1.68 (m, 3H), 1.43 (s, 9H), 0.96-1.15 (m, 2H). ESI-LCMS m/z for $C_{17}H_{25}BrN_2O_4S$: calculated 432.07, found 455.5/457.5 (M+Na$^+$), 431.3/433.3 (M−H)−.

Step 2: 4-bromo-N-(piperidin-4-ylmethyl)benzenesulfonamide

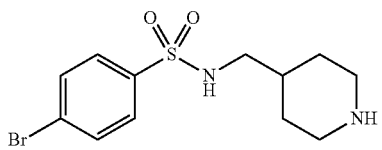 [SMILES: O=S(=O)(NCC1CCNCC1)c1ccc(Br)cc1]

Prepared in a manner similar to Example 5 (step 3) from tert-butyl 4-((4-bromophenyl sulfonamido)methyl)piperidine-1-carboxylate to give the hydrochloride salt of the title compound, 1.160 g (92%). ESI-LCMS m/z for $C_{12}H_{17}BrN_2O_2S$: calculated 332.02, found: 333.3/335.3 (M+H$^+$). The hydrochloride salt (1.150 g, 3.11 mmol) was dissolved in aqueous 1M NaOH and the free amine was extracted into dichloromethane. The organic layer was washed with brine and dried over MgSO$_4$. The solvent was removed under reduced pressure to the title compound as white solid. Yield: 0.935 g (90%).

Step 3: methyl 4-((4-bromophenylsulfonamido)methyl)-N-cyanopiperidine-1-carbimidothioate

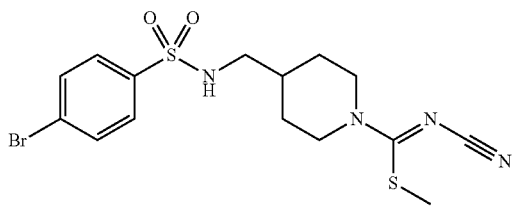 [SMILES: CS/C(=N\C#N)N1CCC(CNS(=O)(=O)c2ccc(Br)cc2)CC1]

Prepared in a manner similar to Example 1 (step 1) from 4-bromo-N-(piperidin-4-ylmethyl)benzenesulfonamide. ESI-LCMS m/z for $C_{15}H_{19}BrN_4O_2S_2$: calculated 430.01, found 429.1/431.1 [M−H]−.

Step 4: N-((1-(3-amino-1H-1,2,4-triazol-5-yl)piperidin-4-yl)methyl)-4-bromobenzene sulfonamide Preparation and purification in a manner similar to Example 1 (step 2) from methyl 4-((4-bromophenylsulfonamido)methyl)-N-cyanopiperidine-1-carbimidothioate gave the desired product as a white solid, 0.375 g (32% per two steps, based on free 4-bromo-N-(piperidin-4-ylmethyl)benzenesulfonamide). $^1$H NMR (DMSO-d$_6$, 500 MHz) δ (ppm) 10.91 (bs, 1H), 7.82 (d, J=8.6 Hz, 2H), 7.71 (d, J=8.6 Hz, 2H), 5.63 (bs, 2H), 3.70-3.76 (m, 2H), 3.63-3.69 (m, 2H), 2.57-2.64 (m, 2H), 1.45-1.61 (m, 3H), 0.97-1.14 (m, 2H). ESI-LCMS m/z for $C_{14}H_{19}BrN_6O_2S$: calculated 414.05; found: 415.4/417.4 [M+H]$^+$, 413.1/415.2 (M−H)−.

Example 13: N-(1-(3-amino-1H-1,2,4-triazol-5-yl)piperidin-4-yl)-1-(4-bromophenyl)methanesulfonamide

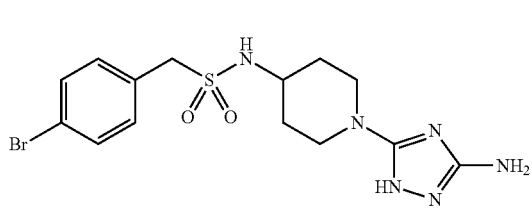

Step 1: tert-butyl 4((4-bromophenyl)methylsulfonamido)piperidine-1-carboxylate

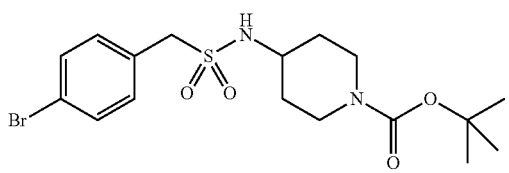 [SMILES: CC(C)(C)OC(=O)N1CCC(NS(=O)(=O)Cc2ccc(Br)cc2)CC1]

Prepared in a manner similar to Example 12 (step 1) from 1-BOC-4-aminopiperidine and (4-bromophenyl)methanesulfonyl chloride (0.917 g, 53% yield). $^1$H NMR (DMSO, 600 MHz) δ (ppm) 7.55 (d, J=8.5 Hz, 2H), 7.30 (d, J=8.5 Hz, 2H), 7.16 (d, J=7.5 Hz, 1H), 4.31 (s, 2H), 3.83-3.73 (m, 2H), 3.27-3.20 (m, 1H), 2.86-2.65 (m, 2H), 1.77-1.71 (m, 2H), 1.34 (s, 9H), 1.25-1.17 (m, 2H). ESI-LCMS m/z for $C_{17}H_{25}BrN_2O_4S$: calculated 432.07, found 431.3/433.1 [M−H]$^-$.

Step 2: 1-(4-bromophenyl)-N-(piperidin-4-yl)methanesulfonamide

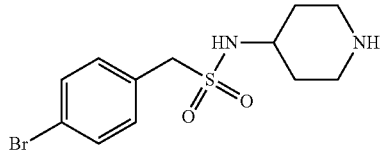 [SMILES: O=S(=O)(Cc1ccc(Br)cc1)NC1CCNCC1]

Prepared in a manner similar to Example 5 (step 3) from tert-butyl 4-((4-bromophenyl) methylsulfonamido)piperidine-1-carboxylate to give the hydrochloride salt of the title compound, (0.302 g, 87% yield). ESI-LCMS m/z for $C_{19}H_{29}BrN_2O_2$: calculated 332.02 found 333.3/335.3 [M+H]$^+$.

Step 3: methyl 4-((4-bromophenyl)methylsulfonamido)-N-cyanopiperidine-1-carbimidothioate

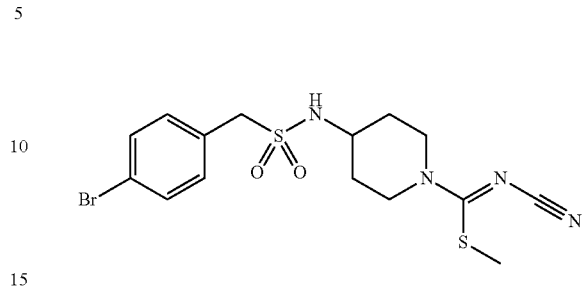

Prepared in a manner similar to Example 1 (step 1) from 1-(4-bromophenyl)-N-(piperidin-4-yl)methanesulfonamide; (0.316 g, 81% yield). ESI-LCMS m/z for $C_{15}H_{19}BrN_4O_2S_2$: calculated 430.01, found 431.4/433.4 [M+H]$^+$.

Step 4: N-(1-(3-amino-1H-1,2,4-triazol-5-yl)piperidin-4-yl)-1-(4-bromophenyl)methanesulfonamide Preparation and purification in a manner similar to Example 1 (step 2) from methyl 4-((4-bromophenyl)methylsulfonamido)-N-cyanopiperidine-1-carbimidothioate gave the desired product as a white solid, 0.189 g (62% yield). $^1$H NMR (DMSO, 600 MHz) δ (ppm) 10.92 (bs, 1H), 7.57 (d, J=8.3 Hz, 2H), 7.33 (d, J=8.3 Hz, 2H), 7.17 (bs, 1H), 5.65 (bs, 2H), 4.33 (s, 2H), 3.75-3.66 (m, 2H), 3.26-3.17 (m, 1H), 2.75-2.61 (m, 2H), 1.80-1.71 (m, 2H), 1.43-1.30 (m, 2H). ESI-LCMS m/z for $C_{14}H_{19}BrN_6O_2S$: calculated 414.05, found 415.3/417.3 [M+H]+.

Example 14: N-(1-(3-amino-1H-1,2,4-triazol-5-yl)piperidin-4-yl)-1-(4-chlorophenyl)methanesulfonamide dihydrochloride

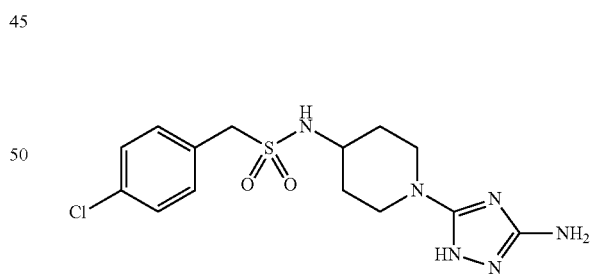

Prepared in a manner similar to Example 13 (all steps) starting from 1-Boc-4-aminopiperidine and (4-chlorophenyl)methanesulfonyl chloride. 0.030 g final product obtained as the dihydrochloride salt. $^1$H NMR (DMSO-$d_6$, 600 MHz) δ (ppm) 7.42 (d, J=8.5 Hz, 2H), 7.37 (d, J=8.5 Hz, 2H), 7.25 (d, J=8.3 Hz, 2H), 4.32 (s, 2H), 3.72-3.63 (m, 2H), 3.44 (bs, 3H), 3.36-3.27 (m, 1H), 3.02-2.92 (m, 2H), 1.87-1.79 (m, 2H), 1.45-1.36 (m, 2H). ESI-LCMS m/z for $C_{14}H_{19}ClN_6O_2S$: calculated 370.10, found 371.4 [M+H]$^+$.

Example 15: N-(1-(3-amino-1H-1,2,4-triazol-5-yl)piperidin-4-yl)-1-(3,4-dichlorophenyl)methanesulfonamide

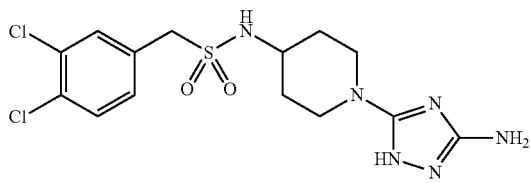 [SMILES: Nc1n[nH]c(N2CCC(NS(=O)(=O)Cc3ccc(Cl)c(Cl)c3)CC2)n1]

Prepared in a manner similar to Example 13 (all steps) starting from 1-Boc-4-aminopiperidine and (3,4-dichlorophenyl)methanesulfonyl chloride. 0.01 g final product obtained, $^1$H NMR (DMSO-d$_6$, 600 MHz) δ (ppm) 7.67-7.61 (m, 2H), 7.39-7.34 (m, 1H), 7.24 (brs, 1H), 5.54 (brs, 1H), 4.39 (s, 2H), 3.75-3.64 (m, 2H), 3.27-3.17 (m, 1H), 2.74-2.63 (m, 2H), 1.82-170 (m, 2H), 1.43-1.30 (m, 2H). ESI-LCMS m/z for C$_{14}$H$_{18}$Cl$_2$N$_6$O$_2$S: calculated 404.06, found 405.4/407.4 [M+H]+.

Example 16: N-(1-(3-amino-1H-1,2,4-triazol-5-yl)piperidin-4-yl)-2-(4-bromophenyl)acetamide

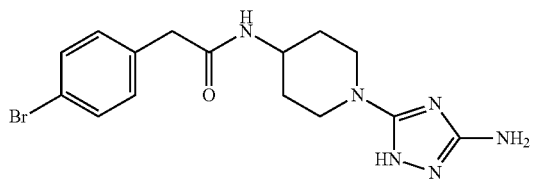 [SMILES: Nc1n[nH]c(N2CCC(NC(=O)Cc3ccc(Br)cc3)CC2)n1]

Step 1: tert-butyl 4-(2-(4-bromophenyl)acetamido)piperidine-1-carboxylate

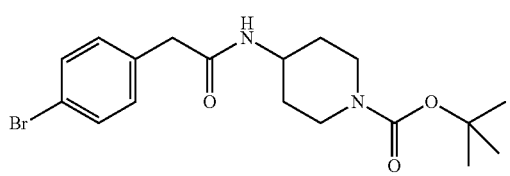 [SMILES: CC(C)(C)OC(=O)N1CCC(NC(=O)Cc2ccc(Br)cc2)CC1]

To a solution of 4-bromophenylacetic acid (1 g, 4.99 mmol) in dichloromethane (50 ml) was added diisopropylethylamine (0.85 ml, 4.99 mmol), O-Benzotriazol-1-yl-N,N,N',N'-tetramethyluronium tetrafluoroborate (TBTU) (1.6 g, 4.99 mmol) and 1-Boc-4-aminopiperidine (1 g, 4.99 mmol). The mixture was stirred at room temperature overnight, then washed with water, 1M NaOH and brine. Dried over MgSO$_4$, filtered, concentrated, and residue crystallized from Et$_2$O to give 1.8 g product, (99%). ESI-LCMS m/z for C$_{18}$H$_{25}$BrN$_2$O$_3$: calculated 396.10, found 341.4/343.4 [M-tBu+H]+.

Step 2: 2-(4-bromophenyl)-N-(piperidin-4-yl)acetamide

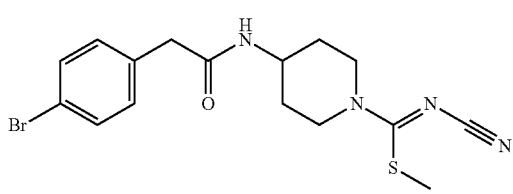 [SMILES: CS/C(=N\C#N)N1CCC(NC(=O)Cc2ccc(Br)cc2)CC1]

Prepared in a manner similar to Example 5 (step 3) from tert-butyl 4-(2-(4-bromophenyl)acetamido)piperidine-1-carboxylate to give 54% yield. Product used without further characterization.

Step 3: methyl 4-(2-(4-bromophenyl)acetamido)-N-cyanopiperidine-1-carbimidothioate

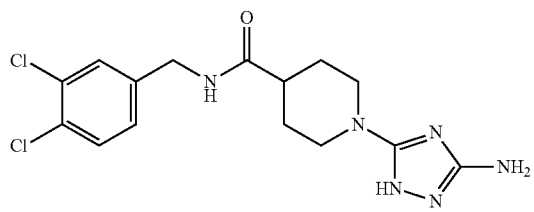 [SMILES: Nc1n[nH]c(N2CCC(C(=O)NCc3ccc(Cl)c(Cl)c3)CC2)n1]

Prepared in a manner similar to Example 1 (step 1) from 2-(4-bromophenyl)-N-(piperidin-4-yl)acetamide. Reaction mixture used without further characterization.

Step 4: N-(1-(3-amino-1H-1,2,4-triazol-5-yl)piperidin-4-yl)-2-(4-bromophenyl)acetamide Preparation and purification in a manner similar to Example 1 (step 2) from methyl 4-(2-(4-bromophenyl)acetamido)-N-cyanopiperidine-1-carbimidothioate gave the desired product as a white solid, 330 mg (37%). $^1$H NMR (DMSO-d$_6$, 500 MHz) δ (ppm) 10.91 (bs, 1H), 8.02 (d, J=7.58, 1H), 7.47-7.43 (m, 2H), 7.19-7.15 (m, 2H), 5.56 (bs, 2H), 3.70-3.55 (m, 3H), 2.77-2.59 (m, 2H), 1.68-1.61 (m, 2H), 1.43-1.20 (m, 2H). ESI-LCMS m/z for C$_{15}$H$_{19}$BrN$_6$O: calculated 378.08, found 379.4/381.4 [M+H]+.

Example 17: 1-(3-amino-1H-1,2,4-triazol-5-yl)-N-(3,4-dichlorobenzyl)piperidine-4-carboxamide

Step 1: ethyl 1-((cyanoimino)(methylthio)methyl)piperidine-4-carboxylate

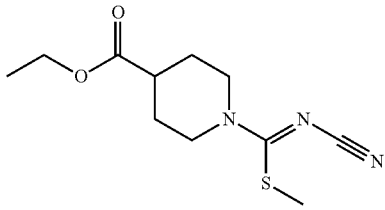 [SMILES: CCOC(=O)C1CCN(/C(=N/C#N)SC)CC1]

Prepared in a manner similar to Example 1 (step 1) from ethyl isonipecotate (10.00 g, 63.61 mmol). Reaction mixture used without further characterization.

Step 2: ethyl 1-(3-amino-1H-1,2,4-triazol-5-yl)piperidine-4-carboxylate

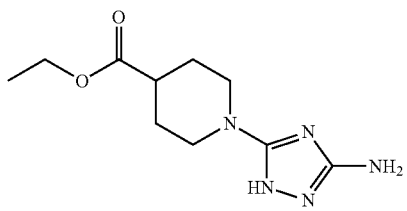 [SMILES: CCOC(=O)C1CCN(c2nc(N)n[nH]2)CC1]

Preparation and purification in a manner similar to Example 1 (step 2) from methyl 4-((4-bromophenyl)methylsulfonamido)-N-cyanopiperidine-1-carbimidothioate gave the desired product as a white solid (11.70 g, 78% yield over two steps). ESI MS found for $C_{10}H_{17}N_5O_2$; calculated 239.14, found 240.3 [M+H]+.

Step 3: 1-(3-amino-1H-1,2,4-triazol-5-yl)piperidine-4-carboxylic acid hydrochloride

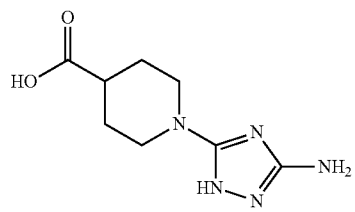 [SMILES: Nc1n[nH]c(N2CCC(C(=O)O)CC2)n1]

Ethyl 1-(3-amino-1H-1,2,4-triazol-5-yl)piperidine-4-carboxylate (3.00 g, 12.54 mmol) was refluxed with 3 M HCl (90 ml, 270 mmol) for 4 h. Solvent was evaporated. Crude product was washed several times with $Et_2O$ and dried on the air to give 3.95 g of product as white solid-yield—98%. ESI MS for $C_8H_{13}N_5O_2$ calculated 211.11, found 212.2 [M+H]+.

Step 4: 1-(3-amino-1H-1,2,4-triazol-5-yl)-N-(3,4-dichlorobenzyl)piperidine-4-carboxamide To a suspension of 1-(3-amino-1H-1,2,4-triazol-5-yl)piperidine-4-carboxylic acid hydrochloride (200 mg, 0.62 mmol) in $CH_2Cl_2$ (20 ml), DIPEA (0.64 ml, 3.72 mmol) was added. Then sequentially, O-(7-azabenzotriazol-1-yl)-N,N,N',N'-tetramethyluronium hexafluorophosphate (HATU) (130 mg, 0.34 mmol) and 3,4-dichloro-benzylamine (55 mg, 0.31 mmol) were added. Reaction mixture was stirred at room temperature for 20 h. Precipitate was filtered, washed with several times with $Et_2O$, dissolved in 4M NaOH (20 ml) and extracted with ethyl acetate (5×40 ml). Combined organic layers were washed with brine (2×20 ml), dried over $MgSO_4$ and stripped to give 85 mg of crude product. Crystallization with MeOH/AcOEt/$Et_2O$ gave 46 mg of pure product (yield 40%) $^1$H NMR (DMSO-$d_6$, 200 MHz) δ (ppm): 10.95 (bs, 1H), 8.37 (t, J=5.6 Hz, 1H), 7.55 (d, J=8.6 Hz, 1H), 7.43 (d, J=1.5 Hz, 1H), 7.18 (dd, $J_1$=8.6 Hz, $J_2$=1.5 Hz, 1H), 5.57 (bs, 1H), 4.21 (d, J=5.6 Hz, 2H), 3.77 (d, J=13.1 Hz, 2H), 2.61-2.52 (m, 2H), 2.35-2.19 (m, 1H), 1.72-1.41 (m, 4H). ESI MS for $C_{15}H_{18}Cl_2N_6O$ calculated 368.09, found 369.5/371.5 [M+H]+.

Example 18: 1-(3-amino-1H-1,2,4-triazol-5-yl)-N-(4-bromobenzyl)piperidine-4-carboxamide

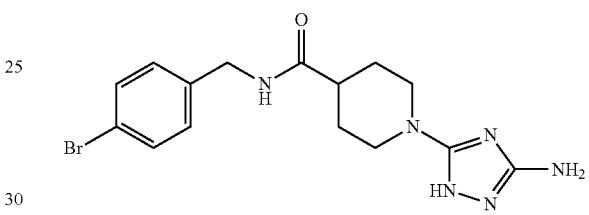

Prepared in a manner similar to Example 17 (step 4) using 4-bromobenzylamine and 1-(3-amino-1H-1,2,4-triazol-5-yl)piperidine-4-carboxylic acid to give white solid, 8 mg (10% yield). Yield 8 mg (10%), $^1$H NMR (DMSO, 200 MHz) δ (ppm) 10.92 (brs, 1H), 8.35 (m, 1H), 7.49 (d, J=8.2 Hz, 2H), 7.17 (d, J=8.2 Hz, 2H), 5.84-5.49 (brs, 2H), 4.20 (d, J=5.5 Hz, 2H), 3.84-3.73 (m, 2H), 2.70-2.54 (m, 2H), 2.34-2.21 (m, 1H), 1.70-1.61 (m, 2H), 1.61-1.48, (m, 2H). ESI-LCMS m/z for $C_{15}H_{19}BrN_6O$: calculated 378.08, found 379/381 [M+H]+.

Example 19: 5-(4-(4-(4-bromophenyl)butan-2-yl)piperazin-1-yl)-1H-1,2,4-triazol-3-amine

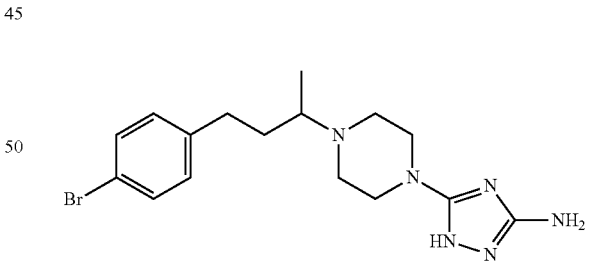

Step 1: 4-(4-bromophenyl)butan-2-one

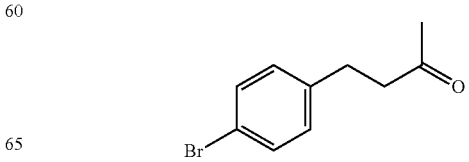

To a solution of 4-bromoaniline-5.00 g (29.07 mmol) in MeCN (125 ml) was added 6M H₂SO₄ [3.26 mL conc. H₂SO₄. (61.22 mmol) and 60 mL H₂O] at room temperature. White solid precipitated. 1-buten-3-ol-5.50 ml (63.79 mmol) and a solution of PdCl₂ (33 mg (0.18 mmol) in MeCN (25 ml)) were added. [This solution was prepared by stirring PdCl₂ and MeCN for 18 h at reflux; brown suspension changed to a dark-yellow solution.]

A solution of NaNO₂ (2.45 g (35.51 mmol) in 10 mL water) was added dropwise over 2 hr to vigorously stirred reaction mixture at 0-5° C. After addition complete, allowed to warm to room temperature and continued stirring for 50 hours. Reaction mixture changed from yellow to dark-brown, and finally to dark-green. The layers were separated and the water-layer was extracted with ethyl acetate (3×100 ml). Combined organic layers were washed with brine (2×50 ml), dried over MgSO₄, and stripped to give 6.38 g of crude product as dark-green oil. Purified by column chromatography (silica-gel, gradient hexane/ethyl acetate 50:1→20:1) to give 4.22 g (64% yield).

Step 2: 4-(4-bromophenyl)butan-2-ol

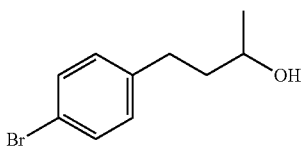

4-(4-Bromophenyl)butan-2-one (2.00 g, 8.88 mmol) was dissolved in methanol (50 ml), and sodium borohydride (0.67 g, 17.71 mmol) was carefully added at room temperature. Reaction was stirred for 3 hr, then quenched by adding 1M NaOH$_{aq}$ (2 ml). Solvent was evaporated and reaction mixture was taken up in water, extracted with ethyl acetate, washed with brine, dried over MgSO₄ and evaporated to give 1.81 g of product (yield 90%). Used without further characterization.

Step 3: 4-(4-bromophenyl)butan-2-yl methanesulfonate

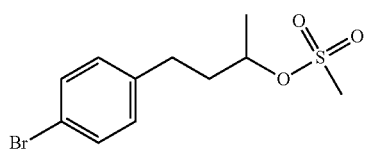 [SMILES: CC(CCc1ccc(Br)cc1)OS(C)(=O)=O]

4-(4-bromophenyl)butan-2-ol (1.50 g, 6.55 mmol) and triethylamine (1.13 g, 11.14 mmol) were dissolved in dichloromethane (50 ml) and the solution was cooled to 0° C. Methanesulfonyl chloride (1.12 g, 9.82 mmol) was dropwise to the cold reaction mix, and the reaction was stirred at room temperature for 3 hours. Diluted with CH₂Cl₂ (150 ml), washed with 2 M NaOH (2×20 ml), 1M HCl (2×20 ml), and brine (2×20 ml), dried over MgSO₄ and evaporated to give 1.94 g of product (96% yield). Used without further characterization.

Step 5: tert-butyl 4-(4-(4-bromophenyl)butan-2-yl) piperazine-1-carboxylate

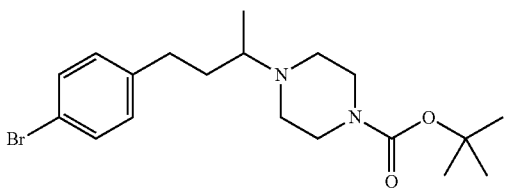 [SMILES: CC(CCc1ccc(Br)cc1)N1CCN(C(=O)OC(C)(C)C)CC1]

A mixture of 3-(4-bromophenyl)-1-methylpropyl methanesulfonate (1.50 g, 4.88 mmol), N-Boc-piperazine (1.52 g, 8.16 mmol), and K₂CO₃ (2.81 g, 20.33 mmol) in acetonitrile (60 ml) was heated to reflux overnight. Excess K₂CO₃ was filtered off and washed with acetonitrile several times. Solvent was evaporated, residue was dissolved in ethyl acetate (200 ml), washed with solution of 2.5% citric acid in brine (1 volume of 5% citric acid in water and 1 volume of saturated brine) (3×40 ml) and saturated brine (2×40 ml) and evaporated. New residue was dissolved in Et₂O (300 ml), washed with 2 M HCl (10×25 ml). Precipitate from both layers was filtered, dissolved in 1M NaOH, extracted with ethyl acetate, dried over MgSO₄ and evaporated to give 1.02 g of product (53% yield). ESI MS m/z for C₁₉H₂₉BrN₂O₂; calculated 396.14, found 341.4/343.4 [M-tBu+H]⁺, 297.3/299.3 [M-Boc+H]⁺.

Step 6: 1-(4-(4-bromophenyl)butan-2-yl)piperazine

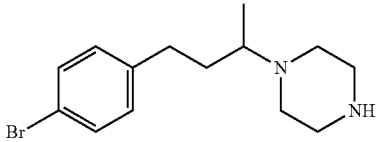 [SMILES: CC(CCc1ccc(Br)cc1)N1CCNCC1]

Prepared in a manner similar to Example 5 (step 3) from tert-butyl 4-(4-(4-bromophenyl)butan-2-yl)piperazine-1-carboxylate to give 0.31 g product (9 yield %). ESI MS m/z for C₁₄H₂₁BrN₂; calculated 296.09, found 297.3/299.3 [M+H]⁺.

Step 7: methyl 4-(4-(4-bromophenyl)butan-2-yl)-N-cyanopiperazine-1-carbimidothioate

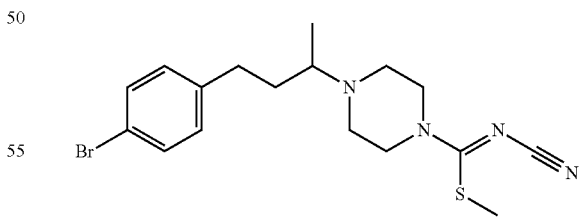

Prepared in a manner similar to Example 1 (step 1) from 1-(4-(4-bromophenyl)butan-2-yl)piperazine, used without further characterization.

Step 8: 5-(4-(4-(4-bromophenyl)butan-2-yl)piperazin-1-yl)-1H-1,2,4-triazol-3-amine Preparation and purification in a manner similar to Example 1 (step 2) from methyl 4-(4-(4-bromophenyl)butan-2-yl)-N-cyanopiperazine-1-carbimidothioate gave the desired product as a white solid, 28 mg (7% yield over two steps). ¹H NMR (DMSO-d₆, 500 MHz) δ (ppm): 10.92 (bs, 1H), 7.42 (d, J=8.2 Hz, 2H), 7.16 (d, J=8.2 Hz, 2H), 5.64 (bs, 2H), 3.38-3.29 (m, 1H), 3.18-3.07 (m, 4H), 2.59-2.55 (m, 2H), 2.54-2.44 (m, 2H), 1.77-1.69 (m, 1H), 1.51-1.44 (m 1H), 0.89 (d, J=6.5 Hz, 3H). ESI MS for $C_{16}H_{23}BrN_6$; calculated 379.30, found 379.4/381.4 [M+H]⁺.

Example 20-1 and 20-2

5-(4-(2-(4-bromophenoxy)propyl)piperazin-1-yl)-1H-1,2,4-triazol-3-amine; and 5-(4-(1-(4-bromophenoxy)propan-2-yl)piperazin-1-yl)-1H-1,2,4-triazol-3-amine

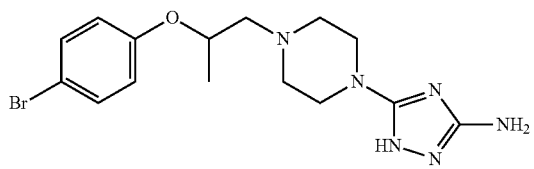 [SMILES: CC(CN1CCN(c2nc(N)n[nH]2)CC1)Oc1ccc(Br)cc1]

5-(4-(2-(4-bromophenoxy)propyl)piperazin-1-yl)-1H-1,2,4-triazol-3-amine

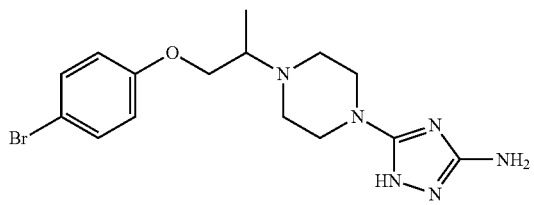

5-(4-(1-(4-bromophenoxy)propan-2-yl)piperazin-1-yl)-1H-1,2,4-triazol-3-amine

Step 1: tert-butyl 4-(1-hydroxypropan-2-yl)piperazine-1-carboxylate; tert-butyl 4-(2-hydroxypropyl)piperazine-1-carboxylate

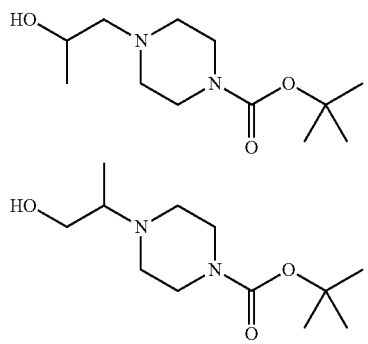

To a solution of Boc-piperazine (1 g, 5.36 mmol) in water at 0° C., propylene oxide (1.1 ml, 16.08 mmol) was added. The resulting mixture was stirred at rt overnight. TLC indicated total consumption of substrate. Product was extracted with ether, dried over MgSO₄ and concentrated to give 1 g of colorless oil (77%) as a mixture of regioisomers (1:1). ¹H NMR (CDCl₃, 500 MHz) δ (ppm) 3.86-3.80 (m, 1H), 3.48-3.32 (m, 5H), 2.64-2.52 (m, 2H), 2.36-2.29 (m, 3H), 2.26-2.20 (m, 1H), 1.44 (s, 9H), 1.12 (d, J=6 Hz, 3H).

Step 2: tert-butyl 4-(1-(4-bromophenoxy)propan-2-yl)piperazine-1-carboxylate; tert-butyl 4-(2-(4-bromophenoxy)propyl)piperazine-1-carboxylate

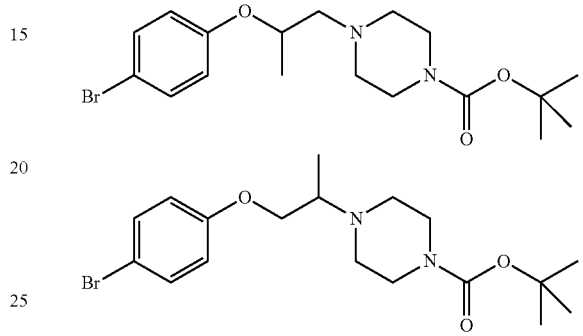

Triphenylphosphine (1.6 g, 6.14 mmol) was suspended in methylene chloride and cooled to −5° C. Then diisopropyl azodicarboxylate (1.2 ml, 6.14 mmol) (DIAD) was added dropwise; after 15 minutes 4-bromophenol (1 g, 6.14 mmol) was added in the same manner. Finally, after 15 minutes, mixture of regioisomers tert-butyl 4-(1-hydroxypropan-2-yl)piperazine-1-carboxylate compound with tert-butyl 4-(2-hydroxypropyl)piperazine-1-carboxylate (1 g, 4.09 mmol) was added at −5° C., and reaction was allowed to warm to rt overnight. Reaction progress was monitored by means of TLC (dichloromethane/methanol 9:1). The reaction mixture was concentrated, diluted with ether, and triphenylphosphine oxide was removed by filtration. The filtrate was concentrated in vacuo, and the residue was purified by flash chromatography ethyl acetate/hexane (1/10 to 1/1) to give 1 g (62%) of colorless oil. ¹H NMR (CDCl₃, 500 MHz) δ (ppm) 7.39-7.36 (m, 2H), 6.82-6.78 (m, 2H), 5.02-4.96 (m, 1H), 4.53-4.48 (m, 1H), 4.04-4.01 (m, 1H), 3.88-3.80 (m, 1H), 3.48-3.38 (m, 4H), 3.06-3.01 (m, 1H), 2.72-2.68 (m, 1H), 2.66-2.55 (m, 2H), 2.53-2.30 (m, 3H), 1.47 (s, 9H), 1.46 (s, 9H), 1.30 (d, J=6.2 Hz, 3H), 1.28 (d, J=6.4 Hz, 2H).

Step 3: 1-(1-(4-bromophenoxy)propan-2-yl)piperazine compound with 1-(2-(4-bromophenoxy)propyl)piperazine

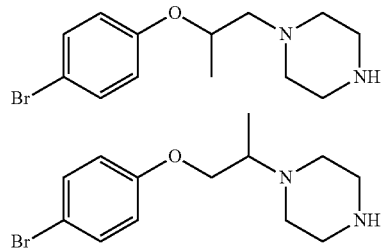

Prepared in a manner similar to Example 5 (step 3) from mixture of regioisomers tert-butyl 4-(1-(4-bromophenoxy)propan-2-yl)piperazine-1-carboxylate and tert-butyl 4-(2-(4-bromophenoxy)propyl)piperazine-1-carboxylate to give 0.7 g (94%). Used without further characterization.

Step 4: methyl 4-(1-(4-bromophenoxy)propan-2-yl)-N-cyanopiperazine-1-carbimidothioate compound with methyl 4-(2-(4-bromophenoxy)propyl)-N-cyanopiperazine-1-carbimidothioate

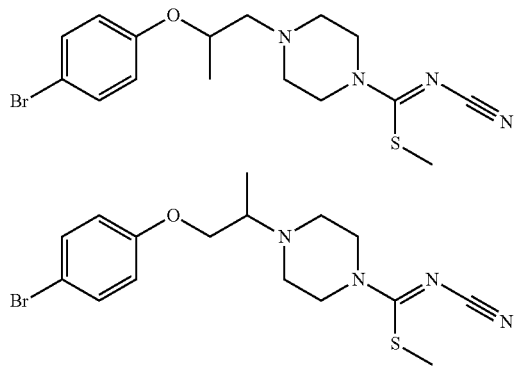

Prepared in a manner similar to Example 1 (step 1) from mixture of regioisomers 1-(1-(4-bromophenoxy)propan-2-yl)piperazine and 1-(2-(4-bromophenoxy)propyl) piperazine, reaction mixture used without further characterization.

Step 5: 5-(4-(1-(4-bromophenoxy)propan-2-yl)piperazin-1-yl)-1H-1,2,4-triazol-3-amine compound with 5-(4-(2-(4-bromophenoxy)propyl)piperazin-1-yl)-1H-1,2,4-triazol-3-amine

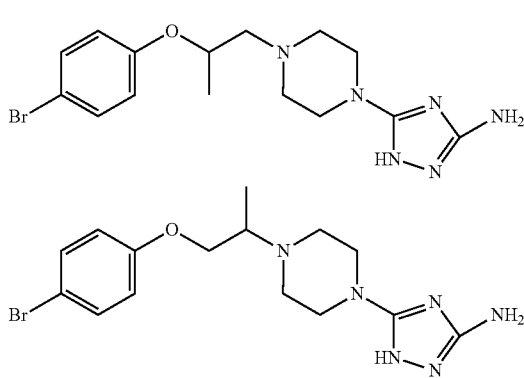

Preparation in a manner similar to Example 1 (step 2) from mixture of regioisomers ethyl 4-(1-(4-bromophenoxy)propan-2-yl)-N-cyanopiperazine-1-carbimidothioate and methyl 4-(2-(4-bromophenoxy)propyl)-N-cyanopiperazine-1-carbimidothioate gave 0.8 g (88% yield) of a mixture of the two regioisomers of the product.

Step 6: Separation of Example 20-1 and Example 20-2

110 mg mixture of isomers 5-(4-(1-(4-bromophenoxy)propan-2-yl)piperazin-1-yl)-1H-1,2,4-triazol-3-amine and 5-(4-(2-(4-bromophenoxy)propyl)piperazin-1-yl)-1H-1,2,4-triazol-3-amine were separated by preparative HPLC (10-40% acetonitrile/water) to give:

Example 20-1

5-(4-(2-(4-bromophenoxy)propyl)piperazin-1-yl)-1H-1,2,4-triazol-3-amine

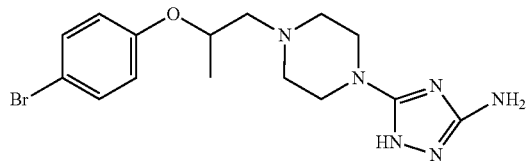 [SMILES: CC(CN1CCN(c2nc(N)n[nH]2)CC1)Oc1ccc(Br)cc1]

Yield 10 mg (10%). $^1$H NMR (D$_2$O, 500 MHz) δ (ppm) 7.41 (d, J=9 Hz, 2H), 6.85 (d, J=9 Hz, 2H), 4.31 (dd, J1=11.5 Hz, J2=3 Hz, 1H), 4.16 (dd, J1=11.5 Hz, J2=6 Hz, 1H), 3.86-3.79 (m, 1H), 3.70-3.17 (m, 7H), 1.41 (d, J=7 Hz, 3H). ESI-LCMS m/z for C$_{15}$H$_{21}$BrN$_6$O: calculated 380.10, found 381/383 [M+H]+.

Example 20-2

5-(4-(1-(4-bromophenoxy)propan-2-yl)piperazin-1-yl)-1H-1,2,4-triazol-3-amine

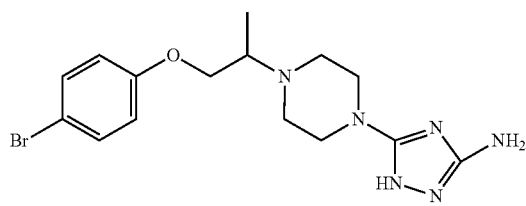 [SMILES: CC(COc1ccc(Br)cc1)N1CCN(c2nc(N)n[nH]2)CC1]

Yield 4 mg (4%). $^1$H NMR (D$_2$O, 500 MHz) δ (ppm) 7.37 (d, J=9 Hz, 2H), 6.84 (d, J=9 Hz, 2H), 4.88-4.80 (m, 1H), 3.85-3.08 (m, 10H), 1.18 (d, J=6 Hz, 3H). ESI-LCMS m/z for C$_{15}$H$_{21}$BrN$_6$O: calculated 380.10, found 381/383 [M+H]$^+$.

Example 21: 1-(3-amino-1H-1,2,4-triazol-5-yl)-N-(4-bromophenethyl)-N-methyl piperidin-4-amine

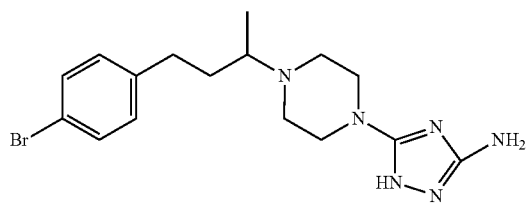 [SMILES: CC(CCc1ccc(Br)cc1)N1CCN(c2nc(N)n[nH]2)CC1]

Step 1: tert-butyl 4-((4-bromophenethyl)(methyl)amino)piperidine-1-carboxylate

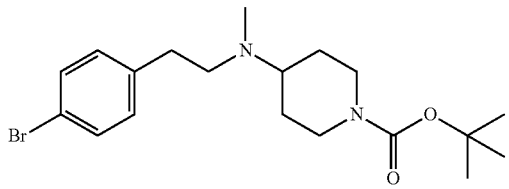 [SMILES: CN(CCc1ccc(Br)cc1)C1CCN(C(=O)OC(C)(C)C)CC1]

Boc-piperidone (1.78 g, 8.96 mmol) and 2-(4-bromophenyl)ethanamine (1.79 g, 8.96 mmol) in dichloroethane were stirred for 1.5 h at room temperature. Then NaBH(OAc)$_3$ (5.70 g, 26.87 mmol) was added in several portions. The mixture was stirred at room temperature for 1.5 h. TLC (CHCl$_3$/MeOH 9/1) indicated total consumption of substrate. ESI-LCMS m/z for C$_{18}$H$_{27}$BrN$_2$O$_2$: found 383.5/385.4 [M+H]+. To the above reaction mixture formaldehyde (36% in water) (0.82 mL, 10.75 mmol) and NaBH(OAc)$_3$ (3.80 g, 17.92 mmol) were added. The resulting mixture was stirred at room temperature for 40 minutes. Reaction progress was monitored by means of TLC (CHCl$_3$/MeOH 9/1). The mixture was treated with 5% aq NaHCO$_3$, organic components were extracted with CH$_2$Cl$_2$. The combined extracts were washed with 1M aq HCl, brine and dried over MgSO$_4$. The solvent was evaporated and product was obtained as a white crystals. Yield 3.39 g (95%). ESI-LCMS m/z for C$_{19}$H$_{29}$BrN$_2$O$_2$: calculated 396.14, found 397.4/399.4 [M+H]$^+$.

Step 2: N-(4-bromophenethyl)-N-methylpiperidin-4-amine

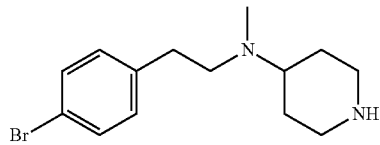 [SMILES: CN(CCc1ccc(Br)cc1)C1CCNCC1]

Prepared in a manner similar to Example 5 (step 3) from tert-butyl 4-((4-bromophenethyl)(methyl)amino)piperidine-1-carboxylate to give 1.62 g (63% yield). ESI-LCMS m/z for C$_{14}$H$_{21}$BrN$_2$: calculated 296.09, found 297.3/299.3 [M+H]$^+$.

Step 3: methyl 4-((4-bromophenethyl)(methyl)amino)-N-cyanopiperidine-1-carbimidothioate

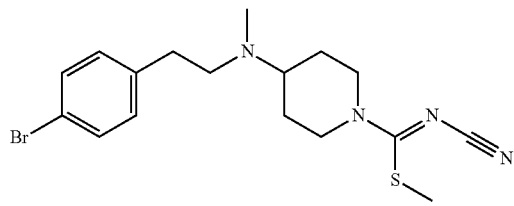

Prepared in a manner similar to Example 1 (step 1) from N-(4-bromophenethyl)-N-methylpiperidin-4-amine. Reaction mixture was used without further characterization.

Step 4: 1-(3-amino-1H-1,2,4-triazol-5-yl)-N-(4-bromophenethyl)-N-methylpiperidin-4-amine Preparation and purification in a manner similar to Example 1 (step 2) from methyl 4-((4-bromophenethyl)(methyl)amino)-N-cyanopiperidine-1-carbimidothioate gave the desired product as a white solid, 1.09 g (52% yield). $^1$H NMR (DMSO, 500 MHz) δ (ppm) 10.81 (bs, 1H), 7.40 (d, J=8.3 Hz, 2H), 7.15 (d, J=8.3 Hz, 2H), 5.55 (bs, 2H), 3.80-3.72 (m, 2H), 2.65-2.59 (m, 2H), 2.59-2.50 (m, 4H), 2.45-2.36 (m, 1H), 2.17 (s, 3H), 1.61-1.54 (m, 2H), 1.38-1.27 (m, 2H). ESI-LCMS m/z for C$_{16}$H$_{23}$BrN$_6$: calculated 378.12, found 379.4/381.4 [M+H]$^+$.

Example 22: 1-(3-amino-1H-1,2,4-triazol-5-yl)-N-(4-bromophenethyl)piperidin-4-amine

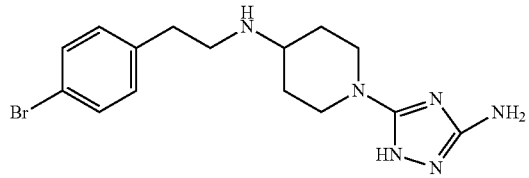 [SMILES: Nc1n[nH]c(N2CCC(NCCc3ccc(Br)cc3)CC2)n1]

Step 1: tert-butyl 4-(((benzyloxy)carbonyl)(4-bromophenethyl)amino)piperidine-1-carboxylate

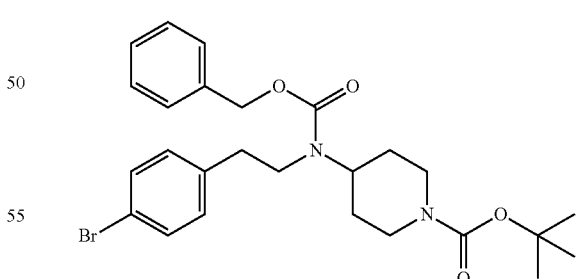

Benzyloxycarbonyl group was added to tert-butyl 4-{[2-(4-bromophenyl)ethyl] amino}piperidine-1-carboxylate using Cbz-Cl. Yield of pure product 26% after column chromatography (hexane/ethyl acetate 20/1→5/1 (v/v)). ESI MS for C$_{26}$H$_{33}$BrN$_2$O$_4$; calculated 516.16, found 417.4/419.4 [M-Boc+H]$^+$.

Step 2: benzyl 4-bromophenethyl(piperidin-4-yl)carbamate

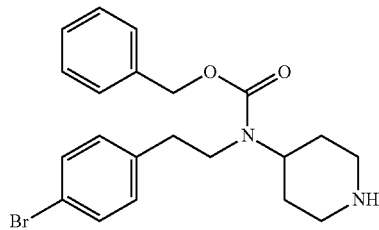 [SMILES: O=C(OCc1ccccc1)N(CCc1ccc(Br)cc1)C1CCNCC1]

Prepared in a manner similar to Example 5 (step 3) from tert-butyl 4-(((benzyloxy) carbonyl)(4-bromophenethyl) amino)piperidine-1-carboxylate to give 243 mg of expected product (yield 89%). ESI MS m/z for $C_{21}H_{25}BrN_2O_2$ calculated 416.11, found 417.5/419.5 $[M+H]^+$.

Step 3: methyl 4-(((benzyloxy)carbonyl)(4-bromophenethyl)amino)-N-cyanopiperidine-1-carbimidothioate

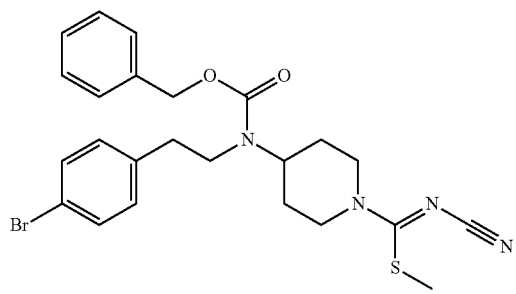 [SMILES: CS/C(=N\C#N)N1CCC(N(CCc2ccc(Br)cc2)C(=O)OCc2ccccc2)CC1]

Prepared in a manner similar to Example 1 (step 1) from methyl 4-(((benzyloxy) carbonyl)(4-bromophenethyl) amino)-N-cyanopiperidine-1-carbimidothioate, used without further characterization.

Step 4: benzyl (1-(3-amino-1H-1,2,4-triazol-5-yl)piperidin-4-yl)(4-bromophenethyl)carbamate

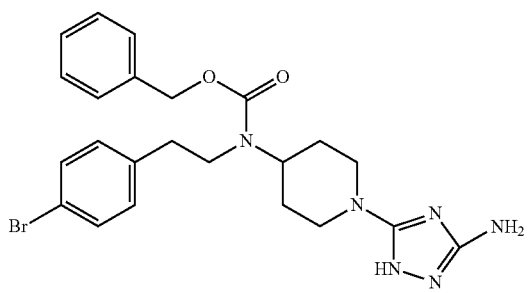 [SMILES: Nc1n[nH]c(N2CCC(N(CCc3ccc(Br)cc3)C(=O)OCc3ccccc3)CC2)n1]

Prepared in a manner similar to Example 1 (step 2) from 235 mg of methyl 4-(((benzyloxy)carbonyl)(4-bromophenethyl)amino)-N-cyanopiperidine-1-carbimidothioate to give 276 mg product after recrystallization from acetonitrile/diethyl ether. ESI MS found for $C_{23}H_{27}BrN_6O_2$; calculated 498.14, found 497.5/499.4 $[M+H]^+$.

Step 5: 1-(3-amino-1H-1,2,4-triazol-5-yl)-N-(4-bromophenethyl)piperidin-4-amine hydrochloride Benzyl (1-(3-amino-1H-1,2,4-triazol-5-yl)piperidin-4-yl) (4-bromophenethyl) carbamate (250 mg, 0.50 mmol) was shaken with 5.7 M solution of HBr in acetic acid in 50° C. and stirred for 2 h at room temperature. Crystals appeared. $Et_2O$ (20 ml) was added. Crystals were filtered and washed with $Et_2O$ to give 236 mg of crude product as amine hydrobromide. Product was purified in by crystallization from ethyl followed by preparative HPLC on C-18 column, gradient 10-50% MeCN in water, HCOOH 0.1%. Proper fraction was evaporated, 1M aqueous HCl was added and again evaporated to give 40 mg of pure product as hydrochloride (yield 18%). $^1H$ NMR (MeOD-$d_4$, 500 MHz) δ (ppm): 7.48 (d, J=8.0 Hz, 2H), 7.25 (d, J=8.0 Hz, 2H), 3.94-3.86 (m, 2H), 3.46-3.38 (m, 1H), 3.33-3.27 (m, 2H), 3.60-3.12 (m, 4H), 2.25-2.16 (m, 2H), 1.80-1.70 (m, 2H). ESI MS found for $C_{15}H_{21}BrN_6$ calculated 364.10, found 365.4/367.4 $[M+H]^+$.

Example 23: 5-(4-(2-((4-chloronaphthalen-1-yl)oxy)ethyl)piperazin-1-yl)-1H-1,2,4-triazol-3-amine

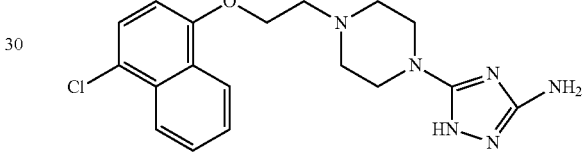

Step 1: methyl 4-(2-((4-chloronaphthalen-1-yl)oxy)ethyl)-N-cyanopiperazine-1-carbimidothioate

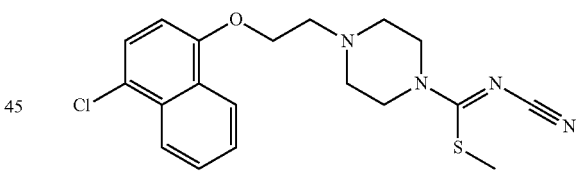

To a 100 mL single neck RBF equipped with nitrogen inlet tube, reflux condenser, and bleach trap were added 1-[2-[(4-chloro-1-naphthalenyl)oxy]ethyl]-piperazine hydrochloride (0.1227 g, 0.3750 mmol) and anhydrous acetonitrile (10 mL). 1.5 eq of triethylamine (0.0570 g, 0.5625 mmol) were added, and the system was stirred at RT for 15 min. Dimethyl cyanocarbonimidodithioate (0.0591 g, 0.4042 mmol) was dissolved in anhydrous acetonitrile (10 mL) and added to the reaction. The reaction was refluxed overnight under nitrogen. TLC and MS confirmed presence of the desired intermediate. The reaction solution was carried forward without purification. ESI-LCMS m/z calculated for $C_{15}H_{19}FN_4OS$: expected 388.9; found 389.2 $[M+H]^+$.

Step 2: 5-(4-(2((4-chloronaphthalen-1-yl)oxy)ethyl)piperazin-1-yl)-1H-1,2,4-triazol-3-amine To the reaction solution from step 1 was added hydrazine hydrate monohydrate (0.2933 g, 3.75 mmol, 284 μL). The reaction was refluxed for 16 hours. The solvent was removed and the residue was purified by reverse-phase HPLC to give the desired product as a white solid (0.028 g, 20.0% yield). $^1$H NMR (CD$_3$OD, 300 MHz) δ (ppm) 8.36 (dd, J=8.2 Hz, J=5.4 Hz, J=1.7 Hz, J=1.2 Hz, 1H), 8.07 (dd, J=8.6 Hz, J=5.2 Hz, J=1.8 Hz, J=1.2 Hz, 1H), 7.65-7.36 (m, 3H), 6.95 (dd, J=8.9, J=5.4, 1H), 4.32 (t, J=5.8, 2H), 3.41-3.22 (m, 4H), 2.89 (t, J=5.8, 2H), 2.62-2.54 (m, 4H); ESI-LCMS m/z calculated for C$_{14}$H$_{19}$FN$_6$O: expected 372.9; found 373.2 [M+H]$^+$.

Example 24: 1-(4-(3-amino-1H-1,2,4-triazol-5-yl) piperazin-1-yl)-2-(4-chlorophenoxy)-ethanone

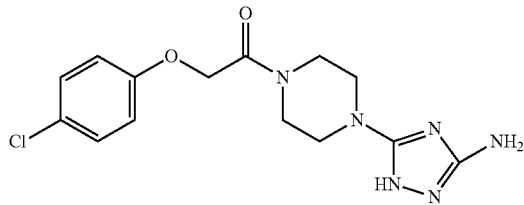 [SMILES: Nc1n[nH]c(N2CCN(C(=O)COc3ccc(Cl)cc3)CC2)n1]

Step 1: methyl 4-(2-(4-chlorophenoxy)acetyl)-N-cyanopiperazine-1-carbimidothioate

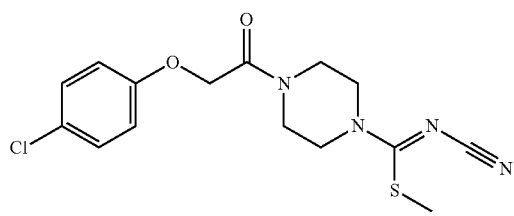 [SMILES: CS/C(=N\C#N)N1CCN(C(=O)COc2ccc(Cl)cc2)CC1]

Prepared in a manner similar to Example 23 (step 1) from 2-(4-chlorophenoxy)-1-(1-piperazinyl)ethanone hydrochloride (0.1274 g, 0.4375 mmol), ESI-LCMS m/z calculated for C$_{15}$H$_{17}$ClN$_4$O$_2$S: expected 352.85; found 353.2 [M+H]$^+$.

Step 2: 1-(4-(3-amino-1H-1,2,4-triazol-5-yl)piperazin-1-yl)-2-(4-chlorophenoxy)-ethanone Preparation and purification in a manner similar to Example 23 (step 2) from methyl 4-(2-(4-chlorophenoxy) acetyl)-N-cyanopiperazine-1-carbimidothioate gave the desired product as a white solid (0.055 g, 36% yield). $^1$H NMR (CD$_3$OD, 400 MHz) δ (ppm) 7.13 (d, J=7.0, 2H), 6.83 (d, J=7.0, 2H), 4.70 (s, 2H), 3.60 (bs, 4H), 3.29 (d, J=12.0, 2H), 3.24 (d, J=12.0, 2H); ESI-LCMS m/z calculated for C$_{14}$H$_{17}$ClN$_6$O$_2$: expected 336.8; found 337.2 [M+H]$^+$.

Example 25: 1-(4-(3-amino-1H-1,2,4-triazol-5-yl) piperazin-1-yl)-2-(naphthalen-2-yloxy) ethanone

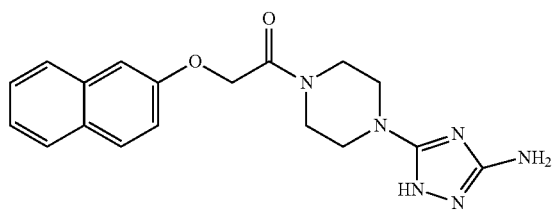 [SMILES: Nc1n[nH]c(N2CCN(C(=O)COc3ccc4ccccc4c3)CC2)n1]

Step 1: methyl N-cyano-4-(2-(naphthalen-2-yloxy) acetyl)piperazine-1-carbimidothioate

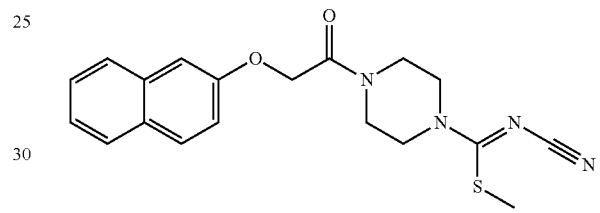

Prepared in a manner similar to Example 23 (step 1) from 2-(naphthalen-2-yloxy)-1-piperazin-1-yl-ethanone trifluoroacetate (0.1922 g, 0.50 mmol). ESI-LCMS m/z calculated for C$_{19}$H$_{20}$N$_4$O$_2$S: expected 368.46; found 369.2 [M+H]$^+$.

Step 2: 1-(4-(3-amino-1H-1,2,4-triazol-5-yl)piperazin-1-yl)-2-(naphthalen-2-yloxy)ethanone Preparation and purification in a manner similar to Example 23 (step 2) from methyl N-cyano-4-(2-(naphthalen-2-yloxy)acetyl)piperazine-1-carbimidothioate gave the desired product as a white solid (0.011 g, 6.0% yield). $^1$H NMR (CD$_3$OD, 400 MHz) δ (ppm) 7.66-7.62 (m, 3H), 7.30-7.08 (m, 4H), 4.84 (s, 2H), 3.63 (bs, 4H), 3.31 (bs, 2H), 3.22 (bs, 2H); ESI-LCMS m/z calculated for C$_{19}$H$_{20}$N$_6$O$_2$: expected 352.40; found 353.2 [M+H]$^+$.

Example 26: 5-(4-(2-(4-bromophenoxy)ethyl)-3-methylpiperazin-1-yl)-1H-1,2,4-triazol-3-amine

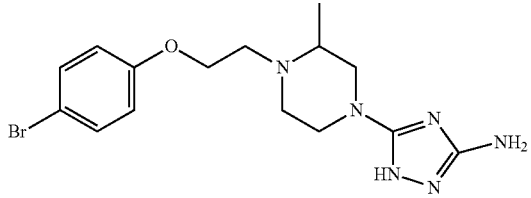 [SMILES: CC1CN(c2nc(N)n[nH]2)CCN1CCOc1ccc(Br)cc1]

Step 1: tert-butyl 4-(2-(4-bromophenoxy)ethyl)-3-methylpiperazine-1-carboxylate

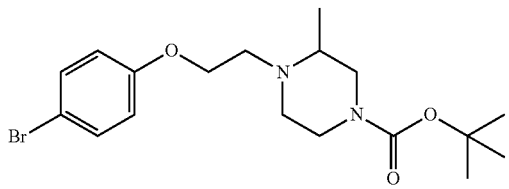 [SMILES: CC1CN(C(=O)OC(C)(C)C)CCN1CCOc1ccc(Br)cc1]

To an 8 mL scintillation vial were added 1-bromo-4-(2-bromoethoxy)benzene (2.80 g, 10.0 mmol), 4-N-Boc-2-methylpiperazine (2.00 g, 10.0 mmol), and cesium carbonate (7.5 g, 20.0 mmol) in anhydrous dimethylformamide (5.0 mL). Reaction slurry was stirred at RT for 48 hrs, TLC and MS confirming presence of the desired intermediate. Quenched with water (50 mL) and extracted with ethyl acetate (3×100 mL). Organics were combined, washed with additional water (50 mL), brine (50 mL), dried over $Na_2SO_4$ and filtered. Solvent was removed and yellow oil was carried forward without purification. ESI-LCMS m/z calculated for $C_{18}H_{27}BrN_2O_3$: expected 399.33; found 400.2 $[M+H]^+$.

Step 2: 1-(2-(4-bromophenoxy)ethyl)-2-methylpiperazine trifluoroacetate

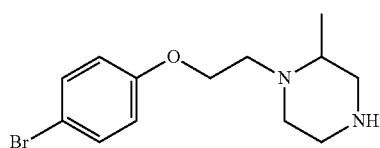 [SMILES: CC1CNCCN1CCOc1ccc(Br)cc1]

Tert-butyl 4-(2-(4-bromophenoxy)ethyl)-3-methylpiperazine-1-carboxylate (4.0 g, 10.0 mmol) was dissolved in anhydrous dichloromethane (20 mL). Added trifluoroacetic acid (15 mL) and stirred at RT under nitrogen for 15 hrs. Solvent was removed, the residue was treated with sat'd $NaHCO_3$ (25 mL), and extracted with dichloromethane (3×100 mL). Combined organic phases were dried over $Na_2SO_4$, filtered, and stripped to give the desired product as a yellow oil (3.37 g, 81% yield). $^1$H NMR ($CD_3OD$, 400 MHz) δ (ppm) 7.41 (d, J=6.8 Hz, 2H), 6.90 (d, J=6.8 Hz, 2H), 4.14 (m, 2H), 3.34 (bs, 4H), 3.15 (bs, 3H), 2.50 (t, J=12.9 Hz, 1H), 2.27 (t, J=12.9 Hz, 1H), 1.30 (d, J=4.8 Hz, 3H); ESI-LCMS m/z calculated for $C_{13}H_{19}BrN_2O$: expected 299.21; found 300.2 $[M+H]^+$.

Step 3: methyl 4-(2-(4-bromophenoxy)ethyl)-N-cyano-3-methylpiperazine-1-carbimidothioate

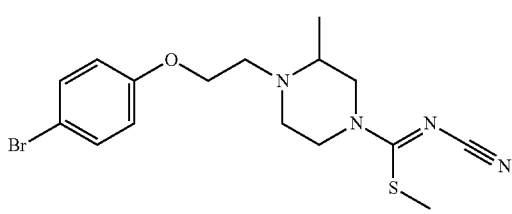 [SMILES: CS/C(=N\C#N)N1CCN(CCOc2ccc(Br)cc2)C(C)C1]

Prepared in a manner similar to Example 23 (step 1) from 1-(2-(4-bromophenoxy) ethyl)-2-methylpiperazine trifluoroacetate (0.2066 g, 0.50 mmol). ESI-LCMS m/z calculated for $C_{16}H_{21}BrN_4OS$: expected 397.34; found 398.2 $[M+H]^+$.

Step 4: 5-(4-(2-(4-bromophenoxy)ethyl)-3-methylpiperazin-1-yl)-1H-1,2,4-triazol-3-amine Preparation and purification in a manner similar to Example 23 (step 2) from methyl 4-(2-(4-bromophenoxy)ethyl)-N-cyano-3-methylpiperazine-1-carbimidothioate gave the desired product as a white solid (0.027 g, 14% yield). $^1$H NMR ($CD_3OD$, 400 MHz) δ (ppm) 7.46 (d, J=8.0 Hz, 2H), 6.97 (d, J=8.0 Hz, 2H), 4.41 (m, 2H), 3.89 (bs, 3H), 3.76 (bs, 2H), 3.64-3.51 (m, 3H), 3.40 (bs, 1H), 1.53 (d, J=5.0 Hz, 3H); ESI-LCMS m/z calculated for $C_{15}H_{21}BrN_6O$: expected 381.28; found 382.2 $[M+H]^+$.

Example 27-1 and 27-2

3-(4-(2-(4-bromophenoxy)ethyl)piperazin-1-yl)-1-methyl-1H-1,2,4-triazol-5-amine; and 5-(4-(2-(4-bromophenoxy)ethyl)piperazin-1-yl)-1-methyl-1H-1,2,4-triazol-3-amine

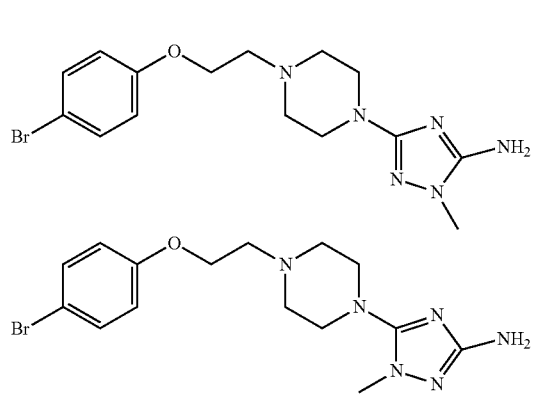

Step 1: methyl 4-(2-(4-bromophenoxy)ethyl)-N-cyanopiperazine-1-carbimidothioate

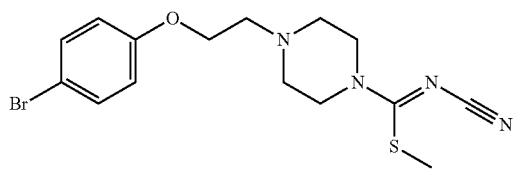

Prepared in a manner similar to Example 23 (step 1) from 1-(2-(4-bromophenoxy)ethyl) piperazine. Reaction mixture was used without further characterization.

Step 2: 3-(4-(2-(4-bromophenoxy)ethyl)piperazin-1-yl)-1-methyl-1H-1,2,4-triazol-5-amine; 5-(4-(2-(4-bromophenoxy)ethyl)piperazin-1-yl)-1-methyl-1H-1,2,4-triazol-3-amine

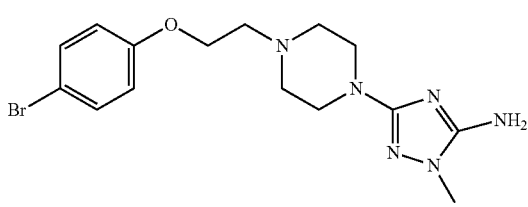

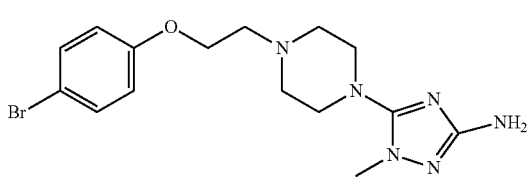

Prepared in a manner similar to Example 23 (step 2) from methyl 4-(2-(4-bromophenoxy) ethyl)-N-cyanopiperazine-1-carbimidothioate using methyl hydrazine. Obtained a mixture of regioisomers which was separated by flash chromatography through silica gel, eluted with a gradient of 2-20% methanol in dichloromethane. Structures were assigned based on NOESY.

Example 28: 5-{4-[2-(4-bromophenoxy)ethyl]-[1,4]-diazepan-1-yl}-1H-1,2,4-triazol-3-amine

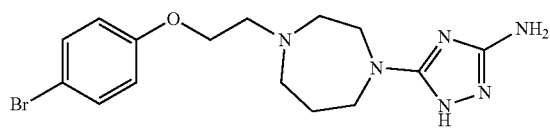 [SMILES: Nc1n[nH]c(N2CCCN(CCOc3ccc(Br)cc3)CC2)n1]

Step 1: 4-[2-(4-Bromophenoxy)ethyl]-[1,4]-diazepane-1-carboxylic acid tert-butyl ester

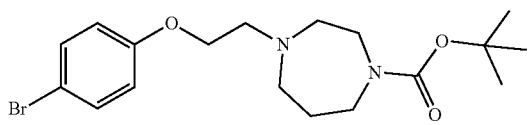 [SMILES: CC(C)(C)OC(=O)N1CCCN(CCOc2ccc(Br)cc2)CC1]

Prepared in a manner similar to Example 26 (step 1) from 1-bromo-4-(2-bromoethoxy)benzene (2.80 g, 10.0 mmol), and [1,4]diazepane-1-carboxylic acid tert-butyl ester (2.00 g, 10.0 mmol), yellow oil was carried forward without purification. ESI-LCMS m/z calculated for $C_{18}H_{27}BrN_2O_3$: expected 399.33; found 400.2 [M+H]$^+$.

Step 2: 4-[2-(4-Bromophenoxy)ethyl]-[1,4]-diazepane

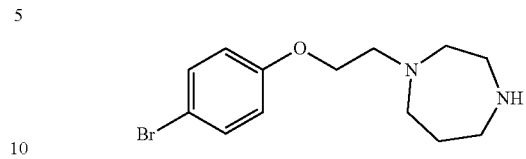

Prepared in a manner similar to Example 26 (step 2) from 4-[2-(4-bromophenoxy) ethyl][1,4]diazepane-1-carboxylic acid tert-butyl ester (4.0 g, 10.0 mmol) to give the desired product as a yellow oil. (2.37 g, 77% yield) $^1$H NMR (CD$_3$OD, 400 MHz) δ 7.10 (d, J=8.5, 2H), 6.82 (d, J=8.5, 2H), 4.11 (t, J=2.7, 2H), 3.04-2.74 (m, 10H), 1.79 (bs, 1H), 1.65 (bs, 1H); ESI-LCMS m/z calculated for $C_{13}H_{19}BrN_2O$: expected 299.21; found 300.2 [M+H]$^+$.

Step 3: N-cyano-{4-[2-(4-bromophenoxy)ethyl]-[1,4]-diazepan-1-yl}carboximido-thioic Acid methyl ester

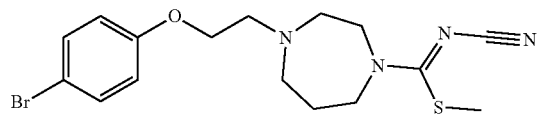 [SMILES: CS/C(=N\C#N)N1CCCN(CCOc2ccc(Br)cc2)CC1]

Prepared in a manner similar to Example 23 (step 1) from 4-[2-(4-bromophenoxy) ethyl]-[1,4]-diazepane trifluoroacetate (0.2066 g, 0.50 mmol). ESI-LCMS m/z calculated for $C_{16}H_{21}BrN_4OS$: expected 397.34; found 398.2 [M+H]$^+$.

Step 4: 5-{4-[2-(4-bromophenoxy)ethyl]-[1,4]-diazepan-1-yl}-1H-1,2,4-triazol-3-amine Preparation and purification in a manner similar to Example 23 (step 2) gave the desired product as a white solid. (0.090 g, 47% yield). $^1$H NMR (CD$_3$OD, 400 MHz) δ (ppm) 7.44 (d, J=8.4 Hz, 2H), 6.95 (d, J=8.4 Hz, 2H), 4.40 (bs, 2H), 3.93 (bs, 2H), 3.71-3.62 (m, 8H), 2.36 (bs, 2H); ESI-LCMS m/z calculated for $C_{15}H_{21}BrN_6O$: expected 381.28; found 382.2 [M+H]$^+$.

Example 29: 5-(5-(2-(4-bromophenoxy)ethyl)hexahydropyrrolo[3,4-c]pyrrol-2(1H)-yl)-1H-1,2,4-triazol-3-amine

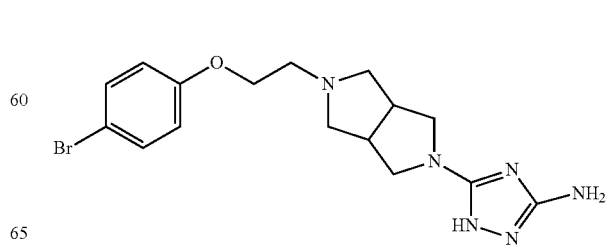

Step 1: tert-butyl 5-(2-(4-bromophenoxy)ethyl)hexahydropyrrolo[3,4-c]pyrrole-2(1H)-carboxylate

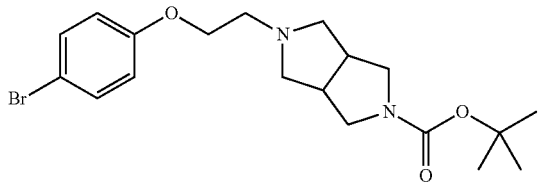 [SMILES: CC(C)(C)OC(=O)N1CC2CN(CCOc3ccc(Br)cc3)CC2C1]

Prepared in a manner similar to Example 26 (step 1) from 1-bromo-4-(2-bromoethoxy)benzene and 2-Boc-hexahydropyrrolo[3,4-c]pyrrole (2.00 g, 10.0 mmol). ESI-LCMS m/z calculated for $C_{19}H_{27}BrN_2O_3$: expected 411.34; found 412.2 [M+H]$^+$.

Step 2: 2-(2-(4-bromophenoxy)ethyl)octahydropyrrolo[3,4-c]pyrrole

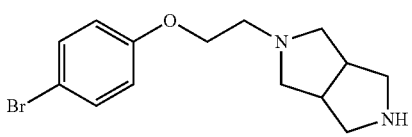 [SMILES: Brc1ccc(OCCN2CC3CNCC3C2)cc1]

Preparation and purification in a manner similar to Example 26 (step 2) from tert-butyl 5-(2-(4-bromophenoxy)ethyl)hexahydropyrrolo[3,4-c]pyrrole-2(1H)-carboxylate gave the desired product as a pale yellow oil. (0.8885 g, 99% yield). $^1$H NMR (CD$_3$OD, 400 MHz) δ (ppm) 7.10 (d, J=8.5, 2H), 6.98 (d, J=8.5, 2H), 4.12 (t, J=2.7, 2H), 3.13-2.98 (m, 8H), 2.90 (t, J=2.7, 2H), 2.77 (m, 2H); ESI-LCMS m/z calculated for $C_{13}H_{19}BrN_2O$: expected 299.21; found 300.2 [M+H]$^+$.

Step 3: methyl 5-(2-(4-bromophenoxy)ethyl)-N-cyanohexahydropyrrolo[3,4-c]pyrrole-2(1H)-carbimidothioate

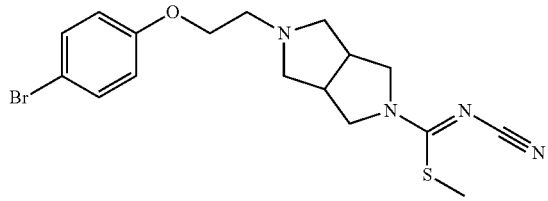 [SMILES: CS/C(=N\C#N)N1CC2CN(CCOc3ccc(Br)cc3)CC2C1]

Preparation and purification in a manner similar to Example 26 (step 3) from 2-(2-(4-bromophenoxy)ethyl)octahydropyrrolo[3,4-c]pyrrole gave the desired product by TLC and MS. ESI-LCMS m/z calculated for $C_{17}H_{21}BrN_4OS$: expected 409.35; found 410.2 [M+H]$^+$.

Step 4: 5-(5-(2-(4-bromophenoxy)ethyl)hexahydropyrrolo[3,4-c]pyrrol-2(1H)-yl)-1H-1,2,4-triazol-3-amine Preparation and purification in a manner similar to Example 26 (step 4) from methyl 5-(2-(4-bromophenoxy)ethyl)-N-cyanohexahydropyrrolo[3,4-c]pyrrole-2(1H)-carbimidothioate gave the desired product as a white solid (0.0662 g, 33% yield). $^1$H NMR (CD$_3$OD, 400 MHz) δ (ppm) 7.44 (d, J=8.0 Hz, 2H), 6.93 (d, J=8.0 Hz, 2H), 4.05 (m, 2H), 3.33 (s, 1H), 3.23 (m, 2H), 3.02 (d, J=9.2 Hz, 2H), 2.76 (m, 5H), 2.35 (m, 2H); ESI-LCMS m/z calculated for $C_{15}H_{21}BrN_6O$: expected 381.28; found 382.2 [M+H]$^+$.

Example 30: 1-(4-(3-amino-1H-1,2,4-triazol-5-yl)piperazin-1-yl)-2-phenoxyethanone

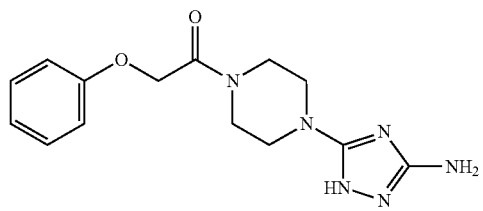 [SMILES: Nc1n[nH]c(N2CCN(C(=O)COc3ccccc3)CC2)n1]

Step 1: methyl N-cyano-4-(2-phenoxyacetyl)piperazine-1-carbimidothioate

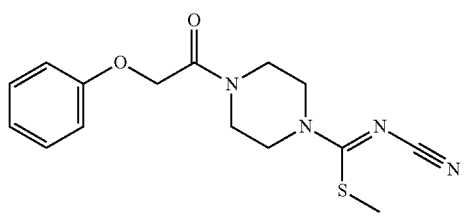 [SMILES: CS/C(=N\C#N)N1CCN(C(=O)COc2ccccc2)CC1]

2-phenoxy-1-(1-piperazinyl)ethanone (0.0551 g, 0.25 mmol), dimethyl cyanocarbonimidodithioate (0.0366 g, 0.25 mmol), and anhydrous acetonitrile (10 mL) were combined in a Biotage 10-20 mL microwave vial and irradiated at 160° C. for 1 hour. TLC and MS confirmed presence of the desired intermediate. The reaction solution was carried forward without purification. ESI-LCMS m/z calculated for $C_{15}H_{18}N_4O_2S$: expected 318.4; found 319.2 [M+H]$^+$.

Step 2: 1-(4-(3-amino-1H-1,2,4-triazol-5-yl)piperazin-1-yl)-2-phenoxyethanone

To the reaction solution from step 1 was added hydrazine hydrate monohydrate (0.1955 g, 2.50 mmol, 190 μL). Reaction was irradiated at 160° C. for 1 hour. The solvent was removed and the residue was purified by reverse-phase HPLC to give the desired product as a white solid. (0.018 g, 24% yield). $^1$H NMR (CD$_3$OD, 400 MHz) δ (ppm) 7.3-6.8 (m, 1H), 4.21 (s, 2H), 3.59 (m, 4H), 3.46 (bs, 2H), 3.07 (bs, 2H); ESI-LCMS m/z calculated for $C_{14}H_{17}BrN_6O_2$: expected 381.2; found 382.2 [M+H]$^+$.

Example 31: 1-(4-(3-amino-1H-1,2,4-triazol-5-yl)piperazin-1-yl)-2-(4-ethylphenoxy)propan-1-one

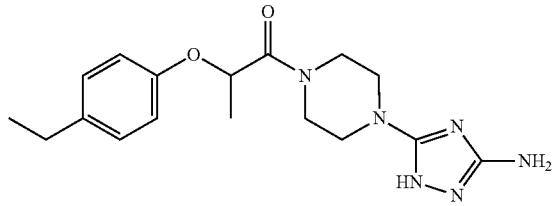 [SMILES: CCc1ccc(OC(C)C(=O)N2CCN(c3nc(N)n[nH]3)CC2)cc1]

Step 1: methyl N-cyano-4-(2-(4-ethylphenoxy)propanoyl)piperazine-1-carbimidothioate

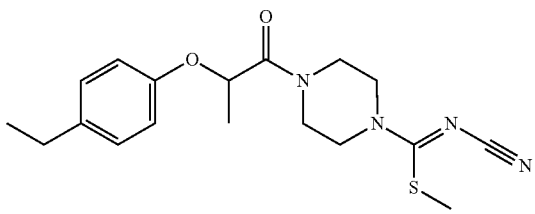 [SMILES: CCc1ccc(OC(C)C(=O)N2CCN(/C(=N/C#N)SC)CC2)cc1]

Prepared in a manner similar to Example 30 (step 1) from 1-[2-(4-ethylphenoxy)-propanoyl]-piperazine. ESI-LCMS m/z calculated for $C_{18}H_{24}N_4O_2S$: expected 360.48; found 361.2 $[M+H]^+$.

Step 2: 1-(4-(3-amino-1H-1,2,4-triazol-5-yl)piperazin-1-yl)-2-(4-ethylphenoxy)propan-1-one Preparation and purification in a manner similar to Example 30 (step 2) from methyl N-cyano-4-(2-(4-ethylphenoxy)propanoyl)piperazine-1-carbimidothioate gave the desired product as a white solid (0.0273 g, 24% yield). $^1$H NMR (CD$_3$OD, 400 MHz) δ (ppm) 7.10 (d, J=8.4, 2H), 6.77 (d, J=8.4, 2H), 5.73 (s, 3H), 5.20 (q, J=13.1, J=6.5, 1H), 3.69-3.45 (m, 4H), 3.21-3.10 (m, 4H), 1.42 (d, J=6.3, 2H), 1.14 (t, J=7.7, 3H); ESI-LCMS m/z calculated for $C_{17}H_{24}N_6O_2$: expected 344.42; found 345.2 $[M+H]^+$.

Example 32: 1-(4-(3-amino-1H-1,2,4-triazol-5-yl)piperazin-1-yl)-2-(o-tolyloxy)propan-1-one

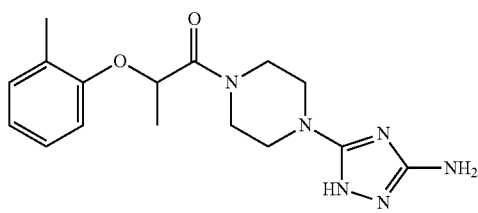 [SMILES: Cc1ccccc1OC(C)C(=O)N1CCN(c2nc(N)n[nH]2)CC1]

Step 1: methyl N-cyano-4-(2-(o-tolyloxy)propanoyl)piperazine-1-carbimidothioate

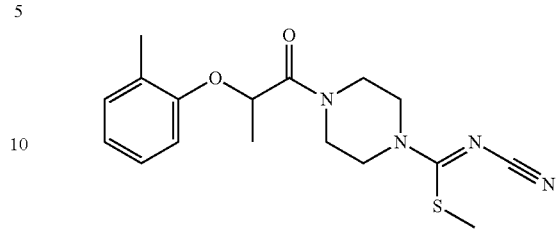

Prepared in a manner similar to Example 30 (step 1) from 1-(piperazin-1-yl)-2-(o-tolyloxy)propan-1-one. ESI-LCMS m/z calculated for $C_{17}H_{22}N_4O_2S$: expected 346.45; found 347.2 $[M+H]^+$.

Step 2: 1 1-(4-(3-amino-1H-1,2,4-triazol-5-yl)piperazin-1-yl)-2-(o-tolyloxy)propan-1-one Preparation and purification in a manner similar to Example 30 (step 2) from methyl N-cyano-4-(2-(o-tolyloxy)propanoyl)piperazine-1-carbimidothioate gave the desired product as a white solid (0.0525 g, 47% yield). $^1$H NMR (CD$_3$OD, 400 MHz) δ (ppm) 7.16-7.10 (m, 2H), 6.83 (t, J=7.2, 1H), 6.76 (d, J=7.9 Hz, 1H), 5.22 (q, J=13.2, J=6.1, 1H), 3.65 (bs, 2H), 3.52 (bs, 2H), 3.20-3.00 (m, 4H), 2.18 (s, 3H), 1.47 (d, J=6.3 Hz, 3H); ESI-LCMS m/z calculated for $C_{16}H_{22}N_6O_2$: expected 330.39; found 331.2 $[M+H]^+$.

Example 33: 1-(4-(3-amino-1H-1,2,4-triazol-5-yl)piperazin-1-yl)-2-(2-ethylphenoxy)propan-1-one

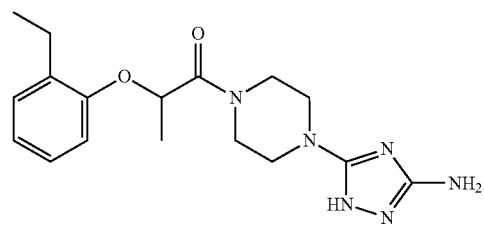 [SMILES: CCc1ccccc1OC(C)C(=O)N1CCN(c2nc(N)n[nH]2)CC1]

Step 1: methyl N-cyano-4-(2-(2-ethylphenoxy)propanoyl)piperazine-1-carbimidothioate

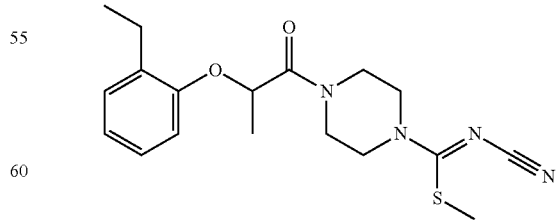

Prepared in a manner similar to Example 30 (step 1) from 2-(2-ethylphenoxy)-1-(piperazin-1-yl)propan-1-one. ESI-LCMS m/z calculated for $C_{18}H_{24}N_4O_2S$: expected 360.48; found 361.2 $[M+H]^+$.

Step 2: 1-(4-(3-amino-1H-1,2,4-triazol-5-yl)piperazin-1-yl)-2-(2-ethylphenoxy)propan-1-one Preparation and purification in a manner similar to Example 30 (step 2) from methyl N-cyano-4-(2-(2-ethylphenoxy)propanoyl)piperazine-1-carbimidothioate gave the desired product as a white solid (0.0156 g, 14% yield). $^1$H NMR (CD$_3$OD, 400 MHz) δ (ppm) 7.16-7.10 (m, 2H), 6.83 (t, J=7.2, 1H), 6.76 (d, J=7.9 Hz, 1H), 5.24 (q, J=13.2, J=6.1, 1H), 3.66 (bs, 2H), 3.53 (bs, 2H), 3.20-3.00 (m, 4H), 2.22 (s, 2H), 1.45 (d, J=6.0 Hz, 3H), 1.15 (t, J=7.6 Hz, 3H); ESI-LCMS m/z calculated for C$_{17}$H$_{24}$N$_6$O$_2$: expected 344.42; found 345.2 [M+H]$^+$.

Example 34: 1-(4-(3-amino-1H-1,2,4-triazol-5-yl)piperazin-1-yl)-2-(2,5-dimethyl phenoxy)propan-1-one

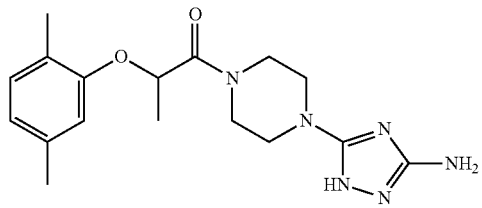 [SMILES: Cc1ccc(C)c(OC(C)C(=O)N2CCN(c3nc(N)n[nH]3)CC2)c1]

Step 1: methyl N-cyano-4-(2-(2,5-dimethylphenoxy)propanoyl)piperazine-1-carbimidothioate

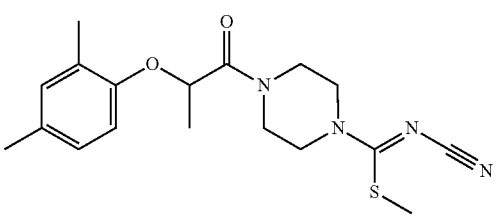 [SMILES: CS/C(=N\C#N)N1CCN(C(=O)C(C)Oc2ccc(C)cc2C)CC1]

Prepared in a manner similar to Example 30 (step 1) from 2-(2,5-dimethylphenoxy)-1-(piperazin-1-yl)propan-1-one. ESI-LCMS m/z calculated for C$_{18}$H$_{24}$N$_4$O$_2$S: expected 360.48; found 361.2 [M+H]$^+$.

Step 2: 1-(4-(3-amino-1H-1,2,4-triazol-5-yl)piperazin-1-yl)-2-(2,5-dimethylphenoxy)propan-1-one Preparation and purification in a manner similar to Example 30 (step 2) from methyl N-cyano-4-(2-(2,5-dimethylphenoxy)propanoyl)piperazine-1-carbimidothioate gave the desired product as a white solid (0.0748 g, 57% yield). $^1$H NMR (CD$_3$OD, 400 MHz) δ (ppm) 7.01 (d, J=7.0 Hz, 1H), 6.64 (d, J=7.0 Hz, 1H), 6.60 (s, 1H), 5.22 (q, J=13.2, J=6.1, 1H), 3.70-3.57 (m, 3H), 3.13 (bs, 3H), 3.53 (bs, 2H), 2.22 (s, 3H), 2.12 (s, 3H), 1.44 (d, J=6.0 Hz, 3H); ESI-LCMS m/z calculated for C$_{17}$H$_{24}$N$_6$O$_2$: expected 344.42; found 345.2 [M+H]$^+$.

Example 35: 1-(4-(3-amino-1H-1,2,4-triazol-5-yl)piperazin-1-yl)-2-(2,4-dimethyl phenoxy)propan-1-one

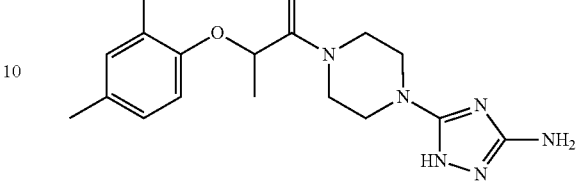

Step 1: methyl N-cyano-4-(2-(2,4-dimethylphenoxy)propanoyl)piperazine-1-carbimidothioate

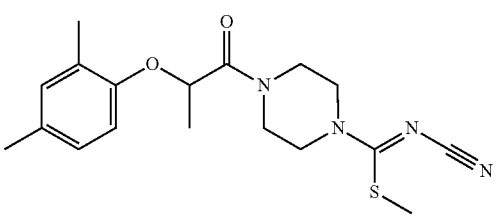 [SMILES: CS/C(=N\C#N)N1CCN(C(=O)C(C)Oc2ccc(C)cc2C)CC1]

Prepared in a manner similar to Example 30 (step 1) from 2-(2,4-dimethylphenoxy)-1-(piperazin-1-yl)propan-1-one. ESI-LCMS m/z calculated for C$_{18}$H$_{24}$N$_4$O$_2$S: expected 360.48; found 361.2 [M+H]$^+$.

Step 2: 1-(4-(3-amino-1H-1,2,4-triazol-5-yl)piperazin-1-yl)-2-(2,4-dimethylphenoxy)propan-1-one Preparation and purification in a manner similar to Example 30 (step 2) from methyl N-cyano-4-(2-(2,4-dimethylphenoxy)propanoyl)piperazine-1-carbimidothioate gave the desired product as a white solid (0.0587 g, 45% yield). $^1$H NMR (CD$_3$OD, 400 MHz) δ (ppm) 6.96 (s, 1H), 6.90 (d, J=8.0 Hz, 1H), 6.67 (d, J=8.0 Hz, 1H), 5.15 (q, J=13.2, J=6.1, 1H), 3.64 (bs, 2H), 3.51 (bs, 2H), 3.20-3.03 (m, 4H), 2.18 (s, 3H), 2.14 (s, 3H), 1.44 (d, J=6.0 Hz, 3H); ESI-LCMS m/z calculated for C$_{17}$H$_{24}$N$_6$O$_2$: expected 344.42; found 345.2 [M+H]$^+$.

Example 36: 1-(4-(3-amino-1H-1,2,4-triazol-5-yl)piperazin-1-yl)-2-(m-tolyloxy)propan-1-one

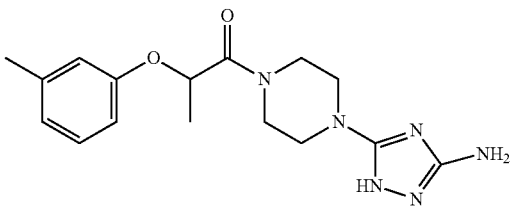 [SMILES: Cc1cccc(OC(C)C(=O)N2CCN(c3nc(N)n[nH]3)CC2)c1]

Step 1: methyl N-cyano-4-(2-(m-tolyloxy)propanoyl)piperazine-1-carbimidothioate

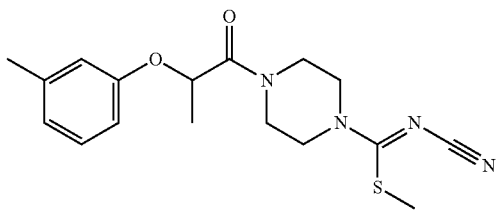 [SMILES: CS/C(=N\C#N)N1CCN(C(=O)C(C)Oc2cccc(C)c2)CC1]

Prepared in a manner similar to Example 30 (step 1) from 1-(piperazin-1-yl)-2-(m-tolyloxy)propan-1-one confirmed presence by TLC and MS of the desired intermediate. The reaction solution was carried forward without purification. ESI-LCMS m/z calculated for $C_{17}H_{22}N_4O_2S$: expected 346.45; found 347.2 [M+H]$^+$.

Step 2: 1-(4-(3-amino-1H-1,2,4-triazol-5-yl)piperazin-1-yl)-2-(m-tolyloxy)propan-1-one Preparation and purification in a manner similar to Example 30 (step 2) from methyl N-cyano-4-(2-(m-tolyloxy)propanoyl)piperazine-1-carbimidothioate gave the desired product as a white solid (0.0155 g, 14% yield). $^1$H NMR (CD$_3$OD, 400 MHz) δ (ppm) 7.05 (t, J=7.7 Hz, 1H), 6.65 (d, J=6.2, 1H), 6.60 (s, 1H), 6.55 (d, J=7.7 Hz, 1H), 5.22 (m, 1H), 3.65 (bs, 2H), 3.52 (bs, 2H), 3.20-3.00 (m, 4H), 2.18 (s, 3H), 1.47 (d, J=6.3 Hz, 3H); ESI-LCMS m/z calculated for $C_{16}H_{22}N_6O_2$: expected 330.39; found 331.2 [M+H]$^+$.

Example 37: 1-(4-(3-amino-1H-1,2,4-triazol-5-yl)piperazin-1-yl)-2-(2,3-difluorophenoxy)propan-1-one

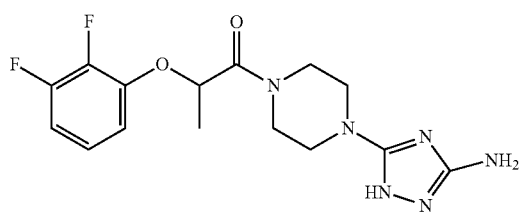 [SMILES: CC(Oc1cccc(F)c1F)C(=O)N1CCN(c2nc(N)n[nH]2)CC1]

Step 1: methyl N-cyano-4-(2-(2,3-difluorophenoxy)propanoyl)piperazine-1-carbimidothioate

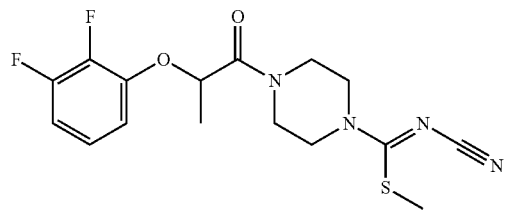 [SMILES: CS/C(=N\C#N)N1CCN(C(=O)C(C)Oc2cccc(F)c2F)CC1]

Prepared in a manner similar to Example 30 (step 1) from 2-(2,3-difluorophenoxy)-1-(piperazin-1-yl)propan-1-one, confirmed presence by TLC and MS of the desired intermediate. The reaction solution was carried forward without purification. ESI-LCMS m/z calculated for $C_{16}H_{18}F_2N_4O_2S$: expected 368.41; found 369.2 [M+H]$^+$.

Step 2: 1-(4-(3-amino-1H-1,2,4-triazol-5-yl)piperazin-1-yl)-2-(2,3-difluorophenoxy)propan-1-one Preparation and purification in a manner similar to Example 30 (step 2) from methyl N-cyano-4-(2-(2,3-difluorophenoxy)propanoyl)piperazine-1-carbimidothioate gave the desired product as a white solid (0.0415 g, 39% yield). $^1$H NMR (CD$_3$OD, 400 MHz) δ (ppm) 7.07-7.04 (m, 1H), 6.91-6.85 (m, 1H), 6.81-6.76 (m, 1H), 5.35-5.25 (m, 1H), 3.67 (t, J=40.8 Hz), 4H), 3.32 (m, 2H), 2.91-2.81 (m, 2H), 1.91 (s, 3H); ESI-LCMS m/z calculated for $C_{16}H_{22}N_6O_2$: expected 352.35; found 353.2 [M+H]$^+$.

Comparative Example 38

5-(piperazin-1-yl)-1H-1,2,4-triazol-3-amine trihydrochloride

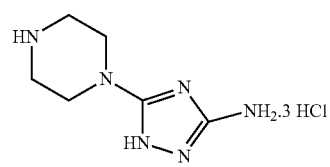

Step 1: tert-butyl 4-((cyanoimino)(methylthio)methyl)piperazine-1-carboxylate

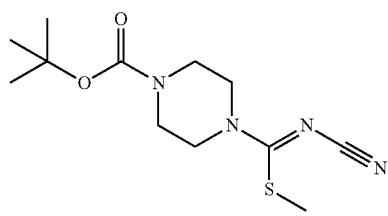 [SMILES: CS/C(=N\C#N)N1CCN(C(=O)OC(C)(C)C)CC1]

Prepared in a manner similar to Example 1 (step 1) from 5 g (26.85 mmol) BOC-piperazine to give 7.21 g (94%). ESI MS for $C_{12}H_{20}N_4O_2S$ calculated m/z 284.13, found 229.2 [M-tBu]$^+$, 307.4 [M+Na]$^+$.

Step 2: tert-butyl 4-(3-amino-1H-1,2,4-triazol-5-yl)piperazine-1-carboxylate

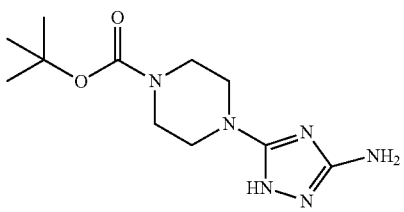 [SMILES: CC(C)(C)OC(=O)N1CCN(c2nc(N)n[nH]2)CC1]

Preparation and purification in a manner similar to Example 1 (step 2) tert-butyl 4-((cyanoimino)(methylthio)methyl)piperazine-1-carboxylate gave the desired product as a white solid, 5.95 g (88%). ESI MS for $C_{11}H_{20}N_6O_2$ m/z calculated 268.16, found 269.4 [M+H]$^+$.

Step 3: 5-(piperazin-1-yl)-1H-1,2,4-triazol-3-amine trihydrochloride

Tert-butyl 4-(3-amino-1H-1,2,4-triazol-5-yl)piperazine-1-carboxylate (5.95 g, 22.17 mmol) was stirred with 5.6M HCl/AcOEt (50 mL) 2 h at ambient temperature, evaporated to dryness. Residue was washed with diethyl ether, dried to give 5.5 g (90%) as white solid. ESI MS for $C_6H_{12}N_6$ calculated m/z 168.11, found 169.1 [M+H]$^+$.

Example 39: 5-(4-(3-(4-bromophenyl)-2-methylpropyl)piperazin-1-yl)-1H-1,2,4-triazol-3-amine dihydrochloride

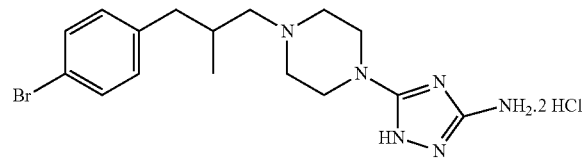

Step 1: 3-(4-bromophenyl)-2-methylpropanal

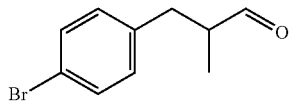

To a solution of 4-bromoaniline (8 g, 46.5 mmol) in MeCN (150 mL) a mixture of $H_2SO_4$ (5.2 mL, 97.66 mmol) in 70 mL $H_2O$ was added at room temperature. White solid was formed. Added β-methallyl alcohol (8.68 mL, 102.3 mmol), and a solution of $PdCl_2$ (0.052 g, 0.293 mmol) in MeCN (5 mL) (this solution was prepared by refluxing for 5 h to dissolve $PdCl_2$). Finally $NaNO_2$ in $H_2O$ (20 mL) was added in one portion (solution turned brown) and the mixture was stirred at room temperature overnight. TLC showed no substrate (aniline). Reaction was diluted with water, extracted with ethyl acetate, washed with brine, dried over $MgSO_4$, filtered and concentrated to dryness to give 6 g (57%). This material was used without further characterization.

Step 2: 5-(4-(3-(4-bromophenyl)-2-methylpropyl)piperazin-1-yl)-1H-1,2,4-triazol-3-amine dihydrochloride A mixture of 3-(4-bromophenyl)-2-methylpropanal (0.14 g, 0.616 mmol), (5-piperazin-1-yl-1H-1,2,4-triazol-3-amine trihydrochloride) (0.17 g, 0.616 mmol), and triethylamine (0.427 mL, 3.08 mmol) in 1,2 dichloroethane (5 mL) were stirred for 1 h at room temperature. Sodium triacetoxyborohydride (0.39 g, 1.85 mmol) was added by portions and the mixture was stirred overnight. The mixture was taken into 1M NaOH and ethyl acetate. Organic layer was washed with 1M NaOH and brine, dried over $MgSO_4$, filtered, evaporated to dryness to give 0.12 g material, which was separated by preparative chromatography (10-50% MeCN, 220 nm, 120 min). Proper fractions were combined, stirred with 1M HCl (5 mL) for 30 minutes, and evaporated to dryness to give 50 mg of white solid (21%). $^1$H NMR (DMSO, 600 MHz) δ (ppm) 10.97 (brs, 1H), 7.48 (d, J=8 Hz, 2H), 7.22 (d, J=8 Hz, 2H), 3.92-3.81 (m, 2H), 3.6-3.52 (m, 4H), 3.17-3.08 (m, 1H). 3.08-2.95 (m, 3H), 2.95-2.89 (m, 1H), 2.39-2.3 (m, 1H), 2.3-2.22 (m, 1H), 0.89 (d, J=6.4, 3H). ESI MS for $C_{16}H_{23}BrN_6$ calculated m/z 378.12, found 379.5/381.5 [M+H]$^+$.

Example 40: 3-amino-1-(4-(3-amino-1H-1,2,4-triazol-5-yl)piperazin-1-yl)-3-(4-chlorophenyl)propan-1-one

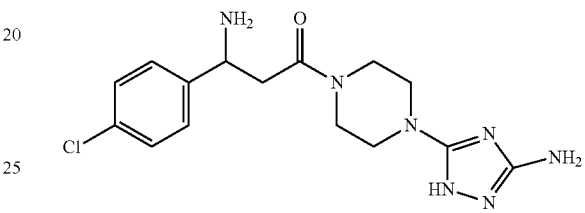

Step 1: tert-butyl (3-(4-(3-amino-1H-1,2,4-triazol-5-yl)piperazin-1-yl)-1-(4-chlorophenyl)-3-oxopropyl)carbamate

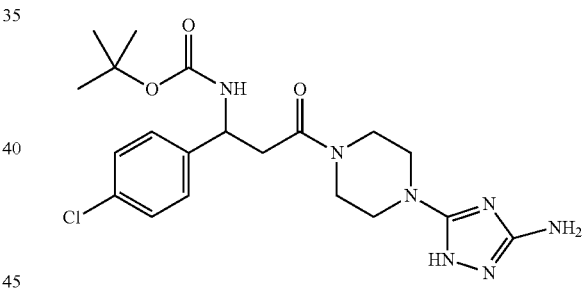

2-Chloro-4,6-dimethoxy-1,3,5-triazine (CDMT) (0.07 g, 0.396 mmol) in dichloromethane (5 mL) was cooled to 0° C., N-methylmorpholine (0.163 mL, 1.48 mmol) was added and stirred at 0° C. for 20 min. 3-[(tert-butoxycarbonyl)amino]-3-(4-chloro phenyl)propanoic acid (0.108 g, 0.36 mmol) was added and stirred for 1 h at 0° C. 5-Piperazin-1-yl-1H-1,2,4-triazol-3-amine trihydrochloride (0.1 g, 0.36 mmol) was added by portions for 1 h at 0° C. and stirred for 2 h at 0° C. After 2 h LCMS showed only a 1:1 mixture of 2 products (mono and di-coupled). The mixture was washed with water, brine, dried over $MgSO_4$. Filtered, concentrated, and separated using flash chromatography with silica gel ($CH_2Cl_2$:MeOH 30:1). Yield 0.045 g (28%) as white foam. ESI MS m/z for $C_{20}H_{28}ClN_7O$: calculated 449.19, found 450.5/452.5 [M+H]$^+$.

Step 2: 3-amino-1-(4-(3-amino-1H-1,2,4-triazol-5-yl)piperazin-1-yl)-3-(4-chlorophenyl)propan-1-one Tert-butyl (3-(4-(3-amino-1H-1,2,4-triazol-5-yl)piperazin-1-yl)-1-(4-chlorophenyl)-3-oxopropyl)carbamate in 5.5M HCl/ethyl acetate was stirred for 30 minutes at room temperature, then evaporated to dryness. Residue was washed with diethyl ether, dried to give 0.039 g of yellow solid (93%). $^1$H NMR (DMSO, 600 MHz) δ (ppm) 8.76-8.58 (m, 3H), 7.59 (d, J=7.5 Hz, 2H), 7.44 (d, J=7.7 Hz, 2H), 4.62-4.48 (m, 1H), 3.43-3.38 (m, 1H), 3.38-3.3 (m, 2H). 3.3-3.15 (m, 4H), 3.14-3.09 (m, 2H), 3.05-2.97 (m, 1H). ESI MS m/z for $C_{15}H_{20}ClN_7O$: calculated 349.14, found 350.5/352.5 $[M+H]^+$, 352.5 $[M-H]^-$.

Example 41: 5-(4-(3-(benzo[d][1,3]dioxol-5-yl)-1,2,4-oxadiazol-5-yl)piperidin-1-yl)-1H-1,2,4-triazol-3-amine

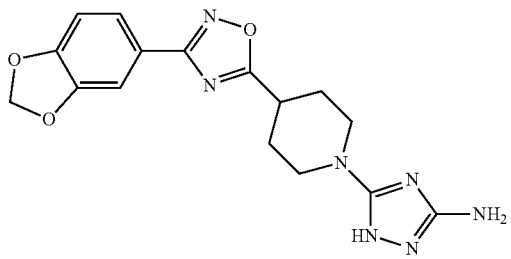 [SMILES: Nc1n[nH]c(N2CCC(c3nc(-c4ccc5c(c4)OCO5)no3)CC2)n1]

Prepared from 3-(benzo[d][1,3]dioxol-5-yl)-5-(piperidin-4-yl)-1,2,4-oxadiazole, intermediate carried through without characterization to give 5-(4-(3-(benzo[d][1,3]dioxol-5-yl)-1,2,4-oxadiazol-5-yl)piperidin-1-yl)-1H-1,2,4-triazol-3-amine $^1$H NMR (DMSO-$d_6$, 400 MHz): δ (ppm) 10.90 (bs, 1H), 7.60-7.54 (m, 1H), 7.45 (bs, 1H), 7.12-7.07 (m, 1H), 6.14 (bs, 2H), 5.75 (bs, 2H), 3.86-3.79 (m, 2H), 3.35-3.24 (m, 1H), 2.95-2.80 (m, 2H), 2.11-2.03 (m, 2H), 1.87-1.74 (m, 2H). ESI MS for $C_{16}H_{17}N_7O_3$; expected 355.14; found m/z 356.0 $[M+H]^+$.

Example 42: 5-(4-(3-(4-(methylsulfonyl)phenyl)-1,2,4-oxadiazol-5-yl)piperidin-1-yl)-1H-1,2,4-triazol-3-amine

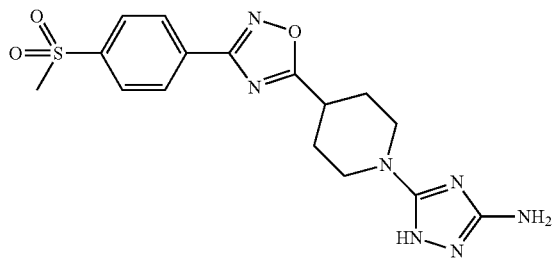 [SMILES: CS(=O)(=O)c1ccc(-c2noc(C3CCN(c4nc(N)n[nH]4)CC3)n2)cc1]

Prepared from 3-(4-(methylsulfonyl)phenyl)-5-(piperidin-4-yl)-1,2,4-oxadiazole, intermediate was carried through without characterization to give 5-(4-(3-(4-(methylsulfonyl) phenyl)-1,2,4-oxadiazol-5-yl)piperidin-1-yl)-1H-1,2,4-triazol-3-amine $^1$H NMR (DMSO-$d_6$, 400 MHz): δ (ppm) 11.00 (bs, 1H), 8.27 (bd, J=7.5 Hz, 2H), 8.12 (bd, J=7.5 Hz, 2H), 5.80 (bs, 2H), 3.89-3.80 (m, 2H), 3.40-3.32 (m, 1H), 2.97-2.86 (m, 2H), 2.14-2.06 (m, 2H), 1.90-1.78 (m, 2H). ESI MS for $C_{16}H_{19}N_7O_3S$; expected 389.13; found m/z 390.2 $[M+H]^+$.

Example 43: 5-(4-(5-(4-fluorophenyl)-1,3,4-oxadiazol-2-yl)piperidin-1-yl)-1H-1,2,4-triazol-3-amine

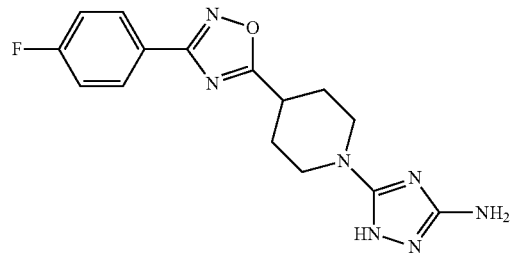 [SMILES: Nc1n[nH]c(N2CCC(c3nc(-c4ccc(F)cc4)no3)CC2)n1]

Prepared from 2-(4-fluorophenyl)-5-(piperidin-4-yl)-1,3,4-oxadiazole, intermediate was carried through without characterization to give 5-(4-(5-(4-fluorophenyl)-1,3,4-oxadiazol-2-yl)piperidin-1-yl)-1H-1,2,4-triazol-3-amine $^1$H NMR (DMSO-$d_6$, 400 MHz): δ (ppm) 11.0 (bs, 1H), 8.10-8.02 (m, 2H), 7.48-7.41 (m, 2H), 5.75 (bs, 2H), 3.85-3.78 (m, 2H), 3.20-3.14 (m, 1H), 2.97-2.85 (m, 2H), 2.15-2.10 (m, 2H), 1.86-1.76 (m, 2H). ESI MS for $C_{15}H_{16}FN_7O$; expected 329.33; found m/z 330.3 $[M+H]^+$.

Example 44: 1-(4-(3-amino-1H-1,2,4-triazol-5-yl)piperazin-1-yl)-2-(2-fluorophenoxy)propan-1-one

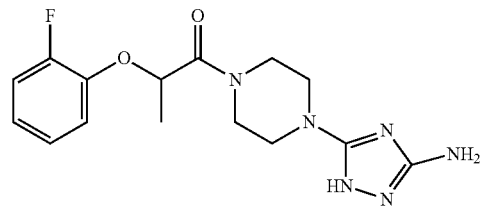 [SMILES: CC(Oc1ccccc1F)C(=O)N1CCN(c2nc(N)n[nH]2)CC1]

Prepared from 2-(2-fluorophenoxy)-1-(piperazin-1-yl)propan-1-one, intermediate was carried through without characterization to give 1-(4-(3-amino-1H-1,2,4-triazol-5-yl)piperazin-1-yl)-2-(2-fluorophenoxy)propan-1-one, $^1$H NMR (CD$_3$OD, 400 MHz) δ 7.174 (m, 2H), 6.917 (m, 2H), 5.212 (m, 1H), 3.65 (bs, 2H), 3.52 (bs, 2H), 3.20-3.00 (m, 4H), 1.47 (d, J=6.3 Hz, 3H); ESI-LCMS m/z calculated for $C_{15}H_{19}FN_6O_2$: expected 334.16; found 335.2 $[M+H]^+$.

Example 45: 1-(4-(3-amino-1H-1,2,4-triazol-5-yl)piperazin-1-yl)-2-(2-chloro-4-methyl phenoxy)propan-1-one

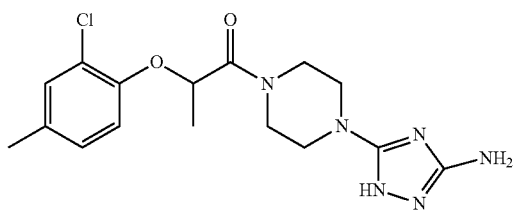 [SMILES: Cc1ccc(OC(C)C(=O)N2CCN(c3nc(N)n[nH]3)CC2)c(Cl)c1]

Prepared from 2-(2-fluorophenoxy)-1-(piperazin-1-yl)propan-1-one, intermediate was carried through without characterization to give 1-(4-(3-amino-1H-1,2,4-triazol-5- yl)piperazin-1-yl)-2-(2-chloro-4-methylphenoxy)propan-1-one. $^1$H NMR (CD$_3$OD, 400 MHz) δ (ppm) 7.240 (m, 1H), 7.057 (m, 1H), 6.864 (m, 1H), 5.158 (m, 1H), 3.846 (m, 1H), 3.598 (m, 2H), 3.518 (m, 1H), 3.148 (m, 2H), 2.679 (m, 1H), 2.274 (bs, 3H), 1.916 (s, 1H), 1.610 (m, 3H); ESI-LCMS m/z calculated for C$_{16}$H$_{21}$ClN$_6$O$_2$: expected 364.14; found 365.2/367.2 [M+H]$^+$.

Example 47: benzyl 4-(3-amino-1H-1,2,4-triazol-5-yl)piperazine-1-carboxylate

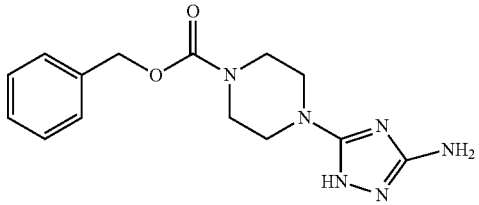 [SMILES: Nc1n[nH]c(N2CCN(C(=O)OCc3ccccc3)CC2)n1]

Prepared from benzyl piperazine-1-carboxylate, intermediate was carried through without characterization to give the titled compound; $^1$H NMR (CD$_3$OD, 400 MHz) δ 7.359 (m, 5H), 5.102 (bs, 2H), 3.457 (bs, 4H), 3.165 (bs, 4H); ESI-LCMS m/z calculated for C$_{14}$H$_{18}$N$_6$O$_2$: expected 302.15; found 303.2 [M+H]$^+$.

Example 48: (4-(3-amino-1H-1,2,4-triazol-5-yl)piperazin-1-yl)(benzofuran-2-yl)methanone

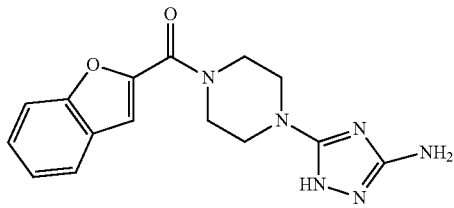 [SMILES: Nc1n[nH]c(N2CCN(C(=O)c3cc4ccccc4o3)CC2)n1]

Prepared from benzofuran-2-yl(piperazin-1-yl)methanone, intermediate was carried through without characterization to give the titled compound; $^1$H NMR (CD$_3$OD, 400 MHz) δ 7.751 (m, 1H), 7.618 (m, 1H), 7.477 (m, 1H), 7.434 (bs, 1H), 7.354 (m, 1H), 3.955 (bs, 4H), 3.439 (bs, 4H); ESI-LCMS m/z calculated for C$_{15}$H$_{16}$N$_6$O$_2$: expected 312.13; found 313.2 [M+H]$^+$.

Example 49: 1-(3-amino-1H-1,2,4-triazol-5-yl)-N-(4-fluorobenzyl)piperidine-4-carboxamide

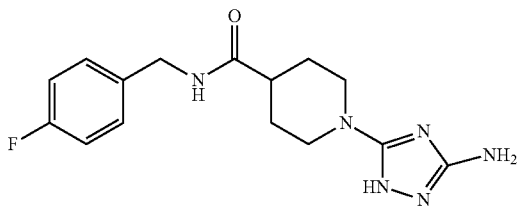 [SMILES: Nc1n[nH]c(N2CCC(C(=O)NCc3ccc(F)cc3)CC2)n1]

Prepared from (4-fluorophenyl)methanamine and 1-(3-amino-1H-1,2,4-triazol-5-yl)piperidine-4-carboxylic acid as described in Example 5 (step 3) to give 1-(3-amino-1H-1,2,4-triazol-5-yl)-N-(4-fluorobenzyl)piperidine-4-carboxamide. Yield: 0.077 g (39%). $^1$H NMR (DMSO, 500 MHz) δ (ppm) 10.97 (bs, 1H), 8.33 (t, J=5.8 Hz, 1H), 7.24-7.20 (m, 2H), 7.16-7.08 (m, 2H), 5.58 (bs, 2H), 4.22 (d, J=5.5 Hz, 2H), 3.83-3.76 (m, 2H), 2.68-2.57 (m, 2H), 2.32-2.25 (m, 1H), 1.69-1.62 (m, 2H), 1.61-1.49 (m, 2H). $^{19}$F NMR (DMSO, 200 MHz) δ −115.77 (s, 1F). ESI-LCMS m/z for C$_{15}$H$_{19}$FN$_6$O$_2$: expected 318.4; found 319.4 [M+H]$^+$, 317.4 [M−H]$^−$.

Example 50: 1-(3-amino-1H-1,2,4-triazol-5-yl)-N-(4-fluoro-2-(trifluoromethyl)benzyl)piperidine-4-carboxamide

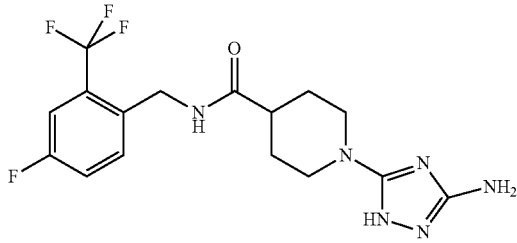 [SMILES: Nc1n[nH]c(N2CCC(C(=O)NCc3ccc(F)cc3C(F)(F)F)CC2)n1]

Prepared from (4-fluoro-2-trifluoromethyl)benzylamine and 1-(3-amino-1H-1,2,4-triazol-5-yl)piperidine-4-carboxylic acid as described in Example 5 (step 3) to give the titled compound. Yield: 0.16 g (53%). $^1$H NMR (DMSO, 500 MHz) δ 11.10 (bs, 1H), 8.44 (t, J=5.7 Hz, 1H), 7.60-7.56 (m, 1H), 7.55-7.49 (m, 1H), 7.49-7.45 (m, 1H), 5.50 (s, 2H), 4.37 (d, J=5.2 Hz, 2H), 3.85-3.75 (m, 2H), 2.68-2.59 (m, 2H), 2.39-2.32 (m, 1H), 1.74-1.65 (m, 2H), 1.60-1.51 (m, 2H). $^{19}$F NMR (DMSO, 200 MHz) δ −58.74 (s, 3F), −113.64 (s, 1F). ESI-LCMS m/z for C$_{16}$H$_{18}$F$_4$N$_6$O: expected 386.4; found 387.5 [M+H]$^+$, 385.4 [M−H]$^−$.

Example 51: 1-(3-amino-1H-1,2,4-triazol-5-yl)-N-(2-fluorobenzyl)piperidine-4-carboxamide

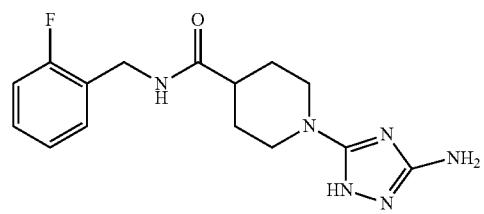 [SMILES: Nc1n[nH]c(N2CCC(C(=O)NCc3ccccc3F)CC2)n1]

Prepared from 2-fluorobenzylamine and 1-(3-amino-1H-1,2,4-triazol-5-yl)piperidine-4-carboxylic acid as described in Example 5 (step 3). $^1$H NMR (DMSO-d$_6$, 200 MHz) δ (ppm) 10.99 (bs, 1H), 8.35 (t, J=5.8 Hz, 1H), 7.40-7.11 (m, 4H), 5.56 (bs, 2H), 4.31 (d, J=5.6 Hz, 2H), 3.80-3.75 (m, 2H), 2.76-2.56 (m, 2H), 2.47-2.25 (m, 1H), 1.80-1.45 (m, 4H). ESI-LCMS m/z calculated for C$_{15}$H$_{19}$FN$_6$O: expected 318.4; found [M+H]$^+$=319.5.

Example 52: 1-(3-amino-1H-1,2,4-triazol-5-yl)-N-(4-chlorobenzyl)piperidine-4-carboxamide

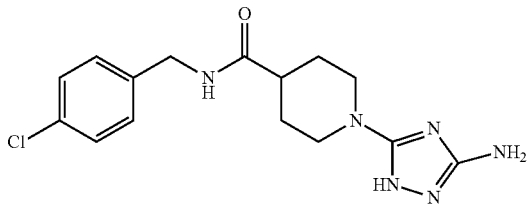 [SMILES: Nc1n[nH]c(N2CCC(C(=O)NCc3ccc(Cl)cc3)CC2)n1]

Prepared from 4-chlorobenzylamine and 1-(3-amino-1H-1,2,4-triazol-5-yl)piperidine-4-carboxylic acid as described in Example 5 (step 3). $^1$H NMR (DMSO-$d_6$, 200 MHz) δ (ppm) 11.00 (bs, 1H), 8.39 (t, J=6.1 Hz, 1H), 7.40 (d, J=8.0 Hz, 2H), 7.26 (d, J=8.1 Hz, 2H), 5.57 (bs, 2H), 4.26 (d, J=5.6 Hz, 2H), 3.93 (m, 2H), 2.77 (m, 2H), 2.44-2.29 (m, 1H), 1.81-1.46 (m, 4H). ESI-LCMS m/z calculated for $C_{15}H_{19}ClN_6O$: expected 334.8; found [M+H]$^+$=335.5.

Example 53: 1-(3-amino-1H-1,2,4-triazol-5-yl)-N-(2-bromobenzyl)piperidine-4-carboxamide

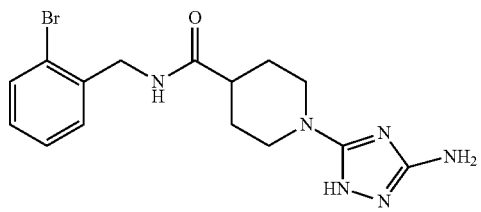 [SMILES: Nc1n[nH]c(N2CCC(C(=O)NCc3ccccc3Br)CC2)n1]

Prepared from 2-bromobenzylamine and 1-(3-amino-1H-1,2,4-triazol-5-yl)piperidine-4-carboxylic acid as described in Example 5 (step 3). $^1$H NMR (CD$_3$OD, 500 MHz) (ppm) 7.63-7.59 (m, 1H), 7.39-7.34 (m, 2H), 7.25-7.19 (m, 1H), 4.47 (brs, 2H), 3.90-3.83 (m, 2H), 3.13-3.04 (m, 2H), 2.63-2.54 (m, 1H), 1.96-1.87 (m, 2H), 1.88-1.78 (m, 2H). ESI MS for $C_{15}H_{19}BrN_6O$; expected 379.26; found m/z 379.4/381.4: [M+H]+; Yield 7 mg, 6%, after HPLC.

Example 54: 1-(3-amino-1H-1,2,4-triazol-5-yl)-N-(4-fluoro-3-(trifluoromethyl)benzyl)piperidine-4-carboxamide

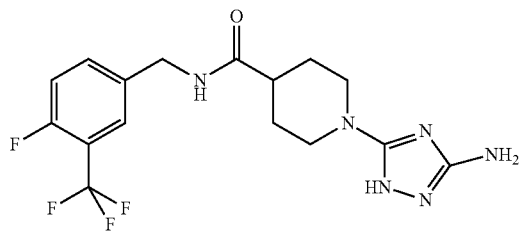 [SMILES: Nc1n[nH]c(N2CCC(C(=O)NCc3ccc(F)c(C(F)(F)F)c3)CC2)n1]

Prepared from (4-fluoro-3-trifluoromethyl)benzylamine and 1-(3-amino-1H-1,2,4-triazol-5-yl)piperidine-4-carboxylic acid as described in Example 5 (step 3); yield 50 mg (17%). $^1$H NMR (DMSO, 500 MHz) δ (ppm) 8.48 (t, J=5.8 Hz, 1H), 7.61-7.54 (m, 2H), 7.47-7.42 (m, 1H), 4.28 (d, J=5.8 Hz, 2H),3.82-3.76 (m, 2H), 2.66-2.55 (m, 2H), 2.35-2.25 (m, 1H). 1.68-1.62 (m, 2H), 1.59-1.48 (m, 2H). ESI MS for $C_{16}H_{18}F_4N_6O$ expected 386.15, found m/z 387.6 [M+H]$^+$, 385.5 [M–H]$^-$.

Example 55: 5-(4-(((4-bromobenzyl)(methyl)amino)methyl)piperidin-1-yl)-1H-1,2,4-triazol-3-amine

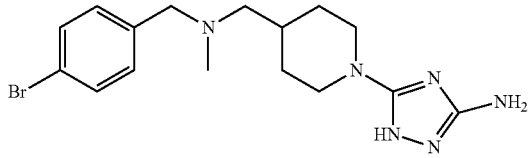 [SMILES: CN(Cc1ccc(Br)cc1)CC1CCN(c2nc(N)n[nH]2)CC1]

Prepared from 4-bromobenzaldehyde and tert-butyl 4-(aminomethyl)piperidine-1-carboxylate via tert-butyl 4-(((4-bromobenzyl)amino)methyl)piperidine-1-carboxylate. Yield: 1.51 g (84%). ESI-LCMS m/z for $C_{18}H_{27}BrN_2O_2$: expected 383.3; found 329.3/329.3 [M–tBu]$^+$. Then, tert-butyl 4-(((4-bromobenzyl)(methyl)amino)methyl)-piperidine-1-carboxylate was obtained; yield: 0.68 g (95%). ESI-LCMS m/z for $C_{19}H_{29}BrN_2O_2$: expected 397.4; found 341.5/343.5 [M-tBu]$^+$, followed by N-(4-bromobenzyl)-N-methyl-1-(piperidin-4-yl)methanamine. Finally, 5-(4-(((4-bromobenzyl)(methyl)amino)methyl)piperidin-1-yl)-1H-1,2,4-triazol-3-amine was obtained in 11% yield (0.080 g) after HPLC. $^1$H NMR (DMSO, 600 MHz) δ (ppm) 10.98 (bs, 1H), 7.68-7.60 (m, 4H), 7.41 (bs, 2H), 4.32-4.23 (m, 2H), 3.83-3.73 (m, 2H), 3.00-2.90 (m, 2H), 2.89-2.83 (m, 2H), 2.69-2.63 (m, 3H), 2.12-1.99 (m, 2H), 1.80-1.74 (m, 1H), 1.25-1.07 (m, 2H). ESI-LCMS m/z for $C_{16}H_{23}BrN_6$: expected 379.3; found 379.3/381.4 [M+H]+.

Example 56: N-(1-(3-amino-1H-1,2,4-triazol-5-yl)piperidin-4-yl)-1-(3-fluorophenyl)methanesulfonamide

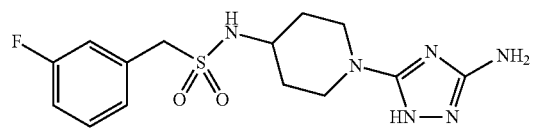 [SMILES: Nc1n[nH]c(N2CCC(NS(=O)(=O)Cc3cccc(F)c3)CC2)n1]

The title compound was prepared via tert-butyl 4-((3-fluorophenyl)-methylsulfonamido)piperidine-1-carboxylate, ESI-LCMS m/z calculated for $C_{17}H_{25}FN_2O_4S$: expected 372.5; found (M)$^-$=372.5, followed by 1-(3-fluorophenyl)-N-(piperidin-4-yl)methanesulfonamide. ESI-LCMS m/z calculated for $C_{12}H_{17}FN_2O_2S$: expected 272.3; found [M+H]$^+$=273.3. Finally, N-(1-(3-amino-1H-1,2,4-triazol-5-yl)piperidin-4-yl)-1-(3-fluorophenyl)methanesulfonamide was obtained: $^1$H NMR (DMSO-$d_6$, 500 MHz) δ (ppm): 10.90 (bs, 1H), 7.43-7.39 (m, 1H), 7.23-7.15 (m, 4H), 5.70 (bs, 2H), 4.37 (s, 2H), 3.72-3.68 (m, 2H), 3.25-3.16 (m, 1H), 2.76-2.60 (m, 2H), 1.80-1.71 (m, 2H), 1.43-1.33 (m, 2H). $^{19}$F NMR (DMSO-$d_6$, 200 MHz) δ (ppm): –113.13 (s, 1F). ESI-LCMS m/z calculated for $C_{14}H_{19}FN_6O_2S$: expected 354.4; found [M+H]$^+$=355.4.

Example 57: N-(1-(3-amino-1H-1,2,4-triazol-5-yl)piperidin-4-yl)-1-(4-fluorophenyl)methanesulfonamide

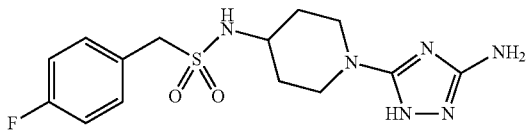 [SMILES: Nc1n[nH]c(N2CCC(NS(=O)(=O)Cc3ccc(F)cc3)CC2)n1]

Step 1: tert-butyl 4-((4-fluorophenyl)methylsulfonamido)piperidine-1-carboxylate

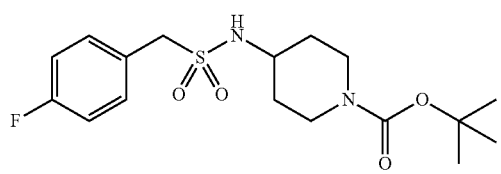 [SMILES: CC(C)(C)OC(=O)N1CCC(NS(=O)(=O)Cc2ccc(F)cc2)CC1]

Prepared from (4-fluorophenyl)methanesulfonyl chloride (0.525 g, 2.516 mmol) and 1-Boc-4-aminopiperidine (0.554 g, 2.768 mmol). Yield: 0.644 g (68.7%). ESI-LCMS m/z for $C_{17}H_{25}FN_2O_4S$: expected 372.15, found 395.5 [M+Na]$^+$, 371.6 [M−H]$^-$.

Step 2: 1-(4-fluorophenyl)-N-(piperidin-4-yl)methanesulfonamide hydrochloride

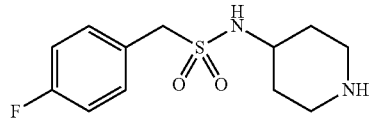 [SMILES: O=S(=O)(Cc1ccc(F)cc1)NC1CCNCC1]

0.330 g of tert-butyl 4-((4-fluorophenyl)methylsulfonamido)piperidine-1-carboxylate was reacted to give the titled compound. Yield: 0.225 g (93%). ESI-LCMS m/z for $C_{12}H_{17}FN_2O_2S$: expected 272.10, found: 273.3 [M+H]$^+$.

Step 3: N-(1-(3-amino-1H-1,2,4-triazol-5-yl)piperidin-4-yl)-1-(4-fluorophenyl)methanesulfonamide Yield 0.165 g (83%). $^1$H NMR (DMSO-d$_6$, 500 MHz) δ (ppm) 10.93 (brs, 1H), 7.41 (dd, J=8.5 Hz; J=5.6 Hz, 2H), 7.20 (t, J=8.8 Hz, 2H), 7.14 (d, J=7.5 Hz, 1H), 5.66 (brs, 2H), 4.33 (s, 2H), 3.68-3.70 (m, 2H), 3.17-3.21 (m, 1H), 2.65-2.67 (m, 2H), 1.75-1.77 (m, 2H), 1.34-1.41 (m, 2H). $^{19}$F NMR (DMSO-d$_6$, 200 MHz) δ (ppm) 113.8. ESI-LCMS expected 354.13, found m/z for $C_{14}H_{19}FN_6O_2S$: found 355.4 [M+H]$^+$; 353.4 [M−H]$^-$.

Example 58: N-(1-(3-amino-1H-1,2,4-triazol-5-yl)piperidin-4-yl)-1-(3,5-dichlorophenyl)methanesulfonamide

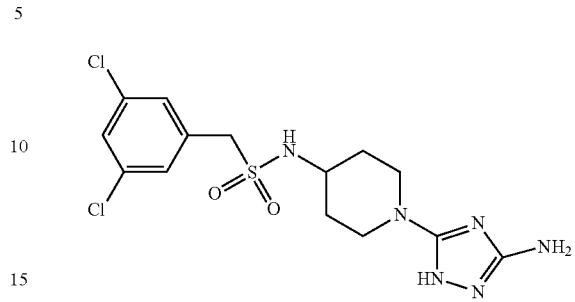

Prepared from (3,5-dichlorophenyl)methanesulfonamide. Yield: 0.107 g (55%). $^1$H NMR (DMSO, 600 MHz) δ (ppm) 10.90 (bs, 1H), 7.62 (s, 1H), 7.45-7.44 (m, 2H), 5.56 (bs, 2H), 4.43 (s, 2H), 3.75-3.68 (m, 2H), 3.26-3.19 (m, 1H), 2.75-2.65 (m, 2H), 1.80-1.73 (m, 2H), 1.45-1.35 (m, 2H). ESI-LCMS m/z for $C_{14}H_{18}Cl_2N_6O_2S$: expected 405.3; found 405.4/407.3 [M+H]$^+$.

Example 59: N-(1-(3-amino-1H-1,2,4-triazol-5-yl)piperidin-4-yl)-1-(3-chlorophenyl)methanesulfonamide

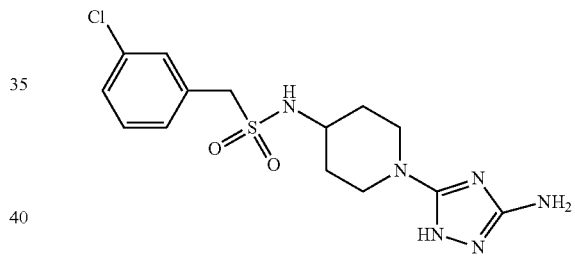

$^1$H NMR (DMSO, 600 MHz) δ (ppm) 7.45 (brs, 1H), 7.42-7.39 (m, 2H), 7.36-7.32 (m, 1H), 7.24-7.2 (M, 1H), 5.6 (brs, 2H), 4.37 (s, 2H), 3.73-3.67 (m, 2H). 3.19 (brs, 1H), 2.67 (brs, 2H), 1.78-1.74 (m, 2H), 1.42-1.34 (m, 2H). Yield 0.24 g (62%). ESI MS found for $C_{16}H_{19}ClN_6O_2S$ expected 370.10, found m/z 371.4/373.3 [M+H]$^+$, 369.3/371.4 [M+H]$^+$.

Example 60: 5-(4-(2-(4-bromophenoxy)butyl)piperazin-1-yl)-1H-1,2,4-triazol-3-amine

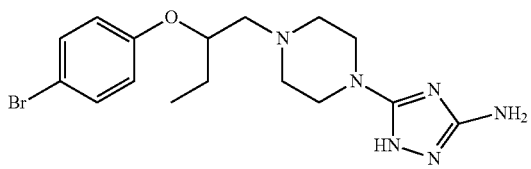 [SMILES: CCC(CN1CCN(c2nc(N)n[nH]2)CC1)Oc1ccc(Br)cc1]

Step 3: tert-butyl 4-(2-(4-bromophenoxy)butyl)piperazine-1-carboxylate

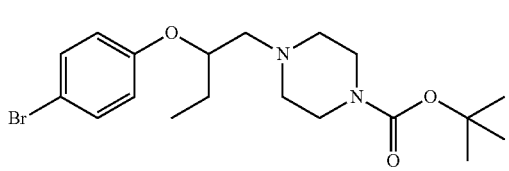 [SMILES: CCC(CN1CCN(C(=O)OC(C)(C)C)CC1)Oc1ccc(Br)cc1]

tert-Butyl 4-(2-(4-bromophenoxy)butanoyl)piperazine-1-carboxylate (Example 5, step 2) (1 eq) was dissolved in dry tetrahydrofuran (5 mL/mmol), and borane dimethylsulfide complex (2 eq) was added dropwise. The reaction mixture was stirred at ambient temperature for 4 h. TLC (eluent DCM/MeOH=20/1; UV, ninhydrin) showed no starting amide. The reaction mixture was carefully quenched with methanol, solvents were removed under reduced pressure, the residue was dissolved in dichloromethane and washed with 1M HCl (twice), 1M NaOH, brine, and dried over anhydrous $MgSO_4$. The drying agent was filtered off, solvent was removed under reduced pressure to give crude products as off-white solid. Products were analyzed by LC/MS and used in the next step without purification. ESI MS for $C_{19}H_{29}BrN_2O_3$; expected 413.36; found m/z 413.4/415.4 in ratio ~1/1 (isotopes of Br) [M+H]$^+$.

Step 4: 1-(2-(4-bromophenoxy)butyl)piperazine

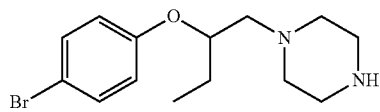 [SMILES: CCC(CN1CCNCC1)Oc1ccc(Br)cc1]

ESI MS for $C_{14}H_{21}BrN_2O$; expected 313.24; found m/z 313.4/315.4 in ratio ~1/1 (isotopes of Br) [M+H]$^+$.

Step 5: 5-(4-(2-(4-bromophenoxy)butyl)piperazin-1-yl)-1H-1,2,4-triazol-3-amine Total yield after all steps 10%; $^1$H NMR (DMSO-$d_6$, 600 MHz): 11.18 (bs, 1H); 7.48 (d, J=9.0 Hz, 2H), 7.04 (d, J=9.0 Hz, 2H), 5.01-4.94 (m, 1H), 3.93-3.82 (m, 2H), 3.59-3.49 (m, 2H), 3.49-3.36 (m, 4H), 3.27-3.14 (m, 2H), 1.67-1.59 (m, 2H), 0.87 (t, J=7.4 Hz, 3H). ESI MS for C16H23BrN6O; expected 395.31; found m/z 395.4/397.4 in ratio ~1/1 (isotopes of Br) [M+H]$^+$.

Example 61: (R)-5-(4-(2-(4-bromophenoxy)propyl)piperazin-1-yl)-1H-1,2,4-triazol-3-amine

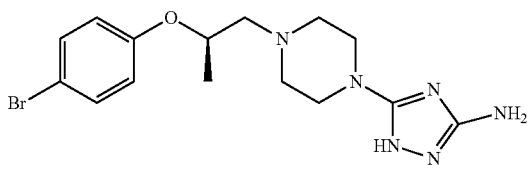 [SMILES: C[C@H](CN1CCN(c2nc(N)n[nH]2)CC1)Oc1ccc(Br)cc1]

Step 3: (R)-tert-butyl 4-(2-(4-bromophenoxy)propyl)piperazine-1-carboxylate

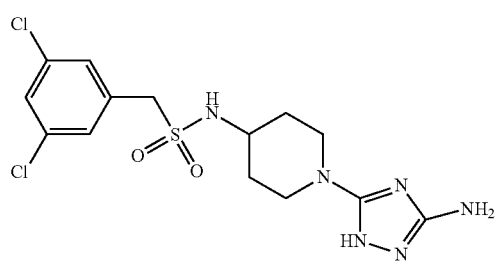 [SMILES: Nc1n[nH]c(N2CCC(NS(=O)(=O)Cc3cc(Cl)cc(Cl)c3)CC2)n1]

Prepared in a manner similar to Example 60 (step 2) from (R)-tert-butyl 4-(2-(4-bromophenoxy)propanoyl)piperazine-1-carboxylate (Example 6, step 2). ESI MS for $C_{18}H_{27}BrN_2O_3$; expected 399.33; found m/z 399.4/401.4 in ratio ~1/1 (isotopes of Br) [M+H]$^+$.

Step 4: (R)-1-(2-(4-bromophenoxy)propyl)piperazine

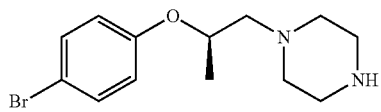

ESI MS for $C_{13}H_{19}BrN_2O$; expected 299.21; found m/z 299.4/301.4 in ratio ~1/1 (isotopes of Br) [M+H]$^+$.

Step 5: (R)-5-(4-(2-(4-bromophenoxy)propyl)piperazin-1-yl)-1H-1,2,4-triazol-3-amine Total yield after all steps 16%; ESI MS for $C_{15}H_{21}BrN_6O$; expected 381.28; found m/z 381.3/383.3 in ratio ~1/1 (isotopes of Br) [M+H]$^+$. $^1$H NMR (DMSO-$d_6$, 600 MHz): 11.29 (bs, 1H); 7.46 (d, J=9.0 Hz, 2H), 7.00 (d, J=9.0 Hz, 2H), 5.12-5.03 (m, 1H), 3.91-3.76 (m, 2H), 3.58-3.44 (m, 6H), 3.25-3.15 (m, 2H), 1.20 (d, J=6.2 Hz, 3H).

Example 62: (S)-5-(4-(2-(4-bromophenoxy)propyl)piperazin-1-yl)-1H-1,2,4-triazol-3-amine

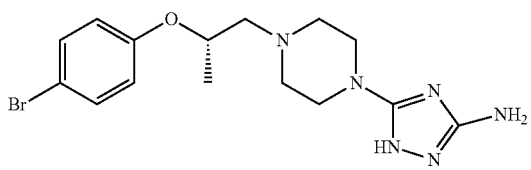 [SMILES: C[C@@H](CN1CCN(c2nc(N)n[nH]2)CC1)Oc1ccc(Br)cc1]

Step 3: (S)-tert-butyl 4-(2-(4-bromophenoxy)propyl)piperazine-1-carboxylate

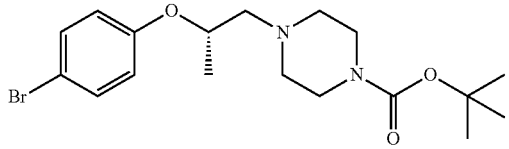 [SMILES: C[C@@H](CN1CCN(C(=O)OC(C)(C)C)CC1)Oc1ccc(Br)cc1]

Prepared in a manner similar to Example 60 (step 2) from (S)-tert-butyl 4-(2-(4-bromophenoxy)propanoyl)piperazine-1-carboxylate (Example 7, step 2). ESI MS for $C_{18}H_{27}BrN_2O_3$; expected 399.33; found m/z 399.4/401.4 in ratio ~1/1 (isotopes of Br) [M+H]$^+$.

Step 4: (S)-1-(2-(4-bromophenoxy)propyl)piperazine

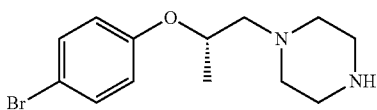

ESI MS for $C_{13}H_{19}BrN_2O$; expected 299.21; found m/z 299.4/301.4 in ratio ~1/1 (isotopes of Br) [M+H]$^+$.

Step 5: (S)-5-(4-(2-(4-bromophenoxy)propyl)piperazin-1-yl)-1H-1,2,4-triazol-3-amine Total yield after all steps 15%; ESI MS for $C_{15}H_{21}BrN_6O$; expected 381.28; found m/z 381.4/383.4 in ratio ~1/1 (isotopes of Br) [M+H]$^+$. $^1$H NMR (DMSO-d$_6$, 600 MHz): 11.43 (bs, 1H), 7.63 (bs, 2H), 7.46 (d, J=9.0 Hz, 2H), 7.00 (d, J=9.0 Hz, 2H), 5.13-5.03 (m, 1H), 3.93-3.78 (m, 2H), 3.58-3.45 (m, 6H), 3.27-3.15 (m, 2H), 1.20 (d, J=6.2 Hz, 3H).

Example 63: 5-(4-(2-(4-chlorophenoxy)butyl)piperazin-1-yl)-1H-1,2,4-triazol-3-amine

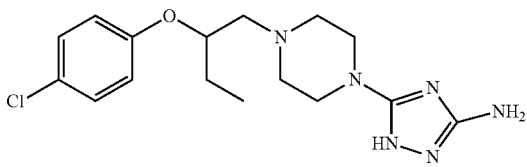 [SMILES: CCC(CN1CCN(c2nc(N)n[nH]2)CC1)Oc1ccc(Cl)cc1]

Step 3: tert-butyl 4-(2-(4-chlorophenoxy)butyl)piperazine-1-carboxylate

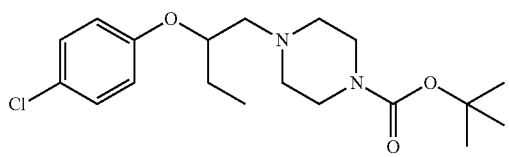 [SMILES: CCC(CN1CCN(C(=O)OC(C)(C)C)CC1)Oc1ccc(Cl)cc1]

Prepared in a manner similar to Example 60 (step 2) from tert-butyl 4-(2-(4-chlorophenoxy)butanoyl)piperazine-1-carboxylate. ESI MS for $C_{19}H_{29}ClN_2O_3$; expected 368.91; found m/z 369.5/371.5 in ratio ~3/1 (isotopes of Cl) [M+H]$^+$.

Step 4: 1-(2-(4-chlorophenoxy)butyl)piperazine

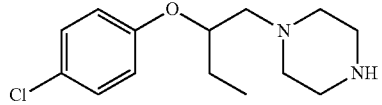 [SMILES: CCC(CN1CCNCC1)Oc1ccc(Cl)cc1]

ESI MS for $C_{14}H_{21}ClN_2O$; expected 268.91; found m/z 269.3/271.3 in ratio ~3/1 (isotopes of Cl) [M+H]$^+$.

Step 5: 5-(4-(2-(4-chlorophenoxy)butyl)piperazin-1-yl)-1H-1,2,4-triazol-3-amine Total yield after all steps 26%; ESI MS for $C_{16}H_{23}ClN_6O$; expected 350.85; found m/z 351.4/353.4 in ratio ~3/1 (isotopes of Cl) [M+H]$^+$. $^1$H NMR (DMSO-d$_6$, 600 MHz): 11.47 (bs, 1H), 7.62 (bs, 2H), 7.33 (d, J=9.0 Hz, 2H), 7.06 (d, J=9.0 Hz, 2H), 5.01-4.94 (m, 1H), 3.93-3.80 (m, 2H), 3.57-3.38 (m, 6H), 3.27-3.14 (m, 2H), 1.65-1.55 (m, 2H), 0.84 (t, J=7.4 Hz, 3H).

Example 64: (R)-5-(4-(2-(4-chlorophenoxy)propyl)piperazin-1-yl)-1H-1,2,4-triazol-3-amine

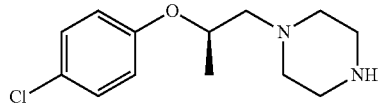 [SMILES: C[C@H](CN1CCNCC1)Oc1ccc(Cl)cc1]

Step 3: (R)-tert-butyl 4-(2-(4-chlorophenoxy)propyl)piperazine-1-carboxylate Prepared in a manner similar to Example 60 (step 2) from (R)-tert-butyl 4-(2-(4-chlorophenoxy)propanoyl)piperazine-1-carboxylate. ESI MS for $C_{18}H_{27}ClN_2O_3$; expected 354.88; found m/z 355.3/357.3 in ratio ~3/1 (isotopes of Cl) [M+H]$^+$.

Step 4: (R)-1-(2-(4-chlorophenoxy)propyl)piperazine

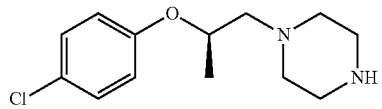 [SMILES: C[C@H](CN1CCNCC1)Oc1ccc(Cl)cc1]

ESI MS for $C_{13}H_{19}ClN_2O$; expected 254.76; found m/z 255.3/257.3 in ratio ~3/1 (isotopes of Cl) [M+H]$^+$.

Step 5: (R)-5-(4-(2-(4-chlorophenoxy)propyl)piperazin-1-yl)-1H-1,2,4-triazol-3-amine Total yield after all steps 30%; ESI MS for $C_{15}H_{21}ClN_6O$; expected 336.83; found m/z 337.4/339.4 in ratio ~3/1 (isotopes of Cl) [M+H]⁺. ¹H NMR (DMSO-d₆, 600 MHz): 11.31 (bs, 1H), 7.52 (bs, 1H), 7.36 (d, J=9.0 Hz, 2H), 7.08 (d, J=9.0 Hz, 2H), 5.13-5.06 (m, 1H), 3.92-3.81 (m, 2H), 3.61-3.40 (m, 6H), 3.28-3.18 (m, 2H), 1.22 (d, J=6.1 Hz, 3H).

Example 65: (S)-5-(4-(2-(4-chlorophenoxy)propyl)piperazin-1-yl)-1H-1,2,4-triazol-3-amine

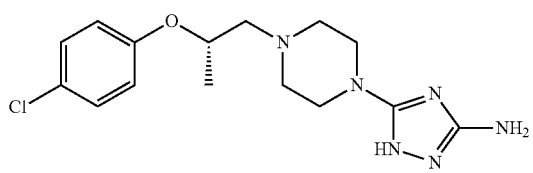 [SMILES: C[C@@H](CN1CCN(c2nc(N)n[nH]2)CC1)Oc1ccc(Cl)cc1]

Step 3: (R)-tert-butyl 4-(2-(4-chlorophenoxy)propyl)piperazine-1-carboxylate

Prepared in a manner similar to Example 60 (step 2) from (S)-tert-butyl 4-(2-(4-chlorophenoxy)propanoyl)piperazine-1-carboxylate. ESI MS for C₁₈H₂₇ClN₂O₃; expected 354.88; found m/z 355.3/357.3 in ratio ~3/1 (isotopes of Cl) [M+H]⁺.

Step 4: (S)-1-(2-(4-chlorophenoxy)propyl)piperazine

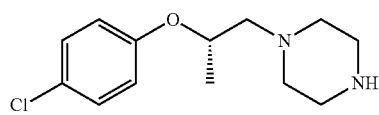 [SMILES: C[C@@H](CN1CCNCC1)Oc1ccc(Cl)cc1]

ESI MS for C₁₃H₁₉ClN₂O; expected 254.76; found m/z 255.3/257.3 in ratio ~3/1 (isotopes of Cl) [M+H]⁺.

Step 5: (S)-5-(4-(2-(4-chlorophenoxy)propyl)piperazin-1-yl)-1H-1,2,4-triazol-3-amine Total yield after all steps 23%; ESI MS for C₁₅H₂₁ClN₆O; expected 336.83; found m/z 337.4/339.4 in ratio ~3/1 (isotopes of Cl) [M+H]⁺. ¹H NMR (DMSO-d₆, 600 MHz): 11.35 (bs, 1H), 7.50 (bs, 1H), 7.36 (d, J=9.0 Hz, 2H), 7.08 (d, J=9.0 Hz, 2H), 5.14-5.06 (m, 1H), 3.95-3.81 (m, 2H), 3.62-3.40 (m, 6H), 3.29-3.17 (m, 2H), 1.22 (d, J=6.1 Hz, 3H).

Example 66: (4-(3-amino-1H-1,2,4-triazol-5-yl)-1-(3-(4-chlorophenyl)propyl)piperazin-2-yl)methanol

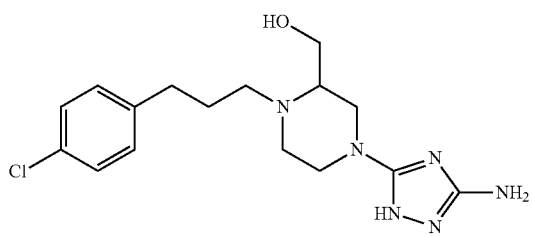 [SMILES: Nc1n[nH]c(N2CCN(CCCc3ccc(Cl)cc3)C(CO)C2)n1]

Step 1: 3-(4-chlorophenyl)propanal

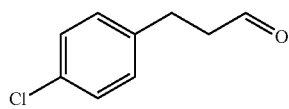 [SMILES: O=CCCc1ccc(Cl)cc1]

Prepared from 4-chloroaniline and allyl alcohol; and used without further characterization.

Step 2: phenyl 4-(3-(4-chlorophenyl)propyl)-3-(hydroxymethyl)piperazine-1-carboxylate

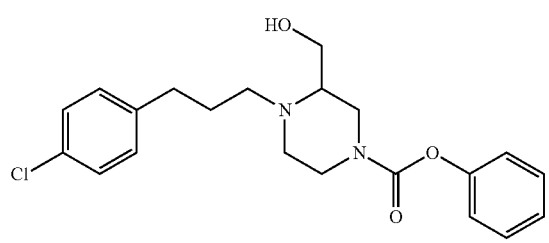 [SMILES: O=C(Oc1ccccc1)N1CCN(CCCc2ccc(Cl)cc2)C(CO)C1]

Prepared from above and phenyl 3-(hydroxymethyl)piperazine-1-carboxylate; ESI-LCMS m/z calculated for C₂₂H₂₇ClN₂O₃: expected 402.9; found [M+H]⁺=403.5.

Step 3: (1-(3-(4-chlorophenyl)propyl)piperazin-2-yl)methanol

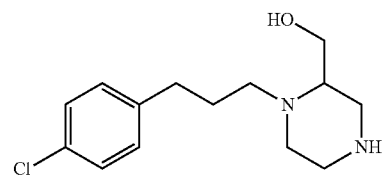 [SMILES: OCC1CNCCN1CCCc1ccc(Cl)cc1]

The compound was prepared and used without characterization.

Step 4: (4-(3-amino-1H-1,2,4-triazol-5-yl)-1-(3-(4-chlorophenyl)propyl)piperazin-2-yl)methanol ¹H NMR (DMSO-d₆, 500 MHz) δ (ppm): 10.97 (bs, 1H), 7.30 (d, J=8.1 Hz, 2H), 7.22 (d, J=8.1 Hz, 2H), 5.63 (bs, 2H), 4.50 (bs, 1H), 3.59-3.47 (m, 2H), 3.40-3.30 (m, 5H), 2.92-2.83 (m, 1H), 2.80-2.65 (m, 2H), 2.63-2.47 (m, 2H), 2.42-2.17 (m, 3H), 1.76-1.63 (m, 2H). ESI-LCMS m/z calculated for C₁₆H₂₃ClN₆O: expected 350.8; found [M+H]⁺=351.4.

Example 67: 1-(1-(3-amino-1H-1,2,4-triazol-5-yl)piperidin-4-yl)-3-(4-chlorophenyl)urea

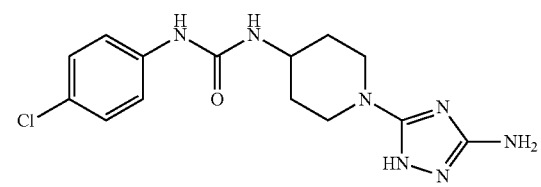 [SMILES: Nc1n[nH]c(N2CCC(NC(=O)Nc3ccc(Cl)cc3)CC2)n1]

Step 1: (4-chlorophenyl)carbamic chloride

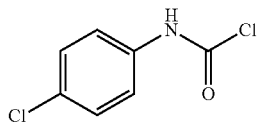 [SMILES: O=C(Cl)Nc1ccc(Cl)cc1]

To a solution of 4-chloroaniline (0.7 g, 5.48 mmol) in toluene, diisopropylethylamine (DIPEA) (1 ml, 5.48 mmol) was added and the mixture was cooled in ice-bath. A 20% solution of $COCl_2$ (3.2 ml, 6.58 mmol) in toluene was added in one portion. Bath was removed and after 40 min at rt TLC (9/1 MeOH/CHCl$_3$) showed no aniline remaining. Reaction mixture was stripped, and crude product was used without further characterization in next step.

Step 2: tert-butyl 4-(3-(4-chlorophenyl)ureido)piperidine-1-carboxylate

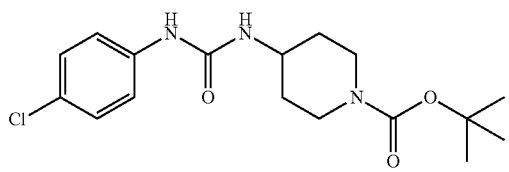 [SMILES: CC(C)(C)OC(=O)N1CCC(NC(=O)Nc2ccc(Cl)cc2)CC1]

(4-chlorophenyl)carbamic chloride was dissolved in dichloromethane, diisopropylethylamine (DIPEA) (3 ml, 16.44 mmol) and 1-Boc-4-aminopiperidine (1.09 g, 5.48 mmol) were added and the reaction was stirred at rt overnight. TLC and LCMS indicated reaction was completed. Reaction was diluted with dichloromethane, washed with 2M HCl, 1M NaOH, and brine, dried over MgSO$_4$ and concentrated. Crystallization from ethyl acetate/hexane gave pure product as light pink solid 1 g (52%). Used without further characterization.

Step 3: 1-(4-chlorophenyl)-3-(piperidin-4-yl)urea

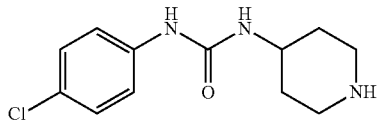 [SMILES: O=C(Nc1ccc(Cl)cc1)NC1CCNCC1]

The compound was prepared and used without characterization.

Step 4: 1-(1-(3-amino-1H-1,2,4-triazol-5-yl)piperidin-4-yl)-3-(4-chlorophenyl)urea Yield 230 mg, 41% for 3 steps. $^1$H NMR (DMSO, 500 MHz) 10.88 (brs, 1H), 8.44 (s, 1H), 7.38 (d, J=8.75 Hz, 2H), 7.22 (d, J=8.75 Hz, 2H), 6.19 (d, J=7.74 Hz, 1H), 5.82-5.60 (brs, 1H), 3.69-3.53 (m, 3H), 2.88-2.71 (m, 2H), 1.81-1.72 (m, 2H), 1.41-1.22 (m, 2H). ESI MS for $C_{14}H_{18}ClN_7O$; expected 335.80; found m/z 336.4: [M+H]$^+$.

Example 68: 1-(1-(3-amino-1H-1,2,4-triazol-5-yl)piperidin-4-yl)-3-(3,4-difluorophenyl)urea

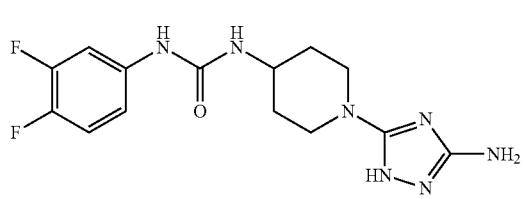 [SMILES: Nc1n[nH]c(N2CCC(NC(=O)Nc3ccc(F)c(F)c3)CC2)n1]

Prepared from 3,4-difluorobenzylamine. Yield: 0.0055 g (1.2%). $^1$H NMR (DMSO, 600 MHz) δ 7.53-7.48 (m, 1H), 7.16-7.08 (m, 1H), 7.00-6.95 (m, 1H), 3.85-3.78 (m, 1H), 3.78-3.73 (m, 2H), 3.21-3.13 (m, 2H), 2.05-1.99 (m, 2H), 1.62-1.53 (m, 2H). $^{19}$F NMR (DMSO, 200 MHz) δ −139.01 (d, J=23.5 Hz, 1F), −113.64 (d, J=21.5 Hz, 1F). ESI-LCMS m/z for $C_{14}H_{17}F_2N_7O$: expected 337.3; found 338.4 [M+H]$^+$, 336.3 [M−H]$^−$.

Example 69: N-((1-(3-amino-1H-1,2,4-triazol-5-yl)piperidin-4-yl)methyl)-3-bromo benzamide

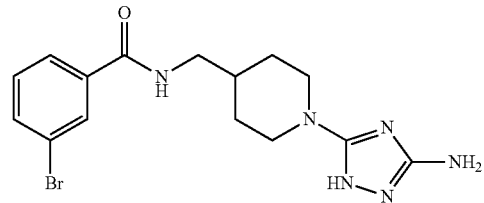 [SMILES: Nc1n[nH]c(N2CCC(CNC(=O)c3cccc(Br)c3)CC2)n1]

Step 1: 5-(4-(aminomethyl)piperidin-1-yl)-1H-1,2,4-triazol-3-amine

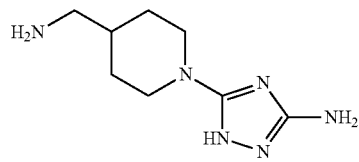 [SMILES: NCC1CCN(c2nc(N)n[nH]2)CC1]

Yield: 2.32 g (98%). ESI-LCMS m/z for $C_8H_{16}N_6$: expected 196.4; found 197.2 [M+H]$^+$.

Step 2: N-((1-(3-amino-1H-1,2,4-triazol-5-yl)piperidin-4-yl)methyl)-3-bromobenzamide Product prepared from 3-bromobenzoic acid. Yield: 0.044 g (18%). $^1$H NMR (DMSO, 500 MHz) δ 11.05 (bs, 1H), 8.64-8.58 (m, 1H), 8.01 (s, 1H), 7.83 (d, J=7.9 Hz, 1H), 7.70 (d, J=7.7 Hz, 1H), 7.41 (dd, J$_1$=7.9 Hz, J$_2$=7.7 Hz, 1H), 5.46 (bs, 2H), 3.76 (d, J=12.3 Hz, 2H), 3.18-3.13 (m, 2H), 2.63-3.53 (m, 2H), 1.71-1.59 (m, 2H), 1.19-1.08 (m, 2H). ESI-LCMS m/z for $C_{15}H_{19}BrN_6O$: expected 379.3; found 379.4/381.4 [M+H]$^+$.

Example 70: 2-(1-(3-amino-1H-1,2,4-triazol-5-yl)piperidin-4-yl)-N-(4-bromophenyl)acetamide

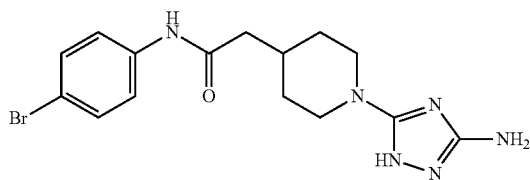 [SMILES: Nc1n[nH]c(N2CCC(CC(=O)Nc3ccc(Br)cc3)CC2)n1]

Step 1: tert-butyl 4-(2-((4-bromophenyl)amino)-2-oxoethyl)piperidine-1-carboxylate

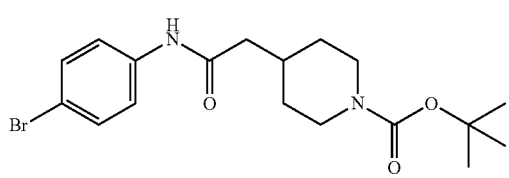 [SMILES: CC(C)(C)OC(=O)N1CCC(CC(=O)Nc2ccc(Br)cc2)CC1]

Prepared from 4-bromoaniline and 2-(1-(tert-butoxycarbonyl)piperidin-4-yl)acetic acid; ESI-LCMS m/z calculated for $C_{18}H_{25}BrN_2O_3$: expected 397.3; found $(M)^-$=397.3.

Step 2: N-(4-bromophenyl)-2-(piperidin-4-yl)acetamide

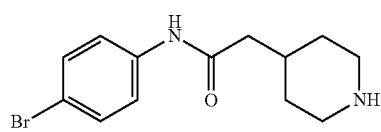 [SMILES: O=C(CC1CCNCC1)Nc1ccc(Br)cc1]

ESI-LCMS m/z calculated for $C_{13}H_{17}BrN_2O$: expected 297.2; found $[M+H]^+$=298.3/300.3.

Step 3: 2-(1-(3-amino-1H-1,2,4-triazol-5-yl)piperidin-4-yl)-N-(4-bromophenyl)acetamide $^1$H NMR (DMSO-$d_6$, 600 MHz) δ (ppm) 10.94 (bs, 1H), 10.02 (s, 1H), 7.58-7.54 (m, 2H), 7.47-7.44 (m, 2H), 5.56 (bs, 2H), 3.77-3.72 (m, 2H), 2.68-2.57 (m, 2H), 2.23 (d, J=7.2 Hz, 2H), 1.92-1.84 (m, 1H), 1.65-1.59 (m, 2H), 1.24-1.16 (m, 2H). ESI-LCMS m/z calculated for $C_{15}H_{19}BrN_6O$: expected 379.3; found $[M+H]^+$=379.4/381.4.

Example 71: N-(1-(3-amino-1H-1,2,4-triazol-5-yl)piperidin-4-yl)-2-(4-chlorophenyl)-2-hydroxyacetamide

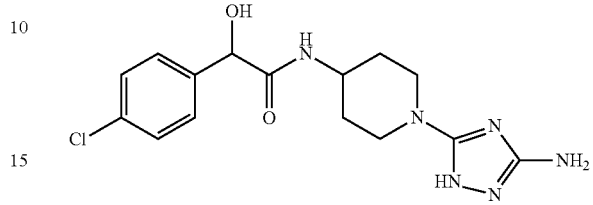

Step 1: tert-butyl 4-(2-(4-chlorophenyl)-2-hydroxyacetamido)piperidine-1-carboxylate

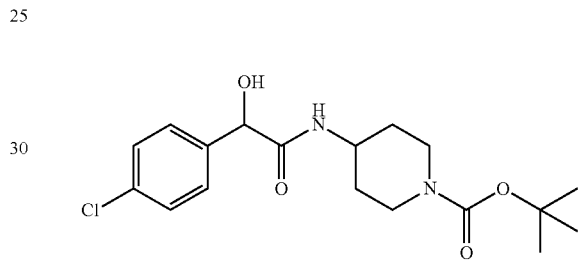

Prepared from 2-(4-chlorophenyl)-2-hydroxyacetic acid and tert-butyl 4-aminopiperidine-1-carboxylate; 0.36 g of white solid was obtained (94%), and used without characterization.

Step 2: 2-(4-chlorophenyl)-2-hydroxy-N-(piperidin-4-yl)acetamide

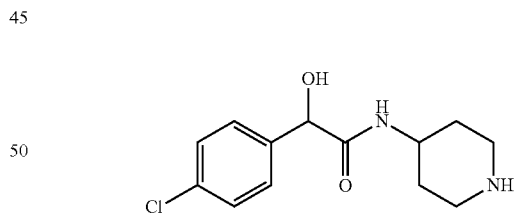

The compound was used without characterization.

Step 3: N-(1-(3-amino-1H-1,2,4-triazol-5-yl)piperidin-4-yl)-2-(4-chlorophenyl)-2-hydroxyacetamide Yield 0.12 g (45%) for 3 steps. $^1$H NMR (DMSO, 600 MHz) δ 7.92 (d, J=8.3 Hz, 1H), 7.43-7.34 (AA'XX', J=8.5 Hz, 4H), 6.21 (d, J=4.7 Hz, 1H), 5.65-5.43 (brs, 2H), 4.90 (d, J=4.1 Hz, 1H), 3.74-3.68 (m, 2H), 3.69-3.61 (m, 1H), 2.74-2.62 (m, 2H), 1.65-1.55 (m, 2H), 1.54-1.42 (m, 2H). ESI MS for $C_{15}H_{19}ClN_6O_2$; expected 350.81; found m/z 351.4/353.4 $[M+H]^+$.

Example 72: (R)-1-(4-(3-amino-1H-1,2,4-triazol-5-yl)piperazin-1-yl)-3-(4-chlorophenyl)-2-hydroxypropan-1-one

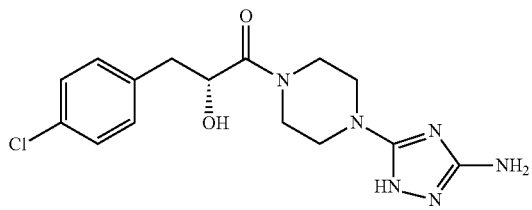 [SMILES: Nc1n[nH]c(N2CCN(C(=O)[C@H](O)Cc3ccc(Cl)cc3)CC2)n1]

Step 1: (R)-2-amino-3-(4-chlorophenyl)propanoic acid hydrochloride

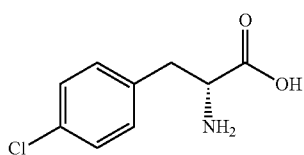 [SMILES: N[C@H](Cc1ccc(Cl)cc1)C(=O)O]

(2R)-2-(acetylamino)-3-(4-chlorophenyl)propanoic acid (8 g, 33 mmol) was treated with 6N HCl (100 mL), refluxed for 2 h and evaporated to dryness to give 7.8 g (99.8%), and was used without further characterization.

Step 2: (R)-3-(4-chlorophenyl)-2-hydroxypropanoic Acid

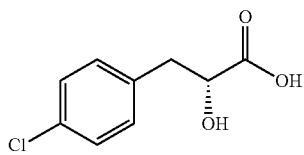 [SMILES: O=C(O)[C@H](O)Cc1ccc(Cl)cc1]

(R)-2-amino-3-(4-chlorophenyl)propanoic acid hydrochloride (7.8 g, 33 mmol) was suspended in water (150 mL) and cooled to 2° C.; sulfuric acid (26.6 mL, 495.5 mmol) in 180 mL of water was added dropwise. NaNO$_2$ (9.12 g, 132.15 mmol) in water (66 mL) was added dropwise and the mixture was stirred overnight at ambient temperature and extracted with ethyl acetate. Organic layers were combined, washed with brine, dried over MgSO$_4$, filtered, and evaporated to dryness to give crude product as colorless oil. Product was crystallized with diethyl ether/hexane. Yield 3.71 g (56%). ESI MS for C$_9$H$_9$ClO$_3$ expected 200.02, found m/z 199.1/201.2 [M–H].

Step 3: (R)-tert-butyl 4-(3-(4-chlorophenyl)-2-hydroxypropanoyl)piperazine-1-carboxylate

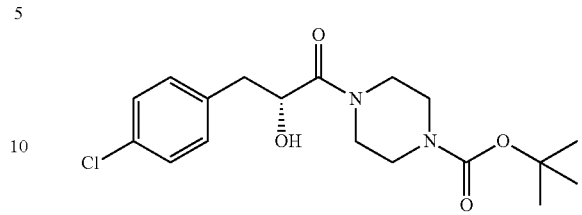

(R)-3-(4-chlorophenyl)-2-hydroxypropanoic acid (0.5 g, 2.49 mmol), 1-Boc-piperazine (1.39 g, 7.477 mmol), DIPEA (0.48 mL, 2.74 mmol), and HATU (0.945 g, 2.49 mmol) in dry CH$_2$Cl$_2$ (10 mL) were stirred overnight at ambient temperature. The mixture was washed with 2N HCl, brine, dried over MgSO$_4$, filtered, and concentrated to give 0.82 g (89%). ESI MS for C$_{18}$H$_{25}$ClN$_2$O$_4$ expected 368.15, found m/z 269.3 (M-Boc), 313.3 (M-tBu).

Final step: (R)-1-(4-(3-amino-1H-1,2,4-triazol-5-yl)piperazin-1-yl)-3-(4-chlorophenyl)-2-hydroxypropan-1-one $^1$H NMR (DMSO, 600 MHz) δ 7.3 (d, J=8.3 Hz, 2H), 7.26 (d, J=8.5 Hz, 2H), 5.78 (brs, 2H), 5.16-5.11 (m, 1H), 4.53-4.47 (m, 1H). 3.6-3.52 (m, 2H), 3.5-3.38 (m, 2H), 3.18-3.04 (m, 4H), 2.9-2.84 (m, 1H), 2.76-2.69 (m, 1H). Yield 0.21 g (73%). ESI MS for C$_{15}$H$_{19}$ClN$_6$O$_2$ expected 350.13, found m/z 351.4/353.4 (M+1), 349.4/351.3 [M–H].

Example 73: 1-(4-(3-amino-1H-1,2,4-triazol-5-yl)piperazin-1-yl)-3-(2-chlorophenyl)-2-hydroxypropan-1-one

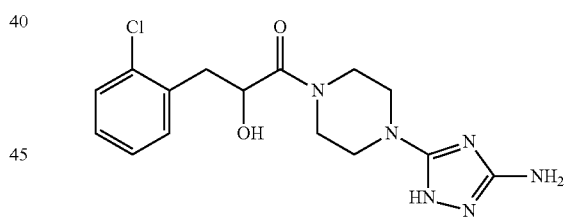

Step 1: tert-butyl 4-(3-(2-chlorophenyl)-2-hydroxypropanoyl)piperazine-1-carboxylate

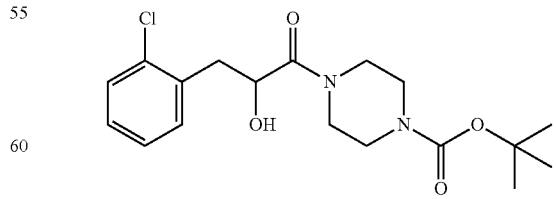

Prepared from 3-(2-chlorophenyl)-2-hydroxypropanoic acid and tert-butyl piperazine-1-carboxylate to yield 1.05 g (57%). $^1$H NMR (CDCl$_3$, 500 MHz) δ 7.36-7.38 (m, 1H), 7.30-7.32 (m, 1H), 7.21-7.23 (m, 2H), 4.69-4.72 (m, 1H), 3.66-3.71 (m, 2H), 3.57-3.60 (m, 1H), 3.37-3.44 (m, 4H), 3.24-3.32 (m, 2H), 3.10 (dd, J=4.9 Hz, J=13.7 Hz, 1H), 2.91 (dd, J=8.5 Hz, J=13.6 Hz, 1H), 1.49 (s, 9H). ESI-LCMS m/z for $C_{18}H_{25}ClN_2O_4$: expected 368.15, found 391.3/393.3 (M+Na)$^+$.

Step 2: 1-(4-(3-amino-1H-1,2,4-triazol-5-yl)piperazin-1-yl)-3-(2-chlorophenyl)-2-hydroxypropan-1-one Yield 0.202 g (53%) for 3 steps. $^1$H NMR (DMSO-$d_6$, 500 MHz) δ (ppm) 11.00 (brs, 1H), 7.35-7.41 (m, 2H), 7.21-7.26 (m, 2H), 5.78 (brs, 2H), 5.24 (d, J=8.0 Hz, 1H), 4.55-4.60 (m, 1H), 3.42-3.58 (m, 4H), 3.11-3.15 (m, 3H), 3.03 (dd, J=5.1 Hz, J=13.8 Hz, 1H), 2.97-3.00 (m, 1H), 2.86 (dd, J=8.5 Hz, J=13.8 Hz, 1H). ESI-LCMS m/z for $C_{15}H_{19}ClN_6O_2$: expected 350.13, found: 351.3/353.3 [M+H]$^+$; 349.4/351.5 [M−H]$^-$.

Example 74: 1-(4-(3-amino-1H-1,2,4-triazol-5-yl) piperazin-1-yl)-2-(4-chloro-3-nitro phenoxy)ethanone

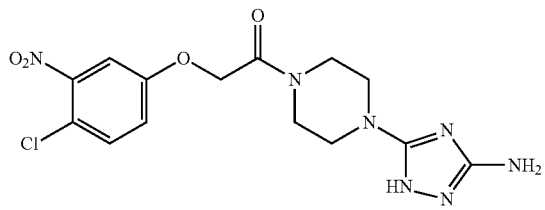 [SMILES: Nc1n[nH]c(N2CCN(C(=O)COc3ccc(Cl)c([N+](=O)[O-])c3)CC2)n1]

Step 1: 2-(4-chloro-3-nitrophenoxy)acetic Acid

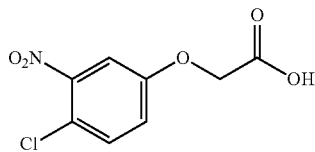 [SMILES: O=C(O)COc1ccc(Cl)c([N+](=O)[O-])c1]

Sodium hydride (3 g (60% in oil), 0.075 mmol) was suspended in THF (95 ml) and cooled to −10° C.; a solution of 4-chloro-3-nitrophenol (4.34 g, 0.025 mmol) in THF (20 ml) added dropwise, followed by a solution of bromoacetic acid (4.17 g, 0.030 mmol) in THF (20 ml) added dropwise. The reaction mixture was stirred overnight at ambient temperature, then quenched with 1M NaOH and Et$_2$O and vigorously stirred for 5 minutes. Phases were separated, the aqueous phase extracted with Et$_2$O, then acidified with aqueous 6M HCl to pH 3. The resulting mixture was extracted three times with Et$_2$O, dried over MgSO$_4$ and concentrated. The residue was refluxed in hexane (100 ml) for 30 minutes. After cooling to ambient temperature beige solid was filtered off, washed with fresh hexane and dried on air in 45° C. Yield 3.6 g (62%). $^1$H NMR (DMSO-$d_6$, 500 MHz) δ 13.2 (brs, 1H), 7.66-7.68 (m, 2H), 7.29 (d, J=3.0 Hz, J=8.8 Hz, 1H), 4.84, (s, 2H). ESI-LCMS m/z for $C_8H_6ClNO_5$: expected 230.99, found: 230.2/232.2 [M−H]$^-$.

Step 2: tert-butyl 4-(2-(4-chloro-3-nitrophenoxy) acetyl)piperazine-1-carboxylate

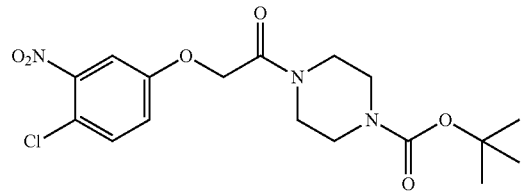 [SMILES: CC(C)(C)OC(=O)N1CCN(C(=O)COc2ccc(Cl)c([N+](=O)[O-])c2)CC1]

Yield 3.93 g (91%). ESI-LCMS m/z for $C_{17}H_{22}ClN_3O_6$: expected 399.12, found: 300.3/302.3 [M+H−Boc]$^+$.

Step 3: 1-(4-(3-amino-1H-1,2,4-triazol-5-yl)piperazin-1-yl)-2-(4-chloro-3-nitrophenoxy)ethanone Yield 1.473 g (47%) for 3 steps. $^1$H NMR (DMSO-$d_6$, 500 MHz) δ: 11.03 (s, 1H), 7.67 (d, J=3.0 Hz, 1H), 7.65 (d, J=9.1 Hz, 1H), 7.27 (dd, J=3.0 Hz, J=9.1 Hz, 1H), 5.81, (s, 2H), 5.03, (s, 2H), 3.47-3.50 (m, 4H), 3.16-3.23 (m, 4H). ESI-LCMS m/z for 4: expected 381.10, found: 382.5/384.5 [M+H]$^+$, 380.5/382.5 [M−H]$^-$.

Example 75-1 and 75-2

(S)-2-amino-1-(4-(3-amino-1H-1,2,4-triazol-5-yl) piperazin-1-yl)-3-(2,4-dichlorophenyl)propan-1-one; (S)-2-amino-1-(4-(3-amino-1H-1,2,4-triazol-5-yl) piperazin-1-yl)-3-(2-chlorophenyl)propan-1-one

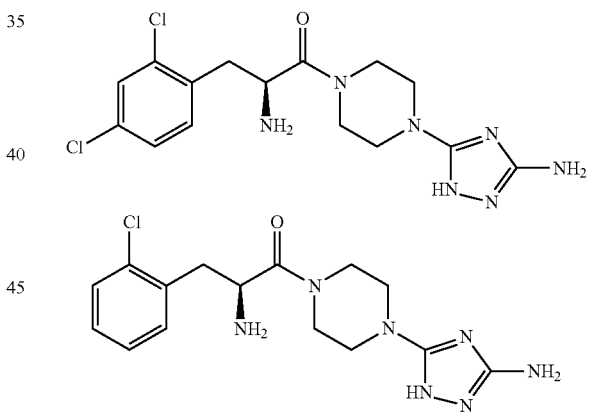

Step 1: (S)-benzyl 4-(2-((tert-butoxycarbonyl) amino)-3-(2,4-dichlorophenyl)propanoyl)piperazine-1-carboxylate

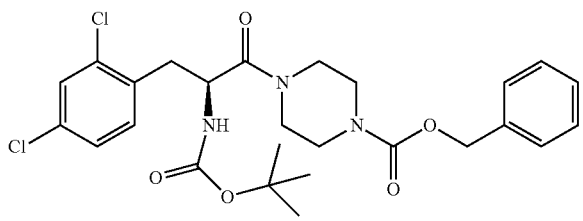 [SMILES: CC(C)(C)OC(=O)N[C@@H](Cc1ccc(Cl)cc1Cl)C(=O)N1CCN(C(=O)OCc2ccccc2)CC1]

Prepared from (2S)-2-[(tert-butoxycarbonyl)amino]-3-(2,4-dichlorophenyl)propanoic acid (1 g, 3 mmol), and benzyl piperazine-1-carboxylate. HCl (0.77 g, 3 mmol) to give 1.1 g (69%). ESI MS found for $C_{26}H_{31}Cl_2N_3O_5$, expected 535.16, found m/z 436.5/438.5 [M-Boc+H]$^+$.

Step 2: mixture of (S)-tert-butyl (3-(2,4-dichlorophenyl)-1-oxo-1-(piperazin-1-yl)propan-2-yl)carbamate compound and (S)-tert-butyl (3-(2-chlorophenyl)-1-oxo-1-(piperazin-1-yl)propan-2-yl)carbamate

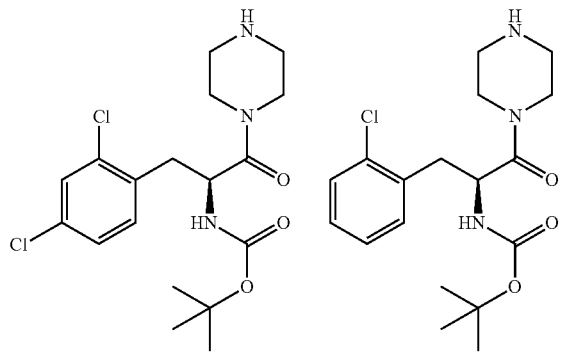

(S)-benzyl 4-(2-((tert-butoxycarbonyl)amino)-3-(2,4-dichlorophenyl)propanoyl)-piperazine-1-carboxylate (0.51 g, 0.95 mmol) was dissolved in MeOH (5 mL), flushed with argon and palladium 10% on barium sulfate (catalytic amount) was added. Air was removed and the mixture was stirred overnight under $H_2$ (balloon). The mixture was filtered through celite, washed with MeOH, and evaporated to dryness to give 0.33 g of mixture containing ~70% dichloro, 30% monochloro product. ESI MS expected for $C_{18}H_{25}Cl_2N_3O_3$ 401.13 (dichloro) and for $C_{18}H_{26}ClN_3O_3$ 367.17 (monochloro), found m/z 302.4/304.3 [dichloro-Boc+H]$^+$ and 268.3/270.3 [monochloro-Boc+H]$^+$.

Step 3: (S)-methyl 4-(2-((tert-butoxycarbonyl)amino)-3-(2,4-dichlorophenyl)propanoyl)-N-cyanopiperazine-1-carbimidothioate; (S)-methyl 4-(2-((tert-butoxycarbonyl)amino)-3-(2-chlorophenyl)propanoyl)-N-cyanopiperazine-1-carbimidothioate

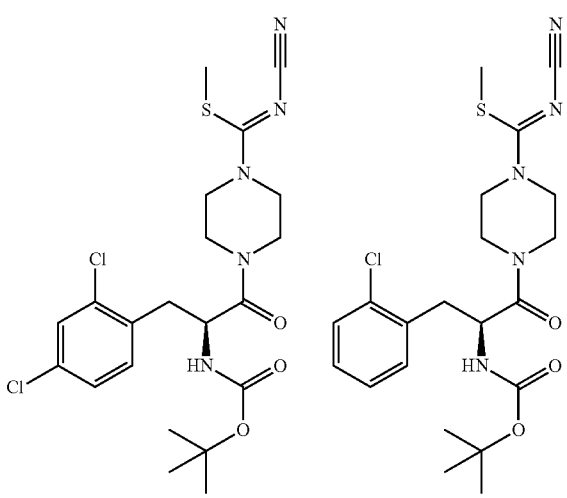

ESI MS expected for $C_{21}H_{27}Cl_2N_5O_3S$ 499.12 (dichloro) and for $C_{21}H_{28}ClN_5O_3S$ 465.16; found m/z 500.5/502.5 [dichloro+H]$^+$, 400.4/402.4 [dichloro-Boc+H]$^+$, m/z 366.4/368.4 [monochloro-Boc+H]$^+$.

Final products are prepared as previously described, separated by prep HPLC and isolated as dihydrochloride salts to give:

Example 75-1, dichloro compound: (S)-2-amino-1-(4-(3-amino-1H-1,2,4-triazol-5-yl)piperazin-1-yl)-3-(2,4-dichlorophenyl)propan-1-one dihydrochloride; $^1$H NMR (DMSO, 600 MHz) δ 8.53 (brs, 3H), 7.65 (s, 1H), 7.46-7.42 (m, 2H), 4.68-4.61 (m, 1H), 3.72-3.65 (m, 1H). 3.53-3.50 (m, 1H), 3.39-3.34 (m, 2H), 3.3-3.24 (m, 2H), 3.23-3.17 (m, 1H), 3.16-3.10 (m, 1H), 3.08-3.02 (m, 1H), 2.96 (brs, 1H). ESI MS for $C_{15}H_{19}Cl_2N_7O$ expected 383.10, found m/z 384.4/386.4 [M+H]$^+$, 382.3/384.2 (M−H)$^-$.

Example 75-2, monochloro compound: (S)-2-amino-1-(4-(3-amino-1H-1,2,4-triazol-5-yl)piperazin-1-yl)-3-(2-chlorophenyl)propan-1-one dihydrochloride; $^1$H NMR (CD$_3$OD, 600 MHz) δ 7.50-7.46 (m, 1H), 7.39-7.33 (m, 3H), 7.32-7.28 (m, 1H), 4.79-4.73 (m, 1H), 3.71-3.64 (m, 1H). 3.63-3.56 (m, 1H), 3.48-3.42 (m, 1H), 3.36-3.31 (m, 2H), 3.26-3.22 (m, 1H), 3.22-3.14 (m, 2H), 3.02-2.96 (m, 1H), 2.67-2.6 (m, 1H). ESI MS for $C_{15}H_{20}ClN_7O$ expected 349.14, found m/z 350.3/352.3 [M+H]$^+$, 348.4/350.3 (M−H)$^-$.

Example 76: N-(3-(4-(3-amino-1H-1,2,4-triazol-5-yl)piperazin-1-yl)-1-(4-fluorophenyl)-3-oxopropyl)acetamide

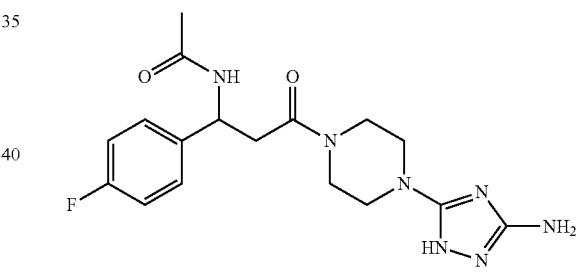

Step 1: benzyl 4-(3-acetamido-3-(4-fluorophenyl)propanoyl)piperazine-1-carboxylate

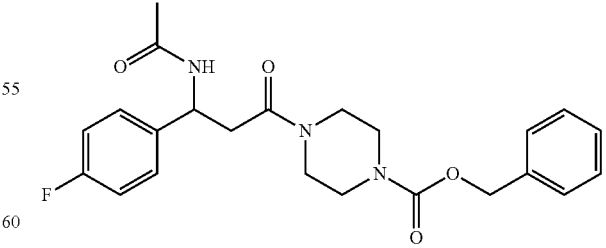

Benzyl 4-(3-amino-3-(4-fluorophenyl)propanoyl)piperazine-1-carboxylate. HCl (0.47 g, 1.114 mmol) was suspended in dry CH$_2$Cl$_2$ (10 mL); Et$_3$N (0.39 mL, 2.785 mmol) was added and the mixture was cooled to 0° C. Acetic anhydride (0.105 mL, 1.114 mmol) was added dropwise and the mixture was stirred overnight. Washed with 2N HCl and brine, dried over MgSO₄, filtered, and evaporated to dryness to give 0.41 g (85%) of product. ESI MS found for $C_{23}H_{26}FN_3O_4$ expected 427.19, found m/z 428.6 [M+H]⁺, 450.5 [M+Na]⁺.

Remaining steps are carried out without intermediate purification or characterization to give N-(3-(4-(3-amino-1H-1,2,4-triazol-5-yl)piperazin-1-yl)-1-(4-fluorophenyl)-3-oxopropyl)acetamide. ¹H NMR (DMSO, 500 MHz) δ 8.24 (d, J=8.1 Hz, 1H), 7.33-7.28 (m, 2H), 7.11-7.05 (m, 2H), 5.67 (brs, Hz, 2H), 5.155 (q, J=7.5, J=14.9, 1H), 3.46-3.35 (m, 4H), 3.14-3.08 (m, 1H), 3.08-2.96 (m, 3H), 2.775 (dd, J=7.5, J=15.4, 1H), 2.695 (dd, J=6.6, J=15.4, 1H), 1.765 (s, 3H). ESI MS found for $C_{17}H_{22}FN_7O_2$ expected 375.18, found m/z 376.5 [M+H]⁺, 374.4 [M–H]⁻.

Comparative Example 77

2-(4-(3-amino-1H-1,2,4-triazol-5-yl)piperazin-1-yl)ethanol

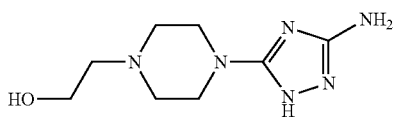 [SMILES: Nc1n[nH]c(N2CCN(CCO)CC2)n1]

Step 1: methyl N-cyano-4-(2-hydroxyethyl)piperazine-1-carbimidothioate

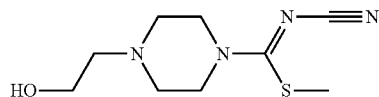

ESI-LCMS m/z calculated for $C_9H_{16}N_4OS$: expected 228.3; found 229.2 [M+H]⁺.

Step 2: 2-(4-(3-amino-1H-1,2,4-triazol-5-yl)piperazin-1-yl)ethanol

¹H NMR (CD₃OD, 400 MHz) δ 4.399 (2H, bs), 3.511 (4H, m), 3.148 (2H, bs), 2.440 (4H, bs), 2.398 (2H, m); ESI-LCMS m/z calculated for $C_8H_{16}N_6O$: expected 212.3; found 213.2 [M+H]⁺.

Example 78: 5-(4-(2-phenoxyethyl)piperazin-1-yl)-1H-1,2,4-triazol-3-amine

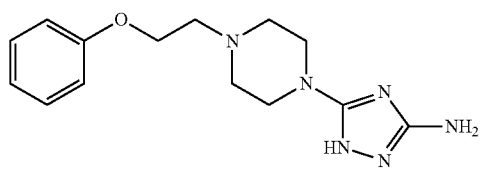 [SMILES: Nc1n[nH]c(N2CCN(CCOc3ccccc3)CC2)n1]

Prepared from phenol and 2-(4-(3-amino-1H-1,2,4-triazol-5-yl)piperazin-1-yl)ethanol (Example 77); ¹H NMR (CD₃OD, 400 MHz) δ 7.221-6.75 (5H, m), 4.142 (2H, t, J=2.670), 2.909 (2H, t, J=2.670), 3.626 (4H, bs), 2.581 (4H, bs); ESI-LCMS m/z calculated for $C_{14}H_{20}N_6O$: expected 288.17; found 289.2 [M+H]⁺.

Example 79: 5-(4-(2-(2-chlorophenoxy)ethyl)piperazin-1-yl)-1H-1,2,4-triazol-3-amine

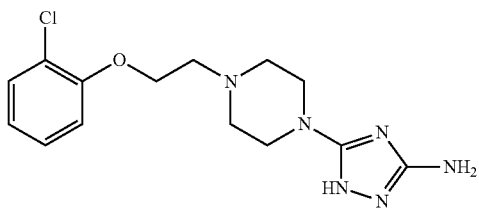

Prepared from 2-chlorophenol and 2-(4-(3-amino-1H-1,2,4-triazol-5-yl)piperazin-1-yl)ethanol (Example 77); ¹H NMR (CD₃OD, 400 MHz) δ 7.367 (d, J=8.0 Hz, 1H), 7.267 (t, J=8.2 Hz, 1H), 7.090 (d, J=8.0, 1H), 6.940 (t, J=8.2, 1H), 4.241 (t, J=5.49 Hz, 2H), 3.352 (m, 4H), 2.934 (t, J=5.49, 2H), 2.784 (m, 4H); ESI-LCMS m/z calculated for $C_{14}H_{19}ClN_6O$: expected 322.13; found 323.2/325.2 [M+H]⁺.

Example 80: 5-(4-(2-(benzyloxy)ethyl)piperazin-1-yl)-1H-1,2,4-triazol-3-amine

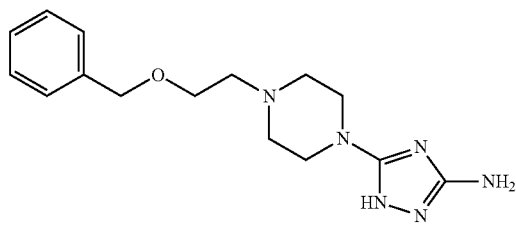 [SMILES: Nc1n[nH]c(N2CCN(CCOCc3ccccc3)CC2)n1]

Prepared from benzyl alcohol and 2-(4-(3-amino-1H-1,2,4-triazol-5-yl)piperazin-1-yl)ethanol (Example 77); ¹H NMR (CD₃OD, 400 MHz) δ 7.366-7.295 (m, 5H), 4.546 (bs, 2H), 3.666 (t, J=5.463, 2H), 3.309 (bs, 4H), 2.677 (t, J=5.463, 2H), 2.617 (bs, 4H); ESI-LCMS m/z calculated for $C_{15}H_{22}N_6O$: expected 302.09; found 203.2 [M+H]⁺.

Example 81: 5-(4-(2-(4-methoxyphenoxy)ethyl)piperazin-1-yl)-1H-1,2,4-triazol-3-amine

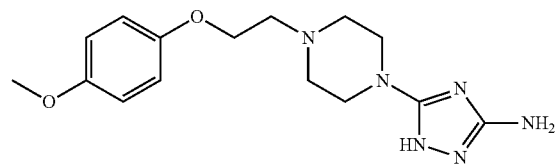 [SMILES: COc1ccc(OCCN2CCN(c3nc(N)n[nH]3)CC2)cc1]

Prepared from 4-methoxyphenol and 2-(4-(3-amino-1H-1,2,4-triazol-5-yl)piperazin-1-yl)ethanol (Example 77); ¹H NMR (CD₃OD, 400 MHz) δ 6.865 (m, 4H), 4.064 (t, J=2.670, 2H), 3.792 (s, 3H), 3.625 (bs, 4H), 2.914 (t, J=2.670, 2H), 2.572 (bs, 4H); ESI-LCMS m/z calculated for $C_{15}H_{22}N_6O_2$: expected 318.18; found 319.2 [M+H]⁺.

Example 82: 5-(4-(2-((1H-indol-5-yl)oxy)ethyl)piperazin-1-yl)-1H-1,2,4-triazol-3-amine

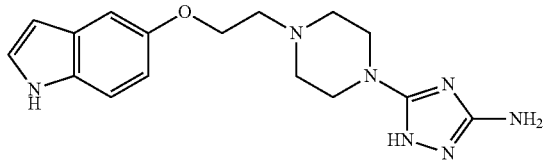 [SMILES: Nc1n[nH]c(N2CCN(CCOc3ccc4[nH]ccc4c3)CC2)n1]

Prepared from 1H-indol-5-ol and 2-(4-(3-amino-1H-1,2,4-triazol-5-yl)piperazin-1-yl)ethanol (Example 77); $^1$H NMR (CD$_3$OD, 400 MHz) δ 7.759 (m, 2H), 7.643 (m, 1H), 7.755 (m, 2H), 4.072 (t, J=2.670, 2H), 3.626 (bs, 4H), 2.916 (t, J=2.670, 2H), 2.566 (bs, 4H); ESI-LCMS m/z calculated for C$_{16}$H$_{21}$N$_7$O: expected 327.18; found 328.2 [M+H]$^+$.

Example 83: 5-(4-(2-([1,1'-biphenyl]-2-yloxy)ethyl)piperazin-1-yl)-1H-1,2,4-triazol-3-amine

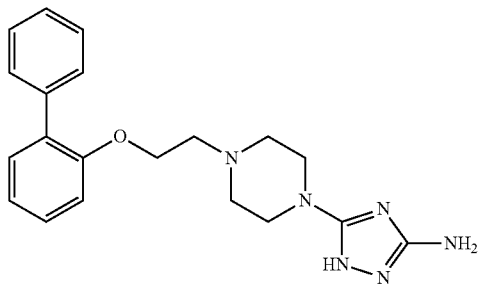 [SMILES: Nc1n[nH]c(N2CCN(CCOc3ccccc3-c3ccccc3)CC2)n1]

Prepared from [1,1'-biphenyl]-2-ol and 2-(4-(3-amino-1H-1,2,4-triazol-5-yl)piperazin-1-yl)ethanol (Example 77); $^1$H NMR (CD$_3$OD, 400 MHz) δ 7.510-7.395 (m, 7H), 7.190 (m, 1H), 7.151 (m, 1H), 4.261 (t, J=5.79, 2H), 3.627 (bs, 4H), 2.896 (t, J=5.79, 2H), 2.620 (bs, 4H); ESI-LCMS m/z calculated for C$_{20}$H$_{24}$N$_6$O: expected 364.20; found 365.2 [M+H]$^+$.

Example 84: 5-(4-(2-(2-isopropylphenoxy)ethyl)piperazin-1-yl)-1H-1,2,4-triazol-3-amine

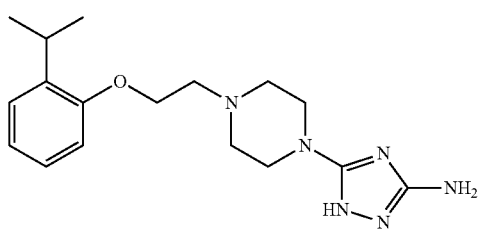 [SMILES: CC(C)c1ccccc1OCCN1CCN(c2nc(N)n[nH]2)CC1]

Prepared from 2-isopropylphenol and 2-(4-(3-amino-1H-1,2,4-triazol-5-yl)piperazin-1-yl)ethanol (Example 77); $^1$H NMR (CD$_3$OD, 400 MHz) δ 7.213 (d, J=7.43 Hz, 1H), 7.142 (t, J=7.43 Hz, 1H), 6.921 (m, 2H), 4.196 (t, J=5.53, 2H), 3.506 (m, 1H), 3.368 (bs, 4H), 2.967 (t, J=5.53, 2H), 2.797 (bs, 4H), 1.222 (d, J=6.86 Hz, 6H); ESI-LCMS m/z calculated for C$_{17}$H$_{26}$N$_6$O: expected 330.22; found 331.2 [M+H]$^+$.

Example 85: 5-(4-(2-(2-fluorophenoxy)ethyl)piperazin-1-yl)-1H-1,2,4-triazol-3-amine

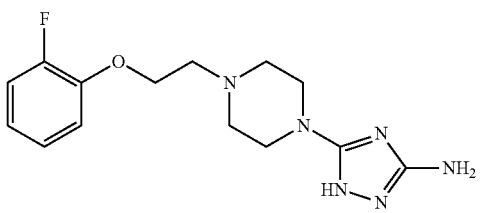

Prepared from 2-fluorophenol and 2-(4-(3-amino-1H-1,2,4-triazol-5-yl)piperazin-1-yl)ethanol (Example 77); $^1$H NMR (CD$_3$OD, 400 MHz) δ 7.108 (m, 3H), 6.942 (m, 1H), 4.235 (t, J=5.22, 2H), 3.349 (m, 4H), 2.895 (t, J=5.22, 2H), 2.729 (m, 4H); ESI-LCMS m/z calculated for C$_{14}$H$_{19}$FN$_6$O: expected 306.16; found 307.2 [M+H]$^+$.

Example 86: 5-(4-(2-(3-chlorophenoxy)ethyl)piperazin-1-yl)-1H-1,2,4-triazol-3-amine

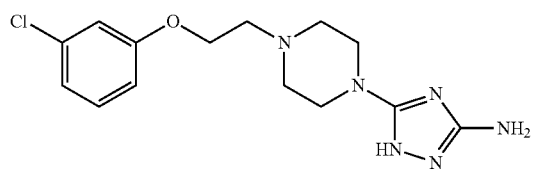 [SMILES: Nc1n[nH]c(N2CCN(CCOc3cccc(Cl)c3)CC2)n1]

Prepared from 2-chlorophenol and 2-(4-(3-amino-1H-1,2,4-triazol-5-yl)piperazin-1-yl)ethanol (Example 77); $^1$H NMR (CD$_3$OD, 400 MHz) δ 7.263 (t, J=8.29, 1H), 6.999 (m, 1H), 6.958 (d, J=7.86, 1H), 6.906 (d, J=8.35, 1H), 4.179 (t, J=5.37, 2H), 3.360 (m, 4H), 2.898 (t, J=5.37, 2H), 2.729 (m, 4H); ESI-LCMS m/z calculated for C$_{14}$H$_{19}$ClN$_6$O: expected 322.13; found 323.2 [M+H]$^+$.

Example 87: 5-(4-(2-(2-chloro-6-methylphenoxy)ethyl)piperazin-1-yl)-1H-1,2,4-triazol-3-amine

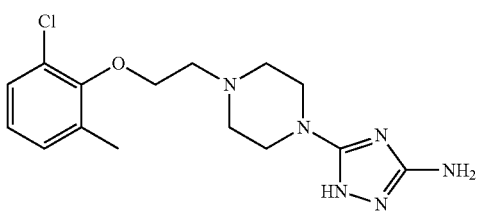

$^1$H NMR (CD$_3$OD, 400 MHz) δ 7.240 (m, 1H), 7.159 (m, 1H), 7.009 (m, 1H), 4.122 (t, J=5.70, 2H), 3.368 (m, 4H), 2.962 (t, J=5.70, 2H), 2.800 (m, 4H), 2.352 (s, 3H); ESI-LCMS m/z calculated for C$_{15}$H$_{21}$ClN$_6$O: expected 336.83; found 337.2 [M+H]$^+$.

Example 88: 1-(3-amino-1H-1,2,4-triazol-5-yl)-N-(4-chlorophenethyl)piperidin-4-amine

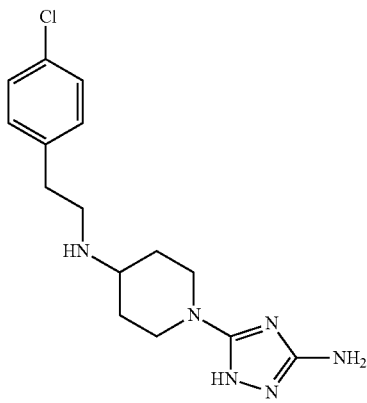 [SMILES: Nc1n[nH]c(N2CCC(NCCc3ccc(Cl)cc3)CC2)n1]

Prepared in a manner similar to Example 22 using 2-(4-bromophenyl)ethanamine; $^1$H NMR (DMSO, 600 MHz) δ 7.28 (d, J=8.4 Hz, 2H), 7.21 (d, J=8.1 Hz, 2H), 5.42 (brs, 2H), 3.68-3.6 (m, 2H), 2.76-2.7 (m, 2H). 2.68-2.58 (m, 4H), 2.53-2.48 (m, 1H), 1.76-1.68 (m, 2H), 1.22-1.1 (m, 2H). Yield 0.62 (79%). ESI MS for $C_{15}H_{21}ClN_6$ expected 320.15, found m/z 321.4/323.4 [M+H], 319.2/321.5 [M−H].

Example 89: 1-(3-amino-1H-1,2,4-triazol-5-yl)-N-(4-chlorophenethyl)-N-ethylpiperidin-4-amine

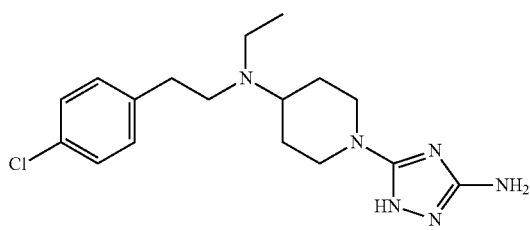 [SMILES: CCN(CCc1ccc(Cl)cc1)C1CCN(c2nc(N)n[nH]2)CC1]

Prepared in a manner similar to Example 21 using 2-(4-bromophenyl)ethanamine and acetaldehyde; $^1$H NMR (DMSO, 600 MHz) δ 7.26 (d, J=8.1 Hz, 2H), 7.20 (d, J=8.4 Hz, 2H), 5.64 (brs, 2H), 3.8-3.73 (m, 2H), 2.64-2.51 (m, 7H). 2.51-2.47 (m, 2H), 1.58-1.52 (m, 2H), 1.36-1.25 (m, 2H), 0.89 (t, J=7.1, 3H). Yield 0.31 g (67%). ESI MS for $C_{17}H_{25}ClN_6$ expected 348.18, found m/z 349.4/351.4 [M+H], 347.4 [M−H].

Example 90: (R)-5-(4-(2-(4-bromophenoxy)propyl)piperazin-1-yl)-1H-1,2,4-triazol-3-amine

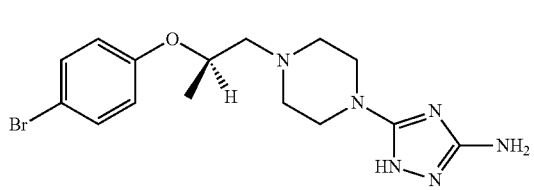 [SMILES: C[C@H](CN1CCN(c2nc(N)n[nH]2)CC1)Oc1ccc(Br)cc1]

$^1$H NMR (DMSO-$d_6$, 600 MHz) δ 11.43 (bs, 1H), 7.63 (bs, 2H), 7.46 (d, J=9.0 Hz, 2H), 7.00 (d, J=9.0 Hz, 2H), 5.13-5.03 (m, 1H), 3.93-3.78 (m, 2H), 3.58-3.45 (m, 6H), 3.27-3.15 (m, 2H), 1.20 (d, J=6.2 Hz, 3H). ESI MS for $C_{15}H_{21}BrN_6O$; expected 381.28; found m/z 381.4/383.4 in ratio ~1/1 (isotopes of Br) [M+H]$^+$.

Example 91: 1-(3-amino-1H-1,2,4-triazol-5-yl)-N-(4-chlorobenzyl)-N,4-dimethyl piperidine-4-carboxamide

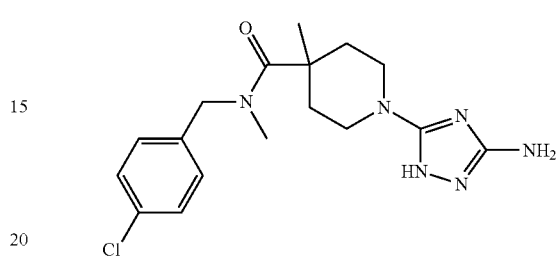

$^1$H NMR (DMSO, 500 MHz) δ 10.88 (bs, 1H), 7.38 (d, J=8.0 Hz, 2H), 7.19 (d, J=8.0 Hz, 2H), 5.56 (bs, 2H), 4.54 (s, 2H), 3.33-3.25 (m, 2H), 3.10-3.02 (m, 2H), 2.93 (s, 3H) 1.99-1.92 (m, 2H), 1.39-1.31 (m, 2H), 1.08 (s, 3H). ESI-LCMS m/z for $C_{17}H_{23}ClN_6O$: expected 362.9; found 363.5 [M+H]+, 361.4 (M−H)$^−$.

In non-limiting embodiments, Examples 92-153 and 155-190 were prepared according to the method described for Example 21. In non-limiting embodiments, Example 154 was prepared according to the method described for Example 107. In non-limiting embodiments, Examples 191-192 were prepared according to the method described for Example 13. In non-limiting embodiments, Examples 193-194 were prepared according to the method described for Example 1. In non-limiting embodiments, Examples 195-207 were prepared according to the method described for Example 17. In non-limiting embodiments, Examples 208-213 were prepared according to the method described for Example 11. In non-limiting embodiments, Examples 214-215 were prepared according to the method described for Example 40. In non-limiting embodiments, Example 216 was prepared according to the method described for Example 60. In non-limiting embodiments, Examples 217-219 were prepared according to the method described for Example 67. In non-limiting embodiments, Example 220 was prepared according to the method described for Example 70. In non-limiting embodiments, Example 221 was prepared according to the method described for Example 72. In non-limiting embodiments, Example 222 was prepared according to the method described for Example 76.

Example 223: 3-(4-(3-amino-1H-1,2,4-triazol-5-yl)-1-(3-(4-(trifluoromethyl)phenyl)propyl)piperazin-2-yl)propan-1-ol

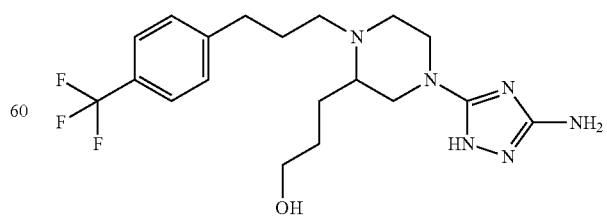

This compound was prepared according to the synthetic pathway described for Example 226, with the exception that the acidolytic removal of Boc was performed under conditions whereby no acetylation of the hydroxy group took place. ¹H NMR (DMSO-d₆, 500 MHz) δ 10.88 (bs, 1H), 7.64 (AA'BB', 2H, J=8 Hz), 7.46 (AA'BB', 2H, J=8 Hz), 3.94-3.86 (m, 1H) 3.82-3.74 (m, 1H), 3.71-3.37 (m, 7H), 3.18-3.09 (m, 1H), 3.08-2.98 (m, 1H), 2.81-2.63 (m, 2H), 2.09-1.87 (m, 3H), 1.68-1.48 (m, 2H), 1.47-1.33 (m, 2H). ¹⁹F (DMSO-d₆, 200 MHz) δ −60.06. ESI MS for $C_{19}H_{27}F_3N_6O$; expected 412.46; found m/z 413.3

¹H NMR (CD₃OD, 500 MHz) δ (ppm) 7.26-7.20 (m, 2H), 7.20-7.15 (m, 2H), 7.15-7.10 (m, 1H), 3.54-3.46 (m, 2H), 3.46-3.40 (m, 1H), 3.29-3.27 (m, 2H), 3.09-3.01 (m, 1H), 2.90-2.82 (m, 2H), 2.77-2.70 (m, 1H), 2.66-2.54 (m, 2H), 2.47-2.37 (m, 2H), 1.86-1.71 (m, 2H), 1.68-1.56 (m, 2H), 1.48-1.36 (m, 2H). ESI MS for $C_{18}H_{28}N_6O$; expected 344.45; found m/z 345.3.

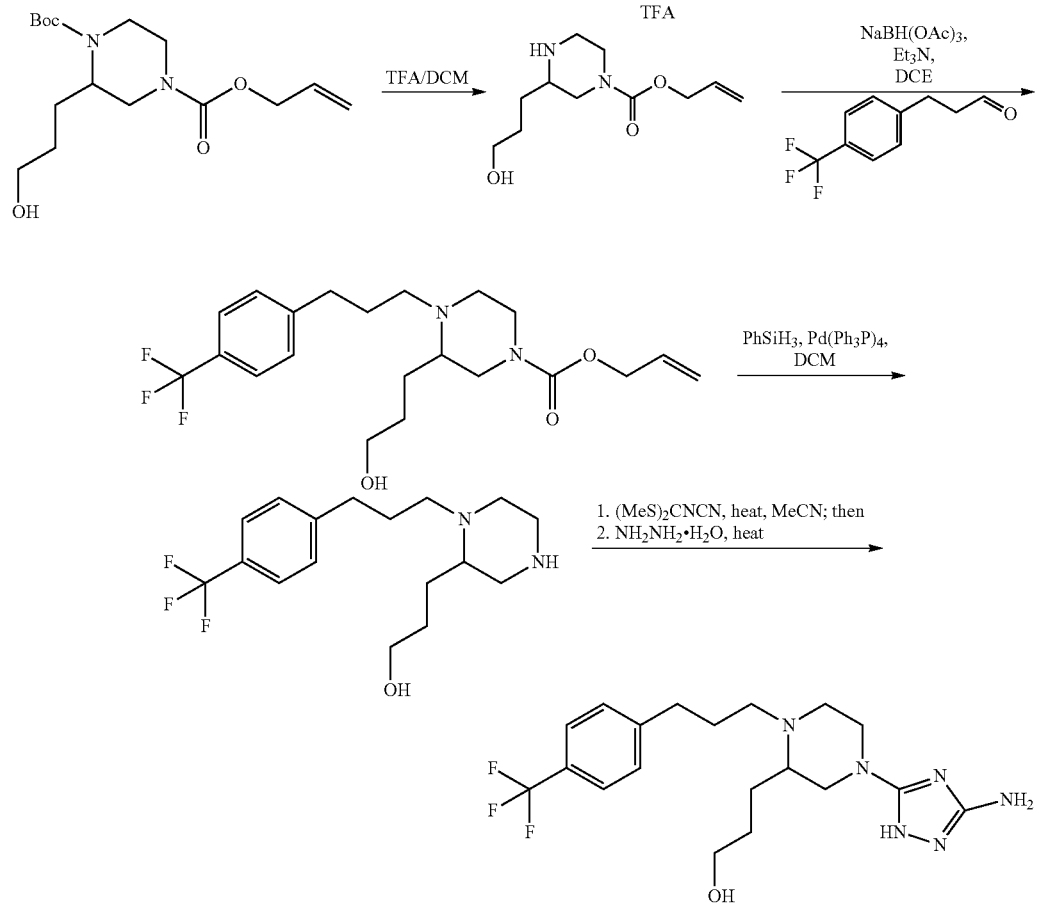

Example 226: 3-(4-(3-amino-1H-1,2,4-triazol-5-yl)-1-(3-(4-bromophenyl)propyl)piperazin-2-yl)propan-1-ol

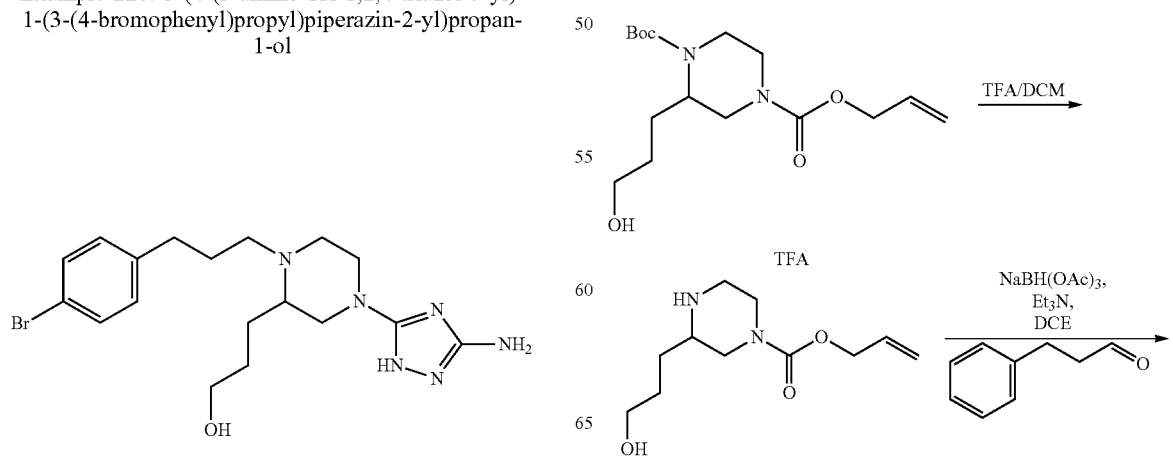

Step 2: tert-butyl 4-amino-4-(2-hydroxyethyl)piperidine-1-carboxylate

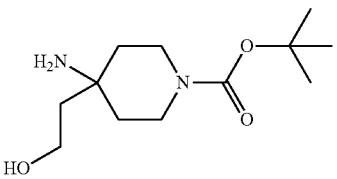

Removal of benzyloxycarbonyl group was accomplished according to the previously reported procedure (Example 225, Step 4). From 1.0 g (2.6 mmol) of starting material 0.56 g (2.3 mmol, 88% yield) of product were obtained. ESI-MS m/z for $C_{12}H_{24}N_2O_3$ expected 244.34, found 245.3 [M+H].

Step 3: tert-butyl 4-((4-chlorophenethyl)(methyl)amino)-4-(2-hydroxyethyl)piperidine-1-carboxylate

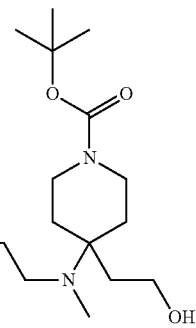

The sequential double reductive alkylation of the amino group with (4-chlorophenyl) acetaldehyde followed by formaldehyde was accomplished according to the procedure described elsewhere herein. From 0.56 g (2.3 mmol) of starting material, 0.8 g (2.0 mmol, 88% yield) of the title compound were obtained. ESI-MS m/z for $C_{20}H_{31}ClN_2O_3$ expected 396.96, found 396.7/398.7 [M+H].

Step 4: 2-(1-(3-amino-1H-1,2,4-triazol-5-yl)-4-((4-chlorophenethyl)(methyl)amino)piperidin-4-yl)ethanol Removal of the Boc-protecting group and installation of the 3-amino-1H-1,2,4-triazole moiety were accomplished according to the previously described procedures (Example 5, Step 3, and Example 1 respectively). 73 mg of product (0.19 mmol, 10% yield over 2 steps) were obtained. ¹H NMR (DMSO-d₆, 500 MHz) δ (ppm) 7.36 (d, 2H, J=8.5 Hz), 7.32 (d, 2H, J=8.5 Hz), 3.78 (brs, 3H), 3.61 (t, 2H, J=6.2 Hz), 3.49-3.41 (m, 1H), 3.12-3.04 (m, 4H), 2.8 (d, 3H, J=4.9 Hz), 2.14-2.08 (m, 2H), 2.07-2.0 (m, 4H). ESI-MS m/z for $C_{17}H_{25}ClN_6O$ expected 378.91; found 379.5/381.4 [M+H], 377.3/379.4 [M−H].

---

-continued

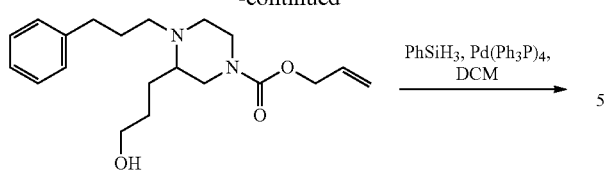

PhSiH₃, Pd(Ph₃P)₄, DCM

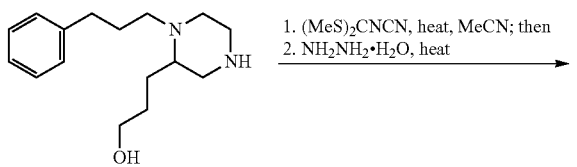

1. (MeS)₂CNCN, heat, MeCN; then
2. NH₂NH₂·H₂O, heat

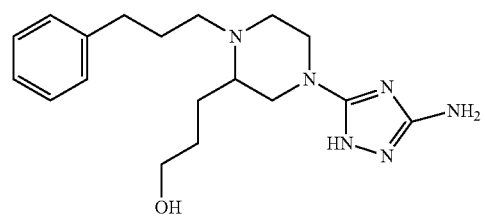

Example 228: 2-(1-(3-amino-1H-1,2,4-triazol-5-yl)-4-((4-chlorophenethyl)(methyl)amino)piperidin-4-yl)ethanol

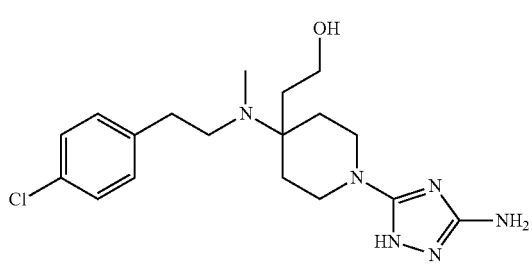 [SMILES: CN(CCc1ccc(Cl)cc1)C1(CCO)CCN(c2nc(N)n[nH]2)CC1]

Step 1: tert-butyl 4-(((benzyloxy)carbonyl)amino)-4-(2-hydroxyethyl)piperidine-1-carboxylate

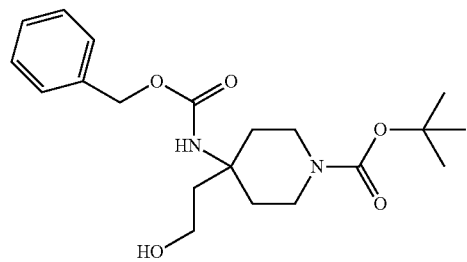 [SMILES: CC(C)(C)OC(=O)N1CCC(CCO)(NC(=O)OCc2ccccc2)CC1]

1-tert-butoxycarbonyl-4-allyl-4-[(benzyloxycarbonyl)amino]piperidine (see Example 256, Step 1) was subjected to the sequential ozonolysis-ozonide reduction procedure as described for Example 228, Step 4). 2.5 g (6.7 mmol) were obtained. ESI-MS m/z for $C_{20}H_{30}N_2O_5$ expected 378.47; found 349.4 [M+H].

Example 229: 4-(4-(3-amino-1H-1,2,4-triazol-5-yl)-1-(3-(4-bromophenyl)propyl)piperazin-2-yl)-2-methylbutan-2-ol

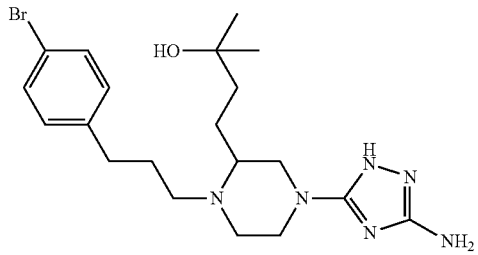 [SMILES: CC(C)(O)CCC1CN(c2nc(N)n[nH]2)CCN1CCCc1ccc(Br)cc1]

Step 1: 2-methyl-4-(N$^1$-Boc-N$^4$-Alloc-piperazin-2)-ylbutan-2-ol

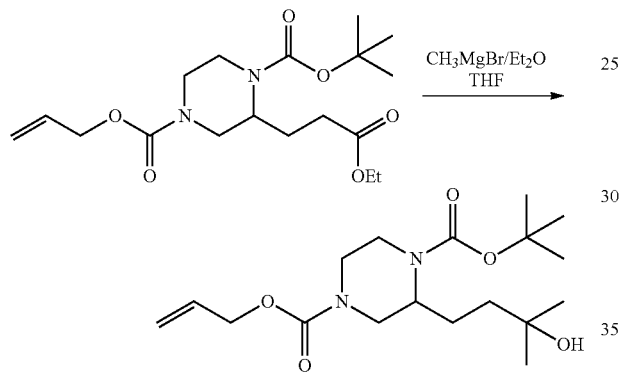

Ethyl 3-[N$^1$-Boc-N4-Alloc-piperazin)-2-yl] propanoate (0.5 g; 1.345 mmol) was dissolved in THF under argon (15 ml), and the mixture was placed into an ice/water bath. Methylmagnesium bromide 3M in ether (1.125 ml; 3.375 mmol) was carefully added via syringe. The reaction mixture was stirred for 2 hrs in a cooling bath and was quenched with saturated aqueous ammonium chloride solution. This mixture was subsequently extracted several times with ethyl acetate. An organic phase was dried over MgSO$_4$ and concentrated to yield the yellow oil. LC/MS analysis of this crude material revealed that aside the desired product, the Alloc-deprotected product formed as well. LC/MS indicated desired product; R$_T$=4.41 min; ES(+): [M+Na$^+$]=379.3; product without an Alloc protecting group; R$_T$=2.32 min; ES(+): [M+H$^+$]=273.3. This crude material was Alloc-deprotected without further purification.

Step 2: 2-methyl-4-(N$^1$-Boc-piperazin-2)-ylbutan-2-ol

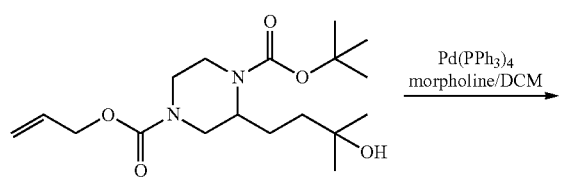

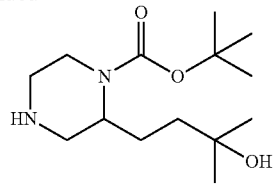

The crude 2-methyl-4-(N$^1$-Boc-N$^4$-Alloc-piperazin-2)-ylbutan-2-ol was dissolved in DCM (20 ml) with morpholine (220 μl; 2.52 mmol), followed by addition of tetrakis (triphenylphosphine) palladium (0) (20 mg; catalyst). The system was stirred overnight at ambient temperature. The reaction mixture was washed with water, dried over MgSO$_4$ and concentrated. The product was purified by flash silica-gel column chromatography using gradient CHCl$_3$/MeOH 15/1 to 5/1 (v/v) to yield pure product (136 mg; 0.5 mmol). 37% yield over two steps. LC/MS: R$_T$=2.24 min; ES(+): [M+Na]=295.3; [M+H]=273.3.

Step 3: 2-methyl-4-[N$^1$-Boc-N4-(5-amino-1,2,4-triazol-3-yl)-piperazin-2]-ylbutan-2-ol

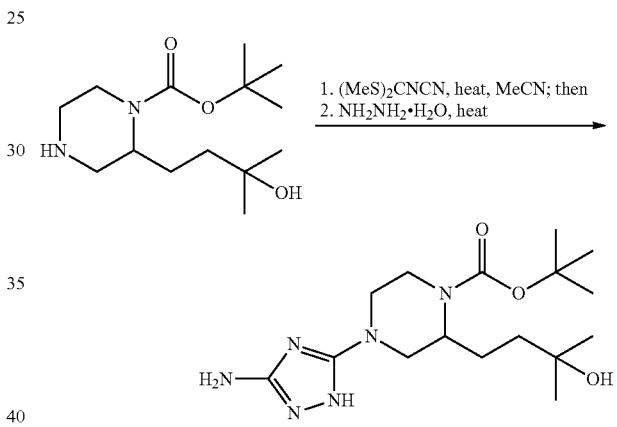

The aminotriazole synthesis (reaction with S,S'-dimethyl-N-cyano-dithioimino carbonate and cyclization with hydrazine) was done according to the procedure described elsewhere herein. From 135 mg (0.495 mmol) of the starting material, 145 mg of the desired product (82% yield) was obtained. Product was purified by flash silica-gel column chromatography using CH$_3$Cl/MeOH 9/1 (v/v) solvent system. LC/MS: R$_T$=2.92 min; ES(+): [M+H]=355.3; ES(−): [M−H]=353.4. $^1$H NMR (DMSO-d$_6$, 500 MHz) δ (ppm) 10.97 (brs, 1H); 5.77 (brs, 2H); 4.14 (s, 1H); 3.97 (brs, 1H); 3.79 (brd, 1H, J=12.8 Hz); 3.67 (brd, 2H, J=11.9 Hz); 2.95 (brs, 1H); 1.67-1.73 (m, 1H); 1.49-1.56 (m, 1H); 1.34-1.43 (m, 2H); 1.40 (s, 9H); 1.17 (dt, 1H, J=13.0 Hz, J=4.1 Hz); 1.01 (s, 3H); 1.00 (s, 3H); 0.78-0.81 (m, 1H).

Step 4: 2-methyl-4-[N$^4$-(5-amino-1,2,4-triazol-3-yl)-piperazin-2]-ylbutan-2-ol

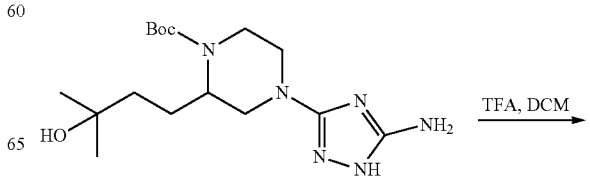

143

-continued

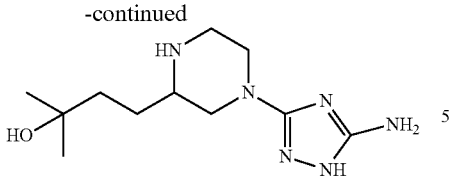

The starting material (142 mg; 0.40 mmol) was dissolved in DCM/TFA (8 ml/1 ml) and stirred at ambient temperature for 5 hrs, after which time the reaction mixture was concentrated in vacuo to give colorless oil. The crude product was taken for next step without the further purification. LC/MS: $R_T$=0.80 min; ES(+): [M+H]=255.2.

Step 5: 2-methyl-4-{[$N^1$-(4-bromophenyl)prop-3-yl]-$N^4$-(5-amino-1,2,4-triazol-3-yl)-piperazin-2]}-ylbutan-2-ol

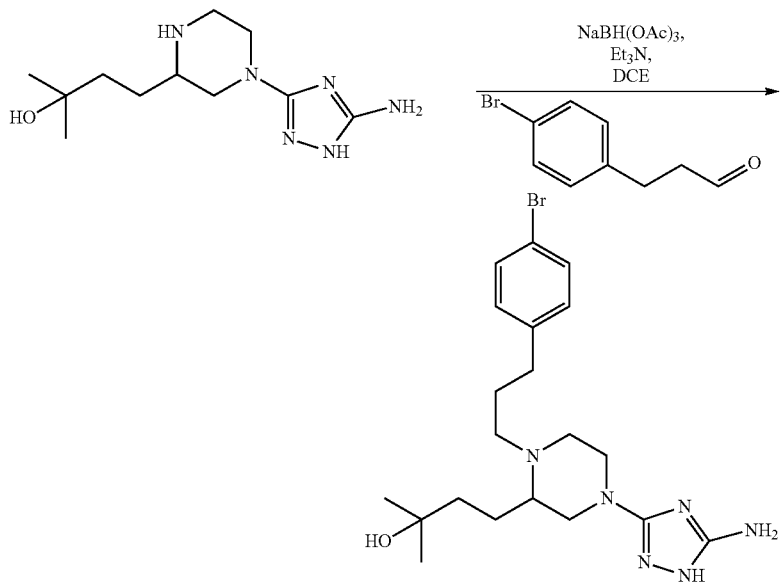

The reductive amination with 3-(4-bromophenyl)propanal was performed according to the procedure described elsewhere herein. The crude mixture was purified by preparative HPLC in gradient 10-80% CH$_3$CN (without addition of TFA). 100 mg of product were obtained. Yield 55%. LC/MS: $R_T$=2.92 min; ES(+): [M+H]=451.3/453.2; ES(−): [M−H]=449.3/451.3. $^1$H NMR (DMSO-d$_6$+D$_2$O, 500 MHz) δ (ppm) 7.41 (d, 2H, $J_{AA'BB'}$=7.7 Hz); 7.15 (d, 2H, $J_{AA'BB'}$=7.7 Hz); 3.00-3.20 (m, 6H); 2.78-2.87 (m, 1H); 1.72-1.94 (m, 3H); 1.25-1.60 (m, 4H); 1.01 (s, 3H); 0.99 (s, 3H).

Examples 231 & 234

1-(3-amino-1H-1,2,4-triazol-5-yl)-N-(4-chlorophenethyl)-3-propylpiperidin-4-amine (Diastereoisomer A and diastereoisomer B)

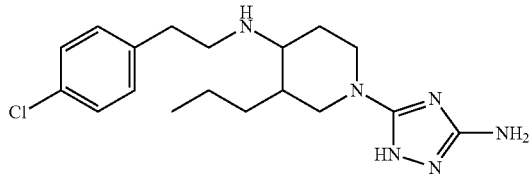 [SMILES: CCCC1CN(c2nc(N)n[nH]2)CCC1NCCc1ccc(Cl)cc1]

144

Step 1: 1-Benzyl-3-allyl-4-oxopiperidine

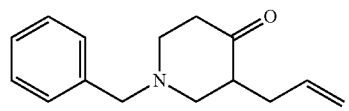 [SMILES: C=CCC1CN(Cc2ccccc2)CCC1=O]

To 1-benzyl-4-piperidone (5 g, 25 mmol), a solution of KHMDS (55 mL of 0.5M solution in toluene, 27.6 mmol) was added at ambient temperature under argon. The reaction mixture was stirred for 1 h. Allyl bromide (2.5 ml, 30 mmol) was then added in one portion, and the system was stirred overnight at room temperature. The reaction mixture was diluted with AcOEt, washed with water, brine, died over MgSO$_4$ and concentrated. The title product was purified by column chromatography AcOEt/hexane (1:2). Yield 3.15 g (55%). $^1$H NMR (CDCl$_3$, 600 MHz) δ (ppm) 7.38-7.25 (m, 5H), 5.76-5.67 (m, 1H), 5.0 (dd, 2H, J=17.6 Hz, 11.1 Hz), 3.68 (AA'BB', 1H, J=13.1 Hz), 3.54 (AA'BB', 1H, J=13.1 Hz), 3.09-3.03 (m, 1H), 3.03-2.96 (m, 1H), 2.65-2.50 (m, 3H), 2.50-2.43 (m, 1H), 2.37 (dt, 1H, J=13.9 Hz, 3.9 Hz), 2.24 (t, 1H, J=10.5 Hz), 2.07-2.0 (m, 1H). ESI-MS m/z for C$_{15}$H$_{19}$NO expected 229.32; found 230.3 [M+H].

Step 2: 1-Boc-4-oxo-3-propylpiperidine

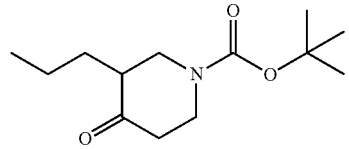 [SMILES: CCCC1CN(C(=O)OC(C)(C)C)CCC1=O]

A mixture of 1-benzyl-3-allyl-4-oxopiperidine (0.6 g, 2.61 mmol), Boc$_2$O (0.62 g, 2.87 mmol), Pd(OH)$_2$/C (cat. amount) in AcOEt was stirred under hydrogen atmosphere (balloon pressure) for 2 h in room temperature. The reaction was filtered through a pad of Celite and concentrated to give 0.62 g of light yellow oil, which was pure enough to be taken to the next step without further purification. ESI-MS m/z for $C_{13}H_{23}NO_3$ expected 241.33; found 142.3 [M+H-Boc].

Step 3: 1-Boc-N-[2-(4-chlorophenyl)ethyl]-3-propylpiperidin-4-amine (racemic cis and trans)

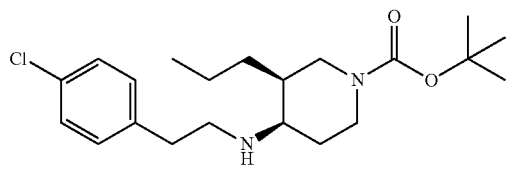

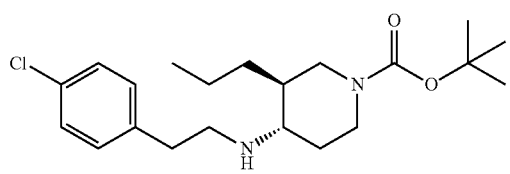

Racemic Cis & Racemic Trans

1-Boc-4-oxo-3-propylpiperidine 0.7 g (3.19 mmol) was subjected to the reductive amination with 2-(4-chlorophenyl)ethyl amine, according to the procedure previously described (Example 21, Step 1). Diastereoisomers were separated by crystallization from $Et_2O$/hexanes to give 0.50 g of diasteroisomer A and 0.53 g diastereoisomer B (combined yield 83%).

Diasteroisomer A:
$^1$H NMR (CDCl$_3$, 600 MHz) δ (ppm) 7.26 (AA'BB', 2H, J=8.1 Hz), 7.14 (AA'BB', 2H, J=8.3 Hz), 4.14-4.03 (m, 1H), 3.99-3.78 (m, 2H), 3.03-2.73 (m, 7H), 1.83-1.73 (m, 1H), 1.71-1.41 (m, 3H), 1.43 (s, 9H), 1.23-1.03 (m, 3H), 0.95-0.80 (m, 3H). ESI-MS m/z for $C_{21}H_{33}ClN_2O_2$: expected 380.96; found 380.7.1/382.7 [M+H].

Diasteroisomer B:
$^1$H NMR (CDCl$_3$, 600 MHz) δ (ppm) 7.26 (AA'BB', 2H, J=8.3 Hz), 7.14 (AA'BB', 2H, J=8.3 Hz), 4.02-3.92 (m, 1H), 3.89-3.79 (m, 1H), 3.73-3.68 (m, 1H), 2.93-2.63 (m, 6H), 1.76-1.64 (m, 1H), 1.58-1.46 (m, 2H), 1.43 (s, 9H), 1.23-1.03 (m, 3H), 0.94-0.83 (m, 3H). ESI-MS m/z for $C_{21}H_{33}ClN_2O_2$: expected 380.96; found 380.7.1/382.7 [M+H].

Example 231: 1-(3-amino-1H-1,2,4-triazol-5-yl)-N-(4-chlorophenethyl)-3-propylpiperidin-4-amine (Diastereoisomer A)

Removal of the Boc-protecting group and installation of the 3-amino-1H-1,2,4-triazole moiety were accomplished according to the procedures described elsewhere herein (Example 5, Step 3 and Example 1, Steps 1 and 2, respectively). $^1$H NMR (DMSO-d$_6$, 600 MHz) δ (ppm) 9.54 (brs, 1H), 9.24 (brs, 1H), 7.36 (AA'BB', 2H, J=8.1 Hz), 7.28 (AA'BB', 2H, J=8.1 Hz), 3.88-3.78 (m, 2H), 3.39-3.32 (m, 1H), 3.18-3.08 (m, 2H), 3.07-2.98 (m, 4H), 2.17-2.11 (m, 1H), 1.99-1.92 (m, 1H), 1.83-1.73 (m, 1H), 1.50-1.41 (m, 1H), 1.40-1.32 (m, 1H), 1.29-1.16 (m, 2H), 0.84 (t, 3H, J=6.8 Hz). ESI-MS m/z for $C_{18}H_{27}ClN_6$: expected 362.91; found 362.7/364.7 [M+H].

Example 234: 1-(3-amino-1H-1,2,4-triazol-5-yl)-N-(4-chlorophenethyl)-3-propylpiperidin-4-amine (Diastereoisomer B)

Removal of the Boc-protecting group and installation of the 3-amino-1H-1,2,4-triazole moiety were accomplished according to the procedures described elsewhere herein (Example 5, Step 3 and Example 1, Steps 1 and 2, respectively). $^1$H NMR (DMSO-d$_6$, 600 MHz) δ (ppm) 9.58 (brs, 1H), 9.30 (brs, 1H), 7.39 (AA'BB', 2H, J=8.3 Hz), 7.31 (AA'BB', 2H, J=8.1 Hz), 3.91-3.82 (m, 2H), 3.41-3.34 (m, 1H), 3.20-3.12 (m, 1H), 3.12-2.91 (m, 5H), 2.21-2.13 (m, 1H), 2.02-1.94 (m, 1H), 1.86-1.73 (m, 1H), 1.52-1.44 (m, 1H), 1.43-1.34 (m, 1H), 1.33-1.29 (m, 2H), 0.86 (t, 3H, J=6.6 Hz). ESI-MS m/z for $C_{18}H_{27}ClN_6$: expected 362.91; found 362.7/364.7 [M+H].

Example 238: N-(1-(3-amino-1H-1,2,4-triazol-5-yl)piperidin-4-yl)-1-(3-chlorophenyl)-N-ethylmethanesulfonamide

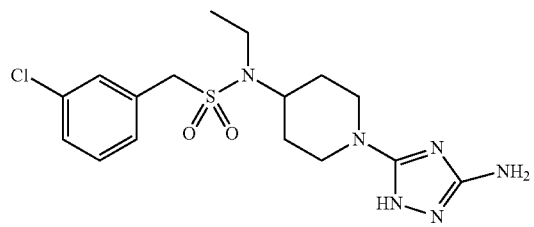 [SMILES: CCN(C1CCN(c2nc(N)n[nH]2)CC1)S(=O)(=O)Cc1cccc(Cl)c1]

Step 1: tert-butyl 4-{[(3-chlorobenzyl)sulfonyl]amino}piperidine-1-carboxylate

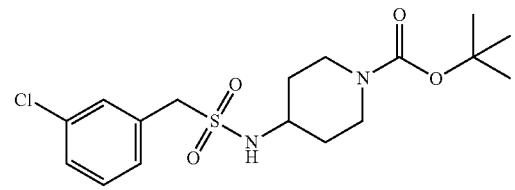 [SMILES: CC(C)(C)OC(=O)N1CCC(NS(=O)(=O)Cc2cccc(Cl)c2)CC1]

3-chlorophenylmethanesulfonyl chloride (1 g, 4.44 mol), 1-Boc-4-aminopiperidine (0.89 g, 4.44 mmol), and Et$_3$N (0.68 mL, 4.89 mmol) in DCM (10 mL) were stirred overnight in room temperature. The mixture was diluted with AcOEt (50 mL) washed with 2M HCl (2×), brine, dried over MgSO$_4$, filtered and evaporated to dryness to give 1.6 g of pure product. ESI-MS m/z for $C_{17}H_{25}ClN_2O_4S$ calculated 388.92, found 387.4/389.3 [M–H].

Step 2: tert-butyl 4-((1-(3-chlorophenyl)-N-ethylmethyl)sulfonamido)piperidine-1-carboxylate

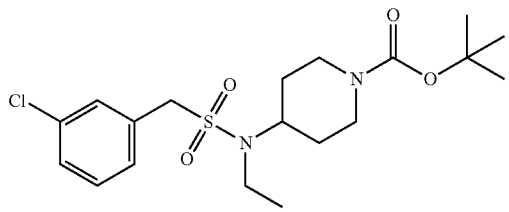 [SMILES: CCN(C1CCN(C(=O)OC(C)(C)C)CC1)S(=O)(=O)Cc1cccc(Cl)c1]

tert-butyl 4-{[(3-chlorobenzyl)sulfonyl]amino}piperidine-1-carboxylate (0.4 g, 1.03 mmol) was suspended in DMF (10 mL), and Cs$_2$CO$_3$ (1 g, 3.09 mmol) was added followed by EtI (0.17 mL, 2.06 mmol). The mixture was heated at 80° C. under stopper overnight, cooled to ambient temperature, and extracted with AcOEt (50 mL) and 10% Na$_2$S$_2$O$_3$ (aq). The organic layer was washed with additional portion of 10% Na$_2$S$_2$O$_3$, water, brine, dried over MgSO$_4$, filtered and evaporated to dryness to give 0.27 g of the title compound (yield 63%). ESI-MS m/z for C$_{19}$H$_{29}$ClN$_2$O$_4$S expected 416.97, found 317.4/319.4 [M+H-Boc], 415.5 [M−H].

Step 3: N-(1-(3-amino-1H-1,2,4-triazol-5-yl)piperidin-4-yl)-1-(3-chlorophenyl)-N-ethylmethanesulfonamide Removal of the Boc-protecting group and installation of the 3-amino-1H-1,2,4-triazole moiety were accomplished according to the previously described procedures (Example 5, Step 3 and Example 1, Steps 1 and 2, respectively). $^1$H NMR (DMSO, 600 MHz) δ (ppm) 7.48 (brs, 1H), 7.44-7.39 (m, 2H), 7.39-7.35 (m, 1H), 5.6 (brs, 2H), 4.43 (s, 2H), 3.86-3.79 (m, 2H), 3.55-3.46 (m, 1H), 3.12-3.05 (m, 2H), 2.64-2.54 (m, 2H), 1.69-1.55 (m, 4H), 0.96 (t, J=7 Hz, 3H). ESI MS m/z for C$_{16}$H$_{23}$ClN$_6$O$_2$S expected 398.92, found 399.4/401.4 [M+H], 397.4/399.4 [M−H].

Example 245: 3-(1-(3-amino-1H-1,2,4-triazol-5-yl)-4-((4-chlorophenethyl)(methyl)amino)piperidin-4-yl)propan-1-ol

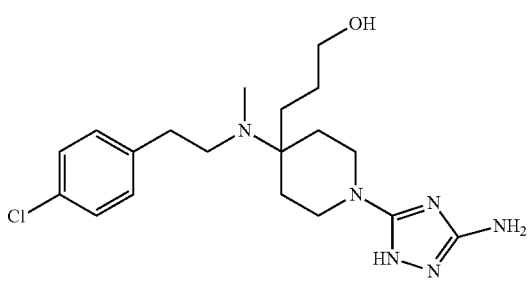 [SMILES: CN(CCc1ccc(Cl)cc1)C1(CCCO)CCN(c2nc(N)n[nH]2)CC1]

Step 1: ethyl 4-amino-4-(3-hydroxypropyl)piperidine-1-carboxylate

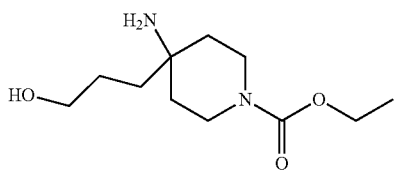 [SMILES: CCOC(=O)N1CCC(N)(CCCO)CC1]

1-ethoxycarbonyl-4-[(benzyloxycarbonyl)amino]-4-(3-hydroxypropyl)piperidine was subjected to the removal of carbobenzyloxycarbonyl group according to the procedure reported elsewhere herein. From 1.0 g (2.75 mmol) of starting material, 0.6 g (2.6 mmol, 95% yield) of product was obtained. ESI-MS m/z for C$_{11}$H$_{22}$N$_2$O$_3$ expected 230.31, found 231.2 [M+H].

Step 2: ethyl 4-((4-chlorophenethyl)(methyl)amino)-4-(3-hydroxypropyl)piperidine-1-carboxylate

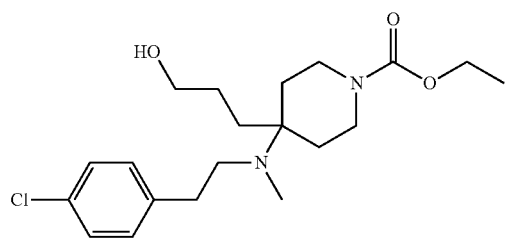 [SMILES: CCOC(=O)N1CCC(CCCO)(N(C)CCc2ccc(Cl)cc2)CC1]

The sequential double reductive alkylation of the amino group with (4-chlorophenyl)acetaldehyde followed by formaldehyde was accomplished according to the procedure described elsewhere herein. From 0.6 g (2.75 mmol) of starting material, 0.82 g (2.1 mmol, 78% yield) of the title compound was obtained. ESI-MS m/z for C$_{20}$H$_{31}$ClN$_2$O$_3$ expected 382.93, found 382.7/384.7 [M+H].

Step 3. 3-(1-(3-amino-1H-1,2,4-triazol-5-yl)-4-((4-chlorophenethyl)(methyl)amino)piperidin-4-yl)propan-1-ol Removal of ethoxycarbonyl group and installation of the 3-amino-1H-1,2,4-triazole moiety were accomplished according to the procedure described elsewhere herein. 90 mg (0.2 mmol, 11% over three steps) of the title compound was obtained after purification by reversed-phase chromatography. $^1$H NMR (DMSO, 500 MHz) δ (ppm) 7.40-7.34 (m, 4H), 3.90-3.75 (m, 2H), 3.50-3.38 (m, 4H), 3.25-3.05 (m, 4H), 2.82 (s, 3H), 2.24-189 (m, 6H), 1.66-1.53 (m, 2H). ESI-MS m/z for C$_{19}$H$_{29}$ClN$_6$O expected 392.9, found 393.5/395.5 [M+H].

Example 246: 3-(1-(3-amino-1H-1,2,4-triazol-5-yl)-4-((4-bromophenethyl)(methyl)amino)piperidin-3-yl)propan-1-ol

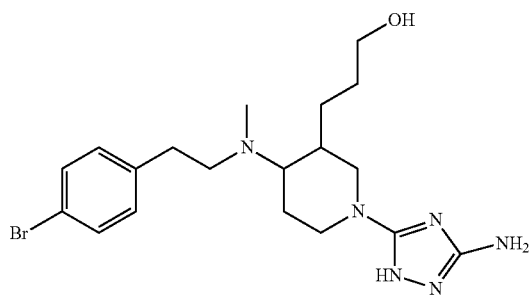 [SMILES: CN(CCc1ccc(Br)cc1)C1CCN(c2nc(N)n[nH]2)CC1CCCO]

Step 1. ethyl 3-allyl-4-((4-bromophenethyl)(methyl)amino)piperidine-1-carboxylate

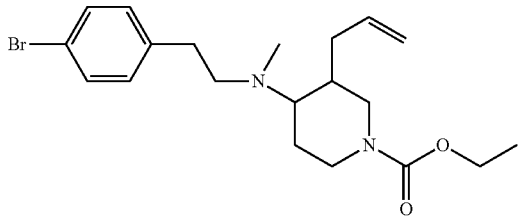 [SMILES: C=CCC1CN(C(=O)OCC)CCC1N(C)CCc1ccc(Br)cc1]

Ethyl 3-allyl-4-oxopiperidine-1-carboxylate (see Example 228, Step 1) was subjected to the sequential double reductive alkylation of the carbonyl group with 2-(4-bromophenyl) ethylamine followed by formaldehyde. 0.35 g (0.85 mmol) of the title compound was synthesized. ESI-MS m/z for $C_{20}H_{29}BrN_2O_2$ expected 409.37, found 409.2/411.2 [M+H].

Step 2: ethyl 4-((4-bromophenethyl)(methyl)amino)-3-(3-hydroxypropyl)piperidine-1-carboxylate

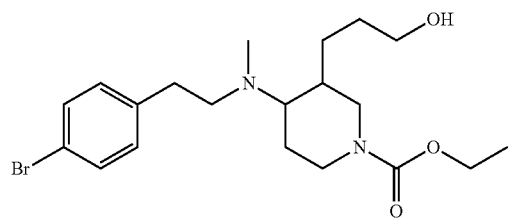 [SMILES: CCOC(=O)N1CCC(N(C)CCc2ccc(Br)cc2)C(CCCO)C1]

0.35 g (0.85 mmol) of ethyl 4-[[2-(4-bromophenyl)ethyl](methyl)amino]-3-allylpiperidine-1-carboxylate was subjected to the hydroboration-oxidation procedure described elsewhere herein. From 0.35 g (0.85 mmol) of starting material, 0.26 g (0.6 mmol, 71% yield) of the title compound were obtained.

Step 3: 3-(1-(3-amino-1H-1,2,4-triazol-5-yl)-4-((4-bromophenethyl)(methyl)amino)piperidin-3-yl)propan-1-ol Removal of ethoxycarbonyl group and installation of the 3-amino-1H-1,2,4-triazole moiety were accomplished according to the procedure described elsewhere herein. 25 mg (0.057 mmol, 9% over three steps) of the title compound were obtained after purification by reversed-phase chromatography. $^1$H NMR (DMSO-d$_6$, 75° C., 500 MHz) δ (ppm) 7.55-7.48 (m, 2H), 7.36-7.29 (m, 2H), 4.09-4.03 (m, 1H), 4.03-3.88 (m, 2H), 3.55-3.41 (m, 3H), 3.4-3.29 (m, 2H), 3.17-3.06 (m, 2H), 3.0-2.9 (m, 2H), 2.85 (s, 3H), 2.33-2.17 (m, 1H), 2.15-2.04 (m, 1H), 2.0-1.9 (m, 1H), 1.72-1.6 (m, 2H), 1.54-1.4 (m, 1H). ESI-MS m/z for $C_{19}H_{29}BrN_6O$ expected 437.39, found 437.5/439.5 [M+H], 435.4/437.3 [M−H].

Example 247: 1-(3-amino-1H-1,2,4-triazol-5-yl)-N-(4-bromophenethyl)1-4-propyl piperidin-4-amine

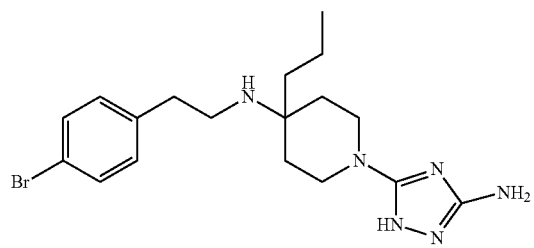 [SMILES: CCCC1(NCCc2ccc(Br)cc2)CCN(c2nc(N)n[nH]2)CC1]

Step 1: ethyl 4-amino-4-propylpiperidine-1-carboxylate

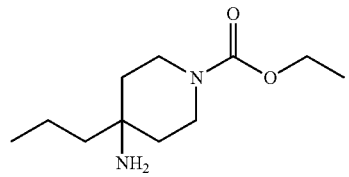

1-ethoxycarbonyl-4-allyl-4-[(benzyloxycarbonyl)amino] piperidine was subjected to the hydrogenolytic removal of Cbz-protecting group (concomitant with saturation of the double bond) according to the procedure reported elsewhere herein. 0.75 g (3.5 mmol) of the title compound were synthesized. ESI MS m/z for $C_{11}H_{22}N_2O_2$ expected 214.31, found 215.4 [M+H].

Step 2: ethyl 4-[2-(4-bromophenyl)ethyl]amino-4-propylpiperidine-1-carboxylate

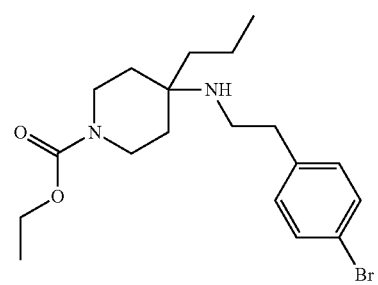 [SMILES: CCCC1(NCCc2ccc(Br)cc2)CCN(C(=O)OCC)CC1]

The reductive alkylation of the amino group with (4-bromophenyl)acetaldehyde was accomplished according to the procedure reported elsewhere herein. From 0.75 g (3.5 mmol) of starting material 0.81 g (2.0 mmol, 58% yield) of the title compound were obtained. ESI MS m/z for $C_{19}H_{29}BrN_2O_2$ expected 397.36, found 397.2/399.2 [M+H], 397.4/395.4 [M–H].

Step 3: 1-(3-amino-1H-1,2,4-triazol-5-yl)-N-(4-bromophenethyl)1-4-propylpiperidin-4-amine Removal of ethoxycarbonyl group and installation of the 3-amino-1H-1,2,4-triazole moiety were accomplished according to the procedure reported elsewhere herein. 150 mg (0.37 mmol, 18% over three steps) of the title compound were obtained after purification by silica-gel chromatography. $^1$H NMR (DMSO-$d_6$, 500 MHz) δ (ppm) 9.17 (brs, 2H), 7.49 (d, 2H, J=8.1 Hz), 7.24 (d, 2H, J=8.1 Hz), 3.72 (brs, 3H), 3.12 (brs, 3H), 3.01 (brs, 3H), 1.98-1.91 (m, 2H), 1.9-1.84 (m, 2H), 1.73 (m, 2H), 1.34-1.26 (m, 2H), 0.87 (t, 3H, J=7 Hz). ESI MS m/z for $C_{18}H_{27}BrN_6$ expected 407.36, found 407.5/409.4 [M+H], 405.4/407.6 [M–H].

Example 256: N-(1-(3-amino-1H-1,2,4-triazol-5-yl)-4-(4-hydroxybutyl)piperidin-4-yl)-1-(4-bromophenyl)methanesulfonamide

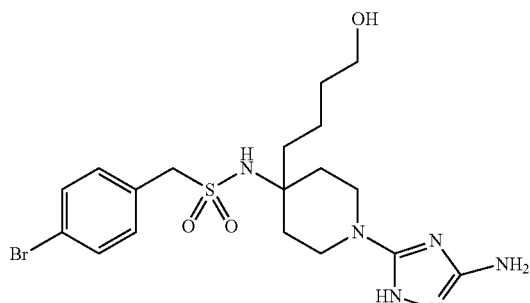

Step 1: 1-tert-butoxycarbonyl-4-allyl-4-[(benzyloxycarbonyl)amino]piperidine

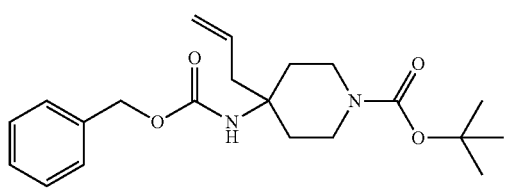 [SMILES: C=CCC1(NC(=O)OCc2ccccc2)CCN(C(=O)OC(C)(C)C)CC1]

To a cooled solution of piperid-4-one (10 g, 50.2 mmol), benzyl carbamate (9 g, 60.2 mmol) and allyltrimethylsilane (11 ml, 70.3 mmol) in DCM (100 mL), BF$_3$·Et$_2$O (7.3 ml, 60.2 mmol) was added dropwise at 0° C. The reaction was stirred at 0° C. for 40 min, and then overnight in room temperature. The reaction was concentrated to dryness, and taken into 1M NaOH/acetone mixture (200 mL, 1:1 v/v). 50.2 mmol (10.8 g) of Boc$_2$O were then added and the system was stirred for 5 hours in room temperature. The product was isolated by standard aqueous acid/base wash and purified by column chromatography (AcOEt/hexanes 1/10) to yield 11 g (58% yield) of white crystalline solid. $^1$H NMR (CDCl$_3$, 500 MHz) δ (ppm) 7.37-7.27 (m, 5H), 5.75-5.65 (m, 1H), 5.08-4.98 (m, 4H), 4.50 (bs, 1H), 3.79-3.70 (m, 2H), 3.05-2.97 (m, 2H), 2.48-2.43 (m, 2H), 2.02-1.92 (m, 2H), 1.53-1.44 (m, 2H), 1.42 (s, 9H). ESI-MS m/z for $C_{21}H_{30}N_2O_4$ expected 374.48; found 397.3 [M+Na].

Step 2: tert-butyl 4-(((benzyloxy)carbonyl)amino)-4-(4-methoxy-4-oxobut-2-en-1-yl)piperidine-1-carboxylate

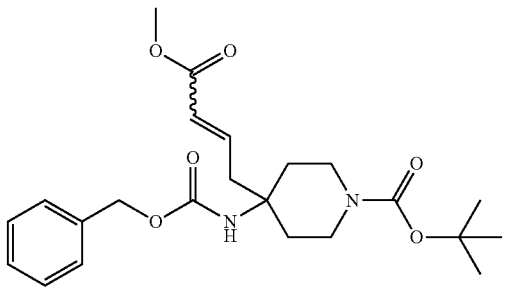 [SMILES: COC(=O)C=CCC1(NC(=O)OCc2ccccc2)CCN(C(=O)OC(C)(C)C)CC1]

To the mixture of 1-tert-butoxycarbonyl-4-allyl-4-[(benzyloxycarbonyl) amino]piperidine (1 g, 2.67 mmol), methyl acrylate (0.7 mL, 8.01 mmol) in DCM (5 mL), Grubbs $2^{nd}$ generation catalyst 90 mg (4% mol) was added and the reaction was refluxed for 1 h under argon. Then the reaction was concentrated in vacuo and product was isolated by column chromatography (hexanes/AcOEt, 100/0 to 1/6). 1.04 g (94% yield) of product was obtained. $^1$H NMR (CDCl$_3$, 500 MHz) δ (ppm) 7.38-7.28 (m, 5H), 6.86 (dt, 1H, J=15.6 Hz, J=7.7 Hz), 5.83 (d, 1H, J=15.6 Hz), 5.04 (s, 2H), 4.59 (bs, 1H), 3.85-4.72 (m, 2H), 3.69 (s, 3H), 2.98 (dd, 2H, J=12 Hz, J=12 Hz), 2.65 (d, 2H, J=6.7 Hz), 2.02-1.92 (m, 2H), 1.55-1.46 (m, 2H), 1.42 (s, 9H). ESI-MS m/z for $C_{23}H_{32}N_2O_6$ expected 432.52; found 455.3 [M+Na].

Step 3: tert-butyl 4-amino-4-(4-methoxy-4-oxobutyl)piperidine-1-carboxylate

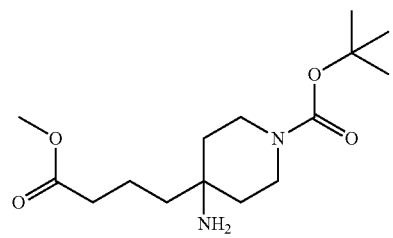 [SMILES: COC(=O)CCCC1(N)CCN(C(=O)OC(C)(C)C)CC1]

Removal of benzyloxycarbonyl group with concomitant hydrogenation of the double bond was accomplished according to the procedure recited elsewhere herein. From 1 g (2.31 mmol) of starting material, 0.63 g (91% yield) of product were obtained. ESI-MS m/z for $C_{15}H_{28}N_2O_4$ expected 300.40; found 301.4 [M+H], 323.3 [M+Na].

Step 4: tert-butyl 4-(((4-bromophenyl)methyl)sulfonamido)-4-(4-methoxy-4-oxobutyl)piperidine-1-carboxylate

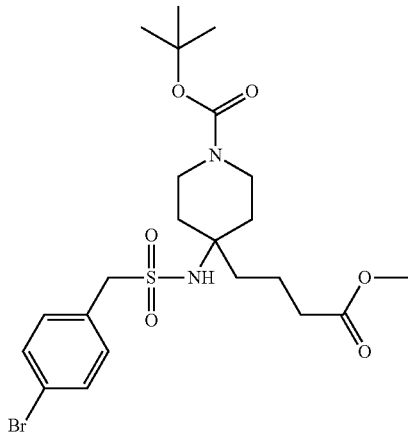 [SMILES: COC(=O)CCCC1(NS(=O)(=O)Cc2ccc(Br)cc2)CCN(C(=O)OC(C)(C)C)CC1]

Sulfonylation of the 4-amino group was accomplished according to the procedure recited elsewhere herein using (4-bromophenyl)methanesulfonyl chloride. From 0.38 g (0.83 mmol) of starting material 0.35 g (79% yield) of product were obtained as white solid. $^1$H NMR (CDCl$_3$, 500 MHz) δ (ppm) 7.49 (AA'BB', 2H, J=8 Hz), 7.29 (AA'BB', 2H, J=8 Hz), 4.21 (s, 2H), 3.91 (bs, 1H), 3.64 (s, 3H), 3.49-3.40 (m, 2H), 3.39-3.30 (m, 2H), 2.35-2.28 (m, 2H), 1.89-1.81 (m, 2H), 1.79-1.72 (m, 2H), 1.68-1.59 (m, 4H), 1.44 (s, 9H). ESI-MS m/z for C$_{22}$H$_{33}$BrN$_2$O$_6$S expected 533.49; found 533.3/535.3 [M+H], 531.3/533.3 [M−H].

Step 5: tert-butyl 4-(((4-bromophenyl)methyl)sulfonamido)-4-(4-hydroxybutyl)piperidine-1-carboxylate

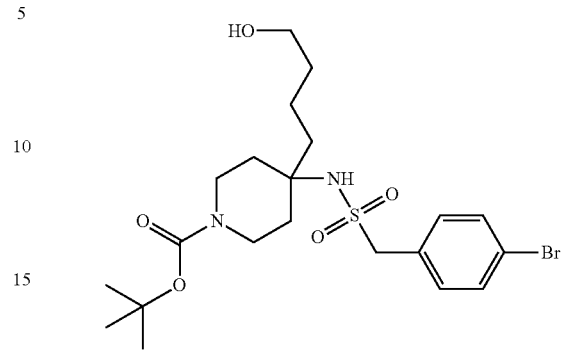

Reduction of the methyl ester group to the primary alcohol was accomplished according to the procedure recited elsewhere herein. From 0.2 g (0.37 mmol) of starting material, 0.18 g (99% yield) of product was obtained as a white foam. $^1$H NMR (CDCl$_3$, 500 MHz) δ (ppm) 7.49 (AA'BB', 2H, J=8.2 Hz), 7.26 (AA'BB', 2H, J=8.2 Hz), 4.19 (s, 2H), 3.89 (bs, 1H), 3.65-3.61 (m, 2H), 3.53-3.45 (m, 2H), 3.32-3.24 (m, 2H), 1.87-1.80 (m, 2H), 1.79-1.73 (m, 2H), 1.64-1.51 (m, 6H), 1.44 (s, 9H). ESI-MS m/z for C$_{22}$H$_{33}$BrN$_2$O$_6$S expected 505.48; found 505.3/507.3 [M+H], 503.3/505.3 [M−H].

Step 6: N-(1-(3-amino-1H-1,2,4-triazol-5-yl)-4-(4-hydroxybutyl)piperidin-4-yl)-1-(4-bromophenyl)methanesulfonamide Removal of the Boc-protecting group and installation of the 3-amino-1H-1,2,4-triazole moiety were accomplished according to the procedure recited elsewhere herein. 21 mg of product (23% yield over 2 steps) were obtained. $^1$H NMR (DMSO-d$_6$, 600 MHz) δ (ppm) 7.38 (AA'BB', 2H, J=8.5 Hz), 7.24 (AA'BB', 2H, J=8.3 Hz), 4.35 (s, 2H), 3.52-3.47 (m, 2H), 3.08-3.02 (m, 2H), 2.36-2.28 (m, 2H), 1.93-1.86, (m, 2H), 1.58-1.52 (m, 2H), 1.48-1.39 (m, 4H), 1.39-1.30 (m, 2H). ESI-MS m/z for C$_{18}$H$_{27}$BrN$_6$O$_3$S expected 487.42; found 487.3/489.3 [M+H], 485.3/487.3 [M−H].

TABLE 1

| Example | Structure | IUPAC Name | Activity | Analytical Data |
|---|---|---|---|---|
| 1 | 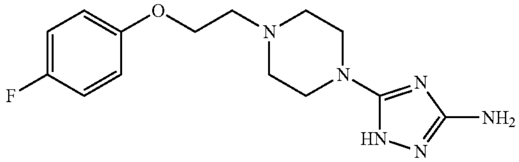 [SMILES: Nc1n[nH]c(N2CCN(CCOc3ccc(F)cc3)CC2)n1] | 5-(4-(2-(4-fluorophenoxy)ethyl)piperazin-1-yl)-1H-1,2,4-triazol-3-amine | E | $^1$H NMR (CD$_3$OD, 300 MHz) δ (ppm) 7.09-6.99 (m, 4 H), 5.48 (s, 2 H), 4.38 (t, J = 5.0 Hz, 2 H), 3.67 (t, J = 5.0 Hz, 6 H), 3.35 (s, 2 H); ESI-LCMS m/z calculated for C$_{14}$H$_{19}$FN$_6$O: expected 306.4; found 307.2 [M + H]$^+$ |
| 2 | 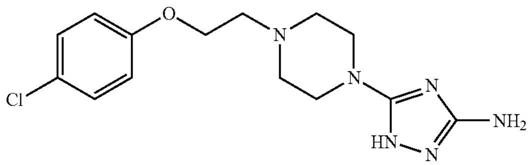 [SMILES: Nc1n[nH]c(N2CCN(CCOc3ccc(Cl)cc3)CC2)n1] | 5-(4-(2-(4-chlorophenoxy)ethyl)piperazin-1-yl)-1H-1,2,4-triazol-3-amine | C | $^1$H NMR (CD$_3$OD, 300 MHz) δ (ppm) 7.09-6.99 (m, 4 H), 5.48 (s, 2 H), 4.38 (t, J = 5.0 Hz, 2 H), 3.67 (t, J = 5.0 Hz, 6 H), 3.35 (s, 2 H); ESI-LCMS m/z calculated for C$_{14}$H$_{19}$ClN$_6$O: expected 322.8; found 323.2 [M + H]$^+$. |

TABLE 1-continued

| Example | Structure | IUPAC Name | Activity | Analytical Data |
|---|---|---|---|---|
| 3 | 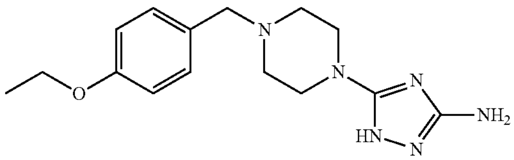 [SMILES: CCOc1ccc(CN2CCN(c3nc(N)n[nH]3)CC2)cc1] | 5-(4-(4-ethoxybenzyl)piperazin-1-yl)-1H-1,2,4-triazol-3-amine | E | $^1$H NMR (CD$_3$OD, 400 MHz) δ (ppm) 7.26 (dd, J = 8.4, J = 5.2, 2 H), 7.00 (dd, J = 8.4, J = 5.2, 2 H), 4.02 (2H, q, J = 7.003), 3.70-3.61 (m, 6 H), 2.62-2.56 (bs, 4 H), 1.24 (t, J = 7.003, 3H); ESI-LCMS m/z calculated for C$_{15}$H$_{22}$N$_6$O: expected 302.4; found 303.2 [M + H]$^+$. |
| 4 | 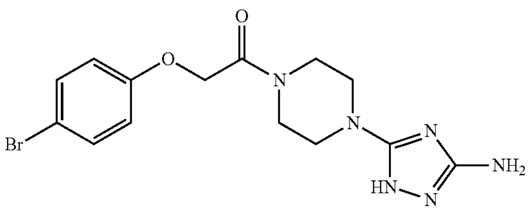 | 1-(4-(3-amino-1H-1,2,4-triazol-5-yl)piperazin-1-yl)-2-(4-bromophenoxy)ethan-1-one | E | $^1$H NMR (CD$_3$OD, 400 MHz) δ (ppm) 7.12 (dd, J = 8.5, J = 5.5, 2 H), 6.893 (dd, J = 8.5, J = 5.5, 2 H), 4.18 (s, 2H), 3.59 (m, 4H), 3.46 (dd, J = 12.0, J = 3.2, 2 H), 3.06 (dd, J = 12.0, J = 3.2, 2 H); ESI-LCMS m/z calculated for C$_{14}$H$_{17}$BrN$_6$O$_2$: expecied 381.2; found 382.2 [M + H]$^+$. |
| 5 | 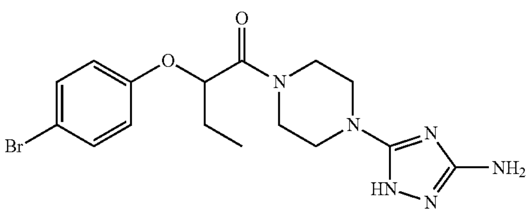 | 1-(4-(3-amino-1H-1,2,4-triazol-5-yl)piperazin-1-yl)-2-(4-bromophenoxy)butan-1-one | E | ESI MS for C$_{16}$H$_{21}$BrN$_6$O$_2$; expected 409.29; found m/z 409.4/411.4 in ratio ~1/1 (isotopes of Br) [M + H]$^+$. $^1$H NMR (DMSO-d$_6$, 600 MHz): δ (ppm) 10.99 (bs, 1H); 7.39 (d, J = 9.0 Hz, 2H), 6.77 (d, J = 9.0 Hz, 2H), 5.76 (bs, 2H); 5.05-5.01 (m, 1H), 3.71-3.63 (m, 1H), 3.61-3.55 (m, 1H), 3.55-3.48 (m, 1H), 3.45-3.38 (m, 1H), 3.19-3.02 (m, 4H), 1.83-1.71 (m, 2H), 0.95 (t, J = 7.3 Hz, 3H). |
| 6 | 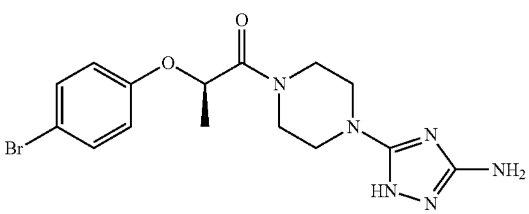 | (R)-1-(4-(3-amino-1H-1,2,4-triazol-5-yl)piperazin-1-yl)-2-(4-bromophenoxy)propan-1-one | E | $^1$H NMR (DMSO-d$_6$, 600 MHz): δ (ppm) 11.00 (bs, 1H); 7.40 (d, J = 9.0 Hz, 2H), 6.78 (d, J = 9.0 Hz, 2H), 5.76 (bs, 2H), 5.24 (q, J = 6.4 Hz, J = 13.1 Hz, 1H), 3.66-3.60 (m, 1H), 3.58-3.48 (m, 2H), 3.43-3.37 (m, 1H), 3.21-3.03 (m, 4H), 1.39 (d, J = 6.6 Hz, 3H). ESI MS for C$_{15}$H$_{19}$BrN$_6$O$_2$; expected 395.26; found m/z 395.3/397.3 in ratio ~1/1 (isotopes of Br) [M + H]$^+$. |
| 7 | 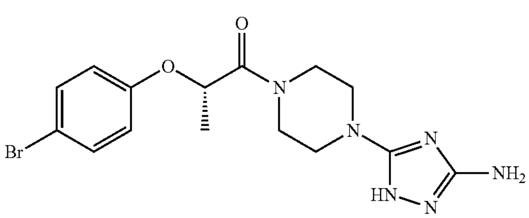 | (S)-1-(4-(3-amino-1H-1,2,4-triazol-5-yl)piperazin-1-yl)-2-(4-bromophenoxy)propan-1-one | E | ESI MS for C$_{15}$H$_{19}$BrN$_6$O$_2$; expected 395.26; found m/z 395.3/397.3 in ratio ~1/1 (isotopes of Br) [M + H]$^+$. $^1$H NMR (DMSO-d$_6$, 600 MHz): δ (ppm) 10.99 (bs, 1H); 7.40 (d, J = 9.0 Hz, 2H), 6.78 (d, J = 9.0 Hz, 2H), 5.75 (bs, 2H); 5.24 (q, J = 6.4 Hz, J = 13.1 Hz, 1H), 3.66-3.59 (m, 1H), 3.58-3.47 (m, 2H), 3.45-3.37 (m, 1H), 3.22-3.03 (m, 4H), 1.39 (d, J = 6.6 Hz, 3H). |
| 8 | 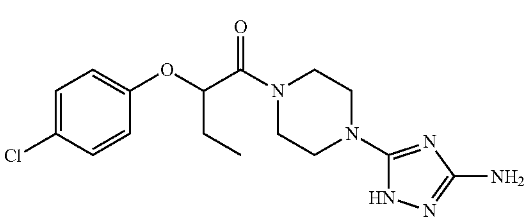 | 1-(4-(3-amino-1H-1,2,4-triazol-5-yl)piperazin-1-yl)-2-(4-chlorophenoxy)butan-1-one | E | ESI MS for C$_{16}$H$_{21}$ClN$_6$O$_2$; expected 364.84; found m/z 365.4/367.4 in ratio ~3/1 (isotopes of Cl) [M + H]$^+$. $^1$H NMR (DMSO-d$_6$, 600 MHz): δ (ppm) 10.99 (bs, 1H); 7.28 (d, J = 9.0 Hz, 2H), 6.82 (d, J = 9.0 Hz, 2H), 5.76 (bs, 2H); 5.05-5.00 (m, 1H), |

TABLE 1-continued

| Example | Structure | IUPAC Name | Activity | Analytical Data |
|---|---|---|---|---|
| | | | | 3.71-3.63 (m, 1H), 3.62-3.55 (m, 1H), 3.55-3.46 (m, 1H), 3.46-3.39 (m, 1H), 3.21-3.01 (m, 4H), 1.83-1.70 (m, 2H), 0.95 (t, J = 7.4 Hz, 3H). |
| 9 | 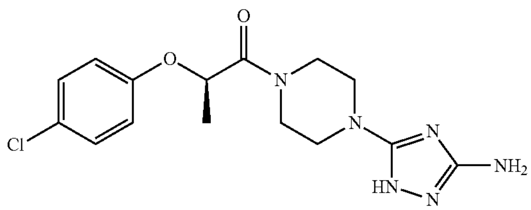 | (R)-1-(4-(3-amino-1H-1,2,4-triazol-5-yl)piperazin-1-yl)-2-(4-chlorophenoxy)propan-1-one | E | ESI MS for $C_{15}H_{19}ClN_6O_2$; expected 350.81; found m/z 351.4/353.4 in ratio ~3/1 (isotopes of Cl) [M + H]$^+$. $^1$H NMR (DMSO-d$_6$, 600 MHz): δ (ppm) 7.28 (d, J = 8.8 Hz, 2H), 6.85 (d, J = 8.8 Hz, 2H), 5.28 (q, J = 6.4 Hz, J = 13.0 Hz, 1H), 3.74-3.64 (m, 1H), 3.64-3.55 (m, 2H), 3.47-3.41 (m, 1H), 3.31-3.19 (m, 4H), 1.38 (d, J = 6.6 Hz, 3H). |
| 10 | 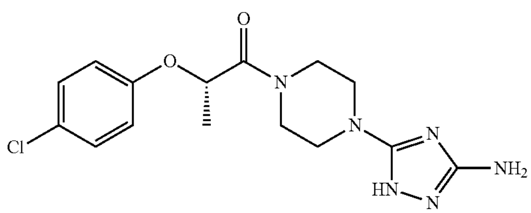 | (S)-1-(4-(3-amino-1H-1,2,4-triazol-5-yl)piperazin-1-yl)-2-(4-chlorophenoxy)propan-1-one | E | ESI MS for $C_{15}H_{19}ClN_6O_2$; expected 350.81; found m/z 351.4/353.4 in ratio ~3/1 (isotopes of Cl) [M + H]$^+$. $^1$H NMR (DMSO-d$_6$, 600 MHz): δ (ppm) 7.28 (d, J = 9.0 Hz, 2H), 6.85 (d, J = 9.0 Hz, 2H), 5.28 (q, J = 6.4 Hz, J = 13.0 Hz, 1 H), 3.74-3.67 (m, 1H), 3.63-3.54 (m, 2H), 3.49-3.43 (m, 1H), 3.32-3.19 (m, 4H), 1.38 (d, J = 6.6 Hz, 3H). |
| 11 | 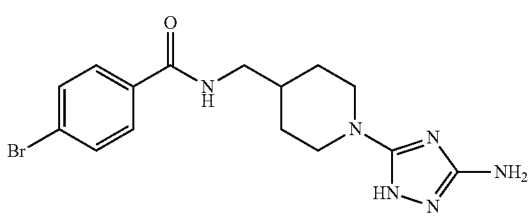 [SMILES: Nc1n[nH]c(N2CCC(CNC(=O)c3ccc(Br)cc3)CC2)n1] | N-((1-(3-amino-1H-1,2,4-triazol-5-yl)piperidin-4-yl)methyl)-4-bromobenzamide | E | $^1$H NMR (DMSO-d$_6$, 500 MHz): δ (ppm) 10.86 (brs, 1 H), 8.65-8.42 (m, 1 H), 7.81-7.65 (m, 4 H), 5.80-5.34 (brs, 1 H), 3.87-3.60 (m, 2 H), 3.17-2.94 (m, 2 H), 2.71-2.49 (m, 2 H), 1.76-146 (m, 3 H), 1.26-0.95 (m, 2 H). ESI-LCMS m/z for $C_{15}H_{19}BrN_6O$: calculated 378.08, found 379/381 [M + H]+. |
| 12 | 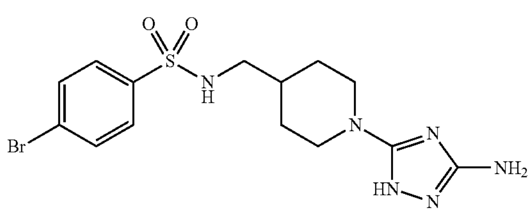 [SMILES: Nc1n[nH]c(N2CCC(CNS(=O)(=O)c3ccc(Br)cc3)CC2)n1] | N-((1-(3-amino-1H-1,2,4-triazol-5-yl)piperidin-4-yl)methyl)-4-bromobenzenesulfonamide | E | $^1$H NMR (DMSO-d$_6$, 500 MHz): δ (ppm) 10.91 (bs, 1 H), 7.82 (d, J = 8.6 Hz, 2 H), 7.71 (d, J = 8.6 Hz, 2 H), 5.63 (bs, 2 H), 3.70-3.76 (m, 2 H), 3.63-3.69 (m, 2 H), 2.57-2.64 (m, 2 H), 1.45-1.61 (m, 3 H), 0.97-1.14 (m, 2 H). ESI-LCMS m/z for $C_{14}H_{19}BrN_6O_2S$: calculated 414.05; found: 415.4/417.4 [M + H]$^+$, 413.1/415.2 [M − H]$^-$. |
| 13 | 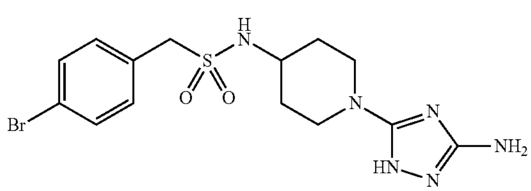 [SMILES: Nc1n[nH]c(N2CCC(NS(=O)(=O)Cc3ccc(Cl)cc3)CC2)n1] | N-(1-(3-amino-1H-1,2,4-triazol-5-yl)piperidin-4-yl)-1-(4-bromophenyl)methanesulfonamide | C | $^1$H NMR (DMSO, 600 MHz) δ (ppm) 10.92 (bs, 1H), 7.57 (d, J = 8.3 Hz, 2 H), 7.33 (d, J = 8.3 Hz, 2 H), 7.17 (bs, 1 H), 5.65 (bs, 2H), 4.33 (s, 2 H), 3.75-3.66 (m, 2H), 3.26-3.17 (m, 1H), 2.75-2.61 (m, 2H), 1.80-1.71 (m, 2H), 1.43-1.30 (m, 2H). ESI-LCMS m/z for $C_{14}H_{19}BrN_6O_2S$: calculated 414.05, found 415.3/417.3 [M + H]+. |

TABLE 1-continued

| Example | Structure | IUPAC Name | Activity | Analytical Data |
|---|---|---|---|---|
| 14 | 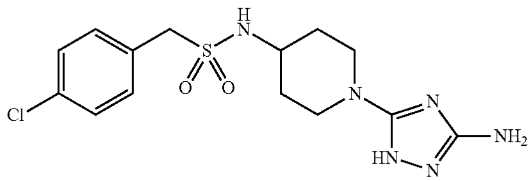 | N-(1-(3-amino-1H-1,2,4-triazol-5-yl)piperidin-4-yl)-1-(4-chlorophenyl)methanesulfonamide | C | $^1$H NMR (DMSO, 600 MHz) δ (ppm) 7.42 (d, J = 8.5 Hz, 2 H), 7.37 (d, J = 8.5 Hz, 2 H), 7.25 (d, J = 8.3 Hz, 2 H), 4.32 (s, 2H), 3.72-3.63 (m, 2 H), 3.44 (bs, 3H), 3.36-3.27 (m, 1H), 3.02-2.92 (m, 2H), 1.87-1.79 (m, 2H), 1.45-1.36 (m, 2H). ESI-LCMS m/z for $C_{14}H_{19}ClN_6O_2S$: calculated 370.10, found 371.4 [M + H]$^+$. |
| 15 | 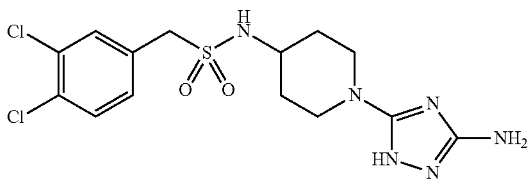 [SMILES: Nc1n[nH]c(N2CCC(NS(=O)(=O)Cc3ccc(Cl)c(Cl)c3)CC2)n1] | N-(1-(3-amino-1H-1,2,4-triazol-5-yl)piperidin-4-yl)-1-(3,4-dichlorophenyl)methanesulfonamide | D | $^1$H NMR (DMSO, 600 MHz) δ (ppm) 7.67-7.61 (m, 2 H), 7.39-7.34 (m, 1 H), 7.24 (brs, 1 H), 5.54 (brs, 1 H), 4.39 (s, 2 H), 3.75-3.64 (m, 2 H), 3.27-3.17 (m, 1 H), 2.74-2.63 (m, 2 H), 1.82-170 (m, 2 H), 1.43-1.30 (m, 2 H). ESI-LCMS m/z for $C_{14}H_{18}Cl_2N_6O_2S$: calculated 404.06, found 405.4/407.4 [M + H]+. |
| 16 | 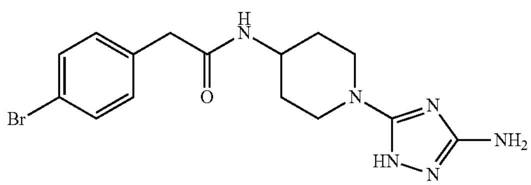 [SMILES: Nc1n[nH]c(N2CCC(NC(=O)Cc3ccc(Br)cc3)CC2)n1] | N-(1-(3-amino-1H-1,2,4-triazol-5-yl)piperidin-4-yl)-2-(4-bromophenyl)acetamide | E | $^1$H NMR (DMSO-$d_6$, 500 MHz) δ (ppm) 10.91 (bs, 1 H), 8.02 (d, J = 7.58, 1 H), 7.47-7.43 (m, 2 H), 7.19-7.15 (m, 2 H), 5.56 (bs, 2 H), 3.70-3.55 (m, 3 H), 2.77-2.59 (m, 2 H), 1.68-1.61 (m, 2 H), 1.43-1.20 (m, 2 H). ESI-LCMS m/z for $C_{15}H_{19}BrN_6O$: calculated 378.08, found 379.4/381.4 [M + H]+. |
| 17 | 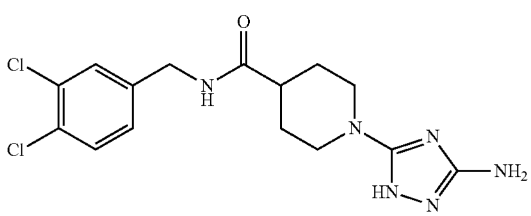 [SMILES: Nc1n[nH]c(N2CCC(C(=O)NCc3ccc(Cl)c(Cl)c3)CC2)n1] | 1-(3-amino-1H-1,2,4-triazol-5-yl)-N-(3,4-dichlorobenzyl)piperidine-4-carboxamide | E | $^1$H NMR (DMSO-$d_6$, 200 MHz) δ (ppm): 10.95 (bs, 1 H), 8.37 (t, J = 5.6 Hz, 1H), 7.55 (d, J = 8.6 Hz, 1 H), 7.43 (d, J = 1.5 Hz, 1 H), 7.18 (dd, J$_1$ = 8.6 Hz, J$_2$ = 1.5 Hz, 1 H), 5.57 (bs, 1 H), 4.21 (d, J = 5.6 Hz, 2 H), 3.77 (d, J = 13.1 Hz, 2 H), 2.61-2.52 (m, 2 H), 2.35-2.19 (m, 1 H), 1.72-1.41 (m, 4 H), ESI MS for $C_{15}H_{18}Cl_2N_6O$ calculated 368.09, found 369.5/371.5 [M + H]$^+$. |
| 18 | 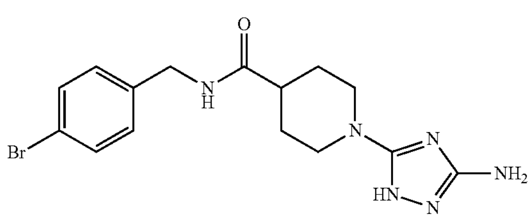 | 1-(3-amino-1H-1,2,4-triazol-5-yl)-N-(4-bromobenzyl)piperidine-4-carboxamide | E | $^1$H NMR (DMSO, 200 MHz) δ (ppm) 10.92 (brs, 1 H), 8.35 (m, 1 H), 7.49 (d, J = 8.2 Hz, 2 H), 7.17 (d, J = 8.2 Hz, 2 H), 5.84-5.49 (brs, 2 H), 4.20 (d, J = 5.5 Hz, 2 H), 3.84-3.73 (m, 2 H), 2.70-2.54 (m, 2 H), 2.34-2.21 (m, 1 H), 1.70-1.61 (m, 2 H), 1.61-1.48, (m, 2 H). ESI-LCMS m/z for $C_{15}H_{19}BrN_6O$: calculated 378.08, found 379/381 [M + H]+. |
| 19 | 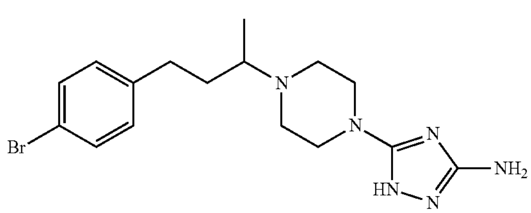 [SMILES: CC(CCc1ccc(Br)cc1)N1CCN(c2nc(N)n[nH]2)CC1] | 5-(4-(4-(4-bromophenyl)butan-2-yl)piperazin-1-yl)-1H-1,2,4-triazol-3-amine | D | $^1$H NMR (DMSO-$d_6$, 500 MHz) δ (ppm): 10.92 (bs, 1 H), 7.42 (d, J = 8.2 Hz, 2 H), 7.16 (d, J = 8.2 Hz, 2 H), 5.64 (bs, 2 H), 3.38-3.29 (m, 1 H), 3.18-3.07 (m, 4 H), 2.59-2.55 (m, 2 H), 2.54-2.44 (m, 2 H), 1.77-1.69 (m, 1 H), 1.51-1.44 (m 1 H), 0.89 (d, J = 6.5 Hz, 3 H). ESI MS for $C_{16}H_{23}BrN_6$; calculated 379.30, found 379.4/381.4 [M + H]$^+$. |

TABLE 1-continued

| Example | Structure | IUPAC Name | Activity | Analytical Data |
|---|---|---|---|---|
| 20-1 | 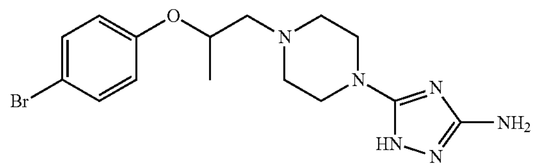 | 5-(4-(2-(4-bromophenoxy)propyl)piperazin-1-yl)-1H-1,2,4-triazol-3-amine | D | $^1$H NMR (D$_2$O, 500 MHz) δ (ppm) 7.41 (d, J = 9 Hz, 2 H), 6.85 (d, J = 9 Hz, 2 H), 4.31 (dd, J1 = 11.5 Hz, J2 = 3 Hz, 1 H), 4.16 (dd, J1 = 11.5 Hz, J2 = 6 Hz, 1 H), 3.86-3.79 (m, 1 H), 3.70-3.17 (m, 7 H), 1.41 (d, J = 7 Hz, 3 H), ESI-LCMS m/z for C$_{15}$H$_{21}$BrN$_6$O: calculated 380.10, found 381/383 [M + H]+. |
| 20-2 | 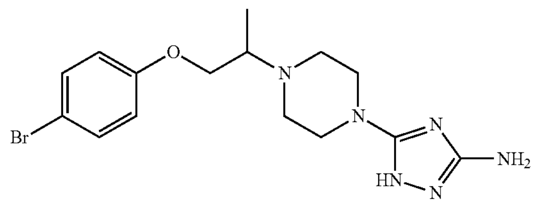 [SMILES: CC(COc1ccc(Br)cc1)N1CCN(c2nc(N)n[nH]2)CC1] | 5-(4-(1-(4-bromophenoxy)propan-2-yl)piperazin-1-yl)-1H-1,2,4-triazol-3-amine | D | $^1$H NMR (D$_2$O, 500 MHz) δ (ppm) 7.37 (d, J = 9 Hz, 2 H), 6.84 (d, J = 9 Hz, 2 H), 4.88-4.80 (m, 1 H), 3.85-3.08 (m, 10 H), 1.18 (d, J = 6 Hz, 3 H). ESI-LCMS m/z for C$_{15}$H$_{21}$BrN$_6$O: calculated 380.10, found 381/383 [M + H]$^+$. |
| 21 | 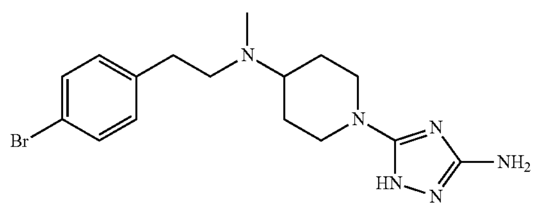 [SMILES: CN(CCc1ccc(Br)cc1)C1CCN(c2nc(N)n[nH]2)CC1] | 1-(3-amino-1H-1,2,4-triazol-5-yl)-N-(4-bromophenethyl)-N-methylpiperidin-4-amine | B | $^1$H NMR (DMSO, 500 MHz) δ (ppm) 10.81 (bs, 1H), 7.40 (d, J = 8.3 Hz, 2 H), 7.15 (d, J = 8.3 Hz, 2 H), 5.55 (bs, 2H), 3.80-3.72 (m, 2 H), 2.65-2.59 (m, 2H), 2.59-2.50 (m, 4H), 2.45-2.36 (m, 1H), 2.17 (s, 3H), 1.61-1.54 (m, 2H), 1.38-1.27 (m, 2H). ESI-LCMS m/z for C$_{16}$H$_{25}$BrN$_6$: calculated 378.12, found 379.4/381.4 [M + H]$^+$. |
| 22 | 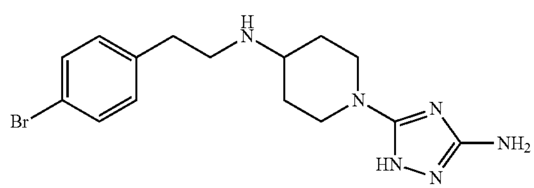 | 1-(3-amino-1H-1,2,4-triazol-5-yl)-N-(4-bromophenethyl)piperidin-4-amine | C | $^1$H NMR (MeOD-d$_4$, 500 MHz) δ (ppm): 7.48 (d, J = 8.0 Hz, 2 H), 7.25 (d, J = 8.0 Hz, 2 H), 3.94-3.86 (m, 2 H), 3.46-3.38 (m, 1 H), 3.33-3.27 (m, 2 H), 3.60-3.12 (m, 4 H), 2.25-2.16 (m, 2 H), 1.80-1.70 (m, 2 H). ESI MS found for C$_{15}$H$_{21}$BrN$_6$ calculated 364.10, found 365.4/367.4 [M + H]$^+$. |
| 23 | 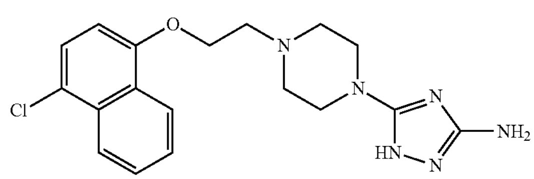 [SMILES: Nc1n[nH]c(N2CCN(CCOc3ccc(Cl)c4ccccc34)CC2)n1] | 5-(4-(2-((4-chloronaphthalen-1-yl)oxy)ethyl)piperazin-1-yl)-1H-1,2,4-triazol-3-amine | C | $^1$H NMR (CD$_3$OD, 300 MHz) δ (ppm) 8.36 (dd, J = 8.2 Hz, J = 5.4 Hz, J = 1.7 Hz, J = 1.2 Hz, 1 H), 8.07 (dd, J = 8.6 Hz, J = 5.2 Hz, J = 1.8 Hz, J = 1.2 Hz, 1 H), 7.65-7.36 (m, 3H), 6.95 (dd, J = 8.9, J = 5.4, 1 H), 4.32 (t, J = 5.8, 2 H), 3.41-3.22 (m, 4 H), 2.89 (t, J = 5.8, 2 H), 2.62-2.54 (m, 4 H); ESI-LCMS m/z calculated for C$_{14}$H$_{19}$FN$_6$O: expected 372.9; found 373.2 [M + H]$^+$. |
| 24 | 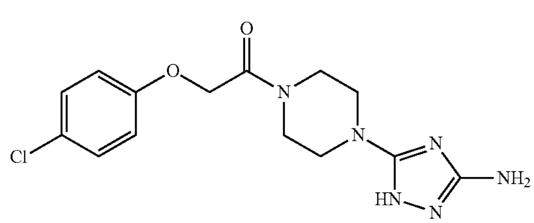 [SMILES: Nc1n[nH]c(N2CCN(C(=O)COc3ccc(Cl)cc3)CC2)n1] | 1-(4-(3-amino-1H-1,2,4-triazol-5-yl)piperazin-1-yl)-2-(4-chlorophenoxy)ethan-1-one | E | $^1$H NMR (CD$_3$OD, 400 MHz) δ (ppm) 7.13 (d, J = 7.0, 2H), 6.83 (d, J = 7.0, 2H), 4.70 (s, 2H), 3.60 (bs, 4H), 3.29 (d, J = 12.0, 2H), 3.24 (d, J = 12.0, 2H); ESI-LCMS m/z calculated for C$_{14}$H$_{17}$ClN$_6$O$_2$: expected 336.8; found 337.2 [M + H]$^+$. |

TABLE 1-continued

| Example | Structure | IUPAC Name | Activity | Analytical Data |
|---|---|---|---|---|
| 25 | 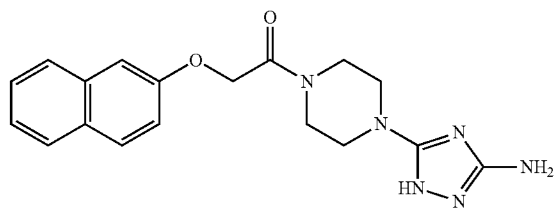 [SMILES: Nc1n[nH]c(N2CCN(C(=O)COc3ccc4ccccc4c3)CC2)n1] | 1-(4-(3-amino-1H-1,2,4-triazol-5-yl)piperazin-1-yl)-2-(naphthalen-2-yloxy)ethan-1-one | E | $^1$H NMR (CD$_3$OD, 400 MHz) δ (ppm) 7.66-7.62 (m, 3H), 7.30-7.08 (m, 4H), 4.84 (s, 2H), 3.63 (bs, 4H), 3.31 (bs, 2H), 3.22 (bs, 2H); ESI-LCMS m/z calculated for C$_{19}$H$_{20}$N$_6$O$_2$: expected 352.40; found 353.2 [M + H]$^+$. |
| 26 | 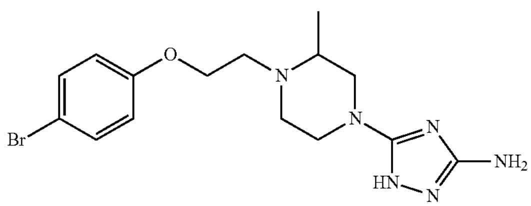 [SMILES: CC1CN(c2nc(N)n[nH]2)CCN1CCOc1ccc(Br)cc1] | 5-(4-(2-(4-bromophenoxy)ethyl)-3-methylpiperazin-1-yl)-1H-1,2,4-triazol-3-amine | C | $^1$H NMR (CD$_3$OD, 400 MHz) δ (ppm) 7.46 (d, J = 8.0 Hz, 2H), 6.97 (d, J = 8.0 Hz, 2H), 4.41 (m, 2H), 3.89 (bs, 3H), 3.76 (bs, 2H), 3.64-3.51 (m, 3H), 3.40 (bs, 1H), 1.53 (d, J = 5.0 Hz, 3H); ESI-LCMS m/z calculated for C$_{15}$H$_{21}$BrN$_6$O: expected 381.28; found 382.2 [M + H]$^+$. |
| 27-1 | 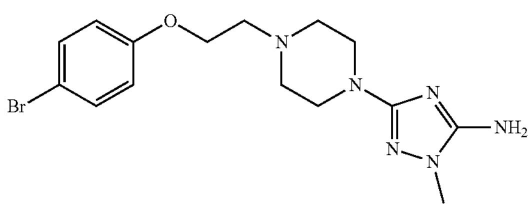 [SMILES: Cn1nc(N2CCN(CCOc3ccc(Br)cc3)CC2)nc1N] | 3-(4-(2-(4-bromophenoxy)ethyl)piperazin-1-yl)-1-methyl-1H-1,2,4-triazol-5-amine | E | |
| 27-2 | 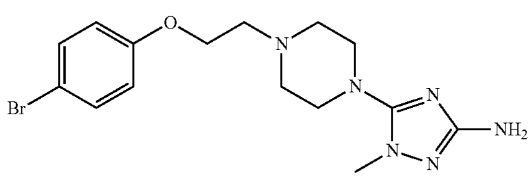 [SMILES: Cn1nc(N)nc1N1CCN(CCOc2ccc(Br)cc2)CC1] | 5-(4-(2-(4-bromophenoxy)ethyl)piperazin-1-yl)-1-methyl-1H-1,2,4-triazol-3-amine | E | |
| 28 | 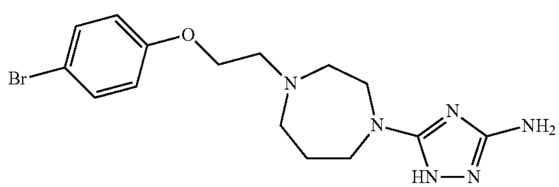 [SMILES: Nc1n[nH]c(N2CCCN(CCOc3ccc(Br)cc3)CC2)n1] | 5-(4-(2-(4-bromophenoxy)ethyl)-1,4-diazepan-1-yl)-1H-1,2,4-triazol-3-amine | E | $^1$H NMR (CD$_3$OD, 400 MHz) δ (ppm) 7.44 (d, J = 8.4 Hz, 2H), 6.95 (d, J = 8.4 Hz, 2H), 4.40 (bs, 2H), 3.93 (bs, 2H), 3.71-3.62 (m, 8H), 2.36 (bs, 2H); ESI-LCMS m/z calculated for C$_{15}$H$_{21}$BrN$_6$O: expected 381.28; found 382.2 [M + H]$^+$. |
| 29 | 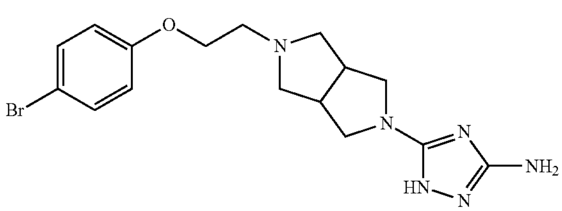 [SMILES: Nc1n[nH]c(N2CC3CN(CCOc4ccc(Br)cc4)CC3C2)n1] | 5-(5-(2-(4-bromophenoxy)ethyl)hexahydropyrrolo[3,4-c]pyrrol-2(1H)-yl)-1H-1,2,4-triazol-3-amine | E | $^1$H NMR (CD$_3$OD, 400 MHz) δ (ppm) 7.44 (d, J = 8.0 Hz, 2 H), 6.93 (d, J = 8.0 Hz, 2 H), 4.05 (m, 2 H), 3.33 (s, 1H), 3.23 (m, 2 H), 3.02 (d, J = 9.2 Hz, 2 H), 2.76 (m, 5 H), 2.35 (m, 2 H); ESI-LCMS m/z calculated for C$_{15}$H$_{21}$BrN$_6$O: expected 381.28; found 382.2 [M + H]$^+$. |
| 30 | 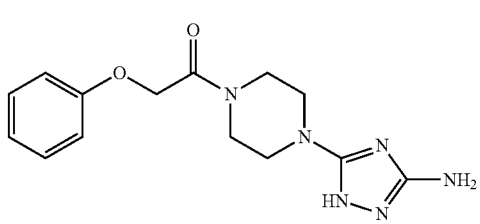 [SMILES: Nc1n[nH]c(N2CCN(C(=O)COc3ccccc3)CC2)n1] | 1-(4-(3-amino-1H-1,2,4-triazol-5-yl)piperazin-1-yl)-2-phenoxyethan-1-one | E | $^1$H NMR (CD$_3$OD, 400 MHz) δ (ppm) 7.3-6.8 (m, 1 H), 4.21 (s, 2H), 3.59 (m, 4H), 3.46 (bs, 2H), 3.07 (bs, 2H); ESI-LCMS m/z calculated for C$_{14}$H$_{17}$BrN$_6$O$_2$: expected 381.2; found 382.2 [M + H]$^+$. |

TABLE 1-continued

| Example | Structure | IUPAC Name | Activity | Analytical Data |
|---|---|---|---|---|
| 31 | 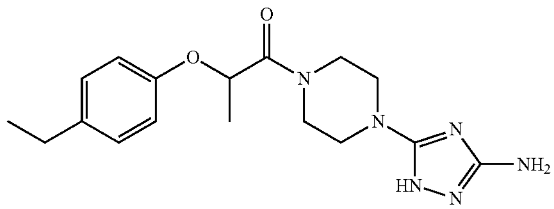 [SMILES: CCc1ccc(OC(C)C(=O)N2CCN(c3nc(N)n[nH]3)CC2)cc1] | 1-(4-(3-amino-1H-1,2,4-triazol-5-yl)piperazin-1-yl)-2-(4-ethylphenoxy)propan-1-one | E | $^1$H NMR (CD$_3$OD, 400 MHz) δ (ppm) 7.10 (d, J = 8.4, 2 H), 6.77 (d, J = 8.4, 2 H), 5.73 (s, 3H), 5.20 (q, J = 13.1, J = 6.5, 1 H), 3.69-3.45 (m, 4H), 3.21-3.10 (m, 4H), 1.42 (d, J = 6.3, 2 H), 1.14 (t, J = 7.7, 3 H); ESI-LCMS m/z calculated for C$_{17}$H$_{24}$N$_6$O$_2$: expected 344.42; found 345.2 [M + H]$^+$. |
| 32 | 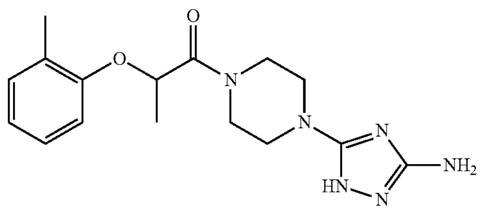 [SMILES: Cc1ccccc1OC(C)C(=O)N1CCN(c2nc(N)n[nH]2)CC1] | 1-(4-(3-amino-1H-1,2,4-triazol-5-yl)piperazin-1-yl)-2-(o-tolyloxy)propan-1-one | E | $^1$H NMR (CD$_3$OD, 400 MHz) δ (ppm) 7.16-7.10 (m, 2 H), 6.83 (t, J = 7.2, 1 H), 6.76 (d, J = 7.9 Hz, 1 H), 5.22 (q, J = 13.2, J = 6.1, 1 H), 3.65 (bs, 2H), 3.52 (bs, 2H), 3.20-3.00 (m, 4H), 2.18 (s, 3 H), 1.47 (d, J = 6.3 Hz, 3H); ESI-LCMS m/z calculated for C$_{16}$H$_{22}$N$_6$O$_2$: expected 330.39; found 331.2 [M + H]$^+$. |
| 33 | 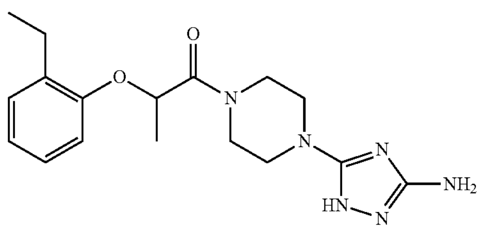 [SMILES: CCc1ccccc1OC(C)C(=O)N1CCN(c2nc(N)n[nH]2)CC1] | 1-(4-(3-amino-1H-1,2,4-triazol-5-yl)piperazin-1-yl)-2-(2-ethylphenoxy)propan-1-one | E | $^1$H NMR (CD$_3$OD, 400 MHz) δ (ppm) 7.16-7.10 (m, 2 H), 6.83 (t, J = 7.2, 1 H), 6.76 (d, J = 7.9 Hz, 1 H), 5.24 (q, J = 13.2, J = 6.1, 1 H), 3.66 (bs, 2H), 3.53 (bs, 2H), 3.20-3.00 (m, 4H), 2.22 (s, 2 H), 1.45 (d, J = 6.0 Hz, 3 H), 1.15 (t, J = 7.6 Hz, 3H); ESI-LCMS m/z calculated for C$_{17}$H$_{24}$N$_6$O$_2$: expected 344.42; found 345.2 [M + H]$^+$. |
| 34 | 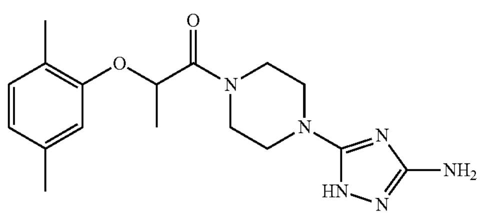 [SMILES: Cc1ccc(C)c(OC(C)C(=O)N2CCN(c3nc(N)n[nH]3)CC2)c1] | 1-(4-(3-amino-1H-1,2,4-triazol-5-yl)piperazin-1-yl)-2-(2,5-dimethylphenoxy)propan-1-one | E | $^1$H NMR (CD$_3$OD, 400 MHz) δ (ppm) 7.01 (d, J = 7.0 Hz, 1 H), 6.64 (d, J = 7.0 Hz, 1 H), 6.60 (s, 1 H), 5.22 (q, J = 13.2, J = 6.1, 1 H), 3.70-3.57 (m, 3 H), 3.13 (bs, 3H), 3.53 (bs, 2H), 2.22 (s, 3 H), 2.12 (s, 3 H), 1.44 (d, J = 6.0 Hz, 3 H); ESI-LCMS m/z calculated for C$_{17}$H$_{24}$N$_6$O$_2$: expected 344.42; found 345.2 [M + H]$^+$. |
| 35 | 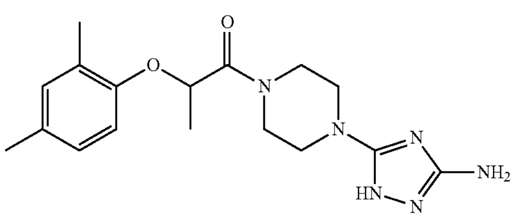 [SMILES: Cc1ccc(OC(C)C(=O)N2CCN(c3nc(N)n[nH]3)CC2)c(C)c1] | 1-(4-(3-amino-1H-1,2,4-triazol-5-yl)piperazin-1-yl)-2-(2,4-dimethylphenoxy)propan-1-one | E | $^1$H NMR (CD$_3$OD, 400 MHz) δ (ppm) 6.96 (s, 1 H), 6.90 (d, J = 8.0 Hz, 1 H), 6.67 (d, J = 8.0 Hz, 1 H), 5.15 (q, J = 13.2, J = 6.1, 1 H), 3.64 (bs, 2H), 3.51 (bs, 2 H), 3.20-3.03 (m, 4 H), 2.18 (s, 3 H), 2.14 (s, 3 H), 1.44 (d, J = 6.0 Hz, 3 H); ESI-LCMS m/z calculated for C$_{17}$H$_{24}$N$_6$O$_2$: expected 344.42; found 345.2 [M + H]$^+$. |
| 36 | 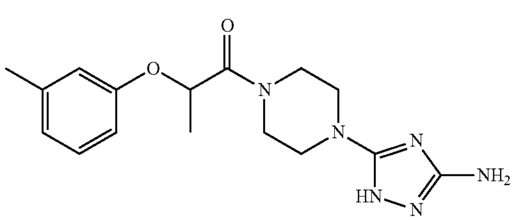 [SMILES: Cc1cccc(OC(C)C(=O)N2CCN(c3nc(N)n[nH]3)CC2)c1] | 1-(4-(3-amino-1H-1,2,4-triazol-5-yl)piperazin-1-yl)-2-(m-tolyloxy)propan-1-one | E | $^1$H NMR (CD$_3$OD, 400 MHz) δ (ppm) 7.05 (t, J = 7.7 Hz, 1 H), 6.65 (d, J = 6.2, 1 H), 6.60 (s, 1 H), 6.55 (d, J = 7.7 Hz, 1 H), 5.22 (m, 1 H), 3.65 (bs, 2H), 3.52 (bs, 2H), 3.20-3.00 (m, 4H), 2.18 (s, 3 H), 1.47 (d, J = 6.3 Hz, 3H); ESI-LCMS m/z calculated for C$_{16}$H$_{22}$N$_6$O$_2$: expected 330.39; found 331.2 [M + H]$^+$. |
| 37 | 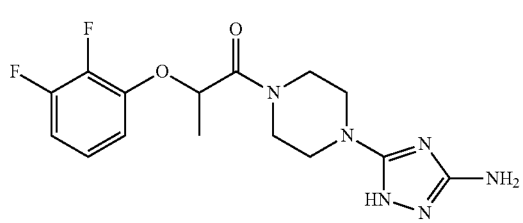 [SMILES: CC(Oc1cccc(F)c1F)C(=O)N1CCN(c2nc(N)n[nH]2)CC1] | 1-(4-(3-amino-1H-1,2,4-triazol-5-yl)piperazin-1-yl)-2-(2,3-difluorophenoxy)propan-1-one | E | $^1$H NMR (CD$_3$OD, 400 MHz) δ (ppm) 7.07-7.04 (m, 1 H), 6.91-6.85 (m, 1 H), 6.81-6.76 (m, 1 H), 5.35-5.25 (m, 1 H), 3.67 (t, J = 40.8 Hz), 4 H), 3.32 (m, 2 H), 2.91-2.81 (m, 2 H), 1.91 (s, 3 H); ESI-LCMS m/z calculated for C$_{16}$H$_{22}$N$_6$O$_2$: expected 352.35; found 353.2 [M + H]$^+$. |

TABLE 1-continued

| Example | Structure | IUPAC Name | Activity | Analytical Data |
|---|---|---|---|---|
| 38 | (structure) ·3HCl | 5-(piperazin-1-yl)-1H-1,2,4-triazol-3-amine trihydrochloride | E | ESI MS for $C_6H_{12}N_6$ calculated m/z 168.11, found 169.1 [M + H]$^+$. |
| 39 | (structure) ·2HCl | 5-(4-(3-(4-bromophenyl)-2-methylpropyl)piperazin-1-yl)-1H-1,2,4-triazol-3-amine dihydrochloride | C | $^1$H NMR (DMSO, 600 MHz) δ (ppm) 10.97 (brs, 1 H), 7.48 (d, J = 8 Hz, 2 H), 7.22 (d, J = 8 Hz, 2 H), 3.92-3.81 (m, 2 H), 3.6-3.52 (m, 4 H), 3.17-3.08 (m, 1 H). 3.08-2.95 (m, 3 H), 2.95-2.89 (m, 1 H), 2.39-2.3 (m, 1 H), 2.3-2.22 (m, 1 H), 0.89 (d, J = 6.4, 3 H). ESI MS for $C_{16}H_{23}BrN_6$ calculated m/z 378.12, found 379.5/381.5 [M + H]$^+$. |
| 40 | (structure) | 3-amino-1-(4-(3-amino-1H-1,2,4-triazol-5-yl)piperazin-1-yl)-3-(4-chlorophenyl)propan-1-one | E | $^1$H NMR (DMSO, 600 MHz) δ (ppm) 8.76-8.58 (m, 3 H), 7.59 (d, J = 7.5 Hz, 2 H), 7.44 (d, J = 7.7 Hz, 2 H), 4.62-4.48 (m, 1 H), 3.43-3.38 (m, 1 H), 3.38-3.3 (m, 2 H), 3.3-3.15 (m, 4 H), 3.14-3.09 (m, 2 H), 3.05-2.97 (m, 1 H). ESI MS m/z for $C_{15}H_{20}ClN_7O$: calculated 349.14, found 350.5/352.5 [M + H]$^+$, 352.5 [M − H]$^-$. |
| 41 | (structure) | 5-(4-(3-(benzo[d][1,3]dioxol-5-yl)-1,2,4-oxadiazol-5-yl)piperidin-1-yl)-1H-1,2,4-triazol-3-amine | E | $^1$H NMR (DMSO-$d_6$, 400 MHz): δ (ppm) 10.90 (bs, 1H), 7.60-7.54 (m, 1H), 7.45 (bs, 1H), 7.12-7.07 (m, 1H), 6.14 (bs, 2H), 5.75 (bs, 2H), 3.86-3.79 (m, 2H), 3.35-3.24 (m, 1H), 2.95-2.80 (m, 2H), 2.11-2.03 (m, 2H), 1.87-1.74 (m, 2H). ESI MS for $C_{16}H_{17}N_7O_3$; expected 355.14; found m/z 356.0 [M + H]$^+$. |
| 42 | (structure) | 5-(4-(3-(4-(methylsulfonyl)phenyl)-1,2,4-oxadiazol-5-yl)piperidin-1-yl)-1H-1,2,4-triazol-3-amine | E | $^1$H NMR (DMSO, 400 MHz) δ (ppm) 11.00 (bs, 1H), 8.27 (bd, J = 7.5 Hz, 2 H), 8.12 (bd, J = 7.5 Hz, 2 H), 5.80 (bs, 2H), 3.89-3.80 (m, 2H), 3.40-3.32 (m, 1H), 2.97-2.86 (m, 2H), 2.14-2.06 (m, 2H), 1.90-1.78 (m, 2H). ESI MS for $C_{16}H_{19}N_7O_3S$; expected 389.13; found m/z 390.2 [M + H]$^+$. |
| 43 | (structure) | 5-(4-(5-(4-fluorophenyl)-1,3,4-oxadiazol-2-yl)piperidin-1-yl)-1H-1,2,4-triazol-3-amine | E | $^1$H NMR (DMSO-$d_6$, 400 MHz): δ (ppm) 11.0 (bs, 1H), 8.10-8.02 (m, 2H), 7.48-7.41 (m, 2H), 5.75 (bs, 2H), 3.85-3.78 (m, 2H), 3.20-3.14 (m, 1H), 2.97-2.85 (m, 2H), 2.15-2.10 (m, 2H), 1.86-1.76 (m, 2H). ESI MS for $C_{15}H_{16}FN_7O$; expected 329.33; found m/z 330.3 [M + H]$^+$. |
| 44 | (structure) | 1-(4-(3-amino-1H-1,2,4-triazol-5-yl)piperazin-1-yl)-2-(2-fluorophenoxy)propan-1-one | E | $^1$H NMR (CD$_3$OD, 400 MHz) δ 7.174 (m, 2 H), 6.917 (m, 2 H), 5.212 (m, 1 H), 3.65 (bs, 2H), 3.52 (bs, 2H), 3.20-3.00 (m, 4H), 1.47 (d, J = 6.3 Hz, 3H); ESI-LCMS m/z calculated for $C_{15}H_{19}FN_6O_2$: expected 334.16; found 335.2 [M + H]$^+$. |

TABLE 1-continued

| Example | Structure | IUPAC Name | Activity | Analytical Data |
|---|---|---|---|---|
| 45 | 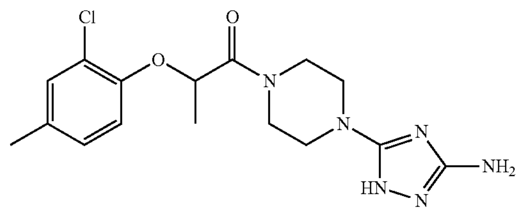 [SMILES: Cc1ccc(OC(C)C(=O)N2CCN(c3nc(N)n[nH]3)CC2)c(Cl)c1] | 1-(4-(3-amino-1H-1,2,4-triazol-5-yl)piperazin-1-yl)-2-(2-chloro-4-methylphenoxy)propan-1-one | E | $^1$H NMR (CD$_3$OD, 400 MHz) δ (ppm) 7.240 (m, 1 H), 7.057 (m, 1 H), 6.864 (m, 1 H), 5.158 (m, 1 H), 3.846 (m, 1 H), 3.598 (m, 2 H), 3.518 (m, 1 H), 3.148 (m, 2 H), 2.679 (m, 1 H), 2.274 (bs, 3 H), 1.916 (s, 1 H), 1.610 (m, 3 H); ESI-LCMS m/z calculated for C$_{16}$H$_{21}$ClN$_6$O$_2$: expected 364.14; found 365.2/367.2 [M + H]$^+$. |
| 47 | 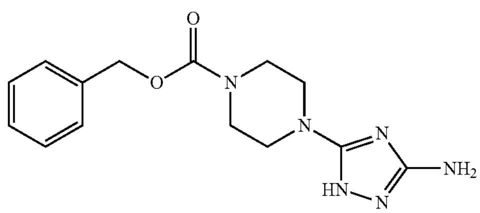 [SMILES: Nc1n[nH]c(N2CCN(C(=O)OCc3ccccc3)CC2)n1] | benzyl 4-(3-amino-1H-1,2,4-triazol-5-yl)piperazine-1-carboxylate | E | $^1$H NMR (CD$_3$OD, 400 MHz) δ 7.359 (m, 5 H), 5.102 (bs, 2 H), 3.457 (bs, 4 H), 3.165 (bs, 4 H); ESI-LCMS m/z calculated for C$_{14}$H$_{18}$N$_6$O$_2$: expected 302.15; found 303.2 [M + H]$^+$. |
| 48 | 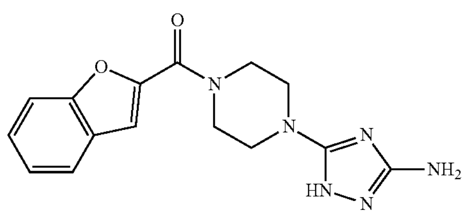 [SMILES: Nc1n[nH]c(N2CCN(C(=O)c3cc4ccccc4o3)CC2)n1] | (4-(3-amino-1H-1,2,4-triazol-5-yl)piperazin-1-yl)(benzofuran-2-yl)methanone | E | $^1$H NMR (CD$_3$OD, 400 MHz) δ 7.751 (m, 1 H), 7.618 (m, 1 H), 7.477 (m, 1 H), 7.434 (bs, 1 H), 7.354 (m, 1 H), 3.955 (bs, 4 H), 3.439 (bs, 4 H); ESI-LCMS m/z calculated for C$_{15}$H$_{16}$N$_6$O$_2$: expected 312.13; found 313.2 [M + H]$^+$. |
| 49 | 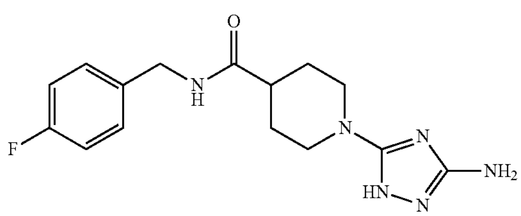 [SMILES: Nc1n[nH]c(N2CCC(C(=O)NCc3ccc(F)cc3)CC2)n1] | 1-(3-amino-1H-1,2,4-triazol-5-yl)-N-(4-fluorobenzyl)piperidine-4-carboxamide | E | $^1$H NMR (DMSO, 500 MHz) δ (ppm) 10.97 (bs, 1 H), 8.33 (t, J = 5.8 Hz, 1 H), 7.24-7.20 (m, 2 H), 7.16-7.08 (m, 2 H), 5.58 (bs, 2 H), 4.22 (d, J = 5.5 Hz, 2 H), 3.83-3.76 (m, 2 H), 2.68-2.57 (m, 2 H), 2.32-2.25 (m, 1 H), 1.69-1.62 (m, 2 H), 1.61-1.49 (m, 2 H). $^{19}$F NMR (DMSO, 200 MHz) δ −115.77 (s, 1 F). ESI-LCMS m/z for C$_{15}$H$_{19}$FN$_6$O$_2$: expected 318.4; found 319.4 [M + H]$^+$, 317.4 [M − H]$^-$. |
| 50 | 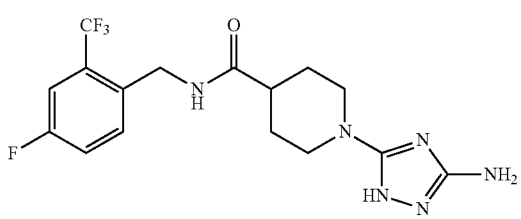 [SMILES: Nc1n[nH]c(N2CCC(C(=O)NCc3ccc(F)cc3C(F)(F)F)CC2)n1] | 1-(3-amino-1H-1,2,4-triazol-5-yl)-N-(4-fluoro-2-(trifluoromethyl)benzyl)piperidine-4-carboxamide | E | $^1$H NMR (DMSO, 500 MHz) δ 11.10 (bs, 1 H), 8.44 (t, J = 5.7 Hz, 1 H), 7.60-7.56 (m, 1 H), 7.55-7.49 (m, 1 H), 7.49-7.45 (m, 1 H), 5.50 (s, 2 H), 4.37 (d, J = 5.2 Hz, 2 H), 3.85-3.75 (m, 2 H), 2.68-2.59 (m, 2 H), 2.39-2.32 (m, 1 H), 1.74-1.65 (m, 2 H), 1.60-1.51 (m, 2 H). $^{19}$F NMR (DMSO, 200 MHz) δ −58.74 (s, 3 F), −113.64 (s, 1 F). ESI-LCMS m/z for C$_{16}$H$_{18}$F$_4$N$_6$O: expected 386.4; found 387.5 [M + H]$^+$, 385.4 [M − H]$^-$. |
| 51 | 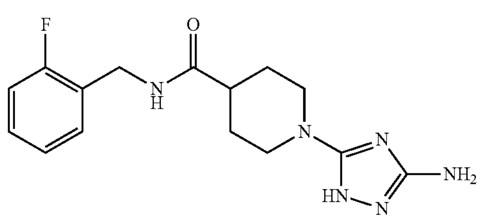 [SMILES: Nc1n[nH]c(N2CCC(C(=O)NCc3ccccc3F)CC2)n1] | 1-(3-amino-1H-1,2,4-triazol-5-yl)-N-(2-fluorobenzyl)piperidine-4-carboxamide | E | $^1$H NMR (DMSO-d$_6$, 200 MHz) δ (ppm) 10.99 (bs, 1 H), 8.35 (t, J = 5.8 Hz, 1 H), 7.40-7.11 (m, 4 H), 5.56 (bs, 2 H), 4.31 (d, J = 5.6 Hz, 2 H), 3.80-3.75 (m, 2 H), 2.76-2.56 (m, 2 H), 2.47-2.25 (m, 1 H), 1.80-1.45 (m, 4 H). ESI-LCMS m/z calculated for C$_{15}$H$_{19}$FN$_6$O: expected 318.4; found [M + H]$^+$ = 319.5. |

TABLE 1-continued

| Example | Structure | IUPAC Name | Activity | Analytical Data |
|---|---|---|---|---|
| 52 | (structure) | 1-(3-amino-1H-1,2,4-triazol-5-yl)-N-(4-chlorobenzyl)piperidine-4-carboxamide | E | $^1$H NMR (DMSO-d$_6$, 200 MHz) δ (ppm) 11.00 (bs, 1 H), 8.39 (t, J = 6.1 Hz, 1H), 7.40 (d, J = 8.0 Hz, 2 H), 7.26 (d, J = 8.1 Hz, 2H), 5.57 (bs, 2 H), 4.26 (d, J = 5.6 Hz, 2 H), 3.93 (m, 2 H), 2.77 (m, 2 H), 2.44-2.29 (m, 1 H), 1.81-1.46 (m, 4 H). ESI-LCMS m/z calculated for C$_{15}$H$_{19}$ClN$_6$O: expected 334.8; found [M + H]$^+$ = 335.5. |
| 53 | (structure) | 1-(3-amino-1H-1,2,4-triazol-5-yl)-N-(2-bromobenzyl)piperidine-4-carboxamide | E | $^1$H NMR (CD$_3$OD, 500 MHz) (ppm) 7.63-7.59 (m, 1 H), 7.39-7.34 (m, 2 H), 7.25-7.19 (m, 1 H), 4.47 (brs, 2 H), 3.90-3.83 (m, 2 H), 3.13-3.04 (m, 2 H), 2.63-2.54 (m, 1 H), 1.96-1.87 (m, 2 H), 1.88-1.78 (m, 2 H). ESI MS for C$_{15}$H$_{19}$BrN$_6$O; expected 379.26; found m/z 379.4/381.4: [M + H]$^+$. |
| 54 | (structure) | 1-(3-amino-1H-1,2,4-triazol-5-yl)-N-(4-fluoro-3-(trifluoromethyl)benzyl)piperidine-4-carboxamide | E | $^1$H NMR (DMSO, 500 MHz) δ (ppm) 8.48 (t, J = 5.8 Hz, 1 H), 7.61-7.54 (m, 2 H), 7.47-7.42 (m, 1 H), 4.28 (d, J = 5.8 Hz, 2H), 3.82-3.76 (m, 2H), 2.66-2.55 (m, 2 H), 2.35-2.25 (m, 1 H), 1.68-1.62 (m, 2 H), 1.59-1.48 (m, 2 H). ESI MS for C$_{16}$H$_{18}$F$_4$N$_6$O expected 386.15, found m/z 387.6 [M + H]$^+$, 385.5 [M − H]$^-$. |
| 55 | (structure) | 5-(4-(((4-bromobenzyl)(methyl)amino)methyl)piperidin-1-yl)-1H-1,2,4-triazol-3-amine | E | $^1$H NMR (DMSO, 600 MHz) δ (ppm) 10.98 (bs, 1 H), 7.68-7.60 (m, 4 H), 7.41 (bs, 2 H), 4.32-4.23 (m, 2 H), 3.83-3.73 (m, 2 H), 3.00-2.90 (m, 2 H), 2.89-2.83 (m, 2 H), 2.69-2.63 (m, 3 H), 2.12-1.99 (m, 2 H), 1.80-1.74 (m, 1 H), 1.25-1.07 (m, 2 H). ESI-LCMS m/z for C$_{16}$H$_{23}$BrN$_6$: expected 379.3; found 379.3/381.4 [M + H]+. |
| 56 | (structure) | N-(1-(3-amino-1H-1,2,4-triazol-5-yl)piperidin-4-yl)-1-(3-fluorophenyl)methanesulfonamide | D | $^1$H NMR (DMSO-d$_6$, 500 MHz) δ (ppm): 10.90 (bs, 1 H), 7.43-7.39 (m, 1H), 7.23-7.15 (m, 4 H), 5.70 (bs, 2 H), 4.37 (s, 2 H), 3.72-3.68 (m, 2 H), 3.25-3.16 (m, 1 H), 2.76-2.60 (m, 2 H), 1.80-1.71 (m, 2 H), 1.43-1.33 (m, 2 H). $^{19}$F NMR (DMSO-d$_6$, 200 MHz) δ (ppm): −113.13 (s, 1F). ESI-LCMS m/z calculated for C$_{14}$H$_{19}$FN$_6$O$_2$S: expected 354.4; found [M + H]$^+$ = 355.4. |
| 57 | (structure) | N-(1-(3-amino-1H-1,2,4-triazol-5-yl)piperidin-4-yl)-1-(4-fluorophenyl)methanesulfonamide | D | $^1$H NMR (DMSO-d$_6$, 500 MHz) δ (ppm) 10.93 (brs, 1 H), 7.41 (dd, J = 8.5 Hz; J = 5.6 Hz, 2 H), 7.20 (t, J = 8.8 Hz, 2 H), 7.14 (d, J = 7.5 Hz, 1 H), 5.66 (brs, 2 H), 4.33 (s, 2 H), 3.68-3.70 (m, 2 H), 3.17-3.21 (m, 1 H), 2.65-2.67 (m, 2 H), 1.75-1.77 (m, 2 H), 1.34-1.41 (m, 2 H). $^{19}$F NMR (DMSO-d$_6$, 200 MHz) δ (ppm) 113.8. ESI-LCMS expected 354.13, found m/z for C$_{14}$H$_{19}$FN$_6$O$_2$S: found 355.4 [M + H]$^+$; 353.4 [M − H]$^-$. |

TABLE 1-continued

| Example | Structure | IUPAC Name | Activity | Analytical Data |
|---|---|---|---|---|
| 58 | 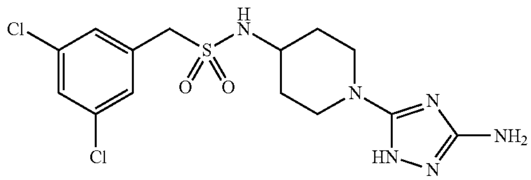 [SMILES: Nc1n[nH]c(N2CCC(NS(=O)(=O)Cc3cc(Cl)cc(Cl)c3)CC2)n1] | N-(1-(3-amino-1H-1,2,4-triazol-5-yl)piperidin-4-yl)-1-(3,5-dichlorophenyl)methane-sulfonamide | C | $^1$H NMR (DMSO, 600 MHz) δ (ppm) 10.90 (bs, 1 H), 7.62 (s, 1 H), 7.45-7.44 (m, 2 H), 5.56 (bs, 2 H), 4.43 (s, 2 H), 3.75-3.68 (m, 2 H), 3.26-3.19 (m, 1 H), 2.75-2.65 (m, 2 H), 1.80-1.73 (m, 2 H), 1.45-1.35 (m, 2 H). ESI-LCMS m/z for $C_{14}H_{18}Cl_2N_6O_2S$: expected 405.3; found 405.4/407.3 [M + H]$^+$. |
| 59 | 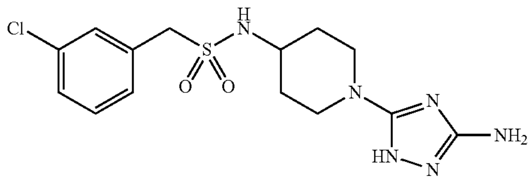 [SMILES: Nc1n[nH]c(N2CCC(NS(=O)(=O)Cc3cccc(Cl)c3)CC2)n1] | N-(1-(3-amino-1H-1,2,4-triazol-5-yl)piperidin-4-yl)-1-(3-chlorophenyl)methane-sulfonamide | C | $^1$H NMR (DMSO, 600 MHz) δ (ppm) 7.45 (brs, 1 H), 7.42-7.39 (m, 2 H), 7.36-7.32 (m, 3 H), 7.24-7.2 (M, 1 H), 5.6 (brs, 2 H), 4.37 (s, 2 H), 3.73-3.67 (m, 2 H), 3.19 (brs, 1 H), 2.67 (brs, 2 H), 1.78-1.74 (m, 2 H), 1.42-1.34 (m, 2 H). ESI MS found for $C_{16}H_{19}ClN_6O_2S$ expected 370.10, found m/z 371.4/373.3 [M + H]$^+$, 369.3/371.4 [M + H]$^+$. |
| 60 | 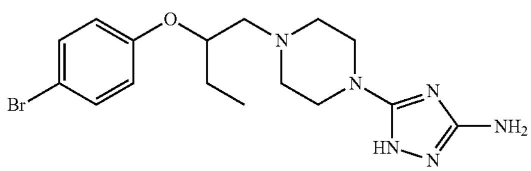 | 5-(4-(2-(4-bromophenoxy)butyl)piperazin-1-yl)-1H-1,2,4-triazol-3-amine | D | $^1$H NMR (DMSO, 600 MHz) δ (ppm): 11.18 (bs, 1H); 7.48 (d, J = 9.0 Hz, 2H), 7.04 (d, J = 9.0 Hz, 2H), 5.01-4.94 (m, 1H), 3.93-3.82 (m, 2H), 3.59-3.49 (m, 2H), 3.49-3.36 (m, 4H), 3.27-3.14 (m, 2H), 1.67-1.59 (m, 2H), 0.87 (t, J = 7.4 Hz, 3H). ESI MS for C16H23BrN6O; expected 395.31; found m/z 395.4/397.4 in ratio ~1/1 (isotopes of Br) [M + H]$^+$. |
| 61 | 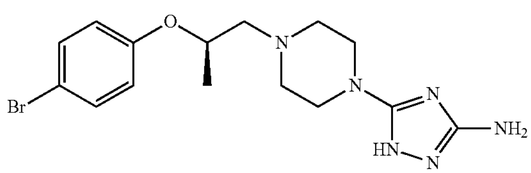 | (R)-5-(4-(2-(4-bromophenoxy)propyl)piperazin-1-yl)-1H-1,2,4-triazol-3-amine | C | ESI MS for $C_{15}H_{21}BrN_6O$; expected 381.28; found m/z 381.3/383.3 in ratio ~1/1 (isotopes of Br) [M + H]$^+$. $^1$H NMR (DMSO-d$_6$, 600 MHz): 11.29 (bs, 1H); 7.46 (d, J = 9.0 Hz, 2H), 7.00 (d, J = 9.0 Hz, 2H), 5.12-5.03 (m, 1H), 3.91-3.76 (m, 2H), 3.58-3.44 (m, 6H), 3.25-3.15 (m, 2H), 1.20 (d, J = 6.2 Hz, 3H). |
| 62 | 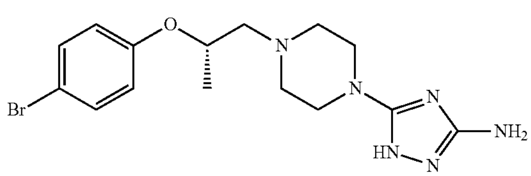 | (S)-5-(4-(2-(4-bromophenoxy)propyl)piperazin-1-yl)-1H-1,2,4-triazol-3-amine | B | ESI MS for $C_{15}H_{21}BrN_6O$; expected 381.28; found m/z 381.4/383.4 in ratio ~1/1 (isotopes of Br) [M + H]$^+$. $^1$H NMR (DMSO-d$_6$, 600 MHz): 11.43 (bs, 1H), 7.63 (bs, 2H), 7.46 (d, J = 9.0 Hz, 2H), 7.00 (d, J = 9.0 Hz, 2H), 5.13-5.03 (m, 1H), 3.93-3.78 (m, 2H), 3.58-3.45 (m, 6H), 3.27-3.15 (m, 2H), 1.20 (d, J = 6.2 Hz, 3H). |
| 63 | 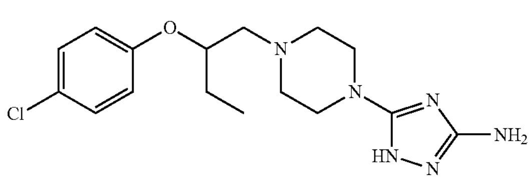 | 5-(4-(2-(4-chlorophenoxy)butyl)piperazin-1-yl)-1H-1,2,4-triazol-3-amine | D | ESI MS for $C_{16}H_{23}ClN_6O$; expected 350.85; found m/z 351.4/353.4 in ratio ~3/1 (isotopes of Cl) [M + H]$^+$. $^1$H NMR (DMSO-d$_6$, 600 MHz): 11.47 (bs, 1H), 7.62 (bs, 2H), 7.33 (d, J = 9.0 Hz, 2H), 7.06 (d, J = 9.0 Hz, 2H), 5.01-4.94 (m, 1H), 3.93-3.80 (m, 2H), 3.57-3.38 (m, 6H), 3.27- |

TABLE 1-continued

| Example | Structure | IUPAC Name | Activity | Analytical Data |
|---|---|---|---|---|
| | | | | 3.14 (m, 2H), 1.65-1.55 (m, 2H), 0.84 (t, J = 7.4 Hz, 3H). |
| 64 | 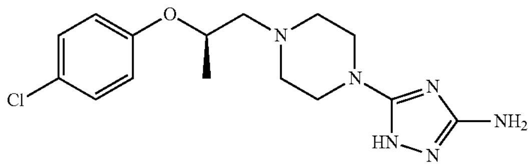 [SMILES: C[C@H](CN1CCN(c2nc(N)n[nH]2)CC1)Oc1ccc(Cl)cc1] | (R)-5-(4-(2-(4-chlorophenoxy)propyl)piperazin-1-yl)-1H-1,2,4-triazol-3-amine | D | ESI MS for $C_{15}H_{21}ClN_6O$; expected 336.83; found m/z 337.4/339.4 in ratio ~3/1 (isotopes of Cl) [M + H]$^+$. $^1$H NMR (DMSO-d$_6$, 600 MHz): 11.31 (bs, 1H), 7.52 (bs, 1H), 7.36 (d, J = 9.0 Hz, 2H), 7.08 (d, J = 9.0 Hz, 2H), 5.13-5.06 (m, 1H), 3.92-3.81 (m, 2H), 3.61-3.40 (m, 6H), 3.28-3.18 (m, 2H), 1.22 (d, J = 6.1 Hz, 3H). |
| 65 | 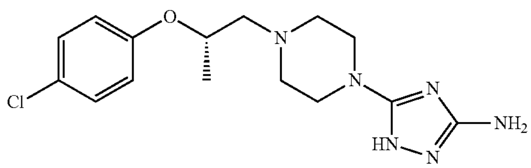 [SMILES: C[C@@H](CN1CCN(c2nc(N)n[nH]2)CC1)Oc1ccc(Cl)cc1] | (S)-5-(4-(2-(4-chlorophenoxy)propyl)piperazin-1-yl)-1H-1,2,4-triazol-3-amine | D | ESI MS for $C_{15}H_{21}ClN_6O$; expected 336.83; found m/z 337.4/339.4 in ratio ~3/1 (isotopes of Cl) [M + H]$^+$. $^1$H NMR (DMSO-d$_6$, 600 MHz): 11.35 (bs, 1H), 7.50 (bs, 1H), 7.36 (d, J = 9.0 Hz, 2H), 7.08 (d, J = 9.0 Hz, 2H), 5.14-5.06 (m, 1H), 3.95-3.81 (m, 2H), 3.62-3.40 (m, 6H), 3.29-3.17 (m, 2H), 1.22 (d, J = 6.1 Hz, 3H). |
| 66 | 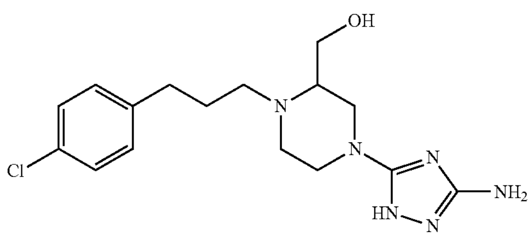 [SMILES: Nc1n[nH]c(N2CCN(CCCc3ccc(Cl)cc3)C(CO)C2)n1] | (4-(3-amino-1H-1,2,4-triazol-5-yl)-1-(3-(4-chlorophenyl)propyl)piperazin-2-yl)methanol | D | $^1$H NMR (DMSO-d$_6$, 500 MHz) δ (ppm): 10.97 (bs, 1 H), 7.30 (d, J = 8.1 Hz, 2H), 7.22 (d, J = 8.1 Hz, 2H), 5.63 (bs, 2 H), 4.50 (bs, 1 H), 3.59-3.47 (m, 2 H), 3.40-3.30 (m, 5 H), 2.92-2.83 (m, 1 H), 2.80-2.65 (m, 2 H), 2.63-2.47 (m, 2 H), 2.42-2.17 (m, 3 H), 1.76-1.63 (m, 2 H). ESI-LCMS m/z calculated for $C_{16}H_{23}ClN_6O$: expected 350.8; found [M + H]$^+$ = 351.4. |
| 67 | 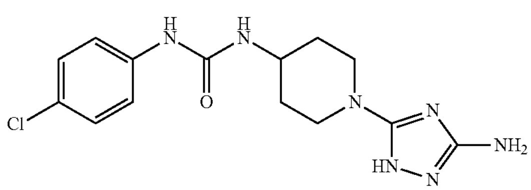 [SMILES: Nc1n[nH]c(N2CCC(NC(=O)Nc3ccc(Cl)cc3)CC2)n1] | 1-(1-(3-amino-1H-1,2,4-triazol-5-yl)piperidin-4-yl)-3-(4-chlorophenyl)urea | E | $^1$H NMR (DMSO, 500 MHz) 10.88 (brs, 1 H), 8.44 (s, 1H), 7.38 (d, J = 8.75 Hz, 2 H), 7.22 (d, J = 8.75 Hz, 2 H), 6.19 (d, J = 7.74 Hz, 1 H), 5.82-5.60 (brs, 1 H), 3.69-3.53 (m, 3 H), 2.88-2.71 (m, 2 H), 1.81-1.72 (m, 2 H), 1.41-1.22 (m, 2 H). ESI MS for $C_{14}H_{18}ClN_7O$; expected 335.80; found m/z 336.4: [M + H]$^+$. |
| 68 | 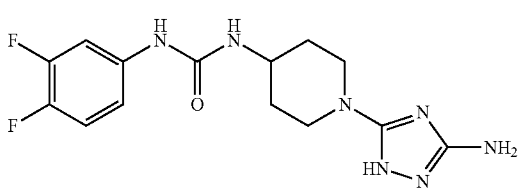 [SMILES: Nc1n[nH]c(N2CCC(NC(=O)Nc3ccc(F)c(F)c3)CC2)n1] | 1-(1-(3-amino-1H-1,2,4-triazol-5-yl)piperidin-4-yl)-3-(3,4-difluorophenyl)urea | E | $^1$H NMR (DMSO, 600 MHz) δ 7.53-7.48 (m, 1 H), 7.16-7.08 (m, 1 H), 7.00-6.95 (m, 1 H), 3.85-3.78 (m, 1 H), 3.78-3.73 (m, 2 H), 3.21-3.13 (m, 2 H), 2.05-1.99 (m, 2 H), 1.62-1.53 (m, 2 H). $^{19}$F NMR (DMSO, 200 MHz) δ −139.01 (d, J = 23.5 Hz, 1 F), −113.64 (d, J = 21.5 Hz, 1 F). ESI-LCMS m/z for $C_{14}H_{17}F_2N_7O$: expected 337.3; found 338.4 [M + H]$^+$, 336.3 [M − H]$^-$. |

TABLE 1-continued

| Example | Structure | IUPAC Name | Activity | Analytical Data |
|---|---|---|---|---|
| 69 | 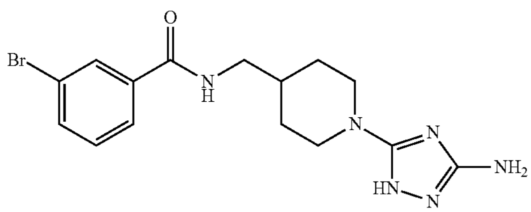 [SMILES: Nc1n[nH]c(N2CCC(CNC(=O)c3cccc(Br)c3)CC2)n1] | N-((1-(3-amino-1H-1,2,4-triazol-5-yl)piperidin-4-yl)methyl)-3-bromobenzamide | E | $^1$H NMR (DMSO, 500 MHz) δ 11.05 (bs, 1 H), 8.64-8.58 (m, 1 H), 8.01 (s, 1 H), 7.83 (d, J = 7.9 Hz, 1 H), 7.70 (d, J = 7.7 Hz, 1 H), 7.41 (dd, $J_1$ = 7.9 Hz, $J_2$ = 7.7 Hz, 1 H), 5.46 (bs, 2 H), 3.76 (d, J = 12.3 Hz, 2 H), 3.18-3.13 (m, 2 H), 2.63-3.53 (m, 2 H), 1.71-1.59 (m, 3 H), 1.19-1.08 (m, 2 H). ESI-LCMS m/z for $C_{15}H_{19}BrN_6O$: expected 379.3; found 379.4/381.4 [M + H]$^+$. |
| 70 | 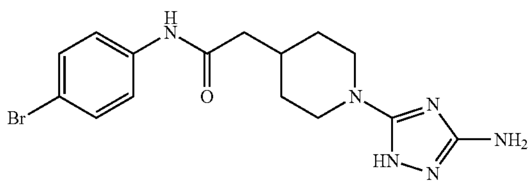 [SMILES: Nc1n[nH]c(N2CCC(CC(=O)Nc3ccc(Br)cc3)CC2)n1] | 2-(1-(3-amino-1H-1,2,4-triazol-5-yl)piperidin-4-yl)-N-(4-bromophenyl)acetamide | E | $^1$H NMR (DMSO, 600 MHz) δ (ppm) 10.94 (bs, 1 H), 10.02 (s, 1 H), 7.58-7.54 (m, 2 H), 7.47-7.44 (m, 2 H), 5.56 (bs, 2H), 3.77-3.72 (m, 2H), 2.68-2.57 (m, 2 H), 2.23 (d, J = 7.2 Hz, 2 H), 1.92-1.84 (m, 1 H), 1.65-1.59 (m, 2 H), 1.24-1.16 (m, 2 H). ESI-LCMS m/z calculated for $C_{15}H_{19}BrN_6O$: expected 379.3; found [M + H]$^+$ = 379.4/381.4. |
| 71 | 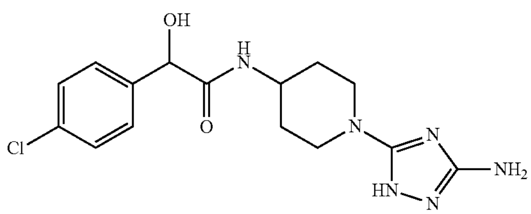 [SMILES: Nc1n[nH]c(N2CCC(NC(=O)C(O)c3ccc(Cl)cc3)CC2)n1] | N-(1-(3-amino-1H-1,2,4-triazol-5-yl)piperidin-4-yl)-2-(4-chlorophenyl)-2-hydroxyacetamide | E | $^1$H NMR (DMSO, 600 MHz) δ 7.92 (d, J = 8.3 Hz, 1 H), 7.43-7.34 (AA'XX', J = 8.5 Hz, 4 H), 6.21 (d, J = 4.7 Hz, 1 H), 5.65-5.43 (brs, 2H), 4.90 (d, J = 4.1 Hz, 1 H), 3.74-3.68 (m, 2 H), 3.69-3.61 (m, 1 H), 2.74-2.62 (m, 2 H), 1.65-1.55 (m, 2 H), 1.54-1.42 (m, 2 H). ESI MS for $C_{15}H_{19}ClN_6O_2$; expected 350.81; found m/z 351.4/353.4 [M + H]$^+$. |
| 72 | 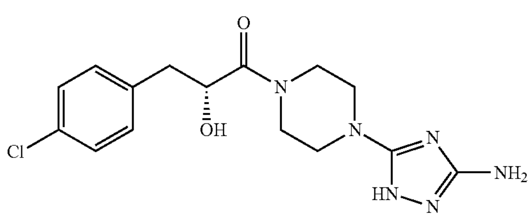 [SMILES: Nc1n[nH]c(N2CCN(C(=O)[C@H](O)Cc3ccc(Cl)cc3)CC2)n1] | (R)-1-(4-(3-amino-1H-1,2,4-triazol-5-yl)piperazin-1-yl)-3-(4-chlorophenyl)-2-hydroxypropan-1-one | E | $^1$H NMR (DMSO, 600 MHz) δ 7.3 (d, J = 8.3 Hz, 2 H), 7.26 (d, J = 8.5 Hz, 2 H), 5.78 (brs, 2 H), 5.16-5.11 (m, 1 H), 4.53-4.47 (m, 1 H), 3.6-3.52 (m, 2H), 3.5-3.38 (m, 2 H), 3.18-3.04 (m, 4 H), 2.9-2.84 (m, 1 H), 2.76-2.69 (m, 1 H). ESI MS for $C_{15}H_{19}ClN_6O_2$ expected 350.13, found m/z 351.4/353.4 (M + 1), 349.4/351.3 [M − H]. |
| 73 | 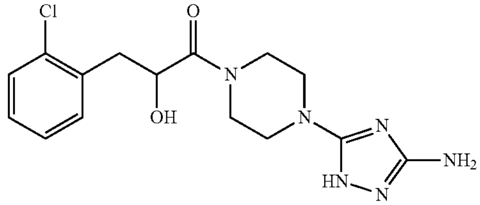 [SMILES: Nc1n[nH]c(N2CCN(C(=O)C(O)Cc3ccccc3Cl)CC2)n1] | 1-(4-(3-amino-1H-1,2,4-triazol-5-yl)piperazin-1-yl)-3-(2-chlorophenyl)-2-hydroxypropan-1-one | E | $^1$H NMR (DMSO-$d_6$, 500 MHz) δ (ppm) 11.00 (brs, 1 H), 7.35-7.41 (m, 2 H), 7.21-7.26 (m, 2 H), 5.78 (brs, 2 H), 5.24 (d, J = 8.0 Hz, 1 H), 4.55-4.60 (m, 1 H), 3.42-3.58 (m, 4 H), 3.11-3.15 (m, 3 H), 3.03 (dd, J = 5.1 Hz, J = 13.8 Hz, 1 H), 2.97-3.00 (m, 1 H), 2.86 (dd, J = 8.5 Hz, J = 13.8 Hz, 1 H). ESI-LCMS m/z for $C_{15}H_{19}ClN_6O_2$: expected 350.13, found: 351.3/353.3 [M + H]$^+$; 349.4/351.5 [M − H]$^-$. |

TABLE 1-continued

| Example | Structure | IUPAC Name | Activity | Analytical Data |
|---|---|---|---|---|
| 74 | 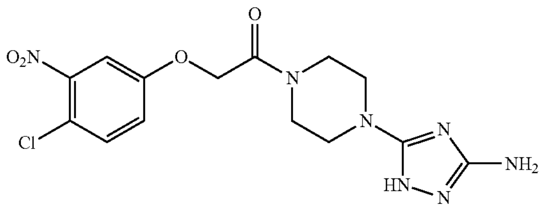 [SMILES: Nc1n[nH]c(N2CCN(C(=O)COc3ccc(Cl)c([N+](=O)[O-])c3)CC2)n1] | 1-(4-(3-amino-1H-1,2,4-triazol-5-yl)piperazin-1-yl)-2-(4-chloro-3-nitrophenoxy)ethan-1-one | E | $^1$H NMR (DMSO-d$_6$, 500 MHz) δ: 11.03 (s, 1 H), 7.67 (d, J = 3.0 Hz, 1 H), 7.65 (d, J = 9.1 Hz, 1 H), 7.27 (dd, J = 3.0 Hz, J = 9.1 Hz, 1 H), 5.81, (s, 2 H), 5.03, (s, 2 H), 3.47-3.50 (m, 4 H), 3.16-3.23 (m, 4 H). ESI-LCMS m/z for 4: expected 381.10, found: 382.5/384.5 [M + H]$^+$, 380.5/382.5 [M − H]$^-$. |
| 75-1 | 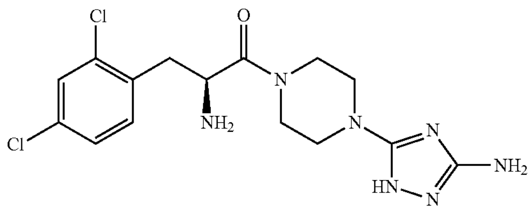 [SMILES: Nc1n[nH]c(N2CCN(C(=O)[C@@H](N)Cc3ccc(Cl)cc3Cl)CC2)n1] | (S)-2-amino-1-(4-(3-amino-1H-1,2,4-triazol-5-yl)piperazin-1-yl)-3-(2,4-dichlorophenyl)propan-1-one | E | $^1$H NMR (DMSO, 600 MHz) δ 8.53 (brs, 3 H), 7.65 (s, 1 H), 7.46-7.42 (m, 2 H), 4.68-4.61 (m, 1 H), 3.72-3.65 (m, 1 H), 3.53-3.50 (m, 1 H), 3.39-3.34 (m, 2 H), 3.3-3.24 (m, 2 H), 3.23-3.17 (m, 1 H), 3.16-3.10 (m, 1 H), 3.08-3.02 (m, 1 H), 2.96 (brs, 1 H). ESI MS for C$_{15}$H$_{19}$Cl$_2$N$_7$O expected 383.10, found m/z 384.4/386.4 [M + H]$^+$, 382.3/384.2 (M − H)$^-$. |
| 75-2 | 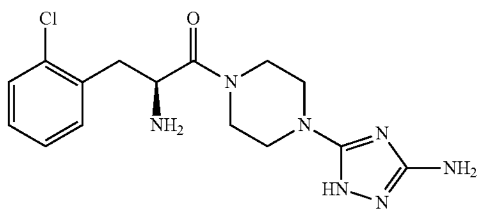 [SMILES: Nc1n[nH]c(N2CCN(C(=O)[C@@H](N)Cc3ccccc3Cl)CC2)n1] | (S)-2-amino-1-(4-(3-amino-1H-1,2,4-triazol-5-yl)piperazin-1-yl)-3-(2-chlorophenyl)propan-1-one | E | $^1$H NMR (CD$_3$OD, 600 MHz) δ 7.50-7.46 (m, 1 H), 7.39-7.33 (m, 3 H), 7.32-7.28 (m, 1 H), 4.79-4.73 (m, 1 H), 3.71-3.64 (m, 1 H), 3.63-3.56 (m, 1 H), 3.48-3.42 (m, 1 H), 3.36-3.31 (m, 2 H), 3.26-3.22 (m, 1 H), 3.22-3.14 (m, 2 H), 3.02-2.96 (m, 1 H), 2.67-2.6 (m, 1 H). ESI MS for C$_{15}$H$_{20}$ClN$_7$O expected 349.14, found m/z 350.3/352.3 [M + H]$^+$, 348.4/350.3 (M − H)$^-$. |
| 76 | 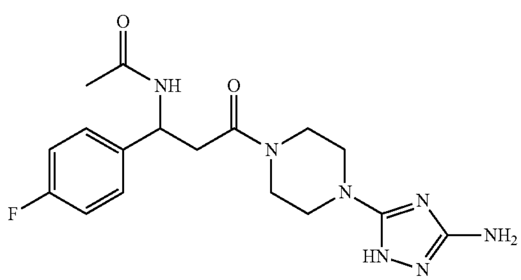 [SMILES: CC(=O)NC(CC(=O)N1CCN(c2nc(N)n[nH]2)CC1)c1ccc(F)cc1] | N-(3-(4-(3-amino-1H-1,2,4-triazol-5-yl)piperazin-1-yl)-1-(4-fluorophenyl)-3-oxopropyl)acetamide | E | $^1$H NMR (DMSO, 500 MHz) δ 8.24 (d, J = 8.1 Hz, 1 H), 7.33-7.28 (m, 2 H), 7.11-7.05 (m, 2 H), 5.67 (brs, Hz, 2 H), 5.155 (q, J = 7.5, J = 14.9, 1 H), 3.46-3.35 (m, 4 H), 3.14-3.08 (m, 1 H), 3.08-2.96 (m, 3 H), 2.775 (dd, J = 7.5, J = 15.4, 1 H), 2.695 (dd, J = 6.6, J = 15.4, 1 H), 1.765 (s, 3H). ESI MS found for C$_{17}$H$_{22}$FN$_7$O$_2$ expected 375.18, found m/z 376.5 [M + H]$^+$, 374.4 [M − H]$^-$. |
| 77 | 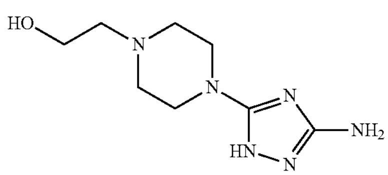 [SMILES: Nc1n[nH]c(N2CCN(CCO)CC2)n1] | 2-(4-(3-amino-1H-1,2,4-triazol-5-yl)piperazin-1-yl)ethan-1-ol | E | $^1$H NMR (CD$_3$OD, 400 MHz) δ 4.399 (2H, bs), 3.511 (4H, m), 3.148 (2H, bs), 2.440 (4H, bs), 2.398 (4H, m); ESI-LCMS m/z calculated for C$_8$H$_{16}$N$_6$O: expected 212.3; found 213.2 [M + H]$^+$. |
| 78 | 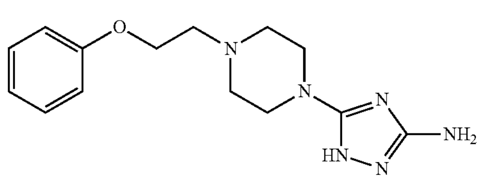 [SMILES: Nc1n[nH]c(N2CCN(CCOc3ccccc3)CC2)n1] | 5-(4-(2-phenoxyethyl)piperazin-1-yl)-1H-1,2,4-triazol-3-amine | E | $^1$H NMR (CD$_3$OD, 400 MHz) δ 7.221-6.75 (5H, m), 4.142 (2H, t, J = 2.670), 2.909 (2H, t, J = 2.670), 3.626 (4H, bs), 2.581 (4H, bs); ESI-LCMS m/z calculated for C$_{14}$H$_{20}$N$_6$O: expected 288.17; found 289.2 [M + H]$^+$. |

TABLE 1-continued

| Example | Structure | IUPAC Name | Activity | Analytical Data |
|---|---|---|---|---|
| 79 | 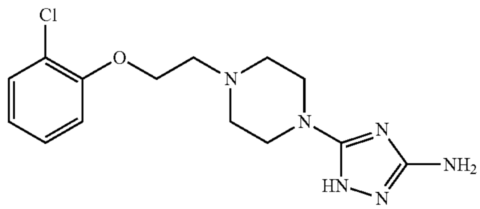 [SMILES: Nc1n[nH]c(N2CCN(CCOc3ccccc3Cl)CC2)n1] | 5-(4-(2-(2-chlorophenoxy)ethyl)piperazin-1-yl)-1H-1,2,4-triazol-3-amine | D | $^1$H NMR (CD$_3$OD, 400 MHz) δ 7.367 (d, J = 8.0 Hz, 1 H), 7.267 (t, J = 8.2 Hz, 1 H), 7.090 (d, J = 8.0, 1 H), 6.940 (t, J = 8.2, 1 H), 4.241 (t, J = 5.49 Hz, 2 H), 3.352 (m, 4H), 2.934 (t, J = 5.49, 2H,), 2.784 (m, 4H); ESI-LCMS m/z calculated for C$_{14}$H$_{19}$ClN$_6$O: expected 322.13; found 323.2/325.2 [M + H]$^+$. |
| 80 | 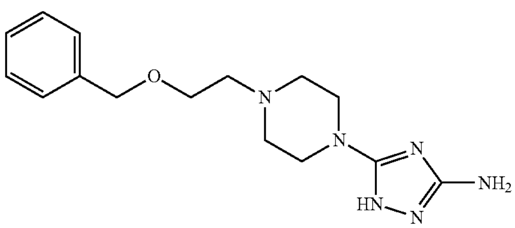 [SMILES: Nc1n[nH]c(N2CCN(CCOCc3ccccc3)CC2)n1] | 5-(4-(2-(benzyloxy)ethyl)piperazin-1-yl)-1H-1,2,4-triazol-3-amine | E | $^1$H NMR (CD$_3$OD, 400 MHz) δ 7.366-7.295 (m, 5H), 4.546 (bs, 2H), 3.666 (t, J = 5.463, 2H), 3.309 (bs, 4H), 2.677 (t, J = 5.463, 2H), 2.617 (bs, 4H); ESI-LCMS m/z calculated for C$_{15}$H$_{22}$N$_6$O: expected 302.09; found 203.2 [M + H]$^+$. |
| 81 | 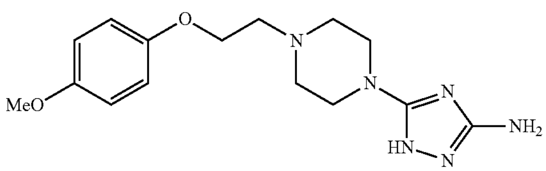 [SMILES: COc1ccc(OCCN2CCN(c3nc(N)n[nH]3)CC2)cc1] | 5-(4-(2-(4-methoxyphenoxy)ethyl)piperazin-1-yl)-1H-1,2,4-triazol-3-amine | D | $^1$H NMR (CD$_3$OD, 400 MHz) δ 6.865 (m, 4 H), 4.064 (t, J = 2.670, 2H), 3.792 (s, 3H), 3.625 (bs, 4H), 2.914 (t, J = 2.670, 2H), 2.572 (bs, 4H); ESI-LCMS m/z calculated for C$_{15}$H$_{22}$N$_6$O$_2$: expected 318.18; found 319.2 [M + H]$^+$. |
| 82 | 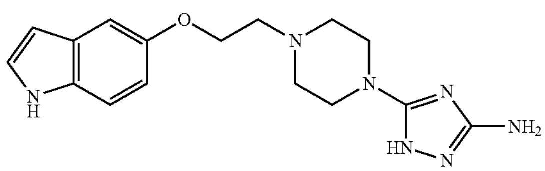 [SMILES: Nc1n[nH]c(N2CCN(CCOc3ccc4[nH]ccc4c3)CC2)n1] | 5-(4-(2-((1H-indol-5-yl)oxy)ethyl)piperazin-1-yl)-1H-1,2,4-triazol-3-amine | E | $^1$H NMR (CD$_3$OD, 400 MHz) δ 7.759 (m, 2 H), 7.643 (m, 1 H), 7.755 (m, 2 H), 4.072 (t, J = 2.670, 2 H), 3.626 (bs, 4 H), 2.916 (t, J = 2.670, 2 H), 2.566 (bs, 4 H); ESI-LCMS m/z calculated for C$_{16}$H$_{21}$N$_7$O: expected 327.18; found 328.2 [M + H]$^+$. |
| 83 | 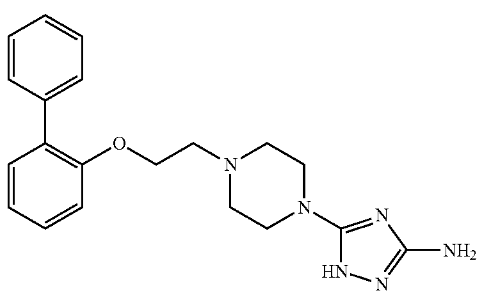 [SMILES: Nc1n[nH]c(N2CCN(CCOc3ccccc3-c3ccccc3)CC2)n1] | 5-(4-(2-([1,1'-biphenyl]-2-yloxy)ethyl)piperazin-1-yl)-1H-1,2,4-triazol-3-amine | D | $^1$H NMR (CD$_3$OD, 400 MHz) δ 7.510-7.395 (m, 7 H), 7.190 (m, 1 H), 7.151 (m, 1 H), 4.261 (t, J = 5.79, 2 H), 3.627 (bs, 4 H), 2.896 (t, J = 5.79, 2 H), 2.620 (bs, 4 H); ESI-LCMS m/z calculated for C$_{20}$H$_{24}$N$_6$O: expected 364.20; found 365.2 [M + H]$^+$. |
| 84 | 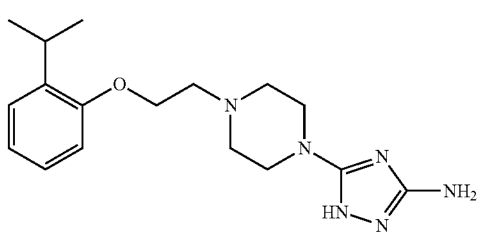 [SMILES: CC(C)c1ccccc1OCCN1CCN(c2nc(N)n[nH]2)CC1] | 5-(4-(2-(2-isopropylphenoxy)ethyl)piperazin-1-yl)-1H-1,2,4-triazol-3-amine | D | $^1$H NMR (CD$_3$OD, 400 MHz) δ 7.213 (d, J = 7.43 Hz, 1 H), 7.142 (t, J = 7.43 Hz, 1 H), 6.921 (m, 2 H), 4.196 (t, J = 5.53, 2 H), 3.506 (m, 1 H), 3.368 (bs, 4 H), 2.967 (t, J = 5.53, 2 H), 2.797 (bs, 4 H), 1.222 (d, J = 6.86 Hz, 6 H); ESI-LCMS m/z calculated for C$_{17}$H$_{26}$N$_6$O: expected 330.22; found 331.2 [M + H]$^+$. |

TABLE 1-continued

| Example | Structure | IUPAC Name | Activity | Analytical Data |
|---|---|---|---|---|
| 85 | 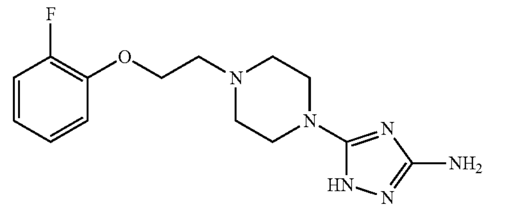 [SMILES: Nc1n[nH]c(N2CCN(CCOc3ccccc3F)CC2)n1] | 5-(4-(2-(2-fluorophenoxy)ethyl)piperazin-1-yl)-1H-1,2,4-triazol-3-amine | D | $^1$H NMR (CD$_3$OD, 400 MHz) δ 7.108 (m, 3 H), 6.942 (m, 1 H), 4.235 (t, J = 5.22, 2 H), 3.349 (m, 4 H), 2.895 (t, J = 5.22, 2 H), 2.729 (m, 4 H); ESI-LCMS m/z calculated for C$_{14}$H$_{19}$FN$_6$O: expected 306.16; found 307.2 [M + H]$^+$. |
| 86 | 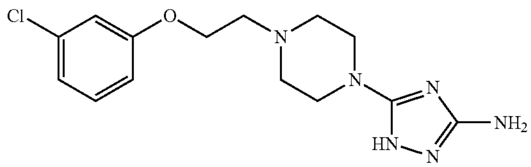 [SMILES: Nc1n[nH]c(N2CCN(CCOc3cccc(Cl)c3)CC2)n1] | 5-(4-(2-(3-chlorophenoxy)ethyl)piperazin-1-yl)-1H-1,2,4-triazol-3-amine | D | $^1$H NMR (CD$_3$OD, 400 MHz) δ 7.263 (t, J = 8.29, 1 H), 6.999 (m, 1 H), 6.958 (d, J = 7.86, 1 H), 6.906 (d, J = 8.35, 1 H), 4.179 (t, J = 5.37, 2 H), 3.360 (m, 4 H), 2.898 (t, J = 5.37, 2 H), 2.729 (m, 4 H); ESI-LCMS m/z calculated for C$_{14}$H$_{19}$ClN$_6$O: expected 322.13; found 323.2 [M + H]$^+$. |
| 87 | 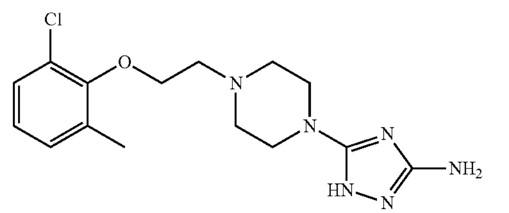 [SMILES: Cc1cccc(Cl)c1OCCN1CCN(c2nc(N)n[nH]2)CC1] | 5-(4-(2-(2-chloro-6-methylphenoxy)ethyl)piperazin-1-yl)-1H-1,2,4-triazol-3-amine | D | $^1$H NMR (CD$_3$OD, 400 MHz) δ 7.240 (m, 1 H), 7.159 (m, 1 H), 7.009 (m, 1 H), 4.122 (t, J = 5.70, 2 H), 3.368 (m, 4 H), 2.962 (t, J = 5.70 2 H), 2.800 (m, 4 H), 2.352 (s, 3 H); ESI-LCMS m/z calculated for C$_{15}$H$_{21}$ClN$_6$O: expected 336.83; found 337.2 [M + H]$^+$. |
| 88 | 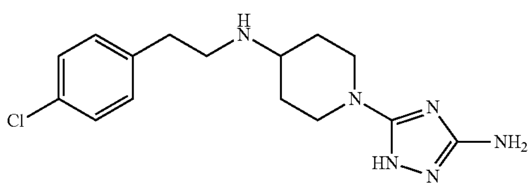 [SMILES: Nc1n[nH]c(N2CCC(NCCc3ccc(Cl)cc3)CC2)n1] | 1-(3-amino-1H-1,2,4-triazol-5-yl)-N-(4-chlorophenethyl)piperidin-4-amine | C | $^1$H NMR (DMSO, 600 MHz) δ 7.28 (d, J = 8.4 Hz, 2 H), 7.21 (d, J = 8.1 Hz, 2 H), 5.42 (brs, 2 H), 3.68-3.6 (m, 2 H), 2.76-2.7 (m, 2 H). 2.68-2.58 (m, 4 H), 2.53-2.48 (m, 1 H), 1.76-1.68 (m, 2 H), 1.22-1.1 (m, 2 H). ESI MS for C$_{15}$H$_{21}$ClN$_6$ expected 320.15, found m/z 321.4/323.4 [M + H], 319.2/321.5 [M − H]. |
| 89 | 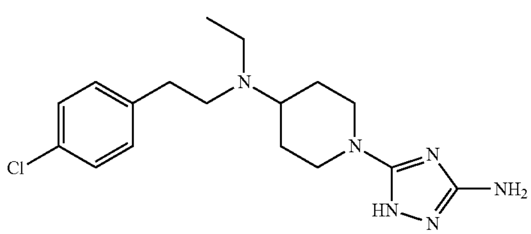 [SMILES: CCN(CCc1ccc(Cl)cc1)C1CCN(c2nc(N)n[nH]2)CC1] | 1-(3-amino-1H-1,2,4-triazol-5-yl)-N-(4-chlorophenethyl)-N-ethylpiperidin-4-amine | B | $^1$H NMR (DMSO, 600 MHz) δ 7.26 (d, J = 8.1 Hz, 2 H), 7.20 (d, J = 8.4 Hz, 2 H), 5.64 (brs, 2 H), 3.8-3.73 (m, 2 H), 2.64-2.51 (m, 7 H), 2.51-2.47 (m, 2 H), 1.58 -1.52 (m, 2 H), 1.36-1.25 (m, 2 H), 0.89 (t, J = 7.1, 3 H). ESI MS for C$_{17}$H$_{25}$ClN$_6$ expected 348.18, found m/z 349.4/351.4 [M + H], 347.4 [M − H]. |
| 90 | 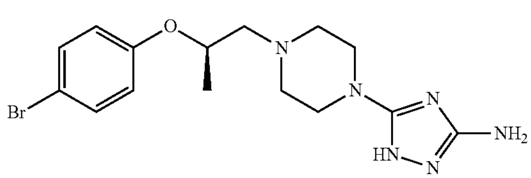 | (R)-5-(4-(2-(4-bromophenoxy)propyl)piperazin-1-yl)-1H-1,2,4-triazol-3-amine | B | $^1$H NMR (DMSO-d$_6$, 600 MHz) δ 11.43 (bs, 1H), 7.63 (bs, 2H), 7.46 (d, J = 9.0 Hz, 2H), 7.00 (d, J = 9.0 Hz, 2H), 5.13-5.03 (m, 1H), 3.93-3.78 (m, 2H), 3.58-3.45 (m, 6H), 3.27-3.15 (m, 2H), 1.20 (d, J = 6.2 Hz, 3H). ESI MS for C$_{15}$H$_{21}$BrN$_6$O; expected 381.28; found m/z 381.4/383.4 in ratio ~1/1 (isotopes of Br) [M + H]$^+$. |

TABLE 1-continued

| Example | Structure | IUPAC Name | Activity | Analytical Data |
|---|---|---|---|---|
| 91 | 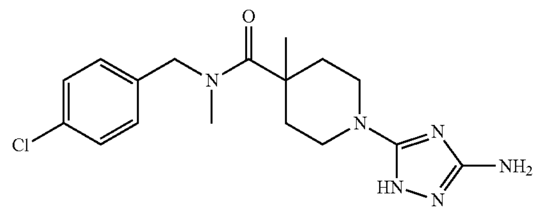 [SMILES: CN(Cc1ccc(Cl)cc1)C(=O)C1(C)CCN(c2nc(N)n[nH]2)CC1] | 1-(3-amino-1H-1,2,4-triazol-5-yl)-N-(4-chlorobenzyl)-N,4-dimethyl-piperidine-4-carboxamide | E | $^1$H NMR (DMSO, 500 MHz) δ 10.88 (bs, 1 H), 7.38 (d, J = 8.0 Hz, 2 H), 7.19 (d, J = 8.0 Hz, 2 H), 5.56 (bs, 2 H), 4.54 (s, 2 H), 3.33-3.25 (m, 2 H), 3.10-3.02 (m, 2 H), 2.93 (s, 3 H) 1.99-1.92 (m, 2 H), 1.39-1.31 (m, 2 H), 1.08 (s, 3 H). ESI-LCMS m/z for $C_{17}H_{21}ClN_6O$: expected 362.9; found 363.5 [M + H]+, 361.4 (M − H)$^-$ |
| 92 | 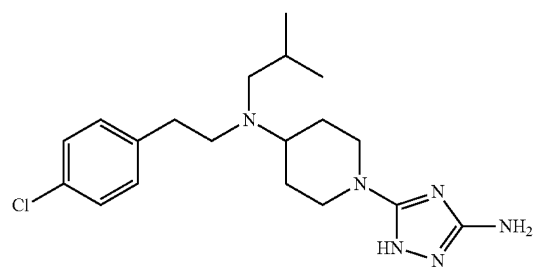 [SMILES: CC(C)CN(CCc1ccc(Cl)cc1)C1CCN(c2nc(N)n[nH]2)CC1] | 1-(3-amino-1H-1,2,4-triazol-5-yl)-N-(4-chlorophenethyl)-N-isobutylpiperidin-4-amine | A | $^1$H NMR (DMSO-d$_6$, 500 MHz) δ 10.86 (brs, 1H), 7.3 (d, 2H, J = 8.3 Hz), 7.23 (d, 2H, J = 8.1 Hz), 5.7 (brs, 2H), 3.83 (brs, 2H), 2.66 2.55 (m, 7H), 2.17-2.13 (m, 2H), 1.6-1.55 (m, 2H), 1.54-1.49 (m, 1H), 1.39-1.29 (m, 2H), 0.77 (d, 6H, J = 6.6 Hz). ESI MS for $C_{19}H_{29}ClN_6$ expected 376.2 found m/z 377.5/379.5 [M + H]. |
| 93 | ·2HCl | 1-(3-amino-1H-1,2,4-triazol-5-yl)-N-(4-chlorophenethyl)-N-(3,3-dimethylbutyl)piperidin-4-amine | A | $^1$H NMR (DMSO-d$_6$, 600 MHz) δ 7.4-7.32 (m, 4H), 3.98-3.87 (m, 2H), 3.61-3.51 (m, 2H), 3.34-3.25 (m, 1H), 3.19-3.05 (m, 4H), 3.04-2.92 (m, 2H), 2.18-2.08 (m, 2H), 1.86-1.73 (m, 2H), 1.72-1.63 (m, 2H), 0.88 (s, 9H). ESI MS for $C_{21}H_{33}ClN_6$ expected 404.3; found m/z 405.5/407.5 [M + H], 403.4 (M − H). |
| 94 | ·2HCl | 1-(3-amino-1H-1,2,4-triazol-5-yl)-N-(4-chlorophenethyl)-N-neopentyl-piperidin-4-amine dihydrochloride | A | $^1$H NMR (DMSO-d$_6$, 500 MHz) δ 9.88 (brs, 1H), 7.37 (d, 2H, J = 8.5 Hz), 7.33 (d, 2H, J = 8.3 Hz), 3.95 (brs, 2H), 3.63-3.55 (m, 1H), 3.4-3.35 (m, 1H), 3.35-3.30 (m, 1H), 3.29-3.24 (m, 1H), 3.2-3.13 (m, 2H), 3.02 (brs, 2H), 2.79 (dd, 1H, J = 4.5 Hz, J = 13.9 Hz), 2.2 (dd, 1H, J = 11.8 Hz, J = 28.8 Hz), 1.92-1.86 (m, 1H), 1.74-1.66 (m, 1H), 1.08 (s, 9H). ESI MS for C20H31ClN6 expected 390.23; found m/z 391.5/393.5 [M + H], 389.4 (M − H). |
| 95 | 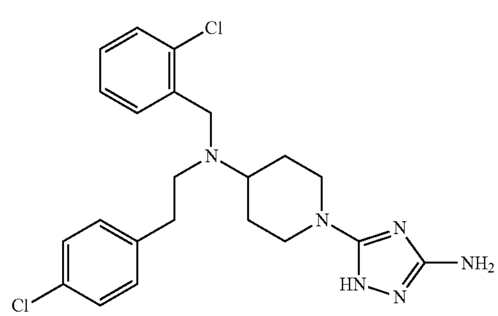 [SMILES: Nc1n[nH]c(N2CCC(N(CCc3ccc(Cl)cc3)Cc3ccccc3Cl)CC2)n1] | 1-(3-amino-1H-1,2,4-triazol-5-yl)-N-(2-chlorobenzyl)-N-(4-chlorophenethyl)piperidin-4-amine | A | $^1$H NMR (DMSO-d$_6$, 500 MHz) δ 11.07 (brs, 1H), 8.02 (brs, 1H), 7.6-7.53 (m, 1H), 7.5-7.4 (m, 2H), 7.33 (d, 2H, J = 7.9 Hz), 7.18 (d, 2H, J = 8.2 Hz), 4.68-4.6 (m, 1H), 4.42 (brs, 1H), 3.94 (brs, 1H), 3.65 (brs, 1H), 3.33 (brs, 1H), 3.2-3.1 (m, 2H), 3.04-2.9 (m, 3H), 2.25 (brs, 2H), 2.01-1.86 (m, 2H). ESI MS for $C_{22}H_{26}Cl_2N_6$ expected 444.2; found m/z 445.4/447.4 [M + H], 443.1/445.4 (M − H). |

TABLE 1-continued

| Example | Structure | IUPAC Name | Activity | Analytical Data |
|---|---|---|---|---|
| 96 | 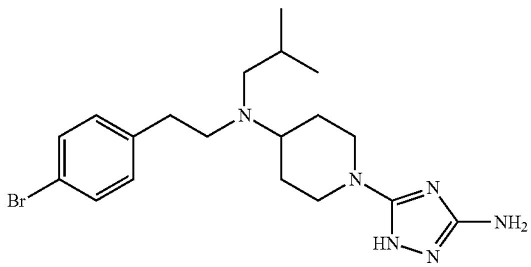 | 1-(3-amino-1H-1,2,4-triazol-5-yl)-N-(4-bromophenethyl)-N-isobutylpiperidin-4-amine | A | $^1$H NMR (DMSO-d$_6$, 500 MHz) δ 10.59 (brs, 1H), 7.385 (dm 2H, J = 8.1 Hz), 7.135 (d, 2H, J = 8.1 Hz), 5.32 (brs, 2H), 3.87-3.8 (m, 2H), 2.66-2.54 (m, 7H), 2.18 (d, 2H, J = 7.1 Hz), 1.6 1.52 (m, 3H), 1.41-1.32 (m, 2H), 0.78 (d, 6H, J = 6.4 Hz) ESI MS found m/z 421.5/423.5[M + H], 419.5/421.4 (M − H). |
| 98 | 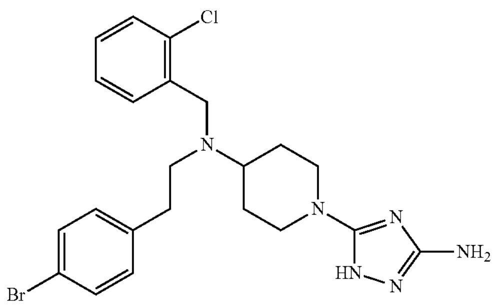 | 1-(3-amino-1H-1,2,4-triazol-5-yl)-N-(4-bromophenethyl)-N-(2-chlorobenzyl)piperidin-4-amine | A | $^1$H NMR (DMSO-d$_6$, 600 MHz) δ 7.44-7.39 (m, 1H), 7.33-7.29 (M, 1H), 7.24-7.16 (m, 2H), 7.21 (J$_{AA'BB'}$, 4H), 3.87-3.79 (m, 2H), 3.75 (J$_{AB}$, 2H), 2.77-2.69 (m, 2H), 2.69-2.62 (m, 1H), 2.62-2.54 (m, 4H), 1.71-1.63 (m, 2H), 1.51-1.40 (m, 2H). ESI MS for C$_{22}$H$_{26}$BrClN$_6$; expected 488.1; found m/z 489.5/491.4 [M + H]. |
| 99 | 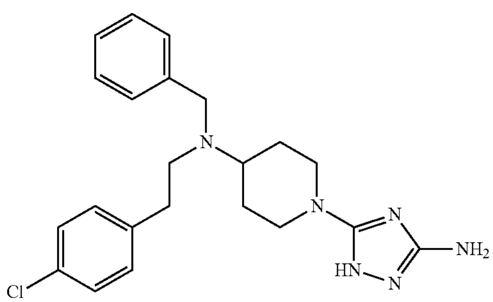 [SMILES: Nc1n[nH]c(N2CCC(N(CCc3ccc(Cl)cc3)Cc3ccccc3)CC2)n1] | 1-(3-amino-1H-1,2,4-triazol-5-yl)-N-benzyl-N-(4-chlorophenethyl)piperidin-4-amine | A | $^1$H NMR (DMSO-d$_6$, 600 MHz) δ 10.87 (brs, 1H), 7.3-7.23 (m, 6H), 7.2 (brs, 1H), 7.14 (d, 2H), 5.7 (brs, 2H), 3.87-3.78 (m, 2H), 3.66 (s, 2H), 2.67-2.6 (m, 7H), 1.68-1.63 (m, 2H), 1.48-1.4 (m, 2H). ESI MS for C$_{22}$H$_{27}$ClN$_6$ expected 410.2; found m/z 411.6 [M + H], 409.4 (M − H). |
| 100 | 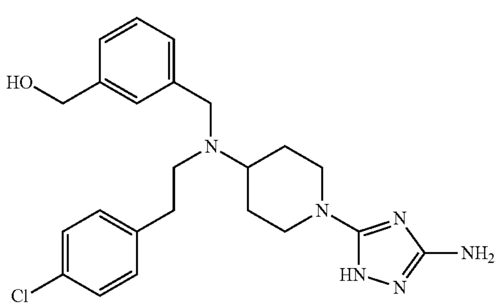 [SMILES: Nc1n[nH]c(N2CCC(N(CCc3ccc(Cl)cc3)Cc3cccc(CO)c3)CC2)n1] | (3-(((1-(3-amino-1H-1,2,4-triazol-5-yl)piperidin-4-yl)(4-chlorophenethyl)amino)methyl)phenyl)methanol | A | $^1$H NMR (DMSO-d$_6$, 600 MHz) δ 7.25-7.20 (m, 2H), 7.19-7.14 (m, 2H), 7.12-7.05 (m, 4H), 4.40 (d, 2H, J = 5.8 Hz), 3.82-3.85 (m, 2H), 3.60 (s, 2H), 2.64-2.54 (m, 6H), 1.64-1.57 (m, 2H), 1.45-1.32 (m, 2H). ESI MS for C$_{23}$H$_{29}$ClN$_6$O; expected 440.2; found m/z 441.4/443.4 [M + H]. |
| 101 | 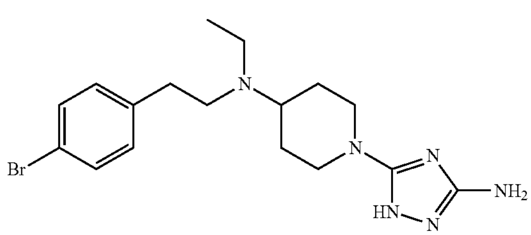 | 1-(3-amino-1H-1,2,4-triazol-5-yl)-N-(4-bromophenethyl)-N-ethylpiperidin-4-amine | A | $^1$H NMR (DMSO-d$_6$, 500 MHz) δ 10.85 (brs, 1H), 7.42 (d, 2H, J = 8.1 Hz), 7.17 (d, 2H, J = 8.3 Hz), 5.68 (brs, 2H), 3.83-3.74 (m, 2H), 2.56 (brs, 2H), 2.51 (q, 2H), 2.5-2.48 (m, 5H), 1.61-1.55 (m, 2H), 1.38-1.29 (m, 2H), 0.914 (t, 3H, J = 7.1 Hz) ESI MS for C$_{17}$H$_{25}$ClN$_6$ expected 392.1; found m/z 393.4/395.5 [M + H], 391.2 (M − H). |

TABLE 1-continued

| Example | Structure | IUPAC Name | Activity | Analytical Data |
|---|---|---|---|---|
| 102 | 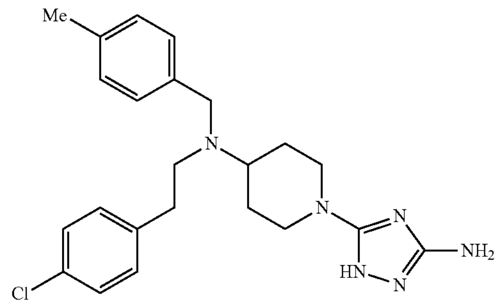 | 1-(3-amino-1H-1,2,4-triazol-5-yl)-N-(4-chlorophenethyl)-N-(4-methylbenzyl)piperidin-4-amine | A | $^1$H NMR (DMSO-$d_6$, 600 MHz) δ 10.72 (bs, 1H), 7.57-7.52 (m, 2H), 7.33 (d, 2H, J = 8.3 Hz), 7.23 (d, 2H, J = 7.7 Hz), 7.15 (d, 2H, J = 8.3 Hz), 4.48-4.41 (m, 1H), 4.28-4.20 (m, 1H), 3.93-3.84 (m, 2H), 3.11-3.01 (m, 2H), 2.97-2.80 (m, 3H), 2.29 (s, 3H), 2.24-2.14 (m, 2H), 1.93-1.79 (m, 2H). ESI MS for $C_{23}H_{29}ClN_6$; expected 424.2; found m/z 425.5/427.5 [M + H] |
| 103 | ·2HCl | (S)-1-(3-amino-1H-1,2,4-triazol-5-yl)-N-(4-chlorophenethyl)-N-(1-phenylethyl)piperidin-4-amine | B | $^1$H NMR (DMSO-$d_6$, 600 MHz): two conformers δ 11.09a, 10.66b (bs, 1H), 7.99-7.91a, 7.88 7.81b (m, 2H), 7.49-7.40 (m, 3H), 7.23a, 6.94b (AA'BB', 4H), 4.90-4.82a, 4.64-4.56b (m, 1H), 4.01-3.77 (m, 2H), 3.23-3.00 (m, 2H), 2.98-2.63 (m, 2H), 2.59-2.52a, 2.39-2.27b (m, 1H), 2.23 2.14a (m, 1H) 2.10-2.00 (m, 1H), 1.98-1.88 (m, 1H), 1.88-1.79b (m, 1H), 1.75a, 1.71b (d, 3H, J = 6.6 Hz), ESI MS for $C_{23}H_{29}ClN_6$; expected 424.2; found m/z 425.5/427.5 [M + H]. |
| 104 | 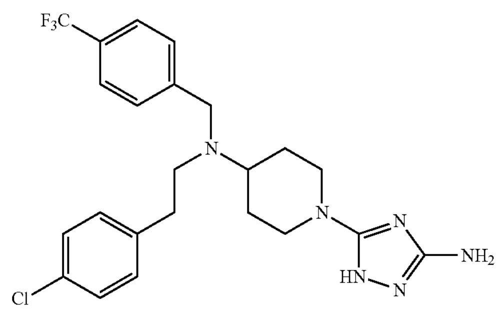 | 1-(3-amino-1H-1,2,4-triazol-5-yl)-N-(4-chlorophenethyl)-N-(4-(trifluoromethyl)benzyl)piperidin-4-amine | A | $^1$H NMR (DMSO-$d_6$, 600 MHz): δ 11.63 (brs, 1H), 8.01-7.97 (m, 2H), 7.81-7.78 (m, 2H), 7.33 (d, 2H, J = 8.3 Hz), 7.16 (d, 2H, J = 8.3 Hz), 4.6 (brs, 1H), 4.44 (brs, 1H), 3.96-3.9 (m, 2H), 3.3-3.2 (m, 2H), 3.2-3.0 (m, 2H), 3.0-2.88 (m, 3H), 2.3-2.22 (m, 2H), 1.95-1.86 (m, 2H). $^{19}$F-NMR (DMSO-$d_6$, 200 MHz): δ −60.53. ESI MS for $C_{23}H_{26}ClF_3N_6$ expected 478.2; found m/z 479.5/481.5 [M + H], 477.5/479.7 (M − H). |
| 105 | 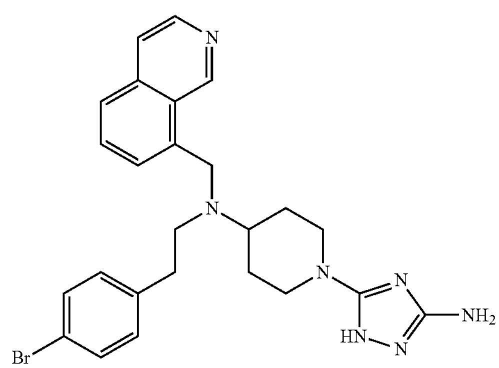 | 1-(3-amino-1H-1,2,4-triazol-5-yl)-N-(4-bromophenethyl)-N-(isoquinolin-8-ylmethyl)piperidin-4-amine | A | $^1$H NMR (DMSO-$d_6$, 500 MHz): 10.89 (brs, 1H), 9.59 (s, 1H), 8.46 (d, J = 5.6 Hz, 1H), 7.81 (d, J = 8.1 Hz, 1H), 7.76 (d, J = 5.6 Hz, 1H), 7.66-7.60 (m, 1H), 7.58 (d, J = 6.9 Hz, 1H), 7.23 (d, J = 8.2 Hz, 2H), 6.88 (d, J = 8.2 Hz, 2H), 4.19 (s, 2H), 3.86 (brs, 2H), 2.73 (brs, 1H), 2.71-2.67 (m, 2H), 1.76 (d, J = 11.3 Hz, 2H), 1.63-1.54 (m, 2H), 1.22 (brs, 2H), 0.86 0.82 (m, 2H). ESI-MS m/z for $C_{25}H_{28}BrN_7$ expected 505.2; found 506.9/507.9 [M + H]. |
| 106 | 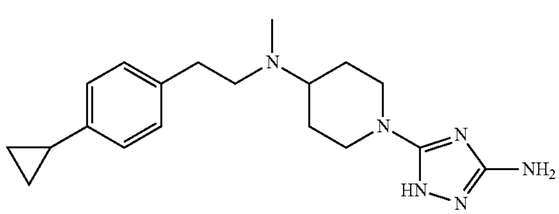 | 1-(3-amino-1H-1,2,4-triazol-5-yl)-N-(4-cyclopropylphenethyl)-N-methylpiperidin-4-amine | C | $^1$H NMR (DMSO-$d_6$, 500 MHz): 510.89 (bs, 1H), 7.04 ($J_{AA'BB'}$, 2H, J = 7.9 Hz), 6.92 ($J_{AA'BB'}$, 2H, J = 7.9 Hz), 5.50 (bs, 1H), 3.81-3.72 (m, 2H), 2.66-2.51 (m, 6H), 2.50-2.43 (m, 1H), 2.27-2.15 (m, 3H), 1.85-1.76 (m, 1H), 1.66-1.57 (m, 2H), 1.42-1.29 (m, 2H), 0.89-0.82 (m, 2H), 0.59-0.53 (m, 2H). ESI MS calculated for |

TABLE 1-continued

| Example | Structure | IUPAC Name | Activity | Analytical Data |
|---|---|---|---|---|
| | | | | $C_{19}H_{26}N_6$ expected 340.3; found m/z 341.4 [M + H]. |
| 107 | 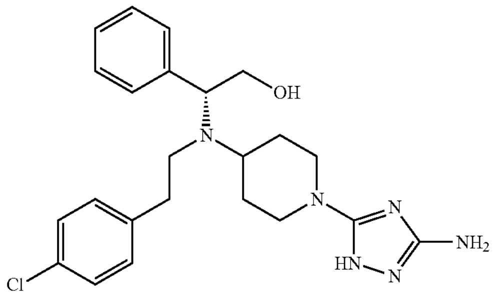 [SMILES: Nc1n[nH]c(N2CCC(N(CCc3ccc(Cl)cc3)[C@@H](CO)c3ccccc3)CC2)n1] | (R)-2-((1-(3-amino-1H-1,2,4-triazol-5-yl)piperidin-4-yl)(4-chlorophenethyl)amino)-2-phenylethan-1-ol | B | $^1$H NMR (DMSO-d$_6$, 600 MHz): two conformers δ 10.92a, 10.61b (bs, 1H), 7.94-7.78 (m, 2H), 7.47-7.40 (m, 3H), 7.37-7.25 (m, 2H), 7.23-7.16 (m, 1H), 6.76-6.68 (m, 1H), 4.77-4.60 (m, 1H), 4.48-4.29 (m, 1H), 4.11-3.92 (m, 2H), 3.91-3.71 (m, 1H), 3.56-3.26 (m, 2H), 3.20-3.09 (m, 1H), 3.08-2.97 (m, 1H), 2.95-2.84 (m, 1H), 2.79-2.20 (m, 1H), 2.63-2.51 (m, 1H), 2.39-2.18 (m, 2H), 2.04-1.55 (m, 2H). ESI MS for $C_{23}H_{29}ClN_6O$; expected 440.2; found m/z 441.5/443.5 [M + H]. |
| 108 | 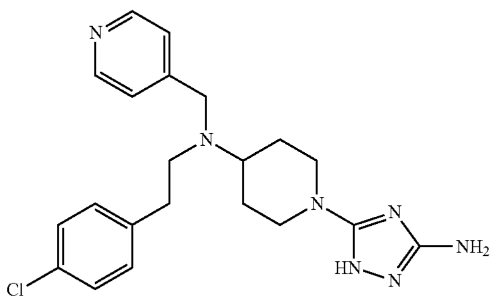 [SMILES: Nc1n[nH]c(N2CCC(N(CCc3ccc(Cl)cc3)Cc3ccncc3)CC2)n1] | 1-(3-amino-1H-1,2,4-triazol-5-yl)-N-(4-chlorophenethyl)-N-(pyridin-4-ylmethyl)piperidin-4-amine | A | $^1$H NMR (DMSO-d$_6$, 600 MHz): δ 8.41-8.38 (m, 2H), 7.27 (d, 2H, J = 8.3 Hz), 7.23-7.19 (m, 2H), 7.14 (d, 2H, J = 8.3 Hz), 5.49 (brs, 2H), 3.85-3.78 (m, 2H), 3.67 (s, 2H), 2.67-2.6 (m, 5H), 2.58-2.51 (m, 2H), 1.67-1.61 (m, 2H), 1.46-1.35 (m, 2H). ESI MS for $C_{21}H_{26}ClN_7$ expected 411.2; found m/z 412.5/414.5 [M + H], 410.5/412.5 (M − H) |
| 109 | 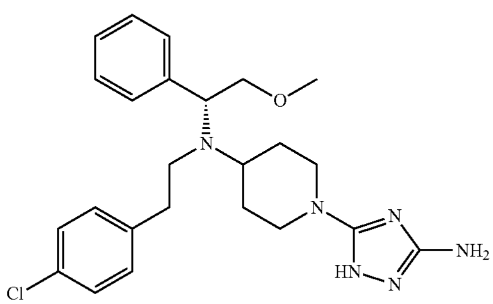 [SMILES: COC[C@@H](c1ccccc1)N(CCc1ccc(Cl)cc1)C1CCN(c2nc(N)n[nH]2)CC1] | (R)-1-(3-amino-1H-1,2,4-triazol-5-yl)-N-(4-chlorophenethyl)-N-(2-methoxy-1-pheny)ethyl)piperidin-4-amine | D | $^1$H NMR (DMSO-d$_6$, 500 MHz): δ 10.81 (bs, 1H), 7.32-7.28 (m, 2H), 7.27-7.22 (m, 4H), 7.20-7.16 (m, 1H), 7.12-7.07 (m, 2H), 5.64 (bs, 1H), 4.04-4.00 (m, 1H), 3.78-3.71 (m, 1H), 3.69-3.59 (m, 3H), 3.20 (s, 3H), 2.74-2.68 (m, 2H), 2.67-2.59 (m, 1H), 2.58-2.50 (m, 3H), 1.52-1.47 (m, 1H), 1.46-1.39 (m, 1H), 1.36-1.27 (m, 1H), 1.25-1.17 (m, 1H). ESI MS for $C_{24}H_{31}ClN_6O$ expected 454.2; found m/z 455.5/457.5 |
| 110 | ·2HCl | 1-(3-amino-1H-1,2,4-triazol-5-yl)-N-(3-chlorobenzyl)-N-(4-chlorophenethyl)piperidin-4-amine dihydrochloride | A | $^1$H NMR (DMSO-d$_6$, 600 MHz): δ 11.54 (bs, 1H), 7.92 (s, 1H), 7.75-7.70 (m, 1H), 7.50-7.42 (m, 2H), 7.32 (d, 2H, J = 8.4 Hz), 7.15 (d, 2H, J = 8.4 Hz), 4.54-4.48 (m, 1H), 4.35-4.28 (m, 1H), 3.97-3.90 (m, 2H), 3.25-3.16 (m, 1H), 3.15-3.03 (m, 2H), 3.02-2.91 (m, 2H), 2.89-2.82 (m, 1H), 2.26 (bs, 2H), 1.95-1.82 (m, 2H). ESI MS $C_{22}H_{26}Cl_2N_6$ expected 444.2/446.2/448.2; found m/z 445.4/447.5 [M + H] |

TABLE 1-continued

| Example | Structure | IUPAC Name | Activity | Analytical Data |
|---|---|---|---|---|
| 111 | 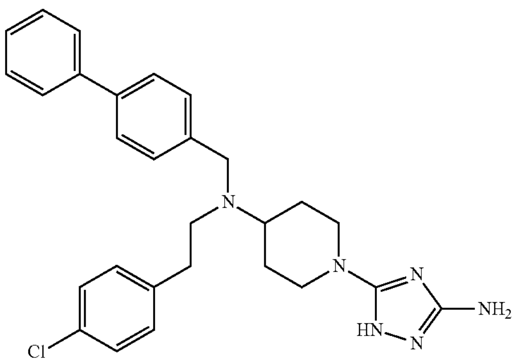 [SMILES: Nc1n[nH]c(N2CCC(N(CCc3ccc(Cl)cc3)Cc3ccc(-c4ccccc4)cc3)CC2)n1] | N-([1,1'-biphenyl]-4-ylmethyl)-1-(3-amino-1H-1,2,4-triazol-5-yl)-N-(4-chlorophenethyl)piperidin-4-amine | A | $^1$H NMR (DMSO-d$_6$, 600 MHz): δ 10.86 (brs, 1H), 7.64 (d, 2H), 7.57-7.51 (m, 2H), 7.46-7.42 (m, 2H), 7.35-7.3 (m, 3H), 7.21 (AA'BB', 4H), 3.86 3.79 (m, 2H), 3.7-3.66 (m, 2H), 2.7-2.61 (m, 5H), 2.59-2.51 (m, 2H), 1.7-1.62 (m, 2H), 1.49-1.4 (m, 2H). ESI MS for C$_{28}$H$_{31}$ClN$_6$ expected 486.2; found m/z 487.6 [M + H], 485.5 (M − H) |
| 112 | 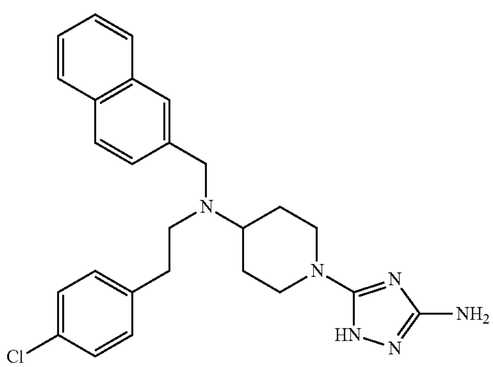 [SMILES: Nc1n[nH]c(N2CCC(N(CCc3ccc(Cl)cc3)Cc3ccc4ccccc4c3)CC2)n1] | 1-(3-amino-1H-1,2,4-triazol-5-yl)-N-(4-chlorophenethyl)-N-(naphthalen-2-ylmethyl)piperidin-4-amine | A | $^1$H NMR (DMSO-d$_6$, 600 MHz): δ 11.2 (brs, 1H), 8.21 (s, 1H), 8.00-7.85 (m, 4H), 7.56-7.53 (m, 2H), 7.28 (d, 2H, J = 7.15 Hz), 7.13 (d, 2H, J = 7.15 Hz), 4.72-4.64 (m, 1H), 4.48 (m, 1H), 3.95-3.86 (m, 2H), 3.28-3.2 (m, 1H), 3.2-3.1 (m, 2H), 3.0-2.88 (m, 3H), 2.32-2.25 (m, 2H), 1.98-1.88 (m, 2H) ESI MS for C$_{26}$H$_{29}$ClN$_6$ expected 460.2/462.2; found m/z 461.6/463.6 [M + H], 459.5/461.4 (M − H) |
| 113 | 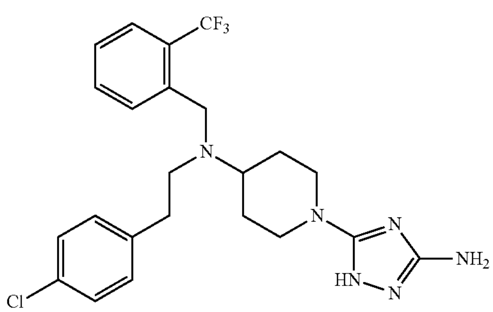 | 1-(3-amino-1H-1,2,4-triazol-5-yl)-N-(4-chlorophenethyl)-N-(2-(trifluoromethyl)benzyl)piperidin-4-amine | A | $^1$H NMR (DMSO-d$_6$, 600 MHz): δ 11.66 (bs, 1H), 8.57-8.48 (m, 1H), 7.86-7.72 (m, 2H), 7.68-7.59 (m, 1H), 7.22 (AA'BB, 4H), 4.77-4.66 (m, 1H), 4.43-4.31 (m, 1H), 4.01-3.89 (m, 2H), 3.86-3.64 (m, 2H), 3.43-3.30 (m, 1H), 3.27-3.14 (m, 1H), 3.10-2.87 (m, 4H), 2.34-2.20 (m, 1H), 2.01-1.83 (m, 1H). $^{19}$F NMR (DMSO-d$_6$, 200 MHz) δ −55.37 ESI MS for C$_{23}$H$_{26}$ClF$_3$N$_6$; expected 478.95; found m/z 479.5/481.5 [M + H] |
| 114 | 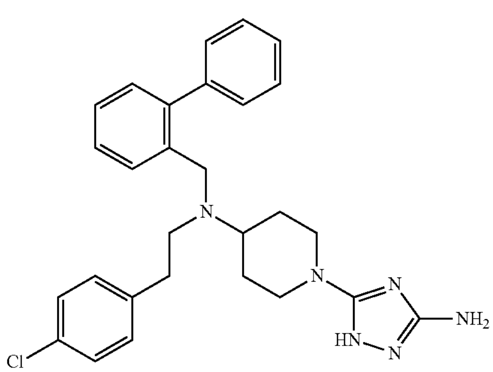 [SMILES: Nc1n[nH]c(N2CCC(N(CCc3ccc(Cl)cc3)Cc3ccccc3-c3ccccc3)CC2)n1] | N-([1,1'-biphenyl]-2-ylmethyl)-1-(3-amino-1H-1,2,4-triazol-5-yl)-N-(4-chlorophenethyl)piperidin-4-amine | A | $^1$H NMR (DMSO-d$_6$, 600 MHz): δ 11.01 (brs, 1H), 8.21-8.16 (m, 1H), 7.55-7.5 (m, 2H), 7.5-7.46 (m, 2H), 7.46-7.42 (m, 1H), 7.39-7.32 (m, 5H), 7.17-7.12 (m, 2H), 4.55-4.48 (m, 1H), 4.46-4.4 (m, 1H), 3.85-3.77 (m, 1H), 3.74-3.67 (m, 1H), 3.31-3.24 (m, 1H), 3.1-2.98 (m, 3H), 2.97-2.9 (m, 1H), 2.9-2.83 (m, 1H), 2.78-2.7 (m, 1H), 2.13-2.06 (m, 1H), 1.71-1.6 (m, 1H), 1.58-1.49 (m, 1H), 1.44-1.38 (m, 1H), ESI MS found m/z 487.6/489.5 [M + H], 485.5/487.6 [M − H]. |

TABLE 1-continued

| Example | Structure | IUPAC Name | Activity | Analytical Data |
|---|---|---|---|---|
| 115 | 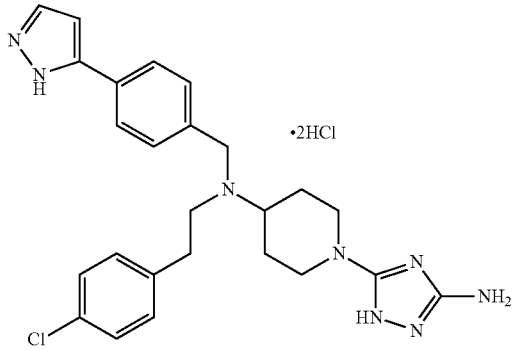 [SMILES: Nc1n[nH]c(N2CCC(N(CCc3ccc(Cl)cc3)Cc3ccc(-c4ccn[nH]4)cc3)CC2)n1] | N-(4-(1H-pyrazol-5-yl)benzyl)-1-(3-amino-1H-1,2,4-triazol-5-yl)-N-(4-chlorophenethyl)piperidin-4-amine dihydrochloride | A | |
| 116 | 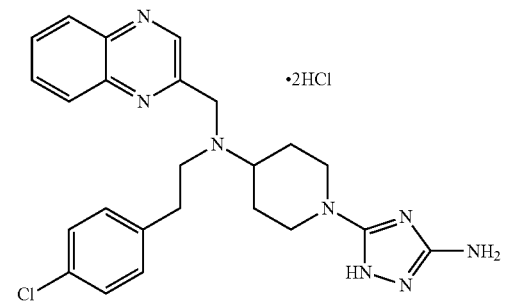 [SMILES: Nc1n[nH]c(N2CCC(N(CCc3ccc(Cl)cc3)Cc3cnc4ccccc4n3)CC2)n1] | 1-(3-amino-1H-1,2,4-triazol-5-yl)-N-(4-chlorophenethyl)-N-(quinoxalin-2-ylmethyl)piperidin-4-amine dihydrochloride | B | $^1$H NMR (D$_2$O, 500 MHz): δ 8.78 (s, 1H); 8.10-8.12 (m, 1H); 8.01-8.03 (m, 1H); 7.91-7.95 (m, 2H); 7.12 (d, 2H, J$_{AA'BB'}$ = 8.5 Hz); 7.03 (d, 2H, J$_{AA'BB'}$ = 8.5 Hz); 4.92 (brs, 2H); 3.90-394 (m, 1H); 3.85 (brd, 2H, J = 12.8 Hz); 3.75 (t, 2H, J = 7.4 Hz); 3.05-3.13 (m, 4H); 2.26 (d, 2H, J = 11.7 Hz); 1.95-1.98 (m, 2H). LC/MS: RT = 3.21 min; ES(+): M + H = 463.3/465.3; ES(−): M − 1 = 461.3/463.3; M+HCOO− = 507.5/509.1 |
| 117 | 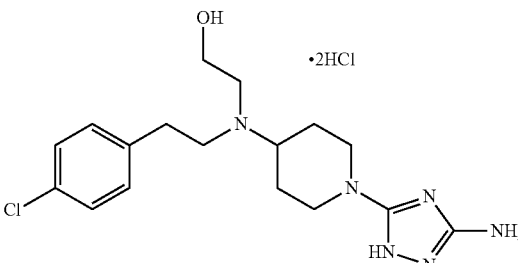 | 2-((1-(3-amino-1H-1,2,4-triazol-5-yl)piperidin-4-yl)(4-chlorophenethyl)amino)ethan-1-ol | B | $^1$H NMR (DMSO-d$_6$, 500 MHz): δ: 10.45 (brs, 1H), 7.37 (d, JAB = 8.2 Hz, 2H), 7.33 (d, JAB = 8.2 Hz, 2H), 3.94-3.89 (m, 2H), 3.80 (brs, 2H), 3.65 (brs, 2H), 3.39-3.22 (m, 2H), 3.21-3.09 (m, 2H), 2.21-2.05 (m, 2H), 1.83 1.72 (m, 2H) ESI-MS for C$_{17}$H$_{25}$ClN$_6$O: expected 364.88, found 364.7/366.7 [M + H] |
| 118 | 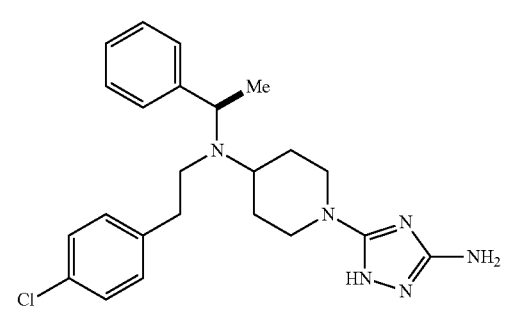 [SMILES: C[C@H](c1ccccc1)N(CCc1ccc(Cl)cc1)C1CCN(c2nc(N)n[nH]2)CC1] | (R)-1-(3-amino-1H-1,2,4-triazol-5-yl)-N-(4-chlorophenethyl)-N-(1-phenylethyl)piperidin-4-amine | A | $^1$H NMR (DMSO-d$_6$, 600 MHz): δ two conformers 10.95, 10.47 (brs, 1H), 7.98-7.94, 7.87-7.84 (m, 2H), 7.52-7.46 (m, 3H), 7.37 7.34,7.25-7.22 (m, 2H), 7.15-7.18, 6.75-6.71 (m, 2H), 4.94-4.87, 4.67-4.6 (m, 1H), 4.0-3.86 (m, 2H), 3.85-3.8,3.5-3.43 (m, 1H), 3.42-3.32 (m, 1H), 3.26-3.14 (m, 1H), 3.13-3.02 (m, 1H), 3.02-2.95,2.9-2.83 (m, 1H), 2.81-2.73 (m, 1H), 2.7-2.61, 2.57-2.5 (m, 1H), 2.35-2.3, 2.23-2.17 (m, 1H), 2.11-2.02 (m, 1H), 2.0-1.92 (m, 1H), 1.87-1.8 (m, 1H), 1.77, 1.73 (d, 3H, J = 6.6 Hz) ESI MS found m/z 425.5/427.5 [M + H], 423.2 [M − H] |

TABLE 1-continued

| Example | Structure | IUPAC Name | Activity | Analytical Data |
|---|---|---|---|---|
| 119 | 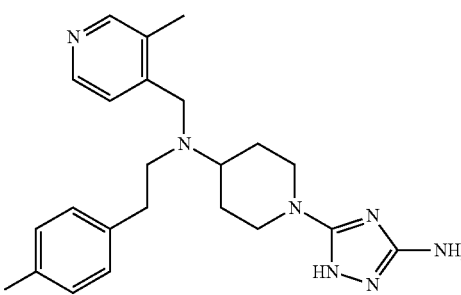 | 1-(3-amino-1H-1,2,4-triazol-5-yl)-N-(4-chlorophenethyl)-N-((3-fluoropyridin-4-yl)methyl)piperidin-4-amine | A | $^1$H NMR (DMSO-$d_6$, 500 MHz): δ 11.52 (bs, 1H), 8.68 (bs, 1H), 8.52 (bs, 1H), 7.99 (bs, 1H), 7.31 (AA'BB', 4H), 4.63 (bs, 1H), 4.45 (bs, 1H), 3.96-3.86 (m, 2H), 3.24-3.12 (m, 1H), 3.14 (s, 3H), 3.10-2.95 (m, 3H), 2.33-2.10 (m, 1H), 1.99-1.77 (m, 1H). ESI MS found m/z 430.5/432.5 |
| 120 | 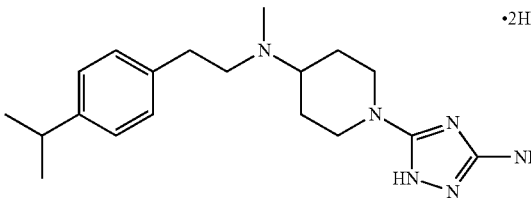 •2HCl | 1-(3-amino-1H-1,2,4-triazol-5-yl)-N-(4-isopropyl-phenethyl)-N-methylpiperidin-4-amine dihydrochloride | C | $^1$H NMR (DMSO-$d_6$, 500 MHz): δ 11.05 (brs, 1H), 7.22-7.13 (m, 4H), 3.95-3.89 (m, 2H), 3.19-3.09 (m, 2H), 3.07-2.96 (m, 3H), 2.95-2.87 (m, 2H), 2.86-2.77 (m, 1H), 2.69 (d, 3H, J = 4.1), 2.15-2.09 (m, 1H), 2.08-2.01 (m, 1H), 1.78-1.62 (m, 2H), 1.13 (d, 6H, J = 6.9 Hz) ESI MS found m/z 343.5 [M + H], 341.3 [M − H] |
| 121 | 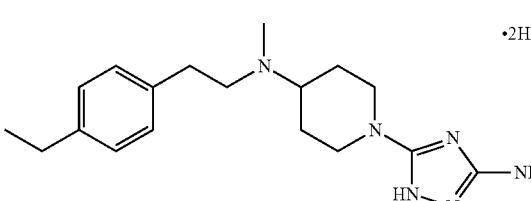 •2HCl | 1-(3-amino-1H-1,2,4-triazol-5-yl)-N-(4-ethylphenethyl)-N-methylpiperidin-4-amine dihydrochloride | D | $^1$H NMR (DMSO-$d_6$, 500 MHz): δ 11.21 (brs, 1H), 7.16 (brs, 1H), 7.13 (brs, 1H), 3.9 (brs, 2H), 3.47 (brs, 1H), 3.5 (brs, 1H), 3.14 (brs, 1H), 3.00-2.90 (m, 4H), 2.69 (s, 3H), 2.57-2.50 (m, 2H), 2.13 (brs, 1H), 2.04 (brs, 1H), 1.77-1.62 (m, 2H), 1.10 (brs, 3H) |
| 122 | 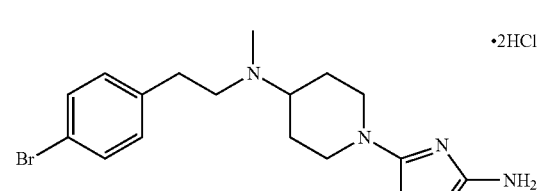 •2HCl | 1-(3-amino-1H-1,2,4-triazol-5-yl)-N-(4-bromophenethyl)-3-methylpiperidin-4-amine dihydrochloride | C | $^1$H NMR (DMSO-$d_6$, 600 MHz): δ 9.43 (brs, 1H), 9.1 (brs, 1H), 7.5-7.46 (m, 2H), 7.26-7.19 (m, 2H), 3.91-3.86 (m, 1H), 3.76 3.72 (m, 1H), 3.4-3.34 (m, 1H), 3.17-3.1 (m, 3H), 3.09-3.03 (m, 2H), 2.99-2.92 (m, 1H), 2.44-2.39 (m, 1H), 2.0-1.95 (m, 1H), 1.92 1.85 (m, 1H), 1.07 (d, J = 6.6 Hz), 1.03 (d, J = 7 Hz), 3H ESI-MS m/z for C16H23BrN6: expected 379.3, found 379.4/381.5 [M + H] |
| 123 | 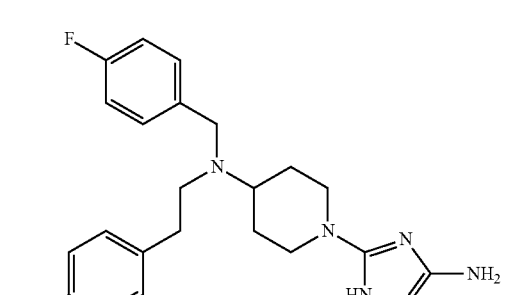 | 1-(3-amino-1H-1,2,4-triazol-5-yl)-N-(4-chlorophenethyl)-N-(4-fluorobenzyl)piperidin-4-amine | A | $^1$H NMR (DMSO-$d_6$, 600 MHz): δ 11.33 (brs, 1H), 7.82-7.77 (m, 2H) 7.33 (d, J = 8.3 Hz), 7.28-7.24 (m, 2H), 7.15 (d, 2H, J = 8.3 Hz), 4.51-4.46 (m, 1H), 4.3 (brs, 1H), 3.94-3.88 (m, 2H), 3.5 (brs, 1H), 3.2 (brs, 1H), 3.11-3.02 (m, 2H), 3.0-2.9 (m, 2H), 2.88-2.82 (m, 1H), 2.27-2.22 (m, 2H), 1.88 (brs, 2H). $^{19}$F NMR (DMSO-$d_6$, 200 MHz) δ −111.24 ESI MS found m/z 429.5/431.5 [M + H], 427.4/429.6 [M − H] |

TABLE 1-continued

| Example | Structure | IUPAC Name | Activity | Analytical Data |
|---|---|---|---|---|
| 125 | 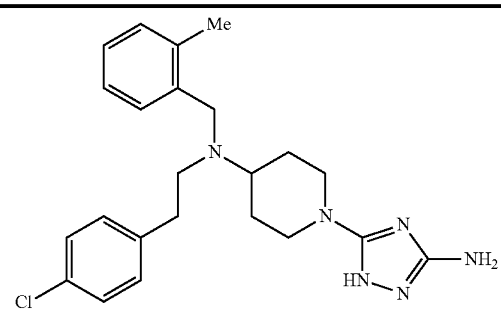 | 1-(3-amino-1H-1,2,4-triazol-5-yl)-N-(4-chlorophenethyl)-N-(2-methylbenzyl)piperidin-4-amine | A | $^1$H NMR (DMSO-$d_6$, 600 MHz):) δ 10.92 (bs, 1H), 7.69 (d, 1H, J = 7.5 Hz), 7.32 (d, 2H, J = 8.4 Hz), 7.29 (d, 1H, J = 7.5 Hz), 7.26-7.19 (m, 2H), 7.15 (d, 2H, 8.4 Hz), 4.56-4.50 (m, 1H), 4.20-4.13 (m, 1H), 4.03-3.93 (m, 2H), 3.72-3.64 (m, 1H), 3.37-3.29 (m, 1H), 3.20-3.12 (m, 1H), 3.09-2.97 (m, 3H), 2.96-2.88 (m, 1H), 2.43 (s, 3H), 2.36-2.30 (m, 1H), 2.30-2.24 (m, 1H), 2.08-1.98 (m, 1H), 1.95-1.85 (m, 1H). ESI MS found m/z 425.5/427.5 |
| 126 | 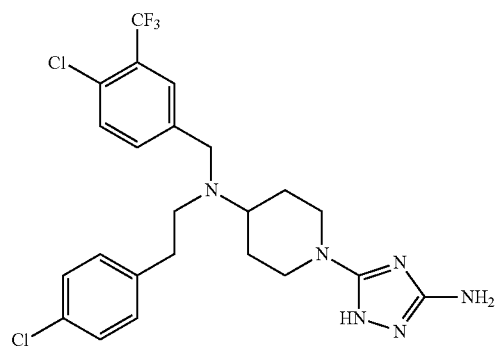 [SMILES: Nc1n[nH]c(N2CCC(N(CCc3ccc(Cl)cc3)Cc3ccc(Cl)c(C(F)(F)F)c3)CC2)n1] | 1-(3-amino-1H-1,2,4-triazol-5-yl)-N-(4-chloro-3-(trifluoromethyl)benzyl)-N-(4-chlorophenethyl)piperidin-4-amine | A | $^1$H NMR (DMSO-$d_6$, 600 MHz): δ 11.73 (brs, 1H), 8.33 (s, 1H), 8.12-8.07 (m, 1H), 7.81-7.77 (m, 1H), 7.32 (d, 2H, J = 8.3 Hz), 7.17 (d, 2H, J = 8.3 Hz), 4.62-4.56 (m, 1H), 4.46-4.41 (m, 1H), 3.93 (brs, 1H), 3.6-3.53 (m, 1H), 3.28-3.21 (m, 1H), 3.18-3.12 (m, 1H), 3.11-3.05 (m, 1H). 2.93-2.87 (m, 1H), 2.3-2.22 (m, 2H), 1.94-1.84 (m, 2H). $^{19}$F-NMR (DMSO-$d_6$, 200 MHz) δ −60.58. ESI MS found m/z 513.4/515.4 [M + H], 511.4/513.5 (M − 1). |
| 127 | 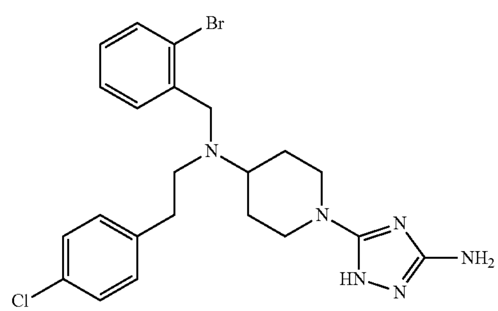 | 1-(3-amino-1H-1,2,4-triazol-5-yl)-N-(2-bromobenzyl)-N-(4-chlorophenethyl)piperidin-4-amine | A | $^1$H NMR (DMSO-$d_6$, 600 MHz): δ 8.08-8.0 (m, 1H), 7.5-7.46 (m, 1H), 7.4 7.35 (m, 1H), 7.35-7.3 (m, 1H), 7.25 (AA'BB', 4H), 4.68-4.6 (m, 1H), 4.48-4.40 (m, 1H), 4.0 3.9 (m, 2H), 3.68-3.6 (m, 2H), 3.36-3.28 (m, 1H), 3.2-3.12 (m, 1H), 3.04-2.88 (m, 3H), 2.32 2.24 (m, 2H), 2.02-1.88 (m, 2H). ESI MS found m/z 489.4/491.4 [M + H], 487.4/489.3 [M − H] |
| 128 | ·2HCl | 1-(3-amino-1H-1,2,4-triazol-5-yl)-N-(4-chlorophenethyl)-N-isopropyl-piperidin-4-amine | B | $^1$H NMR (DMSO-$d_6$, 500 MHz): δ 10.52 (brs, 1H), 7.4-7.36 (m, 4H), 3.94 (brs, 2H), 3.77-3.71 (m, 1H), 3.55 (brs, 1H), 3.31-3.23 (m, 2H), 3.13-3.05 (m, 2H), 3.05-2.98 (m, 2H), 2.16 (brs, 2H), 2.03-1.88 (m, 2H), 1.39 (d, 3H, J = 6.4 Hz), 1.26 (d, 3H, J = 6.4) ESI MS found m/z 363.5 [M + H] |
| 129 | 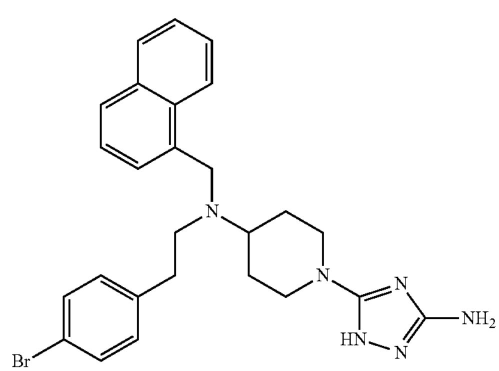 [SMILES: Nc1n[nH]c(N2CCC(N(CCc3ccc(Cl)cc3)Cc3cccc4ccccc34)CC2)n1] | 1-(3-amino-1H-1,2,4-triazol-5-yl)-N-(4-bromophenethyl)-N-(naphthalen-1-ylmethyl)piperidin-4-amine | A | $^1$H NMR (DMSO-$d_6$, 600 MHz): δ 8.27-8.14 (m, 1H), 7.93-7.82 (m, 1H), 7.82-7.71 (m, 1H), 7.58-7.36 (m, 4H), 7.13 (AA'BB', 4H). 4.15 (AB, 2H), 3.92-3.80 (m, 2H), 3.23-3.13 (m, 1H), 2.84-2.68 (m, 3H), 2.63-2.52 (m, 3H), 1.84-1.68 (m, 2H), 1.65-1.49 (m, 2H), 1.34-1.18 (m, 1H). ESI MS found m/z 505.5/507.5 |

TABLE 1-continued

| Example | Structure | IUPAC Name | Activity | Analytical Data |
|---|---|---|---|---|
| 130 | ·2HCl | 2-((1-(3-amino-1H-1,2,4-triazol-5-yl)piperidin-4-yl)(methyl)amino)-3-(4-chlorophenyl)propan-1-ol dihydrochloride | B | $^1$H NMR (DMSO-d$_6$, 500 MHz): d 7.38-7.33 (m, 4H), 3.97-3.87 (m, 2H), 3.67-3.57 (m, 3H), 3.46-3.35 (m, 1H), 3.17-3.11 (m, 1H), 3.01-2.90 (m, 3H), 2.78 (s, 3H), 2.18 (brs, 2H), 1.87 (brs, 2H) |
| 131 | ·3HCl | 1-(3-amino-1H-1,2,4-triazol-5-yl)-N-methyl-N-(2-(pyridin-3-yl)ethyl)piperidin-4-amine dihydrochloride | D | $^1$H NMR (DMSO-d$_6$, 500 MHz): d 11.52 (brs, 1H), 8.96 (s, 1H), 8.81 (d, J = 5.4 Hz, 1H), 8.59 (d, J = 8.1 Hz, 1H), 8.03 (dd, J = 8.1 Hz, J = 5.4 Hz, 1H), 3.99-3.94 (m, 2H), 3.54-3.40 (m, 2H), 3.37-3.27 (m, 3H), 3.00-2.94 (m, 2H), 2.72 (d, J = 4.7 Hz, 3H), 2.21-2.16 (m, 1H), 2.12-2.07 (m, 1H), 1.77-1.68 (m, 2H) |
| 132 | ·2HCl | 1-(3-amino-1H-1,2,4-triazol-5-yl)-N-(4-chlorophenethyl)-3-methylpiperidin-4-amine dihydrochloride (4:1 diastereoisomeric mixture) | B | $^1$H NMR (DMSO-d$_6$, 500 MHz): δ 9.57 (brs, 1H), 9.26 (brs, 1H), 7.36 (d, 2H, J = 8.3 Hz), 7.28 (d, 2H, J = 8.3 Hz), 3.9-3.83 (m, 1H), 3.75-3.7 (m, 1H), 3.39-3.32 (m, 1H), 3.15 3.02 (m, 5H), 2.95-2.87 (m, 1H), 2.43-2.37 (m, 1H), 1.98-1.93 (m, 1H), 1.86-1.77 (m, 1H), 0.98 (d, 3H, J = 6.8 Hz) ESI MS found m/z 337.4/335.4 [M + H], 333.1 [M − H] |
| 133 | 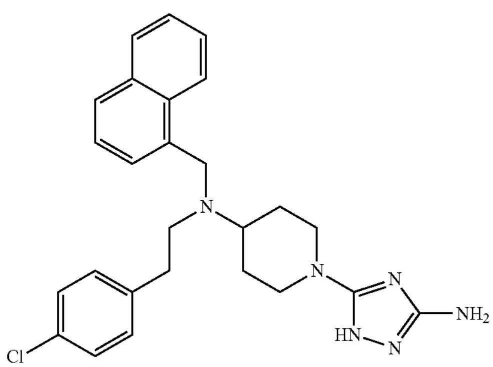 | 1-(3-amino-1H-1,2,4-triazol-5-yl)-N-(4-chlorophenethyl)-N-(naphthalen-1-ylmethyl)piperidin-4-amine | A | $^1$H NMR (DMSO-d$_6$, 500 MHz): 10.85 (brs, 1H), 8.29 (d, J = 8.4 Hz, 1H), 8.06 (d, J = 7.5 Hz, 1H), 8.04 (d, J = 8.0 Hz, 1H), 7.69-7.64 (m, 1H), 7.62 7.58 (m, 2H), 7.27 (d, J = 8.2 Hz, 2H), 7.00 (d, J = 8.2 Hz, 2H), 5.07-5.01 (m, 1H), 4.85-4.74 (m, 1H), 4.00 (brs, 1H), 3.73 (brs, 1H), 3.32 (brs, 2H), 3.13-3.09 (m, 2H), 3.00 (brs, 2H), 2.80-2.73 (m, 2H), 2.35 (brs, 2H), 2.10-2.00 (m, 2H) ESI-MS m/z for C$_{26}$H$_{29}$ClN$_6$ expected 461.0 found 461.2/463.1 [M + H]$^+$ |
| 134 | ·2HCl | 1-(3-amino-1H-1,2,4-triazol-5-yl)-N-(4-chlorobenzyl)-N-(4-chlorophenethyl)piperidin-4-amine | A | $^1$H NMR (DMSO-d$_6$, 600 MHz): δ 7.85-7.72 (m, 2H), 7.54-7.47 (m, 2H), 7.37-7.32 (m, 2H), 7.22-7.16 (m, 2H), 4.55-4-44 (m, 1H), 4.39-4.3 (m, 1H), 3.97-3.88 (m, 2H), 3.58-3.5 (m, 1H), 3.42-3.35 (m, 1H), 3.27-3.2 (m, 1H), 3.17-3.06 (m, 2H), 3.03-2.87 (m, 2H), 2.28-2.1 (m, 2H), 1.95-1.86 (m, 2H). ESI MS for C$_{22}$H$_{26}$Cl$_2$N$_6$ expected 444.4 found m/z 445.4/447.5 [M + H], 443.3/445.4 (M − 1) |

TABLE 1-continued

| Example | Structure | IUPAC Name | Activity | Analytical Data |
|---|---|---|---|---|
| 135 | 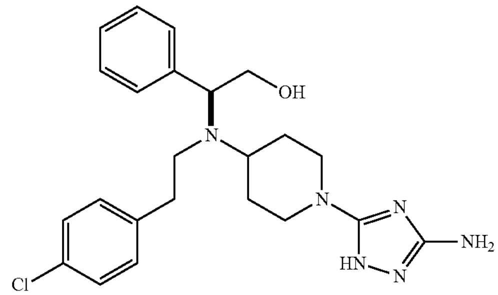 | (S)-2-((1-(3-amino-1H-1,2,4-triazol-5-yl)piperidin-4-yl)(4-chlorophenethyl)amino)-2-phenylethan-1-ol | A | $^1$H NMR (DMSO-d$_6$, 600 MHz: two conformers δ 10.82a, 10.47b (bs, 1H), 4.92-7.76 (m, 2H), 7.48-7.40 (m, 3H), 7.38-7.26 (m, 2H), 7.25 7.17 (m, 1H), 6.79-6.67 (m, 1H), 4.78-4.58 (m, 1H), 4.48-4.26 (m, 1H), 4.09-3.92 (m, 2H), 3.90-3.81 (m, 1H), 3.19-3.08 (m, 1H), 3.08-2.97 (m, 1H), 2.96-2.82 (m, 1H), 2.80-2.69 (m, 1H), 2.63-2.50 (m, 1H), 2.37-2.18 (m, 2H), 2.03-1.54 (m, 2H). ESI MS found m/z 441.5/443.5 |
| 136 | ·3HCl | N-((1H-benzo[d]imidazol-2-yl)methyl)-1-(3-amino-1H-1,2,4-triazol-5-yl)-N-methylpiperidin-4-aminetrihydrochloride | E | $^1$H NMR (DMSO-d$_6$, 500 MHz): d 7.72-7.69 (m, 2H), 7.37-7.34 (m, 2H), 4.66 (s, 2H), 3.96-3.90 (m, 2H), 3.52 (brs, 1H), 3.00-2.90 (m, 2H), 2.80 (s, 3H), 2.21 (brs, 2H), 1.81-1.75 (m, 2H) |
| 137 | ·2HCl | 1-(3-amino-1H-1,2,4-triazol-5-yl)-N-(4-chlorophenethyl)-N-(2-fluorobenzyl)piperidin-4-amine dihydrochloride | A | $^1$H NMR (DMSO-d$_6$, 600 MHz): δ 11.18 (brs, 1H), 7.92-7.88 (m, 1H), 7.55-7.50 (m, 1H), 7.35-7.28 (m, 2H), 7.3 (AA'BB', 4H), 4.62-4.56 (m, 1H), 4.39-4.33 (m, 1H), 4.0-3.93 (m, 2H), 3.66-3.58 (m, 3H), 3.34-3.28 (m, 1H), 3.05-2.95 (m, 3H), 2.32-2.2 (m, 2H), 1.98-1.88 (m, 2H) $^{19}$F NMR (DMSO-d$_6$, 200 MHz) δ −113.81. ESI MS for expected C$_{22}$H$_{26}$ClFN$_6$ 428.9; found m/z 429.5/431.5 [M + H], 427.4/429.5 [M − 1] |
| 138 | ·2HCl | 1-(3-amino-1H-1,2,4-triazol-5-yl)-N-(4-chlorophenethyl)-N-methylpiperidin-4-amine dihydrochloride | B | $^1$H NMR (DMSO-d$_6$, 600 MHz): δ 11.18 (brs, 1H), 7.39 (d, 2H, J = 8.5 Hz), 7.34 (d, 2H, J = 8.5 Hz), 3.94 (brs, 2H), 3.28-3.35 (m, 2H), 3.23-3.16 (m, 1H), 3.14-3.04 (m, 2H), 2.97 (brs, 2H), 2.73 (d, 3H, J = 5 Hz), 2.19-2.14 (m, 1H), 2.11-2.06 (m, 1H), 1.8-1.67 (m, 2H). ESI MS for C$_{16}$H$_{23}$ClN$_6$ expected 334.2 found m/z 335.5/337.5 [M + H], 333.3/335.3 [M − 1]. |
| 139 | ·2HCl | (R)-1-(3-amino-1H-1,2,4-triazol-5-yl)-N-(1-(4-chlorophenyl)propan-2-yl)-N-methylpiperidin-4-amine dihydrochloride | C | $^1$H NMR (DMSO-d$_6$, 500 MHz): δ {[10.98 (rotamer A, brs), 10.80 (rotamer B, brs)], 1H}, 7.40 (d, J = 8.3 Hz, 2H), 7.36-7.32 (m, 2H), 3.97 3.86 (m, 2H), 3.66 (brs, 2H), 3.42 (brs, 2H), 3.04-2.87 (m, 2H), {(2.70 (rotamer B, d, J = 4.8 Hz), 2.68 (rotamer A, d, J = 4.8 Hz)], 3H}, 2.35-2.07 (m, 2H), 1.92-1.82 (m, 2H), {[1.18 (rotamer B, d, J = 6.4 Hz), 1.06 (rotamer A, d, J = 6.4 Hz)], 3H) ESI-MS m/z for C$_{17}$H$_{25}$ClN$_6$, expected 348.9, found 349.1/351.1 [M + H]+ |

TABLE 1-continued

| Example | Structure | IUPAC Name | Activity | Analytical Data |
|---|---|---|---|---|
| 140 | •2HCl | 1-(3-amino-1H-1,2,4-triazol-5-yl)-N-(2-(4-chlorophenyl)propyl)-N-methylpiperidin-4-amine dihydrochloride | D | $^1$H NMR (DMSO-$d_6$, 500 MHz): δ two rotamers {[10.43 (rotamer A, brs), 9.73 (rotamer B, brs)], 1H], 7.42-7.34 (m, 4H), 3.98-3.83 (m, 2H), 3.50 (brs, 1H), 3.43-3.34 (m, 2H), 3.22 3.04 (m, 1H), 2.97-2.78 (m, 2H), {[2.66 (rotamer B, s), 2.59 (rotamer A, s)], 3H], 2.15 2.07 (m, 2H), {[1.84-1.75 (rotamer B, m), 1.70-1.62 (rotamer A, m)], 2H), {[1.31 (1$^{st}$ rotamer, d, J = 5.7 Hz), 1.25 (2$^{nd}$ rotamer, d, J = 5.7 Hz)], 3H} |
| 141 | •2HCl | 1-(3-amino-1H-1,2,4-triazol-5-yl)-N-(1-(4-chlorophenyl)propan-2-yl)-N-methylpiperidin-4-amine dihydrochloride | B | $^1$H NMR (DMSO-$d_6$, 500 MHz): δ {[10.89 (rotamer A, brs), 10.74 (rotamer B, brs)], 1H], 7.40 (d, J = 8.3 Hz, 2H), 7.37-7.32 (m, 2H), 3.96-3.87 (m, 2H), 3.76-3.61 (m, 2H), 3.43 (brs, 2H), 3.06-2.88 (m, 2H), {[2.70 (rotamer B, d, J = 4.8 Hz), 2.68 (rotamer A, d, J = 4.8 Hz)], 3H},2.28-2.07 (m, 2H), 1.88-1.81 (m, 2H), {[1.18 (rotamer B, d, J = 6.4 Hz), 1.06 (rotamer A, d, J = 6.4 Hz)], 3H} ESI-MS m/z for $C_{17}H_{25}ClN_6$, expected 348.9, found 349.1/351.1 [M + H]+ |
| 142 | 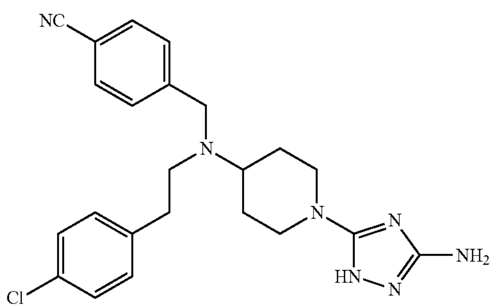 [SMILES: N#Cc1ccc(CN(CCc2ccc(Cl)cc2)C2CCN(c3nc(N)n[nH]3)CC2)cc1] | 4-(((1-(3-amino-1H-1,2,4-triazol-5-yl)piperidin-4-yl)(4-chlorophenethyl)amino)methyl)benzonitrile | A | $^1$H NMR (DMSO-$d_6$, 500 MHz): δ 11.34 (bs, 1H), 7.93 (AA'BB', 4H), 7.26 (AA'BB', 4H), 4.61-4.56 (m, 1H), 4.47-4.39 (m, 1H), 3.94-3.83 (m, 2H), 3.27-3.18 (m, 2H), 3.15-3.04 (m, 2H), 3.01-2.84 (m, 3H), 2.27-2.17 (m, 2H), 1.94-1.79 (m, 2H). ESI MS found m/z 436.5/438.5 |
| 143 | 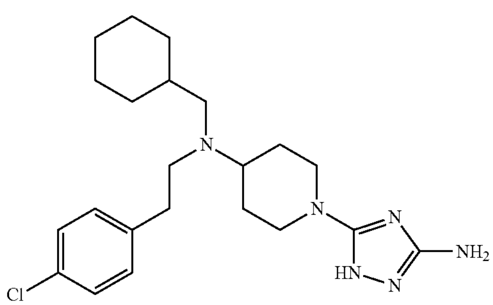 [SMILES: Nc1n[nH]c(N2CCC(N(CCc3ccc(Cl)cc3)CC3CCCCC3)CC2)n1] | 1-(3-amino-1H-1,2,4-triazol-5-yl)-N-(4-chlorophenethyl)-N-(cyclohexylmethyl)piperidin-4-amine | A | $^1$H NMR (DMSO-$d_6$, 500 MHz): δ 10.40 (bs, 1H), 7.37 (AA'BB', 4H), 4.00-3.89 (m, 2H), 3.61-3.51 (m, 2H), 3.28-3.16 (m, 3H), 3.15-2.94 (m, 4H), 2.90-2.80 (m, 1H), 2.14 (bs, 2H), 2.09-2.00 (m, 1H), 1.90-1.69 (m, 4H), 1.69-1.54 (m, 3H), 1.29-1.14 (m, 2H), 1.14-1.03 (m, 1H), 1.02-0.84 (m, 2H). ESI MS found m/z 417.5/419.5 |
| 144 | 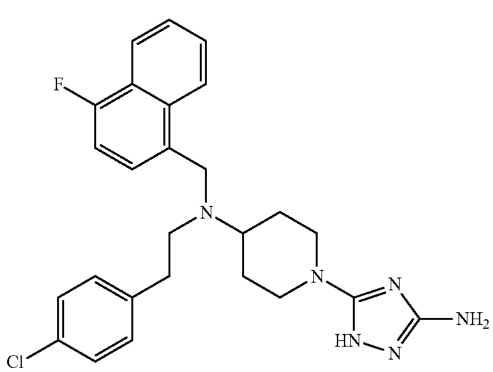 [SMILES: Nc1n[nH]c(N2CCC(N(CCc3ccc(Cl)cc3)Cc3ccc(F)c4ccccc34)CC2)n1] | 1-(3-amino-1H-1,2,4-triazol-5-yl)-N-(4-chlorophenethyl)-N-((4-fluoronaphthalen-1-yl)methyl)piperidin-4-amine | A | $^1$H NMR (DMSO-$d_6$, 600 MHz): δ 11.16-10.90 (m, 1H), 8.38-8.33 (m, 1H), 8.18-8.14 (m, 1H), 8.13-8.07 (m, 1H), 7.8-7.76 (m, 1H), 7.75-7.7 (m, 1H), 7.49-7.44 (m, 1H), 7.32-7.27 (m, 2H), 7.08-7.03 (m, 2H), 5.06-4.95 (m, 1H), 4.9-4.78 (m, 1H), 4.02-3.96 (m, 1H), 3.85-3.78 (m, 1H), 3.75-3.68 (m, 1H), 3.45-3.38 (m, 1H), 3.37-3.32 (m, 1H), 3.2-3.15 (m, 1H), 3.06-2.9 (m, 2H), 2.9-2.79 (m, 1H), 2.4-2.3 (m, 2H), 2.14-1.98 (m, 2H). ESI MS found m/z 479.5/481.5 [M + H], 477.5/479.5 (M − 1). |

TABLE 1-continued

| Example | Structure | IUPAC Name | Activity | Analytical Data |
|---|---|---|---|---|
| 145 | 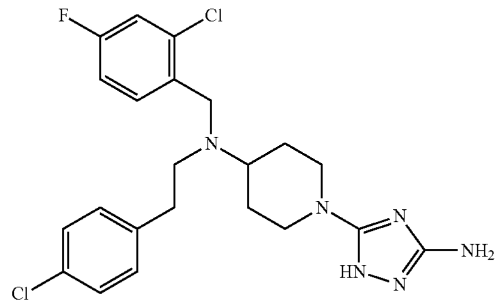 | 1-(3-amino-1H-1,2,4-triazol-5-yl)-N-(2-chloro-4-fluorobenzyl)-N-(4-chlorophenethyl)piperidin-4-amine | A | $^1$H NMR (DMSO-$d_6$, 600 MHz): δ 10.86 (brs, 1H), 7.4 (dd, 1H), 7.33 (dd, 1H), 7.26 (d, 2H, J = 8.3 Hz), 7.13 (d, 2H, J = 8.3 Hz), 7.08 (dt, 1H), 5.68 (brs, 1H), 3.85-3.78 (m, 2H), 3.68 (s, 2H), 2.7-2.65 (m, 2H), 2.65-2.57 (m, 4H), 2.57-2.52 (m, 1H), 1.68-1.62 (m, 2H), 1.47-1.38 (m, 2H) $^{19}$F NMR (DMSO-$d_6$, 200 MHz) δ −113.84. ESI MS found m/z 463.4/465.4 [M + H], 461.3/463.5 [M − H]. |
| 146 | 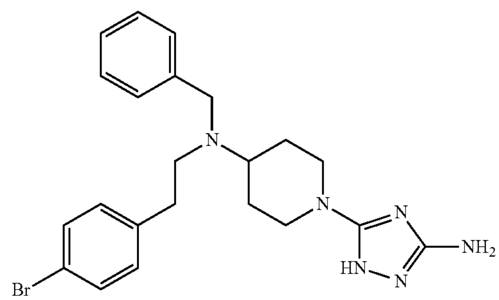 | 1-(3-amino-1H-1,2,4-triazol-5-yl)-N-benzyl-N-(4-bromophenethyl)piperidin-4-amine | A | $^1$H NMR (DMSO-$d_6$, 600 MHz): δ δ 11.37 (bs, 1H), 7.77-7.69 (m, 2H), 7.47-7.38 (m, 5H), 7.09-7.03 (m, 2H), 4.53-4.47 (m, 2H), 4.32-4.24 (m, 1H), 3.98-3.89 (m, 2H), 3.58-3.49 (m, 2H), 3.22-3.14 (m, 1H), 3.12-3.01 (m, 2H), 3.00-2.88 (m, 2H), 2.87-2.78 (m, 1H), 2.32-2.21 (m, 2H), 1.98-1.82 (m, 2H), ESI MS found m/z 455.4/457.4 |
| 147 | •2HCl | 1-(3-amino-1H-1,2,4-triazol-5-yl)-N-(2-(4-chlorophenyl)propyl)piperidin-4-aminedihydrochloride | D | $^1$H NMR (DMSO-$d_6$, 500 MHz): δ (ppm) 9.32 (brs, 1H), 8.88 (brs, 1H), 7.40-7.34 (m, 4H), 3.90-3.80 (m, 2H), 3.32-3.23 (m, 1H), 3.22 (brs, 1H), 3.15-3.08 (m, 2H), 2.90 (brs, 2H), 2.14-2.00 (m, 2H), 1.68-1.57 (m, 2H), 1.26 (d, J = 6.3 Hz, 3H) ESI-MS for $C_{16}H_{25}Cl_3N_6$: expected 334.78, found 334.7/ 336.7 [M + H] |
| 148 | •2HCl | 1-(3-amino-1H-1,2,4-triazol-5-yl)-N-(4-chlorobenzyl)-N-methylpiperidin-4-amine dihydrochloride | E | $^1$H NMR (DMSO-$d_6$, 500 MHz): δ (ppm) 10.95 (brs, 1H), 7.34 (d, JAB = 8.4 Hz, 2H), 7.30 (d, JAB = 8.4 Hz, 2H), 5.56 (brs, 2H), 3.84 (brs, 1H), 3.82 (brs, 2H), 3.51 (s, 2H), 2.52-2.47 (m, 1H), 2.06 (s, 3H), 1.76-1.68 (m, 2H), 1.50-1.44 (m, 2H) ESI-MS for $C_{15}H_{23}Cl_3N_6$: expected 320.18, found 320.3/ 322.3 [M + H] |
| 149 | 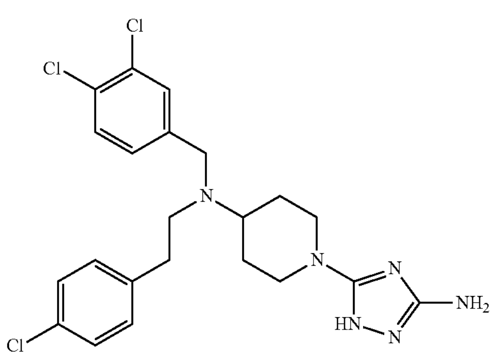 [SMILES: Nc1n[nH]c(N2CCC(N(CCc3ccc(Cl)cc3)Cc3ccc(Cl)c(Cl)c3)CC2)n1] | 1-(3-amino-1H-1,2,4-triazol-5-yl)-N-(4-chlorophenethyl)-N-(3,5-dichlorobenzyl)piperidin-4-amine | A | $^1$H NMR (DMSO-$d_6$, 600 MHz): δ 11.46 (brs, 1H), 8.13 (s, 1H), 7.8-7.71 (m, 2H), 7.36 (d, 2H, J = 8.1 Hz), 7.21 (d, 2H), 8.1 Hz), 4.56-4.49 (m, 1H), 4.4-4.34 (m, 1H), 3.93 (brs, 2H), 3.63-3.5 (m, 2H), 3.3-3.23 (m, 1H), 3.14-3.08 (m, 1H), 3.03-2.9 (m, 3H), 2.25 (brs, 2H), 1.96-1.83 (m, 2H). ESI MS found m/z 479.4/ 481.4 [M + H], 477.2/479.2 [M − H] |

TABLE 1-continued

| Example | Structure | IUPAC Name | Activity | Analytical Data |
|---|---|---|---|---|
| 150 | 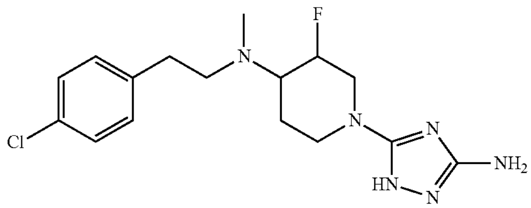 [SMILES: CN(CCc1ccc(Cl)cc1)C1CCN(c2nc(N)n[nH]2)CC1F] | 1-(3-amino-1H-1,2,4-triazol-5-yl)-N-(4-chlorophenethyl)-3-fluoro-N-methylpiperidin-4-amine | C | $^1$H NMR (DMSO-d$_6$, 600 MHz): δ 10.88 (bs, 1H), 7.27 (AA'BB', 2H, J = 8.3 Hz), 7.21 (AA'BB', 2H, J = 8.3 Hz), 5.65 (bs, 1H), 4.90 (d, 2H, J = 49.5 Hz), 4.00-3.91 (m, 1H), 3.88-3.80 (m, 1H), 2.83-2.50 (m, 7H), 2.29 (s, 3H), 1.83-1.72 (m, 1H), 1.52-1.45 (m, 1H). $^{19}$F (DMSO-d$_6$, 200 MHz) δ [ppm] −197.94. ESI-MS m/z for C$_{16}$H$_{22}$ClFN$_6$: expected 352.84, found 353.4/355.4 [M + H] |
| 151 | •2HCl | 1-(3-amino-1H-1,2,4-triazol-5-yl)-N-(1-(4-chlorophenyl)propan-2-yl)piperidin-4-amine dihydrochloride | C | $^1$H NMR (DMSO-d$_6$, 600 MHz): δ 9.55 (brs, 2H), 9.30 (brs, 1H), 9.00 (brs, 1H), 7.36 (d, JAB = 8.2 Hz, 2H), 7.27 (d, JAB = 8.2 Hz, 2H), 3.51 (brs, 1H), 3.45 (brs, 1H), 3.35-3.29 (m, 2H), 3.28-3.26 (m, 1H), 2.89 (brs, 2H), 2.69-2.61 (m, 1H), 2.20 (dd, J = 13 Hz, J = 24 Hz, 1H), 1.95-1.86 (m, 2H), 1.08 (d, J = 6.4 Hz, 3H) ESI-LCMS m/z for C$_{16}$H$_{23}$ClN$_6$ found 335.5/337.5 [M + H] |
| 152 | 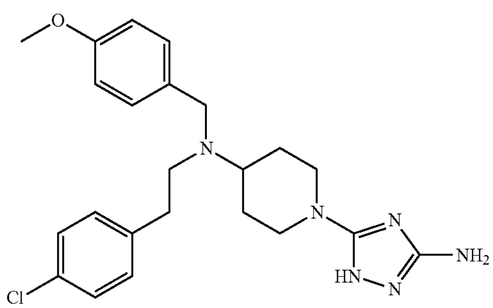 [SMILES: COc1ccc(CN(CCc2ccc(Cl)cc2)C2CCN(c3nc(N)n[nH]3)CC2)cc1] | 1-(3-amino-1H-1,2,4-triazol-5-yl)-N-(4-chlorophenethyl)-N-(4-methoxybenzyl)piperidin-4-amine | A | $^1$H NMR (DMSO-d$_6$, 600 MHz): δ 10.97 (bs, 1H), 7.68-7.63 (m, 2H), 7.37 (d, 2H, J = 8.3 Hz), 7.20 (d, 2H, J = 8.3), 7.01 (d, 2H, 8.1 Hz), 4.49-4.29 (m, 1H), 4.30-4.23 (m, 1H), 3.98-3.90 (m, 2H), 3.78 (s, 3H), 3.59-3.50 (m, 1H), 3.27-3.19 (m, 1H), 3.16-3.05 (m, 2H), 3.03-2.91 (m, 2H), 2.91-2.84 (m, 1H), 2.31-2.21 (m, 2H), 1.98-1.85 (m, 2H). ESI MS found m/z 441.5/443.5 |
| 153 | •2HCl | (S)-2-((1-(3-amino-1H-1,2,4-triazol-5-yl)piperidin-4-yl)(methyl)amino)-3-(4-chlorophenyl)propan-1-ol | B | $^1$H NMR (DMSO-d$_6$, 500 MHz): δ 7.40 (d, JAB = 8.2 Hz, 2H), 7.36 (d, JAB = 8.2 Hz, 2H), 4.01-3.94 (m, 2H), 3.78-3.59 (m, 3H), 3.45 3.22 (m, 2H), 3.04-2.93 (m, 3H), 2.80 (s, 3H), 2.21 (brs, 2H), 1.88 (brs, 2H) ESI-MS m/z for C$_{17}$H$_{25}$ClN$_6$O expected 364.88, found 364.7/366.7 [M + H]+ |
| 154 | •2HCl | 1-(3-amino-1H-1,2,4-triazol-5-yl)-N-(4-chlorophenethyl)-N,3-dimethylpiperidin-4-amine dihydrochloride | B | $^1$H NMR (DMSO-d$_6$, 500 MHz): δ 10.62 (brs, 1H), 7.39-7.33 (m, 4H), 3.96-3.86 (m, 1H), 3.79-3.7 (m, ,3H), 3.5-3.4 (m, 1H), 3.3-3.14 (m, 2H), 3.1-3.0 (m, 3H), 2.95-2.85 (m, 1H), 2.82-2.78 (m, 3H), 2.53-2.48 (m, 1H), 2.1-2.0 (m, 1H), 1.93-1.83 (m, 1H), 1.06 1.02 (m, 3H). ESI-MS m/z for C$_{17}$H$_{25}$ClN$_6$O expected 348.9, found 349.4/351.4 [M + H], 347.4/349.4 [M − H] |
| 155 | •2HCl | 1-(3-amino-1H-1,2,4-triazol-5-yl)-N-(4-chlorophenethyl)-N-ethylpiperidin-4-amine | B | $^1$H NMR (DMSO-d$_6$, 500 MHz): δ 7.26 (d, J = 8.1 Hz, 2H), 7.20 (d, J = 8.4 Hz, 2H), 5.64 (brs, 2H), 3.8-3.73 (m, 2H), 2.64-2.51 (m, 7H), 2.51-2.47 (m, 2H), 1.58-1.52 (m, 2H), 1.36-1.25 (m, 2H), 0.89 (t, J = 7.1 Hz, 3H) ESI-MS m/z for C$_{17}$H$_{25}$ClN$_6$ calculated: 348.88, found 349.4/351.4 [M + H], 347.4/349.4 [M − H] |

TABLE 1-continued

| Example | Structure | IUPAC Name | Activity | Analytical Data |
|---|---|---|---|---|
| 156 | 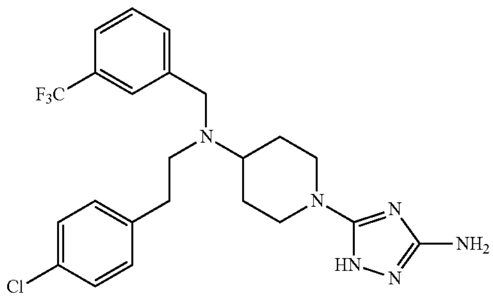 [SMILES: Nc1n[nH]c(N2CCC(N(CCc3ccc(Cl)cc3)Cc3cccc(C(F)(F)F)c3)CC2)n1] | 1-(3-amino-1H-1,2,4-triazol-5-yl)-N-(4-chlorophenethyl)-N-(3-(trifluoromethyl)benzyl)piperidin-4-amine | A | $^1$H NMR (DMSO-d$_6$, 600 MHz): δ 11.78 (brs, 1H), 8.26-8.24 (m, 1H), 8.13 (d. 1H), 7.8 (m, 2H), 7.71-7.66 (m, 1H), 7.33 (d, 2H, J = 8.3 Hz), 7.14 (d, 2H, J = 8.3 Hz), 4.66-4.62 (m, 1H), 4.47-4.42 (m, 1H), 4.0-3.95 (m, 2H), 3.62-3.55 (m, 1H), 3.26-3.19 (m, 1H), 3.18-3.06 (m, 2H), 3.05-2.95 (m, 2H), 2.89-2.83 (m, 1H), 2.35-2.28 (m, 2H), 2.00-1.88 (m, 2H). $^{19}$F NMR (DMSO-d$_6$, 200 MHz) δ −60.43 ESI MS found m/z 479.5/481.5 [M + H], 477.4 (M − H) |
| 157 | •3HCl | 1-(3-amino-1H-1,2,4-triazol-5-yl)-N-methyl-N-(2-(pyridin-2-yl)ethyl)piperidin-4-amine trihydrochloride | D | $^1$H NMR (DMSO-d$_6$, 500 MHz): δ 11.41 (brs, 1H), 8.71 (brs, 1H), 8.27 (brs, 1H), 7.83 (brs, 1H), 7.71 (brs, 1H), 3.95-3.90 (m, 2H), 3.56-3.45 (m, 5H), 3.01-2.92 (m, 2H), 2.75 (s, 3H), 2.19-2.10 (m, 2H), 1.76-1.96 (m, 2H) |
| 158 | 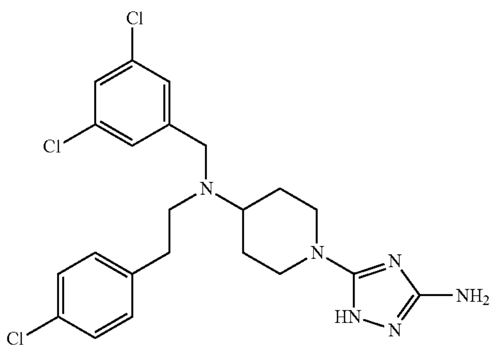 [SMILES: Nc1n[nH]c(N2CCC(N(CCc3ccc(Cl)cc3)Cc3cc(Cl)cc(Cl)c3)CC2)n1] | 1-(3-amino-1H-1,2,4-triazol-5-yl)-N-(4-chlorophenethyl)-N-(2,4-dichlorobenzyl)piperidin-4-amine | A | $^1$H NMR (DMSO-d$_6$, 500 MHz): δ 11.85 (brs, 1H), 7.95 (s, 2H), 7.66 s, 1H), 7.32 (d, 2H, J = 8.1 Hz), 7.17 (d, 2H, J = 8.1 Hz), 4.54-4.47 (m, 1H), 4.37-4.31 (m, 1H), 3.98-3.92 (m, 2H), 3.24-3.12 (m, 3H), 3.10-3.04 (m, 1H), 3.00-2.86 (m, 3H), 2.2-2.22 (m, 2H), 1.92-1.82 (m, 2H) ESI MS found m/z 479.3/481.4 [M + H], 477.3/479.4 [M − H] |
| 159 | •2HCl | 1-(3-amino-1H-1,2,4-triazol-5-yl)-N-benzyl-N-(1-(4-chlorophenyl)propan-2-yl)piperidin-4-amine dihydrochloride | A | $^1$H NMR (DMSO-d$_6$, 600 MHz): δ 10.5 (brs, 1H), 7.8-7.77,7.77-7.74 (m, 2H), 7.45-7.38 (m, 3H), 7.38-7.31 (m, 2H), 7.25-7.19 (m, 2H), 4.6-4.55 (m, 1H), 4.53-4.44 (m, 1H), 3.93-3.86 (m, 2H), 3.7-3.65, 3.65-3.58 (m, 1H), 3.55-3.52, 3.51-3.46 (m, 2H), 3.09-3.02 (m, 1H), 2.99-2.93 (m, 1H), 2.91-2.86, 2.85-2.8 (m, 1H), 2.43-2.37, 2.2-2.15 (m, 1H), 2.3-2.23 (m, 1H), 2.02-1.87 (m, 2H), 1.2, 1.18, (d, 3H, J = 6.6 Hz). ESI MS found m/z 425.5/427.5 [M + H], 423.5/425.4 [M − H] |
| 160 | •2HCl | 1-(3-amino-1H-1,2,4-triazol-5-yl)-N-(1-(4-chlorophenyl)butan-2-yl)-N-methylpiperidin-4-amine | C | $^1$H NMR (DMSO-d$_6$, 500 MHz): δ 7.45-7.39 (m, 4H), 7.43 (br s, 1H), 3.95-3.91 (m, 2H), 3.55-3.41 (m, 9H), 3.24-3.21 (m, 1H), 3.01-2.90 (m, 2H), 2.85-2.81 (m, 1H), 2.73-2.70 (m, 3H), 2.25-2.23 (m, 1H), 2.12-2.10 (m, 1H), 1.92-1.75 (m, 3H), 1.68-1.57 (m, 1H). LC-MS: m/z for C$_{18}$H$_{27}$ClN$_6$: expected 362.9, found 363.1/365.0 [M + H], 361.3/363.3 [M − H] |

TABLE 1-continued

| Example | Structure | IUPAC Name | Activity | Analytical Data |
|---|---|---|---|---|
| 161 | 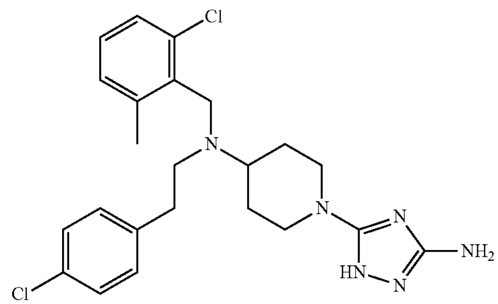 [SMILES: Cc1cccc(Cl)c1CN(CCc1ccc(Cl)cc1)C1CCN(c2nc(N)n[nH]2)CC1] | 1-(3-amino-1H-1,2,4-triazol-5-yl)-N-(2-chloro-6-methylbenzyl)-N-(4-chlorophenethyl)piperidin-4-amine | A | ¹H NMR (DMSO-d₆, 500 MHz): δ 10.88 (bs, 1H), 7.21 (d, 1H, J = 7.9 Hz), 7.16 (d, 2H, J = 8.3 Hz), 7.12 (dd, 1H, J = 7.5 Hz, J = 7.3 Hz) 7.04 (d, 1H, J = 7.3 Hz), 6.92 (d, 2H, J = 8.3 Hz), 3.87-3.80 (m, 2H), 3.78 (s, 2H), 2.63-2.55 (m, 3H), 2.55-2.49 (m, 2H), 2.45-2.40 (m, 2H), 2.28 (s, 3H), 1.68-1.61 (m, 2H), 1.57-1.47 (m, 2H). ESI MS found m/z 459.5/461.4 |
| 162 | 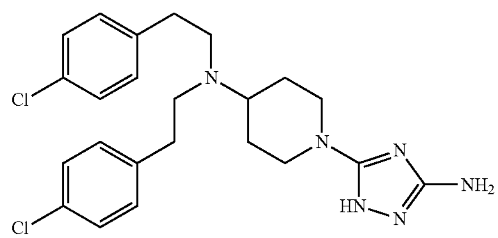 [SMILES: Nc1n[nH]c(N2CCC(N(CCc3ccc(Cl)cc3)CCc3ccc(Cl)cc3)CC2)n1] | 1-(3-amino-1H-1,2,4-triazol-5-yl)-N,N-bis(4-chlorophenethyl)piperidin-4-amine | A | ¹H NMR (CD₃OD, 600 MHz) δ: 7.38-7.33 (m, 8H), 4.0-3.95 (m, 2H), 3.83-3.77 (m, 1H), 3.53 (brs, 2H), 3.45 (brs, 2H), 3.20-3.09 (m, 6H), 2.25-2.21 (m, 2H), 1.99-1.93 (m, 2H). ESI MS found m/z 459.5 [M + H], 457.5 (M − 1). |
| 163 | 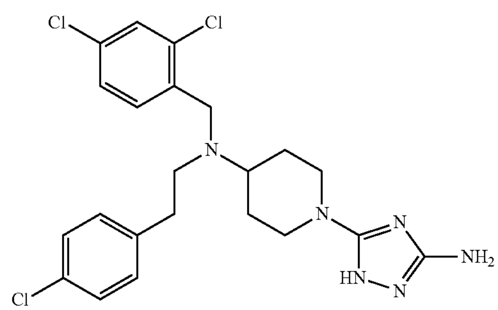 [SMILES: Nc1n[nH]c(N2CCC(N(CCc3ccc(Cl)cc3)Cc3ccc(Cl)cc3Cl)CC2)n1] | 1-(3-amino-1H-1,2,4-triazol-5-yl)-N-(4-chlorophenethyl)-N-(2,4-dichlorobenzyl)piperidin-4-amine | A | ¹H NMR (DMSO-d₆, 500 MHz): δ 11.01 (bs, 1H), 8.05-7.98 (m, 1H), 7.76 (s, 1H), 7.57-7.52 (m, 1H), 7.38-7.31 (m, 2H), 7.26-7.19 (m, 2H), 4.66-4.58 (m, 1H), 4.45-4.36, (m, 1H), 4.00-3.85 (m, 2H), 3.71-3.57 (m, 2H), 3.89-3.28 (m, 1H), 3.22-3.08 (m, 2H), 3.05-2.93 (m, 2H), 2.28-2.16 (m, 2H), 2.00-1.82 (m, 2H). ESI MS found m/z 479.4/481.4 |
| 164 | •2HCl | (2-(((1-(3-amino-1H-1,2,4-triazol-5-yl)piperidin-4-yl)(4-chlorophenethyl)amino)methyl)phenyl)methanol dihydrochloride | A | ¹H NMR (DMSO-d₆, 500 MHz): δ 7.54 (d, 1H, J = 7.15 Hz), 7.42-7.27 (m, 5H), 7.28 (d, 2H, J = 8.47 Hz), 7.10 (d, 2H, 8.28 Hz), 5.09 (q, 1H), 4.66 (s, 2H), 4.36 (s, 2H), 3.92-3.89 (m, 2H), 3.43-3.38 (m, 1H), 3.18 (t, 2H), 2.85-2.80 (m, 2H), 2.75 (t, 2H), 2.00-1.98 (m, 2H), 1.85-1.79 (m, 2H) ESI-MS for C₂₃H₂₉ClN₆O): expected 440.98, found 441.1/443.0 [M + H], 439.3/441.3 [M − H] |
| 165 | 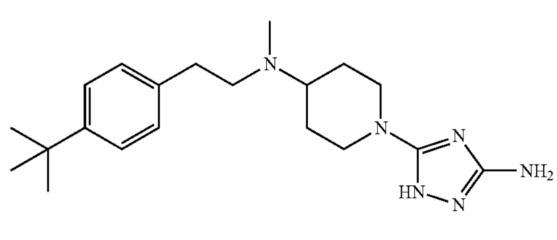 [SMILES: CN(CCc1ccc(C(C)(C)C)cc1)C1CCN(c2nc(N)n[nH]2)CC1] | 1-(3-amino-1H-1,2,4-triazol-5-yl)-N-(4-(tert-butyl)phenethyl)-N-methylpiperidin-4-amine | C | ¹H NMR (DMSO-d₆, 500 MHz): δ 7.31 (d, 2H, J = 8.3 Hz), 7.18 (d, 2H, J = 8.3 Hz), 3.93-3.9 (m, 2H), 3.54-3.4 (m, 1H), 3.28-3.2 (m, 1H), 3.19 3.1 (m, 1H), 3.07-2.98 (m, 2H), 2.98-2.88 (m, 2H), 2.69 (d, 3H, J = 4.5 Hz), 2.15-2.12 (m, 1H), 2.07-2.04 (m, 1H), 1.79-1.63 (m, 2H), 1.22 (s, 9H) ESI MS calculated for C₂₀H₃₂N₆ expected 356.51; found m/z 357.4 [M + H] |

TABLE 1-continued

| Example | Structure | IUPAC Name | Activity | Analytical Data |
|---|---|---|---|---|
| 166 | 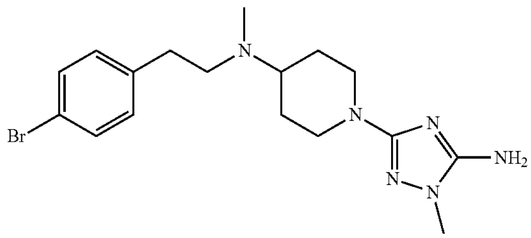 [SMILES: CN(CCc1ccc(Br)cc1)C1CCN(c2nc(N)n(C)n2)CC1] | 1-(5-amino-1-methyl-1H-1,2,4-triazol-3-yl)-N-(4-bromophenethyl)-N-methylpiperidin-4-amine | E | $^1$H NMR (CD$_3$OD, 500 MHz): δ 7.42 (d, 2H, J = 8.3 Hz), 7.16 (d, 2H, J = 8.4 Hz), 6.61 (brs, 1H), 3.48 (s, 3H), 3.48-3.42 (m, 2H), 2.90 2.83 (m, 2H), 2.79-2.73 (m, 4H), 2.69-2.63 (m, 1H), 2.40 (s, 3H), 1.93-1.87 (m, 2H), 1.73-1.63 (m, 2H) ESI-MS m/z for C$_{17}$H$_{25}$BrN$_6$; expected 393.32 found 393.3/395.3 [M + H]+ |
| 167 | 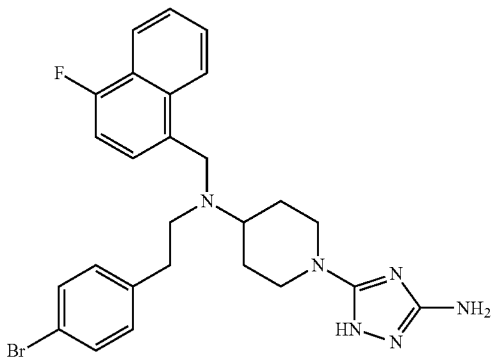 | 1-(3-amino-1H-1,2,4-triazol-5-yl)-N-(4-bromophenethyl)-N-((4-fluoronaphthalen-1-yl)methyl)piperidin-4-amine | A | $^1$H NMR (CD$_3$OD, 500 MHz): δ 8.21 (d, 1H, J = 8.4 Hz), 8.05 (d, 1H, J = 8.3 Hz), 7.57-7.53 (m, 1H), 7.51-7.47(m, 1H), 7.40-7.36 (m, 1H), 7.21 (d, 2H, J = 8.3 Hz), 7.08-7.03 (m, 1H), 6.85 (d, 2H, J = 8.3 Hz), 4.09 (s, 2H), 3.92 3.85 (m, 2H), 2.82-2.76 (m, 2H), 2.76-2.62 (m, 3H), 2.56-2.51 (m, 2H), 1.85-1.79 (m, 2H), 1.73-1.63 (m, 2H) 19F NMR (CD3OD, 500 MHz): δ −126.30 ESI-MS m/z for C$_{26}$H$_{28}$BrFN$_6$; expected 523.4 found 523.1/524.9 [M + H]+ |
| 168 | 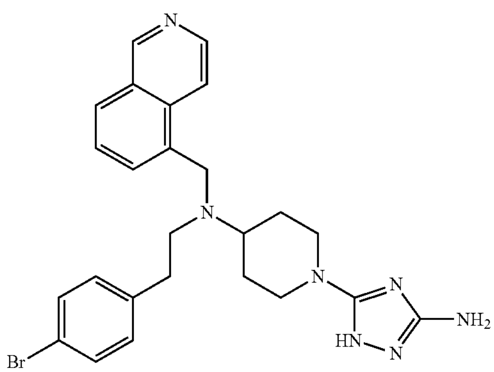 [SMILES: Nc1n[nH]c(N2CCC(N(CCc3ccc(Br)cc3)Cc3cccc4cnccc34)CC2)n1] | 1-(3-amino-1H-1,2,4-triazol-5-yl)-N-(4-bromophenethyl)-N-(isoquinolin-5-ylmethyl)piperidin-4-amine | A | |
| 169 | 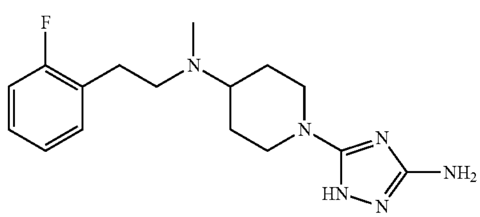 | 1-(3-amino-1H-1,2,4-triazol-5-yl)-N-methyl-N-(2-(trifluoromethyl)phenethyl)piperidin-4-amine | C | $^1$H NMR (DMSO-d$_6$, 500 MHz) δ 11.53 (brs, 1H), 7.73-7.69 (m, 1H), 7.69-7.63 (m, 2H), 7.51-7.46 (m, 1H), 3.99-3.92 (m, 2H), 3.60 3.51 (m, 1H), 3.38-3.10 (m, 4H), 3.04-2.93 (m, 2H), 2.76 (s, 3H), 2.22-2.13 (m, 1H), 2.12-2.04 (m, 1H), 1.82-1.66 (m, 2H) ESI-MS m/z for C$_{17}$H$_{23}$F$_3$N$_6$; expected 368.4 found 369.1/370.1 [M + H]+ |
| 170 | 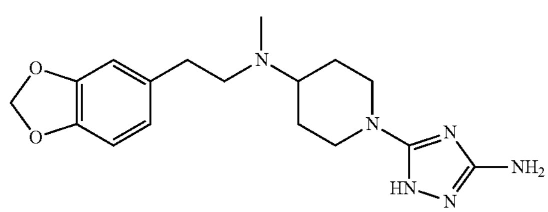 [SMILES: CN(CCc1ccc2c(c1)OCO2)C1CCN(c2nc(N)n[nH]2)CC1] | 1-(3-amino-1H-1,2,4-triazol-5-yl)-N-(2-(benzo[d][1,3]dioxol-5-yl)ethyl)-N-methylpiperidin-4-amine | C | $^1$H NMR (DMSO-d$_6$, 500 MHz) δ 11.06 (brs, 1H), 6.92 (s, 1H), 6.85 (d, 1H, J = 7.9 Hz), 6.75 (d, 1H, J = 7.9 Hz), 5.97 (s, 2H), 3.97 3.87 (m, 2H), 3.54-3.22 (m, 2H) 3.20-3.09 (m, 1H), 3.06-2.91 (m, 4H), 2.71 (s, 3H), 2.18-2.11 (m, 1H), 2.11-2.04 (m, 1H), 1.79 1.74 (m, 2H) ESI-MS m/z for C$_{17}$H$_{24}$N$_6$O$_2$; expected 344.4 found 345.1 [M + H]+ |

TABLE 1-continued

| Example | Structure | IUPAC Name | Activity | Analytical Data |
|---|---|---|---|---|
| 171 | 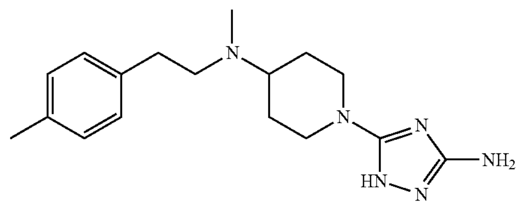 [SMILES: Cc1ccc(CCN(C)C2CCN(c3nc(N)n[nH]3)CC2)cc1] | 1-(3-amino-1H-1,2,4-triazol-5-yl)-N-methyl-N-(4-methylphenethyl)piperidin-4-amine | B | $^1$H NMR (DMSO-d$_6$, 500 MHz) δ 11.19 (brs, 1H), 7.18 (AA'BB', 2H, J = 7.9 Hz), 7.12 (AA'BB', 2H, J = 7.9 Hz), 3.97-3.90 (m, 2H), 3.57-3.22 (m, 2H), 3.21-3.12 (m, 1H), 3.10 2.91 (m, 4H), 2.72 (s, 3H), 2.25 (s, 3H), 2.19 2.12 (m, 1H), 2.11-2.04 (m, 1H), 1.80-1.65 (m, 2H) ESI-MS m/z for C$_{17}$H$_{26}$N$_6$; expected 314.4 found 315.2 [M + H]+ |
| 172 | 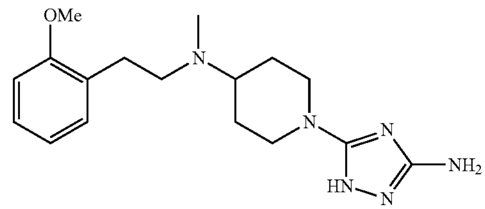 [SMILES: COc1ccccc1CCN(C)C1CCN(c2nc(N)n[nH]2)CC1] | 1-(3-amino-1H-1,2,4-triazol-5-yl)-N-(2-methoxy-phenethyl)-N-methylpiperidin-4-amine | D | $^1$H NMR (DMSO-d$_6$, 500 MHz) δ 11.07 (brs, 1H), 7.27-7.21 (m, 1H), 6.99 (d,1H, J = 7.1 Hz), 6.90 (dd, 1H, J = 7.3 Hz, J = 7.3 Hz), 3.98-3.90 (m, 2H), 3.79 (s, 3H), 3.57-3.20 (m, 3H), 3.16-3.91 (m, 4H), 2.74 (s, 3H), 2.19 2.13 (m, 1H), 2.10-2.04 (m, 1H), 1.81-1.66 (m, 2H) ESI-MS m/z for C$_{17}$H$_{26}$N$_6$O; expected 330.4 found 331.2 [M + H]$^+$ |
| 173 | 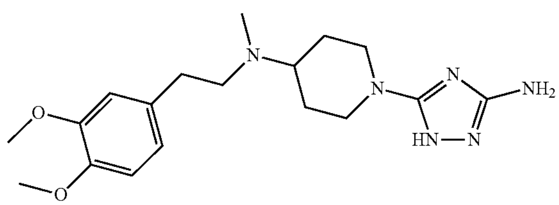 [SMILES: COc1ccc(CCN(C)C2CCN(c3nc(N)n[nH]3)CC2)cc1OC] | 1-(3-amino-1H-1,2,4-triazol-5-yl)-N-(3,4-dimethoxy-phenethyl)-N-methylpiperidin-4-amine | D | $^1$H NMR (DMSO-d$_6$, 500 MHz) δ 11.00 (brs, 1H), 6.91 (d, 1H, J = 1.1 Hz), 6.89 (d, 1H, J = 8.3 Hz), 6.80 (dd, 1H, J = 8.1 Hz, J = 1.1 Hz), 5.74 (brs, 2H), 3.91 (d, 2H, J = 12.8 Hz), 3.75 (s, 3H), 3.72 (s, 3H), 3.16-3.36 (m, 3H), 2.96 2.99 (m, 2H), 2.63-2.72 (m, 5H), 1.95-2.05 (m, 2H), 1.61-1.68 (m, 2H) ESI-MS m/z for C$_{18}$H$_{28}$N$_6$O$_2$; expected 360.4 found 361.2 [M + H]$^+$, 359.3 [M − H]$^-$ |
| 174 | 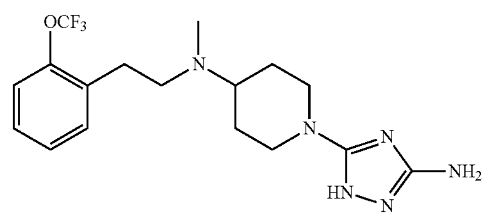 [SMILES: CN(CCc1ccccc1OC(F)(F)F)C1CCN(c2nc(N)n[nH]2)CC1] | 1-(3-amino-1H-1,2,4-triazol-5-yl)-N-methyl-N-(2-(trifluoro-methoxy)phenethyl)piperidin-4-amine | D | $^1$H NMR (DMSO-d$_6$, 500 MHz) δ 11.35 (brs, 1H), 7.53-7.55 (m, 1H), 7.36-7.43 (m, 3H), 3.95 (d, 2H, J = 12.0 Hz), 3.53-3.58 (m, 2H), 3.09-3.26 (m, 3H), 2.97-3.00 (m, 2H), 2.75 (s, 3H), 2.16 (d, 1H, J = 11.7 Hz), 2.08 (d, 1H, J = 11.3 Hz), 1.68-1.81 (m, 2H) ESI-MS m/z for C$_{17}$H$_{23}$F$_3$N$_6$O expected 384.4; found 385.2 [M + H]$^+$, 383.3 [M − H]$^-$ |
| 175 | 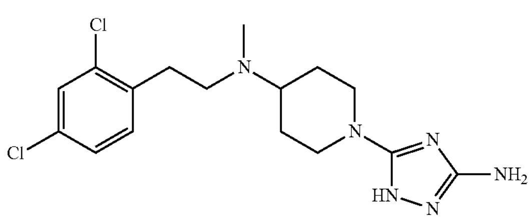 [SMILES: CN(CCc1ccc(Cl)cc1Cl)C1CCN(c2nc(N)n[nH]2)CC1] | 1-(3-amino-1H-1,2,4-triazol-5-yl)-N-(2,4-dichloro-phenethyl)-N-methylpiperidin-4-amine | C | $^1$H NMR (DMSO-d$_6$, 500 MHz) δ 11.04 (brs, 1H), 7.63 (d, 1H, J = 1.9 Hz), 7.50 (d, 1H, J = 8.3 Hz), 7.43 (dd, 1H, J = 8.3 Hz, J = 1.9 Hz), 5.67 (brs, 2H), 3.90 (d, 2H, J = 12.2 Hz), 3.25 3.36 (m, 1H), 3.15-3.20 (m, 4H), 2.63-2.72 (m, 5H), 1.96-2.04 (m, 2H), 1.62-1.66 (m, 2H) ESI-MS m/z for C$_{16}$H$_{22}$Cl$_2$N$_6$ expected 369.3; found 369.0/371.0 [M + H]$^+$ 367.3/369.3 [M − H]$^-$ |
| 176 | 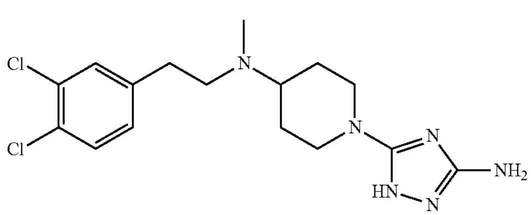 [SMILES: CN(CCc1ccc(Cl)c(Cl)c1)C1CCN(c2nc(N)n[nH]2)CC1] | 1-(3-amino-1H-1,2,4-triazol-5-yl)-N-(3,4-dichloro-phenethyl)-N-methylpiperidin-4-amine | C | $^1$H NMR (DMSO-d$_6$, 500 MHz) δ 11.07 (brs, 1H), 7.64 (d, 1H, J = 1.7 Hz), 7.60 (d, 1H, J = 8.3 Hz), 7.32 (dd, 1H, J = 8.3 Hz, J = 1.7 Hz), 3.93 (d, 2H, J = 12.0 Hz), 3.47-3.52 (m, 1H), 3.18-3.25 (m, 2H), 3.08-3.13 (m, 2H), 2.93 2.98 (m, 2H), 2.73 (s, 3H), 2.15 (d, 2H, J = 12.0 Hz), 2.07-2.10 (m, 2H), 1.67-1.79 (m, 2H) ESI-MS |

TABLE 1-continued

| Example | Structure | IUPAC Name | Activity | Analytical Data |
|---|---|---|---|---|
| | | | | m/z for $C_{16}H_{22}Cl_2N_6$; expected 369.3 found 369.0/371.0 $[M + H]^+$, 367.3/369.3 $[M - H]^-$ |
| 177 | 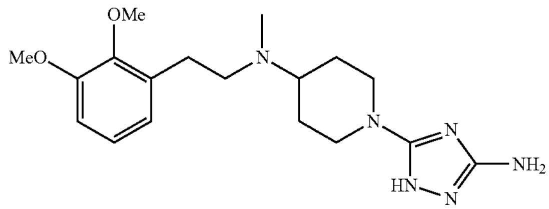 [SMILES: COc1cccc(CCN(C)C2CCN(c3nc(N)n[nH]3)CC2)c1OC] | 1-(3-amino-1H-1,2,4-triazol-5-yl)-N-(2,3-dimethoxyphenethyl)-N-methylpiperidin-4-amine | D | $^1$H NMR (DMSO-$d_6$, 500 MHz) δ 11.20 (s, 1H), 7.44 (brs, 1H), 7.02 (t, 1H, J = 8.0 Hz), 6.96 (d, 1H, J = 7.0 Hz), 6.86 (d, 1H, J = 6.5 Hz), 3.95 (d, 2H, J = 12.0 Hz), 3.78 (s, 3H), 3.75 (s, 3H), 3.54 (t, 1H, J = 11.0 Hz), 3.23 (t, 1H, J = 8.5 Hz), 3.09 (d, 2H, J = 8.5 Hz), 3.00 (m, 3H), 2.74 (d, 3H, J = 4.5 Hz), 2.16 (d, 1H, J = 12.5 Hz), 2.08 (d, 1H, J = 12.0 Hz), 1.74 (m, 2H). ESI-MS m/z for $C_{18}H_{28}N_6O_2$ expected 360.2, found 361.2 $[M + H]^+$ |
| 178 | 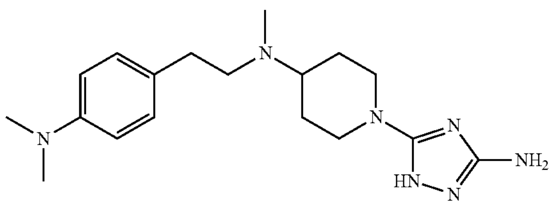 [SMILES: CN(C)c1ccc(CCN(C)C2CCN(c3nc(N)n[nH]3)CC2)cc1] | 1-(3-amino-1H-1,2,4-triazol-5-yl)-N-(4-(dimethylamino)phenethyl)-N-methylpiperidin-4-amine | D | $^1$H NMR (DMSO-$d_6$, 500 MHz) δ 11.20 (brs, 1H), 7.49 (brs, 2H), 7.40 (s, 2H), 3.94 (d, 2H, J = 11.5 Hz), 3.52 (s, 1H), 3.30 (t, 1H, J = 10.5 Hz), 3.17 (m, 2H), 3.09 (m, 2H), 3.02 (s, 6H), 2.97 (m, 2H), 2.73 (d, 3H, J = 4.5 Hz), 2.17 (d, 1H, J = 11.5 Hz), 2.09 (d, 1H, J = 11.5 Hz), 1.74 (m, 2H). ESI-MS m/z for $C_{18}H_{29}N_7$, expected 343.2, found 344.2 $[M + H]^+$ |
| 179 | 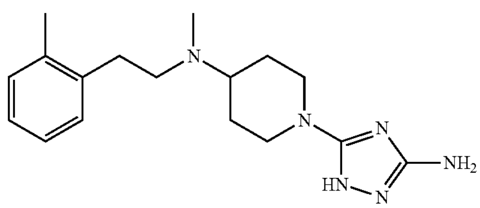 [SMILES: Cc1ccccc1CCN(C)C1CCN(c2nc(N)n[nH]2)CC1] | 1-(3-amino-1H-1,2,4-triazol-5-yl)-N-methyl-N-(2-methylphenethyl)piperidin-4-amine | D | $^1$H NMR (DMSO-$d_6$, 500 MHz) δ 13.01 (brs, 1H), 11.37 (brs, 1H), 7.43 (brs, 1H), 7.23 (m, 1H), 7.16 (m, 3H), 3.95 (d, 2H, J = 12.5 Hz), 3.55 (t, 1H, J = 11.5 Hz), 3.12 (m, 4H), 2.97 (t, 2H, J = 12.0 Hz), 2.75 (d, 3H, J = 4.5 Hz), 2.32 (s, 3H), 2.18 (d, 1H, J = 11.5 Hz), 2.09 (d, 1H, J = 12.0 Hz), 1.74 (m, 2H). ESI-MS m/z for $C_{17}H_{26}N_6$ expected 314.2, found 315.2 $[M + H]^+$ |
| 180 | 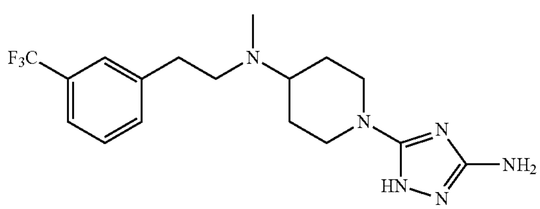 [SMILES: CN(CCc1cccc(C(F)(F)F)c1)C1CCN(c2nc(N)n[nH]2)CC1] | 1-(3-amino-1H-1,2,4-triazol-5-yl)-N-methyl-N-(3-(trifluoromethyl)phenethyl)piperidin-4-amine | B | $^1$H NMR (DMSO-$d_6$, 500 MHz) δ 12.95 (brs, 1H), 11.17 (s, 1H), 7.71 (m, 1H), 7.63 (m, 2H), 7.56 (m, 1H), 7.46 (brs, 1H), 3.94 (d, 2H, J = 12.0 Hz), 3.52 (t, 1H, d = 10.0 Hz), 3.25 (m, 4H), 2.96 (t, 2H, J = 12.0 Hz), 2.75 (d, 3H, J = 4.5 Hz), 2.17 (d, 1H, J = 11.5 Hz), 2.10 (d, 1H, J = 12.5 Hz), 1.74 (m, 2H) $^{19}$F NMR (DMSO-$d_6$, 500 MHz) δ -60.32. ESI-MS m/z for $C_{17}H_{23}F_3N_6$ expected 368.2, found 369.1 $[M + H]^+$ |
| 181 | 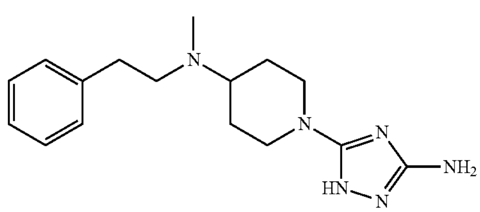 [SMILES: CN(CCc1ccccc1)C1CCN(c2nc(N)n[nH]2)CC1] | 1-(3-amino-1H-1,2,4-triazol-5-yl)-N-methyl-N-phenethylpiperidin-4-amine | D | $^1$H NMR (DMSO-$d_6$, 500 MHz) δ 13.00 (brs, 1H), 11.20 (s, 1H), 7.32 (m, 4H), 7.24 (t, 1H, J = 7.0 Hz), 3.94 (d, 2H, J = 12.0 Hz), 3.52 (t, 1H, J = 10.0 Hz), 3.32 (t, 1H, J = 12.0 Hz), 3.20 (m, 1H), 3.09 (m, 2H), 2.96 (t, 2H, J = 12.0 Hz), 2.73 (d, 3H, J = 4.0 Hz), 2.17 (d, 1H, J = 11.5 Hz), 2.09 (d, 1H, J = 12.0 Hz), 1.74 (m, 2H). ESI-MS m/z for $C_{16}H_{24}N_6$ expected 300.2, found 301.2 $[M + H]^+$ |

TABLE 1-continued

| Example | Structure | IUPAC Name | Activity | Analytical Data |
|---|---|---|---|---|
| 182 | (2,5-dimethoxyphenethyl group, N-methyl, piperidin-4-yl, N-methylpiperidine linked to 3-amino-1H-1,2,4-triazole) | 1-(3-amino-1H-1,2,4-triazol-5-yl)-N-(2,5-dimethoxyphenethyl)-N-methylpiperidin-4-amine | D | $^1$H NMR (DMSO-d$_6$, 500 MHz) δ 11.08 (brs, 1H), 6.91 (d, 1H, J = 8.8 Hz), 6.87 (d, 1H, J = 2.8 Hz), 6.79 (dd, 1H, J = 8.8 Hz, J = 2.8 Hz), 3.98-3.92 (m, 2H), 3.74 (s, 3H), 3.69 (s, 3H), 3.56-3.48 (m, 1H), 3.28-3.2 (m, 1H), 3.14 3.06 (m, 1H), 3.05-2.92 (m, 4H), 2.73 (d, 3H, J = 4.14), 2.19-2.13 (m, 1H), 2.1-2.04 (m, 1H), 1.81-1.66 (m, 2H) ESI-MS m/z for C$_{18}$H$_{28}$N$_6$O$_2$ expected 361.4, found 361.2/[M + H]$^+$ |
| 183 | (4-fluorophenethyl, N-methyl, piperidin-4-yl-N-methylpiperidine linked to 3-amino-1H-1,2,4-triazole) | 1-(3-amino-1H-1,2,4-triazol-5-yl)-N-(4-fluorophenethyl)-N-methylpiperidin-4-amine | C | $^1$H NMR (DMSO-d$_6$, 500 MHz) δ 11.16 (brs, 1H), 7.35 (dd, 2H, J = 8.5 Hz, J = 5.8 Hz), 7.16 (t, 2H, 8.8 Hz), 3.97-3.9 (m, 2H), 3.55-3.48 (m, 1H), 3.34-3.27 (m, 1H), 3.23-3.15 (m, 1H), 3.14-3.02 (m, 2H), 3.01-2.92 (m, 2H), 2.19 2.05 (m, 2H), 1.8-1.66 (m, 2H). $^{19}$F NMR (DMSO-d$_6$, 200 MHz) δ −115.5 ESI-MS m/z for C$_{16}$H$_{23}$FN$_6$; exoected 319.4 found 319.2/ [M + H]$^+$ |
| 184 | (2,6-dichlorophenethyl, N-methyl, piperidin-4-yl-N-methylpiperidine linked to 3-amino-1H-1,2,4-triazole) | 1-(3-amino-1H-1,2,4-triazol-5-yl)-N-(2,6-dichlorophenethyl)-N-methylpiperidin-4-amine | C | $^1$H NMR (DMSO-d$_6$, 500 MHz) d 11.6 (brs, 1H), 7.51 (d, 2H, J = 7.9 Hz), 7.35 (t, 1H, J = 7.9 Hz), 3.98-3.92 (m, 2H), 3.64-3.56 (m, 1H), 3.52-3.44 (m, 1H), 3.39-3.31 (m, 1H), 3.26-3.18 (m, 1H), 2.99 (brs, 3H), 2.8 (s, 3H), 2.22-2.15 (m, 1H), 2.13-2.07 (m, 1H), 1.83 1.68 (m, 2H). ESI-MS m/z for C$_{16}$H$_{22}$Cl$_2$N$_6$ expected 369.29, found 369.1/371.1 [M + H]$^+$. |
| 186 | (4-chlorophenethyl, N-(2,2,2-trifluoroethyl), piperidin-4-yl linked to 3-amino-1H-1,2,4-triazole) •HCl | 1-(3-amino-1H-1,2,4-triazol-5-yl)-N-(4-chlorophenethyl)-N-(2,2,2-trifluoroethyl)piperidin-4-amine hydrochloride | D | $^1$H NMR (DMSO-d$_6$, 500 MHz) δ (ppm) 7.31 (d, 2H, J = 8.3 Hz), 7.25 (d, 2H, J = 8.5 Hz), 3.77-3.74 (m, 2H), 3.32 (q, 2H), 2.92-2.87 (m, 2H), 2.78-2.74 (m, 3H), 2.69-2.66 (m, 2H), 1.70-1.68 (m, 2H), 1.49-1.40 (m, 2H). ESI-MS: m/z for C$_{17}$H$_{22}$ClF$_3$N$_6$: expected 402.85; found 403.1/405.0 [M + H], 401.2/403.2 [M − H] |
| 188 | (4-chlorophenethyl, N-(2-methoxyethyl), piperidin-4-yl linked to 3-amino-1H-1,2,4-triazole) •HCl | 1-(3-amino-1H-1,2,4-triazol-5-yl)-N-(4-chlorophenethyl)-N-(2-methoxyethyl)piperidin-4-amine hydrochloride | B | $^1$H NMR (DMSO-d$_6$, 500 MHz) δ (ppm) 10.90 (brs, 1H), 7.26 (d, 2H, J = 8.47 Hz), 7.20 (d, 2H, J = 8.47 Hz), 5.47 (brs, 2H), 3.78-3.75 (m, 2H), 3.25 (t, 2H), 3.17 (s, 3H), 2.61-2.53 (m, 9H), 1.56-1.54 (m, 2H), 1.34-1.26 (m, 2H). ESI-MS m/z for C$_{17}$H$_{22}$ClF$_3$N$_6$: expected 402.85; found 403.1/405.0 [M + H], 401.2/403.2 [M − H] |
| 191 | (3-bromobenzyl sulfonamide linked to piperidin-4-yl-3-amino-1H-1,2,4-triazole) | N-(1-(3-amino-1H-1,2,4-triazol-5-yl)piperidin-4-yl)-1-(3-bromophenyl)methanesulfonamide | C | $^1$H NMR (DMSO-d$_6$, 500 MHz) δ (ppm) 10.92 (brs, 1H); 7.59 (brs, 1H); 7.54 (d, 1H, J = 7.9 Hz); 7.39 (d, 1H, J = 7.7 Hz); 7.34 (dd, 1H, J = 7.9 Hz, J = 7.7 Hz); 7.22(d, 1H, J = 7.5 Hz); 5.69 (brs, 1H); 4.37 (s, 2H); 3.70 (d, 2H, J = 12.6 Hz), 3.18 (brs, 1H); 2.66 (brs, 1H); 1.76 (d, 2H, J = 10.2 Hz), 1.37 (ddd, 2H, J = 23.1 Hz, J = 12.2 Hz, J = 3.9) LC- |

TABLE 1-continued

| Example | Structure | IUPAC Name | Activity | Analytical Data |
|---|---|---|---|---|
| | | | | MS: m/z for $C_{14}H_{19}BrN_6O_2S$: expected 415.31; found 415.3/417.3 [M + H], 413.2/415.2 [M − H] |
| 192 | 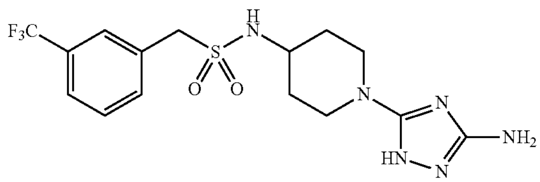 [SMILES: Nc1n[nH]c(N2CCC(NS(=O)(=O)Cc3cccc(C(F)(F)F)c3)CC2)n1] | N-(1-(3-amino-1H-1,2,4-triazol-5-yl)piperidin-4-yl)-1-(3-(trifluoromethyl)phenyl)methanesulfonamide | C | $^1$H NMR (DMSO-$d_6$, 500 MHz) δ (ppm) 10.97 (brs, 1H); 7.75 (brs, 1H); 7.71(d, 1H, J = 7.2 Hz); 7.69 (d, 1H, J = 7.9 Hz); 7.62(dd, 1H, J = 7.9 Hz, J = 7.5 Hz); 7.24 (d, 1H, J = 7.5 Hz); 5.59 (brs, 1H); 4.45 (s, 2H); 3.68-3.71 (m, 2H); 3.20-3.22 (m, 1H); 2.64-2.67 (m, 2H); 1.74 1.77 (m, 2H); 1.38 (ddd, 2H, J = 23.1 Hz, J = 12.4 Hz, J = 3.9). LC-MS: m/z for $C_{15}H_{19}F_3N_6O_2S$: expected 404.4; found 405.4 [M + H], 403.4 [M − H] |
| 193 | 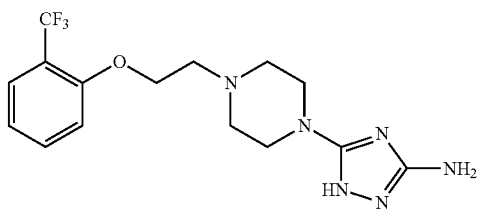 | 5-(4-(2-(2-(trifluoromethyl)phenoxy)ethyl)piperazin-1-yl)-1H-1,2,4-triazol-3-amine | E | $^1$H NMR (DMSO-$d_6$, 500 MHz) δ 11.6 (brs, 1H), 7.63-7.58 (m, 2H), 7.28 (d, 1H, J = 8.3 Hz), 7.08 (t, 1H, J = 7.5 Hz), 5.69 (brs, 2H), 4.25 (brs, 2H), 3.16 (brs, 4H), 2.78 (brs, 2H), 2.57 (brs, 4H). $^{19}$F NMR (DMSO-$d_6$, 200 MHz) δ −60.16. ESI-MS m/z for $C_{15}H_{19}F_3N_6O$ expected 357.3 found 358.2 [M + H]$^+$. |
| 194 | 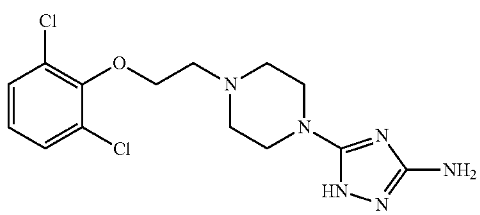 | 5-(4-(2-(2,6-dichlorophenoxy)ethyl)piperazin-1-yl)-1H-1,2,4-triazol-3-amine | D | $^1$H NMR (DMSO-$d_6$, 500 MHz) δ 10.93 (brs, 1H), 7.48 (d, 2H, J = 8.3 Hz), 7.16 (dd, 1H, J = 8.1 Hz, J = 8.1 Hz), 5.73 (brs, 2H), 4.13 (t, 2H, J = 5.6 Hz), 3.35-3.38 (m, 4H), 3.11-3.17 (m, 4H), 2.77 (dd, 2H, J = 5.5 Hz, J = 5.6 Hz). ESI-MS m/z for $C_{14}H_{18}Cl_2N_6O$ expected 357.2; found 357.1/359.0/361.0 [M + H]$^+$. |
| 195 | 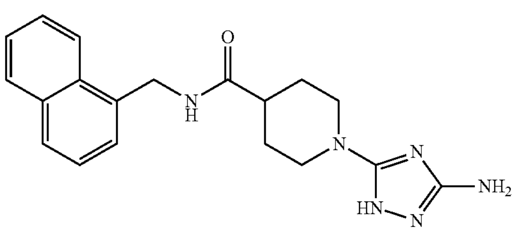 [SMILES: Nc1n[nH]c(N2CCC(C(=O)NCc3cccc4ccccc34)CC2)n1] | 1-(3-amino-1H-1,2,4-triazol-5-yl)-N-(naphthalen-1-ylmethyl)piperidine-4-carboxamide | E | $^1$H NMR (DMSO-$d_6$, 200 MHz) δ 8.38-8.27 (m, 1H), 8.19-7.76 (m, 3H), 7.58-7.32 (m, 4H), 4.67 (d, 2H, J = 7 Hz), 3.85-3.68 (m, 2H), 2.73-2.52 (m, 2H), 2.41-2.23 (m, 1H), 1.72 1.50 (m, 4H), 1.23-1.15 (m, 1H). ESI MS for $C_{19}H_{22}N_6O$ expected 350.49; found m/z 351.5. |
| 196 | 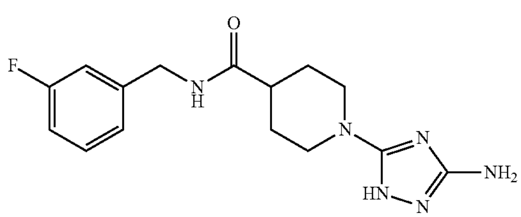 | 1-(3-amino-1H-1,2,4-triazol-5-yl)-N-(3-fluorobenzyl)piperidine-4-carboxamide | E | $^1$H NMR (DMSO-$d_6$, 600 MHz) δ 10.81 (bs, 1H), 7.32-7.28 (m, 2H), 7.27-7.22 (m, 4H), 7.20-7.16 (m, 1H), 7.12-7.07 (m, 2H), 5.64 (bs, 1H), 4.04-4.00 (m, 1H), 3.78-3.71 (m, 1H), 3.69-3.59 (m, 3H), 3.20 (s, 3H), 2.74-2.68 (m, 2H), 2.67-2.59 (m, 1H), 2.58-2.50 (m, 3H), 1.52-1.47 (m, 1H), 1.46-1.39 (m, 1H), 1.36-1.27 (m, 1H), 1.25-1.17 (m, 1H). ESI MS for $C_{24}H_{31}Cl_2N_6O$; expected 455.01; found m/z 455.5/457.5 |

TABLE 1-continued

| Example | Structure | IUPAC Name | Activity | Analytical Data |
|---|---|---|---|---|
| 197 | [structure] | 1-(3-amino-1H-1,2,4-triazol-5-yl)-N-(2-methoxybenzyl)piperidine-4-carboxamide | E | $^1$H NMR (DMSO-$d_6$, 500 MHz) δ 11 (brs, 1H), 8.16-8.1 (m, 1H), 7.2 (t, 1H, J = 7.4 Hz), 7.08 (d, 1H, J = 7.2 Hz), 6.94 (d, 1H, J = 8.2), 6.88 (t, 1H, J = 7.2 Hz), 5.5 (brs, 2H), 4.19 (d, 2H, J = 5.5 Hz), 3.8(brs, 2H), 3.77 (s, 3H), 2.67-2.57 (m, 2H), 2.36-2.28 (m, 1H), 1.7-1.62 (m, 2H), 1.6-1.5 (m, 2H). ESI MS found m/z 331.5 [M + H], 329.5 [M − H] |
| 198 | [structure] | 1-(3-amino-1H-1,2,4-triazol-5-yl)-N-(2-chlorobenzyl)piperidine-4-carboxamide | E | $^1$H NMR (DMSO-$d_6$, 500 MHz) δ 11.00 (bs, 1H), 8.34-8.17 (m, 1H), 7.36-7.32 (m, 1H), 7.26-7.16 (m, 3H), 5.46 (bs, 1H), 4.22 (d, 2H, J = 5.6 Hz), 3.78-3.69 (m, 2H), 2.61-2.51 (m, 2H), 2.32-2.24 (m, 1H), 1.67-1.57 (m, 2H), 1.55-1.46 (m, 2H). ESI MS for $C_{15}H_{19}ClN_6O$; expected 334.80; found m/z 335.3/337.3. |
| 199 | [structure] | 1-(3-amino-1H-1,2,4-triazol-5-yl)-N-(3,4-difluorobenzyl)piperidine-4-carboxamide | E | $^1$H NMR (DMSO-$d_6$, 200 M Hz) δ 7.24-6.97 (m, 3H), 4.29 (s, 2H), 3.86-3.7 (m, 2H), 3.15-2.92 (m, 2H), 2.48 (brs, 1H), 1.9-1.6 (m, 4H). $^{19}$F NMR (DMSO-$d_6$, 200 MHz) δ −140 (d, 1F, J = 19.5 Hz), −142.5 (d, 1F, J = 19.5 Hz). ESI-MS m/z for $C_{15}H_{18}F_2IN_6O$, expected 336.2 found m/z 337.5 [M + H], 335.2 [M − H] |
| 200 | [structure] •2HCl | 1-(3-amino-1H-1,2,4-triazol-5-yl)-N-(1-(4-chlorophenyl)propan-2-yl)-N-methylpiperidin-4-amine | A | $^1$H NMR (DMSO-$d_6$, 500 Hz) d 11.18 (brs, 1H), 7.39-7.33 (m, 4H), 4.00-3.92 (m, 2H), 3.70 (brs, 1H), 3.50 (brs, 1H), 3.28 (brs, 1H), 3.06 2.93 (m, 2H), 2.79 (brs, 1H), 2.70 (s, 3H), 2.33-2.07 (m, 2H), 1.97-1.90 (m, 2H), 1.13 (d, 3H). ESI-LCMS m/z for $C_{17}H_{25}ClN_6$ expected 348.9; found 349.4/351.4 [M + H]$^+$ |
| 201 | [structure] | 1-(3-amino-1H-1,2,4-triazol-5-yl)-N-(2,4-dimethoxybenzyl)piperidine-4-carboxamide | E | $^1$H NMR (DMSO-$d_6$, 500 MHz) δ 8.09 (t, 1H, J = 5.6 Hz), 6.98 (d, 1H, J = 8.3 Hz), 6.49 (d, 1H, J = 2.3 Hz), 6.43 (dd, 1H, J = 2.4 Hz, J = 8.3 Hz), 4.09 (d, 2H, J = 5.6 Hz), 3.78-3.75 (m, 2H), 3.73 (s, 3H), 3.69 (s, 3H), 2.9 (brs, 2H), 2.43 2.35 (m, 1H), 1.74-1.68 (m, 2H), 1.6-1.46 (m, 2H). ESI MS found m/z 361.5 [M + H], 359.5 [M − H] |
| 202 | [structure] | 1-(3-amino-1H-1,2,4-triazol-5-yl)-N-((2-methyl-5-(trifluoromethyl)furan-3-yl)methyl)piperidine-4-carboxamide | E | $^1$H NMR (DMSO-$d_6$, 500 MHz) δ 8.35-8.23 (m, 1H), 6.16 (s, 1H), 5.48 (s, 2H), 4.18-4.1 (m, 2H), 3.83-3.7 (m, 2H), 2.68-2.5 (m, 2H), 2.26 (s, 3H), 1.7-1.4 (m, 4H) 19F NMR (DMSO-d6, 200 MHz) δ −59.4 (s, 3F). ESI MS found m/z 373.5 [M + H], 371.4 [M − H] |

TABLE 1-continued

| Example | Structure | IUPAC Name | Activity | Analytical Data |
|---|---|---|---|---|
| 203 | 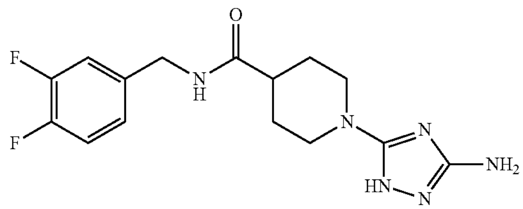 [SMILES: Nc1n[nH]c(N2CCC(C(=O)NCc3ccc(F)c(F)c3)CC2)n1] | 1-(3-amino-1H-1,2,4-triazol-5-yl)-N-(3,4-difluorobenzyl)piperidine-4-carboxamide | E | $^1$H NMR (DMSO-d$_6$, 200 MHz) δ 7.24-6.97 (m, 3H), 4.29 (s, 2H), 3.86-3.7 (m, 2H), 3.15 2.92 (m, 2H), 2.48 (brs, 1H), 1.9-1.6 (m, 4H) 19F NMR (DMSO-d6, 200 MHz) δ −140 (d, 1F, J = 19.5 Hz), −142.5 (d, 1F, J = 19.5 Hz). ESI MS found m/z 337.5 [M + H], 335.2 [M − H] |
| 204 | 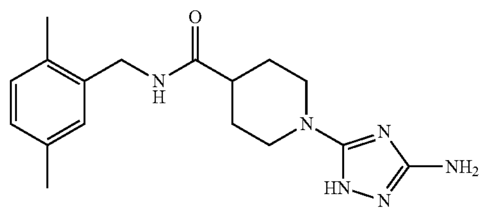 [SMILES: Cc1ccc(C)c(CNC(=O)C2CCN(c3nc(N)n[nH]3)CC2)c1] | 1-(3-amino-1H-1,2,4-triazol-5-yl)-N-(2,5-dimethylbenzyl)piperidine-4-carboxamide | E | $^1$H NMR (DMSO-d$_6$, 500 MHz) δ 7.03 (d, 1H, J = 7.5 Hz), 6.97 (s, 1H), 6.95 (d, 1H, J = 7.5 Hz), 5.5 (brs, 2H), 4.18 (d, 2H, J = 5.5 Hz), 2.67-2.6 (m, 2H), 2.38-2.3 (m, 1H), 2.24 (s, 3H), 2.19 (s, 3H), 1.85 (brs, 2H), 1.69-1.63 (m, 2H), 1.62-1.53 (m, 2H). ESI MS found m/z 329.5 [M + H], 327.4 [M − H] |
| 205 | ·HCl | 1-(3-amino-1H-1,2,4-triazol-5-yl)-N-(4-(trifluoromethoxy)benzyl)piperidine-4-carboxamide | E | $^1$H NMR (DMSO-d$_6$, 500 MHz) δ 11.09 (brs, 1H), 8.4 (s. 1H), 7.32 (brs, 4H), 5.73 (brs, 2H), 4.27 (brs, 2H), 3.8 (brs, 2H), 2.3 (brs, 1H), 1.8-1.5 (m, 4H). ESI MS found m/z 385.5 [M + H], 385.3 [M − H] |
| 206 | 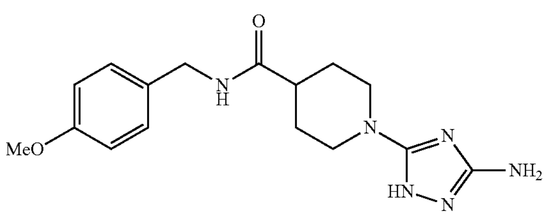 [SMILES: COc1ccc(CNC(=O)C2CCN(c3nc(N)n[nH]3)CC2)cc1] | 1-(3-amino-1H-1,2,4-triazol-5-yl)-N-(4-methoxybenzyl)piperidine-4-carboxamide | E | $^1$H-NMR (DMSO-d$_6$, 200 MHz): δ 8.21 (bs, 1H), 7.11 (J$_{AA'BB'}$, 2H, J = 8.6 Hz), 6.83 (J$_{AA'BB'}$, 2H, J = 8.6 Hz), 5.50 (bs, 1H), 4.14 (d, 2H, J = 5.5 Hz), 3.84-3.71 (m, 2H), 3.68 (s, 3H), 2.70-2.51 (m, 3H), 2.37-2.07 (m, 2H), 1.70-1.40 (m, 5H), 1.38-1.13 (m, 2H) ESI MS for C$_{16}$H$_{22}$N$_6$O$_2$; expected 330.2; found m/z 331.5 |
| 207 | 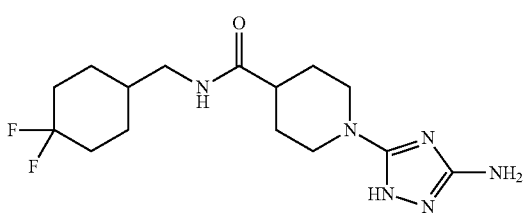 [SMILES: Nc1n[nH]c(N2CCC(C(=O)NCC3CCC(F)(F)CC3)CC2)n1] | 1-(3-amino-1H-1,2,4-triazol-5-yl)-N-((4,4-difluorocyclohexyl)methyl)piperidine-4-carboxamide | E | $^1$H NMR (DMSO-d$_6$, 500 MHz) δ 7.93 (t, 1H, J = 5.8 Hz), 7.42 (brs, 2H), 3.79-3.71 (m, 2H), 2.95-2.88 (m, 4H), 2.36-2.3 (m, 1H), 1.98-1.9 (m, 2H), 1.77-1.72 (m, 1H), 1.71-1.63 (m, 5H), 1.57-1.46 (m, 3H), 1.13-1.05 (m, 2H). ESI MS for C$_{15}$H$_{24}$F$_2$N$_6$O expected 342.39; found m/z 343.5 [M + H], 341.4 [M − H] |
| 208 | 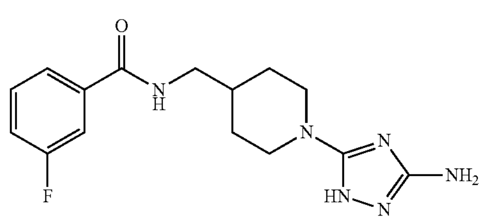 | N-((1-(3-amino-1H-1,2,4-triazol-5-yl)piperidin-4-yl)methyl)-3-fluorobenzamide | E | $^1$H NMR (DMSO-d$_6$, 600 MHz) δ 10.86 (brs, 1H), 7.64 (d, 2H), 7.57-7.51 (m, 2H), 7.46-7.42 (m, 2H), 7.35-7.3 (m, 3H), 7.21 (AA'BB', 4H), 3.86-3.79 (m, 2H), 3.7-3.66 (m, 2H), 2.7-2.61 (m, 5H), 2.59-2.51 (m, 2H), 1.7-1.62 (m, 2H), 1.49-1.4 (m, 2H). ESI MS found m/z 487.6 [M + H], 485.5 (M − 1) |

TABLE 1-continued

| Example | Structure | IUPAC Name | Activity | Analytical Data |
|---|---|---|---|---|
| 209 | 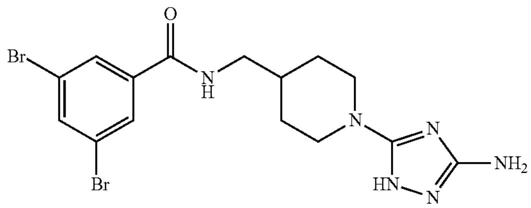 | N-((1-(3-amino-1H-1,2,4-triazol-5-yl)piperidin-4-yl)methyl)-3,5-dibromobenzamide | E | $^1$H NMR (DMSO-$d_6$, 500 MHz) δ 8.75 (t, 1H, J = 5.7), 8.01 (s, 3H), 3.76-3.69 (m, 2H), 2.9 (brs, 2H), 1.9-1.67 (m, 3H), 1.26-1.12 (m, 4H). ESI MS found m/z 459.2/461.3 [M + H], 457.2 [M − H] |
| 210 | 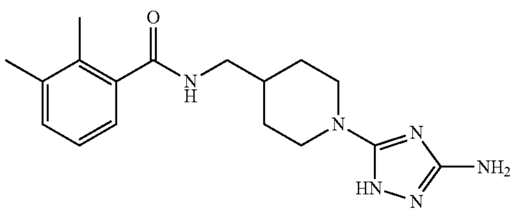 [SMILES: Cc1cccc(C(=O)NCC2CCN(c3nc(N)n[nH]3)CC2)c1C] | N-((1-(3-amino-1H-1,2,4-triazol-5-yl)piperidin-4-yl)methyl)-2,3-dimethylbenzamide | E | $^1$H NMR (DMSO-$d_6$, 500 MHz) δ 10.86 (bs, 1H), 8.25-8.20 (m, 1H), 7.19-7.14 (m, 1H), 7.10-7.04 (m, 2H), 5.68 (bs, 1H), 3.80-3.72 (m, 2H), 3.12-3.06 (m, 2H), 2.69-2.51 (m, 2H), 2.22 (s, 3H), 2.16 (s, 3H), 1.68-1.57 (m, 3H), 1.22-1.10 (m, 2H). ESI MS for $C_{17}H_{24}N_6O$; expected 328.41; found m/z 329.5 |
| 211 | 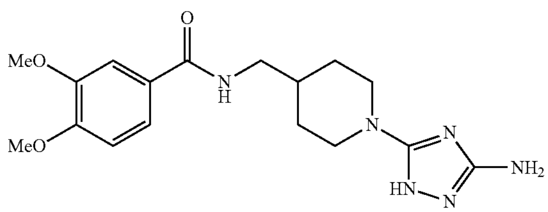 [SMILES: COc1ccc(C(=O)NCC2CCN(c3nc(N)n[nH]3)CC2)cc1OC] | N-((1-(3-amino-1H-1,2,4-triazol-5-yl)piperidin-4-yl)methyl)-3,4-dimethoxybenzamide | E | $^1$H NMR (DMSO-$d_6$, 500 MHz) δ 8.32-8.27 (m, 1H), 7.42-7.38 (m, 1H), 7.37-7.34 (m, 1H), 6.91 (d, 1H, J = 8.5 Hz), 5.45 (brs, 2H), 3.71 (s, 6H), 3.68 (brs, 2H), 3.09-3.03 (m, 2H), 2.56-2.48 (m, 2H), 1.62-1.53 (m, 3H), 1.12-1.02 (m, 2H). ESI MS found m/z 361.4 [M + H], 359.3 [M − H] |
| 212 | 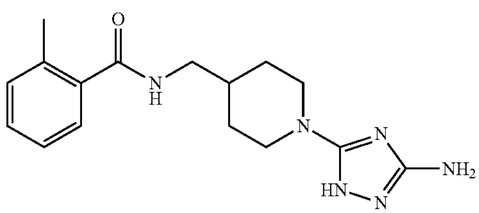 [SMILES: Cc1ccccc1C(=O)NCC1CCN(c2nc(N)n[nH]2)CC1] | N-((1-(3-amino-1H-1,2,4-triazol-5-yl)piperidin-4-yl)methyl)-2-methylbenzamide | E | $^1$H NMR (DMSO-$d_6$, 600 MHz) δ 8.19 (t, 1H), 7.23-7.19 (m, 2H), 7.16-7.12 (m, 2H), 3.73 3.67 (m, 2H), 3.03 (t, 2H), 2.58-2.5 (m, 2H), 2.23 (s, 3H), 1.61-1.55 (m, 3H), 1.14-1.07 (m, 2H) ESI MS for $C_{16}H_{22}N_6O$ calculated 314.38; found m/z 315.4 [M + H], 313.2 [M − H] |
| 213 | 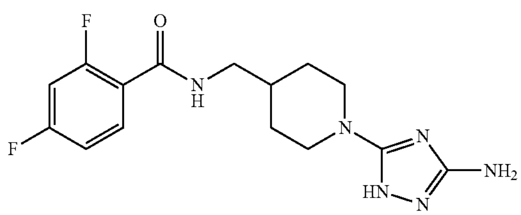 [SMILES: Nc1n[nH]c(N2CCC(CNC(=O)c3ccc(F)cc3F)CC2)n1] | N-((1-(3-amino-1H-1,2,4-triazol-5-yl)piperidin-4-yl)methyl)-2,4-difluorobenzamide | E | $^1$H NMR (DMSO-$d_6$, 500 MHz) δ 10.9 (brs, 1H), 8.33 (t, 1H, J = 5.3 Hz), 7.62 (q, 1H, J = 15.2 Hz), 7.3 (dt, 1H, J = 10.5 Hz, J = 2.3 Hz), 7.12 (dt, 1H, J = 8.5 Hz, J = 2.3 Hz), 5.5 (brs, 2H), 3.74 (d, 2H, J = 12.4 Hz), 3.1 (t, 2H, J = 6 Hz), 2.57 (brs, 2H), 1.66-1.58 (m, 3H), 1.17-1.09 (m, 2H). $^{19}$F NMR (DMSO-$d_6$, 200 MHz) δ −106.44 (d, 1F, J = 9.8 Hz), −109.15 (d, 1F, J = 9.8 Hz). ESI MS for $C_{15}H_{18}F_2N_6O$ calculated 336.34; found m/z 337.5 [M + H], 335.3 [M − H] |
| 214 | •2HCl | 3-amino-1-(4-(3-amino-1H-1,2,4-triazol-5-yl)piperazin-1-yl)-3-(2-fluorophenyl)propan-1-one dihydrochloride | E | $^1$H NMR (DMSO-$d_6$, 500 MHz) δ 8.66 (d, J = 3.9 Hz, 2H), 7.80-7.75 (m, 1H), 7.45-7.10 (m, 1H), 7.30-7.23 (m, 2H), 4.86-4.80 (m, 1H), 3.55 (brs, 4H), 3.40-3.23 (m, 5H), 3.07 (dd, J = 16.7 Hz, J = 5.9 Hz, 1H). $^{19}$F NMR (DMSO-$d_6$, 500 Hz) −116.48, s ESI MS for $C_{15}H_{20}FN_7O$ calculated 333.4, found m/z 334.4 [M + H] |

TABLE 1-continued

| Example | Structure | IUPAC Name | Activity | Analytical Data |
|---|---|---|---|---|
| 215 | ·2HCl | 3-amino-1-(4-(3-amino-1H-1,2,4-triazol-5-yl)piperazin-1-yl)-3-(4-fluorophenyl)propan-1-one dihydrochloride | E | $^1$H NMR (DMSO-d$_6$, 500 MHz) δ 8.52 (brs, 2H), 7.6 (dd, 2H, J = 8.5 Hz), 7.22 (t, 2H, J = 8.5 Hz), 4.62-4.56 (m, 1H), 3.54-3.47 (m, 5H), 3.3-3.19 (m, 3H), 3.07 (ddd, 2H, J = 97.5 Hz, J = 16.5 Hz, J = 5.5 Hz). ESI MS for C$_{15}$H$_{20}$FN$_7$O calculated 333.4, found m/z 334.4 [M + H] |
| 216 | ·2HCl | 5-(4-(2-(4-chlorophenoxy)butyl)piperazin-1-yl)-1H-1,2,4-triazol-3-aminedihydrochloride | C | $^1$H NMR (DMSO-d$_6$, 500 MHz) δ ppm 11.42 (brs, 1H), 7.32 (d, JAB = 8.9 Hz, 2H), 7.06 (d, JAB = 8.9 Hz, 2H), 4.97 (brs, 1H), 3.86 (brs, 2H), 3,56-3.40 (m, 6H), 3.20 (brs, 2H), 1.63 1.58 (m, 2H), 0.84 (t, J = 7.5 Hz, 3H). ESI MS found m/z 380.4/382.4 [M + H], 378.3/380.2 [M − H] |
| 217 | 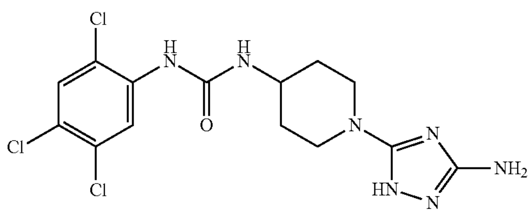 [SMILES: Nc1n[nH]c(N2CCC(NC(=O)Nc3cc(Cl)c(Cl)cc3Cl)CC2)n1] | 1-(1-(3-amino-1H-1,2,4-triazol-5-yl)piperidin-4-yl)-3-(2,4,5-trichlorophenyl)urea | E | $^1$H NMR (DMSO-d$_6$, 600 MHz) δ 8.49 (s, 1H), 8.16 (s, 1H), 7.77 (s, 1H), 7.26-7.21 (m, 1H), 3.65-3.57 (m, 3H), 2.90-2.80 (m, 2H), 1.84 1.77 (m, 2H), 1.41-1.30 (m, 2H). ESI MS for C$_{14}$H$_{16}$Cl$_3$N$_7$O expected 404.69; found m/z 404.3/406.3 |
| 218 | 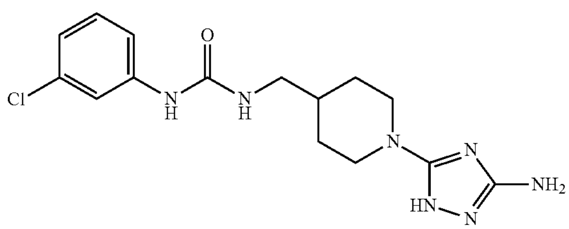 [SMILES: Nc1n[nH]c(N2CCC(CNC(=O)Nc3cccc(Cl)c3)CC2)n1] | 1-(1-(3-amino-1H-1,2,4-triazol-5-yl)piperidin-4-yl)methyl)-3-(3-chlorophenyl)urea | E | $^1$H NMR (DMSO-d$_6$, 500 MHz) δ 8.65 (s, 1H), 7.66 (t, 1H, J = 2.1 Hz), 7.23-7.19 (m, 1H), 6.92-6.89 (m, 1H), 6.32 (t, 1H, J = 5.6 Hz), 5.67 (brs, 2H), 3.81-3.75 (m, 2H), 2.98 (t, 2H, J = 6.2 Hz), 2.58 (brs, 2H), 1.63-1.57 (m, 2H), 1.52 (brs, 1H), 1.16-1.09 (m, 2H). ESI MS for C$_{15}$H$_{20}$ClN$_7$O expected 349.82; found m/z 350.3/352.4 [M + H], 348.3 [M − H] |
| 219 | 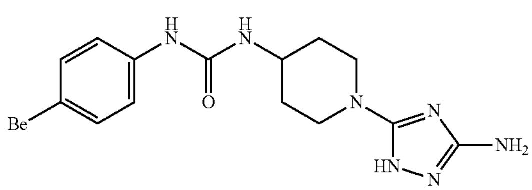 | 1-(1-(3-amino-1H-1,2,4-triazol-5-yl)piperidin-4-yl)-3-(4-bromophenyl)urea | E | $^1$H NMR (DMSO-d$_6$, 500 MHz) δ 8.44 (s, 1H), 7.4 (s, 1H), 7.33 (s, 4H), 6.2 (d, 1H, J = 7.6 Hz), 5.5 (brs, 2H), 3.7-3.5 (m, 3H), 2.88-2.7 (m, 2H), 1.84-1.7 (m, 2H), 1.45-1.22 (m, 2H). ESI MS found m/z 380.4/382.4 [M + H], 378.3/380.2 [M − H] |
| 220 | 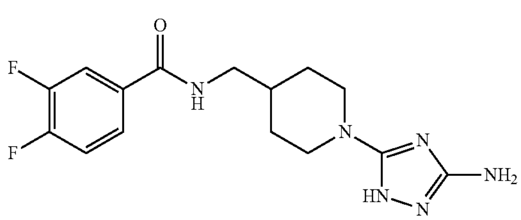 [SMILES: Nc1n[nH]c(N2CCC(CNC(=O)c3ccc(F)c(F)c3)CC2)n1] | N-((1-(3-amino-1H-1,2,4-triazol-5-yl)piperidin-4-yl)methyl)-3,4-difluorobenzamide | E | $^1$H NMR (DMSO-d$_6$, 500 MHz) δ 10.92 (brs, 1H), 10.14 (s, 1H), 7.84-7.77 (m, 1H), 7.4 7.34 (m, 1H), 7.28 (brs, 1H), 5.67 (brs, 2H), 3.8-3.74 (m, 2H), 2.64 (brs, 2H), 2.26-2.23 (m, 2H), 1.9 (brs, 1H), 1.67-1.61 (m, 2H), 1.26-1.17 (m, 2H). $^{19}$F NMR (DMSO-d$_6$, 200 MHz) δ −136.67 (d, 1F, J = 23 Hz), −144.53 (d, 1F, J = 23 Hz). ESI MS found m/z 337.4 [M + H], 335.3 [M − H] |

TABLE 1-continued

| Example | Structure | IUPAC Name | Activity | Analytical Data |
|---|---|---|---|---|
| 221 | 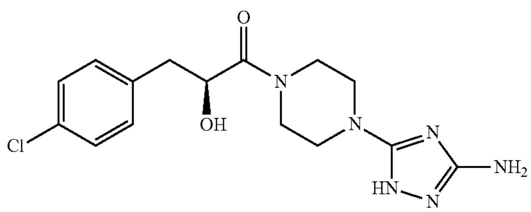 [SMILES: Nc1n[nH]c(N2CCN(C(=O)[C@@H](O)Cc3ccc(Cl)cc3)CC2)n1] | (S)-1-(4-(3-amino-1H-1,2,4-triazol-5-yl)piperazin-1-yl)-3-(4-chlorophenyl)-2-hydroxypropan-1-one | D | $^1$H NMR (DMSO-d$_6$, 500 MHz) δ 7.31 (d, 2H, J = 8.1 Hz), 7.26 (d, 2H, J = 8.1 Hz), 5.67 (brs, 2H), 5.13 (brs, 1H), 4.51 (brs, 1H), 3.60-3.54 (m, 2H), 3.49-3.40 (m, 2H), 3.18-3.12 (m, 1H), 3.1 (brs, 3H), 2.90-2.86 (m, 1H), 2.76 2.70 (m, 1H). ESI MS calculated for C$_{15}$H$_{19}$ClN$_6$O$_2$ found m/z 351.4/353.4 [M + H], 349.2/351.4 [M − H] |
| 222 | 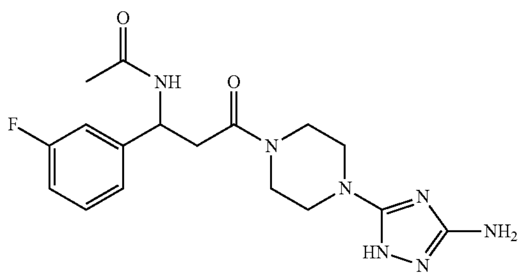 [SMILES: CC(=O)NC(CC(=O)N1CCN(c2nc(N)n[nH]2)CC1)c1cccc(F)c1] | N-(3-(4-(3-amino-1H-1,2,4-triazol-5-yl)piperazin-1-yl)-1-(3-fluorophenyl)-3-oxopropyl)acetamide | E | $^1$H NMR (DMSO-d$_6$, 500 MHz) δ 8.26 (d, 1H, J = 8.1 Hz), 7.34-7.28 (m, 1H), 7.13-7.09 (m, 2H), 7.02-6.98 (m, 1H), 5.63 (brs, 2H), 5.17 (q, 1H, J = 14.5 Hz), 2.75 (ddd, 2H, J = 44 Hz, J = 15.6 Hz, J = 6.4 Hz), 3.47-3.37 (m, 4H), 3.13-3.04 (m, 2H), 3.04-2.97 (m, 2H), 1.78 (s, 3H). $^{19}$F NMR (DMSO-d$_6$, 200 MHz) δ −112.8 (s, 1F). ESI MS calculated for C$_{17}$H$_{22}$FN$_7$O$_2$ expected 375.4; found m/z 376.5 [M + H], 374.4 [M − H] |
| 223 | 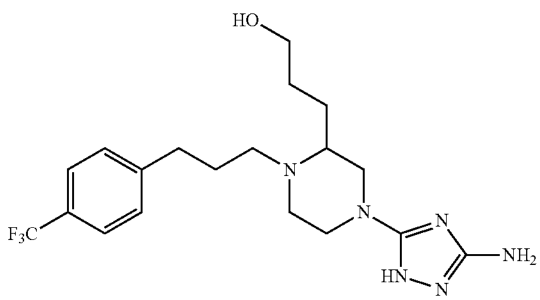 [SMILES: Nc1n[nH]c(N2CCN(CCCc3ccc(C(F)(F)F)cc3)C(CCCO)C2)n1] | 3-(4-(3-amino-1H-1,2,4-triazol-5-yl)-1-(3-(4-(trifluoromethyl)phenyl)propyl)piperazin-2-yl)propan-1-ol | C | $^1$H NMR (DMSO-d$_6$, 500 MHz) δ 10.88 (bs, 1H), 7.64 (AA'BB', 2H, J = 8 Hz), 7.46 (AA'BB', 2H, J = 8 Hz), 3.94-3.86 (m, 1H) 3.82-3.74 (m, 1H), 3.71-3.37 (m,7H), 3.18-3.09 (m, 1H), 3.08-2.98 (m, 1H), 2.81-2.63 (m, 2H), 2.09-1.87 (m, 3H), 1.68-1.48 (m, 2H), 1.47-1.33 (m, 2H). $^{19}$F NMR (DMSO-d$_6$, 200 MHz) δ −60.06. ESI MS for C$_{19}$H$_{27}$F$_3$N$_6$O; expected 412.46; found m/z 413.3 |
| 224 | 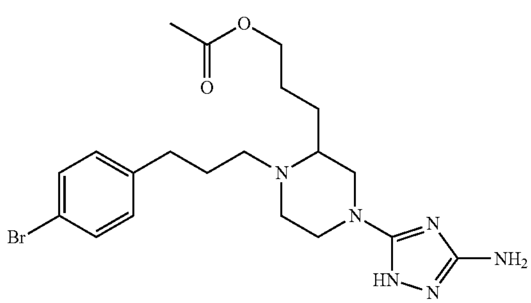 [SMILES: CC(=O)OCCCC1CN(c2nc(N)n[nH]2)CCN1CCCc1ccc(Br)cc1] | 3-(4-(3-amino-1H-1,2,4-triazol-5-yl)-1-(3-(4-bromophenyl)propyl)piperazin-2-yl)propylacetate | B | |
| 225 | 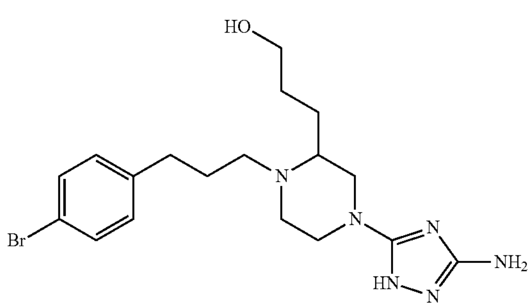 [SMILES: Nc1n[nH]c(N2CCN(CCCc3ccc(Br)cc3)C(CCCO)C2)n1] | 3-(4-(3-amino-1H-1,2,4-triazol-5-yl)-1-(3-(4-bromophenyl)propyl)piperazin-2-yl)propan-1-ol | C | |

TABLE 1-continued

| Example | Structure | IUPAC Name | Activity | Analytical Data |
|---|---|---|---|---|
| 226 | 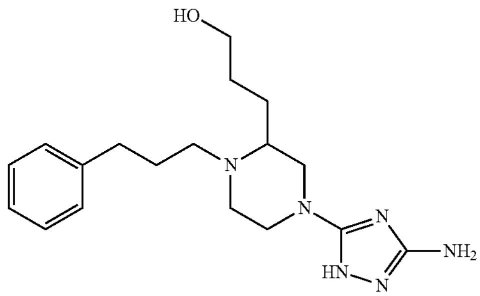 [SMILES: Nc1n[nH]c(N2CCN(CCCc3ccccc3)C(CCCO)C2)n1] | 3-(4-(3-amino-1H-1,2,4-triazol-5-yl)-1-(3-phenylpropyl)piperazin-2-yl)propan-1-ol | D | $^1$H NMR (CD$_3$OD, 500 MHz) δ (ppm) 7.26-7.20 (m, 2H), 7.20-7.15 (m, 2H), 7.15-7.10 (m, 1H), 3.54-3.46 (m, 2H), 3.46-3.40 (m, 1H), 3.29-3.27 (m, 2H), 3.09-3.01 (m, 1H), 2.90-2.82 (m, 2H), 2.77-2.70 (m, 1H), 2.66-2.54 (m, 2H), 2.47-2.37 (m, 2H), 1.86-1.71 (m, 2H), 1.68-1.56 (m, 2H), 1.48-1.36 (m, 2H). ESI MS for C$_{18}$H$_{28}$N$_6$O; expected 344.45; found m/z 345.3 |
| 227 | ·HCl | N-(1-(3-amino-1H-1,2,4-triazol-5-yl)-3-(hydroxymethyl)piperidin-4-yl)-1-(4-bromophenyl)methanesulfonamide hydrochloride | C | $^1$H NMR (CD$_3$OD, 500 MHz) δ (ppm) 7.51 (AA'BB', 2H, J = 8.4 Hz), 7.35 (AA'BB', 2H, J = 8.3 Hz), 4.34 (m, 2H,), 3.90-3.84 (m, 1H), 3.77-3.68(m, 2H), 3.67-3.53 (m, 2H), 3.38 3.30 (m, 1H), 3.06-2.91 (m, 2H), 2.03-1.96 (m, 1H), 1.71-1.54 (m, 2H). ESI-MS m/z for C$_{15}$H$_{22}$BrClN$_6$O$_3$S expected 445.3, found 445.1/447.1 [M + H]$^+$ |
| 228 | 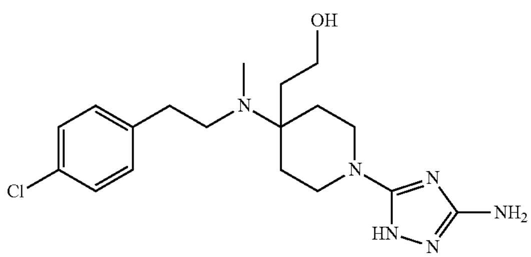 [SMILES: CN(CCc1ccc(Cl)cc1)C1(CCO)CCN(c2nc(N)n[nH]2)CC1] | 2-(1-(3-amino-1H-1,2,4-triazol-5-yl)-4-((4-chlorophenethyl)(methyl)amino)piperidin-4-yl)ethanol | B | $^1$H NMR (DMSO-d$_6$, 500 MHz) δ (ppm) 7.36 (d, 2H, J = 8.5 Hz), 7.32 (d, 2H, J = 8.5 Hz), 3.78 (brs, 3H), 3.61 (t, 2H, J = 6.2 Hz), 3.49-3.41 (m, 1H), 3.12-3.04 (m, 4H), 2.8 (d, 3H, J = 4.9 Hz), 2.14-2.08 (m, 2H), 2.07-2.0 (m, 4H). ESI-MS m/z for C$_{17}$H$_{25}$ClN$_6$O expected 378.91; found 379.5/381.4 [M + H], 377.3/379.4 [M − H]. |
| 229 | 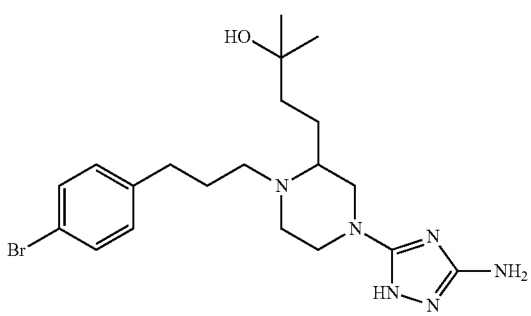 [SMILES: CC(C)(O)CCC1CN(c2nc(N)n[nH]2)CCN1CCCc1ccc(Br)cc1] | 4-(4-(3-amino-1H-1,2,4-triazol-5-yl)-1-(3-(4-bromophenyl)propyl)piperazin-2-yl)-2-methylbutan-2-ol | C | ES(+): [M + H] = 451.3/453.2; ES(−): [M − H] = 449.3/451.3. $^1$H NMR (DMSO-d$_6$ + D$_2$O, 500 MHz) δ (ppm) 7.41 (d, 2H, J$_{AA'BB'}$ = 7.7 Hz); 7.15 (J$_{AA'BB'}$ = 7.7 Hz); 3.00-3.20 (m, 6H); 2.78-2.87 (m, 1H); 1.72-1.94 (m, 3H); 1.25-1.60 (m, 4H); 1.01 (s, 3H); 0.99 (s, 3H). |
| 230 | ·2HCl | 1-(3-amino-1H-1,2,4-triazol-5-yl)-N-(4-bromophenethyl)-N,3-dimethylpiperidin-4-amine dihydrochloride | B | $^1$H NMR (DMSO-d$_6$/+75° C., 500 MHz) δ 7.49 (d, 2H, J = 8.3 Hz), 7.29 (d, 2H, J = 8.3 Hz), 4.0-3.93 (m, 1H), 3.82-3.75 (m, 1H), 3.46 (brs, 1H), 3.23 (brs, 1H), 3.13-3.05 (m, 3H), 2.93 (m, 3H), 2.93 (dt, 1H, J = 12.7 Hz, J = 2.8 Hz), 2.8 (s, 3H), 2.57-2.49 (m, 2H), 2.1-2.01 (m, 1H), 2.01-1.93 (m, 1H), 1.1 (d, 3H), J = 6.8 Hz). ESI MS 393.3 expected for C$_{15}$H$_{27}$BrN$_6$; found m/z 393.4/395.4 [M + H], 391.5/393.3 [M − H] |

TABLE 1-continued

| Example | Structure | IUPAC Name | Activity | Analytical Data |
|---|---|---|---|---|
| 231 | •2HCl | 1-(3-amino-1H-1,2,4-triazol-5-yl)-N-(4-chlorophenethyl)-3-propylpiperidin-4-amine dihydrochloride (diastereoisomer A) | B | $^1$H NMR (DMSO-d$_6$, 600 MHz) δ (ppm) 9.54 (brs, 1H), 9.24 (brs, 1H), 7.36 (AA'BB', 2H, J = 8.1 Hz), 7.28 (AA'BB', 2H, J = 8.1 Hz), 3.88-3.78 (m, 2H), 3.39-3.32 (m, 1H), 3.18-3.08 (m, 2H), 3.07-2.98 (m, 4H), 2.17-2.11 (m, 1H), 1.99-1.92 (m, 1H), 1.83-1.73 (m, 1H), 1.50-1.41 (m, 1H), 1.40-1.32 (m, 1H), 1.29-1.16 (m,2H), 0.84 (t, 3H, J = 6.8 Hz). ESI-MS m/z for C$_{18}$H$_{27}$ClN$_6$: expected 362.91; found 362.7/364.7 [M + H]. |
| 232 | •2HCl | 1-(3-amino-1H-1,2,4-triazol-5-yl)-N-(1-(4-chlorophenyl)butan-2-yl)-N-ethylpiperidin-4-amine dihydrochloride | B | |
| 233 | 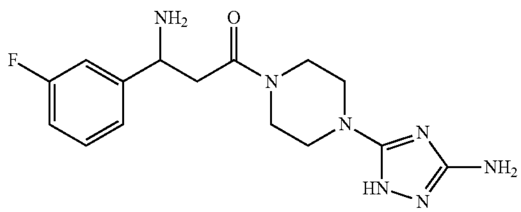 [SMILES: Nc1n[nH]c(N2CCN(C(=O)CC(N)c3cccc(F)c3)CC2)n1] | 3-amino-1-(4-(3-amino-1H-1,2,4-triazol-5-yl)piperazin-1-yl)-3-(3-fluorophenyl)propan-1-one | E | $^1$H NMR (DMSO-d$_6$, 500 MHz) δ (ppm) 8.66 (brs, 1H), 7.51-7.48 (m, 1H), 7.44-7.37 (m, 2H), 7.19-7.15 (m, 1H), 4.63-4.57 (m, 1H), 3.54-3.49 (m, 4H), 3.38-3.32 (m, 1H), 3.32 3.24 (m, 3H), 3.23-3.18 (m, 1H), 3.05-3.0 (m, 1H). $^{19}$F NMR (DMSO-d$_6$, 200 MHz) δ (ppm) 112.0. ESI-MS: m/z for C$_{15}$H$_{20}$FN$_7$O expected 333.36, found 334.4 [M + H] |
| 234 | •2HCl | 1-(3-amino-1H-1,2,4-triazol-5-yl)-N-(4-chlorophenethyl)-3-propylpiperidin-4-amine dihydrochloride (diastereoisomer B) | B | $^1$H NMR (DMSO-d$_6$, 600 MHz) δ (ppm) 9.58 (brs, 1H), 9.30 (brs, 1H), 7.39 (AA'BB', 2H, J = 8.3 Hz), 7.31 (AA'BB', 2H, J = 8.1 Hz), 3.91-3.82 (m, 2H), 3.41-3.34 (m, 1H), 3.20-3.12 (m, 1H), 3.12-2.91 (m, 5H), 2.21-2.13 (m, 1H), 2.02-1.94 (m, 1H), 1.86-1.73 (m, 1H). 1.52-1.44 (m, 1H), 1.43-1.34 (m, 1H), 1.33-1.29 (m, 2H), 0.86 (t, 3H, J = 6.6 Hz). ESI-MS m/z for C$_{18}$H$_{27}$ClN$_6$: expected 362.91; found 362.7/364.7 [M + H]. |
| 235 | 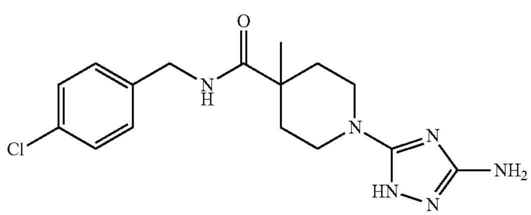 | 1-(3-amino-1H-1,2,4-triazol-5-yl)-N-(4-chlorobenzyl)-4-methylpiperidine-4-carboxamide | E | $^1$H NMR (DMSO-d$_6$, 500 MHz) δ (ppm) 10.9 (brs, 1H), 8.19 (t, 1H, J = 5.6 Hz), 7.33 (d, 2H, J = 8.3 Hz), 7.2 (d, 2H, J = 8.3 Hz), 5.5 (brs, 2H), 4.23 (d, 2H, J = 5.8 Hz), 3.36-3.31 (m, 2H), 2.92-2.86 (m, 2H), 1.98-1.92 (m, 2H), 1.37 1.31 (m, 2H), 1.08 (s, 3H). ESI MS m/z for C$_{17}$H$_{23}$ClN$_6$O expected 362.86, found 362.5 [M + H], 364.5 [M − H] |
| 237 | 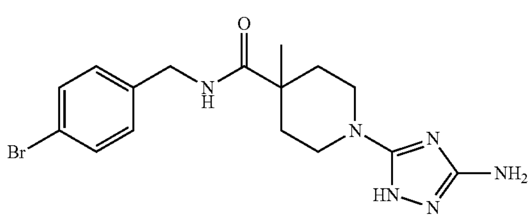 | 1-(3-amino-1H-1,2,4-triazol-5-yl)-N-(4-bromobenzyl)-4-methylpiperidine-4-carboxamide | E | $^1$H NMR (DMSO-d$_6$, 500 MHz) δ (ppm) 10.87 (brs, 1H), 8.19 (t, 1H, J = 5.6 Hz), 7.46 (d, 2H, J = 8.3 Hz), 7.14 (d, 2H, J = 8.3 Hz), 5.62 (brs, 2H), 4.21 (d, 2H, J = 6 Hz), 3.36-3.32 (m, 2H), 2.93-2.86 (m, 2H), 1.98-1.92 (m, 2H), 1.38-1.31 (m, 2H), 1.08 (s, 3H). ESI MS m/z for C$_{16}$H$_{21}$BrN$_6$O expected 392.1, found 393.5/ |

| Example | Structure | IUPAC Name | Activity | Analytical Data |
|---|---|---|---|---|
| | | | | 395.4 [M + H], 391.4/393.3 [M − H]. |
| 238 | 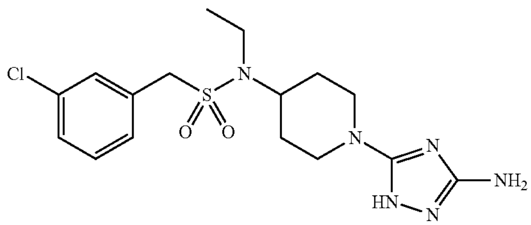 [SMILES: CCN(C1CCN(c2nc(N)n[nH]2)CC1)S(=O)(=O)Cc1cccc(Cl)c1] | N-(1-(3-amino-1H-1,2,4-triazol-5-yl)piperidin-4-yl)-1-(3-chlorophenyl)-N-ethylmethanesulfonamide | B | $^1$H NMR (DMSO-d$_6$, 600 MHz) δ (ppm) 7.48 (brs, 1H), 7.44-7.39 (m, 2H), 7.39-7.35 (m, 1H), 5.6 (brs, 2H), 4.43 (s, 2H), 3.86-3.79 (m, 2H), 3.55-3.46 (m, 1H), 3.12-3.05 (m, 2H), 2.64-2.54 (m, 2H), 1.69-1.55 (m, 4H), 0.96 (t, J = 7 Hz, 3H). ESI MS m/z for C$_{16}$H$_{23}$ClN$_6$O$_2$S expected 398.92, found 399.4/401.4 [M + H], 397.4/399.4 [M − H]. |
| 239 | 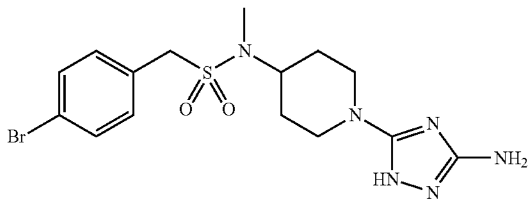 [SMILES: CN(C1CCN(c2nc(N)n[nH]2)CC1)S(=O)(=O)Cc1ccc(Br)cc1] | N-(1-(3-amino-1H-1,2,4-triazol-5-yl)piperidin-4-yl)-1-(4-bromophenyl)-N-methylmethanesulfonamide | E | $^1$H NMR (DMSO-d$_6$, 500 MHz) δ (ppm) 7.55 (d, 2H, J = 8.5 Hz), 7.38 (d, 2H, J = 8.5 Hz), 4.34 (s, 2H), 3.92-3.85 (m, 2H), 3.71-3.64 (m, 1H), 2.8-2.7 (m, 2H), 2.68 (s, 3H), 1.8-1.72 (m, 2H), 1.58-1.52 (m, 2H). ESI MS m/z for C$_{15}$H$_{21}$BrN$_6$O$_2$S expected 429.33, found 429.4/431.4 [M + H], 427.4/429.2 [M − H] |
| 240 | 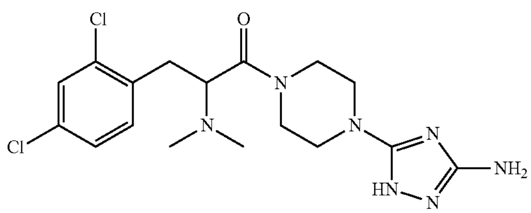 [SMILES: CN(C)C(Cc1ccc(Cl)cc1Cl)C(=O)N1CCN(c2nc(N)n[nH]2)CC1] | 1-(4-(3-amino-1H-1,2,4-triazol-5-yl)piperazin-1-yl)-3-(2,4-dichlorophenyl)-2-(dimethylamino)propan-1-one | E | $^1$H NMR (DMSO-d$_6$, 600 MHz) δ 7.67 (s, 1H), 7.46-7.42 (m, 1H), 7.31 (d, 2H, J = 8.3 Hz), 4.92-4.87 (m, 1H), 3.65-3.6 (m, 1H), 3.59 3.54 (m, 2H), 3.51 (brs, 1H), 3.27-3.21 (m, 2H), 3.18 (brs, 1H), 3.1 (t, 1H, J = 12 Hz), 3.03 (brs, 1H), 2.96 (s, 3H), 2.84 (s, 3H), 2.6 (brs, 1H) ESI-MS m/z for C$_{17}$H$_{23}$Cl$_2$N$_7$O expected 412.33; found 412.4/414.4 [M + H], 410.2/412.3 [M − H]. |
| 241 | 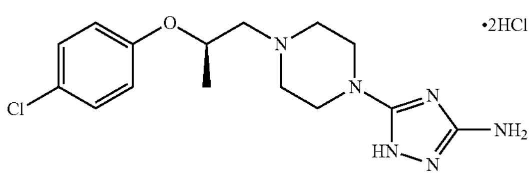 [SMILES: C[C@H](CN1CCN(c2nc(N)n[nH]2)CC1)Oc1ccc(Cl)cc1] | (R)-5-(4-(2-(4-chlorophenoxy)propyl)piperazin-1-yl)-1H-1,2,4-triazol-3-amine dihydrochloride | E | |
| 242 | 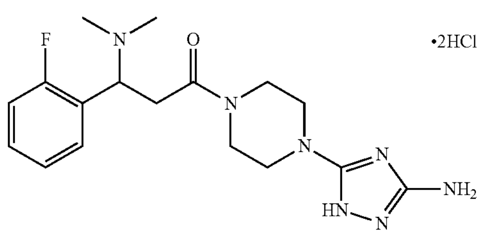 [SMILES: CN(C)C(CC(=O)N1CCN(c2nc(N)n[nH]2)CC1)c1ccccc1F] | 1-(4-(3-amino-1H-1,2,4-triazol-5-yl)piperazin-1-yl)-3-(dimethylamino)-3-(2-fluorophenyl)propan-1-one dihydrochloride | E | $^1$H NMR (CD$_3$OD, 500 MHz) δ (ppm) 7.73 (brs, 1H), 7.60-7.55 (m, 1H), 7.37 (brs, 1H), 7.32 7.29 (m, 1H), 5.25 (brs, 1H), 3.73 (brs, 4H), 3.62 (brs, 1H), 3.47 (brs, 1H), 3.41 (s, 3H), 3.34 (brs, 1H) ESI MS m/z for C$_{17}$H$_{24}$FN$_7$O expected 361.43, found 362.3 [M + H] |
| 243 | 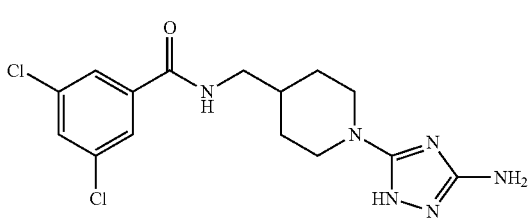 [SMILES: Nc1n[nH]c(N2CCC(CNC(=O)c3cc(Cl)cc(Cl)c3)CC2)n1] | N-((1-(3-amino-1H-1,2,4-triazol-5-yl)piperidin-4-yl)methyl)-3,5-dichlorobenzamide | E | $^1$H NMR (DMSO-d$_6$, 600 MHz) δ 8.68 (t, 1H, J = 5.6 Hz), 7.83 (d, 2H, J = 1.9 Hz), 7.76 (t, 1H, J = 1.9 Hz), 3.75 (brs, 1H), 3.73 (brs, 1H), 3.12 (t, 2H, 6 Hz), 2.56 (brs, 2H), 2.48-2.45 (m, 3H), 1.67-1.59 (m, 3H), 1.16-1.08 (m, 2H) ESI-MS for C$_{15}$H$_{18}$Cl$_2$N$_6$O expected 369.26, found 369.4/371.4 [M + H], 367.3/369.3 [M − H] |

TABLE 1-continued

| Example | Structure | IUPAC Name | Activity | Analytical Data |
|---|---|---|---|---|
| 244 | 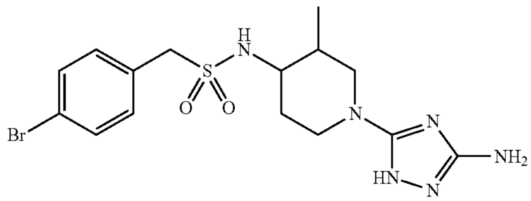 [SMILES: CC1CN(c2nc(N)n[nH]2)CCC1NS(=O)(=O)Cc1ccc(Br)cc1] | N-(1-(3-amino-1H-1,2,4-triazol-5-yl)-3-methylpiperidin-4-yl)-1-(4-bromophenyl)methanesulfonamide | C | $^1$H NMR (DMSO-d$_6$, 500 MHz) δ (ppm) 10.93 (brs, 1H), 7.57 (d, 2H, J = 8.3 Hz), 7.32 (d, 2H, J = 8.3 Hz), 5.53 (brs, 2H), 4.37-4.27 (m, 2H), 3.44-3.38 (m, 2H), 3.2-3.14 (m, 1H), 3.04 2.96 (m, 2H), 1.94-1.85 (m, 1H), 1.61-1.53 (m, 2H). ESI MS m/z for C$_{15}$H$_{21}$BrN$_6$O$_2$S expected 429.34, found 429.3/431.3 [M + H], 427.2/429.3 [M − H]. |
| 245 | •2HCl | 3-(1-(3-amino-1H-1,2,4-triazol-5-yl)-4-((4-chlorophenethyl)(methyl)amino)piperidin-4-yl)propan-1-ol dihydrochloride | C | $^1$H NMR (DMSO, 500 MHz) δ (ppm) 7.40-7.34 (m, 4H), 3.90-3.75 (m, 2H), 3.50-3.38 (m, 4H), 3.25-3.05 (m, 4H), 2.82 (s, 3H), 2.24-189 (m, 6H), 1.66-1.53 (m, 2H). ESI-MS m/z for C$_{19}$H$_{29}$ClN$_6$O expected 392.9, found 393.5/395.5 [M + H]. |
| 246 | •2HCl | 3-(1-(3-amino-1H-1,2,4-triazol-5-yl)-4-((4-bromophenethyl)(methyl)amino)piperidin-3-yl)propan-1-ol dihydrochloride | A | $^1$H NMR (DMSO-d$_6$, 75° C., 500 MHz) δ (ppm) 7.55-7.48 (m, 2H), 7.36-7.29 (m, 2H), 4.09-4.03 (m, 1H), 4.03-3.88 (m, 2H), 3.55-3.41 (m, 3H), 3.4-3.29 (m, 2H), 3.17-3.06 (m, 2H), 3.0-2.9 (m, 2H), 2.85 (s, 3H), 2.33-2.17 (m, 1H), 2.15-2.04 (m, 1H), 2.0-1.9 (m, 1H), 1.72-1.6 (m, 2H), 1.54-1.4 (m, 1H). ESI-MS m/z for C$_{19}$H$_{29}$BrN$_6$O expected 437.39, found 437.5/439.5 [M + H], 435.4/437.3 [M − H]. |
| 247 | •2HCl | 1-(3-amino-1H-1,2,4-triazol-5-yl)-N-(4-bromophenethyl)-4-propylpiperidin-4-amine dihydrochloride | C | $^1$H NMR (DMSO-d$_6$, 500 MHz) δ (ppm) 9.17 (brs, 2H), 7.49 (d, 2H, J = 8.1 Hz), 7.24 (d, 2H, J = 8.1 Hz), 3.72 (brs, 3H), 3.12 (brs, 3H), 3.01 (brs, 3H), 1.98-1.91 (m, 2H), 1.9-1.84 (m, 2H), 1.73 (m, 2H), 1.34-1.26 (m, 2H), 0.87 (t, 3H, J = 7 Hz). ESI MS m/z for C$_{18}$H$_{27}$BrN$_6$ expected 407.36, found 407.5/409.4 [M + H], 405.4/407.6 [M − H]. |
| 248 | •HCl | N-(1-(3-amino-1H-1,2,4-triazol-5-yl)piperidin-4-yl)-2-(3-chlorophenyl)-N-methylmethanesulfonamide hydrochloride | E | $^1$H NMR (DMSO-d$_6$, 600 MHz) δ (ppm) 7.5-7.46 (m, 1H), 7.45-7.39 (m, 2H), 7.39-7.35 (m, 1H), 4.47 (s, 2H), 3.86-3.76 (m, 2H), 3.76 3.67 (m, 1H), 3.15 (s, 3H), 2.94 (brs, 2H), 1.75-1.64 (m, 2H), 1.58-1.5 (m, 2H). ESI MS m/z for C$_{15}$H$_{21}$ClN$_6$O$_2$S expected 384.88, found 385.5/387.5 [M + H], 383.4/385.5 [M − H] |
| 249 | 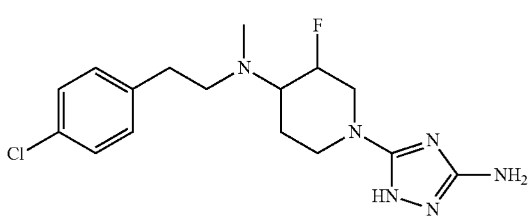 [SMILES: CN(CCc1ccc(Cl)cc1)C1CCN(c2nc(N)n[nH]2)CC1F] | 1-(3-amino-1H-1,2,4-triazol-5-yl)-N-(4-chlorophenethyl)-3-fluoro-N-methylpiperidin-4-amine | C | |

| Example | Structure | | IUPAC Name | Activity | Analytical Data |
|---|---|---|---|---|---|
| 250 | [structure] | ·2HCl | 1-(3-amino-1H-1,2,4-triazol-5-yl)-N-methyl-N-(1,2,3,4-tetrahydronaphthalen-2-yl)piperidin-4-amine dihydrochloride | E | |
| 251 | [structure] | ·2HCl | 3-(1-(3-amino-1H-1,2,4-triazol-5-yl)-4-((4-chlorophenethyl)amino)piperidin-3-yl)propan-1-ol dihydrochloride | A | |
| 252 | [structure] | ·2HCl | 5-(4-(((3,4-dichlorobenzyl)amino)methyl)piperidin-1-yl)-1H-1,2,4-triazol-3-amine dihydrochloride | E | $^1$H NMR (DMSO-$d_6$, 500 MHz) δ (ppm) 9.58 (brs, 1H), 7.9 (s, 1H), 7.62 (d, 1H, J = 8.3 Hz), 7.55 (d, 1H, J = 8.3 Hz), 4.08-4.03 (m, 2H), 3.75-3.68 (m, 2H), 2.85 (t, 2H, J = 12.6 Hz), 2.74-2.68 (m, 2H), 1.95 (brs, 1H), 1.79-1.73 (m, 2H), 1.21-1.11 (m, 2H). ESI-MS m/z for $C_{15}H_{20}Cl_2N_6$ expected 354.1/356.1; found 355.4/357.4 [M + H], 353.5/354.5 [M − H]. |
| 253 | [structure] | ·2HCl | 5-(1-(4-bromophenethyl)octahydro-1,6-naphthyridin-6(2H)-yl)-1H-1,2,4-triazol-3-amine dihydrochloride | A | |
| 254 | [structure] | | 5-(4-(((4-bromobenzyl)amino)methyl)piperidin-1-yl)-1H-1,2,4-triazol-3-amine | E | $^1$H NMR (DMSO-$d_6$, 500 MHz) δ 7.47 (d, 2H, J = 8.1 Hz), 7.27 (d, 2H, J = 8.1 Hz), 5.43 (brs, 2H), 3.77-3.72 (m, 2H), 3.63 (s, 2H), 2.57 (t, 2H, J = 11.9 Hz), 2.31 (d, 2H, J = 6.4 Hz), 1.7 1.64 (m, 2H), 1.49 (brs, 1H), 1.12-1.03 (m, 2H) ESI MS m/z for $C_{15}H_{21}BrN_6$ expected 364.1/366.1, found 365.4/367.5 [M + H]. |
| 255 | [structure] | | 1-(3-amino-1H-1,2,4-triazol-5-yl)-N-(3,5-bis(trifluoromethyl)benzyl)piperidine-4-carboxamide | E | |

TABLE 1-continued

| Example | Structure | IUPAC Name | Activity | Analytical Data |
|---|---|---|---|---|
| 256 | [structure] | N-(1-(3-amino-1H-1,2,4-triazol-5-yl)-4-(4-hydroxybutyl)piperidin-4-yl)-1-(4-bromophenyl)methane sulfonamide | C | $^1$H NMR (DMSO-$d_6$, 600 MHz) δ (ppm) 7.38 (AA'BB', 2H, J = 8.5 Hz), 7.24 (AA'BB', 2H, J = 8.3 Hz), 4.35 (s, 2H), 3.52-3.47 (m, 2H), 3.08-3.02 (m, 2H), 2.36-2.28 (m, 2H), 1.93-1.86, (m, 2H), 1.58-1.52 (m, 2H), 1.48-1.39 (m, 4H), 1.39-1.30 (m, 2H). ESI-MS m/z for $C_{18}H_{27}BrN_6O_3S$ expected 487.42; found 487.3/489.3 [M + H], 485.3/487.3 [M − H]. |
| 257 | [structure] ·CF$_3$CO$_2$H | 5-(4-(4-(4-bromophenyl)-1-phenylbutan-2-yl)piperazin-1-yl)-1H-1,2,4-triazol-3-amine trifluoroacetate | B | |
| 258 | [structure] | 1-(4-(3-amino-1H-1,2,4-triazol-5-yl)piperazin-1-yl)-2-(4-chlorophenoxy)-2-methylpropan-1-one | E | |
| 259 | [structure] | 1-(4-(3-amino-1H-1,2,4-triazol-5-yl)piperazin-1-yl)-2-(4-bromophenoxy)ethan-1-one | E | |

Human AMCase Activity Assay

An enzymatic assay with recombinant human AMCase was used in order to establish inhibitory activity of the compounds (Boot et al, 2001, J. Biol. Chem. 276:6770-6778). The assay was run in the 96-well plate format, each reaction in the total volume of 100 μl. 4-Methylumbelliferyl B-D-N,N' diacetylchitobioside hydrate was used as a substrate for the enzyme. Upon hydrolysis by AMCase, the substrate releases 4-methylumbelliferyl (4MU), when ionized in basic pH, emits fluorescence of 460 nm.

Briefly, 40 μl of a substrate was added to each well, followed by 10 μl of compound dilution and 50 μl of hAMCase recombinant enzyme solution. The reaction was carried out in citrate buffer, pH 5.2, in the dark, at 37° C. for 60 minutes with shaking. After that time the reaction was stopped by adding 195 μl of Stop Buffer (pH 10.5) to each well. The fluorescence of the reaction product was measured in Perkin Elmer Envision fluorescent plate reader at an excitation wavelength of 355 nm.

Compounds disclosed herein have IC$_{50}$ values generally ranging from about 0.01 μM to about 100 μM. IC$_{50}$ value key for values listed in Table 1 is the following: A: <0.1 μM; B: 0.1-1 μM; C: 1-10 μM; D: 10-100 μM; E: >100 μM. Unless otherwise noted in Table 1, compounds in Table 1 demonstrate IC$_{50}$ values of at least about 100 μM (E-value noted above).

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:
1. A compound of formula (I), or a salt, hydrate or solvate thereof:

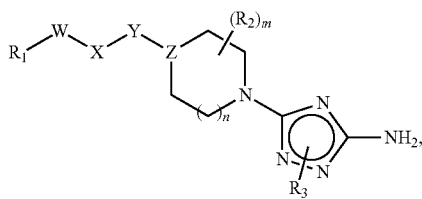

(I)

wherein in (I):
m is 0, 1, 2, 3, or 4;
n is 0, 1, or 2;
$R_1$ is aryl or heteroaryl, each of which is optionally substituted with one or more of $R_4$;
each $R_2$ is individually selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, hydroxy($C_1$-$C_6$ alkyl), $C_1$-$C_6$ acyloxy($C_1$-$C_6$ alkyl), alkoxy($C_1$-$C_6$ alkyl), and $C_1$-$C_6$ haloalkoxy;
$R_3$ is a substituent on one nitrogen atom, and is hydrogen or $C_1$-$C_6$ alkyl;
W is absent, —O—, —N($R_5$)—, —$X_1$—N($R_5$)—, —$X_1$—O—, —N($R_5$)C(=O)—, —C(=O)N($R_5$)—, —N($R_5$)S(=O)$_2$—, or —S(=O)$_2$N($R_5$)—, where $X_1$ is $C_1$-$C_3$ alkylene optionally substituted with one or more substituents selected from the group consisting of $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)N($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);
X is —C(=O)— or $C_1$-$C_6$ alkylene optionally substituted with one or more substituents selected from the group consisting of $C_1$-$C_6$ alkyl, $C_1$-$C_6$ haloalkyl, benzyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);
Y is absent, —C(=O)—, —OC(=O)—, —N($R_5$), —N($R_5$)C(=O)—, —C(=O)N($R_5$)—, —N($R_5$)S(=O)$_2$—, —S(=O)$_2$N($R_5$)—, —N($R_5$)$CH_2$—, or —S(=O)$_2$—;
or W—X—Y represent a heteroarylene, heterocyclylene, or $C_3$-$C_8$ cycloalkylene, each optionally substituted with one or more substituents selected from the group consisting of $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;
Z is CH, C($C_1$-$C_6$ alkyl), or N, wherein the $C_1$-$C_6$ alkyl is optionally substituted with one or more substituents selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)N($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), and —NHC(=O)($C_1$-$C_6$ alkyl);
or Y—Z, together with one carbon atom to which Z is attached, form a heterocyclyl;
or Y—Z, together with the ring containing Z, form a bicyclic heterocycle selected from the group consisting of:

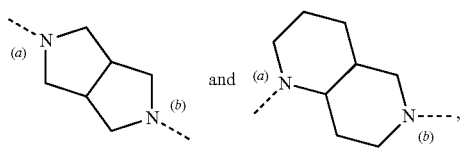

wherein the N labelled as (a) is covalently bonded to X and the N labelled as (b) is covalently bonded to the 1,3,4-triazole ring;
or Y is absent, X is a bond or as defined above, and Z is a carbon atom that is covalently connected to W by a $C_1$-$C_4$ alkylene chain optionally containing a nitrogen, oxygen, or sulfur atom, whereby Z—X—Y—W together form a 3-7 membered carbocyclic or heterocyclic ring;
each $R_4$ is independently selected from the group consisting of halogen, —$NO_2$, —CN, $C_1$-$C_6$ alkyl, $C_3$-$C_7$ cycloalkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S(=O)$_{0-2}$($C_1$-$C_6$ alkyl), hydroxy($C_1$-$C_6$ alkyl), alkoxy($C_1$-$C_6$ alkyl), amino($C_1$-$C_6$ alkyl), —C(=O)$NH_2$, —C(=O)NH($C_1$-$C_6$ alkyl), —C(=O)N($C_1$-$C_6$ alkyl)$_2$, —C(=O)$NHNH_2$, —C(=O)H, —C(=O)O($C_1$-$C_6$ alkyl), —OC(=O)($C_1$-$C_6$ alkyl), —NHC(=O)($C_1$-$C_6$ alkoxy), —NHC(=O)($C_1$-$C_6$ alkyl), —NHC(=O)$NH_2$, —NHC(=O)NH($C_1$-$C_6$ alkyl), —NHC(=NH)$NH_2$, —NH—S(=O)$_{0-2}$—($C_1$-$C_6$ alkyl), —NH—S(=O)$_{0-2}$-aryl, and —NH—S(=O)$_{0-2}$-heteroaryl; and,
each $R_5$ is independently selected from the group consisting of hydrogen and $C_1$-$C_6$ alkyl optionally substituted with at least one substituent selected from the group consisting of halogen, hydroxy, $C_1$-$C_6$ haloalkyl, $C_3$-$C_7$ cycloalkyl, $C_1$-$C_6$ alkoxy, and $R_{5a}$, where $R_{5a}$ is phenyl, naphthyl, or a bicyclic heteroaryl, and $R_{5a}$ is optionally substituted with 1-3 substituents independently selected from the group consisting of halogen, hydroxy, $C_1$-$C_6$ alkyl, cyano, hydroxy $C_1$-$C_6$ alkyl, phenyl, $C_1$-$C_6$ alkoxy, haloalkyl, —$NH_2$, —NH($C_1$-$C_6$ alkyl), —N($C_1$-$C_6$ alkyl)$_2$, and $C_1$-$C_6$ haloalkoxy;
provided the compound of formula (I) is not:
5-[4-(1-naphthalenylmethyl)-1-piperazinyl]-1H-1,2,4-triazol-3-amine;
5-[4-(1,3-benzodioxol-5-ylmethyl)-1-piperazinyl]-1H-1,2,4-triazol-3-amine;
5-[4-(1-phenylethyl)-1-piperazinyl]-1H-1,2,4-triazol-3-amine;
5-[4-[[2-chloro-4-(dimethylamino)phenyl]methyl]-1-piperazinyl]-1H-1,2,4-triazol-3-amine;
5-[4-[[3-bromo-4-(dimethylamino)phenyl]methyl]-1-piperazinyl]-1H-1,2,4-triazol-3-amine;
5-[4-[(2,3,4-trimethoxyphenyl)methyl]-1-piperazinyl]-1H-1,2,4-triazol-3-amine;

5-[4-[(2-chloro-4-fluorophenyl)methyl]-1-piperazinyl]-1H-1,2,4-triazol-3-amine;
5-[4-[[3-(trifluoromethyl)phenyl]methyl]-1-piperazinyl]-1H-1,2,4-triazol-3-amine;
5-[4-[(2,4,6-trimethylphenyl)methyl]-1-piperazinyl]-1H-1,2,4-triazol-3-amine;
5-[4-[(2,5-dimethylphenyl)methyl]-1-piperazinyl]-1H-1,2,4-triazol-3-amine;
5-[4-[(2,6-dichlorophenyl)methyl]-1-piperazinyl]-1H-1,2,4-triazol-3-amine;
5-[4-(2-phenoxyethyl)-1-piperazinyl]-1H-1,2,4-triazol-3-amine;
5-[4-(4-phenoxybutyl)-1-piperazinyl]-1H-1,2,4-triazol-3-amine;
5-[4-[2-(4-bromophenoxy)ethyl]-1-piperazinyl]-1H-1,2,4-triazol-3-amine;
5-[4-[(3,4-dichlorophenyl)methyl]-1-piperazinyl]-1H-1,2,4-triazol-3-amine;
5-[4-(4-pyridinylmethyl)-1-piperazinyl]-1H-1,2,4-triazol-3-amine;
5-[4-[(4-methylphenyl)methyl]-1-piperazinyl]-1H-1,2,4-triazol-3-amine;
5-[4-(phenylmethyl)-1-piperazinyl]-1H-1,2,4-triazol-3-amine;
5-[4-[(4-aminophenyl)methyl]-1-piperazinyl]-1H-1,2,4-triazol-3-amine;
5-[4-[[3-chloro-4-(dimethylamino)phenyl]methyl]-1-piperazinyl]-1H-1,2,4-triazol-3-amine;
5-[4-[(3-chlorophenyl)methyl]-1-piperazinyl]-1H-1,2,4-triazol-3-amine;
5-[4-[[2-bromo-4-(dimethylamino)phenyl]methyl]-1-piperazinyl]-1H-1,2,4-triazol-3-amine;
5-[4-(3-phenylpropyl)-1-piperazinyl]-1H-1,2,4-triazol-3-amine;
5-[4-[[4-(dimethylamino)phenyl]methyl]-1-piperazinyl]-1H-1,2,4-triazol-3-amine;
5-[4-(2-furanylmethyl)-1-piperazinyl]-1H-1,2,4-triazol-3-amine;
5-[4-(2-quinolinylmethyl)-1-piperazinyl]-1H-1,2,4-triazol-3-amine;
4-[[4-(3-amino-1H-1,2,4-triazol-5-yl)-1-piperazinyl]methyl]-benzonitrile;
5-[4-[(2-fluorophenyl)methyl]-1-piperazinyl]-1H-1,2,4-triazol-3-amine;
5-[4-(2-phenylethyl)-1-piperazinyl]-1H-1,2,4-triazol-3-amine;
5-[4-[(4-fluorophenyl)methyl]-1-piperazinyl]-1H-1,2,4-triazol-3-amine;
5-[4-[(2-nitrophenyl)methyl]-1-piperazinyl]-1H-1,2,4-triazol-3-amine;
5-[4-(3-phenoxypropyl)-1-piperazinyl]-1H-1,2,4-triazol-3-amine;
5-[4-[[4-(1,1-dimethylethyl)phenyl]methyl]-1-piperazinyl]-1H-1,2,4-triazol-3-amine;
5-[4-[(4-butylphenyl)methyl]-1-piperazinyl]-1H-1,2,4-triazol-3-amine;
5-[4-[(3-methylphenyl)methyl]-1-piperazinyl]-1H-1,2,4-triazol-3-amine;
benzyl 4-(3-amino-1H-1,2,4-triazol-5-yl)piperazine-1-carboxylate;
5-[4-[(3,4,5-trimethoxyphenyl)methyl]-1-piperazinyl]-1H-1,2,4-triazol-3-amine; or
5-[4-[(2-methylphenyl)methyl]-1-piperazinyl]-1H-1,2,4-triazol-3-amine.

2. The compound of claim 1, which is a compound of formula (II) or a salt, hydrate or solvate thereof:

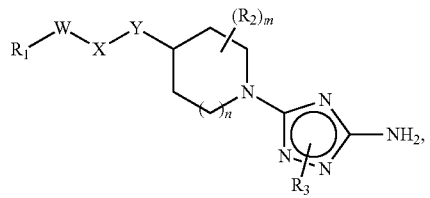

wherein in (II):
W is absent, —O—, —$X_1$—O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more of $C_1$-$C_6$ alkyl, benzyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, or —S($C_1$-$C_6$ alkyl);

Y is absent, —C(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)$CH_2$—, or —S(=O)$_2$—.

3. The compound of claim 1, which is compound of formula (III) or a salt, hydrate or solvate thereof:

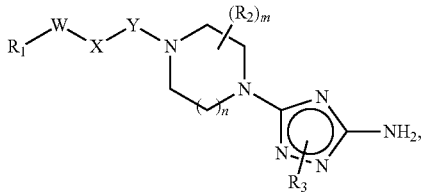

wherein in (III):
W is absent, —O—, —$X_1$O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more substituents selected from the group consisting of $C_1$-$C_6$ alkyl, benzyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, and —S($C_1$-$C_6$ alkyl);

Y is absent, —C(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)$CH_2$—, or —S(=O)$_2$—;

provided that, when both W and Y are absent, X is not optionally substituted methylene;

provided the compound is not:
5-[4-(2-phenoxyethyl)-1-piperazinyl]-1H-1,2,4-triazol-3-amine;
5-[4-(4-phenoxybutyl)-1-piperazinyl]-1H-1,2,4-triazol-3-amine;
5-[4-[2-(4-bromophenoxy)ethyl]-1-piperazinyl]-1H-1,2,4-triazol-3-amine;
5-[4-(3-phenylpropyl)-1-piperazinyl]-1H-1,2,4-triazol-3-amine;
45-[4-(2-phenylethyl)-1-piperazinyl]-1H-1,2,4-triazol-3-amine; or
5-[4-(3-phenoxypropyl)-1-piperazinyl]-1H-1,2,4-triazol-3-amine.

4. The compound of claim 3, wherein:

W is absent, —O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more substituents selected from the group consisting of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, and —S($C_1$-$C_6$ alkyl);

provided that W—X—Y is not —CH$_2$—, and provided that when $R_1$ is phenyl optionally substituted with halogen, W—X—Y is not —CH(CH$_3$)—, —(CH$_2$)$_2$—, —(CH$_2$)$_3$—, —O(CH$_2$)$_2$—, —O(CH$_2$)$_3$—, or —O(CH$_2$)$_4$—.

5. The compound of claim 3, wherein

W is absent, —O—, —N($R_5$)—, —N($R_5$)C(=O)—, —C(=O)N($R_5$)—, —N($R_5$)S(=O)$_2$—, or —S(=O)$_2$N($R_5$)—;

X is $C_1$-$C_6$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, or —S($C_1$-$C_6$ alkyl).

6. The compound of claim 1, which is a compound of formula (IV) or a salt, hydrate or solvate thereof:

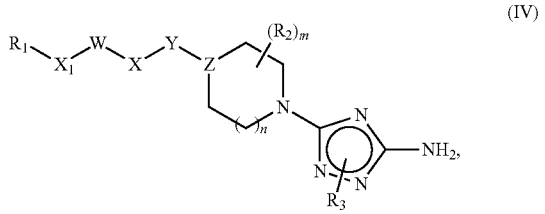

(IV)

wherein in (IV):

W is —O— or —N($R_5$)—;

X is $C_1$-$C_3$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), or —NHC(=O)($C_1$-$C_6$ alkyl);

$X_1$ is $C_1$-$C_3$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), or —NHC(=O)($C_1$-$C_6$ alkyl);

Y is absent, —C(=O)—, —OC(=O)—, —N($R_5$)—, —N($R_5$)C(=O)—, —C(=O)N($R_5$)—, —N($R_5$)S(=O)$_2$—, —S(=O)$_2$N($R_5$)—, —N($R_5$)CH$_2$—, or —S(=O)$_2$—;

provided that the compound is not benzyl 4-(3-amino-1H-1,2,4-triazol-5-yl)piperazine-1-carboxylate.

7. The compound of claim 1, which is a compound of formula (V) or a salt, hydrate or solvate thereof:

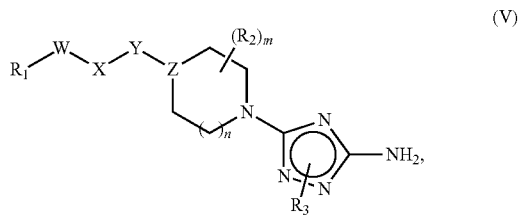

(V)

wherein in (V):

W is —O— or —N($R_5$)—;

X is $C_1$-$C_6$ alkylene optionally substituted with one or more of $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —C(=O)NH$_2$, —C(=O)NH($C_1$-$C_6$ alkyl), —C(=O)N($C_1$-$C_6$ alkyl)$_2$, —C(=O)O($C_1$-$C_6$ alkyl), —NHC(=O)($C_1$-$C_6$ alkoxy), or —NHC(=O)($C_1$-$C_6$ alkyl); or X together with one of $R_4$ forms a $C_1$-$C_3$ alkylene or $C_1$-$C_3$ alkenylene group;

Y is —C(=O)—, —OC(=O)—, —N($R_5$)—, —N($R_5$)C(=O)—, —C(=O)N($R_5$)—, —N($R_5$)SO$_2$—, —S(=O)$_2$N($R_5$)—, —N($R_5$)CH$_2$—, or —S(=O)$_2$—.

8. The compound of claim 1, which is a compound of formula (VI) or a salt, hydrate or solvate thereof:

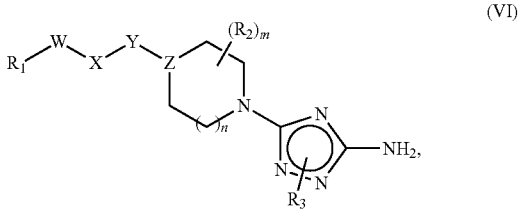

(VI)

wherein in (VI):

W is N($R_5$)—;

X is C(=O)—;

Y is —N($R_5$)—;

Z is CH, C($C_1$-$C_6$ alkyl), or N.

9. The compound of claim 1, wherein W—X—Y form at least one selected from the group consisting of:

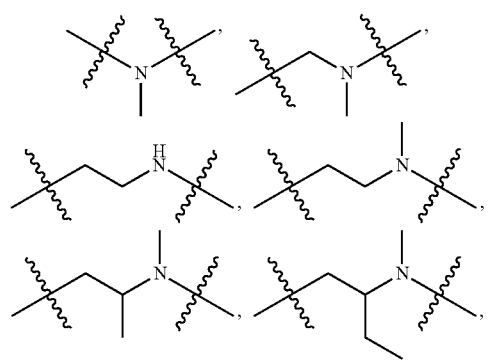

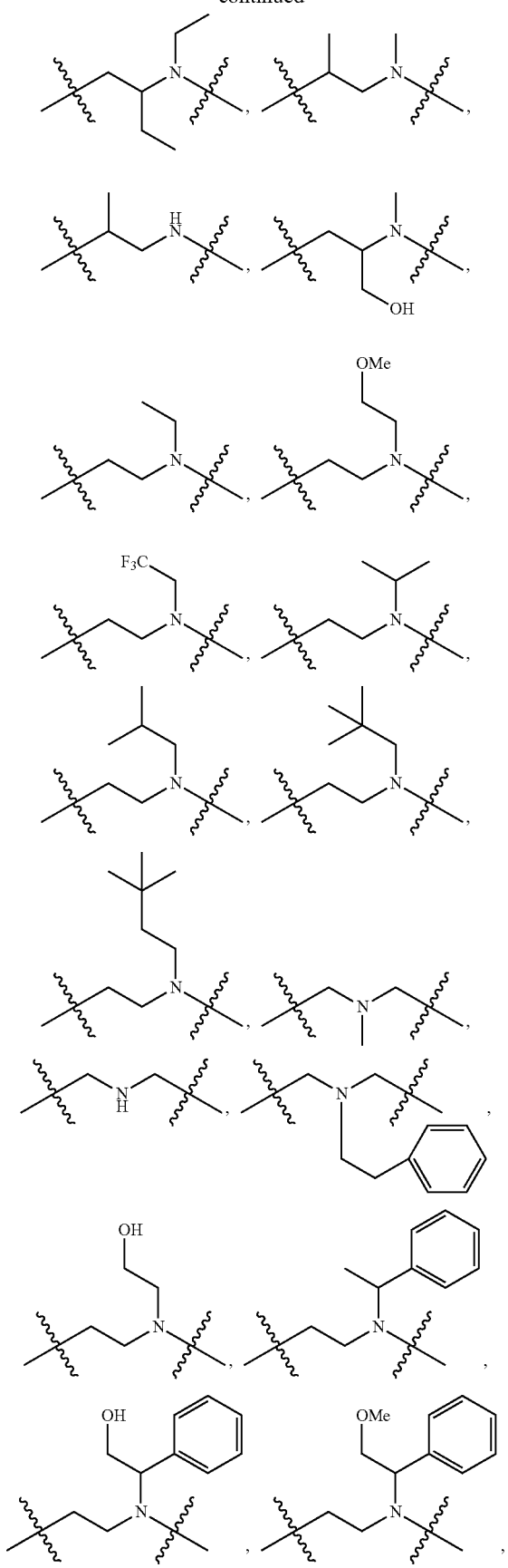
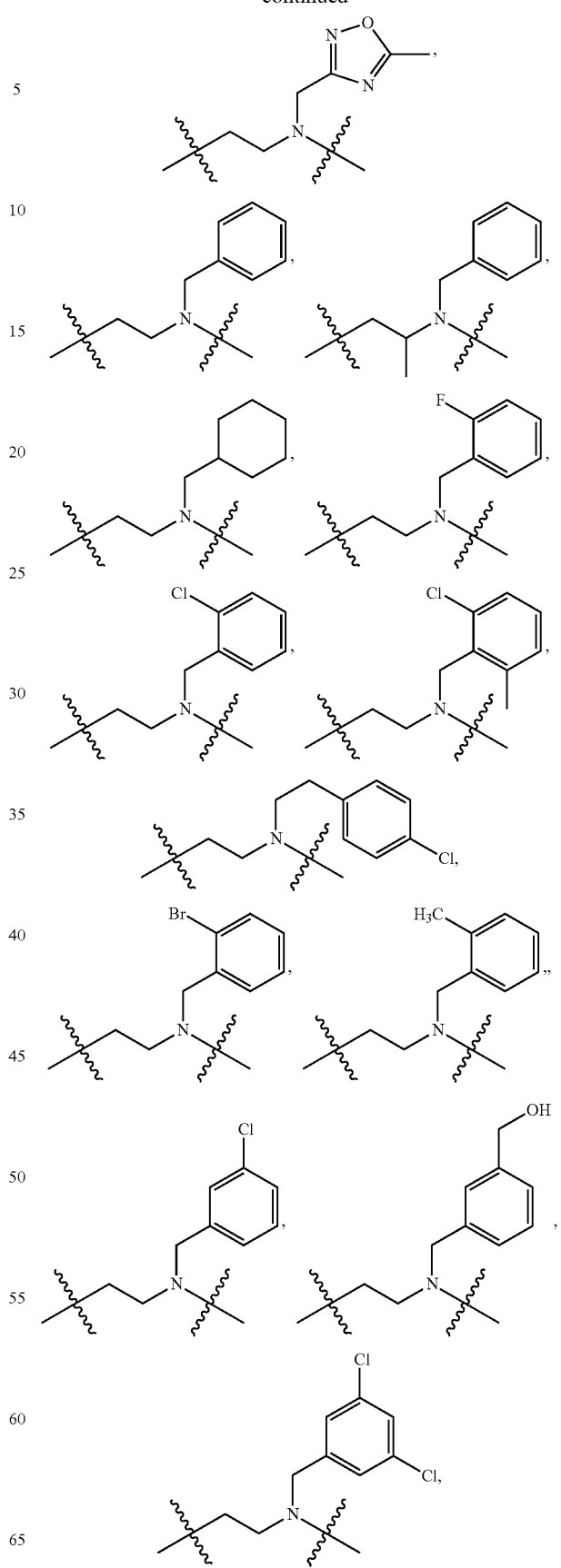

255
-continued
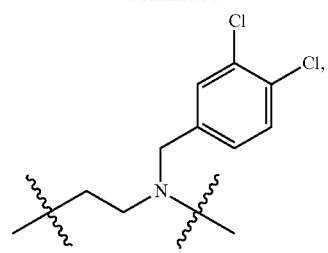
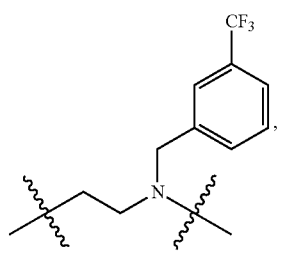
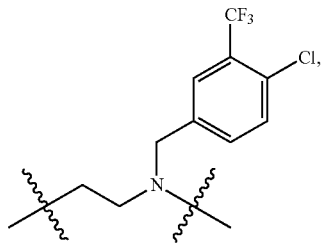
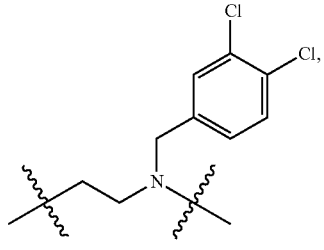
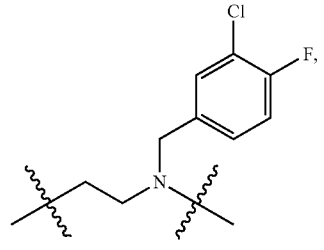
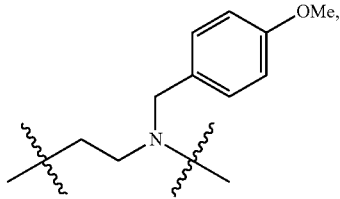
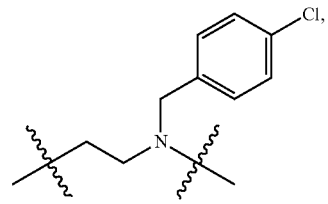
256
-continued
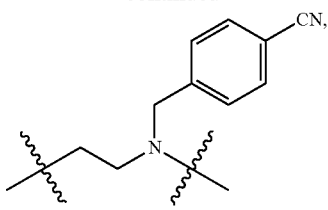
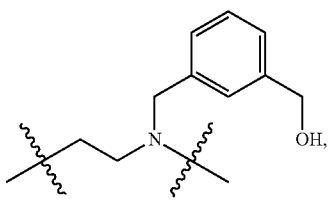
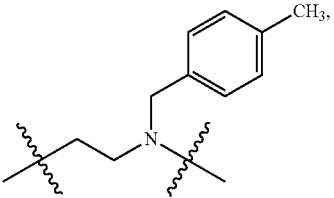
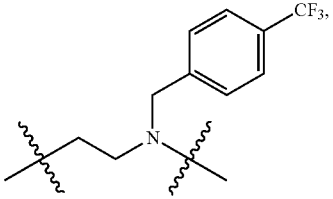
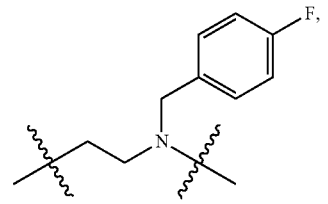
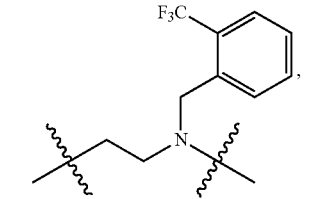
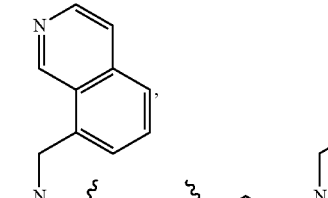
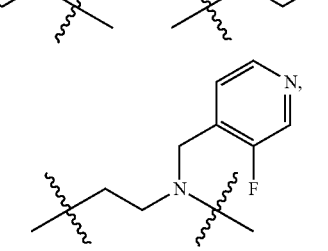

257
-continued
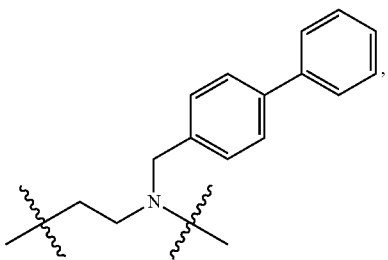
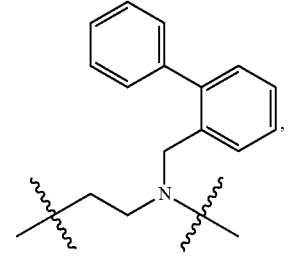
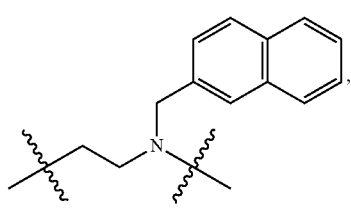
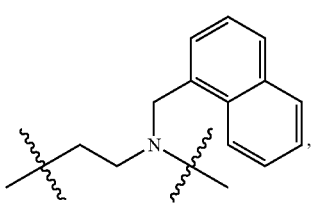
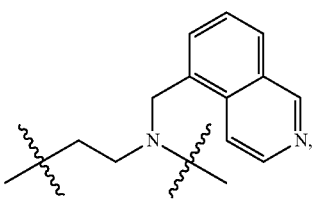
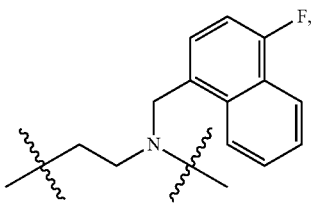
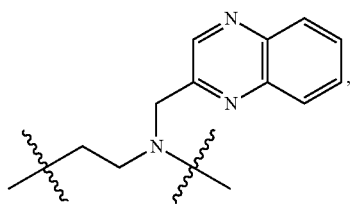
258
-continued
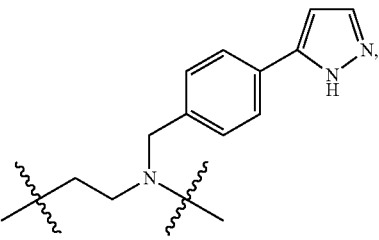
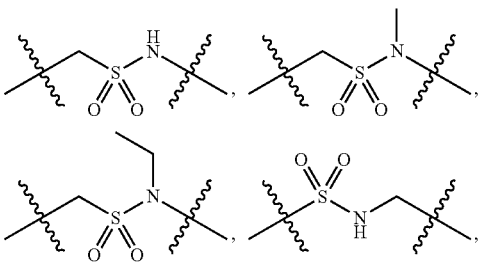
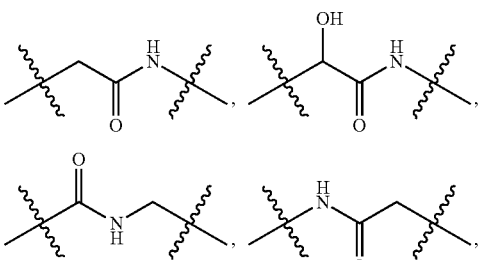
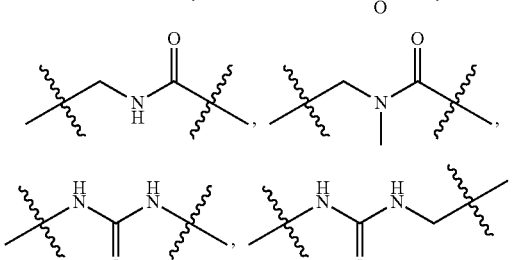
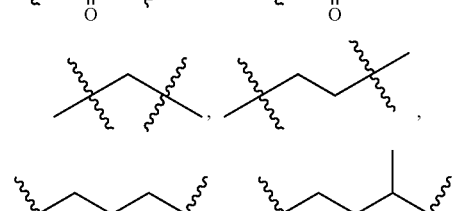
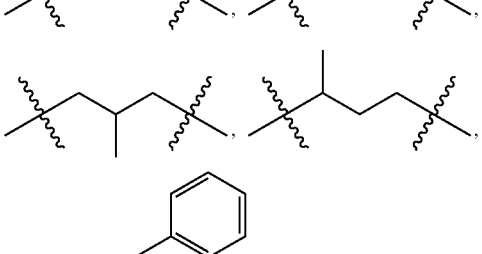
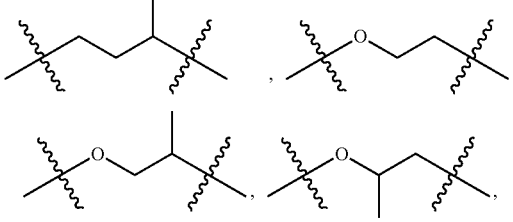

-continued

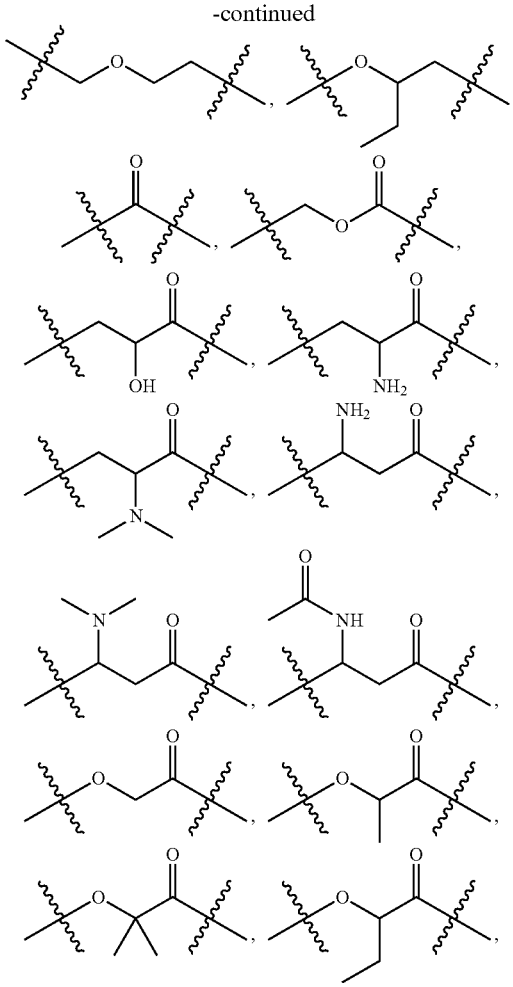

and oxadiazolylene.

10. A compound selected from the group consisting of:
5-(4-(2-(4-fluorophenoxy)ethyl) piperazin-1-yl)-1H-1,2,4-triazol-3-amine;
5-(4-(2-(4-chlorophenoxy)ethyl) piperazin-1-yl)-1H-1,2,4-triazol-3-amine;
5-(4-(4-ethoxybenzyl) piperazin-1-yl)-1H-1,2,4-triazol-3-amine;
1-(4-(3-amino-1H-1,2,4-triazol-5-yl)piperazin-1-yl)-2-(4-bromophenoxy)ethan-1-one;
1-(4-(3-amino-1H-1,2,4-triazol-5-yl)piperazin-1-yl)-2-(4-bromophenoxy)butan-1-one;
(R)-1-(4-(3-amino-1H-1,2,4-triazol-5-yl)piperazin-1-yl)-2-(4-bromophenoxy)propan-1-one;
(S)-1-(4-(3-amino-1H-1,2,4-triazol-5-yl)piperazin-1-yl)-2-(4-bromophenoxy)propan-1-one;
1-(4-(3-amino-1H-1,2,4-triazol-5-yl)piperazin-1-yl)-2-(4-chlorophenoxy)butan-1-one;
(R)-1-(4-(3-amino-1H-1,2,4-triazol-5-yl)piperazin-1-yl)-2-(4-chlorophenoxy)propan-1-one;
(S)-1-(4-(3-amino-1H-1,2,4-triazol-5-yl)piperazin-1-yl)-2-(4-chlorophenoxy)propan-1-one;
N-((1-(3-amino-1H-1,2,4-triazol-5-yl)piperidin-4-yl)methyl)-4-bromobenzamide;
N-((1-(3-amino-1H-1,2,4-triazol-5-yl)piperidin-4-yl)methyl)-4-bromobenzenesulfonamide;
N-(1-(3-amino-1H-1,2,4-triazol-5-yl)piperidin-4-yl)-1-(4-bromophenyl)methanesulfonamide;
N-(1-(3-amino-1H-1,2,4-triazol-5-yl)piperidin-4-yl)-1-(4-chlorophenyl)methanesulfonamide;
N-(1-(3-amino-1H-1,2,4-triazol-5-yl)piperidin-4-yl)-1-(3,4-dichlorophenyl) methanesulfonamide;
N-(1-(3-amino-1H-1,2,4-triazol-5-yl)piperidin-4-yl)-2-(4-bromophenyl)acetamide;
1-(3-amino-1H-1,2,4-triazol-5-yl)-N-(3,4-dichlorobenzyl)piperidine-4-carboxamide;
1-(3-amino-1H-1,2,4-triazol-5-yl)-N-(4-bromobenzyl)piperidine-4-carboxamide;
5-(4-(4-(4-bromophenyl)butan-2-yl)piperazin-1-yl)-1H-1,2,4-triazol-3-amine;
5-(4-(2-(4-bromophenoxy)propyl)piperazin-1-yl)-1H-1,2,4-triazol-3-amine;
5-(4-(1-(4-bromophenoxy)propan-2-yl)piperazin-1-yl)-1H-1,2,4-triazol-3-amine;
1-(3-amino-1H-1,2,4-triazol-5-yl)-N-(4-bromophenethyl)-N-methylpiperidin-4-amine;
1-(3-amino-1H-1,2,4-triazol-5-yl)-N-(4-bromophenethyl)piperidin-4-amine;
5-(4-(2-((4-chloronaphthalen-1-yl)oxy)ethyl)piperazin-1-yl)-1H-1,2,4-triazol-3-amine;
1-(4-(3-amino-1H-1,2,4-triazol-5-yl)piperazin-1-yl)-2-(4-chlorophenoxy)ethan-1-one;
1-(4-(3-amino-1H-1,2,4-triazol-5-yl)piperazin-1-yl)-2-(naphthalen-2-yloxy)ethan-1-one;
5-(4-(2-(4-bromophenoxy)ethyl)-3-methylpiperazin-1-yl)-1H-1,2,4-triazol-3-amine;
3-(4-(2-(4-bromophenoxy)ethyl)piperazin-1-yl)-1-methyl-1H-1,2,4-triazol-5-amine;
5-(4-(2-(4-bromophenoxy)ethyl)piperazin-1-yl)-1-methyl-1H-1,2,4-triazol-3-amine;
5-(4-(2-(4-bromophenoxy)ethyl)-1,4-diazepan-1-yl)-1H-1,2,4-triazol-3-amine;
5-(5-(2-(4-bromophenoxy)ethyl)hexahydropyrrolo[3,4-c]pyrrol-2(1H)-yl)-1H-1,2,4-triazol-3-amine;
1-(4-(3-amino-1H-1,2,4-triazol-5-yl)piperazin-1-yl)-2-phenoxyethan-1-one;
1-(4-(3-amino-1H-1,2,4-triazol-5-yl)piperazin-1-yl)-2-(4-ethylphenoxy)propan-1-one;
1-(4-(3-amino-1H-1,2,4-triazol-5-yl)piperazin-1-yl)-2-(o-tolyloxy)propan-1-one;
1-(4-(3-amino-1H-1,2,4-triazol-5-yl)piperazin-1-yl)-2-(2-ethylphenoxy)propan-1-one;
1-(4-(3-amino-1H-1,2,4-triazol-5-yl)piperazin-1-yl)-2-(2,5-dimethylphenoxy)propan-1-one;
1-(4-(3-amino-1H-1,2,4-triazol-5-yl)piperazin-1-yl)-2-(2,4-dimethylphenoxy)propan-1-one;
1-(4-(3-amino-1H-1,2,4-triazol-5-yl)piperazin-1-yl)-2-(m-tolyloxy)propan-1-one;
1-(4-(3-amino-1H-1,2,4-triazol-5-yl)piperazin-1-yl)-2-(2,3-difluorophenoxy)propan-1-one;
5-(4-(3-(4-bromophenyl)-2-methylpropyl)piperazin-1-yl)-1H-1,2,4-triazol-3-amine;
3-amino-1-(4-(3-amino-1H-1,2,4-triazol-5-yl)piperazin-1-yl)-3-(4-chlorophenyl)propan-1-one;
5-(4-(3-(benzo[d][1,3]dioxol-5-yl)-1,2,4-oxadiazol-5-yl)piperidin-1-yl)-1H-1,2,4-triazol-3-amine;
5-(4-(3-(4-(methylsulfonyl)phenyl)-1,2,4-oxadiazol-5-yl)piperidin-1-yl)-1H-1,2,4-triazol-3-amine;
5-(4-(5-(4-fluorophenyl)-1,3,4-oxadiazol-2-yl)piperidin-1-yl)-1H-1,2,4-triazol-3-amine;
1-(4-(3-amino-1H-1,2,4-triazol-5-yl)piperazin-1-yl)-2-(2-fluorophenoxy)propan-1-one;
1-(4-(3-amino-1H-1,2,4-triazol-5-yl)piperazin-1-yl)-2-(2-chloro-4-methylphenoxy)propan-1-one;

benzyl 4-(3-amino-1H-1,2,4-triazol-5-yl)piperazine-1-carboxylate;
(4-(3-amino-1H-1,2,4-triazol-5-yl)piperazin-1-yl)(benzofuran-2-yl)methanone;
1-(3-amino-1H-1,2,4-triazol-5-yl)-N-(4-fluorobenzyl)piperidine-4-carboxamide;
1-(3-amino-1H-1,2,4-triazol-5-yl)-N-(4-fluoro-2-(trifluoromethyl)benzyl)piperidine-4-carboxamide;
1-(3-amino-1H-1,2,4-triazol-5-yl)-N-(2-fluorobenzyl)piperidine-4-carboxamide;
1-(3-amino-1H-1,2,4-triazol-5-yl)-N-(4-chlorobenzyl)piperidine-4-carboxamide;
1-(3-amino-1H-1,2,4-triazol-5-yl)-N-(2-bromobenzyl)piperidine-4-carboxamide;
1-(3-amino-1H-1,2,4-triazol-5-yl)-N-(4-fluoro-3-(trifluoromethyl)benzyl)piperidine-4-carboxamide;
5-(4-(((4-bromobenzyl)(methyl)amino)methyl)piperidin-1-yl)-1H-1,2,4-triazol-3-amine;
N-(1-(3-amino-1H-1,2,4-triazol-5-yl)piperidin-4-yl)-1-(3-fluorophenyl)methanesulfonamide;
N-(1-(3-amino-1H-1,2,4-triazol-5-yl)piperidin-4-yl)-1-(4-fluorophenyl)methanesulfonamide;
N-(1-(3-amino-1H-1,2,4-triazol-5-yl)piperidin-4-yl)-1-(3,5-dichlorophenyl) methanesulfonamide;
N-(1-(3-amino-1H-1,2,4-triazol-5-yl)piperidin-4-yl)-1-(3-chlorophenyl)methanesulfonamide;
5-(4-(2-(4-bromophenoxy)butyl)piperazin-1-yl)-1H-1,2,4-triazol-3-amine;
(R)-5-(4-(2-(4-bromophenoxy)propyl)piperazin-1-yl)-1H-1,2,4-triazol-3-amine;
(S)-5-(4-(2-(4-bromophenoxy)propyl)piperazin-1-yl)-1H-1,2,4-triazol-3-amine;
5-(4-(2-(4-chlorophenoxy)butyl)piperazin-1-yl)-1H-1,2,4-triazol-3-amine;
(R)-5-(4-(2-(4-chlorophenoxy)propyl)piperazin-1-yl)-1H-1,2,4-triazol-3-amine;
(S)-5-(4-(2-(4-chlorophenoxy)propyl)piperazin-1-yl)-1H-1,2,4-triazol-3-amine;
(4-(3-amino-1H-1,2,4-triazol-5-yl)-1-(3-(4-chlorophenyl)propyl)piperazin-2-yl)methanol;
1-(1-(3-amino-1H-1,2,4-triazol-5-yl)piperidin-4-yl)-3-(4-chlorophenyl)urea;
1-(1-(3-amino-1H-1,2,4-triazol-5-yl)piperidin-4-yl)-3-(3,4-difluorophenyl)urea;
N-((1-(3-amino-1H-1,2,4-triazol-5-yl)piperidin-4-yl)methyl)-3-bromobenzamide;
2-(1-(3-amino-1H-1,2,4-triazol-5-yl)piperidin-4-yl)-N-(4-bromophenyl)acetamide;
N-(1-(3-amino-1H-1,2,4-triazol-5-yl)piperidin-4-yl)-2-(4-chlorophenyl)-2-hydroxyacetamide;
(R)-1-(4-(3-amino-1H-1,2,4-triazol-5-yl)piperazin-1-yl)-3-(4-chlorophenyl)-2-hydroxypropan-1-one;
1-(4-(3-amino-1H-1,2,4-triazol-5-yl)piperazin-1-yl)-3-(2-chlorophenyl)-2-hydroxypropan-1-one;
1-(4-(3-amino-1H-1,2,4-triazol-5-yl)piperazin-1-yl)-2-(4-chloro-3-nitrophenoxy)ethan-1-one;
(S)-2-amino-1-(4-(3-amino-1H-1,2,4-triazol-5-yl)piperazin-1-yl)-3-(2,4-dichlorophenyl)propan-1-one;
(S)-2-amino-1-(4-(3-amino-1H-1,2,4-triazol-5-yl)piperazin-1-yl)-3-(2-chlorophenyl)propan-1-one;
N-(3-(4-(3-amino-1H-1,2,4-triazol-5-yl)piperazin-1-yl)-1-(4-fluorophenyl)-3-oxopropyl)acetamide;
5-(4-(2-phenoxyethyl)piperazin-1-yl)-1H-1,2,4-triazol-3-amine;
5-(4-(2-(2-chlorophenoxy)ethyl)piperazin-1-yl)-1H-1,2,4-triazol-3-amine;
5-(4-(2-(benzyl oxy)ethyl)piperazin-1-yl)-1H-1,2,4-triazol-3-amine;
5-(4-(2-(4-methoxyphenoxy)ethyl)piperazin-1-yl)-1H-1,2,4-triazol-3-amine;
5-(4-(2-((1H-indol-5-yl)oxy)ethyl)piperazin-1-yl)-1H-1,2,4-triazol-3-amine;
5-(4-(2-([1,1'-biphenyl]-2-yloxy)ethyl)piperazin-1-yl)-1H-1,2,4-triazol-3-amine;
5-(4-(2-(2-isopropylphenoxy)ethyl)piperazin-1-yl)-1H-1,2,4-triazol-3-amine;
5-(4-(2-(2-fluorophenoxy)ethyl)piperazin-1-yl)-1H-1,2,4-triazol-3-amine;
5-(4-(2-(3-chlorophenoxy)ethyl)piperazin-1-yl)-1H-1,2,4-triazol-3-amine;
5-(4-(2-(2-chloro-6-methylphenoxy)ethyl)piperazin-1-yl)-1H-1,2,4-triazol-3-amine;
1-(3-amino-1H-1,2,4-triazol-5-yl)-N-(4-chlorophenethyl)piperidin-4-amine;
1-(3-amino-1H-1,2,4-triazol-5-yl)-N-(4-chlorophenethyl)-N-ethylpiperidin-4-amine;
(R)-5-(4-(2-(4-bromophenoxy)propyl)piperazin-1-yl)-1H-1,2,4-triazol-3-amine;
1-(3-amino-1H-1,2,4-triazol-5-yl)-N-(4-chlorobenzyl)-N,4-dimethylpiperidine-4-carboxamide;
1-(3-amino-1H-1,2,4-triazol-5-yl)-N-(4-chlorophenethyl)-N-isobutylpiperidin-4-amine;
1-(3-amino-1H-1,2,4-triazol-5-yl)-N-(4-chlorophenethyl)-N-(3,3-dimethylbutyl)piperidin-4-amine;
1-(3-amino-1H-1,2,4-triazol-5-yl)-N-(4-chlorophenethyl)-N-neopentylpiperidin-4-amine;
1-(3-amino-1H-1,2,4-triazol-5-yl)-N-(2-chlorobenzyl)-N-(4-chlorophenethyl)piperidin-4-amine;
1-(3-amino-1H-1,2,4-triazol-5-yl)-N-(4-bromophenethyl)-N-isobutylpiperidin-4-amine;
1-(3-amino-1H-1,2,4-triazol-5-yl)-N-(4-bromophenethyl)-N-(2-chlorobenzyl)piperidin-4-amine;
1-(3-amino-1H-1,2,4-triazol-5-yl)-N-benzyl-N-(4-chlorophenethyl) piperidin-4-amine;
(3-(((1-(3-amino-1H-1,2,4-triazol-5-yl)piperidin-4-yl)(4-chlorophenethyl)amino) methyl)phenyl)methanol;
1-(3-amino-1H-1,2,4-triazol-5-yl)-N-(4-bromophenethyl)-N-ethylpiperidin-4-amine;
1-(3-amino-1H-1,2,4-triazol-5-yl)-N-(4-chlorophenethyl)-N-(4-methylbenzyl)piperidin-4-amine;
(S)-1-(3-amino-1H-1,2,4-triazol-5-yl)-N-(4-chlorophenethyl)-N-(1-phenylethyl)piperidin-4-amine;
1-(3-amino-1H-1,2,4-triazol-5-yl)-N-(4-chlorophenethyl)-N-(4-(trifluoromethyl)benzyl) piperidin-4-amine;
1-(3-amino-1H-1,2,4-triazol-5-yl)-N-(4-bromophenethyl)-N-(isoquinolin-8-ylmethyl) piperidin-4-amine;
1-(3-amino-1H-1,2,4-triazol-5-yl)-N-(4-cyclopropylphenethyl)-N-methylpiperidin-4-amine;
(R)-2-((1-(3-amino-1H-1,2,4-triazol-5-yl)piperidin-4-yl)(4-chlorophenethyl)amino)-2-phenylethan-1-ol;
1-(3-amino-1H-1,2,4-triazol-5-yl)-N-(4-chlorophenethyl)-N-(pyridin-4-ylmethyl)piperidin-4-amine;
(R)-1-(3-amino-1H-1,2,4-triazol-5-yl)-N-(4-chlorophenethyl)-N-(2-methoxy-1-phenylethyl) piperidin-4-amine;
1-(3-amino-1H-1,2,4-triazol-5-yl)-N-(3-chlorobenzyl)-N-(4-chlorophenethyl)piperidin-4-amine;
N-([1,1'-biphenyl]-4-ylmethyl)-1-(3-amino-1H-1,2,4-triazol-5-yl)-N-(4-chlorophenethyl) piperidin-4-amine;
1-(3-amino-1H-1,2,4-triazol-5-yl)-N-(4-chlorophenethyl)-N-(naphthalen-2-ylmethyl) piperidin-4-amine;

1-(3-amino-1H-1,2,4-triazol-5-yl)-N-(4-chlorophenethyl)-N-(2-(trifluoromethyl)benzyl) piperidin-4-amine;
N-([1,1'-biphenyl]-2-ylmethyl)-1-(3-amino-1H-1,2,4-triazol-5-yl)-N-(4-chlorophenethyl) piperidin-4-amine;
N-(4-(1H-pyrazol-5-yl)benzyl)-1-(3-amino-1H-1,2,4-triazol-5-yl)-N-(4-chlorophenethyl) piperidin-4-amine;
1-(3-amino-1H-1,2,4-triazol-5-yl)-N-(4-chlorophenethyl)-N-(quinoxalin-2-ylmethyl) piperidin-4-amine;
2-((1-(3-amino-1H-1,2,4-triazol-5-yl)piperidin-4-yl)(4-chlorophenethyl)amino)ethan-1-ol;
(R)-1-(3-amino-1H-1,2,4-triazol-5-yl)-N-(4-chlorophenethyl)-N-(1-phenylethyl)piperidin-4-amine;
1-(3-amino-1H-1,2,4-triazol-5-yl)-N-(4-chlorophenethyl)-N-((3-fluoropyridin-4-yl)methyl)piperidin-4-amine;
1-(3-amino-1H-1,2,4-triazol-5-yl)-N-(4-isopropylphenethyl)-N-methylpiperidin-4-amine;
1-(3-amino-1H-1,2,4-triazol-5-yl)-N-(4-ethylphenethyl)-N-methylpiperidin-4-amine;
1-(3-amino-1H-1,2,4-triazol-5-yl)-N-(4-bromophenethyl)-3-methylpiperidin-4-amine;
1-(3-amino-1H-1,2,4-triazol-5-yl)-N-(4-chlorophenethyl)-N-(4-fluorobenzyl)piperidin-4-amine;
1-(3-amino-1H-1,2,4-triazol-5-yl)-N-(4-chlorophenethyl)-N-(2-methylbenzyl)piperidin-4-amine;
1-(3-amino-1H-1,2,4-triazol-5-yl)-N-(4-chloro-3-(trifluoromethyl)benzyl)-N-(4-chlorophenethyl)piperidin-4-amine;
1-(3-amino-1H-1,2,4-triazol-5-yl)-N-(2-bromobenzyl)-N-(4-chlorophenethyl)piperidin-4-amine;
1-(3-amino-1H-1,2,4-triazol-5-yl)-N-(4-chlorophenethyl)-N-isopropylpiperidin-4-amine;
1-(3-amino-1H-1,2,4-triazol-5-yl)-N-(4-bromophenethyl)-N-(naphthalen-1-ylmethyl) piperidin-4-amine;
2-((1-(3-amino-1H-1,2,4-triazol-5-yl)piperidin-4-yl)(methyl)amino)-3-(4-chlorophenyl) propan-1-ol;
1-(3-amino-1H-1,2,4-triazol-5-yl)-N-methyl-N-(2-(pyridin-3-yl)ethyl)piperidin-4-amine;
1-(3-amino-1H-1,2,4-triazol-5-yl)-N-(4-chlorophenethyl)-3-methylpiperidin-4-amine;
1-(3-amino-1H-1,2,4-triazol-5-yl)-N-(4-chlorophenethyl)-N-(naphthalen-1-ylmethyl)piperidin-4-amine;
1-(3-amino-1H-1,2,4-triazol-5-yl)-N-(4-chlorobenzyl)-N-(4-chlorophenethyl)piperidin-4-amine;
(S)-2-((1-(3-amino-1H-1,2,4-triazol-5-yl)piperidin-4-yl)(4-chlorophenethyl)amino)-2-phenylethan-1-ol;
N-((1H-benzo[d]imidazol-2-yl)methyl)-1-(3-amino-1H-1,2,4-triazol-5-yl)-N-methylpiperidin-4-amine;
1-(3-amino-1H-1,2,4-triazol-5-yl)-N-(4-chlorophenethyl)-N-(2-fluorobenzyl)piperidin-4-amine;
1-(3-amino-1H-1,2,4-triazol-5-yl)-N-(4-chlorophenethyl)-N-methylpiperidin-4-amine;
(R)-1-(3-amino-1H-1,2,4-triazol-5-yl)-N-(1-(4-chlorophenyl)propan-2-yl)-N-methylpiperidin-4-amine;
1-(3-amino-1H-1,2,4-triazol-5-yl)-N-(2-(4-chlorophenyl)propyl)-N-methylpiperidin-4-amine;
1-(3-amino-1H-1,2,4-triazol-5-yl)-N-(1-(4-chlorophenyl)propan-2-yl)-N-methylpiperidin-4-amine;
4-(((1-(3-amino-1H-1,2,4-triazol-5-yl)piperidin-4-yl)(4-chlorophenethyl) amino)methyl)benzonitrile;
1-(3-amino-1H-1,2,4-triazol-5-yl)-N-(4-chlorophenethyl)-N-(cyclohexylmethyl)piperidin-4-amine;
1-(3-amino-1H-1,2,4-triazol-5-yl)-N-(4-chlorophenethyl)-N4-fluoronaphthalen-1-yl)methyl)piperidin-4-amine;
1-(3-amino-1H-1,2,4-triazol-5-yl)-N-(2-chloro-4-fluorobenzyl)-N-(4-chlorophenethyl)piperidin-4-amine;
1-(3-amino-1H-1,2,4-triazol-5-yl)-N-benzyl-N-(4-bromophenethyl)piperidin-4-amine;
1-(3-amino-1H-1,2,4-triazol-5-yl)-N-(2-(4-chlorophenyl)propyl)piperidin-4-amine;
1-(3-amino-1H-1,2,4-triazol-5-yl)-N-(4-chlorobenzyl)-N-methylpiperidin-4-amine;
1-(3-amino-1H-1,2,4-triazol-5-yl)-N-(4-chlorophenethyl)-N-(3,5-dichlorobenzyl)piperidin-4-amine;
1-(3-amino-1H-1,2,4-triazol-5-yl)-N-(4-chlorophenethyl)-3-fluoro-N-methylpiperidin-4-amine;
1-(3-amino-1H-1,2,4-triazol-5-yl)-N-(1-(4-chlorophenyl)propan-2-yl)piperidin-4-amine;
1-(3-amino-1H-1,2,4-triazol-5-yl)-N-(4-chlorophenethyl)-N-(4-methoxybenzyl)piperidin-4-amine;
(S)-2-((1-(3-amino-1H-1,2,4-triazol-5-yl)piperidin-4-yl)(methyl)amino)-3-(4-chlorophenyl) propan-1-ol;
1-(3-amino-1H-1,2,4-triazol-5-yl)-N-(4-chlorophenethyl)-N,3-dimethylpiperidin-4-amine;
1-(3-amino-1H-1,2,4-triazol-5-yl)-N-(4-chlorophenethyl)-N-ethylpiperidin-4-amine;
1-(3-amino-1H-1,2,4-triazol-5-yl)-N-(4-chlorophenethyl)-N-(3-(trifluoromethyl)benzyl) piperidin-4-amine;
1-(3-amino-1H-1,2,4-triazol-5-yl)-N-methyl-N-(2-(pyridin-2-yl)ethyl)piperidin-4-amine;
1-(3-amino-1H-1,2,4-triazol-5-yl)-N-(4-chlorophenethyl)-N-(2,4-dichlorobenzyl)piperidin-4-amine;
1-(3-amino-1H-1,2,4-triazol-5-yl)-N-benzyl-N-(1-(4-chlorophenyl)propan-2-yl)piperidin-4-amine;
1-(3-amino-1H-1,2,4-triazol-5-yl)-N-(1-(4-chlorophenyl)butan-2-yl)-N-methylpiperidin-4-amine;
1-(3-amino-1H-1,2,4-triazol-5-yl)-N-(2-chloro-6-methylbenzyl)-N-(4-chlorophenethyl) piperidin-4-amine;
1-(3-amino-1H-1,2,4-triazol-5-yl)-N,N-bis(4-chlorophenethyl) piperidin-4-amine;
1-(3-amino-1H-1,2,4-triazol-5-yl)-N-(4-chlorophenethyl)-N-(2,4-dichlorobenzyl)piperidin-4-amine;
(2-(((1-(3-amino-1H-1,2,4-triazol-5-yl)piperidin-4-yl)(4-chlorophenethyl)amino)methyl) phenyl)methanol;
1-(3-amino-1H-1,2,4-triazol-5-yl)-N-(4-(tert-butyl)phenethyl)-N-methylpiperidin-4-amine;
1-(5-amino-1-methyl-1H-1,2,4-triazol-3-yl)-N-(4-bromophenethyl)-N-methylpiperidin-4-amine;
1-(3-amino-1H-1,2,4-triazol-5-yl)-N-(4-bromophenethyl)-N-((4-fluoronaphthalen-1-yl)methyl)piperidin-4-amine;
1-(3-amino-1H-1,2,4-triazol-5-yl)-N-(4-bromophenethyl)-N-(isoquinolin-5-ylmethyl)piperidin-4-amine;
1-(3-amino-1H-1,2,4-triazol-5-yl)-N-methyl-N-(2-(trifluoromethyl)phenethyl)piperidin-4-amine;
1-(3-amino-1H-1,2,4-triazol-5-yl)-N-(2-(benzo[d][1,3]dioxol-5-yl)ethyl)-N-methylpiperidin-4-amine;
1-(3-amino-1H-1,2,4-triazol-5-yl)-N-methyl-N-(4-methylphenethyl)piperidin-4-amine;
1-(3-amino-1H-1,2,4-triazol-5-yl)-N-(2-methoxyphenethyl)-N-methylpiperidin-4-amine;
1-(3-amino-1H-1,2,4-triazol-5-yl)-N-(3,4-dimethoxyphenethyl)-N-methylpiperidin-4-amine;
1-(3-amino-1H-1,2,4-triazol-5-yl)-N-methyl-N-(2-(trifluoromethoxy)phenethyl)piperidin-4-amine;
1-(3-amino-1H-1,2,4-triazol-5-yl)-N-(2,4-dichlorophenethyl)-N-methylpiperidin-4-amine;
1-(3-amino-1H-1,2,4-triazol-5-yl)-N-(3,4-dichlorophenethyl)-N-methylpiperidin-4-amine;

1-(3-amino-1H-1,2,4-triazol-5-yl)-N-(2,3-dimethoxyphenethyl)-N-methylpiperidin-4-amine;
1-(3-amino-1H-1,2,4-triazol-5-yl)-N-(4-(dimethylamino)phenethyl)-N-methylpiperidin-4-amine;
1-(3-amino-1H-1,2,4-triazol-5-yl)-N-methyl-N-(2-methylphenethyl)piperidin-4-amine;
1-(3-amino-1H-1,2,4-triazol-5-yl)-N-methyl-N-(3-(trifluoromethyl)phenethyl)piperidin-4-amine;
1-(3-amino-1H-1,2,4-triazol-5-yl)-N-methyl-N-phenethylpiperidin-4-amine;
1-(3-amino-1H-1,2,4-triazol-5-yl)-N-(2,5-dimethoxyphenethyl)-N-methylpiperidin-4-amine;
1-(3-amino-1H-1,2,4-triazol-5-yl)-N-(4-fluorophenethyl)-N-methylpiperidin-4-amine;
1-(3-amino-1H-1,2,4-triazol-5-yl)-N-(2,6-dichlorophenethyl)-N-methylpiperidin-4-amine;
1-(3-amino-1H-1,2,4-triazol-5-yl)-N-(4-chlorophenethyl)-N-(2,2,2-trifluoroethyl)piperidin-4-amine;
1-(3-amino-1H-1,2,4-triazol-5-yl)-N-(4-chlorophenethyl)-N-(2-methoxyethyl)piperidin-4-amine;
N-(1-(3-amino-1H-1,2,4-triazol-5-yl)piperidin-4-yl)-1-(3-bromophenyl)methanesulfonamide;
N-(1-(3-amino-1H-1,2,4-triazol-5-yl)piperidin-4-yl)-1-(3-(trifluoromethyl)phenyl) methanesulfonamide;
5-(4-(2-(2-(trifluoromethyl)-phenoxy)ethyl)piperazin-1-yl)-1H-1,2,4-triazol-3-amine;
5-(4-(2-(2,6-dichlorophenoxy)ethyl)piperazin-1-yl)-1H-1,2,4-triazol-3-amine;
1-(3-amino-1H-1,2,4-triazol-5-yl)-N-(naphthalen-1-ylmethyl)piperidine-4-carboxamide;
1-(3-amino-1H-1,2,4-triazol-5-yl)-N-(3-fluorobenzyl)piperidine-4-carboxamide;
1-(3-amino-1H-1,2,4-triazol-5-yl)-N-(2-methoxybenzyl) piperidine-4-carboxamide;
1-(3-amino-1H-1,2,4-triazol-5-yl)-N-(2-chlorobenzyl)piperidine-4-carboxamide;
1-(3-amino-1H-1,2,4-triazol-5-yl)-N-(3,4-difluorobenzyl)piperidine-4-carboxamide;
1-(3-amino-1H-1,2,4-triazol-5-yl)-N-(1-(4-chlorophenyl)propan-2-yl)-N-methylpiperidin-4-amine;
1-(3-amino-1H-1,2,4-triazol-5-yl)-N-(2,4-dimethoxybenzyl)piperidine-4-carboxamide;
1-(3-amino-1H-1,2,4-triazol-5-yl)-N-((2-methyl-5-(trifluoromethyl)furan-3-yl)methyl) piperidine-4-carboxamide;
1-(3-amino-1H-1,2,4-triazol-5-yl)-N-(3,4-difluorobenzyl)piperidine-4-carboxamide;
1-(3-amino-1H-1,2,4-triazol-5-yl)-N-(2,5-dimethylbenzyl)piperidine-4-carboxamide;
1-(3-amino-1H-1,2,4-triazol-5-yl)-N-(4-(trifluoromethoxy)benzyl) piperidine-4-carboxamide;
1-(3-amino-1H-1,2,4-triazol-5-yl)-N-(4-methoxybenzyl) piperidine-4-carboxamide;
N-((1-(3-amino-1H-1,2,4-triazol-5-yl)piperidin-4-yl)methyl)-3-fluorobenzamide;
N-((1-(3-amino-1H-1,2,4-triazol-5-yl)piperidin-4-yl)methyl)-3,5-dibromobenzamide;
N-((1-(3-amino-1H-1,2,4-triazol-5-yl)piperidin-4-yl)methyl)-2,3-dimethylbenzamide;
N-((1-(3-amino-1H-1,2,4-triazol-5-yl)piperidin-4-yl)methyl)-3,4-dimethoxybenzamide;
N-((1-(3-amino-1H-1,2,4-triazol-5-yl)piperidin-4-yl)methyl)-2-methylbenzamide;
N-((1-(3-amino-1H-1,2,4-triazol-5-yl)piperidin-4-yl)methyl)-2,4-difluorobenzamide;
3-amino-1-(4-(3-amino-1H-1,2,4-triazol-5-yl)piperazin-1-yl)-3-(2-fluorophenyl)propan-1-one;
3-amino-1-(4-(3-amino-1H-1,2,4-triazol-5-yl)piperazin-1-yl)-3-(4-fluorophenyl)propan-1-one;
5-(4-(2-(4-chlorophenoxy)butyl) piperazin-1-yl)-1H-1,2,4-triazol-3-amine;
1-(1-(3-amino-1H-1,2,4-triazol-5-yl)piperidin-4-yl)-3-(2,4,5-trichlorophenyl)urea;
1-((1-(3-amino-1H-1,2,4-triazol-5-yl)piperidin-4-yl)methyl)-3-(3-chlorophenyl)urea;
1-(1-(3-amino-1H-1,2,4-triazol-5-yl)piperidin-4-yl)-3-(4-bromophenyl)urea;
N-((1-(3-amino-1H-1,2,4-triazol-5-yl)piperidin-4-yl)methyl)-3,4-difluorobenzamide;
(S)-1-(4-(3-amino-1H-1,2,4-triazol-5-yl)piperazin-1-yl)-3-(4-chlorophenyl)-2-hydroxypropan-1-one;
N-(3-(4-(3-amino-1H-1,2,4-triazol-5-yl)piperazin-1-yl)-1-(3-fluorophenyl)-3-oxopropyl)acetamide;
3-(4-(3-amino-1H-1,2,4-triazol-5-yl)-1-(3-(4-(trifluoromethyl)phenyl)propyl)piperazin-2-yl)propan-1-ol;
3-(4-(3-amino-1H-1,2,4-triazol-5-yl)-1-(3-(4-bromophenyl)propyl)piperazin-2-yl)propyl acetate;
3-(4-(3-amino-1H-1,2,4-triazol-5-yl)-1-(3-(4-bromophenyl)propyl) piperazin-2-yl)propan-1-ol;
3-(4-(3-amino-1H-1,2,4-triazol-5-yl)-1-(3-phenylpropyl) piperazin-2-yl)propan-1-ol;
N-(1-(3-amino-1H-1,2,4-triazol-5-yl)-3-(hydroxymethyl)piperidin-4-yl)-1-(4-bromophenyl) methanesulfonamide;
2-(1-(3-amino-1H-1,2,4-triazol-5-yl)-4-((4-chlorophenethyl)(methyl)amino)piperidin-4-yl)ethanol;
4-(4-(3-amino-1H-1,2,4-triazol-5-yl)-1-(3-(4-bromophenyl)propyl)piperazin-2-yl)-2-methylbutan-2-ol;
1-(3-amino-1H-1,2,4-triazol-5-yl)-N-(4-bromophenethyl)-N,3-dimethylpiperidin-4-amine;
1-(3-amino-1H-1,2,4-triazol-5-yl)-N-(4-chlorophenethyl)-3-propylpiperidin-4-amine;
1-(3-amino-1H-1,2,4-triazol-5-yl)-N-(1-(4-chlorophenyl)butan-2-yl)-N-ethylpiperidin-4-amine;
3-amino-1-(4-(3-amino-1H-1,2,4-triazol-5-yl)piperazin-1-yl)-3-(3-fluorophenyl)propan-1-one;
1-(3-amino-1H-1,2,4-triazol-5-yl)-N-(4-chlorophenethyl)-3-propylpiperidin-4-amine;
1-(3-amino-1H-1,2,4-triazol-5-yl)-N-(4-chlorobenzyl)-4-methylpiperidine-4-carboxamide;
1-(3-amino-1H-1,2,4-triazol-5-yl)-N-(4-bromobenzyl)-4-methylpiperidine-4-carboxamide;
N-(1-(3-amino-1H-1,2,4-triazol-5-yl)piperidin-4-yl)-1-(3-chlorophenyl)-N-ethylmethanesulfonamide;
N-(1-(3-amino-1H-1,2,4-triazol-5-yl)piperidin-4-yl)-1-(4-bromophenyl)-N-methylmethanesulfonamide;
1-(4-(3-amino-1H-1,2,4-triazol-5-yl)piperazin-1-yl)-3-(2,4-dichlorophenyl)-2-(dimethylamino)propan-1-one;
(R)-5-(4-(2-(4-chlorophenoxy)propyl)piperazin-1-yl)-1H-1,2,4-triazol-3-amine;
1-(4-(3-amino-1H-1,2,4-triazol-5-yl)piperazin-1-yl)-3-(dimethylamino)-3-(2-fluorophenyl)propan-1-one;
N-((1-(3-amino-1H-1,2,4-triazol-5-yl)piperidin-4-yl)methyl)-3,5-dichlorobenzamide;
N-(1-(3-amino-1H-1,2,4-triazol-5-yl)-3-methylpiperidin-4-yl)-1-(4-bromophenyl)methanesulfonamide;
3-(1-(3-amino-1H-1,2,4-triazol-5-yl)-4-((4-chlorophenethyl)(methyl)amino)piperidin-4-yl)propan-1-ol;
3-(1-(3-amino-1H-1,2,4-triazol-5-yl)-4-(4-bromophenethyl)(methyl)amino)piperidin-3-yl)propan-1-ol;
1-(3-amino-1H-1,2,4-triazol-5-yl)-N-(4-bromophenethyl)-4-propylpiperidin-4-amine;
N-(1-(3-amino-1H-1,2,4-triazol-5-yl)piperidin-4-yl)-1-(3-chlorophenyl)-N-methylmethanesulfonamide;

1-(3-amino-1H-1,2,4-triazol-5-yl)-N-(4-chlorophenethyl)-3-fluoro-N-methylpiperidin-4-amine;
1-(3-amino-1H-1,2,4-triazol-5-yl)-N-methyl-N-(1,2,3,4-tetrahydronaphthalen-2-yl)piperidin-4-amine;
3-(1-(3-amino-1H-1,2,4-triazol-5-yl)-4-((4-chlorophenethyl)amino)piperidin-3-yl)propan-1-ol;
5-(4-(((3,4-dichlorobenzyl)amino) methyl)piperidin-1-yl)-1H-1,2,4-triazol-3-amine;
5-(1-(4-bromophenethyl)octahydro-1,6-naphthyridin-6(2H)-yl)-1H-1,2,4-triazol-3-amine;
5-(4-(((4-bromobenzyl)amino) methyl)piperidin-1-yl)-1H-1,2,4-triazol-3-amine;
1-(3-amino-1H-1,2,4-triazol-5-yl)-N-(3,5-bis(trifluoromethyl)benzyl) piperidine-4-carboxamide;
N-(1-(3-amino-1H-1,2,4-triazol-5-yl)-4-(4-hydroxybutyl) piperidin-4-yl)-1-(4-bromophenyl)methane sulfonamide;
5-(4-(4-(4-bromophenyl)-1-phenylbutan-2-yl)piperazin-1-yl)-1H-1,2,4-triazol-3-amine trifluoroacetate;
1-(4-(3-amino-1H-1,2,4-triazol-5-yl)piperazin-1-yl)-2-(4-chlorophenoxy)-2-methylpropan-1-one, and 1-(4-(3-amino-1H-1,2,4-triazol-5-yl)piperazin-1-yl)-2-(4-bromophenoxy)ethan-1-one;
or a salt, hydrate or solvate thereof.

\* \* \* \* \*